US011722764B2

(12) United States Patent
Van Os et al.

(10) Patent No.: US 11,722,764 B2
(45) Date of Patent: Aug. 8, 2023

(54) CREATIVE CAMERA

(71) Applicant: Apple Inc., Cupertino, CA (US)

(72) Inventors: Marcel Van Os, San Francisco, CA (US); Jessica L. Aboukasm, San Francisco, CA (US); Jean-Francois M. Albouze, Santa Cruz, CA (US); David R. Black, San Jose, CA (US); Jae Woo Chang, San Jose, CA (US); Robert M. Chinn, Redwood City, CA (US); Gregory L. Dudey, Eagle, ID (US); Katherine K. Ernst, Cedar Rapids, IA (US); Aurelio Guzman, San Jose, CA (US); Christopher J. Moulios, Palo Alto, CA (US); Joanna M. Newman, Santa Clara, CA (US); Grant Paul, San Francisco, CA (US); Nicolas Scapel, Sunnyvale, CA (US); William A. Sorrentino, III, Mill Valley, CA (US); Brian E. Walsh, San Jose, CA (US); Joseph-Alexander P. Weil, Greenbae, CA (US); Christopher Wilson, Sonoma, CA (US)

(73) Assignee: Apple Inc., Cupertino, CA (US)

(*) Notice: Subject to any disclaimer, the term of this patent is extended or adjusted under 35 U.S.C. 154(b) by 0 days.

(21) Appl. No.: 17/525,664

(22) Filed: Nov. 12, 2021

(65) Prior Publication Data
US 2022/0070385 A1 Mar. 3, 2022

Related U.S. Application Data

(63) Continuation of application No. 16/599,433, filed on Oct. 11, 2019, now Pat. No. 11,178,335, which is a
(Continued)

(51) Int. Cl.
H04N 5/232 (2006.01)
H04N 5/262 (2006.01)
(Continued)

(52) U.S. Cl.
CPC ....... H04N 23/631 (2023.01); G06F 3/04845 (2013.01); G06T 13/20 (2013.01);
(Continued)

(58) Field of Classification Search
CPC .......... H04N 5/232933; H04N 5/2226; H04N 5/2621; H04N 23/631; G06F 3/04845; G06T 13/20; G06T 13/40
See application file for complete search history.

(56) References Cited

U.S. PATENT DOCUMENTS 4,518,237 A 5/1985 Mizokami
4,847,819 A 7/1989 Hong
(Continued)

FOREIGN PATENT DOCUMENTS

AU 2015101639 A4 12/2015
AU 2013368443 B2 3/2016
(Continued)

OTHER PUBLICATIONS

Intention to Grant received for Danish Patent Application No. PA202070623, dated Jul. 20, 2022, 2 pages.
(Continued)

Primary Examiner — Mark T Monk
(74) Attorney, Agent, or Firm — DLA Piper LLP (US)

(57) ABSTRACT

The present disclosure generally relates to displaying visual effects in image data. In some examples, visual effects include an avatar displayed on a user's face. In some examples, visual effects include stickers applied to image
(Continued)

data. In some examples, visual effects include screen effects. In some examples, visual effects are modified based on depth data in the image data.

27 Claims, 249 Drawing Sheets

Related U.S. Application Data continuation of application No. 16/143,097, filed on Sep. 26, 2018, now Pat. No. 10,523,879.

(60) Provisional application No. 62/679,934, filed on Jun. 3, 2018, provisional application No. 62/668,227, filed on May 7, 2018.

(51) Int. Cl.
| | |
|---|---|
| *G06F 3/04845* | (2022.01) |
| *G06T 13/40* | (2011.01) |
| *G06T 13/20* | (2011.01) |
| *H04N 5/222* | (2006.01) |
| *A61B 5/00* | (2006.01) |
| *G06T 7/70* | (2017.01) |
| *H04N 23/63* | (2023.01) |
| *H04N 23/62* | (2023.01) |
| *H04N 23/611* | (2023.01) |
| *H04M 1/72439* | (2021.01) |
| *H04M 1/72436* | (2021.01) |
| *G06F 3/04842* | (2022.01) |
| *H04N 7/14* | (2006.01) |
| *G06T 7/50* | (2017.01) |
| *H04N 5/272* | (2006.01) |

(52) U.S. Cl.
CPC .......... *G06T 13/40* (2013.01); *H04M 1/72436* (2021.01); *H04M 1/72439* (2021.01); *H04N 5/2226* (2013.01); *H04N 5/2621* (2013.01); *H04N 23/611* (2023.01); *H04N 23/62* (2023.01); *H04N 23/632* (2023.01); *A61B 5/744* (2013.01); *G06F 3/04842* (2013.01); *G06T 7/50* (2017.01); *G06T 7/70* (2017.01); *G06T 2207/30196* (2013.01); *H04N 2005/2726* (2013.01); *H04N 2007/145* (2013.01)

(56) References Cited

U.S. PATENT DOCUMENTS

| | | | |
|---|---|---|---|
| 4,933,702 A | 6/1990 | Komatsuzaki et al. | |
| 4,945,521 A | 7/1990 | Klaus | |
| 5,463,443 A | 10/1995 | Tanaka et al. | |
| 5,557,358 A | 9/1996 | Mukai et al. | |
| 5,615,384 A | 3/1997 | Allard et al. | |
| 6,084,598 A | 7/2000 | Chekerylla | |
| 6,262,769 B1 | 7/2001 | Anderson et al. | |
| 6,268,864 B1 | 7/2001 | Chen et al. | |
| 6,278,466 B1 | 8/2001 | Chen | |
| 6,621,524 B1 | 9/2003 | Iijima et al. | |
| 6,677,981 B1 | 1/2004 | Mancuso et al. | |
| 6,900,840 B1 | 5/2005 | Schinner et al. | |
| 7,180,524 B1 | 2/2007 | Axelrod | |
| 7,227,976 B1 | 6/2007 | Jung et al. | |
| 7,515,178 B1 | 4/2009 | Fleischman et al. | |
| 7,583,892 B2 | 9/2009 | Okumura | |
| 7,716,057 B2 | 5/2010 | Horvitz | |
| 7,751,285 B1 | 7/2010 | Cain et al. | |
| 7,908,554 B1 | 3/2011 | Blattner | |
| 8,156,060 B2 | 4/2012 | Borzestowski et al. | |
| 8,169,438 B1 | 5/2012 | Baraff et al. | |
| 8,185,839 B2 | 5/2012 | Jalon et al. | |
| 8,234,218 B2 | 7/2012 | Robinson et al. | |
| 8,295,546 B2 | 10/2012 | Craig et al. | |
| 8,390,628 B2* | 3/2013 | Harding | G06T 13/40 345/475 |
| 8,405,680 B1 | 3/2013 | Gomes et al. | |
| 8,423,089 B2 | 4/2013 | Song et al. | |
| 8,493,408 B2 | 7/2013 | Williamson et al. | |
| 8,576,304 B2 | 11/2013 | Ishibashi | |
| 8,638,371 B2 | 1/2014 | Laberge et al. | |
| 8,723,988 B2 | 5/2014 | Thorn | |
| 8,736,704 B2 | 5/2014 | Jasinski et al. | |
| 8,736,716 B2 | 5/2014 | Prentice | |
| 8,848,097 B2 | 9/2014 | Makii | |
| 8,885,978 B2 | 11/2014 | Cote et al. | |
| 8,896,652 B2 | 11/2014 | Ralston | |
| 9,001,226 B1 | 4/2015 | Ng et al. | |
| 9,094,576 B1 | 7/2015 | Karakotsios | |
| 9,153,031 B2 | 10/2015 | El-saban et al. | |
| 9,158,974 B1 | 10/2015 | Laska et al. | |
| 9,207,837 B2 | 12/2015 | Paretti et al. | |
| 9,223,486 B2 | 12/2015 | Shin et al. | |
| 9,230,241 B1 | 1/2016 | Singh et al. | |
| 9,230,355 B1 | 1/2016 | Ahuja et al. | |
| 9,245,177 B2 | 1/2016 | Perez | |
| 9,246,961 B2 | 1/2016 | Walkin et al. | |
| 9,250,797 B2 | 2/2016 | Roberts et al. | |
| 9,264,660 B1 | 2/2016 | Petterson et al. | |
| 9,288,476 B2 | 3/2016 | Sandrew et al. | |
| 9,298,263 B2 | 3/2016 | Geisner et al. | |
| 9,313,397 B2 | 4/2016 | Harris et al. | |
| 9,313,401 B2 | 4/2016 | Frey et al. | |
| 9,342,230 B2 | 5/2016 | Bastien et al. | |
| 9,349,414 B1 | 5/2016 | Furment et al. | |
| 9,360,671 B1 | 6/2016 | Zhou | |
| 9,411,506 B1 | 8/2016 | Marra et al. | |
| 9,448,708 B1 | 9/2016 | Bennett et al. | |
| 9,467,812 B2 | 10/2016 | Jung et al. | |
| 9,542,070 B2 | 1/2017 | Xu et al. | |
| 9,544,563 B1 | 1/2017 | Cheng et al. | |
| 9,592,428 B2 | 3/2017 | Binder | |
| 9,600,178 B2 | 3/2017 | Yun et al. | |
| 9,602,559 B1 | 3/2017 | Barros et al. | |
| 9,609,221 B2 | 3/2017 | Kim et al. | |
| 9,625,987 B1 | 4/2017 | Lapenna et al. | |
| 9,626,589 B1 | 4/2017 | Graham et al. | |
| 9,628,416 B2 | 4/2017 | Henderson | |
| 9,667,881 B2 | 5/2017 | Harris et al. | |
| 9,686,497 B1 | 6/2017 | Terry | |
| 9,704,250 B1 | 7/2017 | Gilmour et al. | |
| 9,716,825 B1 | 7/2017 | Manzari et al. | |
| 9,760,976 B2* | 9/2017 | Kameyama | G06T 5/50 |
| 9,767,613 B1 | 9/2017 | Bedikian et al. | |
| 9,786,084 B1 | 10/2017 | Bhat et al. | |
| 9,819,912 B2 | 11/2017 | Maruta | |
| 9,948,589 B2 | 4/2018 | Gonnen et al. | |
| 9,949,697 B2 | 4/2018 | Iscoe et al. | |
| 10,015,298 B2 | 7/2018 | Yang et al. | |
| 10,021,294 B2 | 7/2018 | Kwon et al. | |
| 10,055,887 B1 | 8/2018 | Gil et al. | |
| 10,062,133 B1 | 8/2018 | Mishra et al. | |
| 10,091,411 B2 | 10/2018 | Ha et al. | |
| 10,095,385 B2 | 10/2018 | Walkin et al. | |
| 10,139,218 B2* | 11/2018 | Matsushita | G01B 11/026 |
| 10,152,222 B2 | 12/2018 | Ozawa et al. | |
| 10,176,622 B1 | 1/2019 | Waggoner et al. | |
| 10,187,587 B2 | 1/2019 | Hasinoff et al. | |
| 10,225,463 B2 | 3/2019 | Yun et al. | |
| 10,230,901 B2 | 3/2019 | Harris et al. | |
| 10,270,983 B1 | 4/2019 | Van Os et al. | |
| 10,289,265 B2 | 5/2019 | Kulkarni | |
| 10,297,034 B2 | 5/2019 | Nash et al. | |
| 10,304,231 B2 | 5/2019 | Saito | |
| 10,313,652 B1 | 6/2019 | Falstrup et al. | |
| 10,325,416 B1 | 6/2019 | Scapel et al. | |
| 10,325,417 B1 | 6/2019 | Scapel et al. | |
| 10,326,942 B2 | 6/2019 | Shabtay et al. | |
| 10,345,592 B2 | 7/2019 | Samec et al. | |
| 10,375,313 B1 | 8/2019 | Van Os et al. | |
| 10,376,153 B2 | 8/2019 | Tzvieli et al. | |
| 10,379,719 B2 | 8/2019 | Scapel et al. | |

(56) References Cited

U.S. PATENT DOCUMENTS

| | | |
|---|---|---|
| 10,397,469 B1 | 8/2019 | Yan et al. |
| 10,397,500 B1 | 8/2019 | Xu et al. |
| 10,410,434 B1 | 9/2019 | Scapel et al. |
| 10,447,908 B2 | 10/2019 | Lee et al. |
| 10,467,729 B1 | 11/2019 | Perera et al. |
| 10,467,775 B1 | 11/2019 | Waggoner et al. |
| 10,505,726 B1 | 12/2019 | Andon et al. |
| 10,521,091 B2 | 12/2019 | Anzures et al. |
| 10,521,948 B2 | 12/2019 | Rickwald et al. |
| 10,523,879 B2 | 12/2019 | Dye et al. |
| 10,574,895 B2 | 2/2020 | Lee et al. |
| 10,580,221 B2 | 3/2020 | Scapel et al. |
| 10,585,551 B2 | 3/2020 | Lee et al. |
| 10,614,139 B2 | 4/2020 | Fujioka et al. |
| 10,620,590 B1 | 4/2020 | Guzman et al. |
| 10,628,985 B2 | 4/2020 | Mishra et al. |
| 10,638,058 B2 | 4/2020 | Matsunaga |
| 10,645,294 B1 | 5/2020 | Manzari et al. |
| 10,652,470 B1 | 5/2020 | Manzari et al. |
| 10,657,695 B2 | 5/2020 | Chand et al. |
| 10,659,405 B1 | 5/2020 | Chang et al. |
| 10,674,072 B1 | 6/2020 | Manzari et al. |
| 10,681,282 B1 | 6/2020 | Manzari et al. |
| 10,698,575 B2 | 6/2020 | Walkin et al. |
| 10,708,545 B2 | 7/2020 | Rivard et al. |
| 10,735,642 B1 | 8/2020 | Manzari et al. |
| 10,735,643 B1 | 8/2020 | Manzari et al. |
| 10,789,753 B2 | 9/2020 | Miller et al. |
| 10,791,273 B1 | 9/2020 | Manzari et al. |
| 10,796,480 B2 | 10/2020 | Chen et al. |
| 10,798,035 B2 | 10/2020 | Lewis et al. |
| 10,810,409 B2 | 10/2020 | Bacivarov et al. |
| 10,817,981 B1 | 10/2020 | Belkin |
| 10,845,968 B2 | 11/2020 | Scapel et al. |
| 10,855,910 B2 * | 12/2020 | Tano ............... H04N 5/2226 |
| 10,902,661 B1 | 1/2021 | Mourkogiannis et al. |
| 10,958,850 B2 | 3/2021 | Kwak et al. |
| 11,039,074 B1 | 6/2021 | Manzari et al. |
| 11,054,973 B1 | 7/2021 | Manzari et al. |
| 11,061,372 B1 | 7/2021 | Chen et al. |
| 11,107,261 B2 | 8/2021 | Scapel et al. |
| 11,120,528 B1 | 9/2021 | Seely et al. |
| 11,212,449 B1 | 12/2021 | Manzari et al. |
| 11,321,857 B2 | 5/2022 | Stauber et al. |
| 11,350,026 B1 | 5/2022 | Manzari et al. |
| 11,418,699 B1 | 8/2022 | Manzari et al. |
| 11,468,625 B2 | 10/2022 | Manzari et al. |
| 11,539,876 B2 | 12/2022 | Manzari et al. |
| 2001/0050689 A1 | 12/2001 | Park |
| 2002/0054157 A1 | 5/2002 | Hayashi et al. |
| 2002/0070945 A1 | 6/2002 | Kage |
| 2002/0167604 A1 | 11/2002 | Ban et al. |
| 2003/0107664 A1 | 6/2003 | Suzuki |
| 2003/0122930 A1 | 7/2003 | Schofield et al. |
| 2003/0135769 A1 | 7/2003 | Loughran |
| 2003/0140309 A1 | 7/2003 | Saito et al. |
| 2003/0160756 A1 | 8/2003 | Numano |
| 2003/0174216 A1 | 9/2003 | Iguchi et al. |
| 2004/0041924 A1 | 3/2004 | White et al. |
| 2004/0061796 A1 | 4/2004 | Honda et al. |
| 2004/0075699 A1 | 4/2004 | Franchi et al. |
| 2004/0090469 A1 | 5/2004 | Moon et al. |
| 2004/0201699 A1 | 10/2004 | Parulski et al. |
| 2004/0203342 A1 | 10/2004 | Sibecas et al. |
| 2004/0225966 A1 | 11/2004 | Besharat et al. |
| 2005/0024517 A1 | 2/2005 | Luciano |
| 2005/0124389 A1 | 6/2005 | Yang |
| 2005/0189419 A1 | 9/2005 | Igarashi et al. |
| 2005/0190653 A1 | 9/2005 | Chen |
| 2005/0206981 A1 | 9/2005 | Hung |
| 2005/0210380 A1 | 9/2005 | Kramer et al. |
| 2005/0210403 A1 | 9/2005 | Satanek |
| 2005/0248574 A1 | 11/2005 | Ashtekar et al. |
| 2005/0248660 A1 | 11/2005 | Stavely et al. |
| 2005/0261031 A1 | 11/2005 | Seo et al. |
| 2005/0270397 A1 | 12/2005 | Battles |
| 2006/0020904 A1 | 1/2006 | Aaltonen et al. |
| 2006/0033831 A1 | 2/2006 | Ejima et al. |
| 2006/0132482 A1 | 6/2006 | Oh et al. |
| 2006/0158730 A1 | 7/2006 | Kira |
| 2006/0166708 A1 | 7/2006 | Kim et al. |
| 2006/0170781 A1 | 8/2006 | Sobol |
| 2006/0187322 A1 | 8/2006 | Janson et al. |
| 2006/0188144 A1 | 8/2006 | Sasaki et al. |
| 2006/0209067 A1 | 9/2006 | Pellacini et al. |
| 2006/0228040 A1 | 10/2006 | Simon et al. |
| 2006/0294465 A1 | 12/2006 | Ronen et al. |
| 2007/0024614 A1 | 2/2007 | Tam et al. |
| 2007/0025723 A1 | 2/2007 | Baudisch et al. |
| 2007/0031062 A1 | 2/2007 | Pal et al. |
| 2007/0052851 A1 | 3/2007 | Ochs et al. |
| 2007/0097088 A1 | 5/2007 | Battles |
| 2007/0101355 A1 | 5/2007 | Chung et al. |
| 2007/0113099 A1 | 5/2007 | Takikawa et al. |
| 2007/0113181 A1 | 5/2007 | Blattner et al. |
| 2007/0140675 A1 | 6/2007 | Yanagi et al. |
| 2007/0153112 A1 | 7/2007 | Ueda et al. |
| 2007/0171091 A1 | 7/2007 | Nisenboim et al. |
| 2007/0192718 A1 | 8/2007 | Voorhees et al. |
| 2007/0222789 A1 | 9/2007 | Yoshio et al. |
| 2007/0226653 A1 | 9/2007 | Moore et al. |
| 2007/0228259 A1 | 10/2007 | Hohenberger |
| 2007/0257992 A1 | 11/2007 | Kato |
| 2007/0260984 A1 | 11/2007 | Marks et al. |
| 2007/0273769 A1 | 11/2007 | Takahashi |
| 2007/0291152 A1 | 12/2007 | Suekane et al. |
| 2008/0030592 A1 | 2/2008 | Border et al. |
| 2008/0052242 A1 | 2/2008 | Merritt et al. |
| 2008/0084484 A1 | 4/2008 | Ochi et al. |
| 2008/0095470 A1 | 4/2008 | Chao et al. |
| 2008/0098031 A1 | 4/2008 | Ducharme |
| 2008/0106601 A1 | 5/2008 | Matsuda |
| 2008/0129759 A1 | 6/2008 | Jeon et al. |
| 2008/0129825 A1 | 6/2008 | Deangelis et al. |
| 2008/0131019 A1 | 6/2008 | Ng |
| 2008/0143840 A1 | 6/2008 | Corkum et al. |
| 2008/0192020 A1 | 8/2008 | Kang et al. |
| 2008/0201438 A1 | 8/2008 | Mandre et al. |
| 2008/0218611 A1 | 9/2008 | Parulski et al. |
| 2008/0222558 A1 | 9/2008 | Cho et al. |
| 2008/0298571 A1 | 12/2008 | Kurtz et al. |
| 2008/0309811 A1 | 12/2008 | Fujinawa et al. |
| 2009/0009612 A1 | 1/2009 | Tico et al. |
| 2009/0021576 A1 | 1/2009 | Linder et al. |
| 2009/0021600 A1 | 1/2009 | Watanabe |
| 2009/0022422 A1 | 1/2009 | Sorek et al. |
| 2009/0027337 A1 | 1/2009 | Hildreth |
| 2009/0027515 A1 | 1/2009 | Maruyama et al. |
| 2009/0027539 A1 | 1/2009 | Kunou |
| 2009/0040332 A1 | 2/2009 | Yoshino et al. |
| 2009/0044113 A1 | 2/2009 | Jones et al. |
| 2009/0046097 A1 | 2/2009 | Franklin |
| 2009/0051783 A1 | 2/2009 | Kim et al. |
| 2009/0066817 A1 | 3/2009 | Sakamaki |
| 2009/0073285 A1 | 3/2009 | Terashima |
| 2009/0077460 A1 | 3/2009 | Li et al. |
| 2009/0077497 A1 | 3/2009 | Cho et al. |
| 2009/0102918 A1 | 4/2009 | Sakamoto et al. |
| 2009/0109316 A1 | 4/2009 | Matsui |
| 2009/0144173 A1 | 6/2009 | Mo et al. |
| 2009/0144639 A1 | 6/2009 | Nims et al. |
| 2009/0167671 A1 | 7/2009 | Kerofsky |
| 2009/0167672 A1 | 7/2009 | Kerofsky |
| 2009/0175511 A1 | 7/2009 | Lee et al. |
| 2009/0202114 A1 | 8/2009 | Morin et al. |
| 2009/0216691 A1 | 8/2009 | Borzestowski et al. |
| 2009/0244318 A1 | 10/2009 | Makii |
| 2009/0251484 A1 | 10/2009 | Zhao et al. |
| 2009/0254859 A1 | 10/2009 | Arrasvuori et al. |
| 2009/0254862 A1 | 10/2009 | Viginisson et al. |
| 2009/0263044 A1 | 10/2009 | Imagawa et al. |
| 2009/0276700 A1 | 11/2009 | Anderson et al. |
| 2009/0297022 A1 | 12/2009 | Pettigrew et al. |
| 2009/0300513 A1 | 12/2009 | Nims et al. |

(56) References Cited

U.S. PATENT DOCUMENTS

| | | |
|---|---|---|
| 2009/0319897 A1 | 12/2009 | Kotler et al. |
| 2009/0322901 A1 | 12/2009 | Subbotin et al. |
| 2009/0325701 A1 | 12/2009 | Andres Del Valle |
| 2010/0009747 A1 | 1/2010 | Reville et al. |
| 2010/0020221 A1 | 1/2010 | Tupman et al. |
| 2010/0020222 A1 | 1/2010 | Jones et al. |
| 2010/0033615 A1 | 2/2010 | Mori |
| 2010/0039522 A1 | 2/2010 | Huang |
| 2010/0042926 A1 | 2/2010 | Bull et al. |
| 2010/0066853 A1 | 3/2010 | Aoki et al. |
| 2010/0066889 A1 | 3/2010 | Ueda et al. |
| 2010/0066890 A1 | 3/2010 | Ueda et al. |
| 2010/0066895 A1 | 3/2010 | Ueda et al. |
| 2010/0093400 A1 | 4/2010 | Ju et al. |
| 2010/0097375 A1 | 4/2010 | Tadaishi et al. |
| 2010/0123737 A1 | 5/2010 | Williamson et al. |
| 2010/0123915 A1 | 5/2010 | Kashimoto |
| 2010/0124941 A1 | 5/2010 | Cho |
| 2010/0149573 A1 | 6/2010 | Pat et al. |
| 2010/0153847 A1 | 6/2010 | Fama |
| 2010/0164893 A1 | 7/2010 | Shin et al. |
| 2010/0188426 A1 | 7/2010 | Ohmori et al. |
| 2010/0194931 A1 | 8/2010 | Kawaguchi et al. |
| 2010/0203968 A1 | 8/2010 | Gill et al. |
| 2010/0208122 A1 | 8/2010 | Yumiki |
| 2010/0211899 A1 | 8/2010 | Fujioka |
| 2010/0218089 A1 | 8/2010 | Chao et al. |
| 2010/0231777 A1 | 9/2010 | Shintani et al. |
| 2010/0232703 A1 | 9/2010 | Aiso |
| 2010/0238327 A1 | 9/2010 | Griffith et al. |
| 2010/0257469 A1 | 10/2010 | Kim et al. |
| 2010/0259645 A1 | 10/2010 | Kaplan et al. |
| 2010/0277470 A1 | 11/2010 | Margolis |
| 2010/0283743 A1 | 11/2010 | Coddington |
| 2010/0289825 A1 | 11/2010 | Shin et al. |
| 2010/0302280 A1 | 12/2010 | Szeliski et al. |
| 2010/0317410 A1 | 12/2010 | Song et al. |
| 2011/0007174 A1 | 1/2011 | Bacivarov et al. |
| 2011/0008033 A1 | 1/2011 | Ichimiya et al. |
| 2011/0013049 A1 | 1/2011 | Thörn |
| 2011/0018970 A1 | 1/2011 | Wakabayashi |
| 2011/0019058 A1 | 1/2011 | Sakai et al. |
| 2011/0072394 A1 | 3/2011 | Victor et al. |
| 2011/0074710 A1 | 3/2011 | Weeldreyer et al. |
| 2011/0074807 A1 | 3/2011 | Inada et al. |
| 2011/0074830 A1 | 3/2011 | Rapp et al. |
| 2011/0109581 A1 | 5/2011 | Ozawa et al. |
| 2011/0119610 A1 | 5/2011 | Hackborn et al. |
| 2011/0138332 A1 | 6/2011 | Miyagawa |
| 2011/0157379 A1 | 6/2011 | Kimura |
| 2011/0176039 A1 | 7/2011 | Lo |
| 2011/0187879 A1 | 8/2011 | Ochiai |
| 2011/0199495 A1 | 8/2011 | Laberge et al. |
| 2011/0221755 A1 | 9/2011 | Geisner et al. |
| 2011/0242369 A1 | 10/2011 | Misawa et al. |
| 2011/0248992 A1 | 10/2011 | Van et al. |
| 2011/0249073 A1 | 10/2011 | Cranfill et al. |
| 2011/0249078 A1 | 10/2011 | Abuan et al. |
| 2011/0252344 A1 | 10/2011 | Van |
| 2011/0256848 A1 | 10/2011 | Bok et al. |
| 2011/0296163 A1 | 12/2011 | Abernethy et al. |
| 2011/0304632 A1 | 12/2011 | Evertt et al. |
| 2012/0002898 A1 | 1/2012 | Côté et al. |
| 2012/0017180 A1 | 1/2012 | Flik et al. |
| 2012/0019551 A1 | 1/2012 | Pettigrew et al. |
| 2012/0026378 A1 | 2/2012 | Pang et al. |
| 2012/0036480 A1 | 2/2012 | Warner et al. |
| 2012/0056830 A1 | 3/2012 | Suzuki et al. |
| 2012/0056997 A1 | 3/2012 | Jang |
| 2012/0069028 A1 | 3/2012 | Bouguerra |
| 2012/0075328 A1 | 3/2012 | Goossens |
| 2012/0079378 A1* | 3/2012 | Goossens ............... G06T 17/10 715/849 |
| 2012/0113762 A1 | 5/2012 | Frost |
| 2012/0127189 A1 | 5/2012 | Park et al. |
| 2012/0127346 A1 | 5/2012 | Sato et al. |
| 2012/0133797 A1 | 5/2012 | Sato et al. |
| 2012/0162242 A1 | 6/2012 | Amano et al. |
| 2012/0169776 A1 | 7/2012 | Rissa et al. |
| 2012/0188394 A1 | 7/2012 | Park et al. |
| 2012/0194559 A1 | 8/2012 | Lim |
| 2012/0206452 A1 | 8/2012 | Geisner et al. |
| 2012/0206495 A1 | 8/2012 | Endo et al. |
| 2012/0206619 A1 | 8/2012 | Nitta et al. |
| 2012/0206621 A1 | 8/2012 | Chen et al. |
| 2012/0210263 A1 | 8/2012 | Perry et al. |
| 2012/0235990 A1 | 9/2012 | Yamaji |
| 2012/0243802 A1 | 9/2012 | Fintel et al. |
| 2012/0256967 A1 | 10/2012 | Baldwin et al. |
| 2012/0274830 A1 | 11/2012 | Kameyama et al. |
| 2012/0293611 A1 | 11/2012 | Lee |
| 2012/0293686 A1 | 11/2012 | Karn et al. |
| 2012/0299945 A1 | 11/2012 | Aarabi |
| 2012/0309520 A1 | 12/2012 | Evertt et al. |
| 2012/0314047 A1 | 12/2012 | Kasahara et al. |
| 2013/0010170 A1 | 1/2013 | Matsuzawa et al. |
| 2013/0038546 A1 | 2/2013 | Mineo |
| 2013/0038759 A1 | 2/2013 | Jo et al. |
| 2013/0055119 A1 | 2/2013 | Luong |
| 2013/0076908 A1 | 3/2013 | Bratton et al. |
| 2013/0083222 A1 | 4/2013 | Matsuzawa et al. |
| 2013/0088413 A1 | 4/2013 | Raffle et al. |
| 2013/0088614 A1 | 4/2013 | Lee |
| 2013/0101164 A1 | 4/2013 | Leclerc et al. |
| 2013/0135315 A1 | 5/2013 | Bares et al. |
| 2013/0141362 A1 | 6/2013 | Asanuma et al. |
| 2013/0141513 A1 | 6/2013 | Setton et al. |
| 2013/0141524 A1 | 6/2013 | Karunamuni et al. |
| 2013/0147933 A1 | 6/2013 | Kulas et al. |
| 2013/0155308 A1 | 6/2013 | Wu et al. |
| 2013/0155474 A1 | 6/2013 | Roach et al. |
| 2013/0157646 A1 | 6/2013 | Ferren et al. |
| 2013/0159900 A1 | 6/2013 | Pendharkar |
| 2013/0165186 A1 | 6/2013 | Choi |
| 2013/0179831 A1 | 7/2013 | Izaki |
| 2013/0194378 A1 | 8/2013 | Brown |
| 2013/0198210 A1 | 8/2013 | Lee et al. |
| 2013/0201104 A1 | 8/2013 | Ptucha et al. |
| 2013/0201203 A1 | 8/2013 | Warner |
| 2013/0201307 A1 | 8/2013 | Schloter et al. |
| 2013/0210563 A1 | 8/2013 | Hollinger |
| 2013/0222663 A1 | 8/2013 | Rydenhag et al. |
| 2013/0234964 A1 | 9/2013 | Kim et al. |
| 2013/0239057 A1 | 9/2013 | Ubillos et al. |
| 2013/0246948 A1 | 9/2013 | Chen et al. |
| 2013/0265467 A1 | 10/2013 | Matsuzawa et al. |
| 2013/0286161 A1 | 10/2013 | Lv et al. |
| 2013/0290905 A1 | 10/2013 | Luvogt et al. |
| 2013/0293686 A1 | 11/2013 | Blow et al. |
| 2013/0305189 A1 | 11/2013 | Kim |
| 2013/0322218 A1 | 12/2013 | Burkhardt et al. |
| 2013/0336545 A1 | 12/2013 | Pritikin et al. |
| 2013/0342730 A1 | 12/2013 | Lee et al. |
| 2013/0346916 A1 | 12/2013 | Williamson et al. |
| 2014/0009639 A1 | 1/2014 | Lee |
| 2014/0022399 A1 | 1/2014 | Rashid et al. |
| 2014/0028872 A1 | 1/2014 | Lee et al. |
| 2014/0028885 A1 | 1/2014 | Ma et al. |
| 2014/0033043 A1 | 1/2014 | Kashima |
| 2014/0033100 A1 | 1/2014 | Noda et al. |
| 2014/0037178 A1 | 2/2014 | Park |
| 2014/0043368 A1 | 2/2014 | Yu |
| 2014/0043517 A1 | 2/2014 | Yim et al. |
| 2014/0047389 A1 | 2/2014 | Aarabi |
| 2014/0049536 A1 | 2/2014 | Neuman et al. |
| 2014/0055554 A1 | 2/2014 | Du et al. |
| 2014/0063175 A1 | 3/2014 | Jafry et al. |
| 2014/0063313 A1 | 3/2014 | Choi et al. |
| 2014/0071061 A1 | 3/2014 | Lin et al. |
| 2014/0071325 A1 | 3/2014 | Kawahara et al. |
| 2014/0078144 A1 | 3/2014 | Berriman et al. |
| 2014/0092272 A1 | 4/2014 | Choi |
| 2014/0095122 A1 | 4/2014 | Appleman et al. |
| 2014/0118560 A1 | 5/2014 | Bala et al. |

(56) References Cited

U.S. PATENT DOCUMENTS

| | | |
|---|---|---|
| 2014/0118563 A1 | 5/2014 | Mehta et al. |
| 2014/0123005 A1 | 5/2014 | Forstall et al. |
| 2014/0132735 A1 | 5/2014 | Lee et al. |
| 2014/0137013 A1 | 5/2014 | Matas |
| 2014/0143693 A1 | 5/2014 | Goossens et al. |
| 2014/0152886 A1 | 6/2014 | Morgan-Mar et al. |
| 2014/0176469 A1 | 6/2014 | Lim |
| 2014/0176565 A1 | 6/2014 | Adeyoola et al. |
| 2014/0192233 A1 | 7/2014 | Kakkori et al. |
| 2014/0205207 A1 | 7/2014 | Bhatt |
| 2014/0218371 A1 | 8/2014 | Du et al. |
| 2014/0229831 A1 | 8/2014 | Chordia et al. |
| 2014/0232838 A1 | 8/2014 | Jorgensen et al. |
| 2014/0240471 A1 | 8/2014 | Srinivasa et al. |
| 2014/0240531 A1 | 8/2014 | Nakai et al. |
| 2014/0267126 A1 | 9/2014 | Aberg et al. |
| 2014/0267618 A1 | 9/2014 | Esteban et al. |
| 2014/0267867 A1 | 9/2014 | Lee et al. |
| 2014/0281983 A1 | 9/2014 | Xian et al. |
| 2014/0282223 A1 | 9/2014 | Bastien et al. |
| 2014/0285698 A1 | 9/2014 | Geiss |
| 2014/0300635 A1 | 10/2014 | Suzuki |
| 2014/0300722 A1 | 10/2014 | Garcia |
| 2014/0300779 A1 | 10/2014 | Yeo et al. |
| 2014/0327639 A1 | 11/2014 | Papakipos et al. |
| 2014/0333671 A1 | 11/2014 | Phang et al. |
| 2014/0333824 A1 | 11/2014 | Xiu |
| 2014/0336808 A1 | 11/2014 | Taylor et al. |
| 2014/0351720 A1 | 11/2014 | Yin |
| 2014/0351753 A1 | 11/2014 | Shin et al. |
| 2014/0354845 A1 | 12/2014 | Mølgaard et al. |
| 2014/0359438 A1 | 12/2014 | Matsuki |
| 2014/0362091 A1 | 12/2014 | Bouaziz et al. |
| 2014/0362274 A1 | 12/2014 | Christie et al. |
| 2014/0364228 A1 | 12/2014 | Rimon |
| 2014/0368601 A1 | 12/2014 | Decharms |
| 2014/0368719 A1 | 12/2014 | Kaneko et al. |
| 2014/0372856 A1 | 12/2014 | Radakovitz et al. |
| 2015/0011204 A1 | 1/2015 | Seo et al. |
| 2015/0022649 A1 | 1/2015 | Koppal |
| 2015/0033192 A1 | 1/2015 | Bohannon et al. |
| 2015/0035825 A1 | 2/2015 | Zhou et al. |
| 2015/0036883 A1 | 2/2015 | Deri et al. |
| 2015/0037545 A1 | 2/2015 | Sun |
| 2015/0042571 A1 | 2/2015 | Lombardi et al. |
| 2015/0042852 A1 | 2/2015 | Lee et al. |
| 2015/0043046 A1 | 2/2015 | Iwamoto |
| 2015/0043806 A1 | 2/2015 | Sunkavalli et al. |
| 2015/0058754 A1 | 2/2015 | Rauh |
| 2015/0062052 A1 | 3/2015 | Bernstein et al. |
| 2015/0067513 A1 | 3/2015 | Zambetti et al. |
| 2015/0070362 A1 | 3/2015 | Hirai |
| 2015/0077502 A1 | 3/2015 | Jordan et al. |
| 2015/0078621 A1 | 3/2015 | Choi et al. |
| 2015/0078726 A1 | 3/2015 | Shakib et al. |
| 2015/0082193 A1 | 3/2015 | Wallace et al. |
| 2015/0082446 A1 | 3/2015 | Flowers et al. |
| 2015/0085174 A1 | 3/2015 | Shabtay et al. |
| 2015/0091896 A1 | 4/2015 | Tarquini et al. |
| 2015/0092077 A1 | 4/2015 | Feder et al. |
| 2015/0109417 A1 | 4/2015 | Zirnheld |
| 2015/0116353 A1 | 4/2015 | Miura et al. |
| 2015/0116448 A1 | 4/2015 | Gottlieb |
| 2015/0135109 A1 | 5/2015 | Zambetti et al. |
| 2015/0135234 A1 | 5/2015 | Hall |
| 2015/0138079 A1 | 5/2015 | Lannsjö |
| 2015/0145950 A1 | 5/2015 | Murphy et al. |
| 2015/0146079 A1 | 5/2015 | Kim |
| 2015/0149899 A1 | 5/2015 | Bernstein et al. |
| 2015/0149927 A1 | 5/2015 | Walkin et al. |
| 2015/0150141 A1 | 5/2015 | Szymanski et al. |
| 2015/0154448 A1 | 6/2015 | Murayama et al. |
| 2015/0172534 A1 | 6/2015 | Miyakawa et al. |
| 2015/0181135 A1 | 6/2015 | Shimosato |
| 2015/0189138 A1 | 7/2015 | Xie et al. |
| 2015/0194186 A1 | 7/2015 | Lee et al. |
| 2015/0208001 A1 | 7/2015 | Nonaka et al. |
| 2015/0212723 A1 | 7/2015 | Lim et al. |
| 2015/0213001 A1 | 7/2015 | Levy et al. |
| 2015/0213604 A1* | 7/2015 | Li ........................ G06T 13/80 |
| | | 345/473 |
| 2015/0220249 A1 | 8/2015 | Snibbe et al. |
| 2015/0248198 A1 | 9/2015 | Somlai-fisher et al. |
| 2015/0248235 A1 | 9/2015 | Offenberg et al. |
| 2015/0248583 A1 | 9/2015 | Sekine et al. |
| 2015/0249775 A1 | 9/2015 | Jacumet |
| 2015/0249785 A1 | 9/2015 | Mehta et al. |
| 2015/0253740 A1 | 9/2015 | Nishijima et al. |
| 2015/0254855 A1 | 9/2015 | Patankar et al. |
| 2015/0256749 A1 | 9/2015 | Frey et al. |
| 2015/0277686 A1 | 10/2015 | Laforge et al. |
| 2015/0281145 A1 | 10/2015 | Ji |
| 2015/0286724 A1 | 10/2015 | Knaapen et al. |
| 2015/0289104 A1 | 10/2015 | Jung et al. |
| 2015/0301731 A1 | 10/2015 | Okamoto et al. |
| 2015/0302624 A1 | 10/2015 | Burke |
| 2015/0310583 A1 | 10/2015 | Hume et al. |
| 2015/0312182 A1 | 10/2015 | Langholz |
| 2015/0312184 A1 | 10/2015 | Langholz et al. |
| 2015/0312185 A1 | 10/2015 | Langholz et al. |
| 2015/0317945 A1 | 11/2015 | Andress et al. |
| 2015/0334075 A1 | 11/2015 | Wang et al. |
| 2015/0334291 A1 | 11/2015 | Cho et al. |
| 2015/0341536 A1 | 11/2015 | Huang et al. |
| 2015/0347824 A1 | 12/2015 | Saari et al. |
| 2015/0350141 A1 | 12/2015 | Yang et al. |
| 2015/0350533 A1 | 12/2015 | Harris et al. |
| 2015/0362998 A1 | 12/2015 | Park et al. |
| 2015/0365587 A1 | 12/2015 | Ha et al. |
| 2015/0370458 A1 | 12/2015 | Chen |
| 2015/0370529 A1 | 12/2015 | Zambetti et al. |
| 2016/0005211 A1 | 1/2016 | Sarkis et al. |
| 2016/0006987 A1 | 1/2016 | Li et al. |
| 2016/0012567 A1 | 1/2016 | Siddiqui et al. |
| 2016/0026371 A1 | 1/2016 | Lu et al. |
| 2016/0030844 A1 | 2/2016 | Nair et al. |
| 2016/0034133 A1 | 2/2016 | Wilson et al. |
| 2016/0044236 A1 | 2/2016 | Matsuzawa et al. |
| 2016/0048598 A1 | 2/2016 | Fujioka et al. |
| 2016/0048599 A1 | 2/2016 | Fujioka et al. |
| 2016/0048725 A1 | 2/2016 | Holz et al. |
| 2016/0048903 A1 | 2/2016 | Fujioka et al. |
| 2016/0050169 A1 | 2/2016 | Ben Atar et al. |
| 2016/0050351 A1 | 2/2016 | Lee et al. |
| 2016/0050446 A1 | 2/2016 | Fujioka et al. |
| 2016/0065832 A1 | 3/2016 | Kim et al. |
| 2016/0065861 A1 | 3/2016 | Steinberg et al. |
| 2016/0065930 A1 | 3/2016 | Chandra et al. |
| 2016/0077725 A1 | 3/2016 | Maeda |
| 2016/0080639 A1 | 3/2016 | Choi et al. |
| 2016/0086387 A1 | 3/2016 | Os et al. |
| 2016/0088280 A1 | 3/2016 | Sadi et al. |
| 2016/0092035 A1 | 3/2016 | Crocker et al. |
| 2016/0092043 A1 | 3/2016 | Missig et al. |
| 2016/0098094 A1 | 4/2016 | Minkkinen |
| 2016/0117829 A1 | 4/2016 | Yoon et al. |
| 2016/0127636 A1 | 5/2016 | Ito et al. |
| 2016/0127638 A1 | 5/2016 | Guo et al. |
| 2016/0132200 A1 | 5/2016 | Walkin et al. |
| 2016/0132201 A1 | 5/2016 | Shaw et al. |
| 2016/0134840 A1 | 5/2016 | Mcculloch |
| 2016/0142649 A1 | 5/2016 | Yim |
| 2016/0148384 A1 | 5/2016 | Bud et al. |
| 2016/0150215 A1 | 5/2016 | Chen et al. |
| 2016/0162039 A1 | 6/2016 | Eilat et al. |
| 2016/0163084 A1 | 6/2016 | Corazza et al. |
| 2016/0173869 A1 | 6/2016 | Srikanth et al. |
| 2016/0187995 A1 | 6/2016 | Rosewall |
| 2016/0188181 A1 | 6/2016 | Smith |
| 2016/0212319 A1 | 7/2016 | Harris et al. |
| 2016/0217601 A1 | 7/2016 | Tsuda et al. |
| 2016/0219217 A1 | 7/2016 | Williams et al. |
| 2016/0225175 A1 | 8/2016 | Kim et al. |
| 2016/0226926 A1 | 8/2016 | Singh et al. |

(56) References Cited

U.S. PATENT DOCUMENTS

| | | |
|---|---|---|
| 2016/0227016 A1 | 8/2016 | Kim et al. |
| 2016/0227121 A1* | 8/2016 | Matsushita ............ G01B 11/22 |
| 2016/0247288 A1 | 8/2016 | Omori et al. |
| 2016/0247309 A1 | 8/2016 | Li et al. |
| 2016/0255268 A1 | 9/2016 | Kang et al. |
| 2016/0259413 A1 | 9/2016 | Anzures et al. |
| 2016/0259497 A1 | 9/2016 | Bauer et al. |
| 2016/0259498 A1 | 9/2016 | Foss et al. |
| 2016/0259499 A1 | 9/2016 | Kocienda et al. |
| 2016/0259518 A1 | 9/2016 | King et al. |
| 2016/0259519 A1 | 9/2016 | Foss et al. |
| 2016/0259527 A1 | 9/2016 | Kocienda et al. |
| 2016/0259528 A1 | 9/2016 | Foss et al. |
| 2016/0267067 A1 | 9/2016 | Mays et al. |
| 2016/0275724 A1 | 9/2016 | Adeyoola et al. |
| 2016/0283097 A1 | 9/2016 | Voss et al. |
| 2016/0284123 A1 | 9/2016 | Hare et al. |
| 2016/0307324 A1 | 10/2016 | Higuchi et al. |
| 2016/0327911 A1 | 11/2016 | Eim et al. |
| 2016/0328875 A1 | 11/2016 | Fang et al. |
| 2016/0337570 A1 | 11/2016 | Tan et al. |
| 2016/0337582 A1 | 11/2016 | Shimauchi et al. |
| 2016/0353030 A1 | 12/2016 | Tang et al. |
| 2016/0357282 A1 | 12/2016 | Block et al. |
| 2016/0357353 A1 | 12/2016 | Miura et al. |
| 2016/0357387 A1 | 12/2016 | Bovet et al. |
| 2016/0360097 A1 | 12/2016 | Penha et al. |
| 2016/0360116 A1 | 12/2016 | Penha et al. |
| 2016/0366323 A1 | 12/2016 | Chen et al. |
| 2016/0366344 A1 | 12/2016 | Pan et al. |
| 2016/0370974 A1 | 12/2016 | Stenneth |
| 2016/0373650 A1 | 12/2016 | Kim et al. |
| 2017/0011773 A1 | 1/2017 | Lee |
| 2017/0013179 A1 | 1/2017 | Kang et al. |
| 2017/0018289 A1 | 1/2017 | Morgenstern |
| 2017/0019604 A1 | 1/2017 | Kim et al. |
| 2017/0024872 A1 | 1/2017 | Olsson et al. |
| 2017/0026565 A1 | 1/2017 | Hong et al. |
| 2017/0034449 A1 | 2/2017 | Eum et al. |
| 2017/0039686 A1 | 2/2017 | Miura et al. |
| 2017/0041677 A1 | 2/2017 | Anderson et al. |
| 2017/0046065 A1 | 2/2017 | Zeng et al. |
| 2017/0048450 A1 | 2/2017 | Lee et al. |
| 2017/0048461 A1 | 2/2017 | Lee et al. |
| 2017/0048494 A1 | 2/2017 | Boyle et al. |
| 2017/0054960 A1 | 2/2017 | Chien et al. |
| 2017/0061635 A1* | 3/2017 | Oberheu ............... G06T 11/60 |
| 2017/0064200 A1 | 3/2017 | Castillo et al. |
| 2017/0064205 A1 | 3/2017 | Choi et al. |
| 2017/0082983 A1 | 3/2017 | Katzer et al. |
| 2017/0083086 A1 | 3/2017 | Mazur et al. |
| 2017/0094019 A1 | 3/2017 | Ahmed et al. |
| 2017/0094161 A1 | 3/2017 | Graham et al. |
| 2017/0109912 A1 | 4/2017 | Lee et al. |
| 2017/0111567 A1 | 4/2017 | Pila |
| 2017/0111616 A1 | 4/2017 | Li et al. |
| 2017/0140214 A1 | 5/2017 | Matas et al. |
| 2017/0164888 A1 | 6/2017 | Matsuda et al. |
| 2017/0178287 A1 | 6/2017 | Anderson |
| 2017/0180811 A1 | 6/2017 | Quirino et al. |
| 2017/0186162 A1 | 6/2017 | Mihic et al. |
| 2017/0193684 A1 | 7/2017 | Du et al. |
| 2017/0206095 A1 | 7/2017 | Gibbs et al. |
| 2017/0220212 A1 | 8/2017 | Yang et al. |
| 2017/0230576 A1 | 8/2017 | Sparks et al. |
| 2017/0230585 A1 | 8/2017 | Nash et al. |
| 2017/0236298 A1 | 8/2017 | Vetter |
| 2017/0237888 A1 | 8/2017 | Harris et al. |
| 2017/0243389 A1 | 8/2017 | Wild et al. |
| 2017/0244896 A1 | 8/2017 | Chien et al. |
| 2017/0244897 A1 | 8/2017 | Jung et al. |
| 2017/0255169 A1 | 9/2017 | Lee et al. |
| 2017/0257596 A1 | 9/2017 | Murata et al. |
| 2017/0264817 A1 | 9/2017 | Yan et al. |
| 2017/0269715 A1 | 9/2017 | Kim et al. |
| 2017/0272654 A1 | 9/2017 | Poindexter, Jr. |
| 2017/0285764 A1 | 10/2017 | Kim et al. |
| 2017/0285916 A1* | 10/2017 | Xu ........................ G06T 11/60 |
| 2017/0286913 A1 | 10/2017 | Liu et al. |
| 2017/0287220 A1 | 10/2017 | Khalid et al. |
| 2017/0302840 A1 | 10/2017 | Hasinoff et al. |
| 2017/0315772 A1 | 11/2017 | Lee et al. |
| 2017/0323266 A1 | 11/2017 | Seo |
| 2017/0324784 A1 | 11/2017 | Taine et al. |
| 2017/0336926 A1 | 11/2017 | Chaudhri et al. |
| 2017/0336928 A1 | 11/2017 | Chaudhri et al. |
| 2017/0336961 A1 | 11/2017 | Heo et al. |
| 2017/0337554 A1 | 11/2017 | Mokhasi et al. |
| 2017/0352379 A1 | 12/2017 | Oh et al. |
| 2017/0354888 A1 | 12/2017 | Benedetto et al. |
| 2017/0358071 A1 | 12/2017 | Yamaoka et al. |
| 2017/0359504 A1 | 12/2017 | Manzari et al. |
| 2017/0359505 A1 | 12/2017 | Manzari et al. |
| 2017/0359506 A1 | 12/2017 | Manzari et al. |
| 2017/0366729 A1 | 12/2017 | Itoh |
| 2018/0004404 A1 | 1/2018 | Delfino et al. |
| 2018/0007315 A1 | 1/2018 | Kim et al. |
| 2018/0021684 A1 | 1/2018 | Benedetto |
| 2018/0034867 A1 | 2/2018 | Zahn et al. |
| 2018/0035031 A1 | 2/2018 | Kwak et al. |
| 2018/0047200 A1 | 2/2018 | O'hara et al. |
| 2018/0052571 A1 | 2/2018 | Seol et al. |
| 2018/0059903 A1 | 3/2018 | Lim et al. |
| 2018/0067633 A1 | 3/2018 | Wilson et al. |
| 2018/0074693 A1 | 3/2018 | Jones et al. |
| 2018/0077332 A1 | 3/2018 | Shimura et al. |
| 2018/0081515 A1 | 3/2018 | Block et al. |
| 2018/0091728 A1 | 3/2018 | Brown et al. |
| 2018/0091732 A1 | 3/2018 | Wilson et al. |
| 2018/0095649 A1 | 4/2018 | Valdivia et al. |
| 2018/0096487 A1 | 4/2018 | Nash et al. |
| 2018/0107367 A1 | 4/2018 | Rinneberg et al. |
| 2018/0109722 A1 | 4/2018 | Laroia et al. |
| 2018/0113577 A1 | 4/2018 | Burns et al. |
| 2018/0114543 A1 | 4/2018 | Novikoff |
| 2018/0120661 A1 | 5/2018 | KiLGore et al. |
| 2018/0121060 A1 | 5/2018 | Jeong et al. |
| 2018/0124299 A1 | 5/2018 | Brook |
| 2018/0129224 A1 | 5/2018 | Hur |
| 2018/0131878 A1 | 5/2018 | Charlton et al. |
| 2018/0146132 A1 | 5/2018 | Manzari et al. |
| 2018/0152611 A1 | 5/2018 | Li et al. |
| 2018/0165862 A1 | 6/2018 | Sawaki |
| 2018/0184008 A1 | 6/2018 | Kondo |
| 2018/0184061 A1 | 6/2018 | Kitsunai et al. |
| 2018/0189549 A1 | 7/2018 | Inomata |
| 2018/0191944 A1 | 7/2018 | Carbonell et al. |
| 2018/0198985 A1 | 7/2018 | Ishitsuka |
| 2018/0199025 A1 | 7/2018 | Holzer et al. |
| 2018/0213144 A1 | 7/2018 | Kim et al. |
| 2018/0213161 A1 | 7/2018 | Kanda et al. |
| 2018/0227479 A1 | 8/2018 | Parameswaran et al. |
| 2018/0227482 A1 | 8/2018 | Holzer et al. |
| 2018/0227505 A1 | 8/2018 | Baltz et al. |
| 2018/0234608 A1 | 8/2018 | Sudo et al. |
| 2018/0246639 A1 | 8/2018 | Han et al. |
| 2018/0253194 A1 | 9/2018 | Javadi |
| 2018/0267703 A1 | 9/2018 | Kamimaru et al. |
| 2018/0268589 A1 | 9/2018 | Grant |
| 2018/0270420 A1 | 9/2018 | Lee et al. |
| 2018/0278823 A1 | 9/2018 | Horesh |
| 2018/0284979 A1 | 10/2018 | Choi et al. |
| 2018/0288310 A1 | 10/2018 | Goldenberg |
| 2018/0302551 A1 | 10/2018 | Yamajo et al. |
| 2018/0302568 A1 | 10/2018 | Kim et al. |
| 2018/0308282 A1 | 10/2018 | Yokoi |
| 2018/0324353 A1 | 11/2018 | Kim et al. |
| 2018/0329587 A1 | 11/2018 | Ko et al. |
| 2018/0335901 A1 | 11/2018 | Manzari et al. |
| 2018/0335927 A1 | 11/2018 | Anzures et al. |
| 2018/0335929 A1 | 11/2018 | Scapel et al. |
| 2018/0335930 A1 | 11/2018 | Scapel et al. |
| 2018/0336715 A1 | 11/2018 | Rickwald et al. |
| 2018/0343383 A1 | 11/2018 | Ito et al. |

(56) References Cited

U.S. PATENT DOCUMENTS

| | | |
|---|---|---|
| 2018/0349008 A1 | 12/2018 | Manzari et al. |
| 2018/0349795 A1 | 12/2018 | Boyle et al. |
| 2018/0352165 A1 | 12/2018 | Zhen et al. |
| 2018/0376122 A1 | 12/2018 | Park et al. |
| 2019/0007589 A1 | 1/2019 | Kadambala et al. |
| 2019/0028650 A1 | 1/2019 | Bernstein et al. |
| 2019/0029513 A1 | 1/2019 | Gunnerson et al. |
| 2019/0050045 A1 | 2/2019 | Jha et al. |
| 2019/0051032 A1 | 2/2019 | Chu et al. |
| 2019/0058827 A1* | 2/2019 | Park .................. G11B 27/00 |
| 2019/0082097 A1 | 3/2019 | Manzari et al. |
| 2019/0089873 A1 | 3/2019 | Misawa et al. |
| 2019/0108684 A1 | 4/2019 | Callaghan |
| 2019/0114740 A1 | 4/2019 | Ogino et al. |
| 2019/0121216 A1 | 4/2019 | Shabtay et al. |
| 2019/0138259 A1 | 5/2019 | Bagaria et al. |
| 2019/0139207 A1 | 5/2019 | Jeong et al. |
| 2019/0141030 A1 | 5/2019 | Cockerill et al. |
| 2019/0149706 A1 | 5/2019 | Rivard et al. |
| 2019/0158735 A1 | 5/2019 | Wilson et al. |
| 2019/0174054 A1 | 6/2019 | Srivastava et al. |
| 2019/0199926 A1 | 6/2019 | An et al. |
| 2019/0205861 A1 | 7/2019 | Bace |
| 2019/0206031 A1 | 7/2019 | Kim et al. |
| 2019/0222769 A1 | 7/2019 | Srivastava et al. |
| 2019/0235743 A1 | 8/2019 | Ono |
| 2019/0235748 A1 | 8/2019 | Seol et al. |
| 2019/0266807 A1 | 8/2019 | Lee et al. |
| 2019/0289201 A1 | 9/2019 | Nishimura et al. |
| 2019/0289271 A1 | 9/2019 | Paulus et al. |
| 2019/0318538 A1 | 10/2019 | Li et al. |
| 2019/0339847 A1 | 11/2019 | Scapel et al. |
| 2019/0342507 A1 | 11/2019 | Dye et al. |
| 2019/0347868 A1 | 11/2019 | Scapel et al. |
| 2019/0379821 A1 | 12/2019 | Kobayashi et al. |
| 2019/0379837 A1 | 12/2019 | Kim et al. |
| 2020/0045245 A1 | 2/2020 | Van Os et al. |
| 2020/0053288 A1 | 2/2020 | Kim et al. |
| 2020/0059605 A1 | 2/2020 | Liu et al. |
| 2020/0068095 A1 | 2/2020 | Nabetani |
| 2020/0068121 A1 | 2/2020 | Wang |
| 2020/0082599 A1 | 3/2020 | Manzari |
| 2020/0089302 A1 | 3/2020 | Kim et al. |
| 2020/0104038 A1 | 4/2020 | Kamath et al. |
| 2020/0105003 A1 | 4/2020 | Stauber et al. |
| 2020/0106952 A1 | 4/2020 | Missig et al. |
| 2020/0128191 A1 | 4/2020 | Sun et al. |
| 2020/0142577 A1 | 5/2020 | Manzari et al. |
| 2020/0204725 A1 | 6/2020 | Li |
| 2020/0221020 A1 | 7/2020 | Manzari et al. |
| 2020/0226848 A1 | 7/2020 | Van Os et al. |
| 2020/0234481 A1 | 7/2020 | Scapel et al. |
| 2020/0234508 A1 | 7/2020 | Shaburov et al. |
| 2020/0236278 A1 | 7/2020 | Yeung et al. |
| 2020/0242788 A1 | 7/2020 | Jacobs et al. |
| 2020/0244879 A1 | 7/2020 | Hohjoh |
| 2020/0285806 A1 | 9/2020 | Radakovitz et al. |
| 2020/0285851 A1 | 9/2020 | Lin et al. |
| 2020/0335133 A1 | 10/2020 | Vaucher |
| 2020/0336660 A1 | 10/2020 | Dong et al. |
| 2020/0358963 A1 | 11/2020 | Manzari et al. |
| 2020/0380768 A1 | 12/2020 | Harris et al. |
| 2020/0380781 A1 | 12/2020 | Barlier et al. |
| 2020/0410763 A1 | 12/2020 | Hare et al. |
| 2020/0412975 A1 | 12/2020 | Al Majid et al. |
| 2021/0005003 A1 | 1/2021 | Chong et al. |
| 2021/0056769 A1 | 2/2021 | Scapel et al. |
| 2021/0058351 A1 | 2/2021 | Viklund et al. |
| 2021/0065448 A1 | 3/2021 | Goodrich et al. |
| 2021/0065454 A1 | 3/2021 | Goodrich et al. |
| 2021/0096703 A1 | 4/2021 | Anzures et al. |
| 2021/0099568 A1 | 4/2021 | Depue et al. |
| 2021/0099761 A1 | 4/2021 | Zhang |
| 2021/0146838 A1 | 5/2021 | Goseberg et al. |
| 2021/0152505 A1 | 5/2021 | Baldwin et al. |
| 2021/0168108 A1 | 6/2021 | Antmen et al. |
| 2021/0195093 A1 | 6/2021 | Manzari et al. |
| 2021/0264656 A1 | 8/2021 | Barlier et al. |
| 2021/0287343 A1* | 9/2021 | Kaida .................. G06T 5/002 |
| 2021/0318798 A1 | 10/2021 | Manzari et al. |
| 2021/0335055 A1 | 10/2021 | Scapel et al. |
| 2021/0349426 A1 | 11/2021 | Chen et al. |
| 2021/0349427 A1 | 11/2021 | Chen et al. |
| 2021/0349611 A1 | 11/2021 | Chen et al. |
| 2021/0349612 A1 | 11/2021 | Triverio |
| 2021/0373750 A1 | 12/2021 | Manzari et al. |
| 2021/0375042 A1* | 12/2021 | Chen .................. G06T 17/10 |
| 2021/0390753 A1 | 12/2021 | Scapel et al. |
| 2022/0006946 A1 | 1/2022 | Missig et al. |
| 2022/0044459 A1 | 2/2022 | Zacharia et al. |
| 2022/0053142 A1 | 2/2022 | Manzari et al. |
| 2022/0103758 A1 | 3/2022 | Manzari et al. |
| 2022/0124241 A1 | 4/2022 | Manzari et al. |
| 2022/0262022 A1 | 8/2022 | Stauber et al. |
| 2022/0264028 A1 | 8/2022 | Manzari et al. |
| 2022/0276041 A1 | 9/2022 | Dryer et al. |
| 2022/0294992 A1 | 9/2022 | Manzari et al. |
| 2022/0319100 A1 | 10/2022 | Manzari et al. |
| 2022/0345785 A1 | 10/2022 | Yang et al. |
| 2022/0353425 A1 | 11/2022 | Manzari et al. |
| 2022/0382440 A1 | 12/2022 | Manzari et al. |
| 2022/0382443 A1 | 12/2022 | Clarke et al. |
| 2022/0392132 A1 | 12/2022 | Sepulveda et al. |
| 2023/0004270 A1 | 1/2023 | Chen et al. |
| 2023/0020616 A1 | 1/2023 | Manzari et al. |
| 2023/0043249 A1 | 2/2023 | Van Os et al. |

FOREIGN PATENT DOCUMENTS

| | | |
|---|---|---|
| AU | 2017100683 B4 | 1/2018 |
| AU | 2015297035 B2 | 6/2018 |
| CA | 2356232 A1 | 3/2002 |
| CA | 2729392 A1 | 8/2011 |
| CA | 2965700 A1 | 5/2016 |
| CA | 2729392 C | 5/2017 |
| CN | 1437365 A | 8/2003 |
| CN | 1499878 A | 5/2004 |
| CN | 1901717 A | 1/2007 |
| CN | 101055646 A | 10/2007 |
| CN | 101068311 A | 11/2007 |
| CN | 101282422 A | 10/2008 |
| CN | 101300830 A | 11/2008 |
| CN | 101310519 A | 11/2008 |
| CN | 101329707 A | 12/2008 |
| CN | 101355655 A | 1/2009 |
| CN | 101364031 A | 2/2009 |
| CN | 101388965 A | 3/2009 |
| CN | 101576996 A | 11/2009 |
| CN | 101681462 A | 3/2010 |
| CN | 101692681 A | 4/2010 |
| CN | 101742053 A | 6/2010 |
| CN | 101778220 A | 7/2010 |
| CN | 101883213 A | 11/2010 |
| CN | 101931691 A | 12/2010 |
| CN | 102035990 A | 4/2011 |
| CN | 201788344 U | 4/2011 |
| CN | 102075727 A | 5/2011 |
| CN | 102084327 A | 6/2011 |
| CN | 102088554 A | 6/2011 |
| CN | 102142149 A | 8/2011 |
| CN | 102271241 A | 12/2011 |
| CN | 102272700 A | 12/2011 |
| CN | 102298797 A | 12/2011 |
| CN | 102428655 A | 4/2012 |
| CN | 102457661 A | 5/2012 |
| CN | 102474560 A | 5/2012 |
| CN | 102567953 A | 7/2012 |
| CN | 202330968 U | 7/2012 |
| CN | 102622085 A | 8/2012 |
| CN | 102625036 A | 8/2012 |
| CN | 102750070 A | 10/2012 |
| CN | 102854979 A | 1/2013 |
| CN | 102855079 A | 1/2013 |
| CN | 103037075 A | 4/2013 |

(56) References Cited

FOREIGN PATENT DOCUMENTS

| | | | |
|---|---|---|---|
| CN | 103051837 A | 4/2013 |
| CN | 103051841 A | 4/2013 |
| CN | 103052961 A | 4/2013 |
| CN | 103297719 A | 9/2013 |
| CN | 103309602 A | 9/2013 |
| CN | 103324329 A | 9/2013 |
| CN | 103516894 A | 1/2014 |
| CN | 103685925 A | 3/2014 |
| CN | 103702039 A | 4/2014 |
| CN | 103703438 A | 4/2014 |
| CN | 103777742 A | 5/2014 |
| CN | 103927190 A | 7/2014 |
| CN | 103947190 A | 7/2014 |
| CN | 103970472 A | 8/2014 |
| CN | 104182741 A | 12/2014 |
| CN | 104246793 A | 12/2014 |
| CN | 104270597 A | 1/2015 |
| CN | 104346080 A | 2/2015 |
| CN | 104346099 A | 2/2015 |
| CN | 104376160 A | 2/2015 |
| CN | 104423946 A | 3/2015 |
| CN | 104461288 A | 3/2015 |
| CN | 104753762 A | 7/2015 |
| CN | 104754203 A | 7/2015 |
| CN | 104813322 A | 7/2015 |
| CN | 104836947 A | 8/2015 |
| CN | 104903834 A | 9/2015 |
| CN | 104952063 A | 9/2015 |
| CN | 105100462 A | 11/2015 |
| CN | 105138259 A | 12/2015 |
| CN | 105190511 A | 12/2015 |
| CN | 105190700 A | 12/2015 |
| CN | 105229571 A | 1/2016 |
| CN | 105245774 A | 1/2016 |
| CN | 105338256 A | 2/2016 |
| CN | 105391937 A | 3/2016 |
| CN | 105474163 A | 4/2016 |
| CN | 105493138 A | 4/2016 |
| CN | 105589637 A | 5/2016 |
| CN | 105611215 A | 5/2016 |
| CN | 105611275 A | 5/2016 |
| CN | 105620393 A | 6/2016 |
| CN | 105630290 A | 6/2016 |
| CN | 105637855 A | 6/2016 |
| CN | 105653031 A | 6/2016 |
| CN | 105765967 A | 7/2016 |
| CN | 105794196 A | 7/2016 |
| CN | 105981372 A | 9/2016 |
| CN | 105991915 A | 10/2016 |
| CN | 106067947 A | 11/2016 |
| CN | 106161956 A | 11/2016 |
| CN | 10625/540 A | 12/2016 |
| CN | 106210184 A | 12/2016 |
| CN | 106210550 A | 12/2016 |
| CN | 106257909 A | 12/2016 |
| CN | 106303280 A | 1/2017 |
| CN | 106303690 A | 1/2017 |
| CN | 106341611 A | 1/2017 |
| CN | 106375662 A | 2/2017 |
| CN | 106412214 A | 2/2017 |
| CN | 106412412 A | 2/2017 |
| CN | 106412445 A | 2/2017 |
| CN | 106445219 A | 2/2017 |
| CN | 106791357 A | 5/2017 |
| CN | 106791377 A | 5/2017 |
| CN | 106791420 A | 5/2017 |
| CN | 106921829 A | 7/2017 |
| CN | 107077274 A | 8/2017 |
| CN | 107079141 A | 8/2017 |
| CN | 107533356 A | 1/2018 |
| CN | 107566721 A | 1/2018 |
| CN | 107580693 A | 1/2018 |
| CN | 107770448 A | 3/2018 |
| CN | 107800945 A | 3/2018 |
| CN | 107820011 A | 3/2018 |
| CN | 107924113 A | 4/2018 |
| CN | 108353126 A | 7/2018 |
| CN | 108391053 A | 8/2018 |
| CN | 108513070 A | 9/2018 |
| CN | 108549522 A | 9/2018 |
| CN | 108668083 A | 10/2018 |
| CN | 108712609 A | 10/2018 |
| CN | 108848308 A | 11/2018 |
| CN | 108886569 A | 11/2018 |
| CN | 109005366 A | 12/2018 |
| CN | 109061985 A | 12/2018 |
| CN | 109313530 A | 2/2019 |
| CN | 109496425 A | 3/2019 |
| CN | 109639970 A | 4/2019 |
| CN | 109644229 A | 4/2019 |
| CN | 111901475 A | 11/2020 |
| DK | 201670652 A1 | 12/2017 |
| DK | 201670753 A1 | 1/2018 |
| DK | 201670755 A1 | 1/2018 |
| DK | 201670627 A1 | 2/2018 |
| EP | 0579093 A1 | 1/1994 |
| EP | 0651543 A2 | 5/1995 |
| EP | 0651543 A3 | 12/1997 |
| EP | 1215867 A2 | 6/2002 |
| EP | 1278099 A1 | 1/2003 |
| EP | 1429291 A1 | 6/2004 |
| EP | 1592212 A1 | 11/2005 |
| EP | 1736931 A2 | 12/2006 |
| EP | 0651543 B1 | 9/2008 |
| EP | 2194508 A1 | 6/2010 |
| EP | 2416563 A2 | 2/2012 |
| EP | 2430766 A2 | 3/2012 |
| EP | 2454872 A1 | 5/2012 |
| EP | 2482179 A2 | 8/2012 |
| EP | 2487613 A1 | 8/2012 |
| EP | 2487913 A2 | 8/2012 |
| EP | 2430766 A4 | 12/2012 |
| EP | 2579572 A1 | 4/2013 |
| EP | 2634751 A1 | 9/2013 |
| EP | 2640060 A1 | 9/2013 |
| EP | 2682855 A2 | 1/2014 |
| EP | 2830297 A1 | 1/2015 |
| EP | 2843530 A1 | 3/2015 |
| EP | 2950198 A1 | 12/2015 |
| EP | 2966855 A2 | 1/2016 |
| EP | 2972677 A1 | 1/2016 |
| EP | 2430766 B1 | 3/2016 |
| EP | 2990887 A2 | 3/2016 |
| EP | 3008575 A1 | 4/2016 |
| EP | 3012732 A1 | 4/2016 |
| EP | 3026636 A1 | 6/2016 |
| EP | 3033837 A1 | 6/2016 |
| EP | 3047884 A1 | 7/2016 |
| EP | 3051525 A1 | 8/2016 |
| EP | 3101958 A1 | 12/2016 |
| EP | 3104590 A1 | 12/2016 |
| EP | 3107065 A1 | 12/2016 |
| EP | 3033837 A4 | 3/2017 |
| EP | 3190563 A1 | 7/2017 |
| EP | 3209012 A1 | 8/2017 |
| EP | 3211587 A1 | 8/2017 |
| EP | 2194508 B1 | 12/2017 |
| EP | 3333544 A1 | 6/2018 |
| EP | 2556665 B1 | 8/2018 |
| EP | 3033837 B1 | 10/2018 |
| EP | 3393119 A1 | 10/2018 |
| EP | 3135028 B1 | 1/2019 |
| EP | 2482179 B1 | 3/2019 |
| EP | 3457680 A1 | 3/2019 |
| EP | 3012732 B1 | 5/2019 |
| EP | 3008575 B1 | 7/2019 |
| EP | 3120217 B1 | 4/2020 |
| EP | 3633975 A1 | 4/2020 |
| EP | 2682855 B1 | 2/2021 |
| EP | 3787285 A1 | 3/2021 |
| GB | 2307383 A | 5/1997 |
| GB | 2515797 A | 1/2015 |
| GB | 2519363 A | 4/2015 |
| GB | 2523670 A | 9/2015 |

(56) References Cited

FOREIGN PATENT DOCUMENTS

| | | |
|---|---|---|
| JP | 53-31170 A | 3/1978 |
| JP | 56-621 A | 1/1981 |
| JP | H02-179078 A | 7/1990 |
| JP | 3007616 U | 2/1995 |
| JP | H099072 A | 1/1997 |
| JP | H09116792 A | 5/1997 |
| JP | 10-506472 A | 6/1998 |
| JP | H11-109066 A | 4/1999 |
| JP | H11355617 A | 12/1999 |
| JP | 2000-76460 A | 3/2000 |
| JP | 2000-162349 A | 6/2000 |
| JP | 2000-207549 A | 7/2000 |
| JP | 2000-244905 A | 9/2000 |
| JP | 2001-144884 A | 5/2001 |
| JP | 2001-245204 A | 9/2001 |
| JP | 2001-273064 A | 10/2001 |
| JP | 2001-298649 A | 10/2001 |
| JP | 2001-313886 A | 11/2001 |
| JP | 2002-251238 A | 9/2002 |
| JP | 2003-008964 A | 1/2003 |
| JP | 2003-9404 A | 1/2003 |
| JP | 2003-018438 A | 1/2003 |
| JP | 2003-032597 A | 1/2003 |
| JP | 2003-219217 A | 7/2003 |
| JP | 2003-233616 A | 8/2003 |
| JP | 2003-241293 A | 8/2003 |
| JP | 2003-248549 A | 9/2003 |
| JP | 2004-015595 A | 1/2004 |
| JP | 2004-28918 A | 1/2004 |
| JP | 2004-135074 A | 4/2004 |
| JP | 2004-184396 A | 7/2004 |
| JP | 2005-031466 A | 2/2005 |
| JP | 2005-191641 A | 7/2005 |
| JP | 2005-191985 A | 7/2005 |
| JP | 2005-521890 A | 7/2005 |
| JP | 2005-311699 A | 11/2005 |
| JP | 2006-520053 A | 8/2006 |
| JP | 3872041 B2 | 1/2007 |
| JP | 2007-028211 A | 2/2007 |
| JP | 2007-124398 A | 5/2007 |
| JP | 2007-528240 A | 10/2007 |
| JP | 2008-066978 A | 3/2008 |
| JP | 2008-236534 A | 10/2008 |
| JP | 2009-105919 A | 5/2009 |
| JP | 2009-212899 A | 9/2009 |
| JP | 2009-273023 A | 11/2009 |
| JP | 2009-545256 A | 12/2009 |
| JP | 2010-117444 A | 5/2010 |
| JP | 2010-119147 A | 5/2010 |
| JP | 2010-160581 A | 7/2010 |
| JP | 2010-182023 A | 8/2010 |
| JP | 2010-268052 A | 11/2010 |
| JP | 2011-087167 A | 4/2011 |
| JP | 2011-091570 A | 5/2011 |
| JP | 2011-124864 A | 6/2011 |
| JP | 2011-517810 A | 6/2011 |
| JP | 2011-525648 A | 9/2011 |
| JP | 2011-209887 A | 10/2011 |
| JP | 2011-211552 A | 10/2011 |
| JP | 2012-038292 A | 2/2012 |
| JP | 2012-079302 A | 4/2012 |
| JP | 2012-089973 A | 5/2012 |
| JP | 2012-124608 A | 6/2012 |
| JP | 2012-147379 A | 8/2012 |
| JP | 2013-3671 A | 1/2013 |
| JP | 2013-070303 A | 4/2013 |
| JP | 2013-92989 A | 5/2013 |
| JP | 2013-97760 A | 5/2013 |
| JP | 2013-101528 A | 5/2013 |
| JP | 2013-106289 A | 5/2013 |
| JP | 2013-232230 A | 11/2013 |
| JP | 2013-546238 A | 12/2013 |
| JP | 2014-023083 A | 2/2014 |
| JP | 2014-206817 A | 10/2014 |
| JP | 2014-212415 A | 11/2014 |
| JP | 2015-001716 A | 1/2015 |
| JP | 2015-005255 A | 1/2015 |
| JP | 2015-022716 A | 2/2015 |
| JP | 2015-25897 A | 2/2015 |
| JP | 2015-050713 A | 3/2015 |
| JP | 2015-076717 A | 4/2015 |
| JP | 2015-091098 A | 5/2015 |
| JP | 2015-146619 A | 8/2015 |
| JP | 2015-149095 A | 8/2015 |
| JP | 2015-180987 A | 10/2015 |
| JP | 2015-201839 A | 11/2015 |
| JP | 2016-066978 A | 4/2016 |
| JP | 2016-072965 A | 5/2016 |
| JP | 2016-129315 A | 7/2016 |
| JP | 2016-136324 A | 7/2016 |
| JP | 2016-175175 A | 10/2016 |
| JP | 2017-034474 A | 2/2017 |
| JP | 2017-527917 A | 9/2017 |
| JP | 2017-531225 A | 10/2017 |
| JP | 6240301 B1 | 11/2017 |
| JP | 6266736 B1 | 1/2018 |
| JP | 2018-514838 A | 6/2018 |
| JP | 2018-106365 A | 7/2018 |
| JP | 2018-107711 A | 7/2018 |
| JP | 2018-116067 A | 7/2018 |
| JP | 2018-121235 A | 8/2018 |
| JP | 2019-062556 A | 4/2019 |
| JP | 2019-145108 A | 8/2019 |
| JP | 2020-42602 A | 3/2020 |
| JP | 6982047 B2 | 11/2021 |
| KR | 10-2004-0046272 A | 6/2004 |
| KR | 10-2004-0107489 A | 12/2004 |
| KR | 10-2005-0086630 A | 8/2005 |
| KR | 10-2008-0050336 A | 6/2008 |
| KR | 10-2010-0086052 A | 7/2010 |
| KR | 10-2011-0028581 A | 3/2011 |
| KR | 10-2012-0025872 A | 3/2012 |
| KR | 10-2012-0048397 A | 5/2012 |
| KR | 10-2012-0054406 A | 5/2012 |
| KR | 10-2012-0057696 A | 6/2012 |
| KR | 10-2012-0093322 A | 8/2012 |
| KR | 10-2012-0132134 A | 12/2012 |
| KR | 10-2013-0033445 A | 4/2013 |
| KR | 101341095 B1 | 12/2013 |
| KR | 10-2014-0019631 A | 2/2014 |
| KR | 10-2014-0033088 A | 3/2014 |
| KR | 10-2014-0049340 A | 4/2014 |
| KR | 10-2014-0049850 A | 4/2014 |
| KR | 10-2014-0062801 A | 5/2014 |
| KR | 10-2015-0008996 A | 1/2015 |
| KR | 10-2015-0014290 A | 2/2015 |
| KR | 10-2015-0024899 A | 3/2015 |
| KR | 20150024899 A * | 3/2015 |
| KR | 10-2015-0067197 A | 6/2015 |
| KR | 101540544 B1 | 7/2015 |
| KR | 101587115 B1 | 1/2016 |
| KR | 10-2016-0016910 A | 2/2016 |
| KR | 10-2016-0019145 A | 2/2016 |
| KR | 10-2016-0020396 A | 2/2016 |
| KR | 10-2016-0020791 A | 2/2016 |
| KR | 20160047891 A * | 5/2016 |
| KR | 10-2016-0075583 A | 6/2016 |
| KR | 101674959 B1 | 11/2016 |
| KR | 10-2017-0081391 A | 7/2017 |
| KR | 10-2017-0123125 A | 11/2017 |
| KR | 10-1799223 B1 | 11/2017 |
| KR | 10-2017-0135975 A | 12/2017 |
| KR | 10-2018-0017227 A | 2/2018 |
| KR | 10-2018-0037076 A | 4/2018 |
| KR | 10-1875907 B1 | 7/2018 |
| KR | 10-2018-0095331 A | 8/2018 |
| KR | 10-2018-0108847 A | 10/2018 |
| KR | 10-2018-0137610 A | 12/2018 |
| KR | 10-2019-0034248 A | 4/2019 |
| KR | 10-2019-0114034 A | 10/2019 |
| KR | 102338576 B1 * | 12/2021 |
| SU | 1610470 A1 | 11/1990 |
| WO | 9840795 A1 | 9/1998 |
| WO | 9939307 A1 | 8/1999 |

(56) References Cited

FOREIGN PATENT DOCUMENTS

| | | |
|---|---|---|
| WO | 03/085460 A2 | 10/2003 |
| WO | 2005/043892 A1 | 5/2005 |
| WO | 2007/120981 A2 | 10/2007 |
| WO | 2007/126707 A1 | 11/2007 |
| WO | 2008/014301 A2 | 1/2008 |
| WO | 2008/020655 A1 | 2/2008 |
| WO | 2008/109644 A2 | 9/2008 |
| WO | 2009/073607 A2 | 6/2009 |
| WO | 2009/114239 A1 | 9/2009 |
| WO | 2009/133710 A1 | 11/2009 |
| WO | 2010/059426 A2 | 5/2010 |
| WO | 2010/077048 A2 | 7/2010 |
| WO | 2010/102678 A1 | 9/2010 |
| WO | 2010/077048 A3 | 10/2010 |
| WO | 2010/131869 A2 | 11/2010 |
| WO | 2010/134275 A1 | 11/2010 |
| WO | 2011/007264 A1 | 1/2011 |
| WO | 2010/131869 A3 | 2/2011 |
| WO | 2010/059426 A3 | 5/2011 |
| WO | 2011/127309 A1 | 10/2011 |
| WO | 2012/001947 A1 | 1/2012 |
| WO | 2012/006251 A1 | 1/2012 |
| WO | 2012/019163 A2 | 2/2012 |
| WO | 2012/051720 A2 | 4/2012 |
| WO | 2012/170354 A2 | 12/2012 |
| WO | 2013/082325 A1 | 6/2013 |
| WO | 2013/120851 A1 | 8/2013 |
| WO | 2013/152453 A1 | 10/2013 |
| WO | 2013/152454 A1 | 10/2013 |
| WO | 2013/152455 A1 | 10/2013 |
| WO | 2013/189058 A1 | 12/2013 |
| WO | 2014/053063 A1 | 4/2014 |
| WO | 2014/066115 A1 | 5/2014 |
| WO | 2014/094199 A1 | 6/2014 |
| WO | 2014/105276 A1 | 7/2014 |
| WO | 2014/159779 A1 | 10/2014 |
| WO | 2014/160819 A1 | 10/2014 |
| WO | 2014/165141 A1 | 10/2014 |
| WO | 2014/200734 A1 | 12/2014 |
| WO | 2014/200798 A1 | 12/2014 |
| WO | 2015/023044 A1 | 2/2015 |
| WO | 2015/026864 A1 | 2/2015 |
| WO | 2015/034960 A1 | 3/2015 |
| WO | 2015/059349 A1 | 4/2015 |
| WO | 2015/080744 A1 | 6/2015 |
| WO | 2015/085042 A1 | 6/2015 |
| WO | 2015/112868 A1 | 7/2015 |
| WO | 2014/200798 A8 | 8/2015 |
| WO | 2015/144209 A1 | 10/2015 |
| WO | 2015/166684 A1 | 11/2015 |
| WO | 2015/183438 A1 | 12/2015 |
| WO | 2015/187494 A1 | 12/2015 |
| WO | 2015/190666 A1 | 12/2015 |
| WO | 2016/022203 A1 | 2/2016 |
| WO | 2016/022204 A1 | 2/2016 |
| WO | 2016/022205 A1 | 2/2016 |
| WO | 2016/028806 A1 | 2/2016 |
| WO | 2016/028807 A1 | 2/2016 |
| WO | 2016/028808 A1 | 2/2016 |
| WO | 2016/028809 A1 | 2/2016 |
| WO | 2016/036218 A1 | 3/2016 |
| WO | 2016/042926 A1 | 3/2016 |
| WO | 2016/045005 A1 | 3/2016 |
| WO | 2016/057062 A1 | 4/2016 |
| WO | 2016/064435 A1 | 4/2016 |
| WO | 2016/073804 A2 | 5/2016 |
| WO | 2016/101124 A1 | 6/2016 |
| WO | 2016/101131 A1 | 6/2016 |
| WO | 2016/101132 A1 | 6/2016 |
| WO | 2016/073804 A3 | 7/2016 |
| WO | 2016/144385 A1 | 9/2016 |
| WO | 2016/145129 A1 | 9/2016 |
| WO | 2016/161556 A1 | 10/2016 |
| WO | 2016/172619 A1 | 10/2016 |
| WO | 2016/203282 A1 | 12/2016 |
| WO | 2016/204936 A1 | 12/2016 |
| WO | 2017/058834 A1 | 4/2017 |
| WO | 2017/071559 A1 | 5/2017 |
| WO | 2017/153771 A1 | 9/2017 |
| WO | 2017/201326 A1 | 11/2017 |
| WO | 2017/218193 A1 | 12/2017 |
| WO | 2018/006053 A1 | 1/2018 |
| WO | 2018/048838 A1 | 3/2018 |
| WO | 2018/049430 A2 | 3/2018 |
| WO | 2018/057268 A1 | 3/2018 |
| WO | 2018/057272 A1 | 3/2018 |
| WO | 2018/099037 A1 | 6/2018 |
| WO | 2018/144339 A2 | 8/2018 |
| WO | 2018/159864 A1 | 9/2018 |
| WO | 2018/212802 A1 | 11/2018 |
| WO | 2019/050562 A1 | 3/2019 |
| WO | 2019/216999 A1 | 11/2019 |
| WO | WO-2019216997 A1 * | 11/2019 ............... G06T 3/40 |
| WO | 2020/227386 A2 | 11/2020 |
| WO | 2021/050190 A1 | 3/2021 |

OTHER PUBLICATIONS

Notice of Allowance received for Japanese Patent Application No. 2020-159338, dated Jul. 19, 2022, 3 pages (1 page of English Translation and 2 pages of Official Copy).

Notice of Allowance received for U.S. Appl. No. 16/144,629, dated Jul. 25, 2022, 10 pages.

Notice of Allowance received for U.S. Appl. No. 17/373,163, dated Jul. 27, 2022, 8 pages.

Examiner-Initiated Interview Summary received for U.S. Appl. No. 17/356,322, dated Sep. 29, 2022, 4 pages.

Intention to Grant received for European Patent Application No. 21733324.4, dated Sep. 13, 2022, 7 pages.

Notice of Allowance received for Danish Patent Application No. PA202070623, dated Sep. 20, 2022, 2 pages.

Office Action received for Danish Patent Application No. PA202070625, dated Sep. 23, 2022, 4 pages.

Office Action received for European Patent Application No. 21163791.3, dated Sep. 20, 2022, 6 pages.

Applicant Initiated Interview Summary received for U.S. Appl. No. 17/031,671, dated Jun. 13, 2022, 7 pages.

Corrected Notice of Allowance received for U.S. Appl. No. 16/144,629, dated Jun. 23, 2022, 5 pages.

Decision on Appeal received for Korean Patent Application No. 10-2021-7002582, mailed on May 13, 2022, 29 pages (2 pages of English Translation and 27 pages of Official Copy).

Office Action received for Japanese Patent Application No. 2021-565919, dated Jun. 13, 2022, 4 pages (2 pages of English Translation and 2 pages of Official Copy).

Office Action received for Korean Patent Application No. 10-2020-0123852, dated Jun. 9, 2022, 10 pages (4 pages of English Translation and 6 pages of Official Copy).

Office Action received for Korean Patent Application No. 10-2020-0123857, dated Jun. 9, 2022, 12 pages (5 pages of English Translation and 7 pages of Official Copy).

Office Action received for Korean Patent Application No. 10-2020-0123887, dated Jun. 9, 2022, 5 pages (2 pages of English Translation and 3 pages of Official Copy).

[B612] Addition of facial recognition bear/cat stamps and AR background function having moving sparkles or hearts, Available Online at: <URL, htpps://apptopi.jp/2017/0I/22/b612>, Jan. 22, 2017, 11 pages.

Advisory Action received for U.S. Appl. No. 13/082,035, dated Jun. 19, 2015, 5 pages.

Advisory Action received for U.S. Appl. No. 13/082,035, dated Oct. 23, 2013, 3 pages.

Advisory Action received for U.S. Appl. No. 16/144,629, dated Dec. 13, 2019, 9 pages.

Advisory Action received for U.S. Appl. No. 16/144,629, dated Jan. 6, 2021, 10 pages.

Advisory Action received for U.S. Appl. No. 16/259,771, dated Feb. 26, 2020, 3 pages.

(56) References Cited

OTHER PUBLICATIONS

Advisory Action received for U.S. Appl. No. 16/259,771, dated Jul. 14, 2020, 6 pages.
Applicant Initiated Interview Summary received for U.S. Appl. No. 16/259,771, dated May 5, 2020, 10 pages.
Applicant Initiated Interview Summary received for U.S. Appl. No. 17/031,671, dated Aug. 2, 2021, 5 pages.
Applicant-Initiated Interview Summary received for U.S. Appl. No. 13/082,035, dated Apr. 4, 2013, 3 pages.
Applicant-Initiated Interview Summary received for U.S. Appl. No. 13/082,035, dated Aug. 1, 2016, 3 pages.
Applicant-Initiated Interview Summary received for U.S. Appl. No. 13/082,035, dated Jan. 29, 2015, 3 pages.
Applicant-Initiated Interview Summary received for U.S. Appl. No. 13/082,035, dated Oct. 30, 2013, 3 pages.
Applicant-Initiated Interview Summary received for U.S. Appl. No. 14/866,560, dated Jan. 30, 2019, 3 pages.
Applicant-Initiated Interview Summary received for U.S. Appl. No. 14/866,560, dated Jul. 26, 2018, 3 pages.
Applicant-Initiated Interview Summary received for U.S. Appl. No. 14/866,560, dated May 14, 2019, 4 pages.
Applicant-Initiated Interview Summary received for U.S. Appl. No. 14/866,560, dated Oct. 21, 2019, 3 pages.
Applicant-Initiated Interview Summary received for U.S. Appl. No. 16/144,629, dated Jul. 2, 2020, 5 pages.
Applicant-Initiated Interview Summary received for U.S. Appl. No. 16/144,629, dated Nov. 23, 2020, 3 pages.
Applicant-Initiated Interview Summary received for U.S. Appl. No. 16/519,850, dated Jun. 26, 2020, 4 pages.
Applicant-Initiated Interview Summary received for U.S. Appl. No. 16/528,941, dated Jun. 19, 2020, 3 pages.
Applicant-Initiated Interview Summary received for U.S. Appl. No. 16/528,941, dated Nov. 10, 2020, 2 pages.
Applicant-Initiated Interview Summary received for U.S. Appl. No. 16/584,100, dated Feb. 19, 2020, 3 pages.
Applicant-Initiated Interview Summary received for U.S. Appl. No. 16/586,344, dated Feb. 27, 2020, 3 pages.
Applicant-Initiated Interview Summary received for U.S. Appl. No. 16/663,062, dated Dec. 18, 2020, 3 pages.
Applicant-Initiated Interview Summary received for U.S. Appl. No. 16/733,718, dated Nov. 2, 2020, 4 pages.
Applicant-Initiated Interview Summary received for U.S. Appl. No. 16/833,436, dated Jul. 1, 2021, 2 pages.
Applicant-Initiated Interview Summary received for U.S. Appl. No. 17/027,317, dated Dec. 21, 2020, 4 pages.
Applicant-Initiated Interview Summary received for U.S. Appl. No. 17/031,654, dated Feb. 1, 2021, 2 pages.
Applicant-Initiated Interview Summary received for U.S. Appl. No. 17/031,765, dated Sep. 22, 2021, 5 pages.
Brief Communication Regarding Oral Proceedings received for European Patent Application No. 19172407.9, mailed on Nov. 9, 2020, 1 page.
Brief Communication Regarding Oral Proceedings received for European Patent Application No. 19172407.9, mailed on Nov. 20, 2020, 2 pages.
Certificate of Examination received for Australian Patent Application No. 2017100683, dated Jan. 16, 2018, 2 pages.
Certificate of Examination received for Australian Patent Application No. 2019100420, dated Jul. 3, 2019, 2 pages.
Certificate of Examination received for Australian Patent Application No. 2019100497, dated Jul. 29, 2019, 2 pages.
Certificate of Examination received for Australian Patent Application No. 2019100794, dated Dec. 19, 2019, 2 pages.
Certificate of Examination received for Australian Patent Application No. 2019101019, dated Nov. 12, 2019, 2 pages.
Certificate of Examination received for Australian Patent Application No. 2019101667, dated Mar. 20, 2020, 2 pages.
Certificate of Examination received for Australian Patent Application No. 2020100189, dated May 12, 2020, 2 pages.
Certificate of Examination received for Australian Patent Application No. 2020100675, dated Jun. 30, 2020, 2 pages.
Certificate of Examination received for Australian Patent Application No. 2020101715, dated Oct. 6, 2020, 2 pages.
Certificate of Examination received for Australian Patent Application No. 2020104220, dated Apr. 1, 2021, 2 pages.
Certificate of Examination received for Australian Patent Application No. 2021103004, dated Sep. 13, 2021, 2 pages.
Corrected Notice of Allowance received for U.S. Appl. No. 15/273,453, dated Dec. 21, 2017, 3 pages.
Corrected Notice of Allowance received for U.S. Appl. No. 15/273,453, dated Feb. 8, 2018, 2 pages.
Corrected Notice of Allowance received for U.S. Appl. No. 15/273,453, dated Nov. 27, 2017. 2 pages.
Corrected Notice of Allowance received for U.S. Appl. No. 15/273,503, dated Nov. 2, 2017, 2 pages.
Corrected Notice of Allowance received for U.S. Appl. No. 15/273,503, dated Nov. 24, 2017. 2 pages.
Corrected Notice of Allowance received for U.S. Appl. No. 15/713,490, dated May 1, 2019, 2 pages.
Corrected Notice of Allowance received for U.S. Appl. No. 15/858,175, dated Sep. 21, 2018, 2 pages.
Corrected Notice of Allowance received for U.S. Appl. No. 16/142,288, dated Jul. 30, 2019, 5 pages.
Corrected Notice of Allowance received for U.S. Appl. No. 16/143,097, dated Nov. 8, 2019, 3 pages.
Corrected Notice of Allowance received for U.S. Appl. No. 16/191,117, dated Dec. 9, 2019, 2 pages.
Corrected Notice of Allowance received for U.S. Appl. No. 16/191,117, dated Feb. 28, 2020, 2 pages.
Corrected Notice of Allowance received for U.S. Appl. No. 16/191,117, dated Nov. 20, 2019, 2 pages.
Corrected Notice of Allowance received for U.S. Appl. No. 16/519,850, dated Nov. 2, 2020, 5 pages.
Corrected Notice of Allowance received for U.S. Appl. No. 16/519,850, dated Sep. 8, 2020, 5 pages.
Corrected Notice of Allowance received for U.S. Appl. No. 16/582,595, dated Apr. 7, 2020, 5 pages.
Corrected Notice of Allowance received for U.S. Appl. No. 16/582,595, dated Apr. 22, 2020, 5 pages.
Corrected Notice of Allowance received for U.S. Appl. No. 16/583,020, dated Mar. 24, 2020, 2 pages.
Corrected Notice of Allowance received for U.S. Appl. No. 16/584,044, dated Apr. 16, 2020, 3 pages.
Corrected Notice of Allowance received for U.S. Appl. No. 16/584,044, dated Jan. 29, 2020, 3 pages.
Corrected Notice of Allowance received for U.S. Appl. No. 16/584,044, dated Mar. 4, 2020. 2 pages.
Corrected Notice of Allowance received for U.S. Appl. No. 16/584,100, dated Feb. 21, 2020, 9 pages.
Corrected Notice of Allowance received for U.S. Appl. No. 16/584,693, dated Feb. 21, 2020, 15 pages.
Corrected Notice of Allowance received for U.S. Appl. No. 16/584,693, dated Mar. 4, 2020, 2 pages.
Corrected Notice of Allowance received for U.S. Appl. No. 16/584,693, dated Mar. 20, 2020, 2 pages.
Corrected Notice of Allowance received for U.S. Appl. No. 16/586,314, dated Apr. 8, 2020, 5 pages.
Corrected Notice of Allowance received for U.S. Appl. No. 16/586,314, dated Mar. 4, 2020, 3 pages.
Corrected Notice of Allowance received for U.S. Appl. No. 16/586,344, dated Apr. 7, 2020, 4 pages.
Corrected Notice of Allowance received for U.S. Appl. No. 16/586,344, dated Jan. 23, 2020, 4 pages.
Corrected Notice of Allowance received for U.S. Appl. No. 16/586,344, dated Mar. 17, 2020, 4 pages.
Corrected Notice of Allowance received for U.S. Appl. No. 16/663,062, dated Jul. 21, 2021, 2 pages.
Corrected Notice of Allowance received for U.S. Appl. No. 16/733,718, dated Aug. 18, 2021, 2 pages.
Corrected Notice of Allowance received for U.S. Appl. No. 16/825,879, dated Aug. 13, 2021, 2 pages.

(56) References Cited

OTHER PUBLICATIONS

Corrected Notice of Allowance received for U.S. Appl. No. 16/825,879, dated Sep. 15, 2021, 2 pages.
Corrected Notice of Allowance received for U.S. Appl. No. 16/835,651, dated Aug. 10, 2021, 4 pages.
Corrected Notice of Allowance received for U.S. Appl. No. 16/835,651, dated Aug. 13, 2021, 2 pages.
Corrected Notice of Allowance received for U.S. Appl. No. 16/835,651, dated Jul. 28, 2021, 4 pages.
Corrected Notice of Allowance received for U.S. Appl. No. 16/835,651, dated Jun. 14, 2021, 2 pages.
Corrected Notice of Allowance received for U.S. Appl. No. 17/027,484, dated May 14, 2021, 5 pages.
Corrected Notice of Allowance received for U.S. Appl. No. 17/027,484, dated May 28, 2021, 5 pages.
Decision of Refusal received for Japanese Patent Application No. 2018-545502, dated Feb. 25, 2019, 11 pages.
Decision on Appeal received for Japanese Patent Application No. 2018-225131, mailed on Mar. 11, 2021, 5 pages.
Decision on Appeal received for Japanese Patent Application No. 2018-545502, mailed on Mar. 25, 2021, 3 pages.
Decision on Appeal received for U.S. Appl. No. 16/259,771, mailed on Aug. 19, 2021, 12 pages.
Decision to Grant received for Danish Patent Application No. PA201670627, dated Nov. 29, 2018, 2 pages.
Decision to Grant received for Danish Patent Application No. PA201670753, dated Mar. 6, 2019, 2 pages.
Decision to Grant received for Danish Patent Application No. PA201670755, dated Mar. 6, 2019, 2 pages.
Decision to Grant received for Danish Patent Application No. PA201870372, dated Jun. 17, 2020, 2 pages.
Decision to Grant received for Danish Patent Application No. PA201870375, dated Jul. 24, 2019, 2 pages.
Decision to Grant received for Danish Patent Application No. PA201870377, dated May 14, 2019, 2 pages.
Decision to Grant received for Danish Patent Application No. PA201970601, dated Feb. 3, 2021, 2 pages.
Decision to Grant received for Danish Patent Application No. PA201970603, dated May 21, 2021, 2 pages.
Decision to Grant received for European Patent Application No. 18176890.4, dated Jul. 9, 2020, 3 pages.
Decision to Grant received for European Patent Application No. 18183054.8, dated Jan. 21, 2021, 3 pages.
Decision to Grant received for European Patent Application No. 18209460.7, dated Apr. 9, 2021, 2 pages.
Decision to Grant received for European Patent Application No. 18214698.5, dated Sep. 10, 2020, 3 pages.
Decision to Grant received for European Patent Application No. 19172407.9, dated Jun. 17, 2021, 2 pages.
Decision to Grant received for Japanese Patent Application No. 2018-243463, dated Aug. 17, 2020, 2 pages.
Decision to Grant received for Japanese Patent Application No. 2020-070418, dated Feb. 8, 2021, 3 pages.
Decision to Grant received for Japanese Patent Application No. 2020-184470, dated Jul. 1, 2021, 3 pages.
Decision to Grant received for Japanese Patent Application No. 2020-184471, dated Jul. 1, 2021, 3 pages.
Decision to Grant received for Japanese Patent Application No. 2020-193703, dated Aug. 10, 2021, 3 pages.
Decision to Grant received for Japanese Patent Application No. 2021-051385, dated Jul. 8, 2021, 3 pages.
Decision to Refuse received for European Patent Application No. 19724959.2, dated Jun. 22, 2021, 13 pages.
Decision to Refuse received for Japanese Patent Application No. 2018-225131, dated Jul. 8, 2019, 6 pages.
Decision to Refuse received for Japanese Patent Application No. 2018-243463, dated Jul. 8, 2019, 5 pages.
Decision to Refuse received for Japanese Patent Application No. 2018-545502, dated Jul. 8, 2019, 5 pages.
European Search Report received for European Patent Application No. 18209460.7, dated Mar. 15, 2019, 4 pages.
European Search Report received for European Patent Application No. 18214698.5, dated Mar. 21, 2019, 5 pages.
European Search Report received for European Patent Application No. 19172407.9, dated Oct. 9, 2019, 4 pages.
European Search Report received for European Patent Application No. 19181242.9, dated Nov. 27, 2019, 4 pages.
European Search Report received for European Patent Application No. 20168021.2, dated Jul. 8, 2020, 4 pages.
European Search Report received for European Patent Application No. 20206196.6, dated Dec. 8, 2020, 4 pages.
European Search Report received for European Patent Application No. 20206197.4, dated Nov. 30, 2020, 4 pages.
European Search Report received for European Patent Application No. 20210373.5, dated Apr. 13, 2021, 4 pages.
European Search Report received for European Patent Application No. 21157252.4, dated Apr. 16, 2021, 4 pages.
European Search Report received for European Patent Application No. 21163791.3, dated May 6, 2021, 5 pages.
Examiner Initiated-Interview Summary received for U.S. Appl. No. 16/528,941, dated Dec. 1, 2020, 2 pages.
Examiner's Answer to Appeal Brief received for U.S. Appl. No. 16/144,629, mailed on Jul. 21, 2021, 21 pages.
Examiner's Answer to Appeal Brief received for U.S. Appl. No. 16/259,771, mailed on Oct. 23, 2020, 15 pages.
Extended European Search Report received for European Patent Application No. 17853657.9, dated May 28, 2020, 9 pages.
Extended European Search Report received for European Patent Application No. 19204230.7, dated Feb. 21, 2020, 7 pages.
Extended European Search Report received for European Patent Application No. 19212057.4, dated Feb. 27, 2020, 8 pages.
Extended European Search Report received for European Patent Application No. 20168009.7, dated Sep. 11, 2020, 12 pages.
Final Office Action received for U.S. Appl. No. 13/082,035, dated Apr. 16, 2015, 24 pages.
Final Office Action received for U.S. Appl. No. 13/082,035, dated Aug. 15, 2013, 24 pages.
Final Office Action received for U.S. Appl. No. 14/866,560, dated Oct. 9, 2018, 22 pages.
Final Office Action received for U.S. Appl. No. 15/728,147, dated Aug. 29, 2018, 39 pages.
Final Office Action received for U.S. Appl. No. 15/728,147, dated May 28, 2019, 45 pages.
Final Office Action received for U.S. Appl. No. 16/116,221, dated Mar. 22, 2019, 35 pages.
Final Office Action received for U.S. Appl. No. 16/144,629, dated Sep. 11, 2020, 22 pages.
Final Office Action received for U.S. Appl. No. 16/528,941, dated Jul. 13, 2020, 15 pages.
Final Office Action received for U.S. Appl. No. 16/833,436, dated Sep. 21, 2021, 29 pages.
Final Office Action received for U.S. Appl. No. 17/031,671, dated Sep. 7, 2021, 27 pages.
Intention to Grant received for Danish Patent Application No. PA201670753, dated Oct. 29, 2018, 2 pages.
Intention to Grant received for Danish Patent Application No. PA201670755, dated Nov. 13, 2018, 2 pages.
Intention to Grant received for Danish Patent Application No. PA201870372, dated Feb. 13, 2020, 2 pages.
Intention to Grant received for Danish Patent Application No. PA201870375, dated Jun. 3, 2019, 2 pages.
Intention to Grant received for Danish Patent Application No. PA201870375, dated Mar. 26, 2019, 2 pages.
Intention to Grant received for Danish Patent Application No. PA201870377, dated Mar. 26, 2019, 2 pages.
Intention to Grant received for Danish Patent Application No. PA201970593, dated Apr. 13, 2021, 2 pages.
Intention to Grant received for Danish Patent Application No. PA201970601, dated Sep. 21, 2020, 2 pages.
Intention to Grant received for Danish Patent Application No. PA201970603, dated Jan. 13, 2021, 2 pages.

(56) References Cited

OTHER PUBLICATIONS

Intention to Grant received for Danish Patent Application No. PA202070611, dated May 5, 2021, 2 pages.
Intention to Grant received for European Patent Application No. 17809168.2, dated Jun. 25, 2021, 8 pages.
Intention to Grant received for European Patent Application No. 18176890.4, dated Feb. 28, 2020, 8 pages.
Intention to Grant received for European Patent Application No. 18183054.8, dated Nov. 5, 2020, 6 pages.
Intention to Grant received for European Patent Application No. 18209460.7, dated Jan. 15, 2021, 8 pages.
Intention to Grant received for European Patent Application No. 18214698.5, dated Apr. 21, 2020, 8 pages.
Intention to Grant received for European Patent Application No. 19172407.9, dated Feb. 11, 2021, 9 pages.
Intention to Grant received for European Patent Application No. 20168021.2, dated Apr. 15, 2021, 8 pages.
Intention to Grant received for European Patent Application No. 20168021.2, dated Sep. 20, 2021, 8 pages.
International Preliminary Report on Patentability received for PCT Patent Application No. PCT/US2017/035321, dated Dec. 27, 2018, 11 Pages.
International Preliminary Report on Patentability received for PCT Patent Application No. PCT/US2017/049795, dated Apr. 4, 2019, 16 pages.
International Preliminary Report on Patentability received for PCT Patent Application No. PCT/US2018/015591, dated Dec. 19, 2019, 10 pages.
International Preliminary Report on Patentability received for PCT Patent Application No. PCT/US2019/023793, dated Nov. 19, 2020, 12 pages.
International Preliminary Report on Patentability received for PCT Patent Application No. PCT/US2019/024067, dated Nov. 19, 2020, 12 pages.
International Preliminary Report on Patentability received for PCT Patent Application No. PCT/US2019/049101, dated Mar. 25, 2021, 17 pages.
International Preliminary Report on Patentability received for PCT Patent Application No. PCT/US2020/014176, dated Jul. 29, 2021, 9 pages.
International Search Report and Written Opinion received for PCT Patent Application No. PCT/US2019/023793, dated Aug. 27, 2019, 17 pages.
International Search Report and Written Opinion received for PCT Patent Application No. PCT/US2019/024067, dated Oct. 9, 2019, 18 pages.
International Search Report and Written Opinion received for PCT Patent Application No. PCT/US2019/049101, dated Dec. 16, 2019, 26 pages.
International Search Report and Written Opinion received for PCT Patent Application No. PCT/US2020/014176, dated Mar. 26, 2020, 12 pages.
International Search Report and Written Opinion received for PCT Patent Application No. PCT/US2020/031643, dated Dec. 2, 2020, 33 pages.
International Search Report and Written Opinion received for PCT Patent Application No. PCT/US2020/031643, dated Nov. 2, 2020, 34 pages.
International Search Report and Written Opinion received for PCT Patent Application No. PCT/US2021/031212, dated Sep. 21, 2021, 21 pages.
Invitation to Pay Addition Fees received for PCT Patent Application No. PCT/US2017/035321, dated Aug. 17, 2017, 3 pages.
Invitation to Pay Additional Fees and Partial International Search Report received for PCT Patent Application No. PCT/US2019/049101, dated Oct. 24, 2019, 17 pages.
Invitation to Pay Additional Fees received for PCT Patent Application No. PCT/US2017/049795, dated Nov. 3, 2017, 3 pages.
Invitation to Pay Additional Fees received for PCT Patent Application No. PCT/US2019/023793, dated Jul. 5, 2019, 11 pages.
Invitation to Pay Additional Fees received for PCT Patent Application No. PCT/US2019/024067, dated Jul. 16, 2019, 13 pages.
Invitation to Pay Additional Fees received for PCT Patent Application No. PCT/US2020/031643, dated Sep. 9, 2020, 30 pages.
Invitation to Pay Additional Fees received for PCT Patent Application No. PCT/US2021/031212, dated Jul. 28, 2021, 19 pages.
Invitation to Pay Additional Fees received for PCT Patent Application No. PCT/US2021/034304, dated Aug. 20, 2021, 16 pages.
Invitation to Pay Search Fees received for European Patent Application No. 18704732.9, dated Jun. 2, 2021, 3 pages.
Invitation to Pay Search Fees received for European Patent Application No. 19724959.2, dated Feb. 25, 2020, 3 pages.
Minutes of the Oral Proceedings received for European Patent Application No. 19181242.9, mailed on Dec. 15, 2020, 6 pages.
Minutes of the Oral Proceedings received for European Patent Application No. 19724959.2, mailed on Jun. 14, 2021, 6 pages.
Non-Final Office Action received for U.S. Appl. No. 16/528,257, dated Jul. 30, 2021, 12 pages.
Non-Final Office Action received for U.S. Appl. No. 13/082,035, dated Apr. 21, 2016, 25 pages.
Non-Final Office Action received for U.S. Appl. No. 13/082,035, dated Dec. 19, 2012, 19 pages.
Non-Final Office Action received for U.S. Appl. No. 13/082,035, dated Sep. 11, 2014, 23 pages.
Non-Final Office Action received for U.S. Appl. No. 14/866,560, dated Apr. 19, 2018, 10 pages.
Non-Final Office Action received for U.S. Appl. No. 14/866,560, dated Apr. 30, 2019, 23 pages.
Non-Final Office Action received for U.S. Appl. No. 15/273,522, dated Nov. 30, 2016, 15 pages.
Non-Final Office Action received for U.S. Appl. No. 15/273,544, dated May 25, 2017, 18 pages.
Non-Final Office Action received for U.S. Appl. No. 15/728,147, dated Feb. 22, 2018, 20 pages.
Non-Final Office Action received for U.S. Appl. No. 15/728,147, dated Jan. 31, 2019, 41 pages.
Non-Final Office Action received for U.S. Appl. No. 16/116,221, dated Nov. 13, 2018, 27 pages.
Non-Final Office Action received for U.S. Appl. No. 16/142,288, dated Nov. 20, 2018, 15 pages.
Non-Final Office Action received for U.S. Appl. No. 16/142,305, dated Nov. 23, 2018, 32 pages.
Non-Final Office Action received for U.S. Appl. No. 16/142,328, dated Nov. 8, 2018, 18 pages.
Non-Final Office Action received for U.S. Appl. No. 16/143,097, dated Feb. 28, 2019, 17 pages.
Non-Final Office Action received for U.S. Appl. No. 16/144,629, dated Mar. 13, 2020, 24 pages.
Non-Final Office Action received for U.S. Appl. No. 16/144,629, dated Mar. 29, 2019, 18 pages.
Non-Final Office Action received for U.S. Appl. No. 16/259,771, dated May 8, 2019, 11 pages.
Non-Final Office Action received for U.S. Appl. No. 16/519,850, dated Mar. 23, 2020, 8 pages.
Non-Final Office Action received for U.S. Appl. No. 16/528,941, dated Dec. 7, 2020, 15 pages.
Non-Final Office Action received for U.S. Appl. No. 16/582,595, dated Nov. 26, 2019, 17 pages.
Non-Final Office Action received for U.S. Appl. No. 16/583,020, dated Nov. 14, 2019, 9 pages.
Non-Final Office Action received for U.S. Appl. No. 16/733,718, dated Sep. 16, 2020, 25 pages.
Non-Final Office Action received for U.S. Appl. No. 16/825,879, dated May 5, 2021, 12 pages.
Non-Final Office Action received for U.S. Appl. No. 16/833,436, dated Mar. 29, 2021, 27 pages.
Non-Final Office Action received for U.S. Appl. No. 17/027,317, dated Nov. 17, 2020, 17 pages.
Non-Final Office Action received for U.S. Appl. No. 17/031,654, dated Nov. 19, 2020, 12 pages.
Non-Final Office Action received for U.S. Appl. No. 17/031,671, dated Apr. 30, 2021, 27 pages.

(56) References Cited

OTHER PUBLICATIONS

Non-Final Office Action received for U.S. Appl. No. 17/031,765, dated Jun. 28, 2021, 32 pages.
Non-Final Office Action received for U.S. Appl. No. 17/091,460, dated Sep. 10, 2021, 10 pages.
Notice of Acceptance received for Australian Patent Application No. 2017286130, dated Apr. 26, 2019, 3 pages.
Notice of Acceptance received for Australian Patent Application No. 2017330212, dated Apr. 28, 2020, 3 pages.
Notice of Acceptance received for Australian Patent Application No. 2018279787, dated Dec. 10, 2019, 3 pages.
Notice of Acceptance received for Australian Patent Application No. 2019213341, dated Aug. 25, 2020, 3 pages.
Notice of Acceptance received for Australian Patent Application No. 2019265357, dated Dec. 24, 2020, 3 pages.
Notice of Acceptance received for Australian Patent Application No. 2019266049, dated Nov. 24, 2020, 3 pages.
Notice of Acceptance received for Australian Patent Application No. 2020213402, dated Sep. 21, 2020, 3 pages.
Notice of Acceptance received for Australian Patent Application No. 2020267151, dated Dec. 9, 2020, 3 pages.
Notice of Acceptance received for Australian Patent Application No. 2020277216, dated Mar. 15, 2021, 3 pages.
Notice of Acceptance received for Australian Patent Application No. 2021201167, dated Mar. 15, 2021, 3 pages.
Notice of Acceptance received for Australian Patent Application No. 2021203210, dated Jul. 9, 2021, 3 pages.
Notice of Allowance received for Brazilian Patent Application No. 112018074765-3, dated Oct. 8, 2019, 2 pages.
Notice of Allowance received for Chinese Patent Application No. 201780002533.5, dated Apr. 14, 2020, 2 pages.
Notice of Allowance received for Chinese Patent Application No. 201810566134.8, dated Apr. 7, 2020, 3 pages.
Notice of Allowance received for Chinese Patent Application No. 201810664927.3, dated Jul. 19, 2019, 2 pages.
Notice of Allowance received for Chinese Patent Application No. 201811512767.7, dated Jul. 27, 2020, 4 pages.
Notice of Allowance received for Chinese Patent Application No. 201910379481.4, dated Nov. 9, 2020, 6 pages.
Notice of Allowance received for Chinese Patent Application No. 201911202668.3, dated Feb. 4, 2021, 5 pages.
Notice of Allowance received for Chinese Patent Application No. 201911219525.3, dated Sep. 29, 2020, 2 pages.
Notice of Allowance received for Chinese Patent Application No. 202010218168.5, dated Aug. 25, 2021, 6 pages.
Notice of Allowance received for Chinese Patent Application No. 202010287953.6, dated Mar. 18, 2021, 7 pages.
Notice of Allowance received for Chinese Patent Application No. 202010287958.9, dated Aug. 27, 2021, 6 pages.
Notice of Allowance received for Chinese Patent Application No. 202010287961.0, dated Mar. 9, 2021, 8 pages.
Notice of Allowance received for Chinese Patent Application No. 202010287975.2, dated Mar. 1, 2021, 7 pages.
Notice of Allowance received for Chinese Patent Application No. 202010600151.6, dated Aug. 13, 2021, 2 pages.
Notice of Allowance received for Japanese Patent Application No. 2018-171188, dated Jul. 16, 2019, 3 pages.
Notice of Allowance received for Japanese Patent Application No. 2018-184254, dated Jun. 15, 2020, 4 pages.
Notice of Allowance received for Japanese Patent Application No. 2019-511767, dated Mar. 30, 2020, 4 pages.
Notice of Allowance received for Korean Patent Application No. 10-2018-7026743, dated Mar. 20, 2019, 7 pages.
Notice of Allowance received for Korean Patent Application No. 10-2018-7028849, dated Feb. 1, 2019, 4 pages.
Notice of Allowance received for Korean Patent Application No. 10-2018-7034780, dated Jun. 19, 2019, 4 pages.
Notice of Allowance received for Korean Patent Application No. 10-2018-7036893, dated Jun. 12, 2019, 4 pages.
Notice of Allowance received for Korean Patent Application No. 10-2019-7005369, dated Oct. 26, 2020, 4 pages.
Notice of Allowance received for Korean Patent Application No. 10-2019-7027042, dated Nov. 26, 2020, 4 pages.
Notice of Allowance received for Korean Patent Application No. 10-2019-7035478, dated Apr. 24, 2020, 4 pages.
Notice of Allowance received for Korean Patent Application No. 10-2020-0052618, dated Mar. 23, 2021, 5 pages.
Notice of Allowance received for Korean Patent Application No. 10-2020-0143726, dated Nov. 10, 2020, 5 pages.
Notice of Allowance received for Korean Patent Application No. 10-2020-0155924, dated Nov. 23, 2020, 7 pages.
Notice of Allowance received for Korean Patent Application No. 10-2020-7021870, dated Apr. 26, 2021, 4 pages.
Notice of Allowance received for Korean Patent Application No. 10-2020-7031855, dated Mar. 22, 2021, 5 pages.
Notice of Allowance received for Korean Patent Application No. 10-2020-7032147, dated May 12, 2021, 4 pages.
Notice of Allowance received for Korean Patent Application No. 10-2021-7000954, dated Aug. 18, 2021, 5 pages.
Notice of Allowance received for Korean Patent Application No. 10-2021-7019525, dated Jul. 13, 2021, 5 pages.
Notice of Allowance received for U.S. Appl. No. 16/528,941, dated Aug. 10, 2021, 5 pages.
Notice of Allowance received for U.S. Appl. No. 16/528,941, dated May 19, 2021, 5 pages.
Notice of Allowance received for U.S. Appl. No. 13/082,035, dated Oct. 5, 2016, 9 pages.
Notice of Allowance received for U.S. Appl. No. 14/866,560, dated Nov. 15, 2019, 9 pages.
Notice of Allowance received for U.S. Appl. No. 15/273,453, dated Oct. 12, 2017. 11 pages.
Notice of Allowance received for U.S. Appl. No. 15/273,503, dated Aug. 14, 2017, 9 pages.
Notice of Allowance received for U.S. Appl. No. 15/273,522, dated Mar. 28, 2017. 9 Pages.
Notice of Allowance received for U.S. Appl. No. 15/273,522, dated May 19, 2017, 2 pages.
Notice of Allowance received for U.S. Appl. No. 15/273,522, dated May 23, 2017, 2 pages.
Notice of Allowance received for U.S. Appl. No. 15/273,544, dated Mar. 13, 2018, 8 pages.
Notice of Allowance received for U.S. Appl. No. 15/273,544, dated Oct. 27, 2017, 8 pages.
Notice of Allowance received for U.S. Appl. No. 15/713,490, dated Mar. 20, 2019, 15 pages.
Notice of Allowance received for U.S. Appl. No. 15/728,147, dated Aug. 19, 2019, 13 pages.
Notice of Allowance received for U.S. Appl. No. 15/858,175, dated Jun. 1, 2018, 8 pages.
Notice of Allowance received for U.S. Appl. No. 15/858,175, dated Sep. 12, 2018, 8 pages.
Notice of Allowance received for U.S. Appl. No. 16/110,514, dated Apr. 29, 2019, 9 pages.
Notice of Allowance received for U.S. Appl. No. 16/110,514, dated Mar. 13, 2019, 11 pages.
Notice of Allowance received for U.S. Appl. No. 16/116,221, dated Nov. 22, 2019, 13 pages.
Notice of Allowance received for U.S. Appl. No. 16/116,221, dated Sep. 20, 2019, 13 pages.
Notice of Allowance received for U.S. Appl. No. 16/142,288, dated Jun. 24, 2019, 10 pages.
Notice of Allowance received for U.S. Appl. No. 16/142,288, dated Mar. 27, 2019, 9 pages.
Notice of Allowance received for U.S. Appl. No. 16/142,288, dated May 1, 2019, 4 pages.
Notice of Allowance received for U.S. Appl. No. 16/142,305, dated Apr. 3, 2019, 5 pages.
Notice of Allowance received for U.S. Appl. No. 16/142,305, dated May 1, 2019, 2 pages.
Notice of Allowance received for U.S. Appl. No. 16/142,328, dated Apr. 5, 2019, 7 pages.

(56) References Cited

OTHER PUBLICATIONS

Notice of Allowance received for U.S. Appl. No. 16/143,097, dated Aug. 29, 2019, 23 pages.
Notice of Allowance received for U.S. Appl. No. 16/143,201, dated Feb. 8, 2019, 9 pages.
Notice of Allowance received for U.S. Appl. No. 16/143,201, dated Nov. 28, 2018, 14 pages.
Notice of Allowance received for U.S. Appl. No. 16/191,117, dated Oct. 29, 2019, 9 pages.
Notice of Allowance received for U.S. Appl. No. 16/519,850, dated Aug. 26, 2020, 8 pages.
Notice of Allowance received for U.S. Appl. No. 16/582,595, dated Mar. 20, 2020, 9 pages.
Notice of Allowance received for U.S. Appl. No. 16/583,020, dated Apr. 1, 2020, 5 pages.
Notice of Allowance received for U.S. Appl. No. 16/583,020, dated Feb. 28, 2020, 5 pages.
Notice of Allowance received for U.S. Appl. No. 16/584,044, dated Dec. 11, 2019, 15 pages.
Notice of Allowance received for U.S. Appl. No. 16/584,044, dated Mar. 30, 2020, 16 pages.
Notice of Allowance received for U.S. Appl. No. 16/584,044, dated Nov. 14, 2019, 13 pages.
Notice of Allowance received for U.S. Appl. No. 16/584,100, dated Apr. 8, 2020, 12 pages.
Notice of Allowance received for U.S. Appl. No. 16/584,100, dated Jan. 14, 2020, 13 pages.
Notice of Allowance received for U.S. Appl. No. 16/584,693, dated Jan. 14, 2020, 15 pages.
Notice of Allowance received for U.S. Appl. No. 16/584,693, dated May 4, 2020, 12 pages.
Notice of Allowance received for U.S. Appl. No. 16/586,314, dated Apr. 1, 2020, 8 pages.
Notice of Allowance received for U.S. Appl. No. 16/586,314, dated Jan. 9, 2020, 10 pages.
Notice of Allowance received for U.S. Appl. No. 16/586,344, dated Dec. 16, 2019, 12 pages.
Notice of Allowance received for U.S. Appl. No. 16/586,344, dated Mar. 27, 2020, 12 pages.
Notice of Allowance received for U.S. Appl. No. 16/663,062, dated Mar. 24, 2021, 8 pages.
Notice of Allowance received for U.S. Appl. No. 16/733,718, dated Feb. 5, 2021, 14 pages.
Notice of Allowance received for U.S. Appl. No. 16/733,718, dated Jul. 29, 2021, 26 pages.
Notice of Allowance received for U.S. Appl. No. 16/825,879, dated Jul. 13, 2021, 9 pages.
Notice of Allowance received for U.S. Appl. No. 16/825,879, dated Sep. 28, 2021, 8 pages.
Notice of Allowance received for U.S. Appl. No. 16/835,651, dated Jul. 23, 2021, 8 pages.
Notice of Allowance received for U.S. Appl. No. 16/835,651, dated Jun. 1, 2021, 10 pages.
Notice of Allowance received for U.S. Appl. No. 17/027,317, dated Apr. 12, 2021, 7 pages.
Notice of Allowance received for U.S. Appl. No. 17/027,317, dated Jan. 13, 2021, 10 pages.
Notice of Allowance received for U.S. Appl. No. 17/027,484, dated May 3, 2021, 11 pages.
Notice of Allowance received for U.S. Appl. No. 17/031,654, dated Feb. 10, 2021, 9 pages.
Notice of Allowance received for U.S. Appl. No. 17/031,654, dated May 27, 2021, 8 pages.
Office Action received for Australian Patent Application No. 2017100683, dated Sep. 20, 2017. 3 pages.
Office Action received for Australian Patent Application No. 2017100684, dated Jan. 24, 2018, 4 pages.
Office Action received for Australian Patent Application No. 2017100684, dated Oct. 5, 2017. 4 pages.
Office Action Received for Australian Patent Application No. 2017286130, dated Jan. 21, 2019, 4 pages.
Office Action received for Australian Patent Application No. 2017330212, dated Feb. 21, 2020, 2 pages.
Office Action received for Australian Patent Application No. 2019100794, dated Oct. 3, 2019, 4 pages.
Office Action received for Australian Patent Application No. 2019213341, dated Jun. 30, 2020, 6 pages.
Office Action received for Australian Patent Application No. 2020100189, dated Apr. 1, 2020, 3 pages.
Office Action received for Australian Patent Application No. 2020100720, dated Jul. 9, 2020, 7 pages.
Office Action received for Australian Patent Application No. 2020100720, dated Sep. 1, 2020, 5 pages.
Office Action received for Australian Patent Application No. 2020101043, dated Aug. 14, 2020, 5 pages.
Office Action received for Australian Patent Application No. 2020101043, dated Oct. 30, 2020, 4 pages.
Office Action received for Australian Patent Application No. 2020201969, dated Sep. 25, 2020, 5 pages.
Office Action received for Australian Patent Application No. 2020239717, dated Jun. 23, 2021, 7 pages.
Office Action received for Australian Patent Application No. 2020239749, dated Jul. 16, 2021, 5 pages.
Office Action received for Australian Patent Application No. 2020260413, dated Jun. 24, 2021, 2 pages.
Office Action received for Australian Patent Application No. 2020277216, dated Dec. 17, 2020, 5 pages.
Office Action received for Australian Patent Application No. 2021103004, dated Aug. 12, 2021, 5 pages.
Office Action received for Chinese Patent Application No. 201780002533.5, dated Apr. 25, 2019, 17 pages.
Office Action received for Chinese Patent Application No. 201780002533.5, dated Feb. 3, 2020, 6 pages.
Office Action received for Chinese Patent Application No. 201780002533.5, dated Sep. 26, 2019, 21 pages.
Office Action received for Chinese Patent Application No. 201810566134.8, dated Aug. 13, 2019, 14 pages.
Office Action received for Chinese Patent Application No. 201810664927.3, dated Mar. 28, 2019, 11 pages.
Office Action received for Chinese Patent Application No. 201811446867.4, dated Dec. 31, 2019, 12.
Office Action received for Chinese Patent Application No. 201811446867.4, dated Sep. 8, 2020, 9 pages.
Office Action received for Chinese Patent Application No. 201811512767.7, dated Dec. 20, 2019, 14 pages.
Office Action received for Chinese Patent Application No. 201811512767.7, dated Jun. 4, 2020, 6 pages.
Office Action received for Chinese Patent Application No. 201910379481.4, dated Mar. 2, 2020, 18 pages.
Office Action received for Chinese Patent Application No. 201910691865.X, dated Aug. 4, 2021, 10 pages.
Office Action received for Chinese Patent Application No. 201910691865.X, dated Feb. 4, 2021, 16 pages.
Office Action received for Chinese Patent Application No. 201910691865.X, dated Jul. 8, 2020, 17 pages.
Office Action received for Chinese Patent Application No. 201910691872.X, dated Jun. 3, 2020, 10 pages.
Office Action received for Chinese Patent Application No. 201910692978.1, dated Apr. 3, 2020, 19 pages.
Office Action received for Chinese Patent Application No. 201910692978.1, dated Nov. 4, 2020, 4 pages.
Office Action received for Chinese Patent Application No. 201911199054.4, dated Jan. 20, 2021, 19 pages.
Office Action received for Chinese Patent Application No. 201911199054.4, dated Jun. 10, 2021, 13 pages.
Office Action received for Chinese Patent Application No. 201911202668.3, dated Aug. 4, 2020, 13 pages.
Office Action received for Chinese Patent Application No. 201911219525.3, dated Jul. 10, 2020, 7 pages.
Office Action received for Chinese Patent Application No. 202010218168.5, dated Feb. 9, 2021, 21 pages.

(56) References Cited

OTHER PUBLICATIONS

Office Action received for Chinese Patent Application No. 202010287950.2, dated Aug. 10, 2021, 12 pages.
Office Action received for Chinese Patent Application No. 202010287950.2, dated Feb. 20, 2021, 22 pages.
Office Action received for Chinese Patent Application No. 202010287953.6, dated Jan. 14, 2021, 14 pages.
Office Action received for Chinese Patent Application No. 202010287958.9, dated Jan. 5, 2021, 16 pages.
Office Action received for Chinese Patent Application No. 202010287961.0, dated Dec. 30, 2020, 16 pages.
Office Action received for Chinese Patent Application No. 202010287975.2, dated Dec. 30, 2020, 17 pages.
Office Action received for Chinese Patent Application No. 202010330318.1, dated Jul. 13, 2021, 12 pages.
Office Action received for Chinese Patent Application No. 202010330318.1, dated Mar. 31, 2021, 13 pages.
Office Action received for Chinese Patent Application No. 202010330318.1, dated Nov. 19, 2020, 18 pages.
Office Action received for Chinese Patent Application No. 202010600151.6, dated Apr. 29, 2021, 11 pages.
Office Action received for Chinese Patent Application No. 202010600197.8, dated Jul. 2, 2021, 14 pages.
Office Action received for Chinese Patent Application No. 202010601484.0, dated Jun. 3, 2021, 13 pages.
Office Action received for Chinese Patent Application No. 202011480411.7, dated Aug. 2, 2021, 12 pages.
Office Action received for Danish Patent Application No. PA201670627, dated Apr. 5, 2017, 3 pages.
Office Action received for Danish Patent Application No. PA201670627, dated Nov. 6, 2017, 2 pages.
Office Action received for Danish Patent Application No. PA201670627, dated Oct. 11, 2016, 8 pages.
Office Action received for Danish Patent Application No. PA201670753, dated Dec. 20, 2016, 7 pages.
Office Action received for Danish Patent Application No. PA201670753, dated Jul. 5, 2017. 4 pages.
Office Action received for Danish Patent Application No. PA201670753, dated Mar. 23, 2018, 5 pages.
Office Action received for Danish Patent Application No. PA201670755, dated Apr. 6, 2017, 5 pages.
Office Action received for Danish Patent Application No. PA201670755, dated Apr. 20, 2018, 2 pages.
Office Action received for Danish Patent Application No. PA201670755, dated Dec. 22, 2016, 6 pages.
Office Action received for Danish Patent Application No. PA201770563, dated Aug. 13, 2018, 5 pages.
Office Action received for Danish Patent Application No. PA201770563, dated Jan. 28, 2020, 3 pages.
Office Action received for Danish Patent Application No. PA201770563, dated Jun. 28, 2019, 5 pages.
Office Action received for Danish Patent Application No. PA201770719, dated Aug. 14, 2018, 6 pages.
Office Action received for Danish Patent Application No. PA201770719, dated Feb. 19, 2019, 4 pages.
Office Action received for Danish Patent Application No. PA201770719, dated Jan. 17, 2020, 4 pages.
Office Action received for Danish Patent Application No. PA201770719, dated Jun. 30, 2021, 3 pages.
Office Action received for Danish Patent Application No. PA201770719, dated Nov. 16, 2020, 5 pages.
Office Action received for Danish Patent Application No. PA201870366, dated Aug. 22, 2019, 3 pages.
Office Action received for Danish Patent Application No. PA201870366, dated Dec. 12, 2018, 3 pages.
Office Action received for Danish Patent Application No. PA201870367, dated Dec. 20, 2018, 5 pages.
Office Action received for Danish Patent Application No. PA201870368, dated Dec. 20, 2018, 5 pages.
Office Action received for Danish Patent Application No. PA201870368, dated Oct. 1, 2019, 6 pages.
Office Action received for Danish Patent Application No. PA201870372, dated Aug. 20, 2019, 2 pages.
Office Action received for Danish Patent Application No. PA201870372, dated Jan. 31, 2019, 4 pages.
Office Action received for Danish Patent Application No. PA201870374, dated Feb. 6, 2019, 5 pages.
Office Action received for Danish Patent Application No. PA201870374, dated Jun. 17, 2019, 5 pages.
Office Action received for Danish Patent Application No. PA201870375, dated Jan. 31, 2019, 4 pages.
Office Action received for Danish Patent Application No. PA201870377, dated Jan. 31, 2019, 4 pages.
Office Action received for Danish Patent Application No. PA201870623, dated Jan. 30, 2020, 2 pages.
Office Action received for Danish Patent Application No. PA201870623, dated Jul. 12, 2019, 4 pages.
Office Action received for Danish Patent Application No. PA201970592, dated Mar. 2, 2020, 5 pages.
Office Action received for Danish Patent Application No. PA201970592, dated Oct. 26, 2020, 5 pages.
Office Action received for Danish Patent Application No. PA201970593, dated Apr. 16, 2020, 2 pages.
Office Action received for Danish Patent Application No. PA201970593, dated Feb. 2, 2021, 2 pages.
Office Action received for Danish Patent Application No. PA201970593, dated Mar. 10, 2020, 4 pages.
Office Action received for Danish Patent Application No. PA201970595, dated Mar. 10, 2020, 4 pages.
Office Action received for Danish Patent Application No. PA201970600, dated Mar. 9, 2020, 5 pages.
Office Action received for Danish Patent Application No. PA201970601, dated Aug. 13, 2020, 3 pages.
Office Action received for Danish Patent Application No. PA201970601, dated Jan. 31, 2020, 3 pages.
Office Action received for Danish Patent Application No. PA201970601, dated Nov. 11, 2019, 8 pages.
Office Action received for Danish Patent Application No. PA201970603, dated Nov. 4, 2020, 3 pages.
Office Action received for Danish Patent Application No. PA201970605, dated Mar. 10, 2020, 5 pages.
Office Action received for Danish Patent Application No. PA202070611, dated Dec. 22, 2020, 7 pages.
Office Action received for Danish Patent Application No. PA202070623, dated Aug. 24, 2021, 3 pages.
Office Action received for Danish Patent Application No. PA202070624, dated Jun. 16, 2021, 5 pages.
Office Action received for Danish Patent Application No. PA202070625, dated Jun. 16, 2021, 3 pages.
Office Action received for European Patent Application 17809168.2, dated Jan. 7, 2020, 5 pages.
Office Action received for European Patent Application 17809168.2, dated Oct. 8, 2020, 4 pages.
Office Action received for European Patent Application No. 17853657.9, dated Apr. 1, 2021, 6 pages.
Office Action received for European Patent Application No. 18176890.4, dated Oct. 16, 2018, 8 pages.
Office Action received for European Patent Application No. 18183054.8, dated Feb. 24, 2020, 6 pages.
Office Action received for European Patent Application No. 18183054.8, dated Nov. 16, 2018, 8 Pages.
Office Action received for European Patent Application No. 18209460.7, dated Apr. 10, 2019, 7 pages.
Office Action received for European Patent Application No. 18209460.7, dated Apr. 21, 2020, 5 pages.
Office Action received for European Patent Application No. 18214698.5, dated Apr. 2, 2019, 8 pages.
Office Action received for European Patent Application No. 18704732.9, dated Sep. 7, 2021, 10 pages.
Office Action received for European Patent Application No. 19172407.9, dated Oct. 18, 2019, 7 pages.

(56) References Cited

OTHER PUBLICATIONS

Office Action received for European Patent Application No. 19204230.7, dated Sep. 28, 2020, 6 pages.
Office Action received for European Patent Application No. 19212057.4, dated Mar. 9, 2021, 6 pages.
Office Action received for European Patent Application No. 19724959.2, dated Apr. 23, 2020, 10 pages.
Office Action received for European Patent Application No. 20168009.7, dated Apr. 20, 2021, 6 pages.
Office Action received for European Patent Application No. 20168009.7, dated Sep. 13, 2021, 8 pages.
Office Action received for European Patent Application No. 20168021.2, dated Jul. 22, 2020, 8 pages.
Office Action received for European Patent Application No. 20206196.6, dated Jan. 13, 2021, 10 pages.
Office Action received for European Patent Application No. 20206197.4, dated Aug. 27, 2021, 6 pages.
Office Action received for European Patent Application No. 20206197.4, dated Jan. 12, 2021, 9 pages.
Office Action received for European Patent Application No. 20210373.5, dated May 10, 2021, 9 pages.
Office Action received for European Patent Application No. 21157252.4, dated Apr. 23, 2021, 8 pages.
Office Action received for European Patent Application No. 21163791.3, dated Jun. 2, 2021, 8 pages.
Office Action received for Indian Patent Application No. 201814036470, dated Feb. 26, 2021, 7 pages.
Office Action received for Indian Patent Application No. 201814036472, dated Jul. 8, 2021, 8 pages.
Office Action received for Indian Patent Application No. 201917053025, dated Mar. 19, 2021, 7 pages.
Office Action received for Indian Patent Application No. 202018006172, dated May 5, 2021, 6 pages.
Office Action received for Japanese Patent Application No. 2018-182607, dated Apr. 6, 2020, 6 pages.
Office Action received for Japanese Patent Application No. 2018-182607, dated Jul. 20, 2020, 5 pages.
Office Action received for Japanese Patent Application No. 2018-182607, dated Sep. 8, 2021, 7 pages.
Office Action received for Japanese Patent Application No. 2018-184254, dated Mar. 2, 2020, 8 pages.
Office Action received for Japanese Patent Application No. 2018-225131, dated Aug. 17, 2020, 21 pages.
Office Action received for Japanese Patent Application No. 2018-225131, dated Mar. 4, 2019, 10 pages.
Office Action received for Japanese Patent Application No. 2018-545502, dated Aug. 17, 2020, 14 pages.
Office Action received for Japanese Patent Application No. 2019-203399, dated Aug. 10, 2021, 4 pages.
Office Action received for Japanese Patent Application No. 2019-215503, dated Feb. 5, 2021, 12 pages.
Office Action received for Japanese Patent Application No. 2019-215503, dated Jul. 3, 2020, 12 pages.
Office Action received for Japanese Patent Application No. 2020-070418, dated Aug. 3, 2020, 22 pages.
Office Action received for Japanese Patent Application No. 2020-120086, dated May 21, 2021, 6 pages.
Office Action received for Japanese Patent Application No. 2020-120086, dated Nov. 20, 2020, 6 pages.
Office Action received for Japanese Patent Application No. 2020-184470, dated May 10, 2021, 3 pages.
Office Action received for Japanese Patent Application No. 2020-184471, dated May 10, 2021, 3 pages.
Office Action received for Japanese Patent Application No. 2020-193703, dated Apr. 19, 2021, 4 pages.
Office Action received for Korean Patent Application No. 10-2018-7026743, dated Jan. 17, 2019, 5 pages.
Office Action received for Korean Patent Application No. 10-2018-7034780, dated Apr. 4, 2019, 11 pages.
Office Action received for Korean Patent Application No. 10-2018-7036893, dated Apr. 9, 2019, 6 pages.
Office Action received for Korean Patent Application No. 10-2019-7005369, dated Mar. 13, 2020, 12 pages.
Office Action received for Korean Patent Application No. 10-2019-7027042, dated May 13, 2020, 6 pages.
Office Action received for Korean Patent Application No. 10-2019-7035478, dated Jan. 17, 2020, 17 pages.
Office Action received for Korean Patent Application No. 10-2020-0052618, dated Aug. 18, 2020, 11 pages.
Office Action received for Korean Patent Application No. 10-2020-7031855, dated Nov. 24, 2020, 6 pages.
Office Action received for Korean Patent Application No. 10-2020-7032147, dated Feb. 16, 2021, 6 pages.
Office Action received for Korean Patent Application No. 10-2021-0022053, dated Mar. 1, 2021, 11 pages.
Office Action received for Korean Patent Application No. 10-2021-7000954, dated Jan. 28, 2021, 5 pages.
Office Action received for Korean Patent Application No. 10-2021-7002582, dated Apr. 16, 2021, 13 pages.
Office Action received for Korean Patent Application No. 10-2021-7020693, dated Jul. 14, 2021, 7 pages.
Office Action received for Taiwanese Patent Application No. 100111887, dated Oct. 7, 2013, 23 pages.
Pre-Appeal Review Report received for Japanese Patent Application No. 2018-182607, mailed on Jan. 21, 2021, 4 pages.
PreAppeal Review Report received for Japanese Patent Application No. 2018-225131, mailed on Jan. 24, 2020, 8 pages.
PreAppeal Review Report received for Japanese Patent Application No. 2018-545502, mailed on Jan. 24, 2020, 8 pages.
Procamera Capture the Moment, Online Available at: http://www.procamera-app.com/procamera_manual/ProCamera_Manual_EN.pdf, Apr. 21, 2016, 63 pages.
Record of Oral Hearing received for U.S. Appl. No. 16/259,771, mailed on Aug. 4, 2021, 15 pages.
Result of Consultation received for European Patent Application No. 19172407.9, dated Nov. 5, 2020, 17 pages.
Result of Consultation received for European Patent Application No. 19204230.7, dated Nov. 16, 2020, 3 pages.
Result of Consultation received for European Patent Application No. 19204230.7, dated Sep. 24, 2020, 5 pages.
Result of Consultation received for European Patent Application No. 19724959.2, dated Sep. 4, 2020, 3 pages.
Result of Consultation received for European Patent Application No. 19181242.9, dated Dec. 1, 2020, 12 pages.
Search Report and Opinion received for Danish Patent Application No. PA201770563, dated Oct. 10, 2017, 9 pages.
Search Report and Opinion received for Danish Patent Application No. PA201870366, dated Aug. 27, 2018, 9 pages.
Search Report and Opinion received for Danish Patent Application No. PA201870367, dated Aug. 27, 2018, 9 pages.
Search Report and Opinion received for Danish Patent Application No. PA201870368, dated Sep. 6, 2018, 7 pages.
Search Report and Opinion received for Danish Patent Application No. PA201870372, dated Sep. 14, 2018, 8 pages.
Search Report and Opinion received for Danish Patent Application No. PA201870372, dated Sep. 17, 2018, 10 pages.
Search Report and Opinion received for Danish Patent Application No. PA201870374, dated Aug. 27, 2018, 9 pages.
Search Report and Opinion received for Danish Patent Application No. PA201870375, dated Aug. 23, 2018, 8 pages.
Search Report and Opinion received for Danish Patent Application No. PA201870377, dated Sep. 4, 2018, 8 pages.
Search Report and Opinion received for Danish Patent Application No. PA201870623, dated Dec. 20, 2018, 8 pages.
Search Report and Opinion received for Danish Patent Application No. PA201970592, dated Nov. 7, 2019, 8 pages.
Search Report and Opinion received for Danish Patent Application No. PA201970593, dated Oct. 29, 2019, 10 pages.
Search Report and Opinion received for Danish Patent Application No. PA201970595, dated Nov. 8, 2019, 16 pages.
Search Report and Opinion received for Danish Patent Application No. PA201970600, dated Nov. 5, 2019, 11 pages.

(56) References Cited

OTHER PUBLICATIONS

Search Report and Opinion received for Danish Patent Application No. PA201970605, dated Nov. 12, 2019, 10 pages.
Search Report and Opinion received for Danish Patent Application No. PA202070623, dated Dec. 21, 2020, 9 pages.
Search Report and Opinion received for Danish Patent Application No. PA202070624, dated Dec. 10, 2020, 10 pages.
Search Report and Opinion received for Danish Patent Application No. PA202070625, dated Dec. 17, 2020, 9 pages.
Search Report received for Danish Patent Application No. PA201770719, dated Oct. 17, 2017, 9 pages.
Summons to Attend Oral Proceedings received for European Patent Application No. 19172407.9, mailed on Jun. 24, 2020, 14 pages.
Summons to Attend Oral Proceedings received for European Patent Application No. 19181242.9, mailed on Jun. 16, 2020, 12 pages.
Summons to Attend Oral Proceedings received for European Patent Application No. 19204230.7, mailed on May 25, 2021, 10 pages.
Summons to Attend Oral Proceedings received for European Patent Application No. 19724959.2, mailed on Feb. 1, 2021, 9 pages.
Summons to Attend Oral Proceedings received for European Patent Application No. 19724959.2, mailed on Mar. 31, 2021, 3 pages.
Supplemental Notice of Allowance received for U.S. Appl. No. 15/713,490, dated May 30, 2019, 2 pages.
Supplemental Notice of Allowance received for U.S. Appl. No. 16/143,201, dated Dec. 13, 2018, 2 pages.
Supplemental Notice of Allowance received for U.S. Appl. No. 16/143,201, dated Dec. 19, 2018, 2 pages.
Supplemental Notice of Allowance received for U.S. Appl. No. 16/143,201, dated Jan. 10, 2019, 2 pages.
Supplemental Notice of Allowance received for U.S. Appl. No. 16/733,718, dated Mar. 9, 2021, 21 pages.
Supplemental Notice of Allowance received for U.S. Appl. No. 16/733,718, dated Mar. 29, 2021, 2 pages.
Supplementary European Search Report received for European Patent Application No. 18176890.4, dated Sep. 20, 2018, 4 pages.
Ali et al. "Facial Expression Recognition Using Human to Animated-Character Expression Translation", Oct. 12, 2019, 8 pages.
Android Police,"Galaxy S9+ In-Depth Camera Review", See Especially 0:43-0:53; 1:13-1:25; 1:25-1:27; 5:11-5:38; 6:12-6:26, Available Online at <https://www.youtube.com/watch?v=GZHYCdMCv-w>, Apr. 19, 2018, 3 pages.
Applivgames,""Super Mario Run" Stickers for iMessage: Free Delivery Started!", Available online at: <https://games.app-liv.jp/archives/178627>, Sep. 13, 2016, 3 pages.
AstroVideo,"AstroVideo enables you to use a low-cost,low-light video camera to capture astronomical images.", Available online at: https://www.coaa.co.uk/astrovideo.htm, Retrieved on: Nov. 18, 2019, 5 pages.
Carretero et al. "Preserving Avatar Genuineness in Different Display Media", Mobile Networks and Applications, Kluwer Academic Publishers, BO, vol. 13, No. 6, Jul. 15, 2008, pp. 627-634.
Channel Highway,"Virtual Makeover in Real-time and in full 3D", Available online at:—https://www.youtube.com/watch?v=NgUbBzb5qZg, Feb. 16, 2016, 1 page.
Clover Juli, "Moment Pro Camera App for iOS Gains Zebra Striping for Displaying Over and Underexposed Areas", Online Available at: https://web.archive.org/web/20190502081353/https://www.macrumors.com/2019/05/01/momentcamera-app-zebra-striping-and-more/, May 1, 2019, 8 pages.
Contents Pocket,"Line Stamp Information", Available online at: <https://web.archive.org/web/20150404080541/http://contents-pocket.net/linestamp.html>, Apr. 2015, 2 pages.
Digital Trends,"ModiFace Partners With Samsung To Bring AR Makeup To The Galaxy S9", Available online at:—https://www.digitaltrends.com/mobile/modiface-samsung-partnership-ar-makeup-galaxy-s9/, 2018, 16 pages.
Enterbrain,"No. 5 Create your own Avatar Mii Studio", vol. 26, No. 11, p. 138, Feb. 24, 2011, 4 pages.
Fedko Daria, "AR Hairstyles", Online Available at <https://www.youtube.com/watch?v=FrS6tHRbFE0>, Jan. 24, 2017, 2 pages.

Feng et al. "3D Direct Human-Computer Interface Paradigm Based on Free Hand Tracking", Chinese Journal of Computers, vol. 37, No. 6, Jun. 30, 2014, 15 pages.
Flatlinevertigo,"Black Desert Online :: Intro to Hair Customization", Online Available at: <https://www.youtube.com/watch?v=9MCbfd_eMEg>, Sep. 9, 2015, 3 pages.
Gadgets Portal,"Galaxy J5 Prime Camera Review! (vs J7 Prime) 4K", Available Online at :—https://www.youtube.com/watch?v=Rf2Gy8QmDqc, Oct. 24, 2016, 3 pages.
Gao et al. "Automatic Unpaired Shape Deformation Transfer", ACM Transactions on Graphics, Online available at: https://doi.org/10.1145/3272127.3275028, 2018, 11 pages.
Gavin's Gadgets,"Honor 10 Camera App Tutorial—How to use All Modes + 90 Photos Camera Showcase", See Especially 2:58-4:32, Available Online at <https://www.youtube.com/watch?v=M5XZwXJcK74>, May 26, 2018, 3 pages.
Gibson Andrews. , "Aspect Ratio: What it is and Why it Matters", Retrieved from <https://web.archive.org/web/20190331225429/https:/digital-photography-school.com/aspect-ratio-what-it-is-and-why-it-matters/>, Paragraphs: "Adjusting aspect ratio in-camera", "Cropping in post-processing", Mar. 31, 2019, 10 pages.
GSM Arena,"Honor 10 Review : Camera", Available Online at <https://web.archive.org/web/20180823142417/https://www.gsmarena.com/honor_10-review-1771p5.php>, Aug. 23, 2018, 11 pages.
Hall Brent, "Samsung Galaxy Phones Pro Mode (S7/S8/S9/Note 8/Note 9): When, why, & How To Use It", See Especially 3:18-5:57, Available Online at <https://www.youtube.com/watch?v=KwPxGUDRkTg>, Jun. 19, 2018, 3 pages.
Helpvideostv,"How to Use Snap Filters on Snapchat", Retrieved from <https://www.youtube.com/watch?v=oR-7cIWPszU&feature=youtu.be>, Mar. 22, 2017, pp. 1-2.
Hernández Carlos, "Lens Blur in the New Google Camera App", Available online at: https://research.googleblog.com/2014/04/lens-blur-in-new-google-camera-app.html, https://ai.googleblog.com/2014/04/1ens-blur-in-new-google-camera-app.html, Apr. 16, 2014, 6 pages.
Huawei Mobile PH,"Huawei P10 Tips & Tricks: Compose Portraits With Wide Aperture (Bokeh)", Available Online at <https://www.youtube.com/watch?v=WM4yo5-hrrE>, Mar. 30, 2017, 2 pages.
Iluvtrading,"Galaxy S10 / S10+: How to Use Bright Night Mode for Photos (Super Night Mode)", Online Available at: https://www.youtube.com/watch?v=SfZ7Us1S1Mk, Mar. 11, 2019, 4 pages.
Iluvtrading,"Super Bright Night Mode: Samsung Galaxy S1O vs Huawei P30 Pro (Review/How to/Explained)", Online Available at: https://www.youtube.com/watch?v=d4r3PWioY4Y, Apr. 26, 2019, 4 pages.
Imagespacetv,"Olympus OM-D E-M1 Mark II—Highlights & Shadows with Gavin Hoey", Online available at: https://www.youtube.com/watch?v=goEhh1n--hQ, Aug. 3, 2018, 3 pages.
KK World,"Redmi Note 7 Pro Night Camera Test I Night Photography with Night Sight & Mode", Online Available at: https://www.youtube.com/watch?v=3EKjGBjX3PY, Mar. 26, 2019, 4 pages.
Koti Kotresh, "Colour with Asian Paints.A Mobail App by Android Application—2018", Available Online at <https://www.youtube.com/watch?v=M6EIO7ErYd0&feature=youtu.be&t=81 >, May 6, 2018, 2 pages.
Kozak Tadeusz, "When You're Video Chatting on Snapchat, How Do You Use Face Filters?", Quora, Online Available at: https://www.quora.com/When-youre-video-chatting-on-Snapchat-how-do-you-use-face-filters, Apr. 29, 2018, 1 page.
Kyoko Makino, "How to Make a Lookalike Face Icon for Your Friend", ASCII, Japan Weekly, ASCII Media Works Inc. vol. 24, pp. 90-93, Jul. 17, 2014, 7 pages.
Lang Brian, "How to Audio & Video Chat with Multiple Users at the Same Time in Groups", Snapchat 101, Online Available at: <https://smartphones.gadgethacks.com/how-to/snapchat-101-audio-video-chat-with-multiple-users-same-time-groups-0184113/>, Apr. 17, 2018, 4 pages.
Mitsuru Takeuchi, "Face Shape Selection for Automatic Avatar Generation", 13th Annual Conference Proceedings of Virtual Reality Society of Japan tournament Papers [DVD-ROM], The Virtual Reality Society of Japan, Sep. 24, 2008, 7 pages.

(56) References Cited

OTHER PUBLICATIONS

Mobiscrub,"Galaxy S4 mini camera review", Available Online at :—https://www.youtube.com/watch?v=KYKOydw8QT8, Aug. 10, 2013, 3 pages.
Mobiscrub,"Samsung Galaxy S5 Camera Review—HD Video", Available Online on:—https://www.youtube.com/watch?v=BFgwDtNKMjg, Mar. 27, 2014, 3 pages.
Modifacechannel,"Sephora 3D Augmented Reality Mirror", Available Online at: https://www.youtube.com/watch?v=wwBO4PU9EXI, May 15, 2014, 1 page.
Neurotechnology,"Sentimask SDK", Available at: https://www.neurotechnology.com/sentimask.html, Apr. 22, 2018, 5 pages.
Noh et al. "Expression Cloning", Proceedings of the 28th annual conference on Computer Graphics and Interactive Techniques, ACM Siggraph, Los Angeles, CA, USA, Aug. 12-17, 2001, 12 pages.
Osxdaily,"How to Zoom the Camera on iPhone", Available Online at: https://osxdaily.com/2012/04/18/zoom-camera-iphone/, Apr. 18, 2012, 6 pages.
Paine Steve, "Samsung Galaxy Camera Detailed Overview—User Interface", Retrieved from: <https://www.youtube.com/watch?v=td8UYSySulo&feature=youtu.be>, Sep. 18, 2012, pp. 1-2.
PC World,"How to make AR Emojis on the Samsung Galaxy S9", You Tube, Available Online: https://www.youtube.com/watch?v=8wQICfulkz0, Feb. 25, 2018, 2 pages.
Phonearena,"Sony Xperia Z5 camera app and UI overview", Retrieved from <https://www.youtube.com/watch?v=UtDzdTsmkfU&feature=youtu.be>, Sep. 8, 2015, pp. 1-3.
Pumarola et al. "GANimation: Anatomically-aware Facial Animation from a Single Image", Proceedings of the European Conference on Computer Vision (ECCV), Jul. 24, 2018, 16 pages.
Pyun et al. "An Example-Based Approach for Facial Expression Cloning", SIGGRAPH Symposium on Computer Animation, The Eurographics Association (2003), 2003, 10 pages.
Rosa et al. "Stripe Generator—a Free Tool for the Web Design Community", Available online at: http://www.stripegenerator.com/, Mar. 28, 2019, 10 pages.
Schiffhauer Alexander, "See the Light with Night Sight", Available online at: https://www.blog.google/products/pixel/see-light-night-sight, Nov. 14, 2018, 6 pages.
Shaw et al. ""Skills for Closeups Photography"", Watson-Guptill Publications, Nov. 1999, 5 pages.
shiftdelete.net,"Oppo Reno 10x Zoom Ön Inceleme—Huawei P30 Pro'ya rakip mi geliyor?", Available online at <https://www.youtube.com/watch?v=ev2wlUztdrg>, See especially 5:34-6:05. Apr. 24, 2019, 2 pages.
Singh Lovepreet, "Samsung Galaxy Watch: How to Change Watch Face—Tips and Tricks", Online available at: <https://www.youtube.com/watch?pp=desktop&v=IN7gPxlZ1qU>, Retrieved on Dec. 10, 2020, Dec. 4, 2018, 1 page.
Slashgear,"Samsung AR Emoji demo on the Galaxy S9", Available Online at <https://www.youtube.com/watch?v=GQwNKzY4C9Y>, Feb. 25, 2018, 3 pages.
Smart Reviews,"Honor10 AI Camera's In Depth Review", See Especially 2:37-2:48; 6:39-6:49, Available Online at <https://www.youtube.com/watch?v=oKFqRvxeDBQ>, May 31, 2018, 2 pages.
Snapchat Lenses,"How To Get All Snapchat Lenses Face Effect Filter on Android", Retrived from: <https://www.youtube.com/watch?v=0PfnF1RIntw&feature=youtu.be>, Sep. 21, 2015, pp. 1-2.
Sony,"User Guide, Xperia XZ3, H8416/H9436/H9493", Sony Mobile Communications Inc. Retrieved from <https://www-support-downloads.sonymobile.com/h8416/userguide_EN_H8416-H9436-H9493_2_Android9.0.pdf>, See pp. 86-102. 2018, 121 pages.
Spellburst,"The Sims 3: Create a Sim With Me | #2—Dark Fairy + Full CC List!", Available online at: <https://www.youtube.com/watch?v=Dy_5g9B-wkA>, Oct. 9, 2017, 2 pages.
Tech With Brett,"How to Create Your AR Emoji on the Galaxy S9 and S9+", Available online at: <https://www.youtube.com/watch?v=HHMdcBpC8MQ>, Mar. 16, 2018, 5 pages.

Techtag,"Samsung J5 Prime Camera Review | True Review", Available online at :—https://www.youtube.com/watch?v=a_p906ai6PQ, Oct. 26, 2016, 3 pages.
Techtag,"Samsung J7 Prime Camera Review (Technical Camera)", Available Online at:—https://www.youtube.com/watch?v=AJPcLP8GpFQ, Oct. 4, 2016, 3 pages.
Telleen et al. "Synthetic Shutter Speed Imaging", University of California, Santa Cruz, vol. 26, No. 3, 2007, 8 pages.
The Nitpicker,"Sony Xperia XZ3 | in-depth Preview", Avalaible online at <https://www.youtube.com/watch?v=TGCKxBuiO5c>, See especially 12:40-17:25, Oct. 7, 2018, 3 pages.
Tico et al. "Robust method of digital image stabilization", Nokia Research Center, ISCCSP, Malta,, Mar. 12-14, 2008, pp. 316-321.
Tsuchihashi et al. "Generation of Caricatures by Automatic Selection of Templates for Shapes and Placement of Facial Parts", Technical Report of the Institute of Image Information and Television Engineers, Japan, The Institute of Image Information and Television Engineers,vol. 33, No. 11, pp. 77-80. Feb. 8, 2009, 7 pages.
Vickgeek,"Canon 80D Live View Tutorial | Enhance your image quality", Available online at:—https://www.youtube.com/watch?v=JGNCiy6Wt9c, Sep. 27, 2016, 3 pages.
Vidstube,"Bitmoji Clockface on Fitbit Versa Sense/Versa 3/Versa 2", Available online at: <https://www.youtube.com/watch?v=4V_xDnSLeHE>, Retrieved on Dec. 3, 2020, Jun. 30, 2019, 1 page.
Vivo India,"Bokeh Mode | Vivo V9", Available Online at <https://www.youtube.com/watch?v=B5AIHhH5Rxs>, Mar. 25, 2018, 3 pages.
Wong Richard, "Huawei Smartphone (P20/P10/P9 ,Mate 10/9) Wide Aperture Mode Demo", Available Online at <https://www.youtube.com/watch?v=eLY3LsZGDPA>, May 7, 2017, 2 pages.
Woolsey Amanda, "How To Customize The Clock on the Apple Watch", Available online at: <https://www.youtube.com/watch?v=t-3Bckdd9B4>, Retrieved on Dec. 11, 2020, Apr. 25, 2015, 1 page.
Xeetechcare,"Samsung Galaxy S10—Super Night Mode & Ultra Fast Charging!", Online Available at: https://www.youtube.com/watch?v=3bguV4FX6aA, Mar. 28, 2019, 4 pages.
X-Tech,"Test Make up via Slick Augmented Reality Mirror Without Putting It on", Available Online at: http://x-tech.am/test-make-up-via-slick-augmented-reality-mirror-without-putting-it-on/, Nov. 29, 2014, 5 pages.
Zhang et al. "Facial Expression Retargeting from Human to Avatar Made Easy", IEEE Transactions On Visualization And Computer Graphics, Aug. 2020, 14 pages.
Zhao et al. "An Event-related Potential Comparison of Facial Expression Processing between Cartoon and Real Faces", Online available at https://www.biorxiv.org/content/10.1101/333898v2, Jun. 18, 2018, 31 pages.
ZY News,"Generate Cartoon Face within Three Seconds, You are the New-generation Expression Emperor", Online available at: <http://inews.ifeng.com/48551936/news.shtml>, Apr. 22, 2016, 3 pages.
Applicant-Initiated Interview Summary received for U.S. Appl. No. 17/093,408, dated Jul. 1, 2022, 3 pages.
Corrected Notice of Allowance received for U.S. Appl. No. 17/373,163, dated Jun. 27, 2022, 5 pages.
Non-Final Office Action received for U.S. Appl. No. 17/370,505, dated Jul. 6, 2022, 14 pages.
Notice of Acceptance received for Australian Patent Application No. 2019338180, dated Jun. 27, 2022, 3 pages.
Office Action received for Australian Patent Application No. 2021202254, dated Jun. 20, 2022, 2 pages.
Office Action received for Indian Patent Application No. 202118028159, dated Jun. 27, 2022, 6 pages.
Office Action received for Korean Patent Application No. 10-2022-7010505, dated Jun. 14, 2022, 5 pages (2 pages of English Translation and 3 pages of Official Copy).
Corrected Notice of Allowance received for U.S. Appl. No. 17/373,163, dated Jul. 15, 2022, 5 pages.
Notice of Acceptance received for Australian Patent Application No. 2021203177, dated Jul. 14, 2022, 3 pages.
Notice of Allowance received for U.S. Appl. No. 16/833,436, dated Jul. 7, 2022, 8 pages.

(56) References Cited

OTHER PUBLICATIONS

Supplemental Notice of Allowance received for U.S. Appl. No. 16/833,436, dated Jul. 14, 2022, 2 pages.
Final Office Action received for U.S. Appl. No. 17/031,765, dated Sep. 12, 2022, 37 pages.
Hourunranta et al., "Video and Audio Editing for Mobile Applications", IEEE International Conference on Multimedia and Expo, ICME 2006, Jul. 9, 2006, pp. 1305-1308.
Hurwitz, Jon, "Interface For Small-Screen Media Playback Control", Online available at: https://www.tdcommons.org/cgi/viewcontent.cgi?article=4231&context=dpubs_series, Technical Disclosure Commons, Apr. 17, 2020, pp. 1-9.
Lein et al., "Patternizer", Available online at: https://patternizer.com/, Apr. 2016, 5 pages.
Non-Final Office Action received for U.S. Appl. No. 17/093,408, dated Sep. 14, 2022, 46 pages.
Notice of Allowance received for Japanese Patent Application No. 2019-215503, dated Aug. 26, 2022, 3 pages (1 page of English Translation and 2 pages of Official Copy).
Notice of Allowance received for U.S. Appl. No. 16/833,436, dated Sep. 8, 2022, 8 pages.
Final Office Action received for U.S. Appl. No. 16/259,771, dated Aug. 12, 2022, 25 pages.
International Search Report and Written Opinion received for PCT Patent Application No. PCT/US2022/024964, dated Aug. 4, 2022, 17 pages.
Non-Final Office Action received for U.S. Appl. No. 17/356,322, dated Aug. 11, 2022, 17 pages.
Notice of Allowance received for U.S. Appl. No. 17/483,684, dated Aug. 16, 2022, 9 pages.
Office Action received for Chinese Patent Application No. 202111323807.5, dated Jul. 15, 2022, 12 pages (6 pages of English Translation and 6 pages of Official Copy).
Office Action received for European Patent Application No. 20206196.6, dated Aug. 10, 2022, 13 pages.
Office Action received for Korean Patent Application No. 10-2022-7023077, dated Jul. 25, 2022, 6 pages (2 pages of English Translation and 4 pages of Official Copy).
Final Office Action received for U.S. Appl. No. 17/093,408, dated May 18, 2022, 41 pages.
Notice of Acceptance received for Australian Patent Application No. 2021201295, dated May 10, 2022, 3 pages.
Notice of Allowance received for Chinese Patent Application No. 202180002106.3, dated May 5, 2022, 6 pages (3 pages of English Translation and 3 pages of Official Copy).
Notice of Allowance received for U.S. Appl. No. 17/373,163, dated May 11, 2022, 8 pages.
Office Action received for Australian Patent Application No. 2021203177, dated May 4, 2022, 7 pages.
Office Action received for Korean Patent Application No. 10-2022-7003364, dated Apr. 22, 2022, 14 pages (6 pages of English Translation and 8 pages of Official Copy).
Applicant-Initiated Interview Summary received for U.S. Appl. No. 16/259,771, dated Apr. 18, 2022, 2 pages.
Applicant-Initiated Interview Summary received for U.S. Appl. No. 16/833,436, dated Jan. 27, 2022, 2 pages.
Applicant-Initiated Interview Summary received for U.S. Appl. No. 17/031,765, dated Dec. 15, 2021, 4 pages.
Applicant-Initiated Interview Summary received for U.S. Appl. No. 17/093,408, dated Mar. 1, 2022, 3 pages.
Applicant-Initiated Interview Summary received for U.S. Appl. No. 17/220,596, dated Aug. 18, 2021, 3 pages.
Applicant-Initiated Interview Summary received for U.S. Appl. No. 17/373,163, dated Apr. 11, 2022, 2 pages.
Corrected Notice of Allowance received for U.S. Appl. No. 16/144,629, dated Apr. 21, 2022, 5 pages.
Corrected Notice of Allowance received for U.S. Appl. No. 16/528,257, dated Feb. 3, 2022, 2 pages.
Corrected Notice of Allowance received for U.S. Appl. No. 17/091,460, dated Feb. 16, 2022, 6 pages.
Corrected Notice of Allowance received for U.S. Appl. No. 17/091,460, dated Feb. 25, 2022, 6 pages.
Corrected Notice of Allowance received for U.S. Appl. No. 17/220,596, dated Nov. 4, 2021, 3 pages.
Corrected Notice of Allowance received for U.S. Appl. No. 17/220,596, dated Nov. 18, 2021, 27 pages.
Corrected Notice of Allowance received for U.S. Appl. No. 17/354,376, dated Apr. 11, 2022, 5 pages.
Corrected Notice of Allowance received for U.S. Appl. No. 17/354,376, dated Feb. 16, 2022, 5 pages.
Corrected Notice of Allowance received for U.S. Appl. No. 17/354,376, dated Mar. 23, 2022, 6 pages.
Decision on Appeal received for U.S. Appl. No. 16/144,629, mailed on Jan. 18, 2022, 8 pages.
Decision to Grant received for Danish Patent Application No. PA201770719, dated Feb. 3, 2022, 2 pages.
Decision to Grant received for European Patent Application No. 20168021.2, dated Feb. 3, 2022, 2 pages.
Decision to Grant received for Japanese Patent Application No. 2018-182607, dated Apr. 13, 2022, 3 pages (1 page of English Translation and 2 pages of Official Copy).
Decision to Grant received for Japanese Patent Application No. 2019-566087, dated Jan. 26, 2022, 2 pages (1 page of English Translation and 1 page of Official Copy).
Decision to Refuse received for European Patent Application No. 19204230.7, dated Feb. 4, 2022, 15 pages.
Examiner-Initiated Interview Summary received for U.S. Appl. No. 17/220,596, dated Oct. 7, 2021, 2 pages.
Extended European Search Report received for European Patent Application No. 22151131.4, dated Mar. 24, 2022, 6 pages.
International Search Report and Written Opinion received for PCT Patent Application No. PCT/US2021/046877, dated Mar. 1, 2022, 17 pages.
Invitation to Pay Additional Fees received for PCT Patent Application No. PCT/US2021/046877, dated Jan. 5, 2022, 10 pages.
Minutes of the Oral Proceedings received for European Patent Application No. 19204230.7, mailed on Feb. 2, 2022, 9 pages.
Non-Final Office Action received for U.S. Appl. No. 16/259,771, dated Jan. 25, 2022, 20 pages.
Non-Final Office Action received for U.S. Appl. No. 17/031,671, dated Apr. 1, 2022, 32 pages.
Non-Final Office Action received for U.S. Appl. No. 17/031,765, dated Mar. 29, 2022, 33 pages.
Non-Final Office Action received for U.S. Appl. No. 17/220,596, dated Jun. 10, 2021, 31 pages.
Non-Final Office Action received for U.S. Appl. No. 17/373,163, dated Jan. 27, 2022, 14 pages.
Notice of Acceptance received for Australian Patent Application No. 2020294208, dated Mar. 2, 2022, 3 pages.
Notice of Acceptance received for Australian Patent Application No. 2022200966, dated Feb. 25, 2022, 3 pages.
Notice of Allowance received for Chinese Patent Application No. 202010287950.2, dated Mar. 22, 2022, 7 pages (03 pages of English Translation and 04 pages of Official Copy).
Notice of Allowance received for Chinese Patent Application No. 202010600197.8, dated Feb. 9, 2022, 5 pages (1 page of English Translation and 4 pages of Official Copy).
Notice of Allowance received for Chinese Patent Application No. 202011480411.7, dated Feb. 18, 2022, 6 pages (3 pages of English Translation and 3 pages of Official Copy).
Notice of Allowance received for Japanese Patent Application No. 2020-159825, dated Mar. 25, 2022, 5 pages (1 page of English Translation and 4 pages of Official Copy).
Notice of Allowance received for Korean Patent Application No. 10-2021-7020693, dated Dec. 27, 2021, 5 pages (1 page of English Translation and 4 pages of Official Copy).
Notice of Allowance received for Korean Patent Application No. 10-2021-7023617, dated Dec. 21, 2021, 6 pages (2 pages of English Translation and 4 pages of Official Copy).
Notice of Allowance received for Korean Patent Application No. 10-2021-7035687, dated Dec. 30, 2021, 5 pages (1 page of English Translation and 4 pages of Official Copy).

(56) References Cited

OTHER PUBLICATIONS

Notice of Allowance received for Korean Patent Application No. 10-2021-7036337, dated Apr. 5, 2022, 4 pages (1 page of English Translation and 3 pages of Official Copy).
Notice of Allowance received for Korean Patent Application No. 10-2022-7002829, dated Feb. 12, 2022, 6 pages (1 page of English Translation and 5 pages of Official Copy).
Notice of Allowance received for U.S. Appl. No. 16/144,629, dated Apr. 7, 2022, 8 pages.
Notice of Allowance received for U.S. Appl. No. 16/528,257, dated Jan. 14, 2022, 10 pages.
Notice of Allowance received for U.S. Appl. No. 17/091,460, dated Apr. 28, 2022, 9 pages.
Notice of Allowance received for U.S. Appl. No. 17/091,460, dated Feb. 4, 2022, 10 pages.
Notice of Allowance received for U.S. Appl. No. 17/220,596, dated Oct. 21, 2021, 43 pages.
Notice of Allowance received for U.S. Appl. No. 17/354,376, dated Jan. 27, 2022, 10 pages.
Notice of Allowance received for U.S. Appl. No. 17/354,376, dated Mar. 4, 2022, 5 pages.
Notice of Allowance received for U.S. Appl. No. 17/354,376, dated Mar. 30, 2022, 5 pages.
Office Action received for Australian Patent Application No. 2019338180, dated Feb. 18, 2022, 3 pages.
Office Action received for Australian Patent Application No. 2020239717, dated Dec. 15, 2021, 6 pages.
Office Action received for Australian Patent Application No. 2020239717, dated Mar. 16, 2022, 4 pages.
Office Action received for Australian Patent Application No. 2020239749, dated Jan. 21, 2022, 4 pages.
Office Action received for Australian Patent Application No. 2020294208, dated Dec. 17, 2021, 2 pages.
Office Action received for Australian Patent Application No. 2021107587, dated Feb. 1, 2022, 6 pages.
Office Action received for Australian Patent Application No. 2021201295, dated Jan. 14, 2022, 3 pages.
Office Action received for Chinese Patent Application No. 201910315328.5, dated Nov. 30, 2021, 21 pages (10 pages of English Translation and 11 pages of Official Copy).
Office Action received for Chinese Patent Application No. 201910691872.X, dated Nov. 10, 2021, 16 pages (9 pages of English Translation and 7 pages of Official Copy).
Office Action received for Chinese Patent Application No. 202010287950.2, dated Nov. 19, 2021, 8 pages (5 pages of English Translation and 3 pages of Official Copy).
Office Action received for Chinese Patent Application No. 202011480411.7, dated Jan. 12, 2022, 7 pages (4 pages of English Translation and 3 pages of Official Copy).
Office Action received for Chinese Patent Application No. 202110766668.7, dated Feb. 16, 2022, 12 pages (6 pages of English Translation and 6 pages of Official Copy).
Office Action received for Chinese Patent Application No. 202110820692.4, dated Mar. 15, 2022, 18 pages (9 pages of English Translation and 9 pages of Official Copy).
Office Action received for Chinese Patent Application No. 202180002106.3, dated Feb. 16, 2022, 12 pages (6 pages of English Translation and 6 pages of Official Copy).
Office Action received for Danish Patent Application No. PA202070624, dated Feb. 4, 2022, 4 pages.
Office Action received for Danish Patent Application No. PA202070625, dated Feb. 8, 2022, 2 pages.
Office Action received for European Patent Application No. 20206197.4, dated Mar. 18, 2022, 7 pages.
Office Action received for Indian Patent Application No. 201818025015, dated Feb. 4, 2022, 7 pages.
Office Action received for Indian Patent Application No. 201818046896, dated Feb. 2, 2022, 7 pages.
Office Action received for Indian Patent Application No. 202014041530, dated Dec. 8, 2021, 7 pages.
Office Action received for Indian Patent Application No. 202118021941, dated Mar. 23, 2022, 5 pages.
Office Action received for Indian Patent Application No. 202118046032, dated Apr. 25, 2022, 6 pages.
Office Action received for Indian Patent Application No. 202118046033, dated Apr. 25, 2022, 7 pages.
Office Action received for Indian Patent Application No. 202118046044, dated Apr. 25, 2022, 6 pages.
Office Action received for Japanese Patent Application No. 2020-159338, dated Dec. 8, 2021, 9 pages (5 pages of English Translation and 4 pages of Official Copy).
Office Action received for Japanese Patent Application No. 2020-159823, dated Dec. 23, 2021, 8 pages (4 pages of English Translation and 4 pages of Official Copy).
Office Action received for Japanese Patent Application No. 2020-159824, dated Dec. 17, 2021, 13 pages (7 pages of English Translation and 6 pages of Official Copy).
Office Action received for Japanese Patent Application No. 2020-159825, dated Dec. 10, 2021, 4 pages (2 pages of English Translation and 2 pages of Official Copy).
Office Action received for Japanese Patent Application No. 2021-092483, dated Apr. 1, 2022, 8 pages (4 pages of English Translation and 4 pages of Official Copy).
Office Action received for Korean Patent Application No. 10-2021-7036337, dated Dec. 8, 2021, 6 pages (2 pages of English Translation and 4 pages of Official Copy).
Office Action received for Korean Patent Application No. 10-2022-7006310, dated Mar. 8, 2022, 6 pages (2 pages of English Translation and 4 pages of Official Copy).
Record of Oral Hearing received for U.S. Appl. No. 16/144,629, mailed on Jan. 28, 2022, 13 pages.
Demetriou Soteris, "Analyzing & Designing the Security of Shared Resources on Smartphone Operating Systems", Dissertation, University of Illinois at Urbana-Champaign Online available at: https://www.ideals.illinois.edu/bitstream/handle/2142/100907/DEMETRIOU-DISSERTATION-2018.pdf?sequence=1&isAllowed=n, 2018, 211 pages.
Dutta Tushars., "Warning! iOS Apps with Camera Access Permission Can Spy on You", Online available at: https://web.archive.org/web/20180219092123/https://techviral.net/ios-apps-camera-can-spy/, Feb. 19, 2018, 3 pages.
Ilovex, "Stripe Generator", a tool that makes it easy to create striped materials, Online available at: https://www.ilovex.co.jp/blog/system/webconsulting/stripe-generator.html, May 2, 2012, 3 pages (Official Copy Only) See Communication Under 37 CFR § 1.98(a) (3).
King Juliea., "How to Check the Exposure Meter on Your Nikon D5500", Online available at: https://www.dummies.com/article/home-auto-hobbies/photography/how-to-check-the-exposuremeter-on-your-nikon-d5500-142677, Mar. 26, 2016, 6 pages.
Messelodi et al., "A Kalman filter based background updating algorithm robust to sharp illumination changes.", International Conference on Image Analysis and Processing. Springer, Berlin, Heidelberg, 2005, pp. 163-170.
Whitacre Michele, "Photography 101 | Exposure Meter", Online available at: https://web.archive.org/web/20160223055834/http://www.michelewhitacrephotographyblog.com, Feb. 23, 2016, 4 pages.
Wu et al., "Security Threats to Mobile Multimedia Applications: Camera-Based Attacks on Mobile Phones", IEEE Communications Magazine, Available online at: http://www.ieeeprojectmadurai.in/BASE/ANDROID/Security%20Threats%20to%20Mobile.pdf, Mar. 2014, pp. 80-87.
Applicant-Initiated Interview Summary received for U.S. Appl. No. 17/031,765, dated May 23, 2022, 5 pages.
Certificate of Examination received for Australian Patent Application No. 2021107587, dated Apr. 29, 2022, 2 pages.
Corrected Notice of Allowance received for U.S. Appl. No. 17/484,279, dated Feb. 15, 2022, 2 pages.
Corrected Notice of Allowance received for U.S. Appl. No. 17/484,279, dated Feb. 28, 2022, 2 pages.
Corrected Notice of Allowance received for U.S. Appl. No. 17/484,307, dated Apr. 20, 2022, 2 pages.
Corrected Notice of Allowance received for U.S. Appl. No. 17/484,307, dated Feb. 10, 2022, 7 pages.

(56) References Cited

OTHER PUBLICATIONS

Corrected Notice of Allowance received for U.S. Appl. No. 17/484,321, dated Mar. 24, 2022, 2 pages.
Extended European Search Report received for European Patent Application No. 22154034.7, dated May 11, 2022, 14 pages.
Intention to Grant received for European Patent Application No. 20168009.7, dated May 17, 2022, 9 pages.
Notice of Acceptance received for Australian Patent Application No. 2020239749, dated May 27, 2022, 3 pages.
Notice of Acceptance received for Australian Patent Application No. 2022202377, dated May 11, 2022, 3 pages.
Notice of Allowance received for Japanese Patent Application No. 2021-510849, dated May 16, 2022, 4 pages (1 page of English Translation and 3 pages of Official Copy).
Notice of Allowance received for U.S. Appl. No. 17/091,460, dated May 23, 2022, 9 pages.
Notice of Allowance received for U.S. Appl. No. 17/483,684, dated Apr. 27, 2022, 10 pages.
Notice of Allowance received for U.S. Appl. No. 17/484,279, dated Jan. 26, 2022, 12 pages.
Notice of Allowance received for U.S. Appl. No. 17/484,279, dated May 13, 2022, 9 pages.
Notice of Allowance received for U.S. Appl. No. 17/484,307, dated Mar. 8, 2022, 11 pages.
Notice of Allowance received for U.S. Appl. No. 17/484,307, dated Nov. 30, 2021, 11 pages.
Notice of Allowance received for U.S. Appl. No. 17/484,321, dated Nov. 30, 2021, 10 pages.
Office Action received for Danish Patent Application No. PA202070623, dated May 23, 2022, 3 pages.
Summons to Attend Oral Proceedings received for European Patent Application No. 19181242.9, mailed on May 19, 2022, 7 pages.
Supplemental Notice of Allowance received for U.S. Appl. No. 17/484,321, dated Mar. 1, 2022, 6 pages.
Applicant Initiated Interview Summary received for U.S. Appl. No. 17/031,671, dated Nov. 8, 2021, 5 pages.
Applicant Initiated Interview Summary received for U.S. Appl. No. 17/190,879, dated Oct. 26, 2021, 3 pages.
Applicant-Initiated Interview Summary received for U.S. Appl. No. 16/528,257, dated Nov. 18, 2021, 2 pages.
Corrected Notice of Allowance received for U.S. Appl. No. 16/733,718, dated Nov. 17, 2021, 2 pages.
Corrected Notice of Allowance received for U.S. Appl. No. 17/190,879, dated Nov. 19, 2021, 2 pages.
Decision to Grant received for European Patent Application No. 17809168.2, dated Oct. 21, 2021, 3 pages.
Decision to Grant received for Japanese Patent Application No. 2019-203399, dated Oct. 20, 2021, 3 pages (1 page of English Translation and 2 pages of Official Copy).
Examiner's Pre-Review Report received for Japanese Patent Application No. 2019-215503, dated Aug. 20, 2021, 15 pages (8 pages of English Translation and 7 pages of Official Copy).
Final Office Action received for U.S. Appl. No. 17/031,765, dated Oct. 29, 2021, 34 pages.
Intention to Grant received for European Patent Application No. 19181242.9, dated Oct. 28, 2021, 16 pages.
International Preliminary Report on Patentability received for PCT Patent Application No. PCT/US2020/031643, dated Nov. 18, 2021, 27 pages.
International Search Report and Written Opinion received for PCT Patent Application No. PCT/US2021/031096, dated Oct. 13, 2021, 16 pages.
International Search Report and Written Opinion received for PCT Patent Application No. PCT/US2021/034304, dated Oct. 11, 2021, 24 pages.
Invitation to Pay Additional Fees received for PCT Patent Application No. PCT/US2021/031096, dated Aug. 19, 2021, 8 pages.
Nikon Digital Camera D7200 User's Manual, Online available at: https://download.nikonimglib.com/archive3/dbHI400jWws903mGr6q98a4k8F90/D7200UM_SG(En)05.pdf, 2005, 416 pages.
Non-Final Office Action received for U.S. Appl. No. 17/093,408, dated Dec. 8, 2021, 37 pages.
Non-Final Office Action received for U.S. Appl. No. 17/190,879, dated Oct. 13, 2021, 10 pages.
Notice of Acceptance received for Australian Patent Application No. 2020260413, dated Oct. 14, 2021, 3 pages.
Notice of Acceptance received for Australian Patent Application No. 2021254567, dated Nov. 17, 2021, 3 pages.
Notice of Allowance received for Chinese Patent Application No. 202010601484.0, dated Nov. 23, 2021, 2 pages (1 page of English Translation and 1 page of Official Copy).
Notice of Allowance received for Japanese Patent Application No. 2020-120086, dated Nov. 15, 2021, 4 pages (1 page of English Translation and 3 pages of Official Copy).
Notice of Allowance received for Korean Patent Application No. 10-2021-0022053, dated Nov. 23, 2021, 5 pages (2 pages of English Translation and 3 pages of Official Copy).
Notice of Allowance received for U.S. Appl. No. 16/733,718, dated Oct. 20, 2021, 24 pages.
Notice of Allowance received for U.S. Appl. No. 16/835,651, dated Nov. 10, 2021, 9 pages.
Notice of Allowance received for U.S. Appl. No. 17/190,879, dated Nov. 10, 2021, 8 pages.
Office Action received for Australian Patent Application No. 2020239717, dated Sep. 28, 2021, 6 pages.
Office Action received for Danish Patent Application No. PA201770719, dated Nov. 16, 2021, 2 pages.
Office Action received for European Patent Application No. 20210373.5, dated Dec. 9, 2021, 7 pages.
Office Action received for Indian Patent Application No. 201817024430, dated Sep. 27, 2021, 8 pages.
Office Action received for Indian Patent Application No. 201818045872, dated Oct. 13, 2021, 7 pages.
Office Action received for Japanese Patent Application No. 2019-566087, dated Oct. 18, 2021, 10 pages (6 pages of English Translation and 4 pages of Official Copy).
Office Action received for Korean Patent Application No. 10-2021-7002582, dated Oct. 29, 2021, 6 pages (3 pages of English Translation and 3 pages of Official Copy).
Theunlockr, "Galaxy Watch Complete Walkthrough: The Best Watch They've Made So Far", Available online at: https://www.youtube.com/watch?v=xiECIfe1SN4, Sep. 11, 2018, 27 pages.
Corrected Notice of Allowance received for U.S. Appl. No. 16/144,629, dated Aug. 24, 2022, 6 pages.
Corrected Notice of Allowance received for U.S. Appl. No. 17/483,684, dated Aug. 24, 2022, 6 pages.
Non-Final Office Action received for U.S. Appl. No. 17/479,897, dated Aug. 30, 2022, 10 pages.
Notice of Allowance received for Chinese Patent Application No. 201910315328.5, dated Aug. 24, 2022, 4 pages (1 page of English Translation and 3 pages of Official Copy).
Office Action received for Japanese Patent Application No. 2020-159823, dated Aug. 15, 2022, 6 pages (3 pages of English Translation and 3 pages of Official Copy).
Notice of Acceptance received for Australian Patent Application No. 2020239717, dated Jun. 1, 2022, 3 pages.
Notice of Allowance received for Korean Patent Application No. 10-2022-7016421, dated May 25, 2022, 6 pages (2 pages of English Translation and 4 pages of Official Copy).
Office Action received for European Patent Application No. 20210373.5, dated May 31, 2022, 5 pages.
Decision to Refuse received for Japanese Patent Application No. 2020-159824, dated Sep. 30, 2022, 6 pages (3 pages of English Translation and 3 pages of Official Copy).
Notice of Acceptance received for Australian Patent Application No. 2022215297, dated Sep. 26, 2022, 3 pages.
Notice of Acceptance received for Australian Patent Application No. 2022220279, dated Sep. 27, 2022, 3 pages.

(56) References Cited

OTHER PUBLICATIONS

Notice of Allowance received for Japanese Patent Application No. 2021-092483, dated Sep. 30, 2022, 4 pages (1 page of English Translation and 3 pages of Official Copy).
Notice of Allowance received for Japanese Patent Application No. 2021-565919, dated Oct. 3, 2022, 3 pages (1 page of English Translation and 2 of pages Official Copy).
Notice of Allowance received for Korean Patent Application No. 10-2022-7006310, dated Sep. 20, 2022, 8 pages (2 pages of English Translation and 6 pages of Official Copy).
Office Action received for Brazilian Patent Application No. BR122018076550-0, dated Sep. 28, 2022, 7 pages (1 page of English Translation and 6 pages of Official Copy).
Office Action received for Japanese Patent Application No. 2021-166686, dated Oct. 3, 2022, 3 pages (2 pages of English Translation and 1 page of Official Copy).
Advisory Action received for U.S. Appl. No. 17/031,765, dated Dec. 12, 2022, 7 pages.
Applicant-Initiated Interview Summary received for U.S. Appl. No. 16/599,433, dated Apr. 20, 2021, 7 pages.
Applicant-Initiated Interview Summary received for U.S. Appl. No. 17/031,671, dated Dec. 9, 2022, 5 pages.
Applicant-Initiated Interview Summary received for U.S. Appl. No. 17/031,765, dated Nov. 16, 2022, 5 pages.
Applicant-Initiated Interview Summary received for U.S. Appl. No. 17/093,408, dated Jan. 5, 2023, 3 pages.
Applicant-Initiated Interview Summary received for U.S. Appl. No. 17/356,322, dated Dec. 27, 2022, 4 pages.
Applicant-Initiated Interview Summary received for U.S. Appl. No. 17/370,505, dated Oct. 17, 2022, 4 pages.
Applicant-Initiated Interview Summary received for U.S. Appl. No. 17/479,897, dated Oct. 31, 2022, 3 pages.
Brief Communication Regarding Oral Proceedings received for European Patent Application No. 19181242.9, dated Oct. 5, 2022, 4 pages.
Certificate of Examination received for Australian Patent Application No. 2020100720, dated Nov. 11, 2020, 2 pages.
Certificate of Examination received for Australian Patent Application No. 2020101043, dated Dec. 22, 2020, 2 pages.
Corrected Notice of Allowance received for U.S. Appl. No. 16/599,433, dated Aug. 13, 2021, 5 pages.
Corrected Notice of Allowance received for U.S. Appl. No. 16/599,433, dated Oct. 14, 2021, 3 pages.
Corrected Notice of Allowance received for U.S. Appl. No. 16/663,062, dated Apr. 14, 2021, 2 pages.
Corrected Notice of Allowance received for U.S. Appl. No. 16/825,879, dated Jul. 23, 2021, 2 pages.
Corrected Notice of Allowance received for U.S. Appl. No. 17/566,094, dated Jan. 5, 2023, 2 pages.
Corrected Notice of Allowance received for U.S. Appl. No. 17/566,094, dated Jan. 23, 2023, 2 pages.
Corrected Notice of Allowance received for U.S. Appl. No. 17/740,032, dated Nov. 3, 2022, 6 pages.
Decision of Refusal received for Japanese Patent Application No. 2018-243463, dated Feb. 25, 2019, 8 pages (5 pages of English Translation and 3 pages of Official Copy).
Decision to Grant received for Danish Patent Application No. PA201970593, dated Sep. 7, 2021, 2 pages.
Drunk Beauty Flower Digital Technology, "iPhone Xs Max Camera Tips, Tricks, Features and Complete Tutorial", Available online at: https://www.ixigua.com/6606874981844386308?wid_try=1, Oct. 2, 2018, 2 pages (Official Copy Only) (See Communication under 37 CFR § 1.98(a) (3)).
European Search Report received for European Patent Application No. 22184844.3, dated Nov. 4, 2022, 4 pages.
European Search Report received for European Patent Application No. 22184853.4, dated Nov. 14, 2022, 5 pages.
Extended Search Report received for European Patent Application 17809168.2, dated Jun. 28, 2018, 9 pages.

Final Office Action received for U.S. Appl. No. 16/144,629, dated Sep. 18, 2019, 22 pages.
Final Office Action received for U.S. Appl. No. 16/259,771, dated Nov. 18, 2019, 13 pages.
Final Office Action received for U.S. Appl. No. 17/031,671, dated Nov. 15, 2022, 27 pages.
Final Office Action received for U.S. Appl. No. 17/356,322, dated Nov. 29, 2022, 19 pages.
Final Office Action received for U.S. Appl. No. 17/479,897, dated Jan. 10, 2023, 15 pages.
Here are Warez Files:Eve Online Character Creator, Online Available at: <http://theherearewarezfiles.blogspot.com/2014/03/eve-online-character-creator-download.html>, Mar. 3, 2014, 7 pages.
Intention to Grant received for Danish Patent Application No. PA201670627, dated Jun. 11, 2018, 2 pages.
Intention to Grant received for European Patent Application No. 18704732.9, dated Dec. 6, 2022, 10 pages.
Intention to Grant received for European Patent Application No. 19181242.9, dated Nov. 17, 2022, 9 pages.
Intention to Grant received for European Patent Application No. 20168009.7, dated Oct. 31, 2022, 9 pages.
Intention to Grant received for European Patent Application No. 20206197.4, dated Dec. 15, 2022, 10 pages.
Intention to Grant received for European Patent Application No. 20210373.5, dated Jan. 10, 2023, 12 pages.
Intention to Grant received for European Patent Application No. 21733324.4, dated Jan. 9, 2023, 9 pages.
International Preliminary Report on Patentability received for PCT Patent Application No. PCT/US2011/031616, dated Oct. 18, 2012, 6 pages.
International Preliminary Report on Patentability received for PCT Patent Application No. PCT/US2017/035321, dated Dec. 27, 2018, 11 Pages.
International Preliminary Report on Patentability received for PCT Patent Application No. PCT/US2021/031096, dated Nov. 24, 2022, 11 pages.
International Preliminary Report on Patentability received for PCT Patent Application No. PCT/US2021/031212, dated Nov. 24, 2022, 16 pages.
International Preliminary Report on Patentability received for PCT Patent Application No. PCT/US2021/034304, dated Dec. 15, 2022, 19 pages.
International Search Report and Written Opinion received for PCT Application No. PCT/US2017/049795, dated Dec. 27, 2017., 26 pages.
International Search Report and Written Opinion received for PCT Patent Application No. PCT/US2011/031616, dated Aug. 30, 2011, 8 pages.
International Search Report and Written Opinion received for PCT Patent Application No. PCT/US2017/035321, dated Oct. 6, 2017., 15 pages.
International Search Report and Written Opinion received for PCT Patent Application No. PCT/US2018/015591, dated Jun. 14, 2018, 14 pages.
International Search Report and Written Opinion received for PCT Patent Application No. PCT/US2022/030589, dated Sep. 5, 2022, 26 pages.
International Search Report and Written Opinion received for PCT Patent Application No. PCT/US2022/030704, dated Nov. 9, 2022, 19 pages.
Invitation to Pay Additional Fees and Partial International Search Report received for PCT Patent Application No. PCT/US2022/030704, dated Sep. 15, 2022, 12 pages.
Non-Final Office Action received for U.S. Appl. No. 16/528,941, dated Jan. 30, 2020, 14 pages.
Non-Final Office Action received for U.S. Appl. No. 16/599,433, dated Jan. 28, 2021, 16 pages.
Non-Final Office Action received for U.S. Appl. No. 16/663,062, dated Oct. 28, 2020, 14 pages.
Non-Final Office Action received for U.S. Appl. No. 17/041,412, dated Dec. 5, 2022, 13 pages.
Non-Final Office Action received for U.S. Appl. No. 17/461,014, dated Dec. 7, 2022, 22 pages.

(56) References Cited

OTHER PUBLICATIONS

Non-Final Office Action received for U.S. Appl. No. 17/510,168, dated Dec. 6, 2022, 11 pages.
Non-Final Office Action received for U.S. Appl. No. 17/944,765, dated Jan. 18, 2023, 9 pages.
Notice of Acceptance received for Australian Patent Application No. 2020201969, dated Mar. 26, 2021, 3 pages.
Notice of Acceptance received for Australian Patent Application No. 2021202254, dated Nov. 16, 2022, 3 pages.
Notice of Allowance received for Brazilian Patent Application No. BR122018076550-0, dated Jan. 3, 2022, 3 pages (1 page of English Translation and 2 pages of Official Copy).
Notice of Allowance received for Chinese Patent Application No. 201910692978.1, dated Feb. 4, 2021, 6 pages (3 pages of English Translation and 3 pages of Official Copy).
Notice of Allowance received for Chinese Patent Application No. 202110820692.4, dated Nov. 16, 2022, 2 pages (1 page of English Translation and 1 page of Official Copy).
Notice of Allowance received for Chinese Patent Application No. 202111323807.5, dated Jan. 10, 2023, 4 pages (1 page of English Translation and 3 pages of Official Copy).
Notice of Allowance received for Korean Patent Application No. 10-2020-0123852, dated Nov. 28, 2022, 7 pages (2 pages of English Translation and 5 pages of Official Copy).
Notice of Allowance received for Korean Patent Application No. 10-2020-0123887, dated Nov. 28, 2022, 7 pages (2 pages of English Translation and 5 pages of Official Copy).
Notice of Allowance received for Korean Patent Application No. 10-2022-7010505, dated Dec. 26, 2022, 7 pages (2 pages of English Translation and 5 pages of Official Copy).
Notice of Allowance received for Korean Patent Application No. 10-2022-7023077, dated Nov. 1, 2022, 8 pages (2 pages of English Translation and 6 pages of Official Copy).
Notice of Allowance received for U.S. Appl. No. 16/599,433, dated May 14, 2021, 11 pages.
Notice of Allowance received for U.S. Appl. No. 16/599,433, dated Oct. 4, 2021, 13 pages.
Notice of Allowance received for U.S. Appl. No. 16/663,062, dated Jul. 13, 2021, 7 pages.
Notice of Allowance received for U.S. Appl. No. 17/483,684, dated Oct. 24, 2022, 9 pages.
Notice of Allowance received for U.S. Appl. No. 17/566,094, dated Nov. 22, 2022, 10 pages.
Notice of Allowance received for U.S. Appl. No. 17/732,191, dated Nov. 9, 2022, 12 pages.
Notice of Allowance received for U.S. Appl. No. 17/740,032, dated Oct. 13, 2022, 11 pages.
Office Action received for Australian Patent Application No. 2021290292, dated Nov. 24, 2022, 2 pages.
Office Action received for Chinese Patent Application No. 201780058426.4, dated Dec. 2, 2022, 11 pages (5 pages of English Translation and 6 pages of Official Copy).
Office Action received for Chinese Patent Application No. 201811446867.4, dated May 6, 2020, 10 pages (5 pages of English Translation and 5 pages of Official Copy).
Office Action received for Chinese Patent Application No. 201910691872.X, dated Jun. 23, 2021, 10 pages (5 pages of English Translation and 5 pages of Official Copy).
Office Action received for Chinese Patent Application No. 201910691872.X, dated Mar. 24, 2021, 19 pages (9 pages of English Translation and 10 pages of Official Copy).
Office Action received for Chinese Patent Application No. 201910692978.1, dated Apr. 3, 2020, 19 pages (8 pages of English Translation and 11 pages of Official Copy).
Office Action received for Chinese Patent Application No. 201911199054.4, dated Jul. 3, 2020, 15 pages (9 pages of English Translation and 6 pages of Official Copy).
Office Action received for Chinese Patent Application No. 202110766668.7, dated Sep. 15, 2022, 18 pages (9 pages of English Translation and 9 pages of Official Copy).
Office Action received for Danish Patent Application No. PA201670755, dated Oct. 20, 2017., 4 pages.
Office Action received for European Patent Application No. 19181242.9, dated Dec. 6, 2019, 9 pages.
Office Action received for European Patent Application No. 19769316.1, dated Jan. 12, 2023, 10 pages.
Office Action received for European Patent Application No. 22184844.3, dated Nov. 16, 2022, 7 pages.
Office Action received for European Patent Application No. 22184853.4, dated Nov. 25, 2022, 7 pages.
Office Action received for Indian Patent Application No. 202215010325, dated Oct. 10, 2022, 7 pages.
Office Action received for Japanese Patent Application No. 2021-153573, dated Oct. 17, 2022, 4 pages (2 pages of English Translation and 2 pages of Official Copy).
Office Action received for Japanese Patent Application No. 2022-027861, dated Nov. 21, 2022, 4 pages (2 pages of English Translation and 2 pages of Official Copy).
Office Action received for Korean Patent Application No. 10-2020-0123857, dated Dec. 16, 2022, 8 pages (4 pages of English Translation and 4 pages of Official Copy).
Office Action received for Korean Patent Application No. 10-2020-7021870, dated Nov. 11, 2020, 11 pages (5 pages of English Translation and 6 pages of Official Copy).
Office Action received for Korean Patent Application No. 10-2021-7006145, dated Oct. 12, 2022, 14 pages (6 pages of English Translation and 8 pages of Official Copy).
Office Action received for Korean Patent Application No. 10-2022-7003364, dated Dec. 26, 2022, 8 pages (3 pages of English Translation and 5 pages of Official Copy).
Office Action received for Korean Patent Application No. 10-2022-7009437, dated Nov. 30, 2022, 6 pages (2 pages of English Translation and 4 pages of Official Copy).
Office Action received for Korean Patent Application No. 10-2022-7043663, dated Jan. 6, 2023, 12 pages (5 pages of English Translation and 7 pages of Official Copy).
Pavlakos et al., "Expressive Body Capture: 3D Hands, Face, and Body from a Single Image", In Proceedings of the IEEE/CVF conference on computer vision and pattern recognition 2019, online available at https://arxiv.org/abs/1904.05866, 2019, pp. 10975-10985.
Search Report and Opinion received for Danish Patent Application No. PA201970603, dated Nov. 15, 2019, 9 pages.
Sony Xperia XZ3 Camera Review—The Colors, Duke, The Colors!, Android Headlines—Android News & Tech News, Available online at <https://www.youtube.com/watch?v=mwpYXzWVOgw>, See especially 1:02-1:27, 2:28-2:30, Nov. 3, 2018, 3 pages.
Supplementary European Search Report received for European Patent Application No. 18183054.8, dated Oct. 11, 2018, 4 pages.
Zollhöfer et al., "State of the Art on Monocular 3D Face Reconstruction, Tracking, and Applications", In Computer graphics forum May 2018 (vol. 37, No. 2), online available at https://studios.disneyresearch.com/wp-content/uploads/2019/03/State-of-the-Art-on-Monocular-3D-Face-Reconstruction-Tracking-and-Applications-1.pdf., 2018, 28 pages.
Applicant-Initiated Interview Summary received for U.S. Appl. No. 17/041,412, dated Jan. 31, 2023, 7 pages.
Corrected Notice of Allowance received for U.S. Patent Application No. 17/566,094, dated Feb. 8, 2023, 2 pages.
Non-Final Office Action received for U.S. Patent Application No. 17/721,039, dated Feb. 2, 2023, 65 pages.
Notice of Acceptance received for Australian Patent Application No. 2021290292, dated Jan. 23, 2023, 3 pages.
Notice of Allowance received for U.S. Patent Application No. 17/356,322, dated Feb. 2, 2023, 11 pages.
Notice of Allowance received for U.S. Appl. No. 17/370,505, dated Feb. 2, 2023, 8 pages.
Notice of Allowance received for U.S. Appl. No. 17/740,032, dated Feb. 1, 2023, 9 pages.
Office Action received for Chinese Patent Application No. 2022100630/0.6, dated Jan. 5, 2023, 12 pages (6 pages of English Translation and 6 pages of Official Copy).

(56) References Cited

OTHER PUBLICATIONS

Office Action received for Korean Patent Application No. 10-2020-0124139, dated Jan. 17, 2023, 10 pages (5 pages of English Translation and 5 pages of Official Copy).
Result of Consultation received for European Patent Application No. 22184844.3, dated Feb. 1, 2023, 3 pages.
Office Action received for Indian Patent Application No. 202015008746, dated Mar. 6, 2023, 7 pages.
Applicant Initiated Interview Summary received for U.S. Appl. No. 17/721,039, dated Mar. 10, 2023, 3 pages.
Applicant-Initiated Interview Summary received for U.S. Appl. No. 17/461,014, dated Feb. 21, 2023, 3 pages.
Board Opinion received for Chinese Patent Application No. 201811446867.4, dated Feb. 14, 2023, 11 pages (4 pages of English Translation and 7 pages of Official Copy).
Corrected Notice of Allowance received for U.S. Appl. No. 17/041,412, dated Mar. 23, 2023, 7 pages.
Corrected Notice of Allowance received for U.S. Appl. No. 17/041,412, dated Mar. 31, 2023, 6 pages.
Corrected Notice of Allowance received for U.S. Appl. No. 17/356,322, dated Feb. 15, 2023, 2 pages.
Corrected Notice of Allowance received for U.S. Appl. No. 17/356,322, dated Mar. 8, 2023, 2 pages.
Corrected Notice of Allowance received for U.S. Appl. No. 17/370,505, dated Apr. 4, 2023, 5 pages.
Corrected Notice of Allowance received for U.S. Appl. No. 17/370,505, dated Mar. 8, 2023, 5 pages.
Corrected Notice of Allowance received for U.S. Appl. No. 17/510,168, dated Mar. 16, 2023, 2 pages.
Corrected Notice of Allowance received for U.S. Appl. No. 17/510,168, dated Mar. 29, 2023, 2 pages.
Corrected Notice of Allowance received for U.S. Appl. No. 17/566,094, dated Mar. 7, 2023, 2 pages.
Corrected Notice of Allowance received for U.S. Appl. No. 17/740,032, dated Feb. 15, 2023, 6 pages.
Decision to Grant received for European Patent Application No. 19181242.9, dated Mar. 23, 2023, 3 pages.
Final Office Action received for U.S. Appl. No. 17/093,408, dated Mar. 2, 2023, 51 pages.
Final Office Action received for U.S. Appl. No. 17/461,014, dated Apr. 6, 2023, 24 pages.
Intention to Grant received for European Patent Application No. 20168009.7, dated Feb. 28, 2023, 10 pages.
International Preliminary Report on Patentability received for PCT Patent Application No. PCT/US2021/046877, dated Apr. 6, 2023, 12 pages.
Non-Final Office Action received for U.S. Appl. No. 17/031,671, dated Mar. 17, 2023, 34 pages.
Non-Final Office Action received for U.S. Appl. No. 17/031,765, dated Mar. 28, 2023, 31 pages.
Non-Final Office Action received for U.S. Appl. No. 17/542,947, dated Mar. 2, 2023, 59 pages.
Notice of Allowance received for Japanese Patent Application No. 2021-153573, dated Feb. 17, 2023, 4 pages (1 page of English Translation and 3 pages of Official Copy).
Notice of Allowance received for Japanese Patent Application No. 2022-027861, dated Feb. 13, 2023, 3 pages (1 page of English Translation and 2 pages of Official Copy).
Notice of Allowance received for Korean Patent Application No. 10-2020-0123852, dated Mar. 9, 2023, 7 pages (2 pages of English Translation and 5 pages of Official Copy).
Notice of Allowance received for Korean Patent Application No. 10-2020-0123857, dated Feb. 21, 2023, 6 pages (1 page of English Translation and 5 pages of Official Copy).
Notice of Allowance received for Korean Patent Application No. 10-2021-7006145, dated Mar. 6, 2023, 5 pages (2 pages of English Translation and 3 pages of Official Copy).
Notice of Allowance received for U.S. Appl. No. 17/041,412, dated Mar. 15, 2023, 13 pages.
Notice of Allowance received for U.S. Appl. No. 17/510,168, dated Feb. 13, 2023, 10 pages.
Notice of Allowance received for U.S. Appl. No. 17/566,094, dated Feb. 23, 2023, 8 pages.
Notice of Allowance received for U.S. Appl. No. 17/732,191, dated Feb. 27, 2023, 12 pages.
Notice of Allowance received for U.S. Appl. No. 17/941,962, dated Mar. 10, 2023, 11 pages.
Notice of Allowance received for U.S. Appl. No. 17/944,765, dated Apr. 5, 2023, 9 pages.
Office Action received for Australian Patent Application No. 2022200965, dated Feb. 14, 2023, 4 pages.
Office Action received for Australian Patent Application No. 2022218463, dated Mar. 17, 2023, 2 pages.
Office Action received for Chinese Patent Application No. 202110766668.7, dated Jan. 20, 2023, 11 pages (6 pages of English Translation and 5 pages of Official Copy).
Office Action received for Chinese Patent Application No. 202210849242.2, dated Jan. 20, 2023, 12 pages (6 pages of English Translation and 6 pages of Official Copy).
Office Action received for European Patent Application No. 20704768.9, dated Mar. 24, 2023, 8 pages.
Office Action received for Indian Patent Application No. 202015008747, dated Mar. 15, 2023, 10 pages.
Office Action received for Indian Patent Application No. 202117009020, dated Feb. 6, 2023, 7 pages.
Office Action received for Indian Patent Application No. 202215026505, dated Feb. 8, 2023, 9 pages.
Office Action received for Japanese Patent Application No. 2021-187533, dated Feb. 6, 2023, 7 pages (4 pages of English Translation and 3 pages of Official Copy).
Pre-Appeal Review Report received for Japanese Patent Application No. 2020-159823, dated Jan. 12, 2023, 4 pages (2 pages of English Translation and 2 pages of Official Copy).
Droid Life, "20+ Galaxy S9, S9+ Tips and Tricks", Available Online at: https://www.youtube.com/watch?v=sso0mYTfV6w, Mar. 22, 2018, pp. 1-33.
Gauging Gadgets, "How to Customize Watch Faces—Garmin Venu Tutorial", Online Available at: https://www.youtube.com/watch?v=dxajKKulaP0, Jan. 7, 2020, 14 pages.
Takahashi et al., "Neural network modeling of altered facial expression recognition in autism spectrum disorders based on predictive processing framework", Scientific reports, online available at:—https://www.nature.com/articles/s41598-021-94067-x, Jul. 26, 2021, 14 pages.
Applicant-Initiated Interview Summary received for U.S. Appl. No. 17/031,765, dated Apr. 17, 2023, 4 pages.
Corrected Notice of Allowance received for U.S. Appl. No. 17/041,412, dated Apr. 12, 2023, 2 pages.
Corrected Notice of Allowance received for U.S. Appl. No. 17/941,962, dated Apr. 14, 2023, 6 pages.
Hearing Notice received for Indian Patent Application No. 201817024430, mailed on Apr. 6, 2023, 2 pages.
Office Action received for Chinese Patent Application No. 202211072958.2, dated Apr. 5, 2023, 11 pages (6 pages of English Translation and 5 pages of Official Copy).
Office Action received for Indian Patent Application No. 202215026045, dated Mar. 31, 2023, 8 pages.
Decision to Grant received for Japanese Patent Application No. 2021-166686, dated Apr. 20, 2023, 2 pages (1 page of English Translation and 1 page of Official Copy).

* cited by examiner

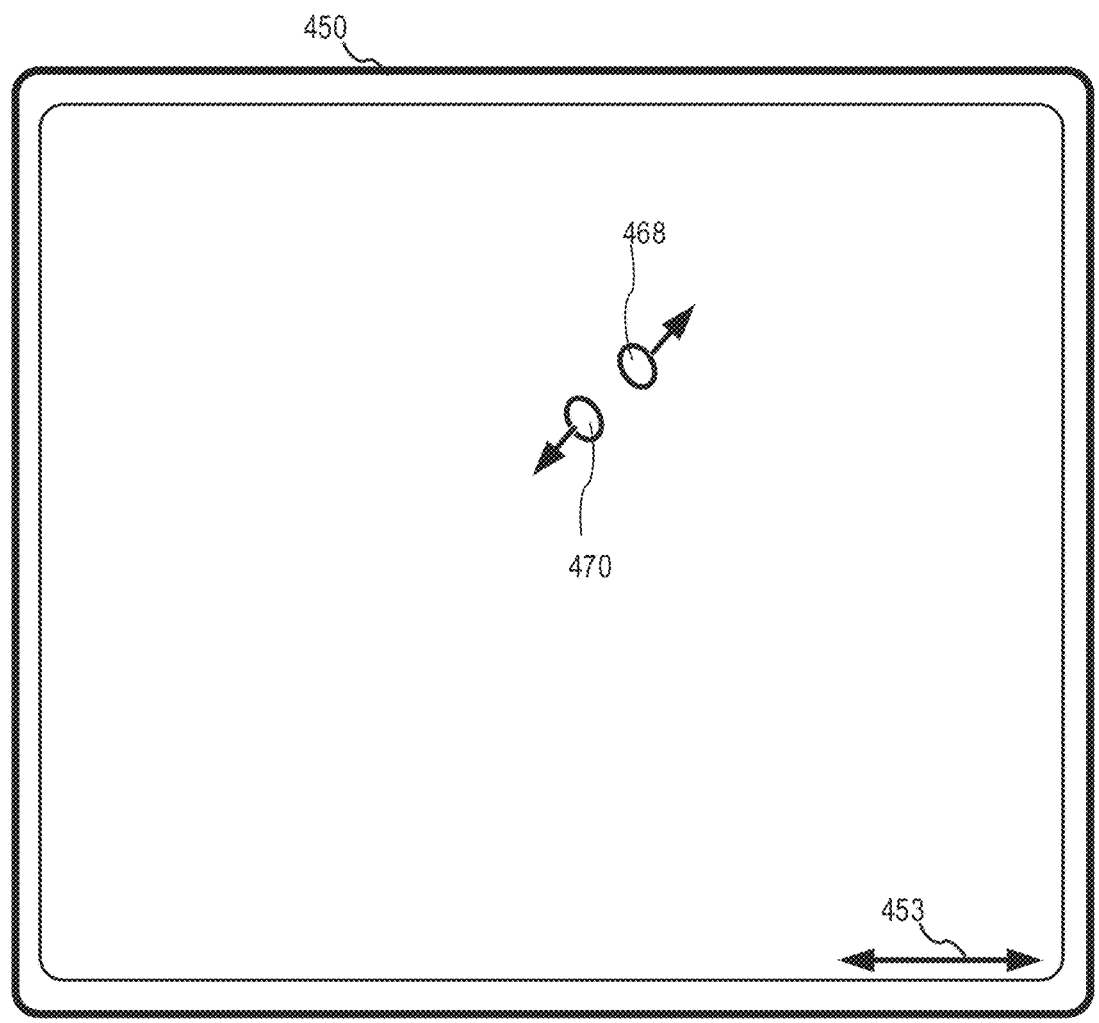
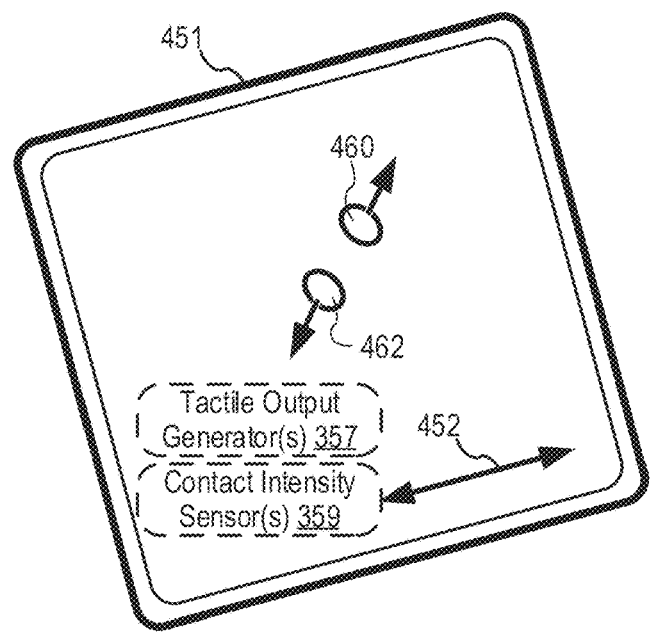
FIG. 4B

700

702
Display, via a display apparatus, a messaging user interface of a message conversation including at least a first participant, the messaging user interface including a camera affordance.

704
Detect, via one or more input devices, a first input directed to the camera affordance.

706
In response to detecting the first input, display a camera user interface, the camera user interface including:

708
A capture affordance.

710
An effects mode affordance associated with a mode in which visual effects are enabled for display in the captured image data.

712
Detect, via the one or more input devices, a second input directed to the capture affordance.

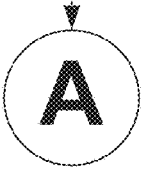

902
Display, via a display apparatus, a camera user interface, the camera user interface including:

904
A camera display region including a representation of image data captured via the camera.

906
The image data includes depth data.

908
A first affordance associated with a first camera display mode.

910
While a subject is positioned within a field of view of the camera and a representation of the subject and a background are displayed in the camera display region, detect a gesture directed to the first affordance.

```
┌─────────────────────────────────────────────────────────────────────┐
│                            1102                                     │
│  Display, via a display apparatus, a media user interface, the      │
│                  media user interface including:                    │
│  ┌───────────────────────────────────────────────────────────────┐  │
│  │                          1104                                 │  │
│  │  A media display region including a representation of a       │  │
│  │                       media item.                             │  │
│  └───────────────────────────────────────────────────────────────┘  │
│  ┌───────────────────────────────────────────────────────────────┐  │
│  │                          1106                                 │  │
│  │                    An effects affordance.                     │  │
│  └───────────────────────────────────────────────────────────────┘  │
└─────────────────────────────────────────────────────────────────────┘
                                   │
                                   ▼
┌─────────────────────────────────────────────────────────────────────┐
│                              1108                                   │
│           Detect a gesture directed to the effects affordance.      │
│  ┌ ─ ─ ─ ─ ─ ─ ─ ─ ─ ─ ─ ─ ─ ─ 1110 ─ ─ ─ ─ ─ ─ ─ ─ ─ ─ ─ ─ ─ ─ ┐  │
│    The respective effects option corresponds to an effect for       │
│  │            displaying an avatar in the media item.            │  │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘  │
│  ┌ ─ ─ ─ ─ ─ ─ ─ ─ ─ ─ ─ ─ ─ ─ 1112 ─ ─ ─ ─ ─ ─ ─ ─ ─ ─ ─ ─ ─ ─ ┐  │
│    The respective effects option corresponds to an effect for       │
│  │   displaying a plurality of virtual objects moving in the     │  │
│                            media item.                              │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘  │
│  ┌ ─ ─ ─ ─ ─ ─ ─ ─ ─ ─ ─ ─ ─ ─ 1114 ─ ─ ─ ─ ─ ─ ─ ─ ─ ─ ─ ─ ─ ─ ┐  │
│    The respective effects option corresponds to an effect for       │
│  │  displaying one or more selectable graphical icons in the     │  │
│                            media item.                              │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘  │
└─────────────────────────────────────────────────────────────────────┘
```

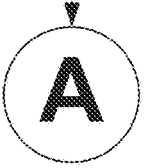

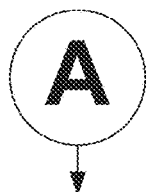

1116
In response to detecting the gesture directed to the effects affordance, display a plurality of effects options for applying effects to the media item concurrently with a representation of the media item, including:

1118
In accordance with a determination that the media item is associated with corresponding depth data, the plurality of effects options include a respective effects option for applying effects based on the depth data.

1120
In accordance with a determination that the image data does not include the depth data, the respective effects option is not available for activation in the plurality of effects options.

*FIG. 11B*

```
                              1300 ─╮
┌─────────────────────────────────────────────────────────────────┐
│                              1302                               │
│ Display, via a display apparatus, a live video communication    │
│ user interface of a live video communication application, the   │
│ live video communication user interface including:              │
│                                                                 │
│   ┌─────────────────────────────────────────────────────────┐   │
│   │                        1304                             │   │
│   │ A representation of a subject participating in a live   │   │
│   │ video communication session.                            │   │
│   │   ┌ ─ ─ ─ ─ ─ ─ ─ ─ ─ ─ ─1306─ ─ ─ ─ ─ ─ ─ ─ ─ ─ ─ ┐    │   │
│   │     The representation of the subject participating       │   │
│   │   │ in the live video communication session includes │    │   │
│   │     image data captured by a camera associated with       │   │
│   │   │ the electronic device.                           │    │   │
│   │   └ ─ ─ ─ ─ ─ ─ ─ ─ ─ ─ ─ ─ ─ ─ ─ ─ ─ ─ ─ ─ ─ ─ ─ ┘    │   │
│   └─────────────────────────────────────────────────────────┘   │
│                                                                 │
│   ┌─────────────────────────────────────────────────────────┐   │
│   │                        1308                             │   │
│   │                   A first affordance.                   │   │
│   └─────────────────────────────────────────────────────────┘   │
└─────────────────────────────────────────────────────────────────┘
                                  │
                                  ▼
┌─────────────────────────────────────────────────────────────────┐
│                              1310                               │
│           Detect a gesture directed to the first affordance.    │
└─────────────────────────────────────────────────────────────────┘
                                  │
                                  ▼
┌─────────────────────────────────────────────────────────────────┐
│                              1312                               │
│   In response to detecting the gesture directed to the first    │
│                           affordance:                           │
│                                                                 │
│   ┌─────────────────────────────────────────────────────────┐   │
│   │                        1314                             │   │
│   │                Activate a camera effects mode.          │   │
│   └─────────────────────────────────────────────────────────┘   │
│                                                                 │
│   ┌─────────────────────────────────────────────────────────┐   │
│   │                        1316                             │   │
│   │ Increase a size of the representation of the subject    │   │
│   │ participating in the live video communication session.  │   │
│   └─────────────────────────────────────────────────────────┘   │
└─────────────────────────────────────────────────────────────────┘
```

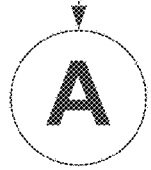

1502
Display, via a display apparatus, a representation of image data captured via the one or more cameras, wherein the representation includes a representation of a subject and the image data corresponds to depth data that includes depth data for the subject.

1504
Display, via the display apparatus, a representation of a virtual avatar that is displayed in place of at least a portion of the representation of the subject, wherein the virtual avatar is placed at simulated depth relative to the representation of the subject as determined based on the depth data for the subject.

1506
In accordance with a determination, based on the depth data, that a first portion of the virtual avatar satisfies a set of depth-based display criteria, include as part of the representation of the virtual avatar, a representation of the first portion of the virtual avatar that is displayed in place of the first portion of the subject.

1508
In accordance with a determination, based on the depth data, that the first portion of the virtual avatar does not satisfy the set of depth-based display criteria, exclude from the representation of the virtual avatar, the representation of the first portion of the virtual avatar and display the first portion of the subject in the region that would have been occupied by the first portion of the virtual avatar.

1504
Display, via a display apparatus, a representation of a virtual avatar that is displayed in place of at least a portion of the representation of the subject, wherein the virtual avatar is placed at simulated depth relative to the representation of the subject as determined based on the depth data for the subject

1510
Detect a change in pose of the subject.

1512
In response to detecting the change in pose of the subject, modify the displayed representation of the virtual avatar based on the change in pose, including:

1514
In accordance with a determination, based on the depth data that takes into account the change in pose of the subject, that the first portion of the virtual avatar satisfies the set of depth-based display criteria, update an appearance of the representation of the virtual avatar from a first appearance that excludes the first portion of the virtual avatar to a second appearance that includes the first portion of the virtual avatar.

1516
In accordance with a determination, based on the depth data that takes into account the change in pose of the subject, that the first portion of the virtual avatar does not satisfy the set of depth-based display criteria, update the appearance of the representation of the virtual avatar from a third appearance that includes the first portion of the virtual avatar to a fourth appearance that excludes the first portion of the virtual avatar.

*FIG. 15B*

CREATIVE CAMERA

CROSS-REFERENCE TO RELATED APPLICATIONS

This application is a continuation of U.S. application Ser. No. 16/599,433, entitled "Creative Camera," filed Oct. 11, 2019, which is a continuation of U.S. application Ser. No. 16/143,097, now U.S. Pat. No. 10,523,879, entitled "Creative Camera," filed Sep. 26, 2018, which claims the benefit of: U.S. Provisional Application No. 62/668,227, entitled "Creative Camera," filed May 7, 2018; and U.S. Provisional Application No. 62/679,934, entitled "Creative Camera," filed Jun. 3, 2018, the contents of which are hereby incorporated by reference in their entireties.

FIELD

The present disclosure relates generally to computer user interfaces, and more specifically to techniques for displaying visual effects.

BACKGROUND

Visual effects are used to enhance a user's experience when capturing and viewing media using electronic devices. Visual effects can alter the appearance of image data or can represent an idealized or completely fictional representation of an environment captured in an image.

BRIEF SUMMARY

Some techniques for displaying visual effects using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for displaying visual effects. Such methods and interfaces optionally complement or replace other methods for displaying visual effects. Such methods and interfaces reduce the cognitive burden on a user and produce a more efficient human-machine interface. For battery-operated computing devices, such methods and interfaces conserve power and increase the time between battery charges.

A method is described. The method is performed at an electronic device having a camera, a display apparatus, and one or more input devices. The method comprises: displaying, via the display apparatus, a messaging user interface of a message conversation including at least a first participant, the messaging user interface including a camera affordance; detecting, via the one or more input devices, a first input directed to the camera affordance; in response to detecting the first input, displaying a camera user interface, the camera user interface including a capture affordance; detecting, via the one or more input devices, a second input directed to the capture affordance; in response to detecting the second input: capturing image data using the camera; ceasing to display the capture affordance; and displaying a send affordance at a location in the camera user interface that was previously occupied by the capture affordance; detecting, via the one or more input devices, a third input directed to the send affordance; and in response to detecting the third input, initiating a process to send the captured image data to the first participant.

A non-transitory computer-readable storage medium is described. The non-transitory computer-readable storage medium stores one or more programs configured to be executed by one or more processors of an electronic device with a camera, a display apparatus, and one or more input devices, the one or more programs including instructions for: displaying, via the display apparatus, a messaging user interface of a message conversation including at least a first participant, the messaging user interface including a camera affordance; detecting, via the one or more input devices, a first input directed to the camera affordance; in response to detecting the first input, displaying a camera user interface, the camera user interface including a capture affordance; detecting, via the one or more input devices, a second input directed to the capture affordance; in response to detecting the second input: capturing image data using the camera; ceasing to display the capture affordance; and displaying a send affordance at a location in the camera user interface that was previously occupied by the capture affordance; detecting, via the one or more input devices, a third input directed to the send affordance; and in response to detecting the third input, initiating a process to send the captured image data to the first participant.

A transitory computer-readable storage medium is described. The transitory computer-readable storage medium stores one or more programs configured to be executed by one or more processors of an electronic device with a camera, a display apparatus, and one or more input devices, the one or more programs including instructions for: displaying, via the display apparatus, a messaging user interface of a message conversation including at least a first participant, the messaging user interface including a camera affordance; detecting, via the one or more input devices, a first input directed to the camera affordance; in response to detecting the first input, displaying a camera user interface, the camera user interface including a capture affordance; detecting, via the one or more input devices, a second input directed to the capture affordance; in response to detecting the second input: capturing image data using the camera; ceasing to display the capture affordance; and displaying a send affordance at a location in the camera user interface that was previously occupied by the capture affordance; detecting, via the one or more input devices, a third input directed to the send affordance; and in response to detecting the third input, initiating a process to send the captured image data to the first participant.

An electronic device is described. The electronic device comprises: a camera; a display apparatus; one or more input devices; one or more processors; and memory storing one or more programs configured to be executed by the one or more processors, the one or more programs including instructions for: displaying, via the display apparatus, a messaging user interface of a message conversation including at least a first participant, the messaging user interface including a camera affordance; detecting, via the one or more input devices, a first input directed to the camera affordance; in response to detecting the first input, displaying a camera user interface, the camera user interface including a capture affordance; detecting, via the one or more input devices, a second input directed to the capture affordance; in response to detecting the second input: capturing image data using the camera; ceasing to display the capture affordance; and displaying a send affordance at a location in the camera user interface that was previously occupied by the capture affordance; detecting, via the one or more input devices, a third input directed to the send affordance; and in response to detecting the third input, initiating a process to send the captured image data to the first participant.

An electronic device is described. The electronic device comprises: a camera; a display apparatus; one or more input devices; means for displaying, via the display apparatus, a messaging user interface of a message conversation including at least a first participant, the messaging user interface including a camera affordance; means for detecting, via the one or more input devices, a first input directed to the camera affordance; means, responsive to detecting the first input, for displaying a camera user interface, the camera user interface including a capture affordance; means for detecting, via the one or more input devices, a second input directed to the capture affordance; means, responsive to detecting the second input, for: capturing image data using the camera; ceasing to display the capture affordance; and displaying a send affordance at a location in the camera user interface that was previously occupied by the capture affordance; means for detecting, via the one or more input devices, a third input directed to the send affordance; and means, responsive to detecting the third input, for initiating a process to send the captured image data to the first participant.

A method is described. The method is performed at an electronic device having a camera and a display apparatus. The method comprises: displaying, via the display apparatus, a camera user interface, the camera user interface including: a camera display region including a representation of image data captured via the camera; and a first affordance associated with a first camera display mode; while a subject is positioned within a field of view of the camera and a representation of the subject and a background are displayed in the camera display region, detecting a gesture directed to the first affordance; in response to detecting the gesture directed to the first affordance, activating the first camera display mode, wherein activating the first camera display mode includes: displaying an avatar selection region including a selected one of a plurality of avatar options; and displaying a representation of the selected avatar option on the representation of the subject in the camera display region; while the first camera display mode is active, detecting a change in pose of the subject; and in response to detecting the change in pose of the subject, changing an appearance of the displayed representation of the selected avatar option based on the detected change in pose of the subject while maintaining display of the background.

A non-transitory computer-readable storage medium is described. The non-transitory computer-readable storage medium stores one or more programs configured to be executed by one or more processors of an electronic device with a camera and a display apparatus, the one or more programs including instructions for: displaying, via the display apparatus, a camera user interface, the camera user interface including: a camera display region including a representation of image data captured via the camera; and a first affordance associated with a first camera display mode; while a subject is positioned within a field of view of the camera and a representation of the subject and a background are displayed in the camera display region, detecting a gesture directed to the first affordance; in response to detecting the gesture directed to the first affordance, activating the first camera display mode, wherein activating the first camera display mode includes: displaying an avatar selection region including a selected one of a plurality of avatar options; and displaying a representation of the selected avatar option on the representation of the subject in the camera display region; while the first camera display mode is active, detecting a change in pose of the subject; and in response to detecting the change in pose of the subject, changing an appearance of the displayed representation of the selected avatar option based on the detected change in pose of the subject while maintaining display of the background.

A transitory computer-readable storage medium is described. The transitory computer-readable storage medium stores one or more programs configured to be executed by one or more processors of an electronic device with a camera and a display apparatus, the one or more programs including instructions for: displaying, via the display apparatus, a camera user interface, the camera user interface including: a camera display region including a representation of image data captured via the camera; and a first affordance associated with a first camera display mode; while a subject is positioned within a field of view of the camera and a representation of the subject and a background are displayed in the camera display region, detecting a gesture directed to the first affordance; in response to detecting the gesture directed to the first affordance, activating the first camera display mode, wherein activating the first camera display mode includes: displaying an avatar selection region including a selected one of a plurality of avatar options; and displaying a representation of the selected avatar option on the representation of the subject in the camera display region; while the first camera display mode is active, detecting a change in pose of the subject; and in response to detecting the change in pose of the subject, changing an appearance of the displayed representation of the selected avatar option based on the detected change in pose of the subject while maintaining display of the background.

An electronic device is described. The electronic device comprises: a camera; a display apparatus; one or more processors; and memory storing one or more programs configured to be executed by the one or more processors, the one or more programs including instructions for: displaying, via the display apparatus, a camera user interface, the camera user interface including: a camera display region including a representation of image data captured via the camera; and a first affordance associated with a first camera display mode; while a subject is positioned within a field of view of the camera and a representation of the subject and a background are displayed in the camera display region, detecting a gesture directed to the first affordance; in response to detecting the gesture directed to the first affordance, activating the first camera display mode, wherein activating the first camera display mode includes: displaying an avatar selection region including a selected one of a plurality of avatar options; and displaying a representation of the selected avatar option on the representation of the subject in the camera display region; while the first camera display mode is active, detecting a change in pose of the subject; and in response to detecting the change in pose of the subject, changing an appearance of the displayed representation of the selected avatar option based on the detected change in pose of the subject while maintaining display of the background.

An electronic device is described. The electronic device comprises: a camera; a display apparatus; one or more input devices; means for displaying, via the display apparatus, a camera user interface, the camera user interface including: a camera display region including a representation of image data captured via the camera; and a first affordance associated with a first camera display mode; means, while a subject is positioned within a field of view of the camera and a representation of the subject and a background are displayed in the camera display region, for detecting a gesture directed to the first affordance; means, responsive to detecting the gesture directed to the first affordance, for activating the first camera display mode, wherein activating the first camera display mode includes: displaying an avatar selection region including a selected one of a plurality of avatar options; and displaying a representation of the selected avatar option on the representation of the subject in the camera display region; means, while the first camera display mode is active, for detecting a change in pose of the subject; and means, responsive to detecting the change in pose of the subject, for changing an appearance of the displayed representation of the selected avatar option based on the detected change in pose of the subject while maintaining display of the background.

A method is described. The method is performed at an electronic device having a display apparatus. The method comprises: displaying, via the display apparatus, a media user interface, the media user interface including: a media display region including a representation of a media item; and an effects affordance; detecting a gesture directed to the effects affordance; in response to detecting the gesture directed to the effects affordance, displaying a plurality of effects options for applying effects to the media item concurrently with a representation of the media item, including: in accordance with a determination that the media item is associated with corresponding depth data, the plurality of effects options include a respective effects option for applying effects based on the depth data; and in accordance with a determination that the image data does not include the depth data, the respective effects option is not available for activation in the plurality of effects options.

A non-transitory computer-readable storage medium is described. The non-transitory computer-readable storage medium stores one or more programs configured to be executed by one or more processors of an electronic device with a display apparatus, the one or more programs including instructions for: displaying, via the display apparatus, a media user interface, the media user interface including: a media display region including a representation of a media item; and an effects affordance; detecting a gesture directed to the effects affordance; in response to detecting the gesture directed to the effects affordance, displaying a plurality of effects options for applying effects to the media item concurrently with a representation of the media item, including: in accordance with a determination that the media item is associated with corresponding depth data, the plurality of effects options include a respective effects option for applying effects based on the depth data; and in accordance with a determination that the image data does not include the depth data, the respective effects option is not available for activation in the plurality of effects options.

A transitory computer-readable storage medium is described. The transitory computer-readable storage medium stores one or more programs configured to be executed by one or more processors of an electronic device with a display apparatus, the one or more programs including instructions for: displaying, via the display apparatus, a media user interface, the media user interface including: a media display region including a representation of a media item; and an effects affordance; detecting a gesture directed to the effects affordance; in response to detecting the gesture directed to the effects affordance, displaying a plurality of effects options for applying effects to the media item concurrently with a representation of the media item, including: in accordance with a determination that the media item is associated with corresponding depth data, the plurality of effects options include a respective effects option for applying effects based on the depth data; and in accordance with a determination that the image data does not include the depth data, the respective effects option is not available for activation in the plurality of effects options.

An electronic device is described. The electronic device comprises: a display apparatus; one or more processors; and memory storing one or more programs configured to be executed by the one or more processors, the one or more programs including instructions for: displaying, via the display apparatus, a media user interface, the media user interface including: a media display region including a representation of a media item; and an effects affordance; detecting a gesture directed to the effects affordance; in response to detecting the gesture directed to the effects affordance, displaying a plurality of effects options for applying effects to the media item concurrently with a representation of the media item, including: in accordance with a determination that the media item is associated with corresponding depth data, the plurality of effects options include a respective effects option for applying effects based on the depth data; and in accordance with a determination that the image data does not include the depth data, the respective effects option is not available for activation in the plurality of effects options.

An electronic device is described. The electronic device comprises: a display apparatus; one or more input devices; means for displaying, via the display apparatus, a media user interface, the media user interface including: a media display region including a representation of a media item; and an effects affordance; means for detecting a gesture directed to the effects affordance; means, responsive to detecting the gesture directed to the effects affordance, for displaying a plurality of effects options for applying effects to the media item concurrently with a representation of the media item, including: in accordance with a determination that the media item is associated with corresponding depth data, the plurality of effects options include a respective effects option for applying effects based on the depth data; and in accordance with a determination that the image data does not include the depth data, the respective effects option is not available for activation in the plurality of effects options.

A method is described. The method is performed at an electronic device having a display apparatus. The method comprises: displaying, via the display apparatus, a live video communication user interface of a live video communication application, the live video communication user interface including: a representation of a subject participating in a live video communication session, and a first affordance; detecting a gesture directed to the first affordance; and in response to detecting the gesture directed to the first affordance: activating a camera effects mode; and increasing a size of the representation of the subject participating in the live video communication session.

A non-transitory computer-readable storage medium is described. The non-transitory computer-readable storage medium stores one or more programs configured to be executed by one or more processors of an electronic device with a display apparatus, the one or more programs including instructions for: displaying, via the display apparatus, a live video communication user interface of a live video communication application, the live video communication user interface including: a representation of a subject participating in a live video communication session, and a first affordance; detecting a gesture directed to the first affordance; and in response to detecting the gesture directed to the first affordance: activating a camera effects mode; and increasing a size of the representation of the subject participating in the live video communication session.

A transitory computer-readable storage medium is described. The transitory computer-readable storage medium stores one or more programs configured to be executed by one or more processors of an electronic device with a display apparatus, the one or more programs including instructions for: displaying, via the display apparatus, a live video communication user interface of a live video communication application, the live video communication user interface including: a representation of a subject participating in a live video communication session, and a first affordance; detecting a gesture directed to the first affordance; and in response to detecting the gesture directed to the first affordance: activating a camera effects mode; and increasing a size of the representation of the subject participating in the live video communication session.

An electronic device is described. The electronic device comprises: a display apparatus; one or more processors; and memory storing one or more programs configured to be executed by the one or more processors, the one or more programs including instructions for: displaying, via the display apparatus, a live video communication user interface of a live video communication application, the live video communication user interface including: a representation of a subject participating in a live video communication session, and a first affordance; detecting a gesture directed to the first affordance; and in response to detecting the gesture directed to the first affordance: activating a camera effects mode; and increasing a size of the representation of the subject participating in the live video communication session.

An electronic device is described. The electronic device comprises: a display apparatus; one or more input devices; means for displaying, via the display apparatus, a live video communication user interface of a live video communication application, the live video communication user interface including: a representation of a subject participating in a live video communication session, and a first affordance; means for detecting a gesture directed to the first affordance; and means, responsive to detecting the gesture directed to the first affordance, for: activating a camera effects mode; and increasing a size of the representation of the subject participating in the live video communication session.

A method is described. The method is performed at an electronic device having a camera and a display apparatus. The method comprises: displaying, via the display apparatus, a representation of image data captured via the one or more cameras, wherein the representation includes a representation of a subject and the image data corresponds to depth data that includes depth data for the subject; displaying, via the display apparatus, a representation of a virtual avatar that is displayed in place of at least a portion of the representation of the subject, wherein the virtual avatar is placed at simulated depth relative to the representation of the subject as determined based on the depth data for the subject, displaying the representation of the virtual avatar includes: in accordance with a determination, based on the depth data, that a first portion of the virtual avatar satisfies a set of depth-based display criteria, wherein the depth-based display criteria include a requirement that the depth data for the subject indicate that the first portion of the virtual avatar has a simulated depth that is in front of a corresponding first portion of the subject, in order for the depth-based display criteria to be met, including as part of the representation of the virtual avatar, a representation of the first portion of the virtual avatar that is displayed in place of the first portion of the subject; and in accordance with a determination, based on the depth data, that the first portion of the virtual avatar does not satisfy the set of depth-based display criteria for the first portion of the subject, excluding, from the representation of the virtual avatar, the representation of the first portion of the virtual avatar and displaying the first portion of the subject in the region that would have been occupied by the first portion of the virtual avatar.

A non-transitory computer-readable storage medium is described. The non-transitory computer-readable storage medium stores one or more programs configured to be executed by one or more processors of an electronic device with a camera and a display apparatus, the one or more programs including instructions for: displaying, via the display apparatus, a representation of image data captured via the one or more cameras, wherein the representation includes a representation of a subject and the image data corresponds to depth data that includes depth data for the subject; displaying, via the display apparatus, a representation of a virtual avatar that is displayed in place of at least a portion of the representation of the subject, wherein the virtual avatar is placed at simulated depth relative to the representation of the subject as determined based on the depth data for the subject, displaying the representation of the virtual avatar includes: in accordance with a determination, based on the depth data, that a first portion of the virtual avatar satisfies a set of depth-based display criteria, wherein the depth-based display criteria include a requirement that the depth data for the subject indicate that the first portion of the virtual avatar has a simulated depth that is in front of a corresponding first portion of the subject, in order for the depth-based display criteria to be met, including as part of the representation of the virtual avatar, a representation of the first portion of the virtual avatar that is displayed in place of the first portion of the subject; and in accordance with a determination, based on the depth data, that the first portion of the virtual avatar does not satisfy the set of depth-based display criteria for the first portion of the subject, excluding, from the representation of the virtual avatar, the representation of the first portion of the virtual avatar and displaying the first portion of the subject in the region that would have been occupied by the first portion of the virtual avatar.

A transitory computer-readable storage medium is described. The transitory computer-readable storage medium stores one or more programs configured to be executed by one or more processors of an electronic device with a camera and a display apparatus, the one or more programs including instructions for: displaying, via the display apparatus, a representation of image data captured via the one or more cameras, wherein the representation includes a representation of a subject and the image data corresponds to depth data that includes depth data for the subject; displaying, via the display apparatus, a representation of a virtual avatar that is displayed in place of at least a portion of the representation of the subject, wherein the virtual avatar is placed at simulated depth relative to the representation of the subject as determined based on the depth data for the subject, displaying the representation of the virtual avatar includes: in accordance with a determination, based on the depth data, that a first portion of the virtual avatar satisfies a set of depth-based display criteria, wherein the depth-based display criteria include a requirement that the depth data for the subject indicate that the first portion of the virtual avatar has a simulated depth that is in front of a corresponding first portion of the subject, in order for the depth-based display criteria to be met, including as part of the representation of the virtual avatar, a representation of the first portion of the virtual avatar that is displayed in place of the first portion of the subject; and in accordance with a determination, based on the depth data, that the first portion of the virtual avatar does not satisfy the set of depth-based display criteria for the first portion of the subject, excluding, from the representation of the virtual avatar, the representation of the first portion of the virtual avatar and displaying the first portion of the subject in the region that would have been occupied by the first portion of the virtual avatar.

An electronic device is described. The electronic device comprises: a camera; a display apparatus; one or more processors; and memory storing one or more programs configured to be executed by the one or more processors, the one or more programs including instructions for: displaying, via the display apparatus, a representation of image data captured via the one or more cameras, wherein the representation includes a representation of a subject and the image data corresponds to depth data that includes depth data for the subject; displaying, via the display apparatus, a representation of a virtual avatar that is displayed in place of at least a portion of the representation of the subject, wherein the virtual avatar is placed at simulated depth relative to the representation of the subject as determined based on the depth data for the subject, displaying the representation of the virtual avatar includes: in accordance with a determination, based on the depth data, that a first portion of the virtual avatar satisfies a set of depth-based display criteria, wherein the depth-based display criteria include a requirement that the depth data for the subject indicate that the first portion of the virtual avatar has a simulated depth that is in front of a corresponding first portion of the subject, in order for the depth-based display criteria to be met, including as part of the representation of the virtual avatar, a representation of the first portion of the virtual avatar that is displayed in place of the first portion of the subject; and in accordance with a determination, based on the depth data, that the first portion of the virtual avatar does not satisfy the set of depth-based display criteria for the first portion of the subject, excluding, from the representation of the virtual avatar, the representation of the first portion of the virtual avatar and displaying the first portion of the subject in the region that would have been occupied by the first portion of the virtual avatar.

An electronic device is described. The electronic device comprises: a camera; and a display apparatus; means for displaying, via the display apparatus, a representation of image data captured via the one or more cameras, wherein the representation includes a representation of a subject and the image data corresponds to depth data that includes depth data for the subject; means for displaying, via the display apparatus, a representation of a virtual avatar that is displayed in place of at least a portion of the representation of the subject, wherein the virtual avatar is placed at simulated depth relative to the representation of the subject as determined based on the depth data for the subject, displaying the representation of the virtual avatar includes: means in accordance with a determination, based on the depth data, that a first portion of the virtual avatar satisfies a set of depth-based display criteria, wherein the depth-based display criteria include a requirement that the depth data for the subject indicate that the first portion of the virtual avatar has a simulated depth that is in front of a corresponding first portion of the subject, in order for the depth-based display criteria to be met, for including as part of the representation of the virtual avatar, a representation of the first portion of the virtual avatar that is displayed in place of the first portion of the subject; and means in accordance with a determination, based on the depth data, that the first portion of the virtual avatar does not satisfy the set of depth-based display criteria for the first portion of the subject, for excluding, from the representation of the virtual avatar, the representation of the first portion of the virtual avatar and displaying the first portion of the subject in the region that would have been occupied by the first portion of the virtual avatar.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for displaying visual effects, thereby increasing the effectiveness, efficiency, and user satisfaction with such devices. Such methods and interfaces may complement or replace other methods for displaying visual effects.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIGS. 7A and 7B are a flow diagram illustrating a method for displaying visual effects in a messaging application.

FIGS. 9A and 9B are a flow diagram illustrating a method for displaying visual effects in a camera application.

FIGS. 11A and 11B are a flow diagram illustrating a method for displaying visual effects in a media item viewing mode.

FIGS. 13A and 13B are a flow diagram illustrating a method for displaying visual effects in a live video communication session.

FIGS. 15A and 15B are a flow diagram illustrating a method for displaying visual effects in a camera application.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for displaying visual effects. For example, while programs already exist for displaying visual effects, these programs are inefficient and difficult to use compared to the techniques below, which allow a user to displaying visual effects in various applications. Such techniques can reduce the cognitive burden on a user who displays visual effects in an application, thereby enhancing productivity. Further, such techniques can reduce processor and battery power otherwise wasted on redundant user inputs.

Below, FIGS. 1A-1B, 2, 3, 4A-4B, and 5A-5B provide a description of exemplary devices for performing the techniques for managing event notifications.

Figure 6A:
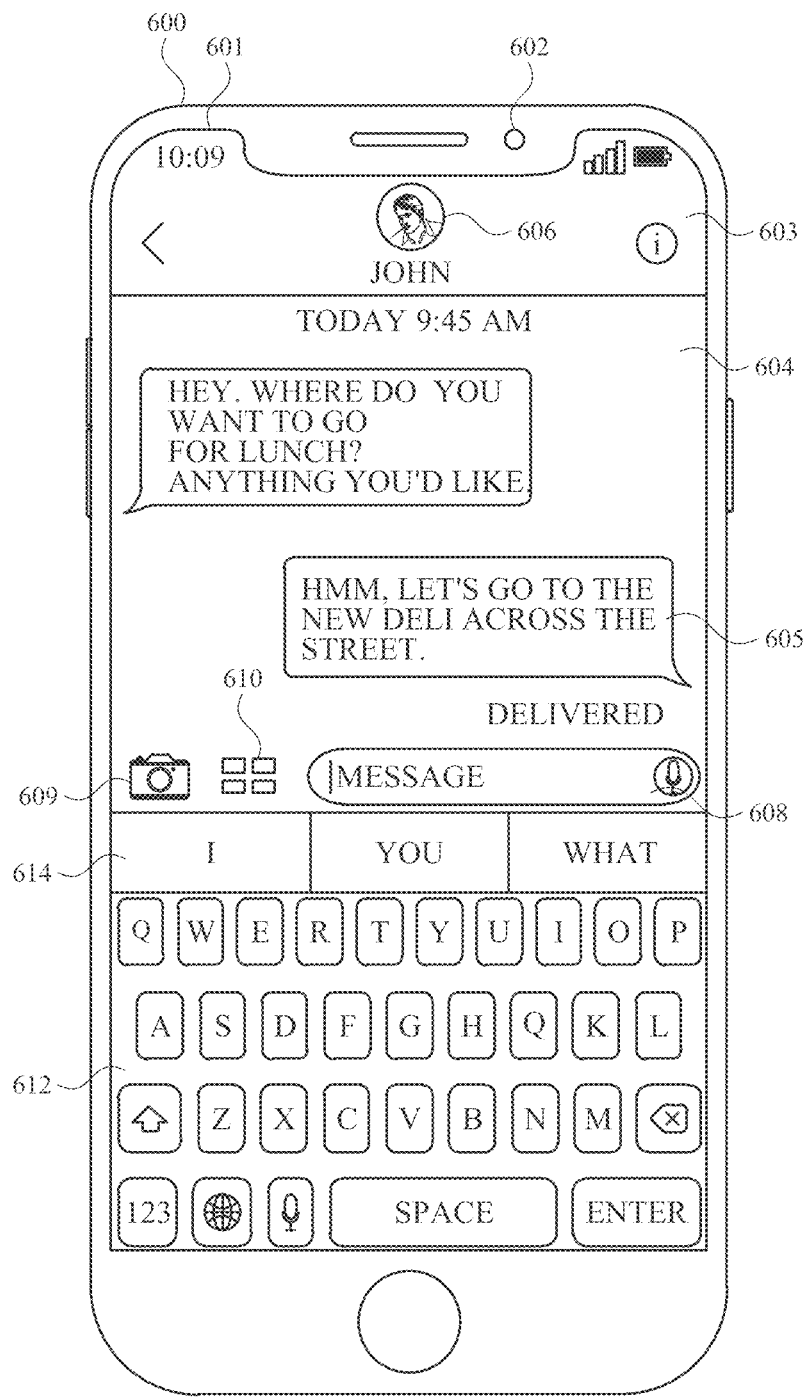
FIGS. 6A-6BQ illustrate exemplary user interfaces for displaying visual effects in a messaging application.
Figure 6B:
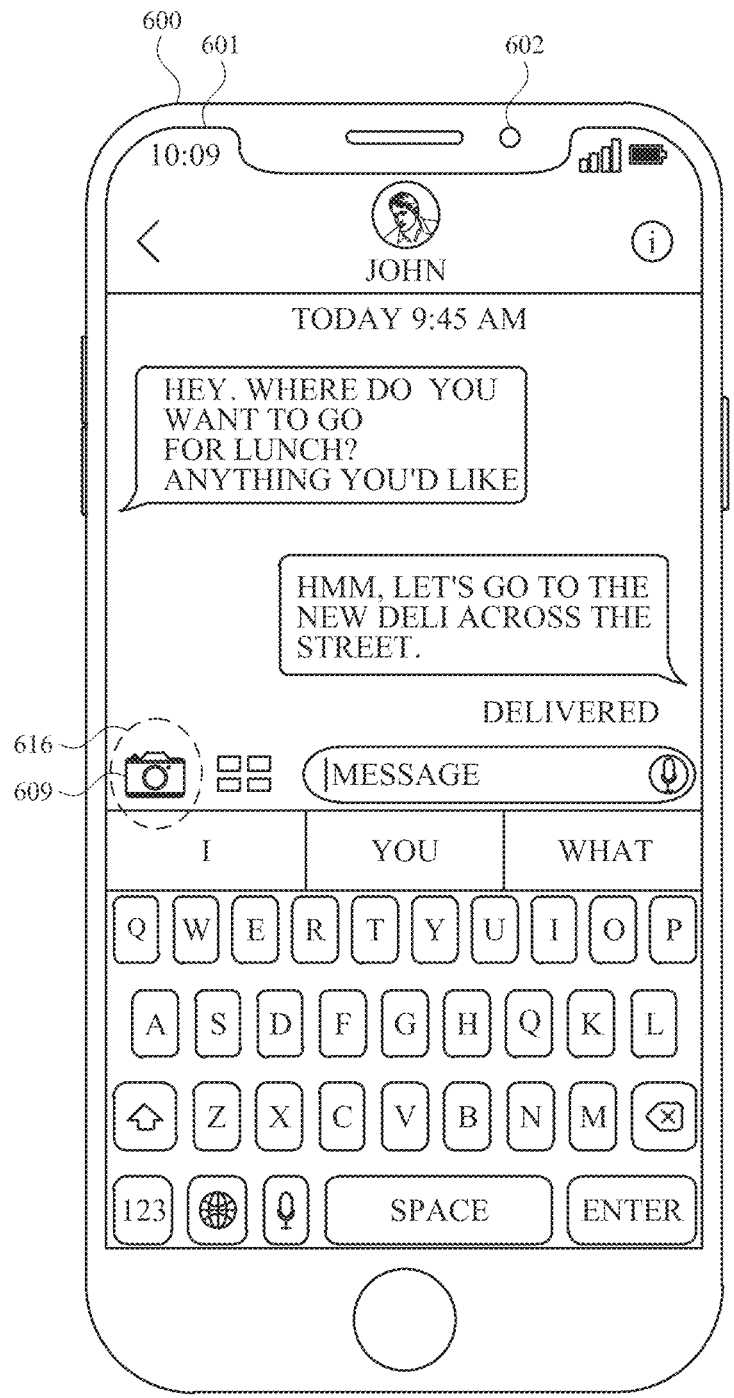
Figure 7B:
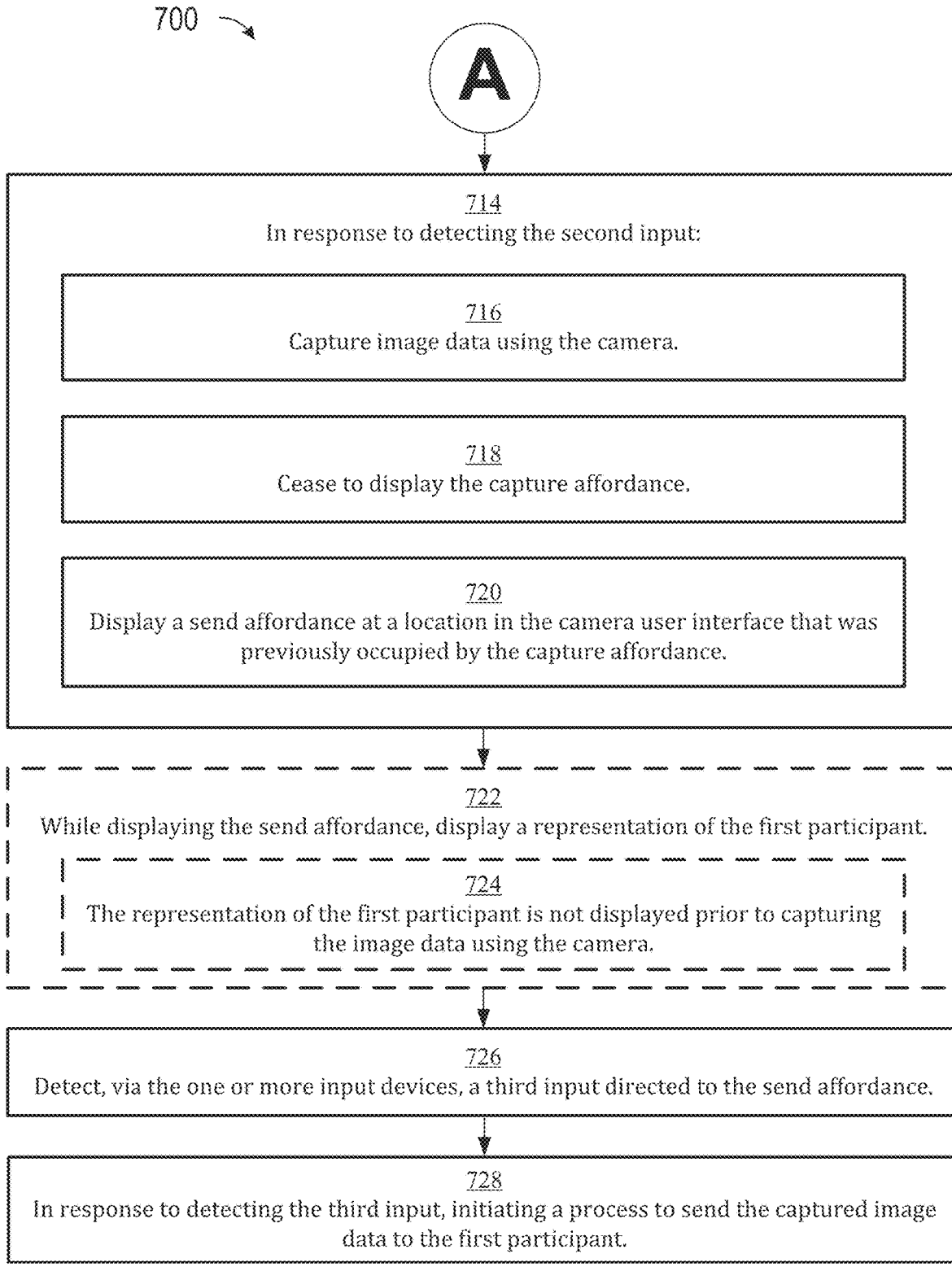

FIGS. 6A-6BQ illustrate exemplary user interfaces for displaying visual effects in a messaging application. FIGS. 7A and 7B are a flow diagram illustrating methods of displaying visual effects in a messaging application in accordance with some embodiments. The user interfaces in FIGS. 6A-6BQ are used to illustrate the processes described below, including the processes in FIGS. 7A and 7B.

Figure 8A:
FIGS. 8A-8BQ illustrate exemplary user interfaces for displaying visual effects in a camera application.
Figure 8B:
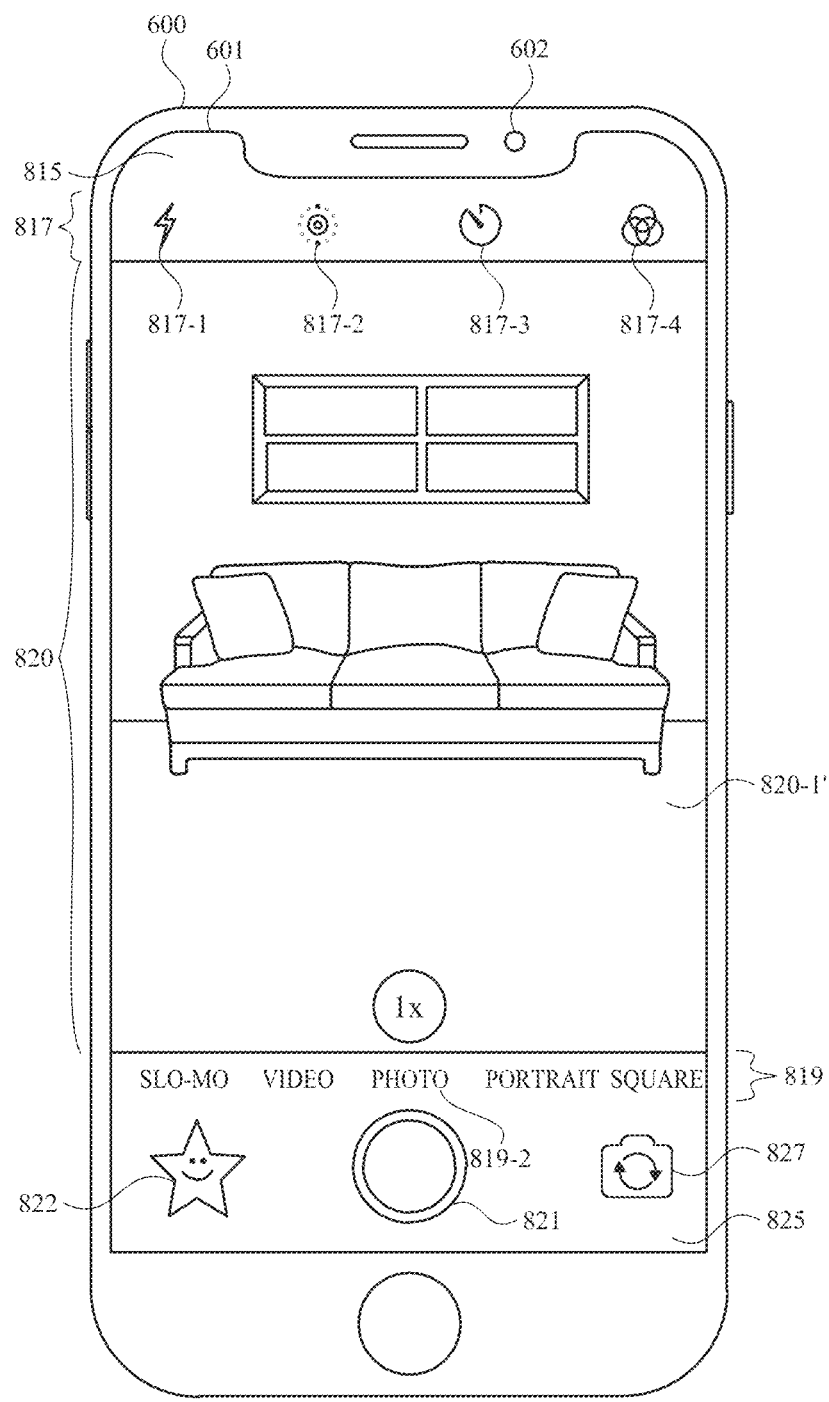
Figure 9B:
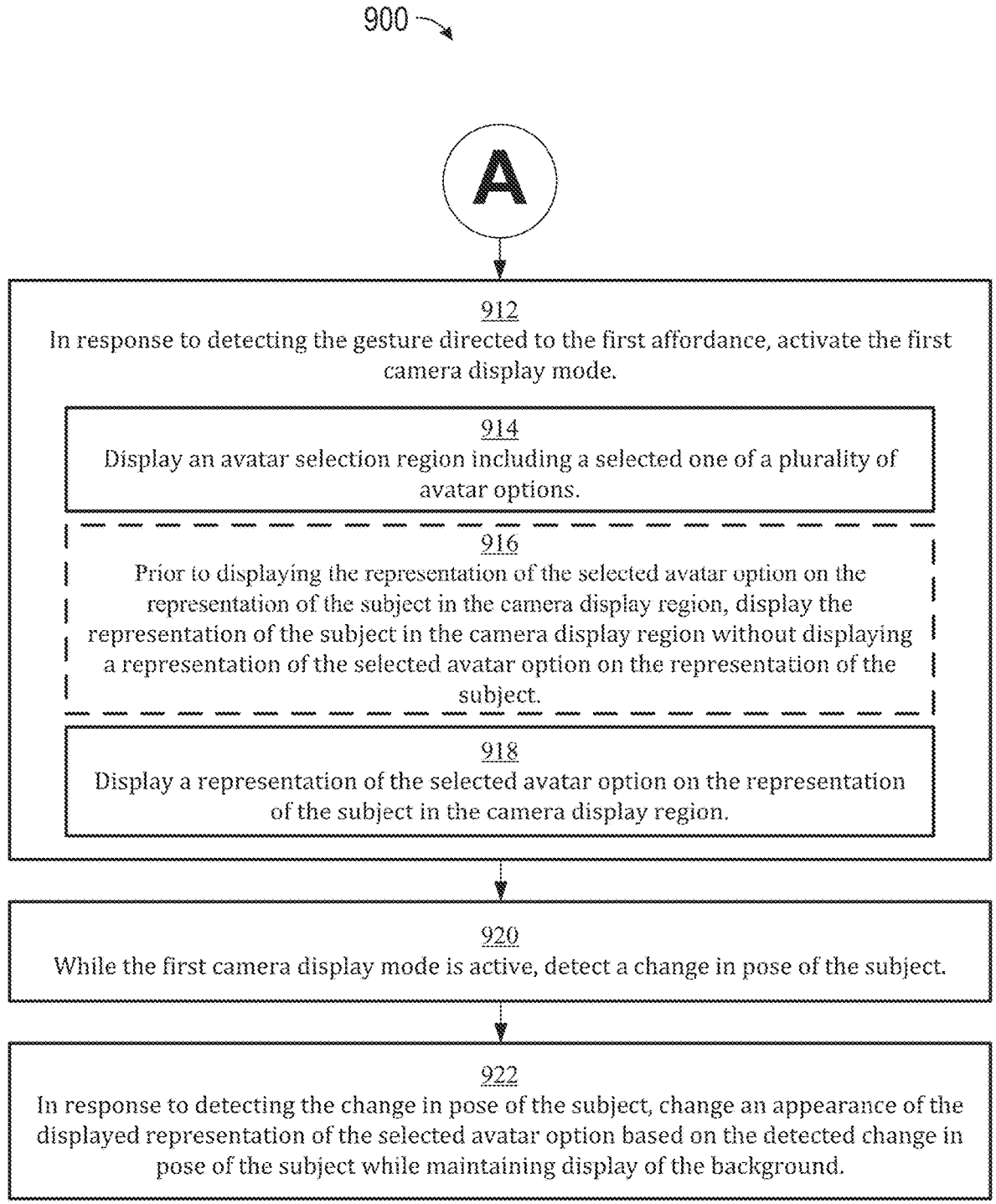

FIGS. 8A-8BQ illustrate exemplary user interfaces for displaying visual effects in a camera application. FIGS. 9A and 9B are a flow diagram illustrating methods of displaying visual effects in a camera application in accordance with some embodiments. The user interfaces in FIGS. 8A-8BQ are used to illustrate the processes described below, including the processes in FIGS. 9A and 9B.

Figure 10A:
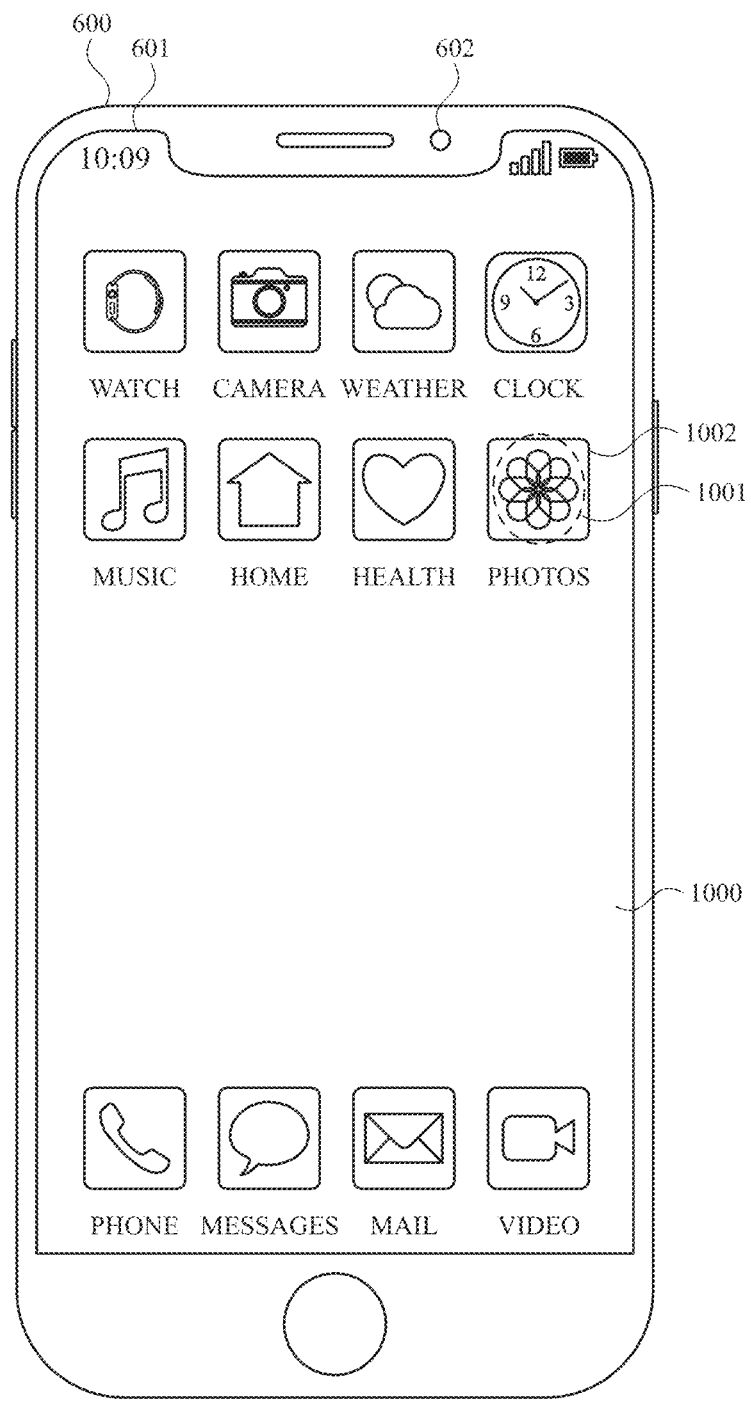
FIGS. 10A-10AL illustrate exemplary user interfaces for displaying visual effects in a media item viewing mode.

FIGS. 10A-10AL illustrate exemplary user interfaces for displaying visual effects in a camera application. FIGS. 11A and 11B are a flow diagram illustrating methods of displaying visual effects in a media item viewing mode in accordance with some embodiments. The user interfaces in FIGS. 10A-10AL are used to illustrate the processes described below, including the processes in FIGS. 11A and 11B.

Figure 12A:
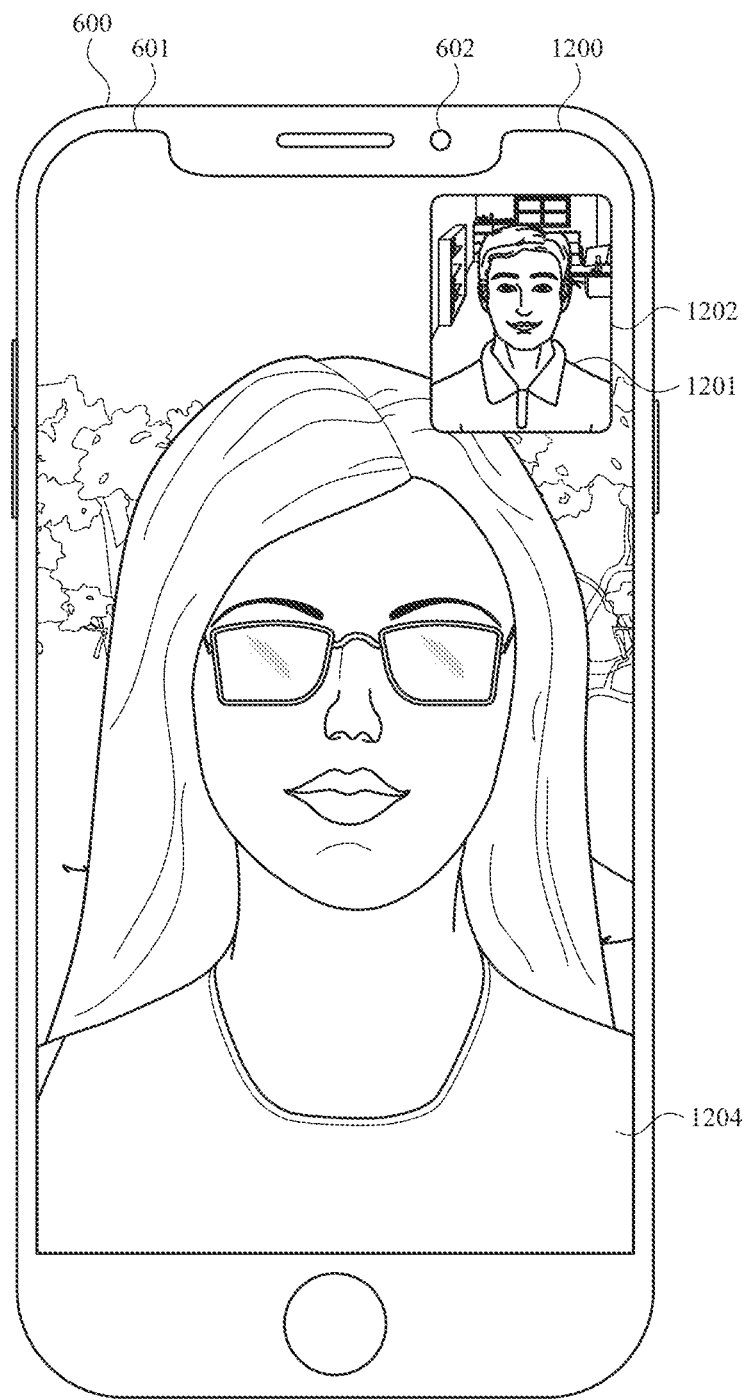
FIGS. 12A-12AP illustrate exemplary user interfaces for displaying visual effects in a live video communication session.
Figure 13B:
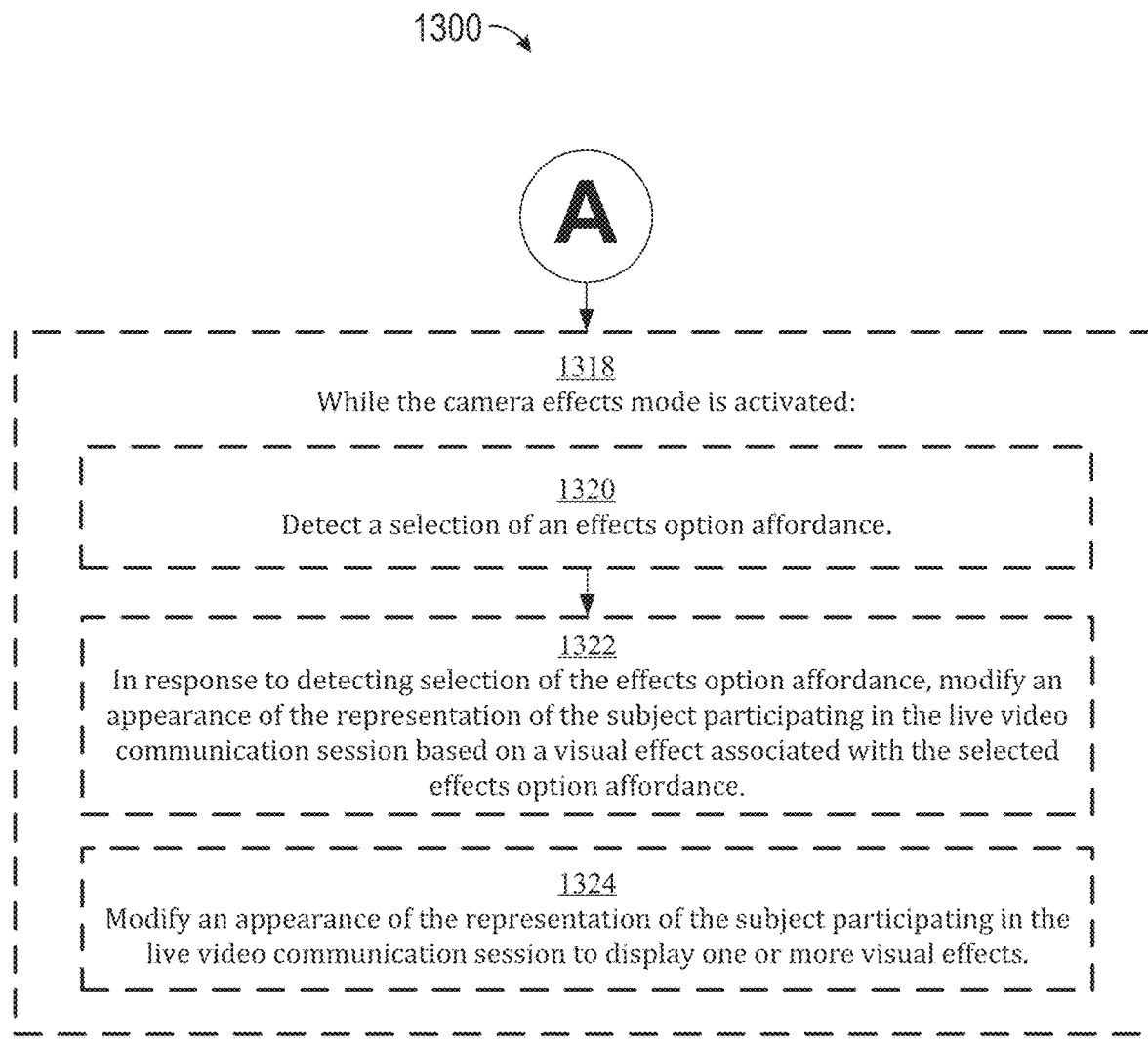

FIGS. 12A-12AP illustrate exemplary user interfaces for displaying visual effects in a live video communication session. FIGS. 13A and 13B are a flow diagram illustrating methods of displaying visual effects in a live video communication session in accordance with some embodiments. The user interfaces in FIGS. 12A-12AP are used to illustrate the processes described below, including the processes in FIGS. 13A and 13B.

FIGS. 14A-14M illustrate exemplary user interfaces for displaying visual effects in a camera application. FIGS. 15A and 15B are a flow diagram illustrating methods of displaying visual effects in a camera application in accordance with some embodiments. The user interfaces in FIGS. 14A-14M are used to illustrate the processes described below, including the processes in FIGS. 15A and 15B.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
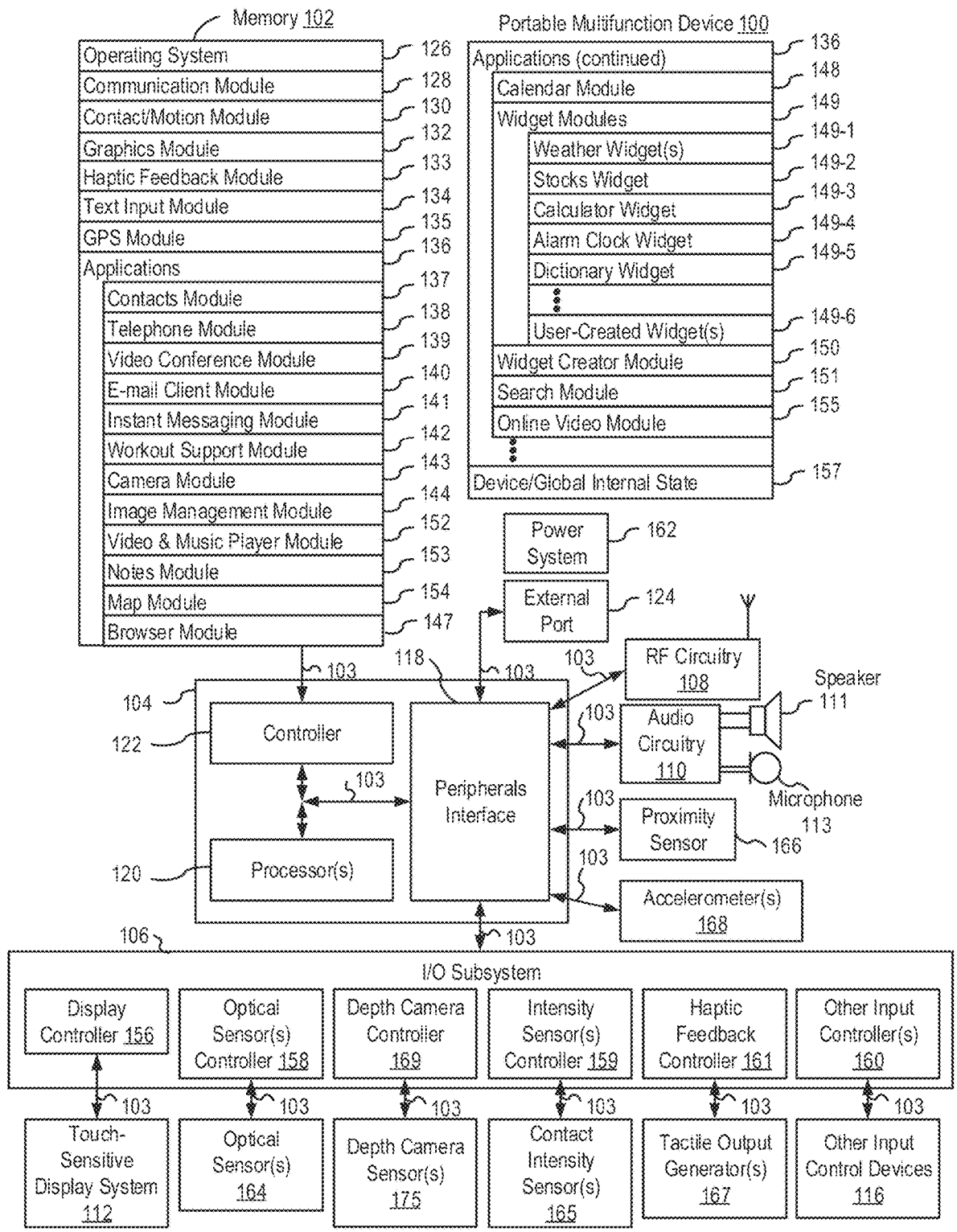
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

In some embodiments, a depth map (e.g., depth map image) contains information (e.g., values) that relates to the distance of objects in a scene from a viewpoint (e.g., a camera, an optical sensor, a depth camera sensor). In one embodiment of a depth map, each depth pixel defines the position in the viewpoint's Z-axis where its corresponding two-dimensional pixel is located. In some embodiments, a depth map is composed of pixels wherein each pixel is defined by a value (e.g., 0-255). For example, the "0" value represents pixels that are located at the most distant place in a "three dimensional" scene and the "255" value represents pixels that are located closest to a viewpoint (e.g., a camera, an optical sensor, a depth camera sensor) in the "three dimensional" scene. In other embodiments, a depth map represents the distance between an object in a scene and the plane of the viewpoint. In some embodiments, the depth map includes information about the relative depth of various features of an object of interest in view of the depth camera (e.g., the relative depth of eyes, nose, mouth, ears of a user's face). In some embodiments, the depth map includes information that enables the device to determine contours of the object of interest in a z direction.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
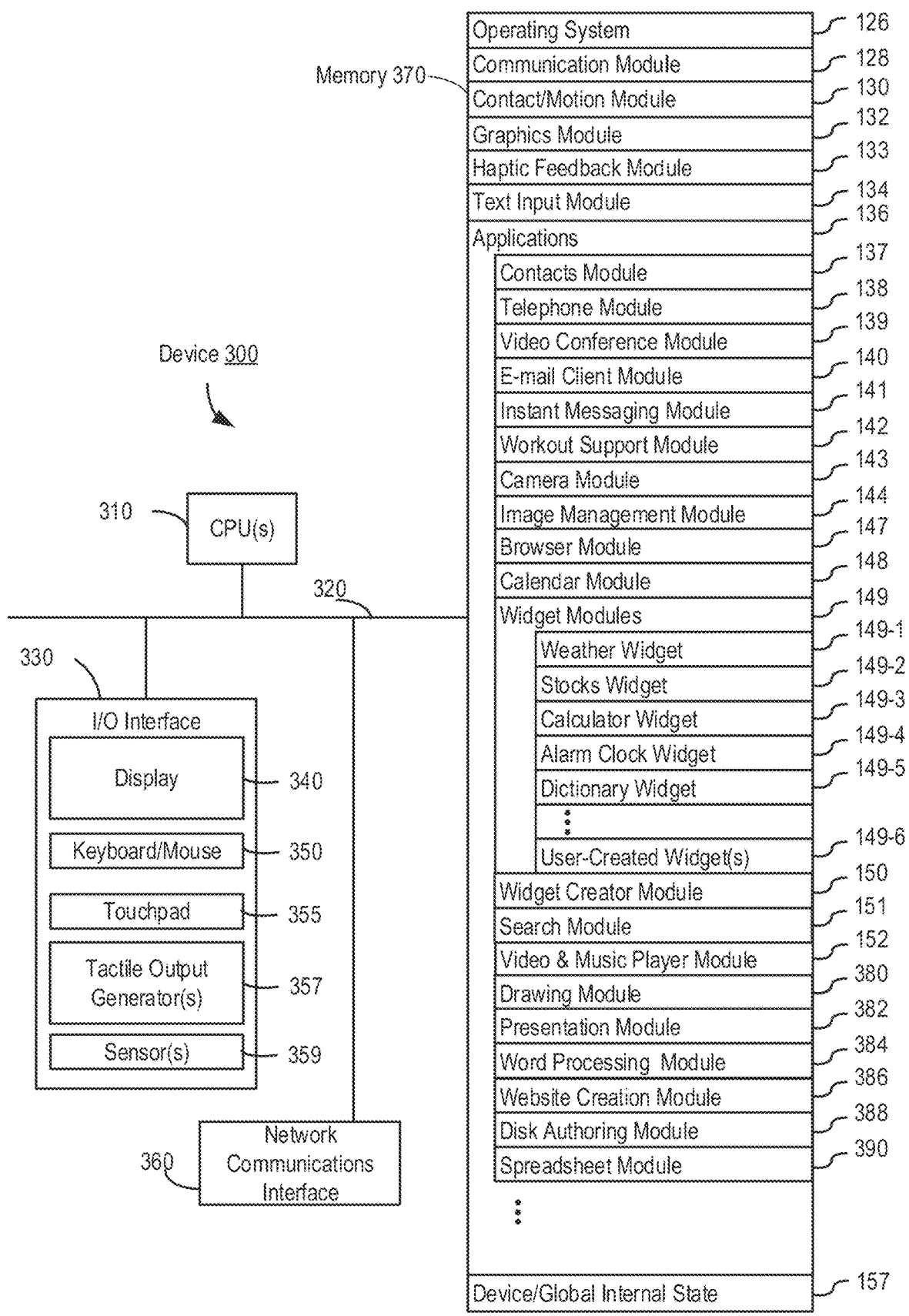
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:

Contacts module 137 (sometimes called an address book or contact list);
Telephone module 138;
Video conference module 139;
E-mail client module 140;
Instant messaging (IM) module 141;
Workout support module 142;
Camera module 143 for still and/or video images;
Image management module 144;
Video player module;
Music player module;
Browser module 147;
Calendar module 148;
Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
Widget creator module 150 for making user-created widgets 149-6;
Search module 151;
Video and music player module 152, which merges video player module and music player module;
Notes module 153;
Map module 154; and/or
Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
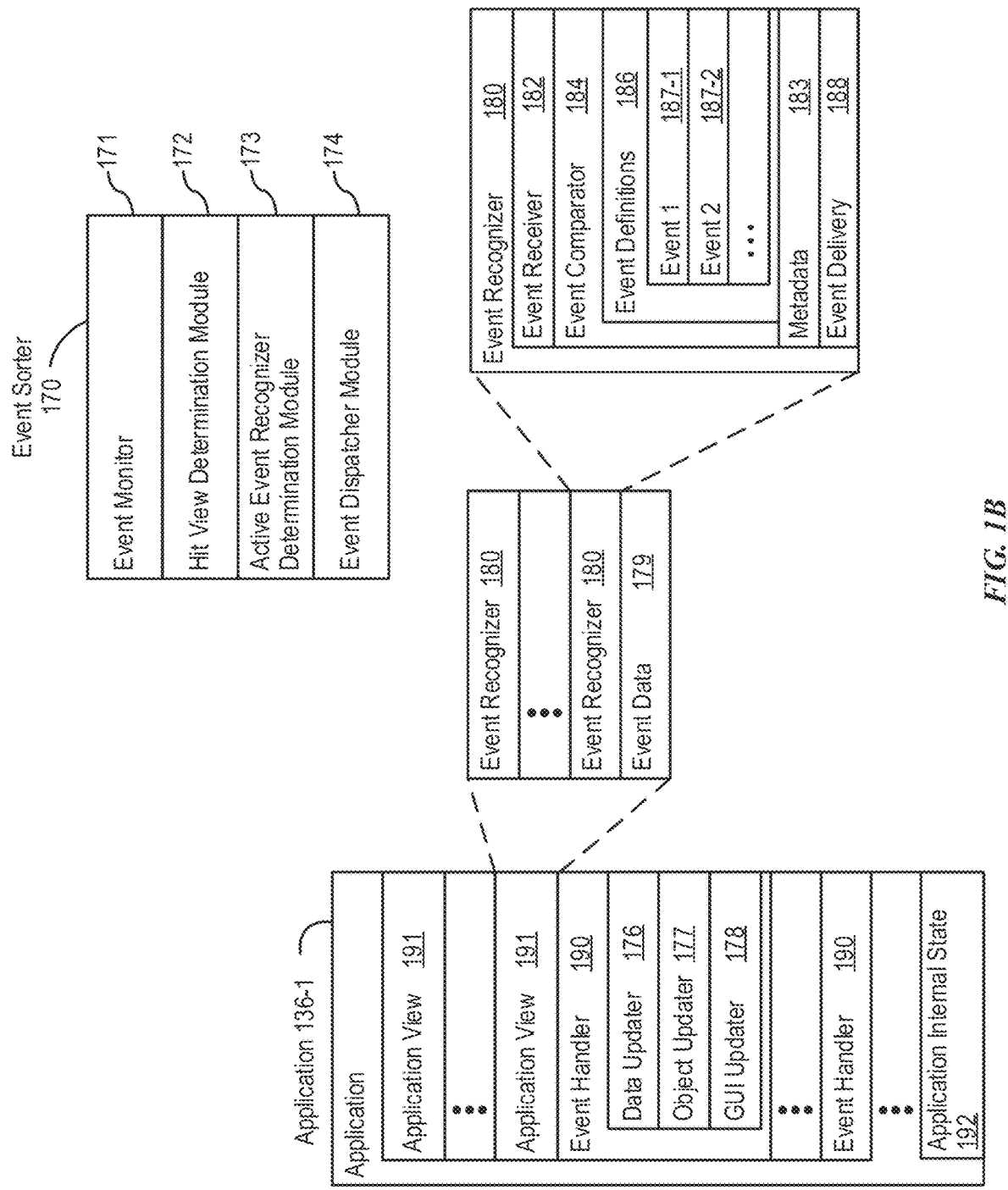
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
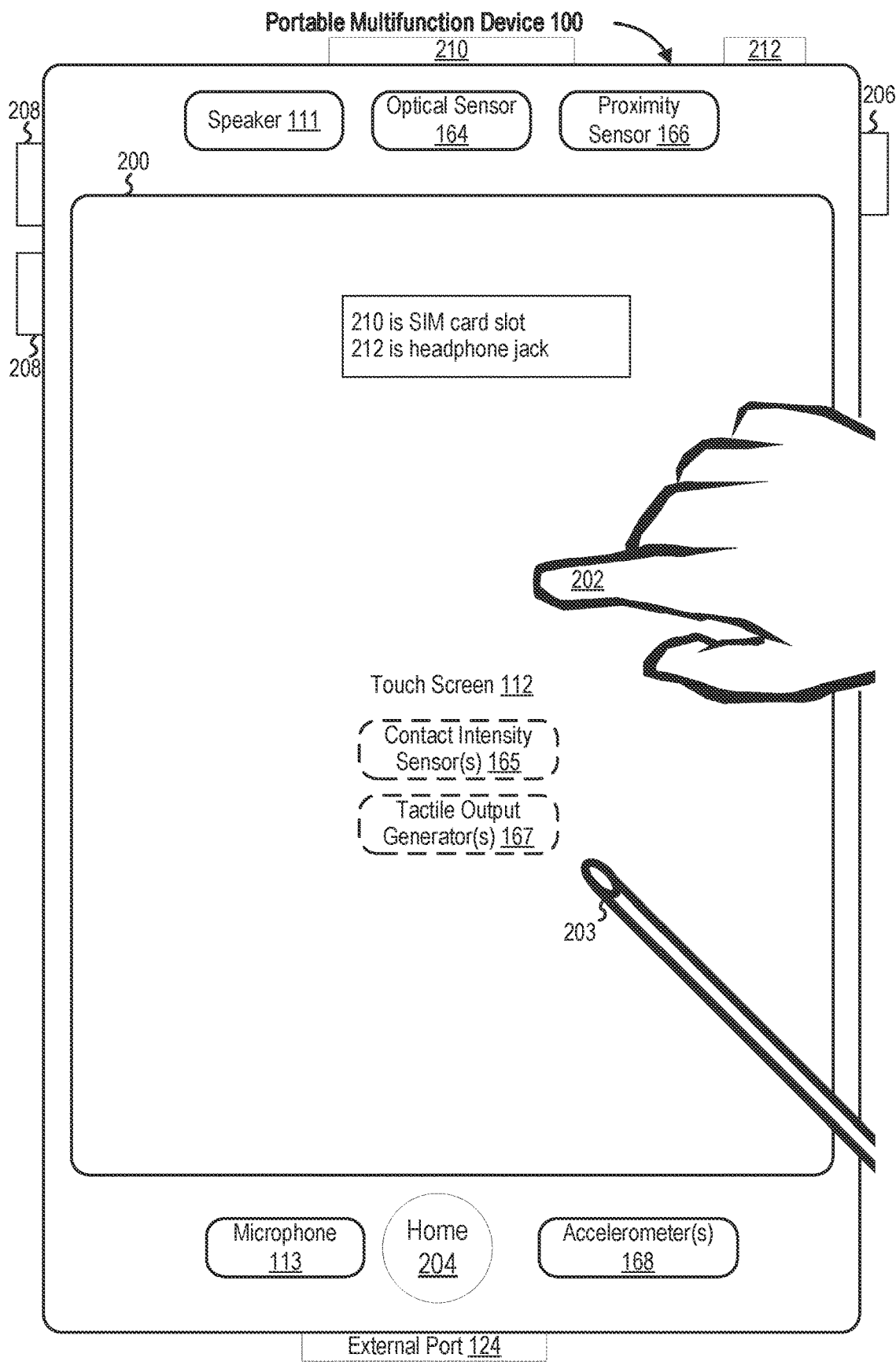
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
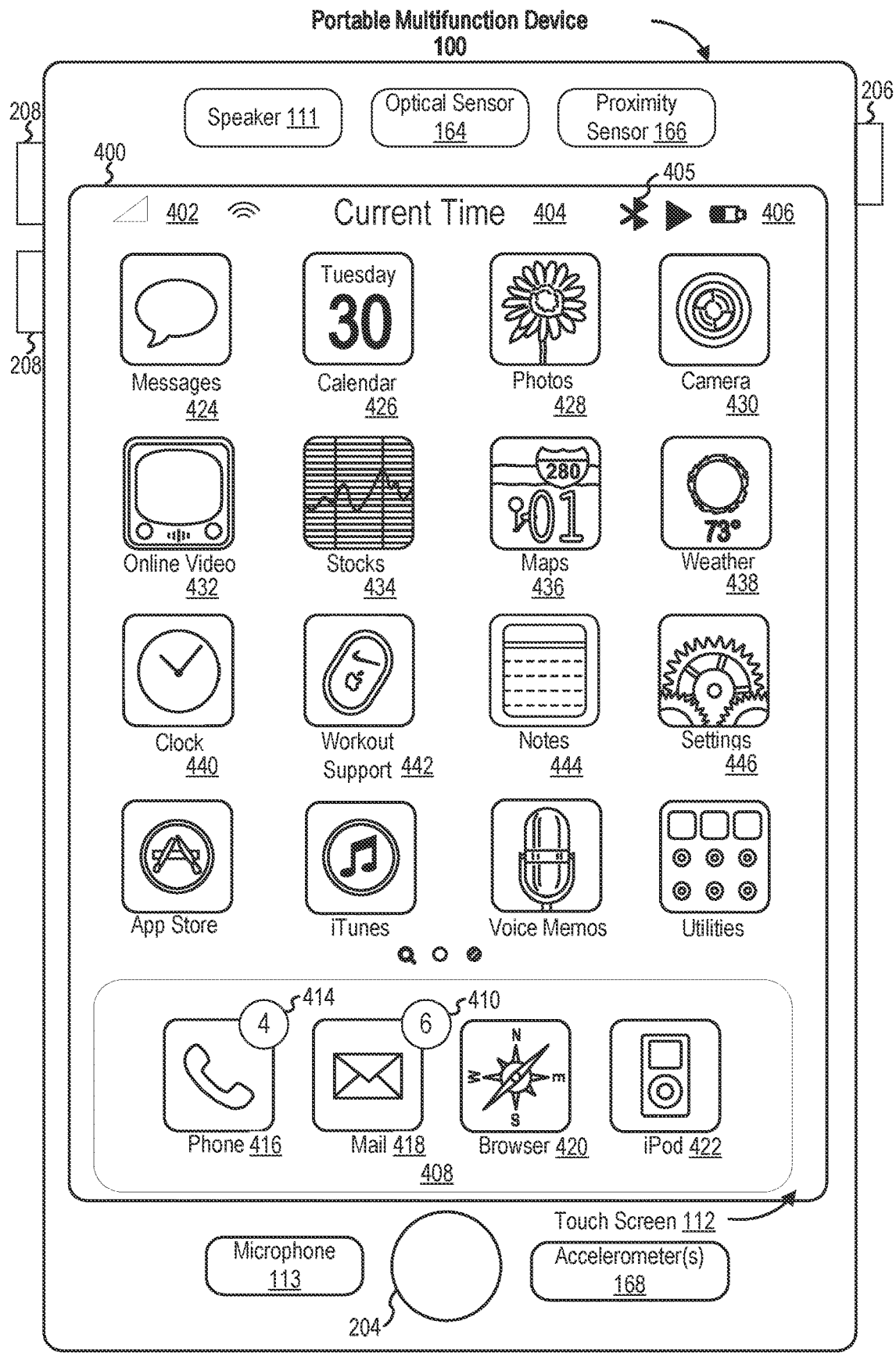
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
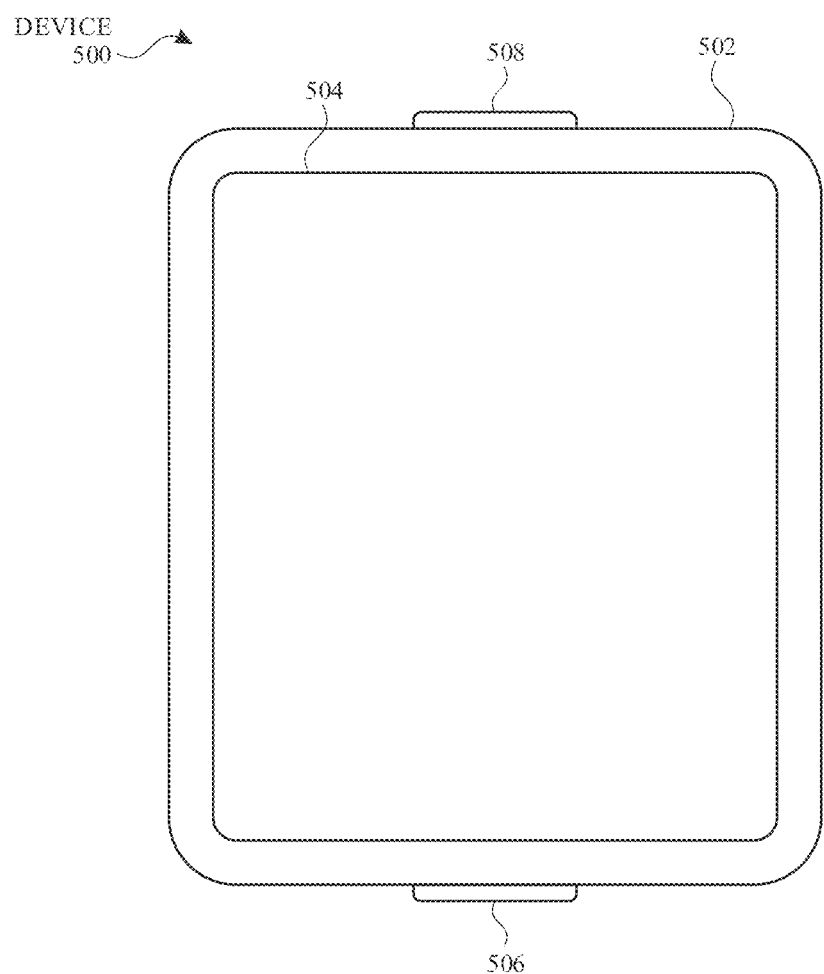
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
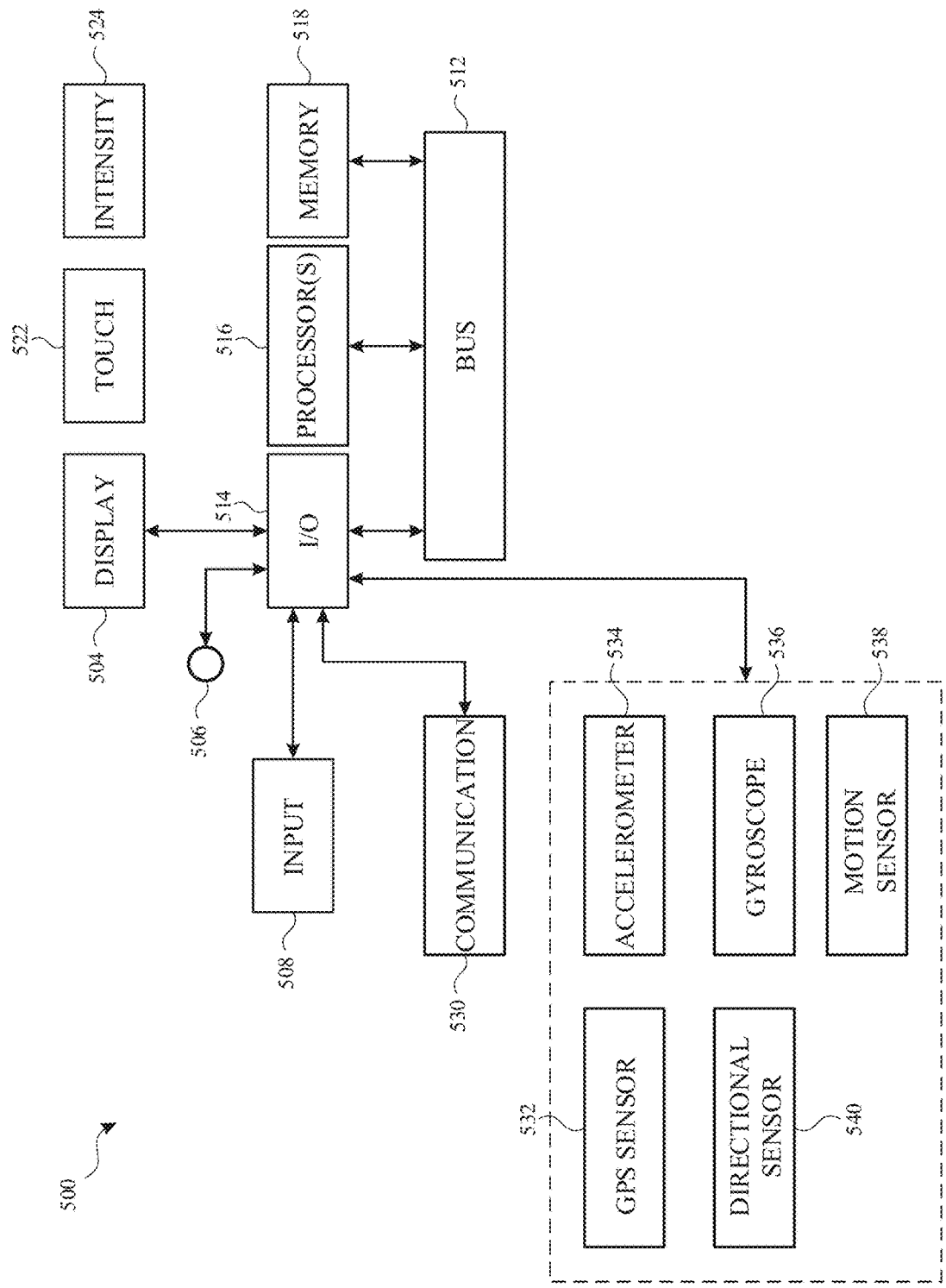
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 900, 1100, 1300, and 1500 (FIGS. 7A-7B, 9A-9B, 11A-11B, 13A-13B, and 15A-15B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

FIGS. 6A-6BQ illustrate exemplary user interfaces for displaying visual effects in a messaging application, in accordance with some embodiments. The user interfaces in these figures are used to illustrate the processes described below, including the processes in FIGS. 7A-7B.

FIG. 6A depicts device 600 having display 601, which in some cases is a touch-sensitive display. In some embodiments, device 600 also includes camera 602, which, at a minimum, includes an image sensor that is capable of capturing data representing a portion of the light spectrum (e.g., visible light, infrared light, or ultraviolet light). In some embodiments, camera 602 includes multiple image sensors and/or other types of sensors. In addition to capturing data representing sensed light, in some embodiments, camera 602 is capable of capturing other types of data, such as depth data. For example, in some embodiments, camera 602 also captures depth data using techniques based on speckle, time-of-flight, parallax, or focus. Image data that device 600 captures using camera 602 includes data corresponding to a portion of the light spectrum for a scene within the field of view of the camera. Additionally, in some embodiments, the captured image data also includes depth data for the light data. In some other embodiments, the captured image data contains data sufficient to determine or generate depth data for the data for the portion of the light spectrum. In some embodiments, device 600 includes one or more features of devices 100, 300, or 500.

In some examples, electronic device 600 includes a depth camera, such as an infrared camera, a thermographic camera, or a combination thereof. In some examples, the device further includes a light-emitting device (e.g., light projector), such an IR flood light, a structured light projector, or a combination thereof. The light-emitting device is, optionally, used to illuminate the subject during capture of the image by a visible light camera and a depth camera (e.g., an IR camera) and the information from the depth camera and the visible light camera are used to determine a depth map of different portions of subject captured by the visible light camera. In some embodiments, a depth map (e.g., depth map image) contains information (e.g., values) that relates to the distance of objects in a scene from a viewpoint (e.g., a camera). In one embodiment of a depth map, each depth pixel defines the position in the viewpoint's Z-axis where its corresponding two-dimensional pixel is located. In some examples, a depth map is composed of pixels wherein each pixel is defined by a value (e.g., 0-255). For example, the "0" value represents pixels that are located at the most distant place in a "three dimensional" scene and the "255" value represents pixels that are located closest to a viewpoint (e.g., camera) in the "three dimensional" scene. In other examples, a depth map represents the distance between an object in a scene and the plane of the viewpoint.) In some embodiments, the depth map includes information about the relative depth of various features of an object of interest in view of the depth camera (e.g., the relative depth of eyes, nose, mouth, ears of a user's face). In some embodiments, the depth map includes information that enables the device to determine contours of the object of interest in a z direction. In some embodiments, the lighting effects described herein are displayed using disparity information from two cameras (e.g., two visual light cameras) for rear facing images and using depth information from a depth camera combined with image data from a visual light camera for front facing images (e.g., selfie images). In some embodiments, the same user interface is used when the two visual light cameras are used to determine the depth information and when the depth camera is used to determine the depth information, providing the user with a consistent experience, even when using dramatically different technologies to determine the information that is used when generating the lighting effects. In some embodiments, while displaying the camera user interface with one of the lighting effects applied, the device detects selection of a camera switching affordance and switches from the front facing cameras (e.g., a depth camera and a visible light camera) to the rear-facing cameras (e.g., two visible light cameras that are spaced apart from each other) (or vice versa) while maintaining display of the user interface controls for applying the lighting effect and replacing display of the field of view of the front facing cameras to the field of view of the rear facing cameras (or vice versa).

In FIG. 6A, device 600 is displaying messaging user interface 603 of a messaging application. Messaging user interface 603 includes message display region 604 including messages 605 transmitted to a participant (represented by recipient identifier 606) in a message conversation. Messaging user interface 603 also includes a message-compose field 608 for displaying input (e.g., text input, multimedia input, etc.) for sending to the participant in the message conversation. Messaging user interface 603 also includes camera application affordance 609, application dock affordance 610, keyboard display region 612, and text-suggestion region 614.

In FIG. 6B, device 600 detects input 616 (e.g., a touch input on display 601) at a location corresponding to camera application affordance 609.

Figure 6C:
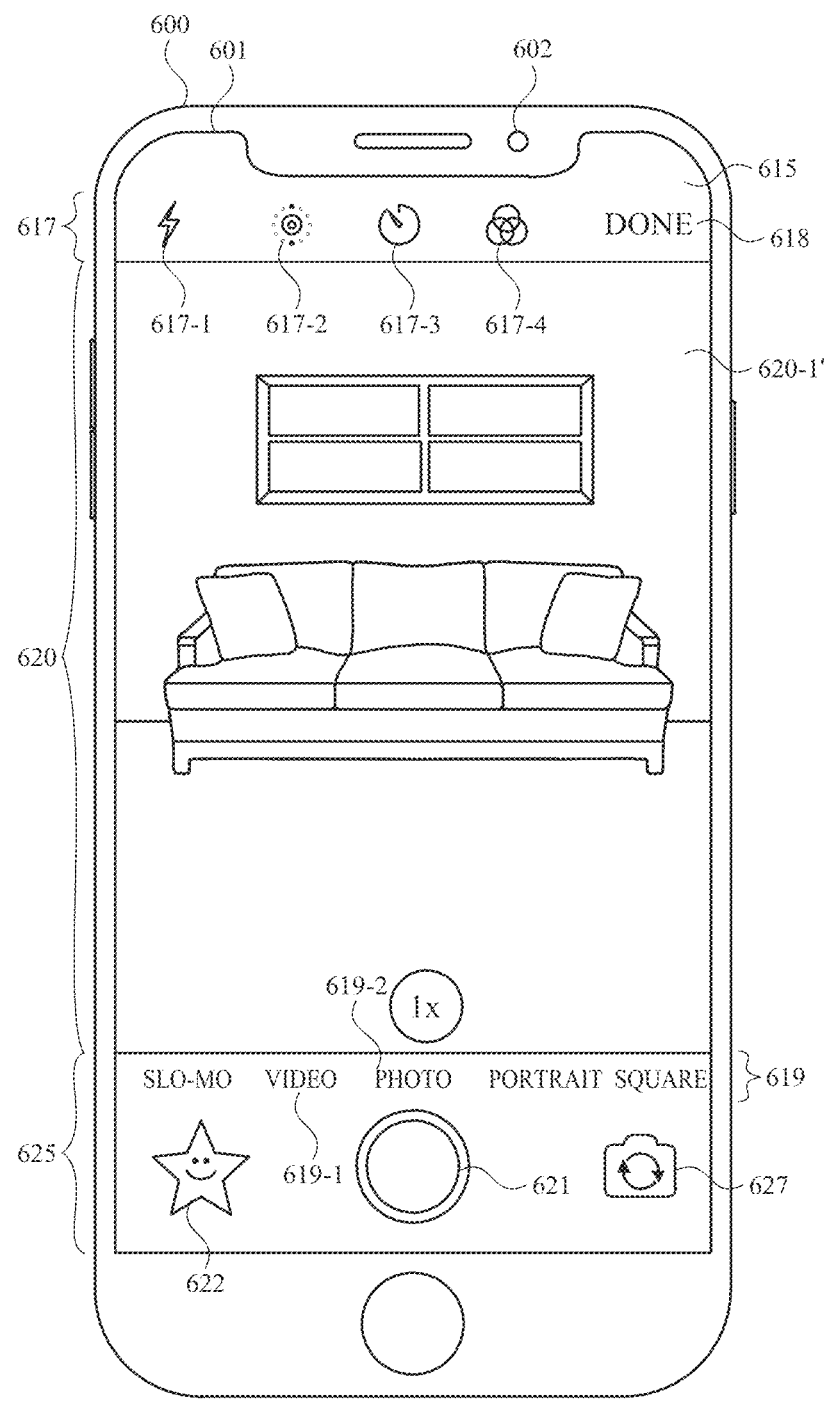

In FIG. 6C, in response to detecting input 616, device 600 launches a camera application associated with camera application affordance 609 and displays camera application user interface 615. Camera application user interface 615 includes image display region 620 which displays a representation of image data such as, for example, streamed image data (e.g., a live camera preview, live camera recording, or live video communications session) representing objects positioned within a field-of-view of a camera (e.g., a rear-facing camera or camera 602), or a media item such as, for example, a photograph or a video recording. In the embodiment illustrated in FIG. 6C, image display region 620 shows live camera preview 620-1' from a rear-facing camera of device 600.

Camera application user interface 615 also includes a region above image display region 620 that includes camera-specific affordances 617 and done affordance 618 for exiting camera application user interface 615. Camera-specific affordances include affordance 617-1 associated with a camera flash function, affordance 617-2 associated with a camera mode function, affordance 617-3 associated with a timer function, and affordance 617-4 associated with a filter function.

Camera application user interface 615 also includes camera options region 625 positioned below image display region 620. Camera options region 625 includes camera selector affordance 627 for switching between cameras (e.g., a rear-facing camera and camera 602), and camera option affordances 619 associated with different capture modes in which a camera can record image data. For example, video affordance 619-1 is associated with a function for activating a video recording capture mode of the camera, and photo affordance 619-2 is associated with a function for activating a still image capture mode of the camera. In the embodiments discussed below with respect to FIGS. 6C-6AX, device 600 is in the still image capture mode of operation associated with photo affordance 619-2. However, unless specified otherwise, these embodiments also apply to the video recording mode associated with video affordance 619-1.

Camera options region 625 further includes effects affordance 622 for enabling and disabling a mode of device 600 in which device 600 is enabled or disabled for displaying visual effects in image display region 620. This mode of device 600 is often referred to herein as an effects mode.

Camera options region 625 also includes capture affordance 621, which can be selected to capture image data represented in image display region 620. In some embodiments, device 600 captures the image data in a manner based on the currently enabled capture mode (e.g., video recording capture mode or image capture mode). In some embodiments, device 600 captures the image data depending on the type of gesture detected on capture affordance 621. For example, if device 600 detects a tap gesture on capture affordance 621, device 600 captures a still image of the image data represented in image display region 620 at the time the tap gesture occurs. If device 600 detects a tap-and-hold gesture on capture affordance 621, device 600 captures a video recording of the image data represented in image display region 620 during a period of time for which the tap-and-hold gesture persists. In some embodiments, the video recording stops when the finger lifts off of the affordance. In some embodiments, the video recording continues until a subsequent input (e.g., a tap input) is detected at a location corresponding to the affordance. In some embodiments, the captured image (e.g., still image or video recording) is then inserted into message-compose field 608 to be subsequently sent to a participant in the message conversation. In some embodiments, the captured image is sent directly to the participant in the message conversation without inserting the captured image in message-compose field 608.

Figure 6D:
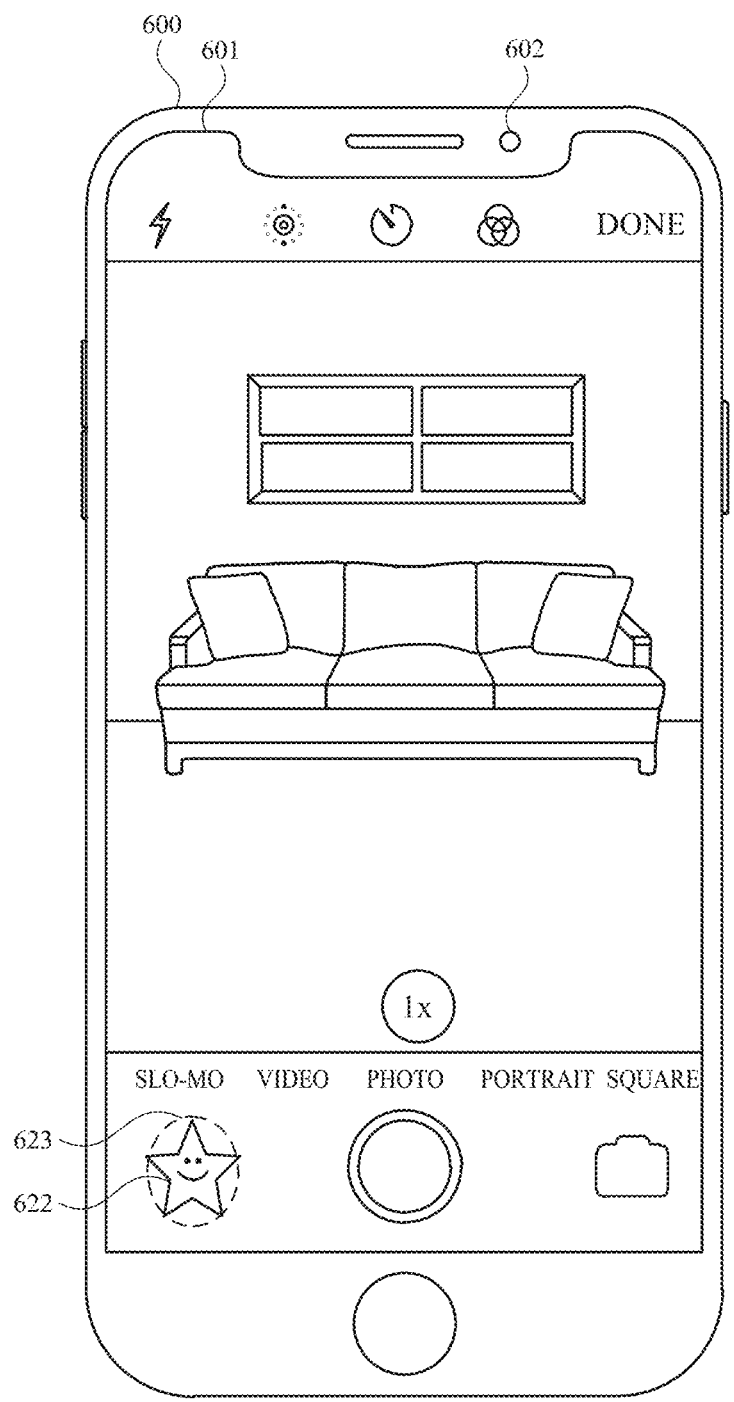

In FIG. 6D, device 600 detects input 623 (e.g., a tap gesture on display 601) on effects affordance 622.

Figure 6E:
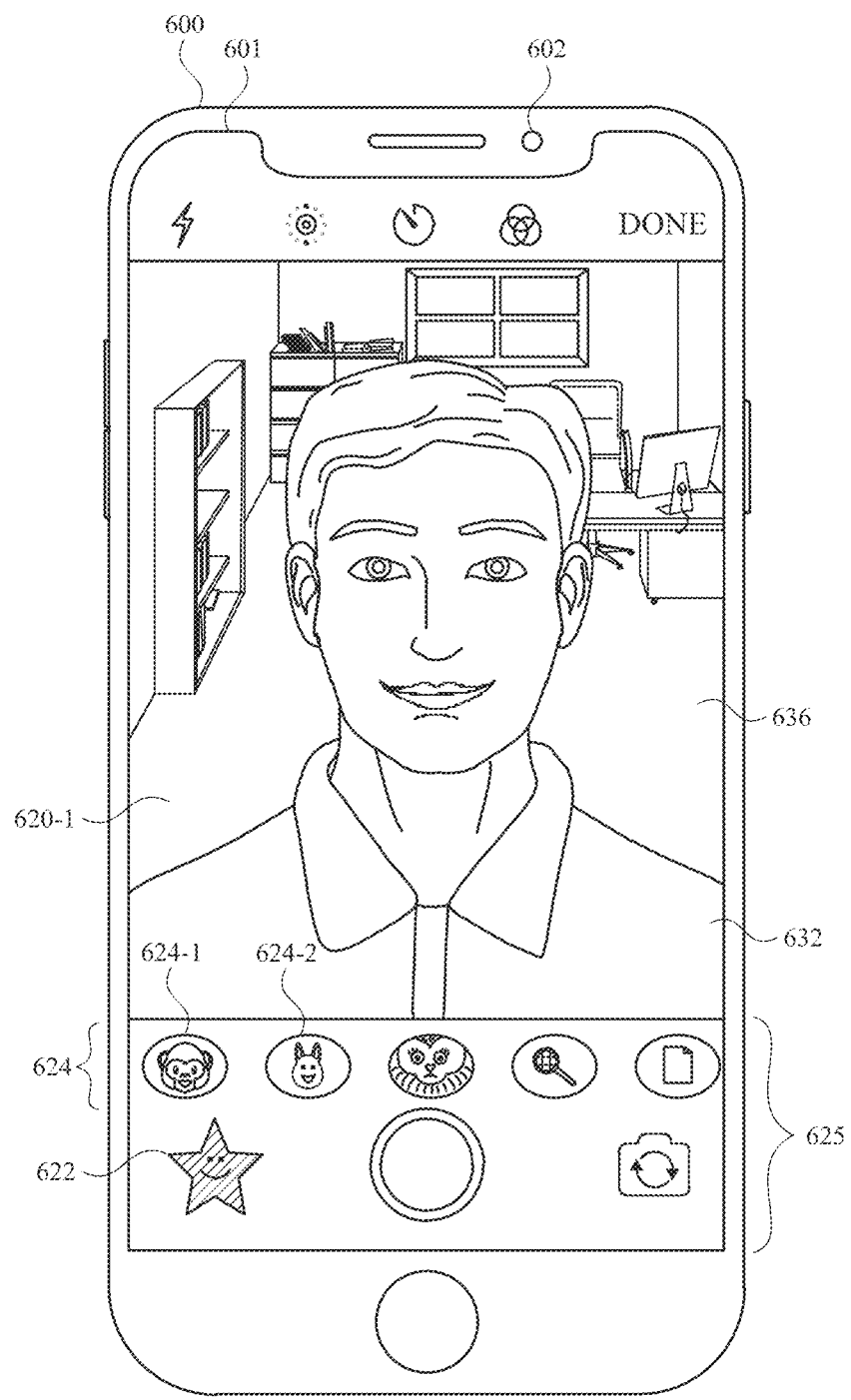

In FIG. 6E, in response to detecting input 623, device 600 activates camera 602 (e.g., switches from the rear-facing camera) and updates image display region 620 to display live camera preview 620-1 from camera 602, showing a representation of subject 632 positioned in the field-of-view of camera 602 and background 636 displayed behind subject 632. As discussed herein, image data captured using camera 602 includes, in some embodiments, depth data that can be used to determine a depth of objects in the field-of-view of camera 602. In some embodiments, device 600 parses objects (e.g., in image data) based on a detected depth of those objects, and uses this determination to apply the visual effects discussed herein. For example, device 600 can categorize subject 632 as being in the foreground of the live camera preview 620-1 and objects positioned behind the user as being in the background of the live camera preview 620-1. These background objects are referred to generally herein as background 636.

Device 600 also highlights effects affordance 622 to indicate visual effects are enabled for display, and updates camera options region 625 by replacing camera option affordances 619 with visual effects option affordances 624. The visual effects option affordances include avatar effects affordance 624-1 and sticker effects affordance 624-2. Visual effects option affordances 624 correspond to different visual effects that can be applied to the image displayed in image display region 620. By selecting one of the visual effect option affordances (e.g., 624-1 or 624-2) a menu is displayed with visual effects options corresponding to the selected visual effects option affordance.

A user can activate or deactivate the effects mode of device 600 by selecting effects affordance 622. When effects affordance 622 is highlighted, an effects mode of device 600 is enabled to display visual effects in image display region 620. If a user taps on highlighted affordance 622, effects affordance 622 is no longer highlighted, and the effects mode is disabled such that visual effects are not enabled for display in image display region 620. In some embodiments, when the effects mode is enabled, device 600 updates the image shown in image display region 620 to display one or more visual effects that have been applied to the image (including visual effects that are applied to a live image stream) and, when the effects mode is disabled, device 600 removes or hides the visual effects from the image shown in image display region 620.

Figure 6F:
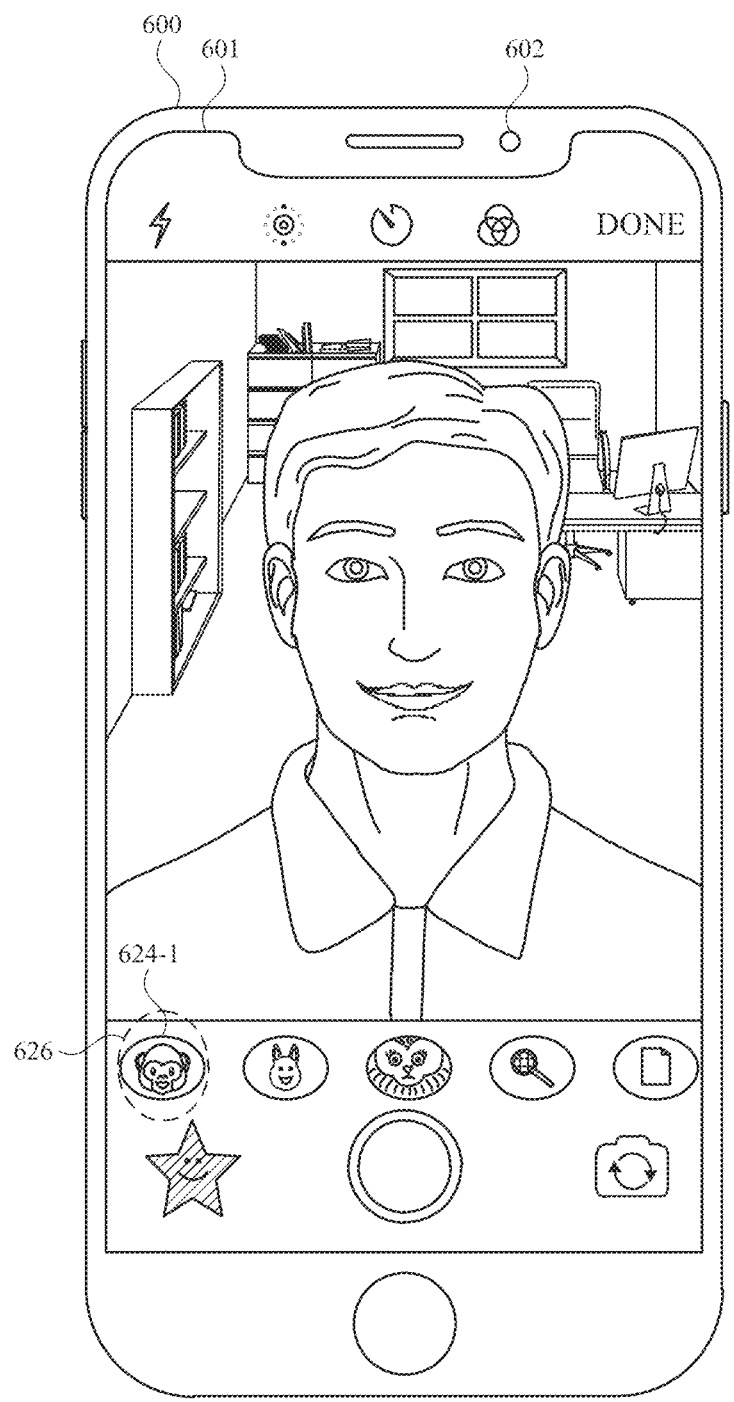

In FIG. 6F, device 600 detects input 626 (e.g., a tap gesture on display 601) on avatar effects affordance 624-1.

Figure 6G:
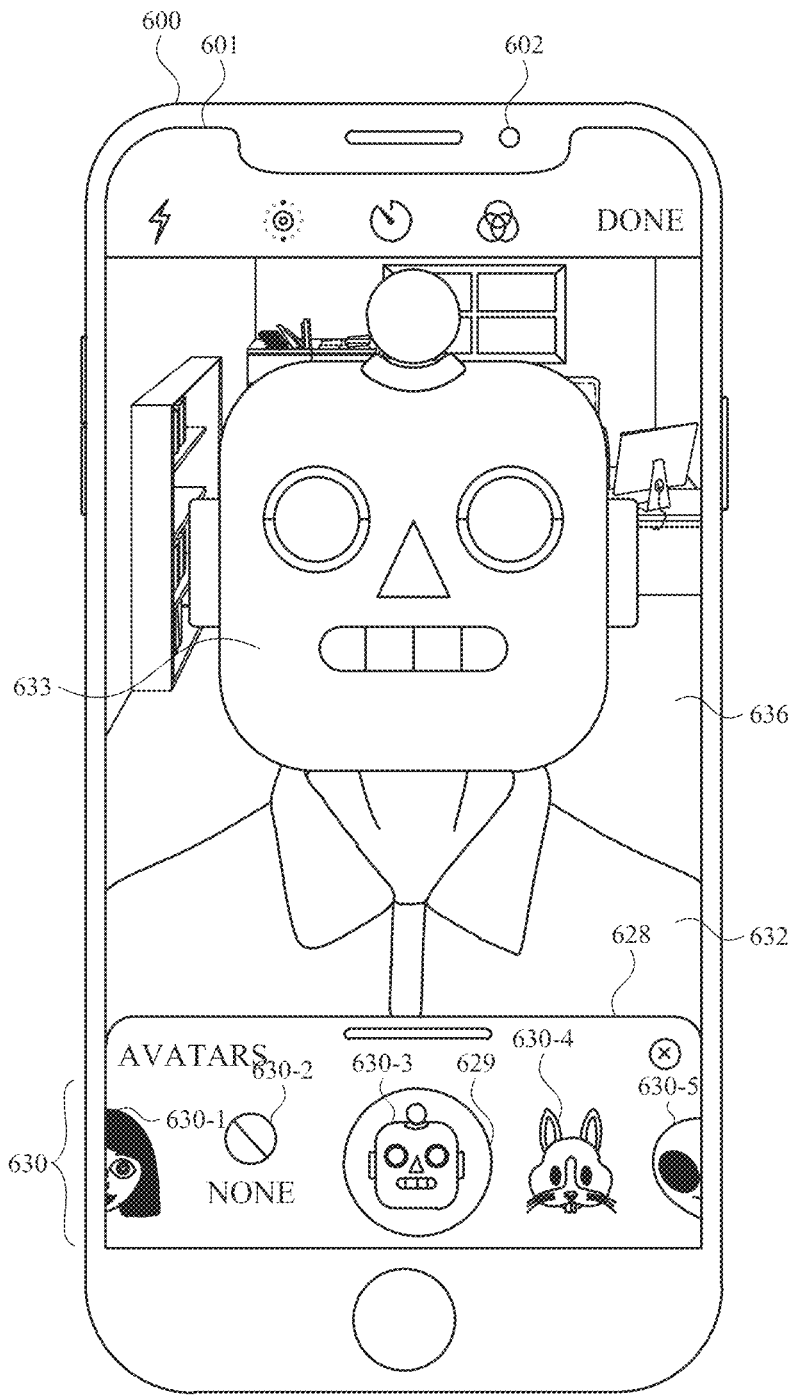

In FIG. 6G, in response to detecting input 626, device 600 displays avatar options menu 628 with a scrollable listing of avatar options 630. Avatar options menu 628 also includes selection region 629 for indicating a selected one of avatar options 630. As shown in FIG. 6G, robot avatar option 630-3 is positioned in selection region 629, which indicates robot avatar option 630-1 is selected. Other avatar options 630 shown in FIG. 6G include customized woman avatar option 630-1, null avatar option 630-2, rabbit avatar option 630-4, and alien avatar option 630-5. As discussed in detail below, null avatar option 630-2 corresponds to an avatar option for which no avatar is displayed on the subject in image display region 620. In some embodiments, null avatar option 630-2 is the default selected avatar option when avatar options menu 628 is displayed.

Avatar options 630 correspond to a virtual avatar visual effect applied to a representation of the subject in image display region 620. Specifically, each avatar option 630 corresponds to a virtual avatar that, when selected, is transposed onto the face of the subject in the image display region, while other portions of the image in image display region (such as a background or other portions of the user, such as their body) remain displayed. A user (e.g., subject 632) positioned in the field-of-view of camera 602 can control visual aspects of the virtual avatar by changing the pose (e.g., rotation or orientation) of their face, including moving various facial features (e.g., winking, sticking out their tongue, smiling, etc.). Details for controlling display and movement of virtual avatars is provided in U.S. patent application Ser. No. 15/870,195, which is hereby incorporated by reference for all purposes.

In some embodiments, a virtual avatar is a representation of the user that can be graphically depicted (e.g., a graphical representation of the user). In some embodiments, the virtual avatar is non-photorealistic (e.g., is cartoonish). In some embodiments, the virtual avatar includes an avatar face having one or more avatar features (e.g., avatar facial features). In some embodiments, the avatar features correspond (e.g., are mapped) to one or more physical features of a user's face such that detected movement of the user's physical features (e.g., as determined based on a camera such as a depth sensing camera) affects the avatar feature (e.g., affects the feature's graphical representation).

In some examples, a user is able to manipulate characteristics or features of a virtual avatar using a camera sensor (e.g., camera module 143, optical sensor 164) and, optionally, a depth sensor (e.g., depth camera sensor 175). As a user's physical features (such as facial features) and position (such as head position, head rotation, or head tilt) changes, the electronic device detects the changes and modifies the displayed image of the virtual avatar to reflect the changes in the user's physical features and position. In some embodiments, the changes to the user's physical features and position are indicative of various expressions, emotions, context, tone, or other non-verbal communication. In some embodiments, the electronic device modifies the displayed image of the virtual avatar to represent these expressions, emotions, context, tone, or other non-verbal communication.

In some embodiments, the virtual avatars are customizable avatars (e.g., customizable avatar 835). Customizable avatars are virtual avatars that can be selected and customized by a user, for example, to achieve a desired appearance (e.g., to look like the user). The customizable avatars generally have an appearance of a human character, rather than a non-human character such as an anthropomorphic construct of an animal or other nonhuman object. Additionally, features of the avatar can be created or changed, if desired, using an avatar editing user interface (e.g., such as the avatar editing user interface discussed below with respect to FIGS. 8AA-8AB). In some embodiments, customizable avatars can be created and configured to achieve a customized physical appearance, physical construct, or modeled behavior.

In some embodiments, the virtual avatars are non-customizable avatars. Non-customizable avatars are virtual avatars that can be selected by a user, but generally are not fundamentally configurable, though their appearance can be altered via face tracking, as described in more detail below. Instead, non-customizable avatars are preconfigured and generally do not have feature components that can be modified by a user. In some embodiments, the non-customizable avatars have an appearance of a non-human character, such as an anthropomorphic construct of an animal or other nonhuman object (e.g., see robot avatar 633, rabbit avatar 634). Non-customizable avatars cannot be created by a user or modified to achieve a significant change in the physical appearance, physical construct, or modeled behavior of non-customizable avatars.

Because robot avatar 630-3 is selected in FIG. 6G, device 600 displays robot avatar 633 positioned on the face of subject 632 (e.g., the user) displayed in image display region 620. Device 600 displays the avatar so that it remains fixed on the subject's face as he moves within the field-of-view of camera 602. Device 600 also continually modifies the avatar based on any detected changes in the user's face, including pose of the face or changes in facial expressions, while maintaining the displayed subject's body and background 636 in the image shown in image display region 620.

Figure 6H:
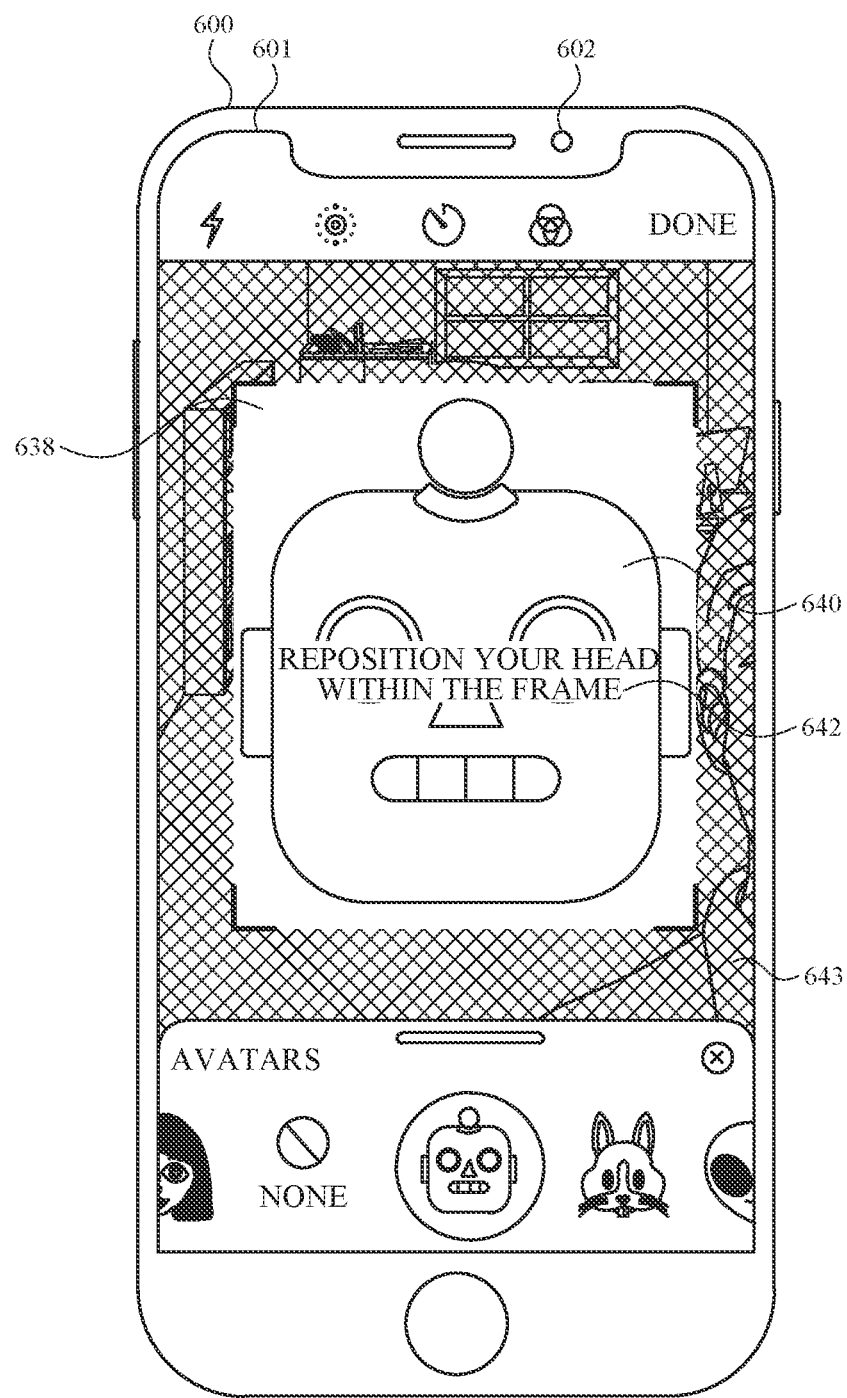

As shown in FIG. 6H, if device 600 detects that the user's head moves beyond the field-of-view of camera 602, device 600 displays, for example, prompt 638 containing representation 640 of the selected avatar (e.g., robot avatar) and message 642 instructing the user to reposition their head in the field-of-view of camera 602. In some embodiments, prompt 638 is displayed with a blurred background 643 (including blurring the user 632 and background 636). In some embodiments, displaying prompt 638 includes displaying an animation of the selected avatar returning to a center location of image display region 620, and showing a slowed movement of the avatar and its features as they appear to settle to a stop based on a physics model of the avatar features.

Figure 6I:
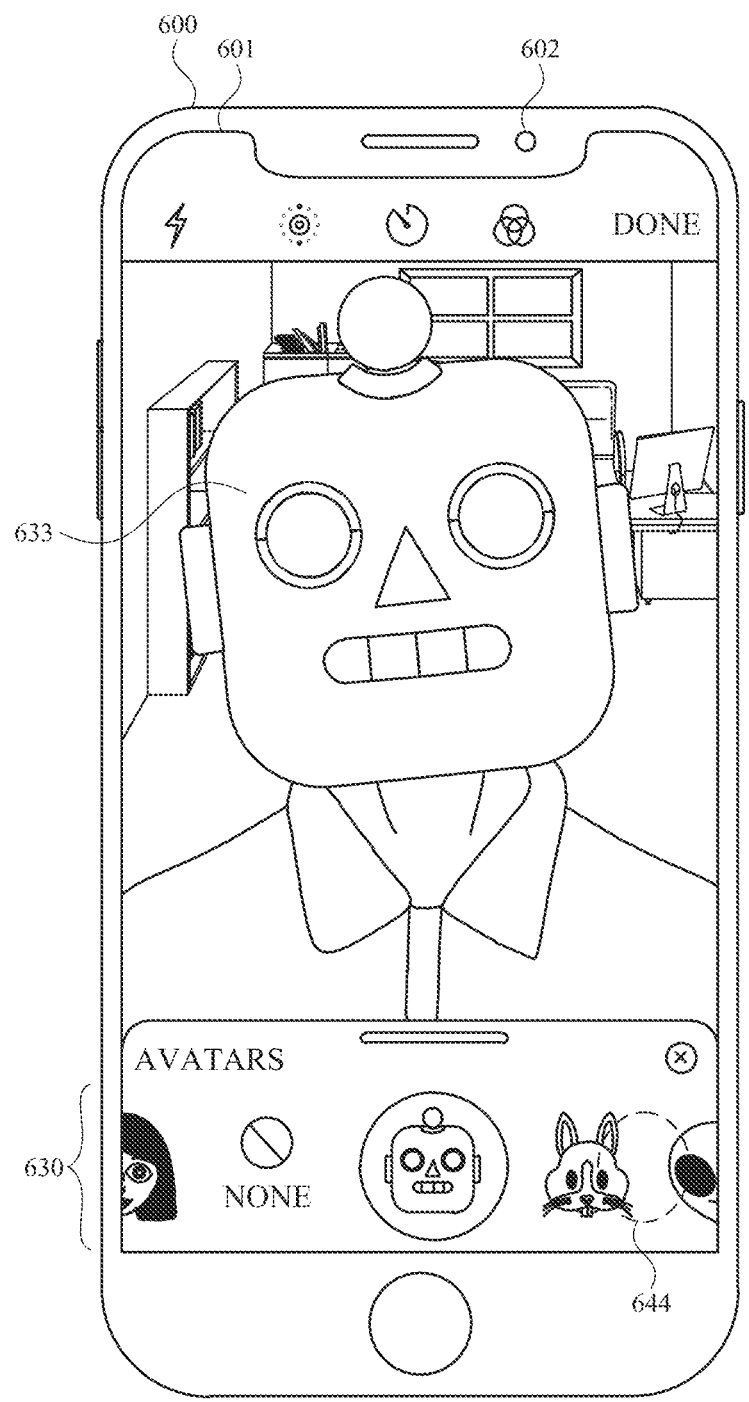

Once device 600 detects the user's head returning to the field-of-view of camera 602, device continues updating the selected avatar (e.g., robot avatar 633) based on changes detected in the user's face, as shown in FIG. 6I. In some embodiments, when device 600 detects the user's face returning to the field-of-view of camera 602, device 600 displays avatar 633 moving from the center position of image display region 620 to the position of the user's face, and resumes modifying the avatar based on detected changes to the user's face.

Figure 6J:
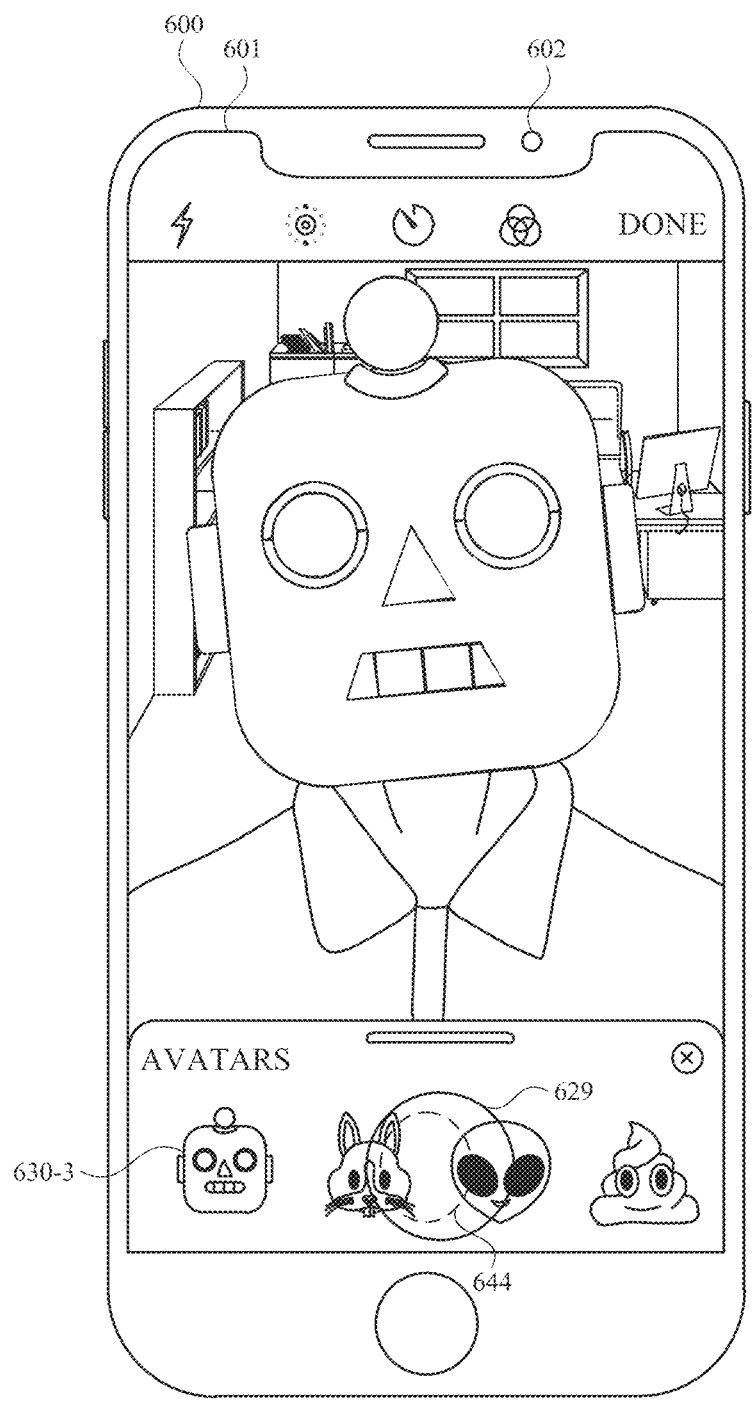
Figure 6K:
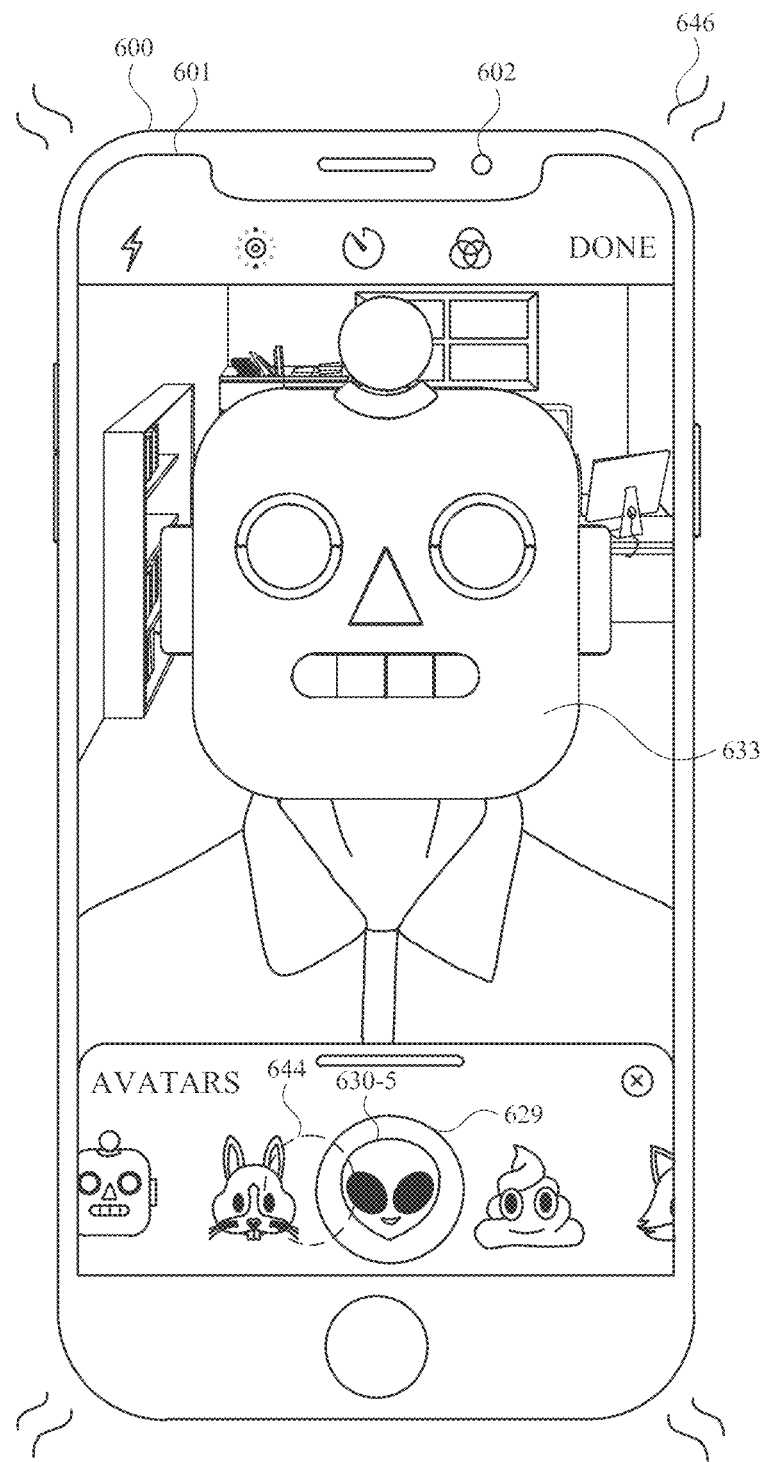
Figure 6L:
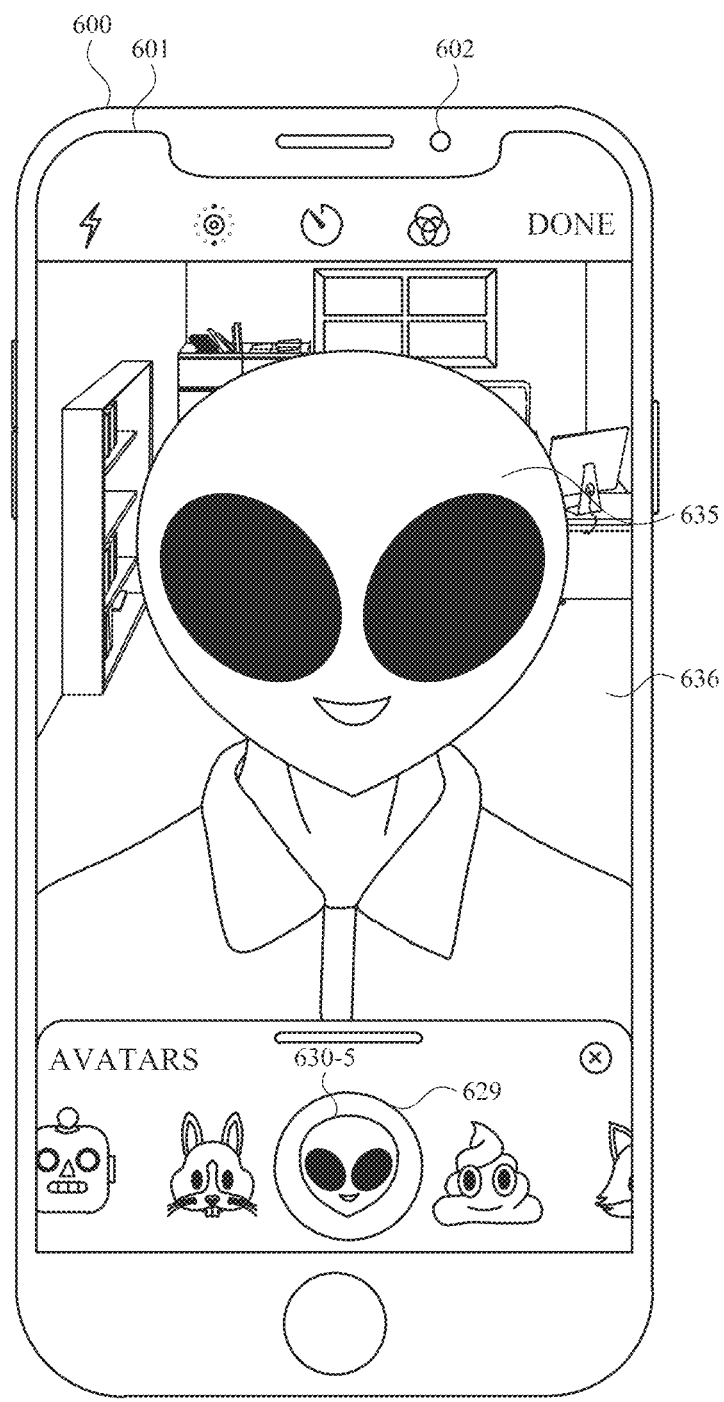

In FIGS. 6I-6K, device 600 detects input 644 (e.g., a scrolling gesture on display 601) on the displayed list of avatar options 630. As input 644 moves in a leftward direction across display 601, device 600 displays avatar options 630 scrolling to the left to reveal additional avatar options (e.g., a poop avatar option and a fox avatar option). In some embodiments, as one of the avatar options enters selection region 629, device produces a haptic feedback (e.g., a tactile output, with or without an audio output) to indicate to the user that termination of input 644 at that time would result in selection of the avatar option currently positioned within selection region 629. For example, in FIG. 6K, device 600 produces haptic feedback 646 when alien avatar option 630-5 is positioned within selection region 629.

In FIG. 6J, device 600 detects termination of input 644 and determines alien avatar option 630-5 is positioned within selection region 629. As a result, device 600 replaces robot avatar 633 with alien avatar 635 corresponding to selected alien avatar option 630-5, while maintaining display of the subject's body and background 636. In some embodiments, replacing the previously selected avatar (e.g., robot avatar 633) with the currently selected avatar (e.g., alien avatar 635) includes displaying an animation of the previously selected avatar moving off-screen (e.g., out of image display region 620) and an animation of currently selected avatar moving from avatar options menu 628 to the user's face in image display region 620. In some embodiments, face tracking of the currently selected avatar begins as the avatar moves from avatar options menu 628 to the user's face. In some embodiments, the background is blurred while the avatar switching operation occurs.

Figure 6M:
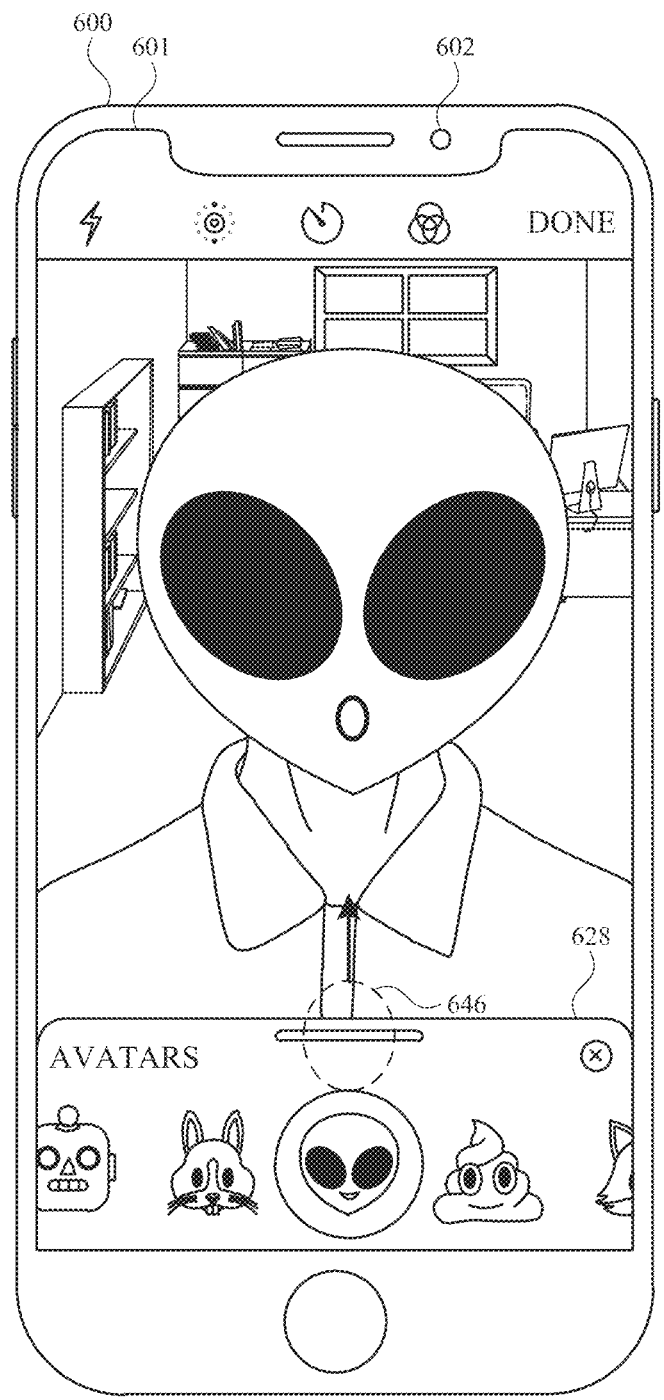
Figure 6N:
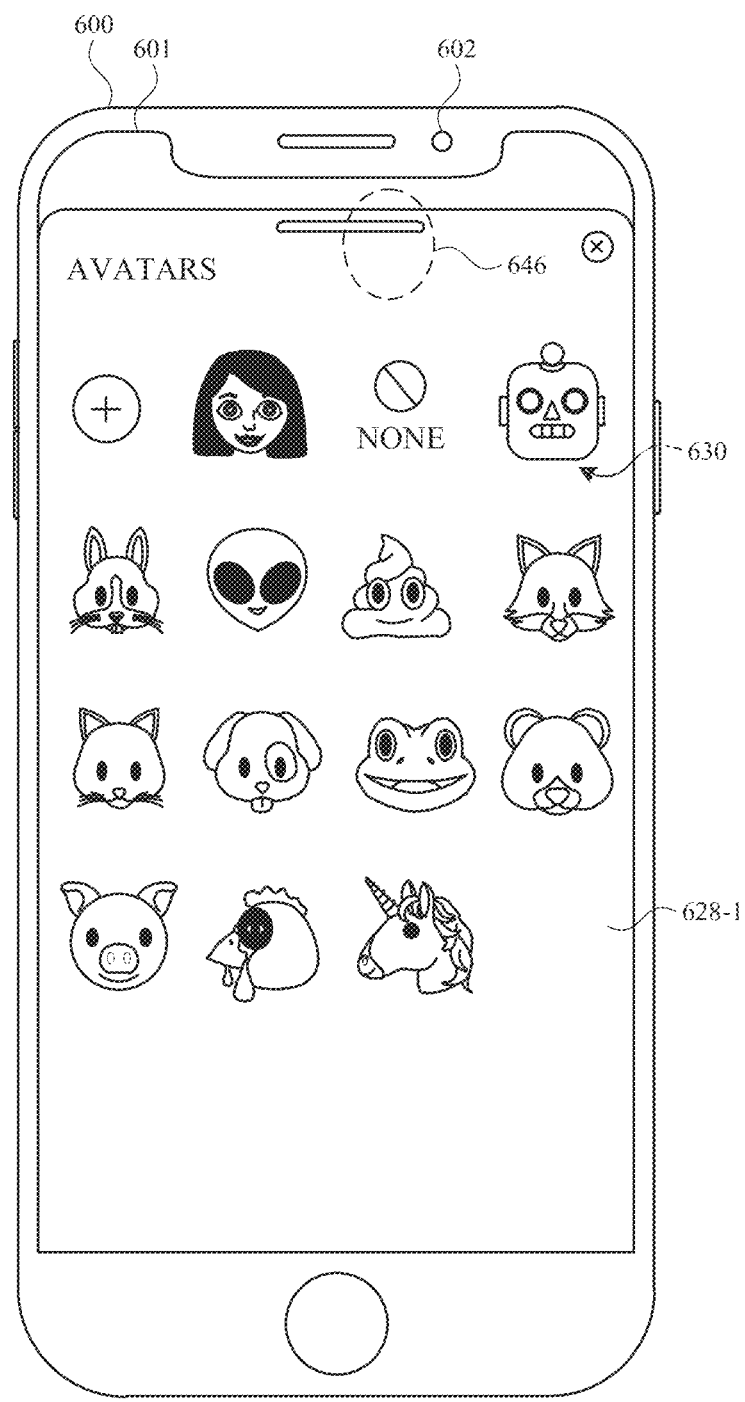

In FIGS. 6M-6N, device 600 detects a vertical gesture 646 (e.g., a vertical swipe or touch-and-drag on display 601) on avatar options menu 628 and, in response, enlarges avatar options menu 628 to enlarged view 628-1, as shown in FIG.

Figure 6O:
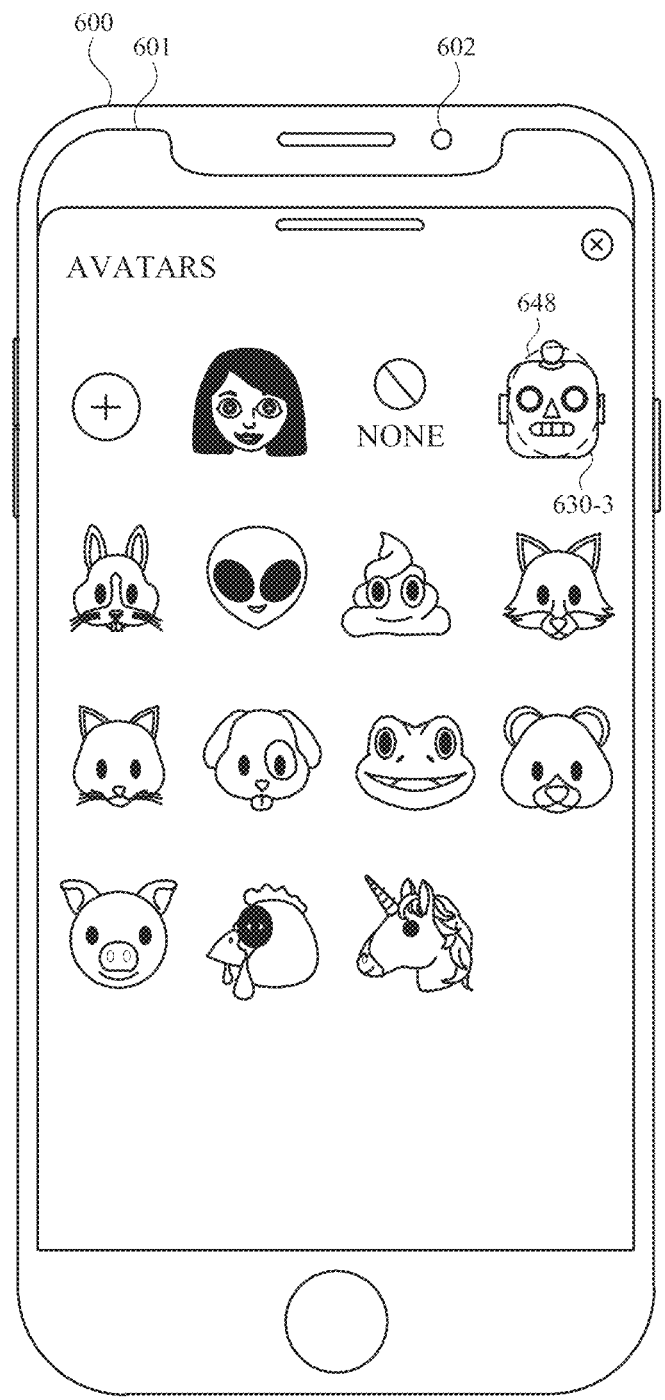

6N. In FIG. 6N, avatar options 630 are arranged in a matrix and can be selected as shown in FIG. 6O (e.g., gesture 648 selects robot avatar option 630-3) to display a different avatar in image display region 620.

Figure 6P:

In FIG. 6P, in response to gesture 648, device 600 shows (e.g., by de-enlarging the meu) the avatar options menu 628 with selected robot avatar option 630-3 (positioned in selection region 629) and robot avatar 633 displayed on the user's head in image display region 620.

Figure 6Q:
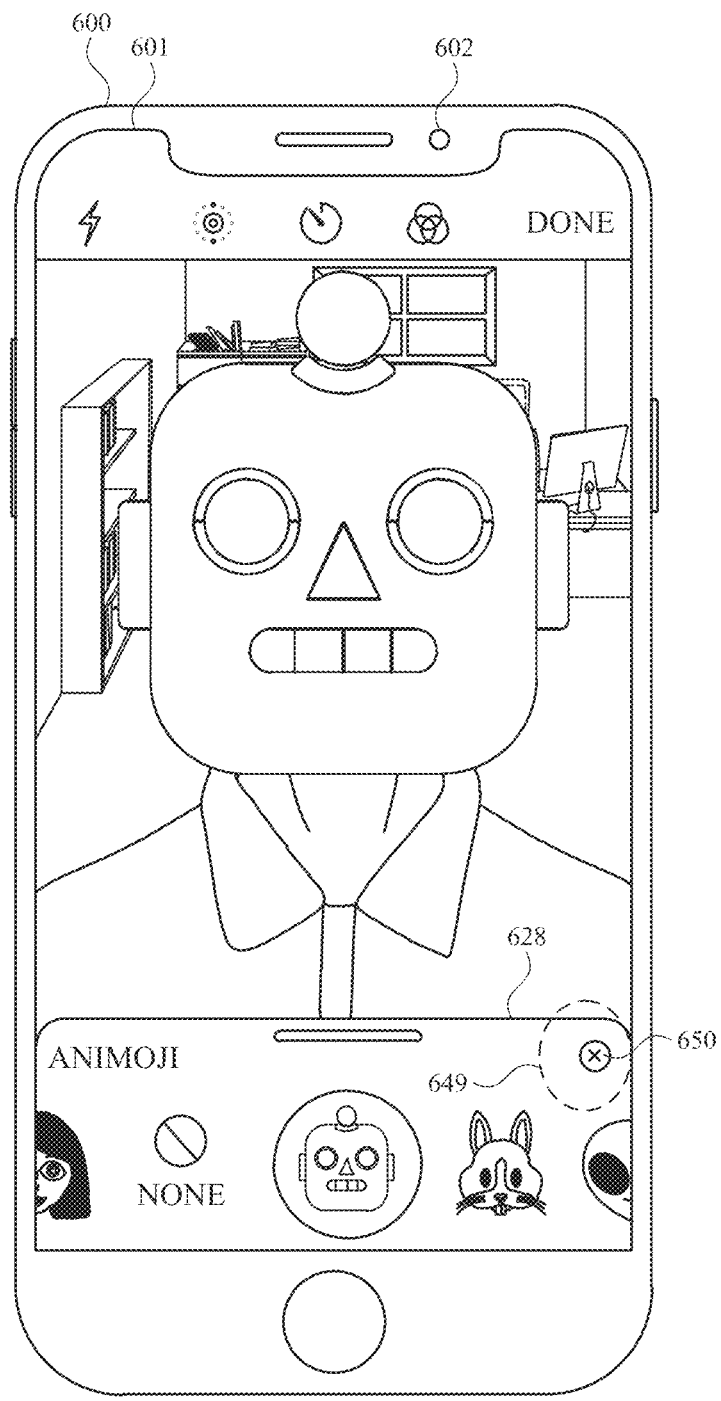
Figure 6R:
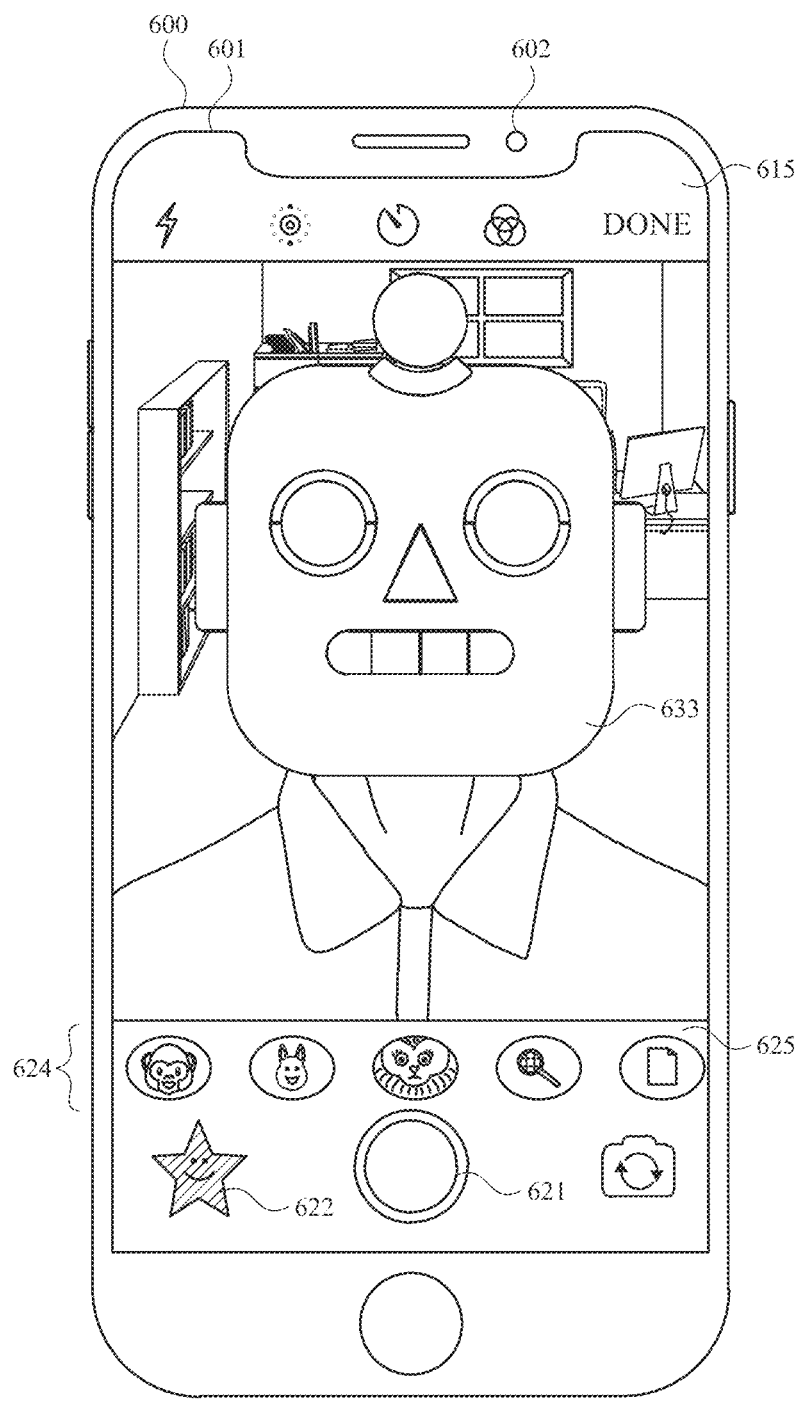

In FIG. 6Q, device 600 detects input 649 (e.g., a tap gesture on display 601) on close icon 650 to close application options menu 628 and return to the camera user interface 615 shown in FIG. 6R, showing camera options region 625, while maintaining display of robot avatar 633 on the user's face in an image stream (e.g., live camera preview) on image display region 620. Camera options region 625 shows capture affordance 621, visual effects option affordances 624, and highlighted effects affordance 622. The user can select avatar menu affordance 624-1 to again display avatar options menu 628, as shown below in FIGS. 6S and 6T.

Figure 6S:
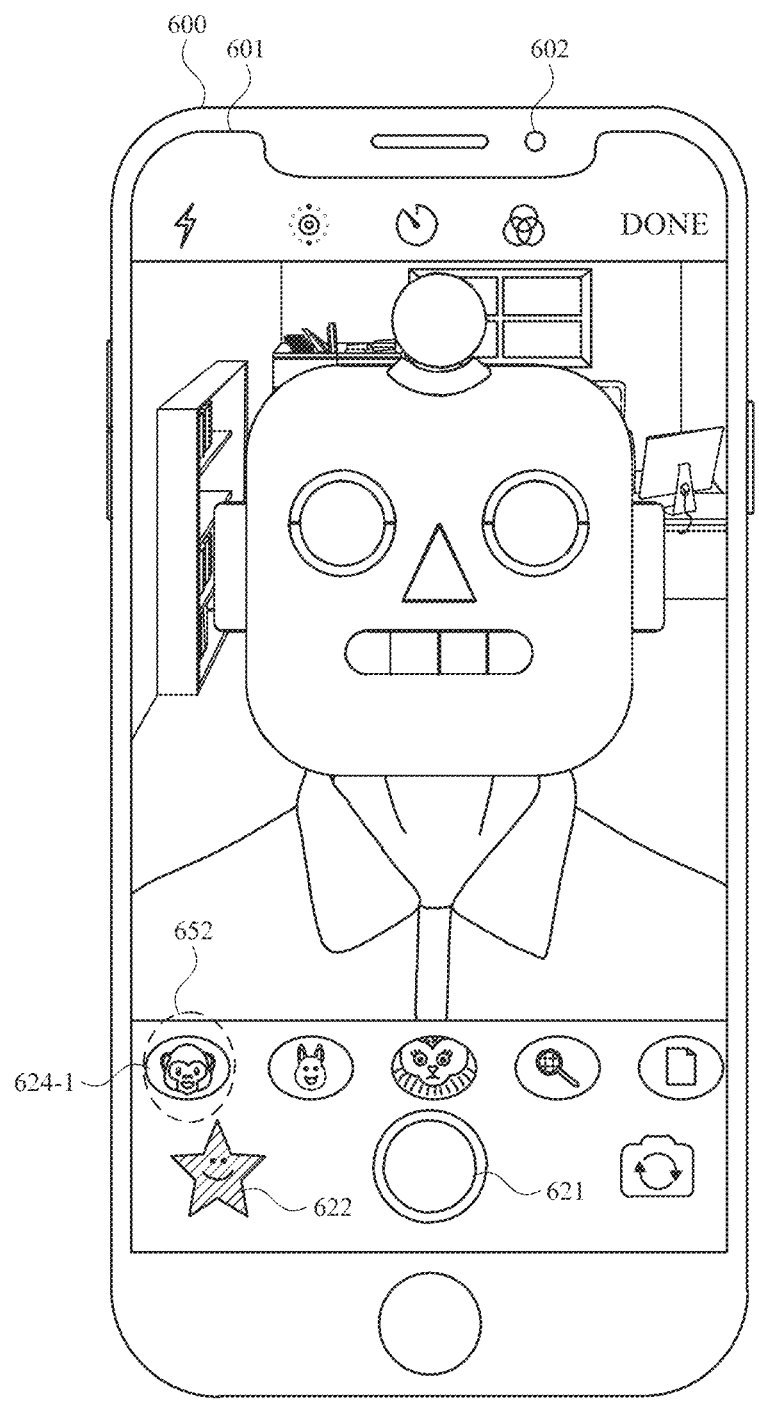
Figure 6T:
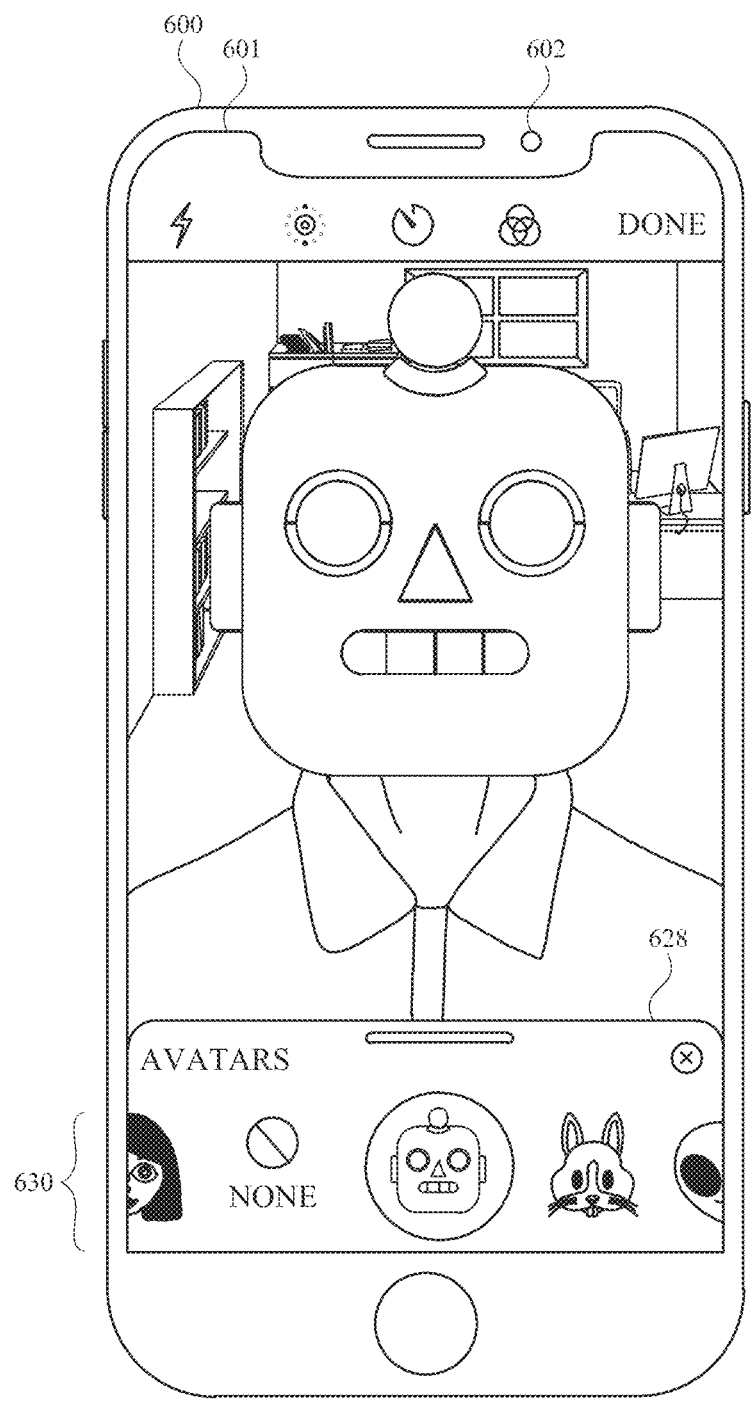

For example, in FIG. 6S, device 600 detects input 652 (e.g., tap gesture on display 601) on avatar effects affordance 624-1. In FIG. 6T, in response to detecting input 652, device 600 displays avatar options menu 628 having avatar options 630, which replaces camera options region 625, including capture affordance 621, effects affordance 622, and visual effects option affordances 624. The avatar options menu 628 can be closed again by selecting close affordance 650, as previously discussed, returning again to the camera application user interface 615 as shown in FIG. 6U.

Figure 6U:
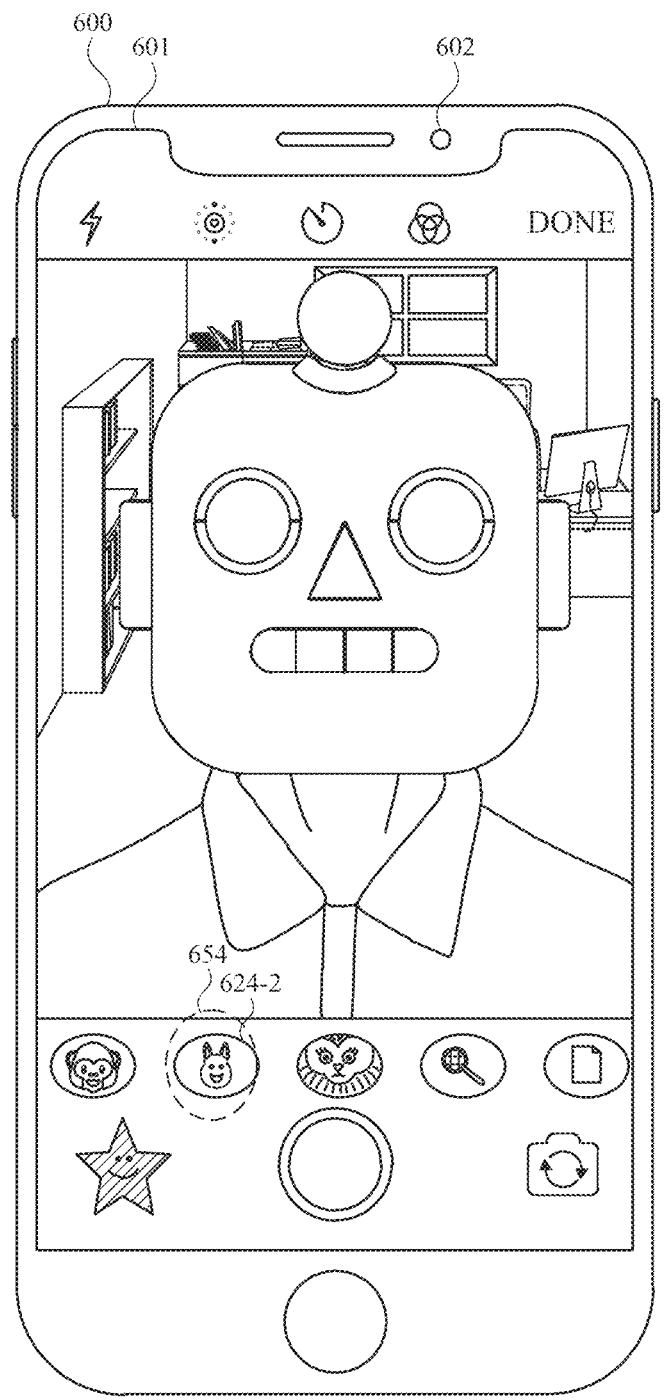
Figure 6V:
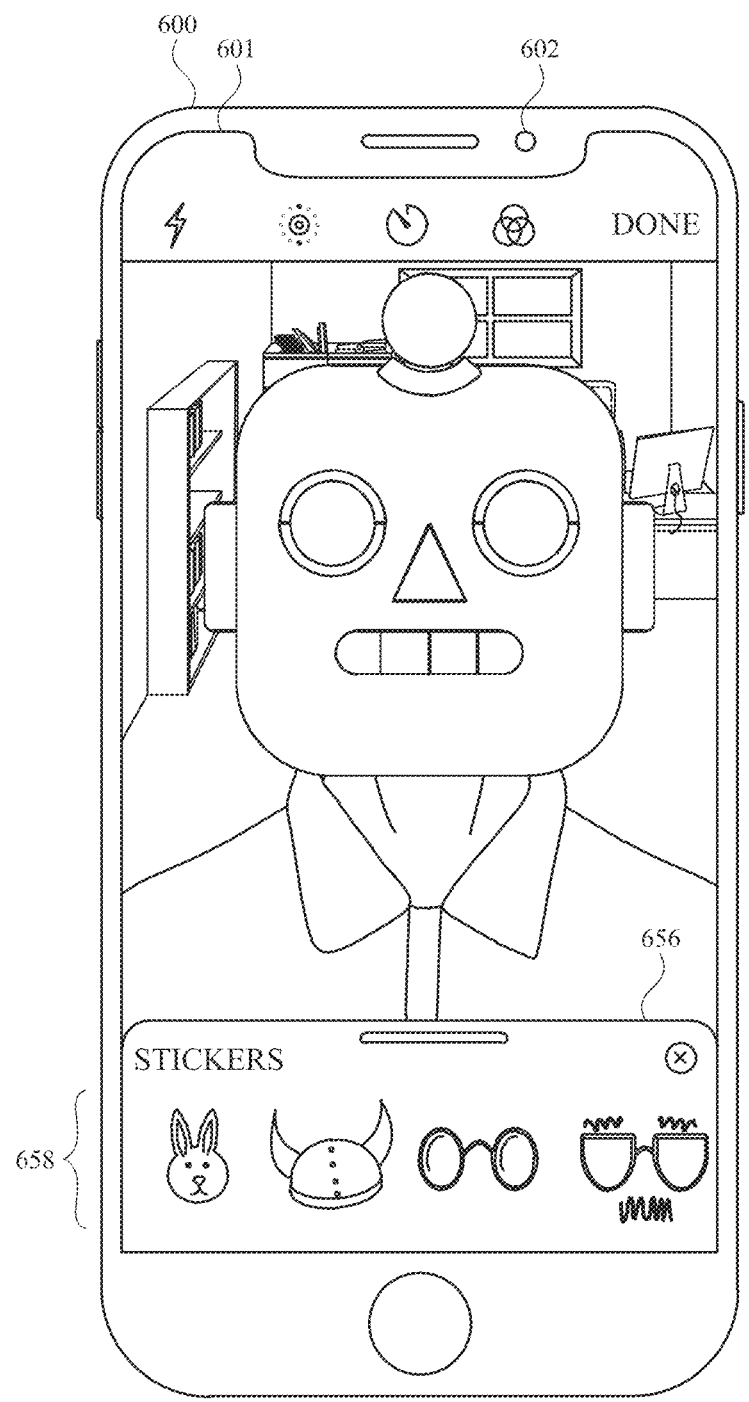
Figure 6W:
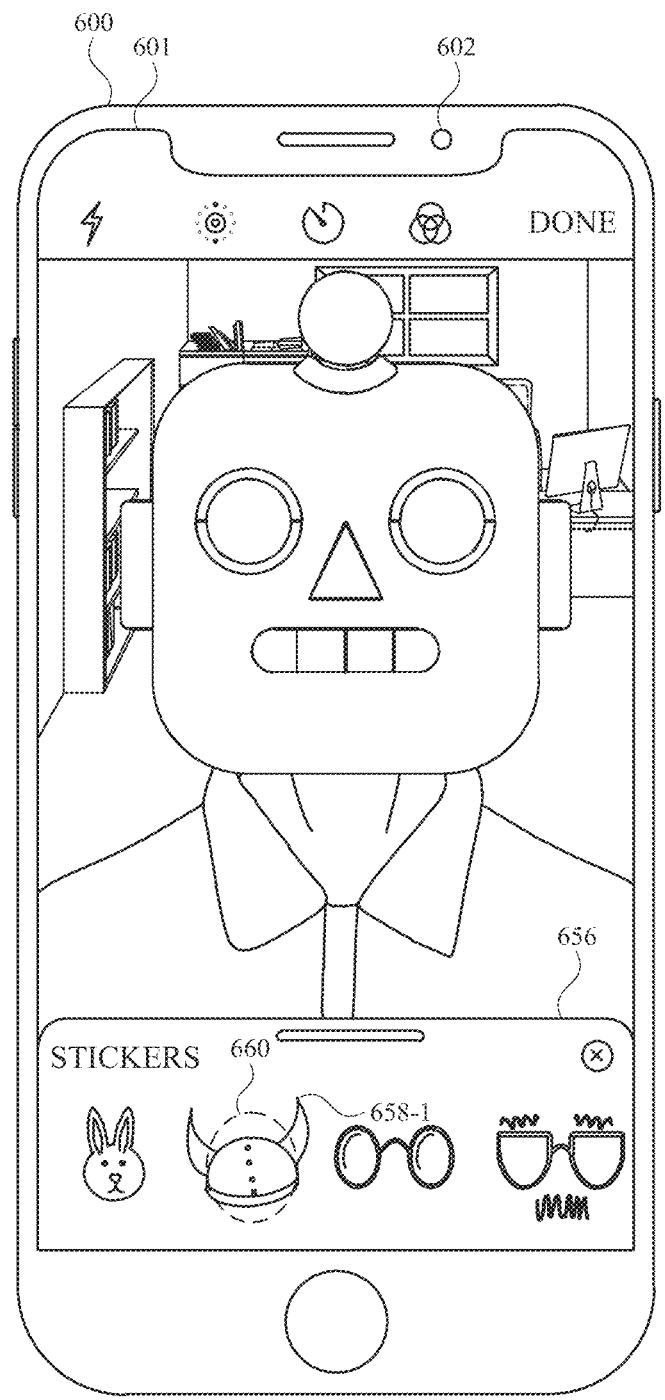
Figure 6X:
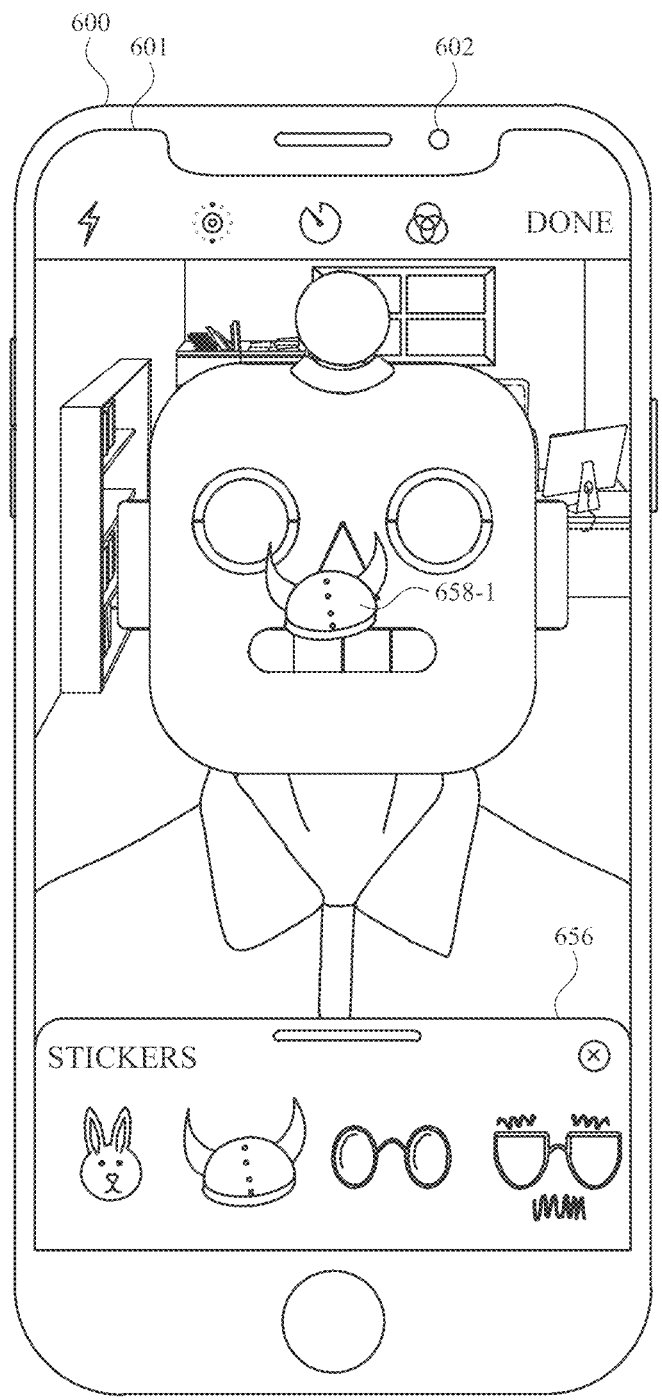

In FIG. 6U, device 600 detects input 654 (e.g., tap gesture on display 601) on sticker effects affordance 624-2. In FIG. 6V, in response to detecting input 654, device 600 displays sticker options menu 656 having a scrollable listing of stickers 658. The stickers are static graphical objects that may be selected by a user and applied to the image in image display region 620. In some embodiments, a sticker can be selected by a touch-and-drag gesture that initiates on the selected sticker, drags the sticker to a desired location, and then places the sticker at the desired location by terminating the drag (e.g., lifting finger). In some embodiments a sticker can be selected by a tap gesture, and the corresponding sticker is then displayed at a position on the image display region 620. An example of such an embodiment is shown in FIGS. 6W-6X, showing tap gesture 660 on helmet sticker 658-1, which is then displayed in the center of image display region 620.

Figure 6Y:
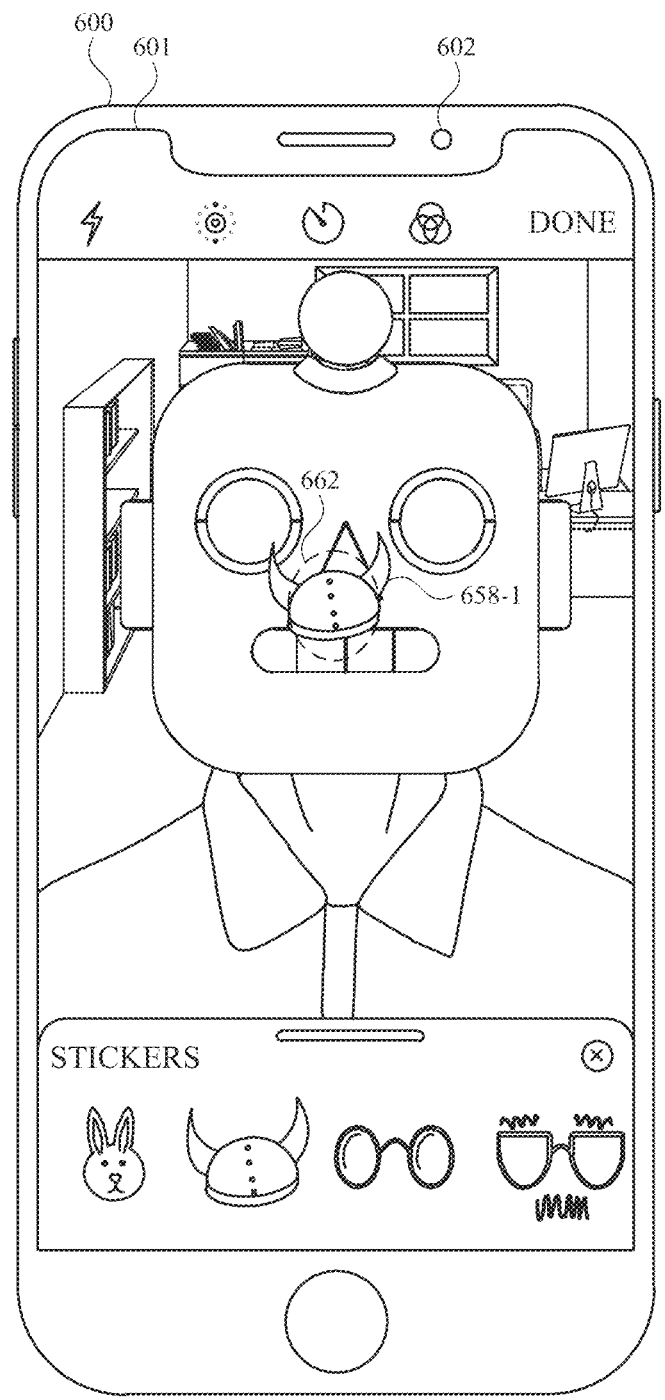
Figure 6Z:
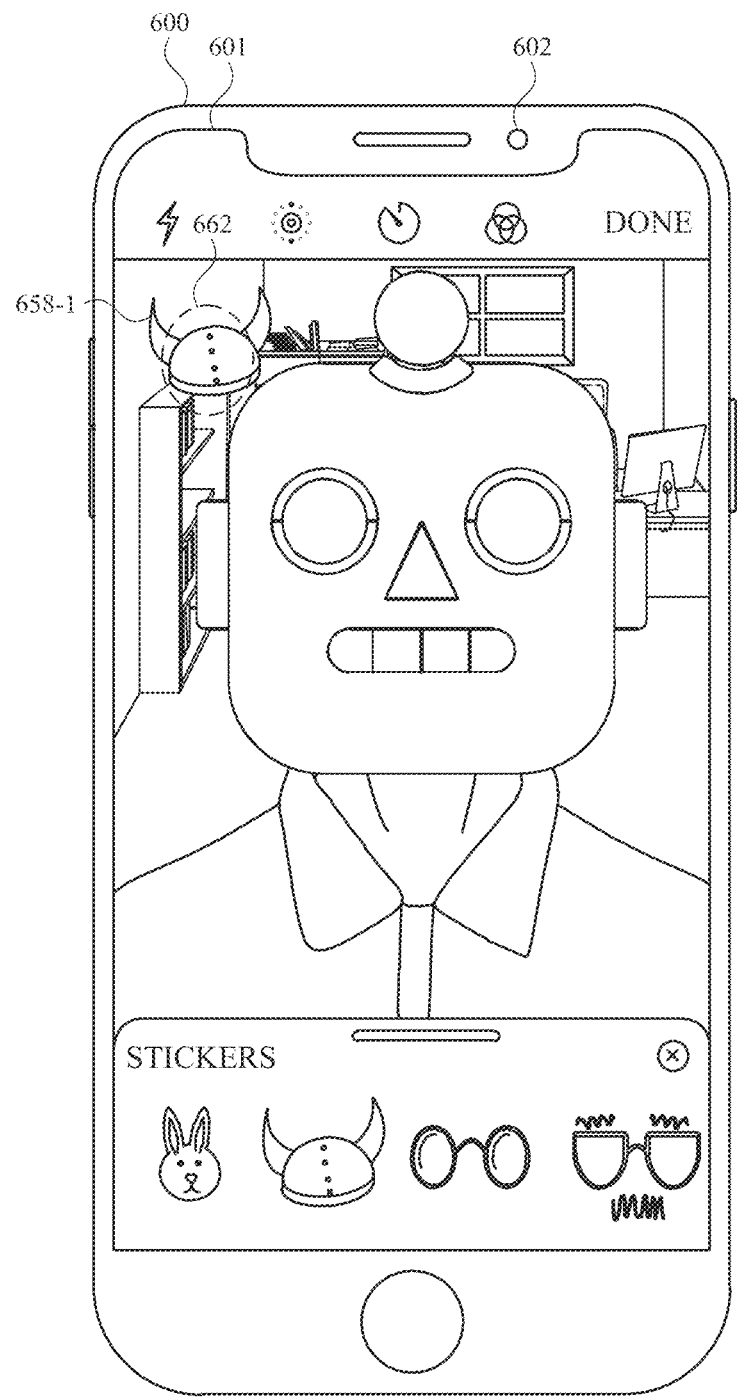
Figure 6A:
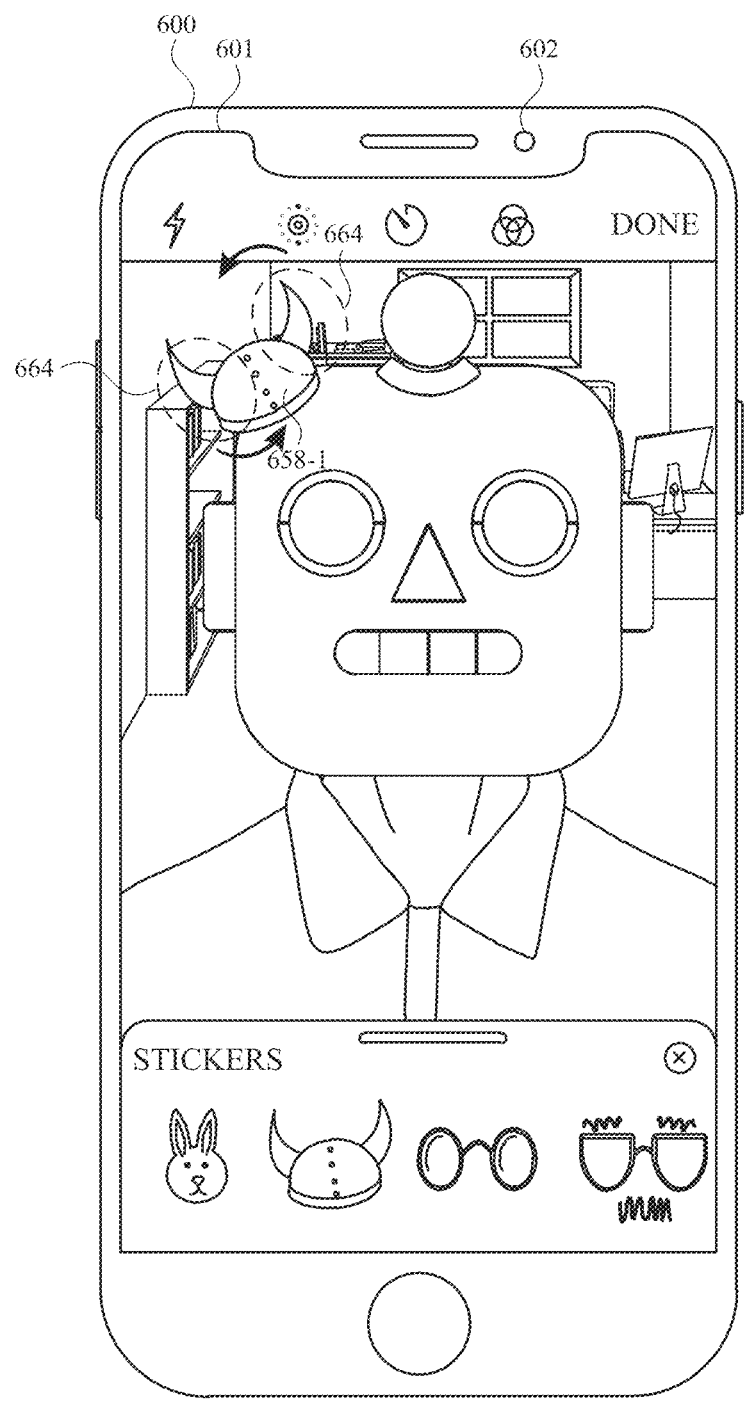
Figure 6A:
Figure 6A:
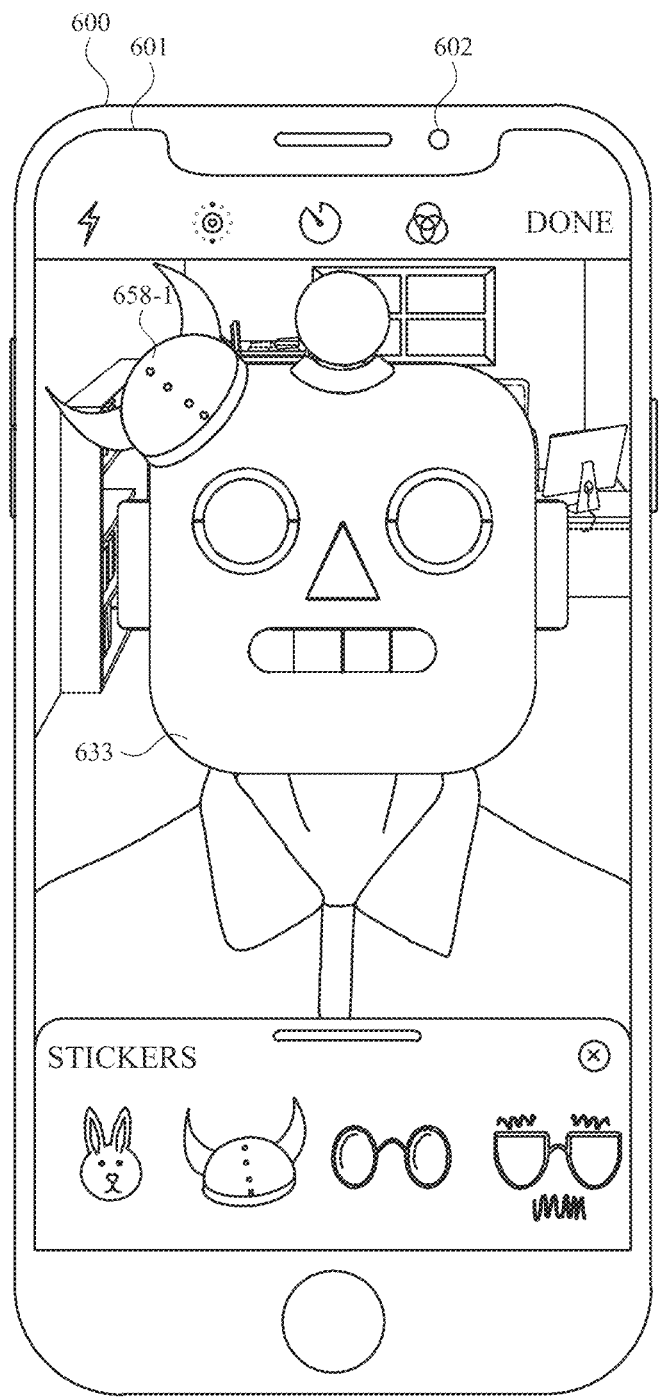
Figure 6A:
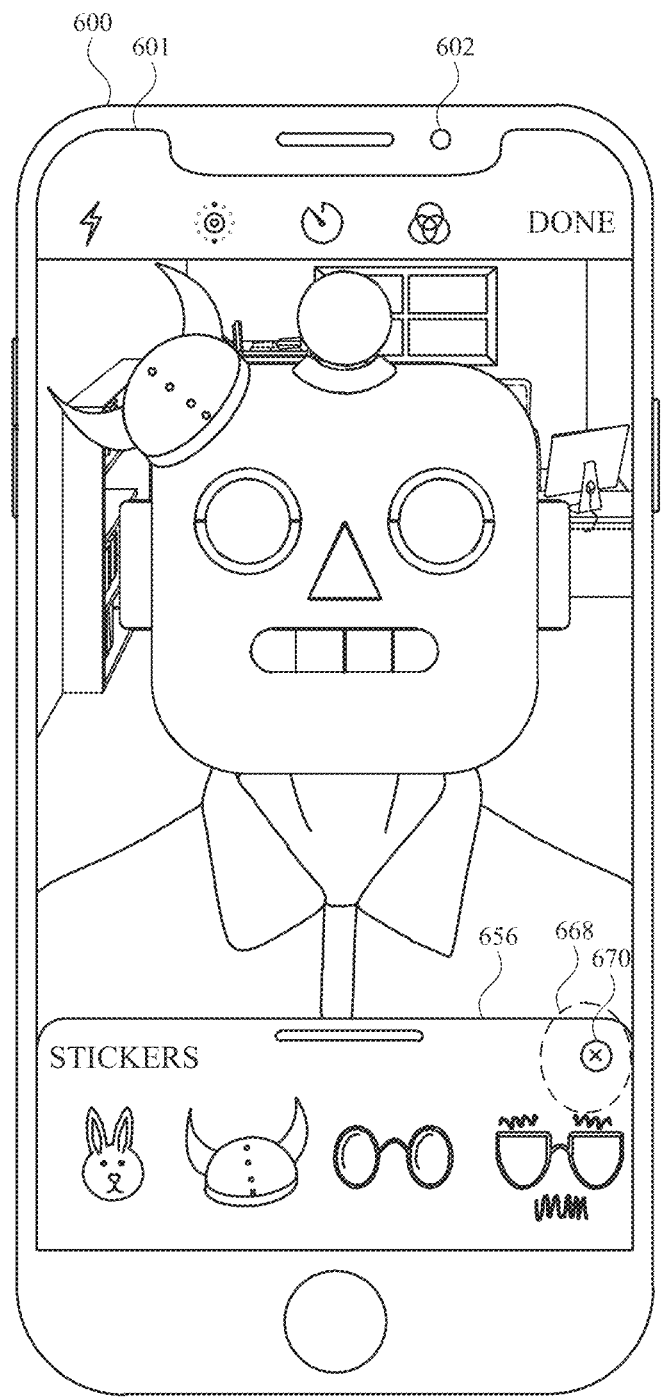
Figure 6A:
Figure 6A:
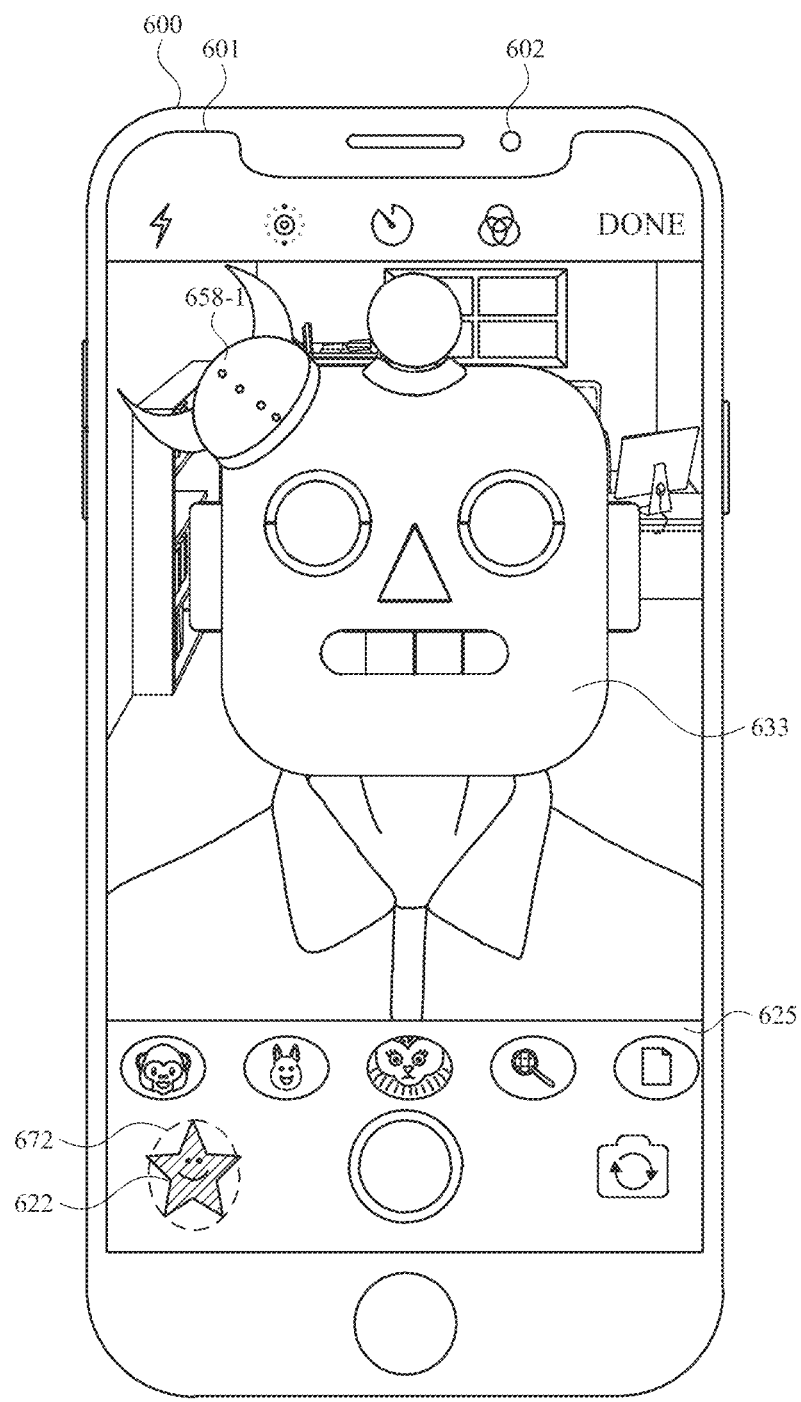
Figure 6A:
Figure 6A:
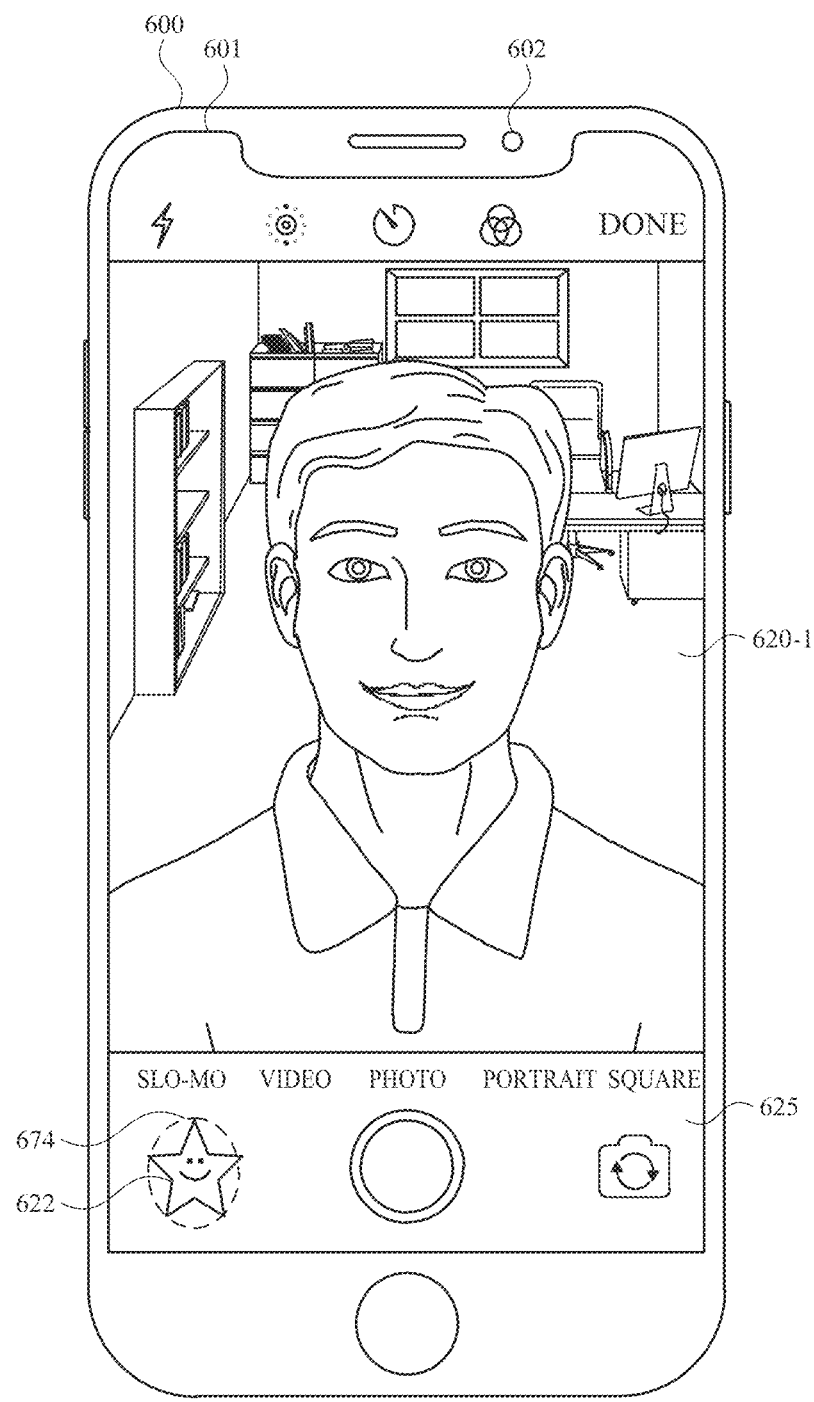
Figure 6A:
Figure 6A:
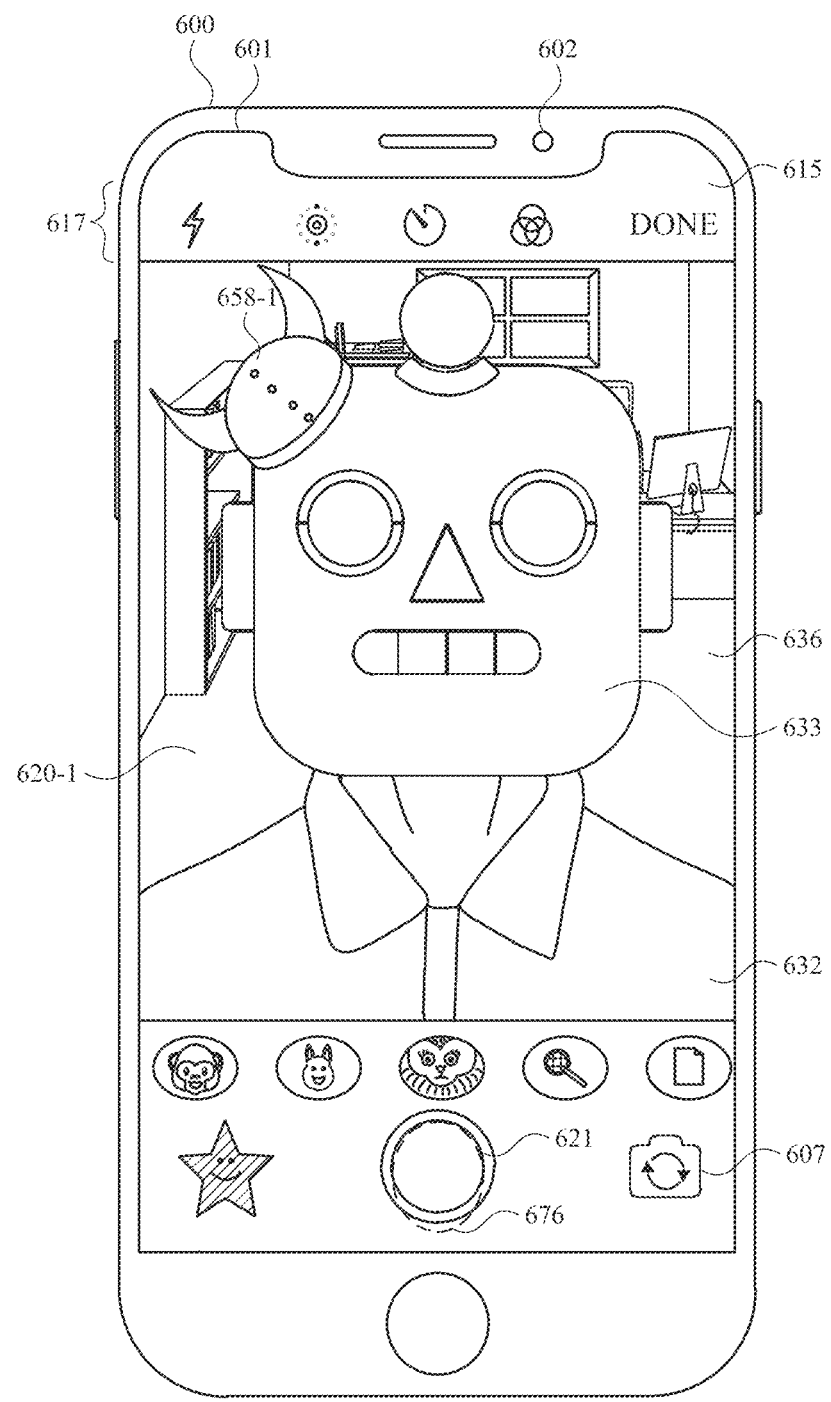
Figure 6A:
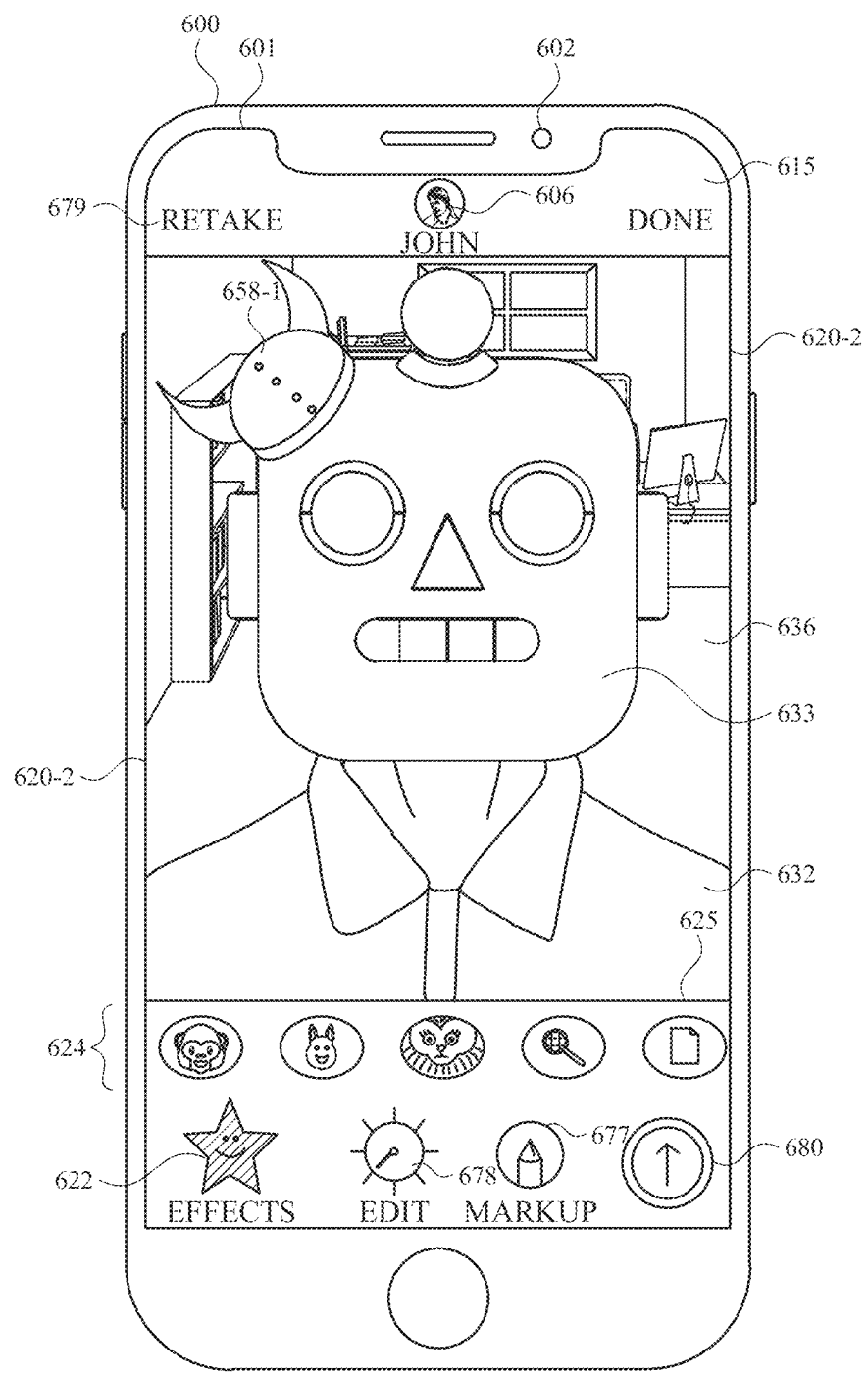
Figure 6A:
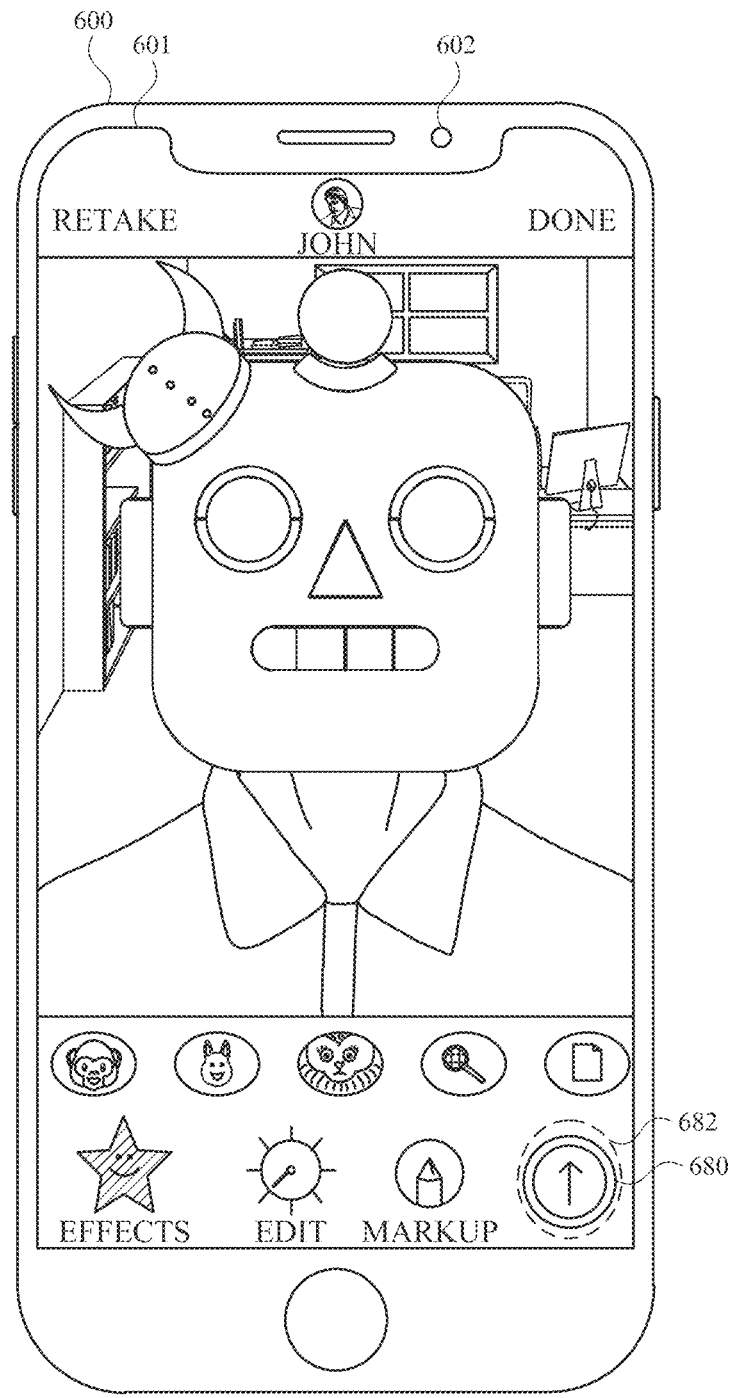
Figure 6A:
Figure 6A:
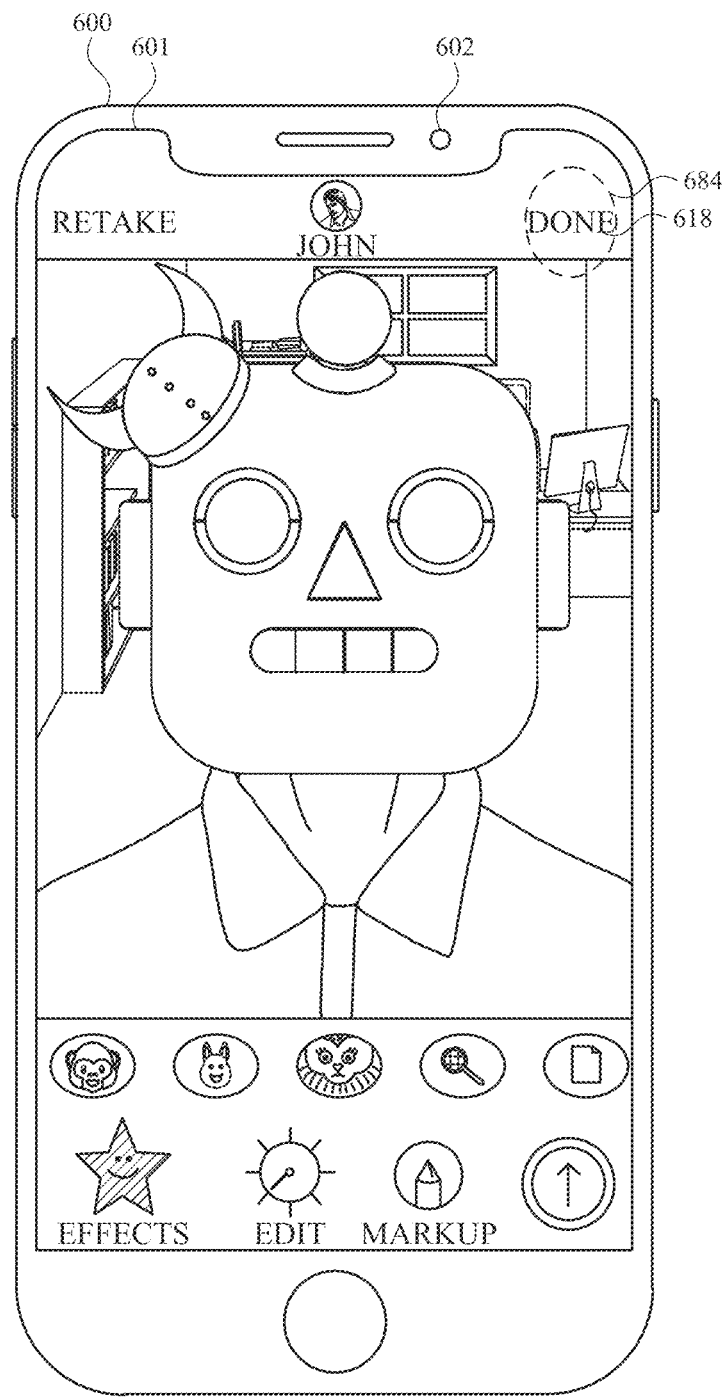
Figure 6A:
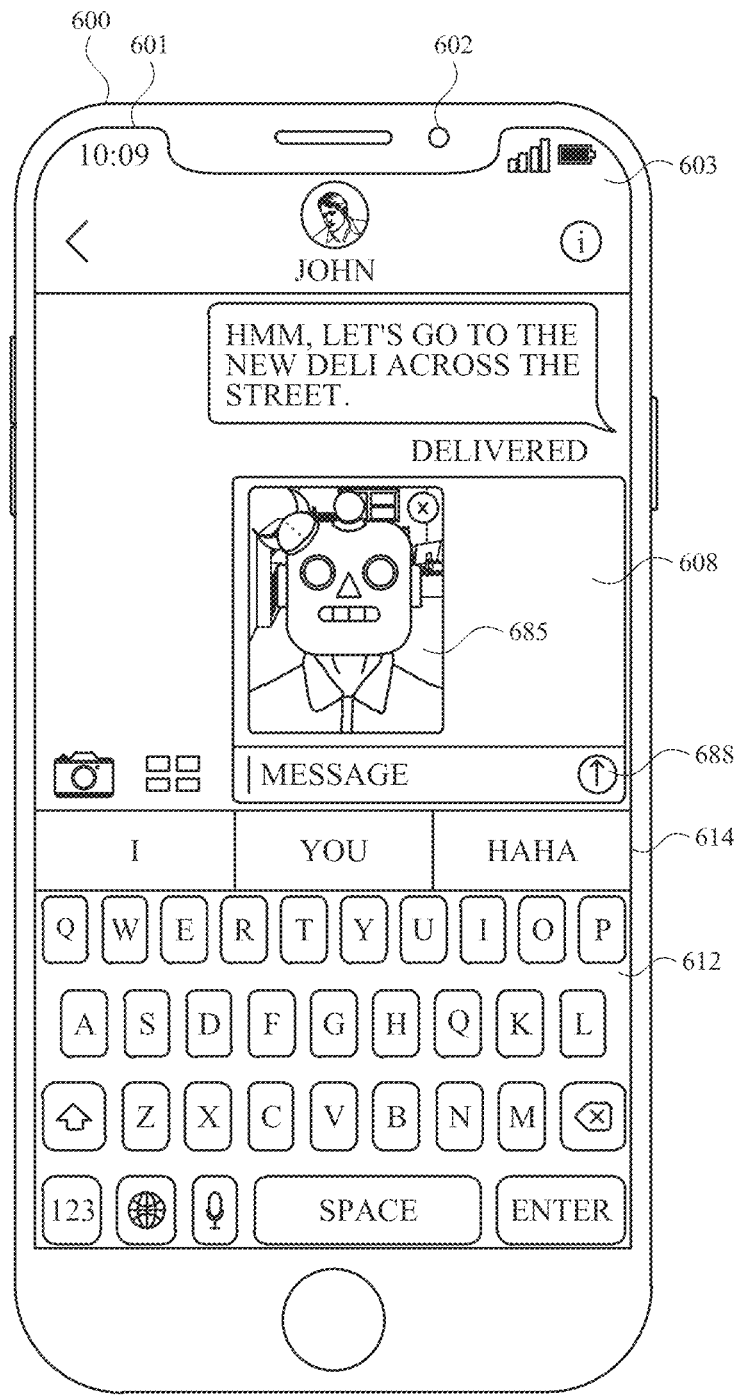
Figure 6A:
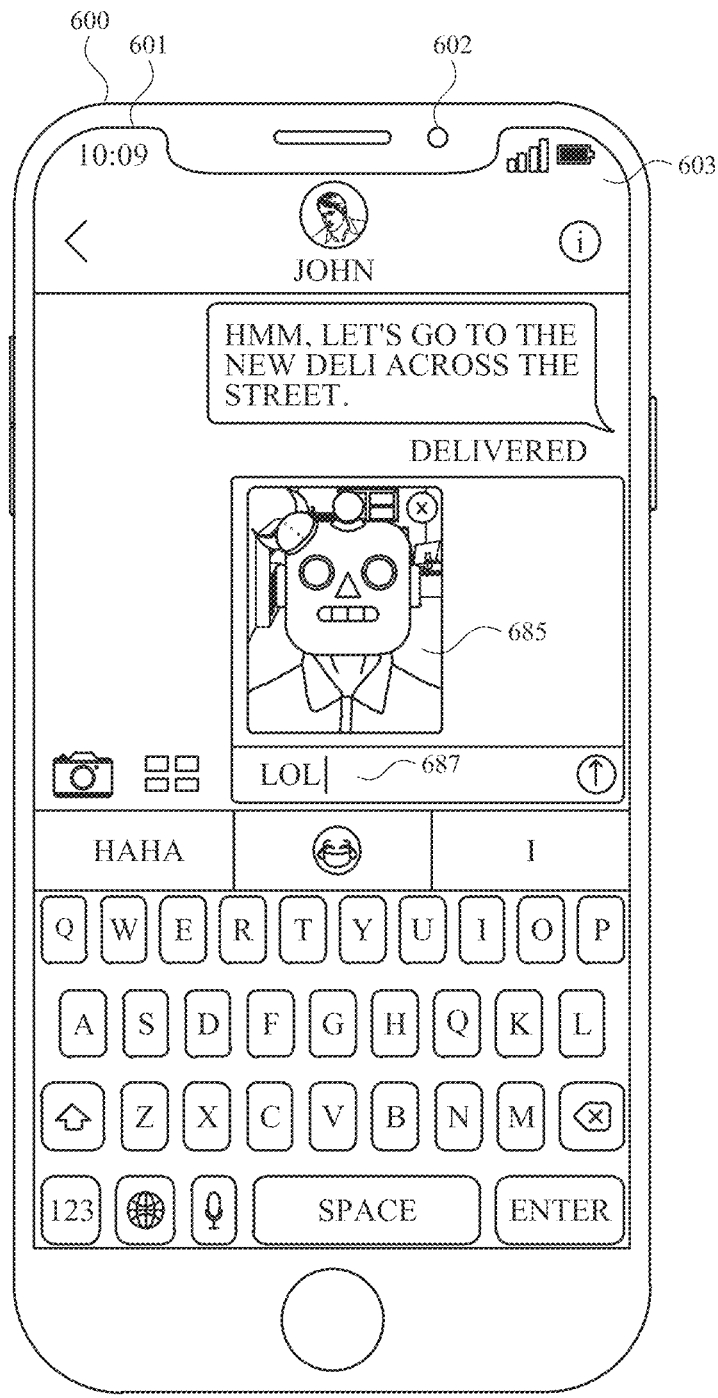
Figure 6A:
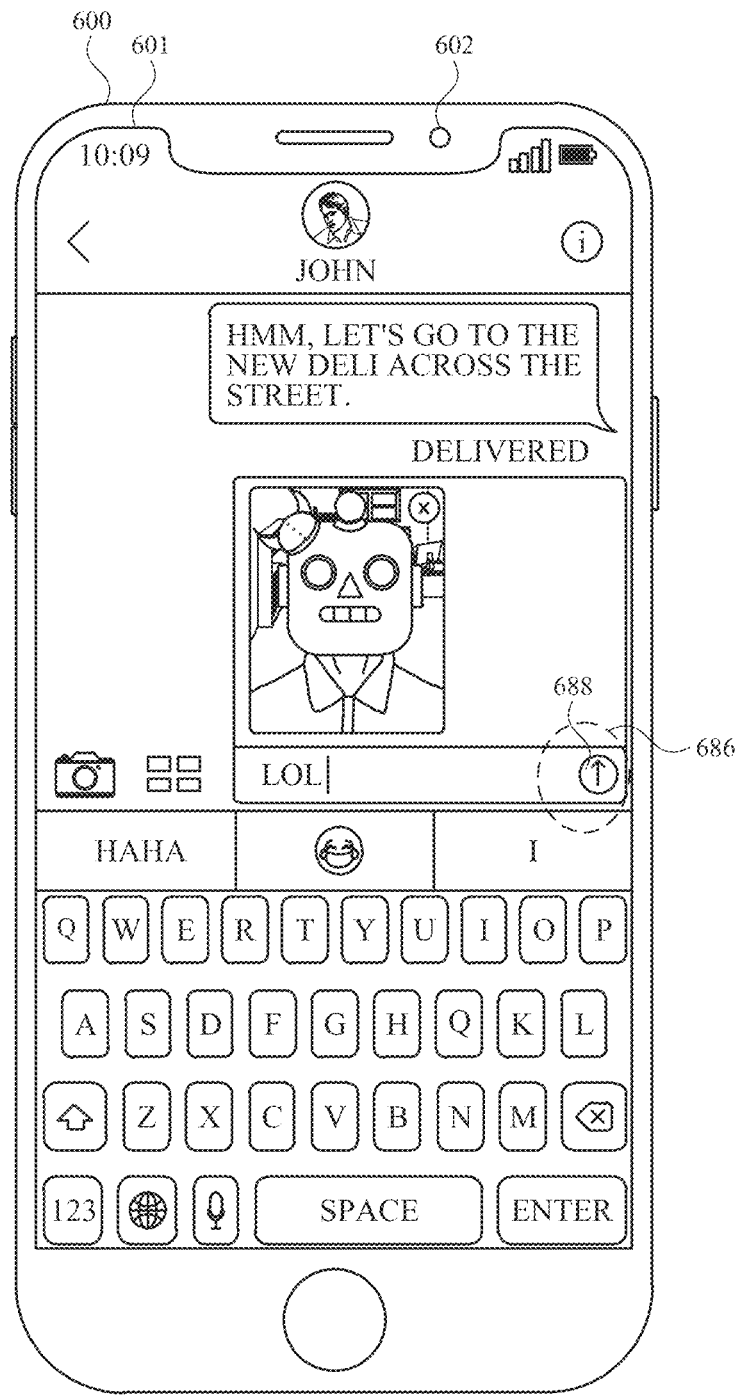
Figure 6A:
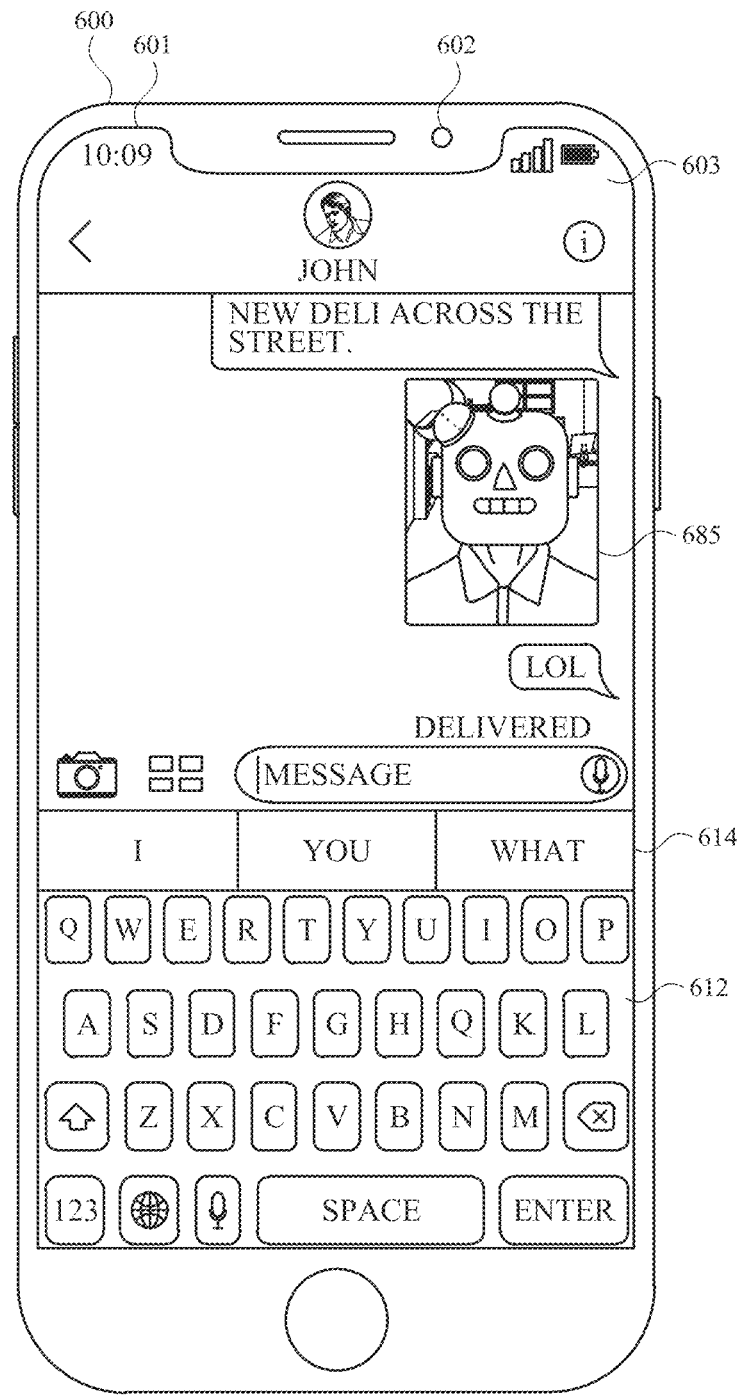
Figure 6A:
Figure 6A:
Figure 6A:
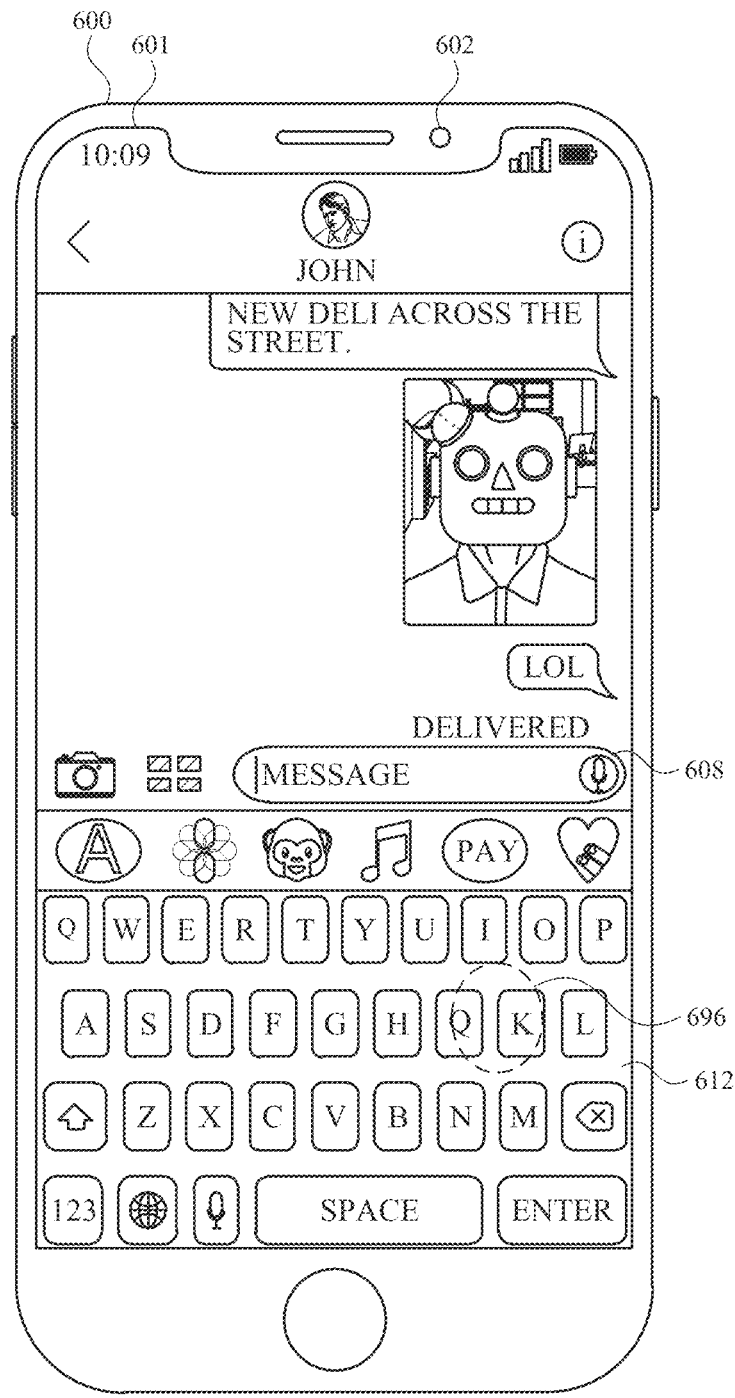
Figure 6A:
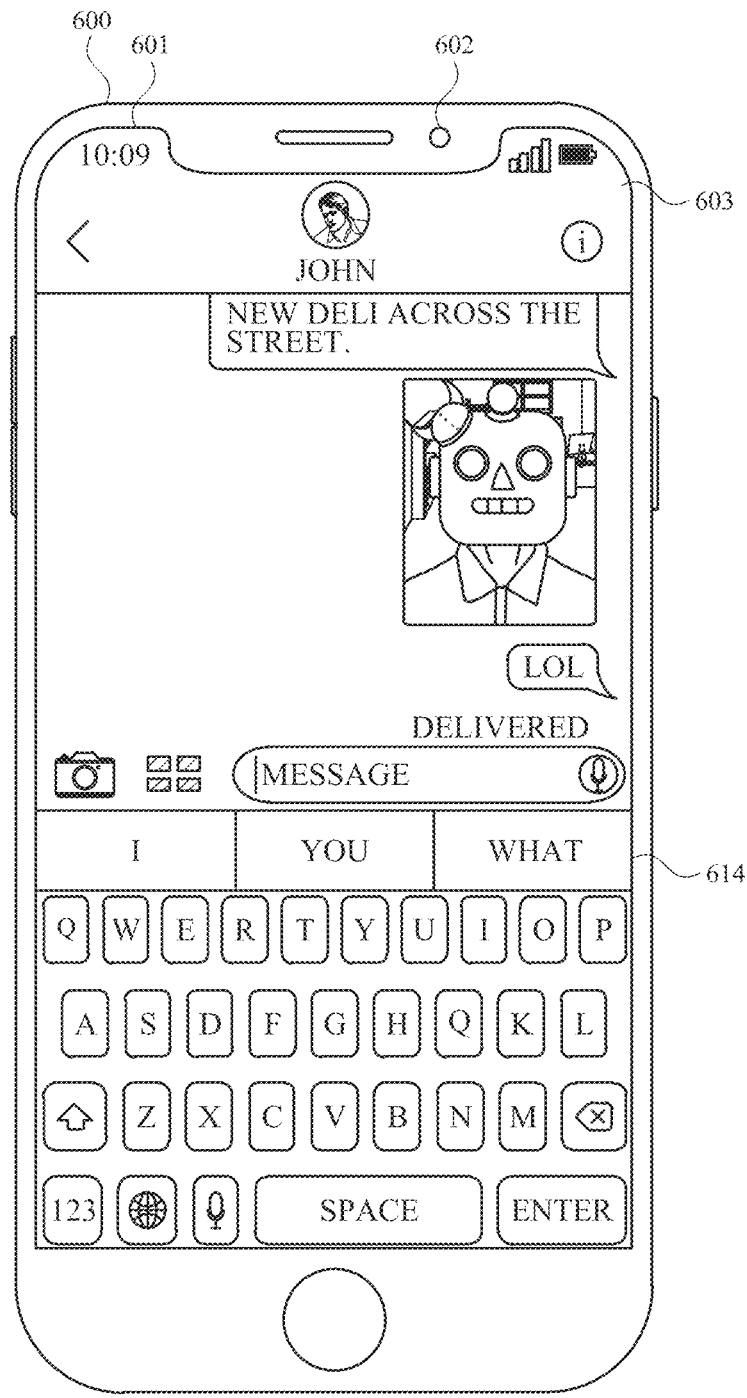
Figure 6A:
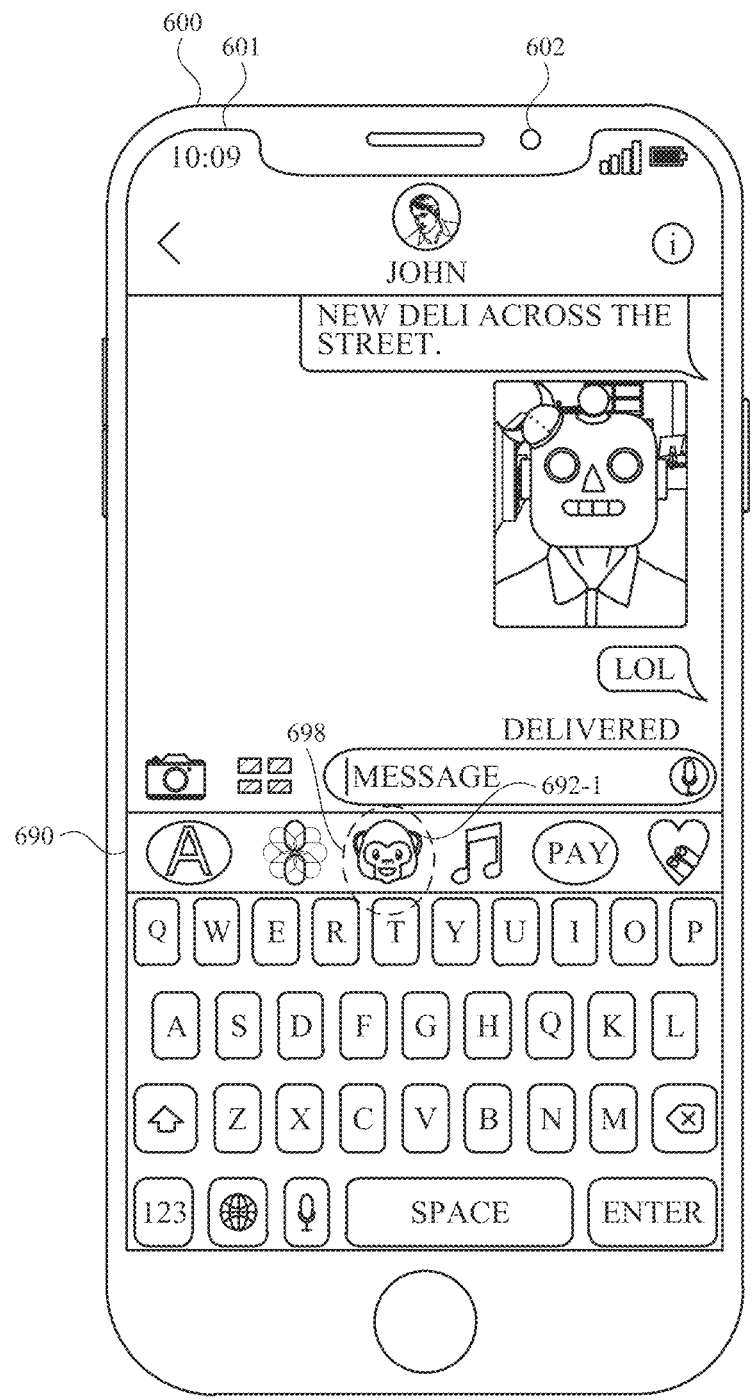
Figure 6A:
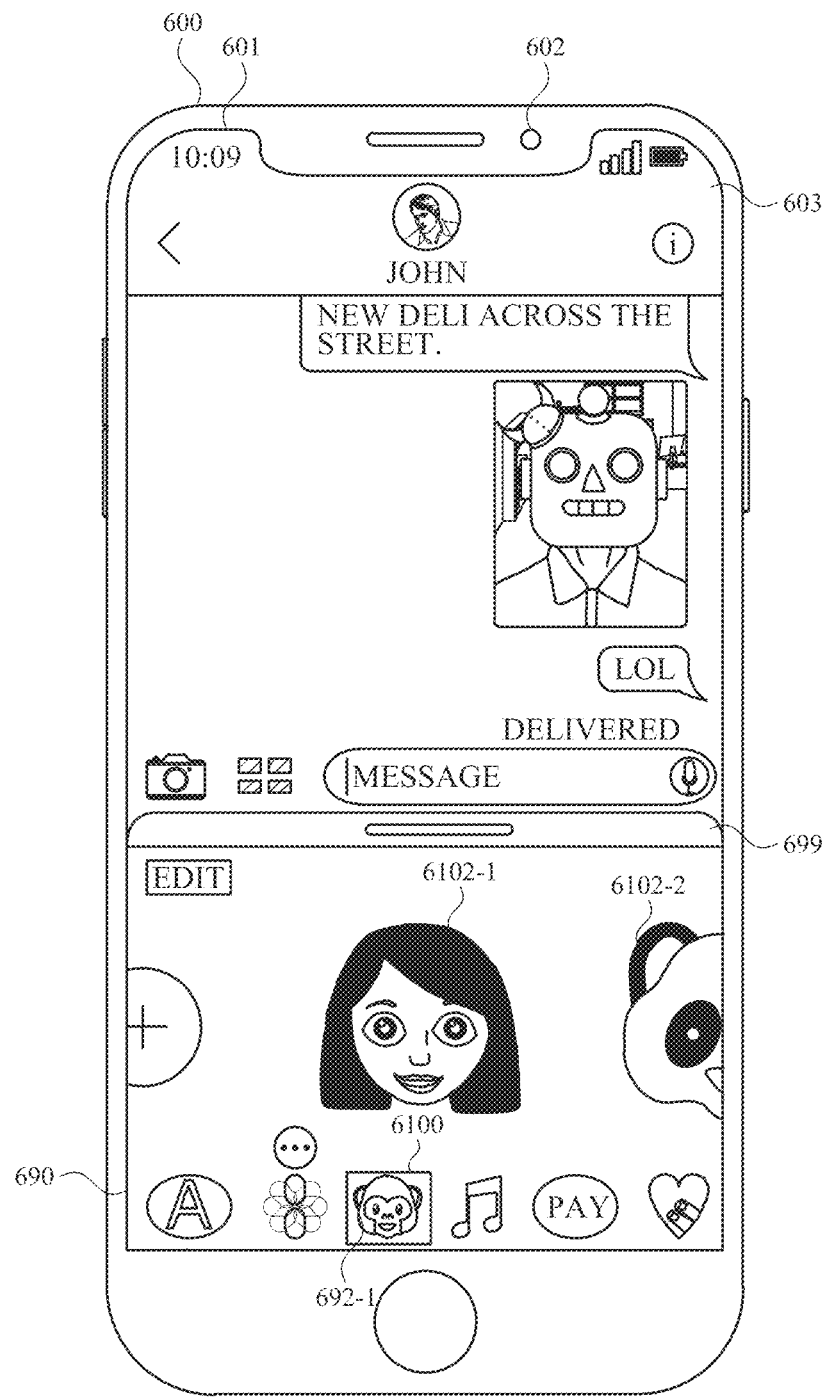
Figure 6A:
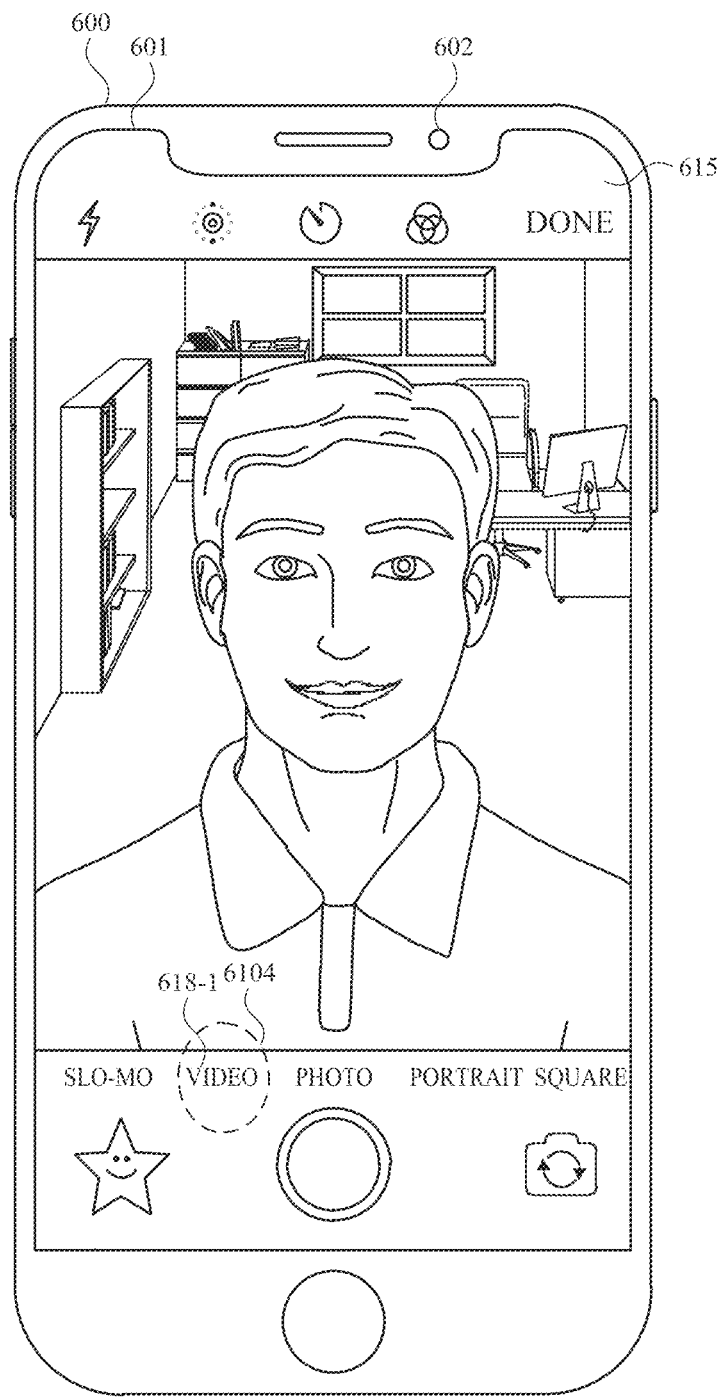
Figure 6A:
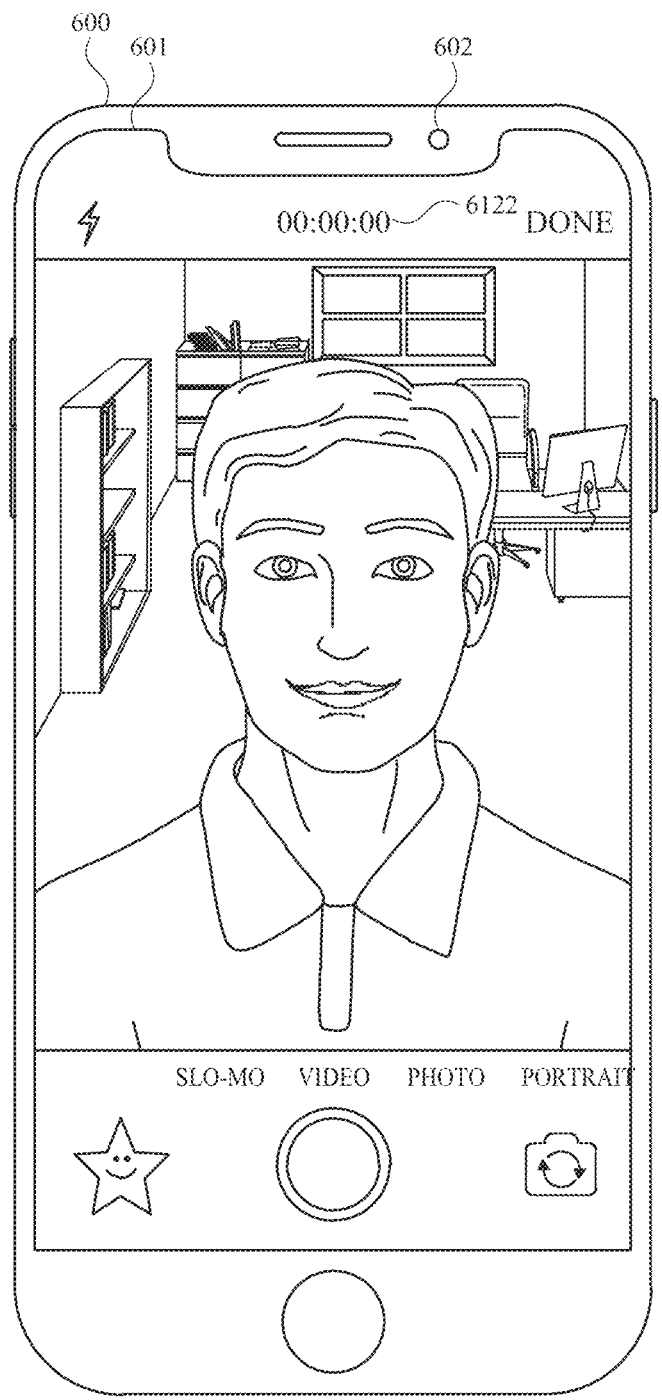
Figure 6B:
Figure 6B:
Figure 6B:
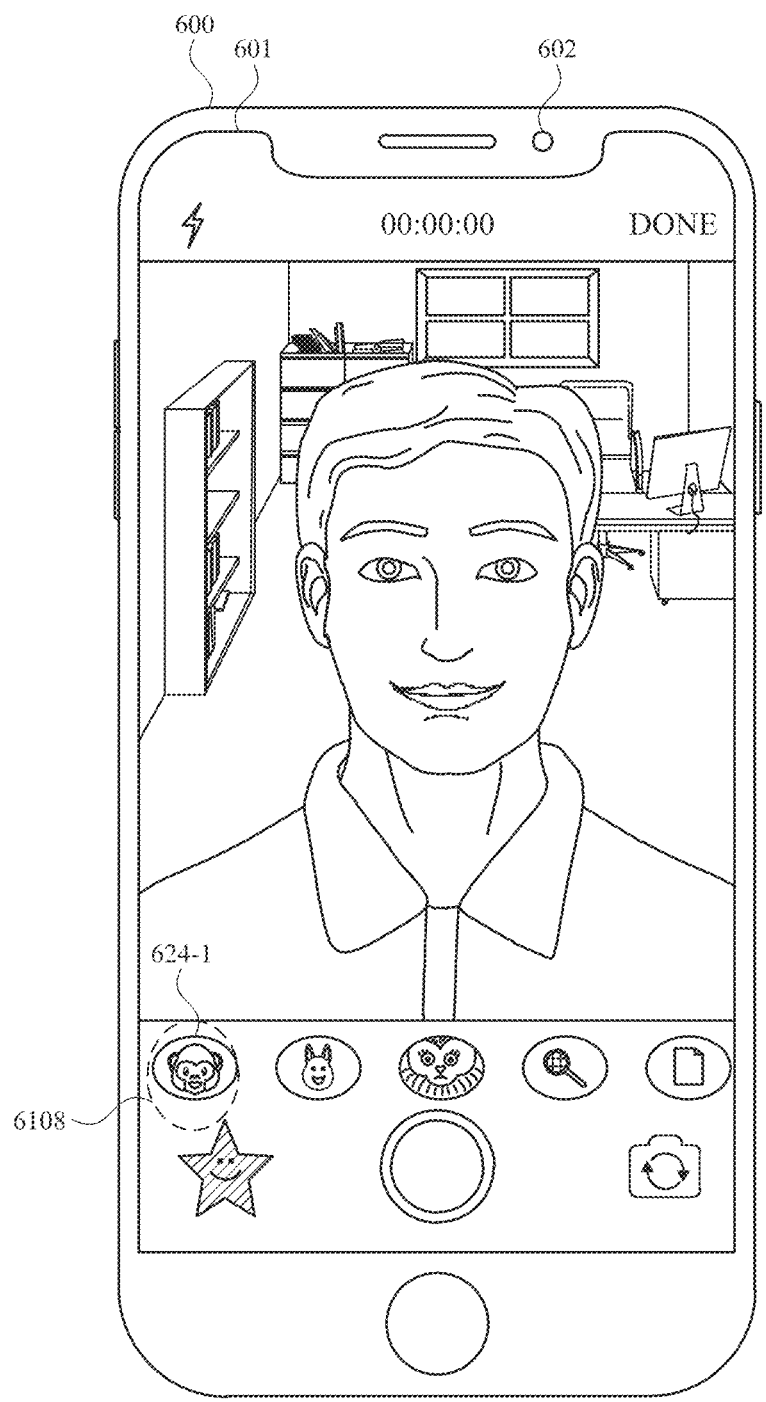
Figure 6B:
Figure 6B:
Figure 6B:
Figure 6B:
Figure 6B:
Figure 6B:
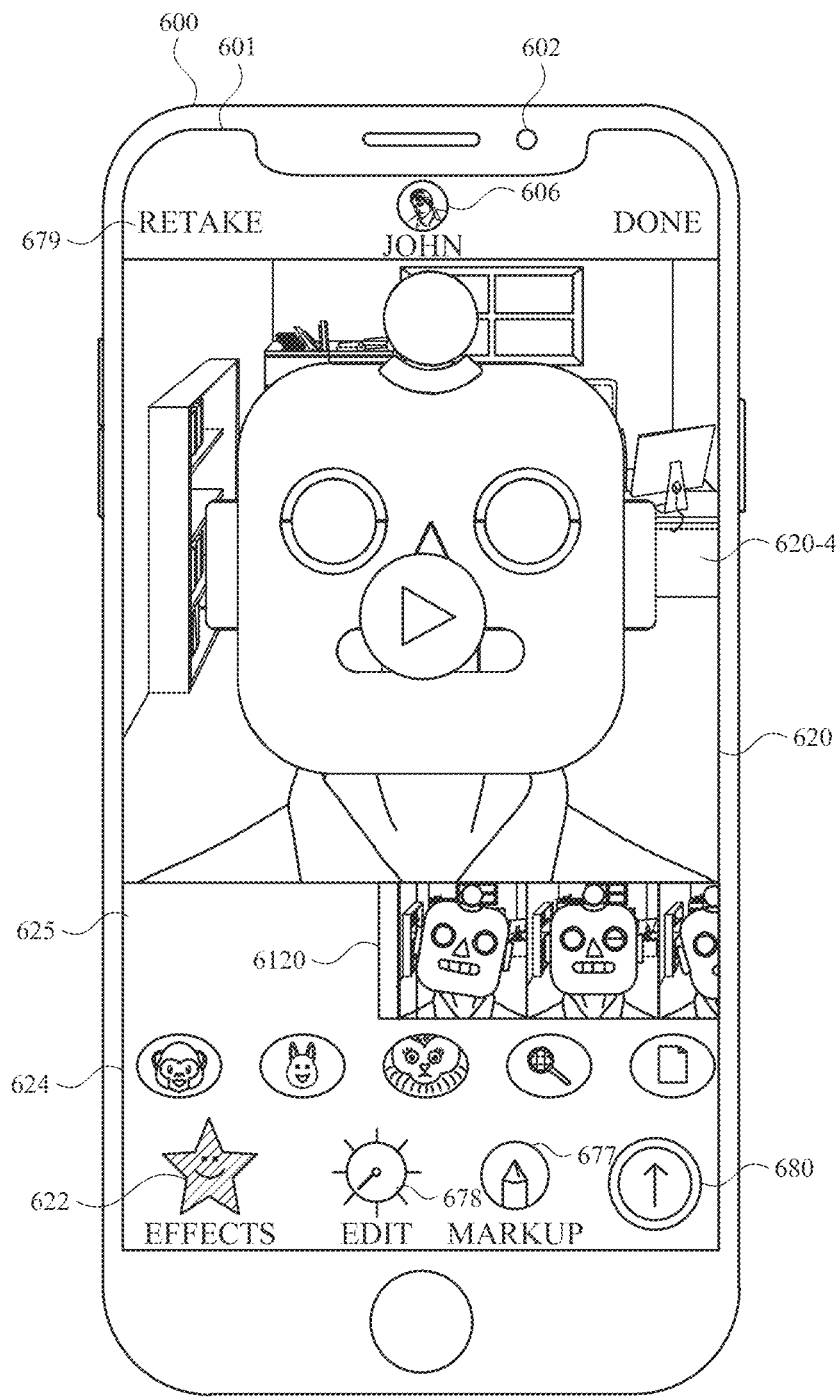
Figure 6B:
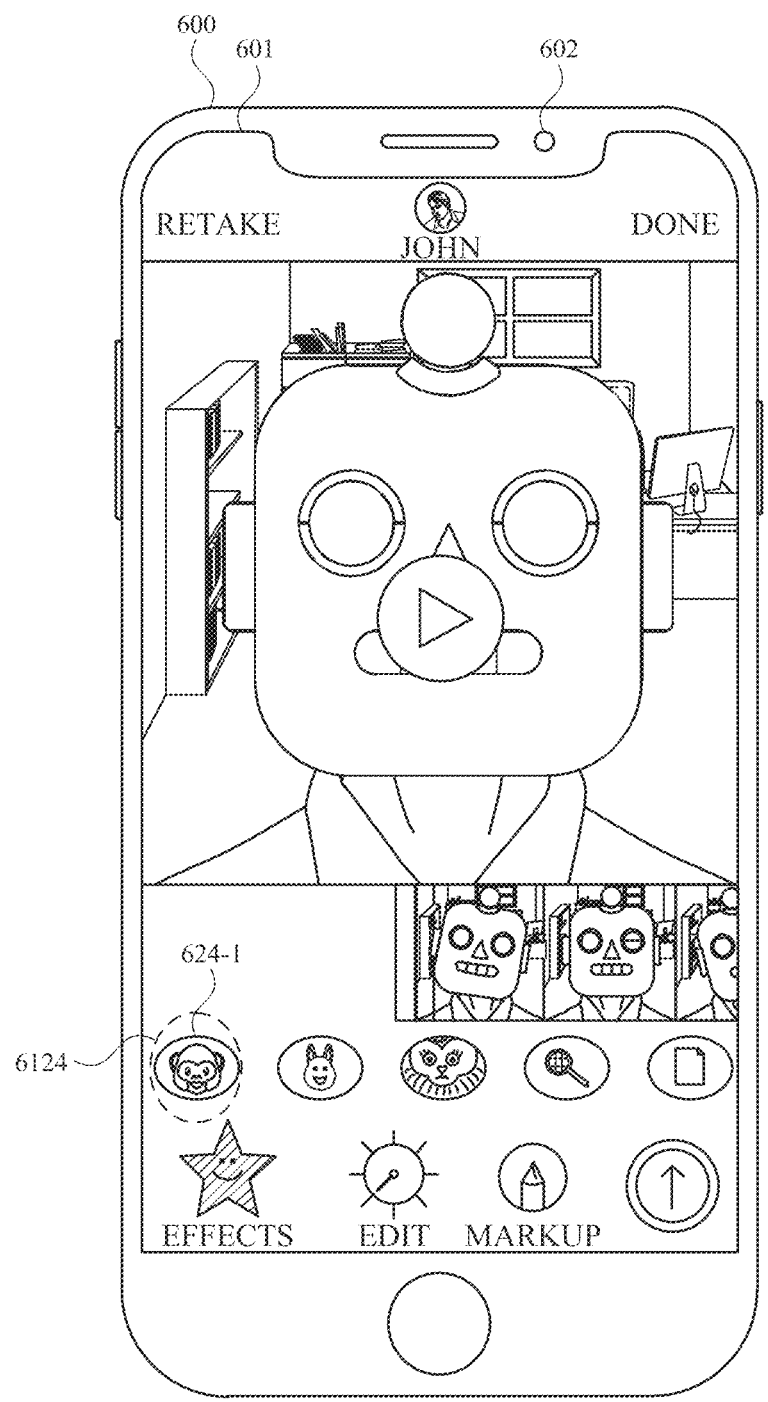
Figure 6B:
Figure 6B:
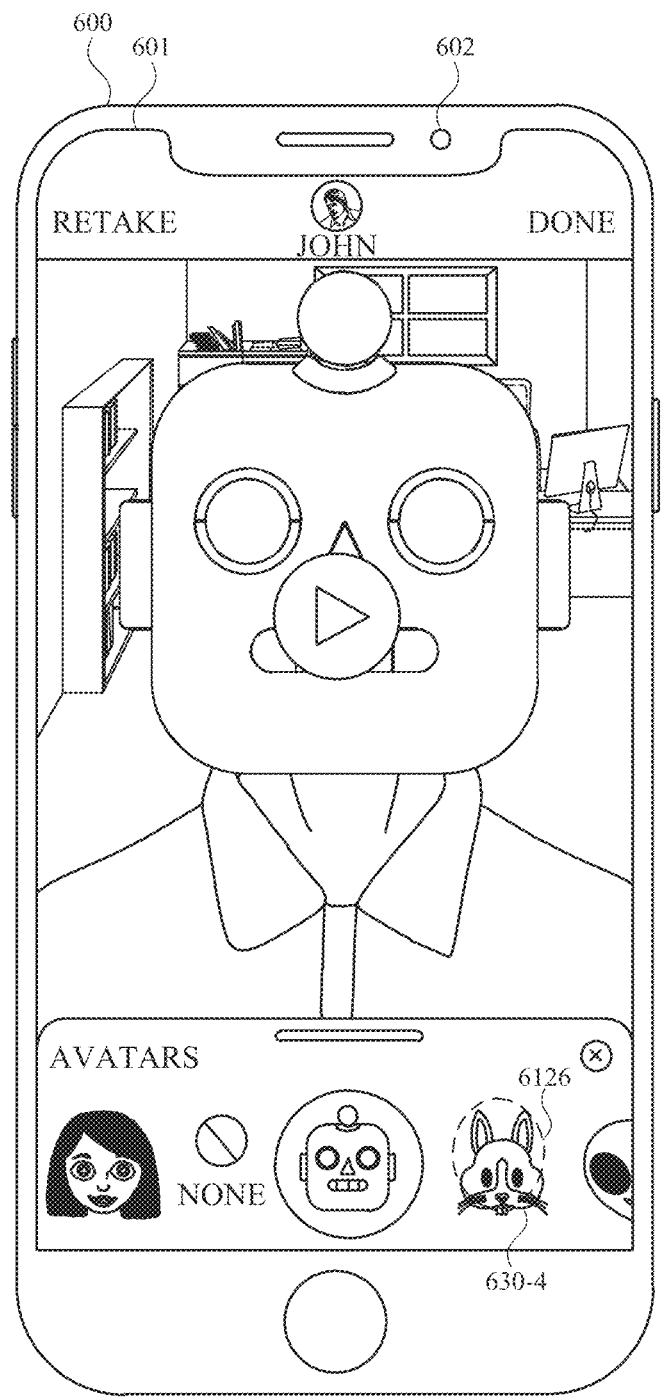
Figure 6B:
Figure 6B:
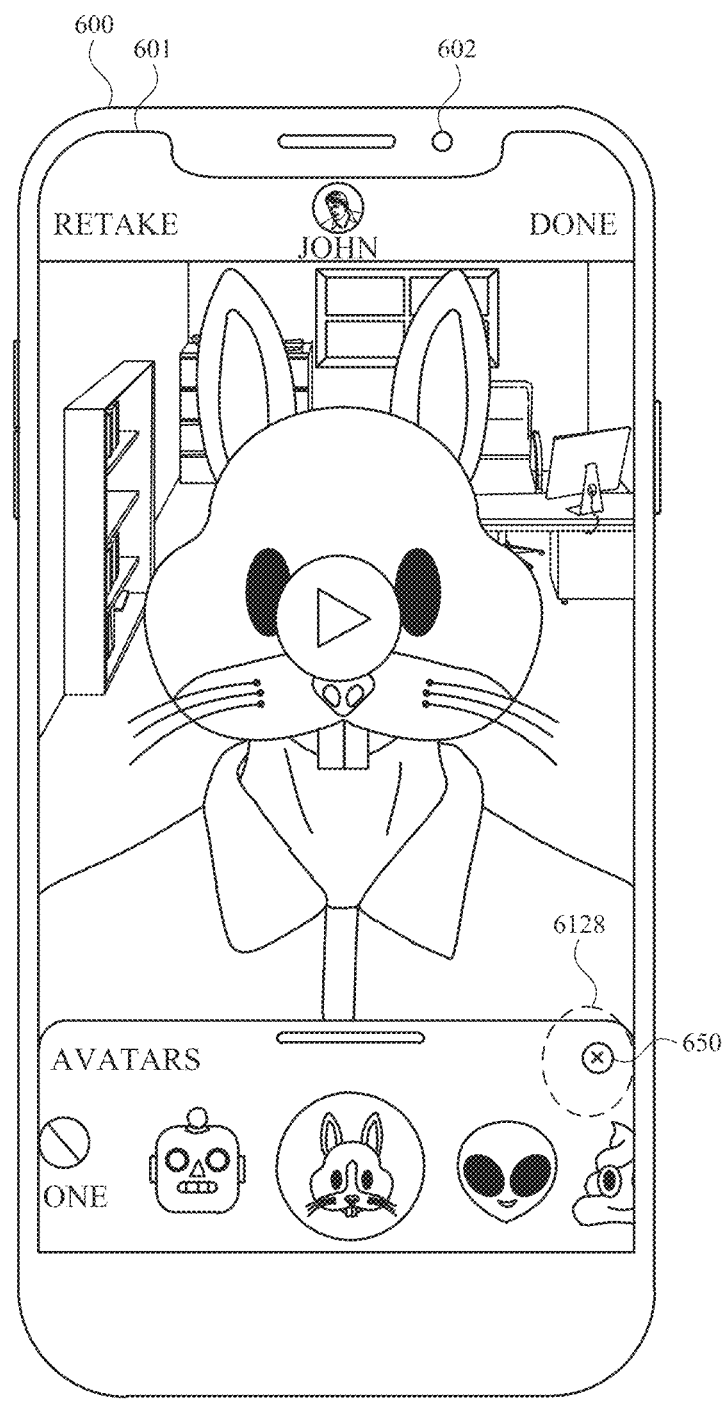
Figure 6B:
Figure 6B:
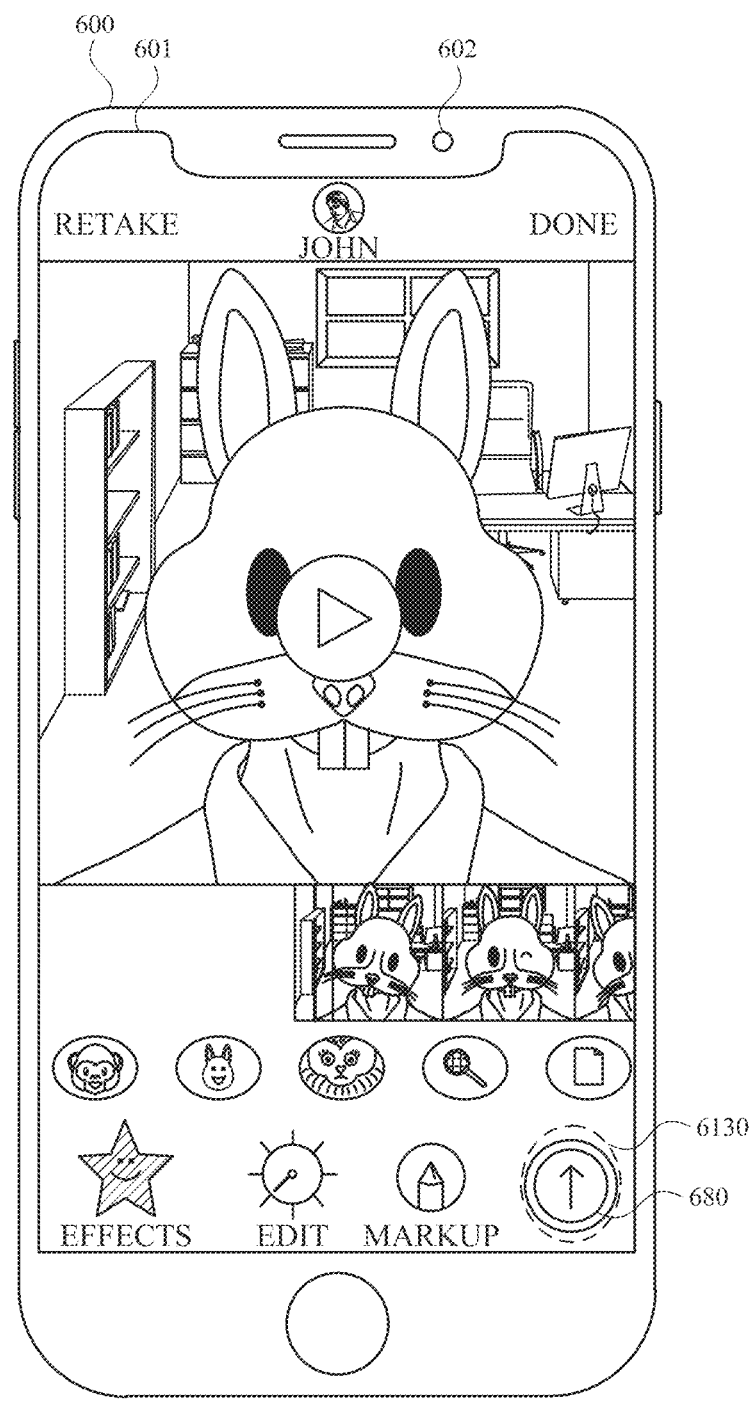
Figure 6B:
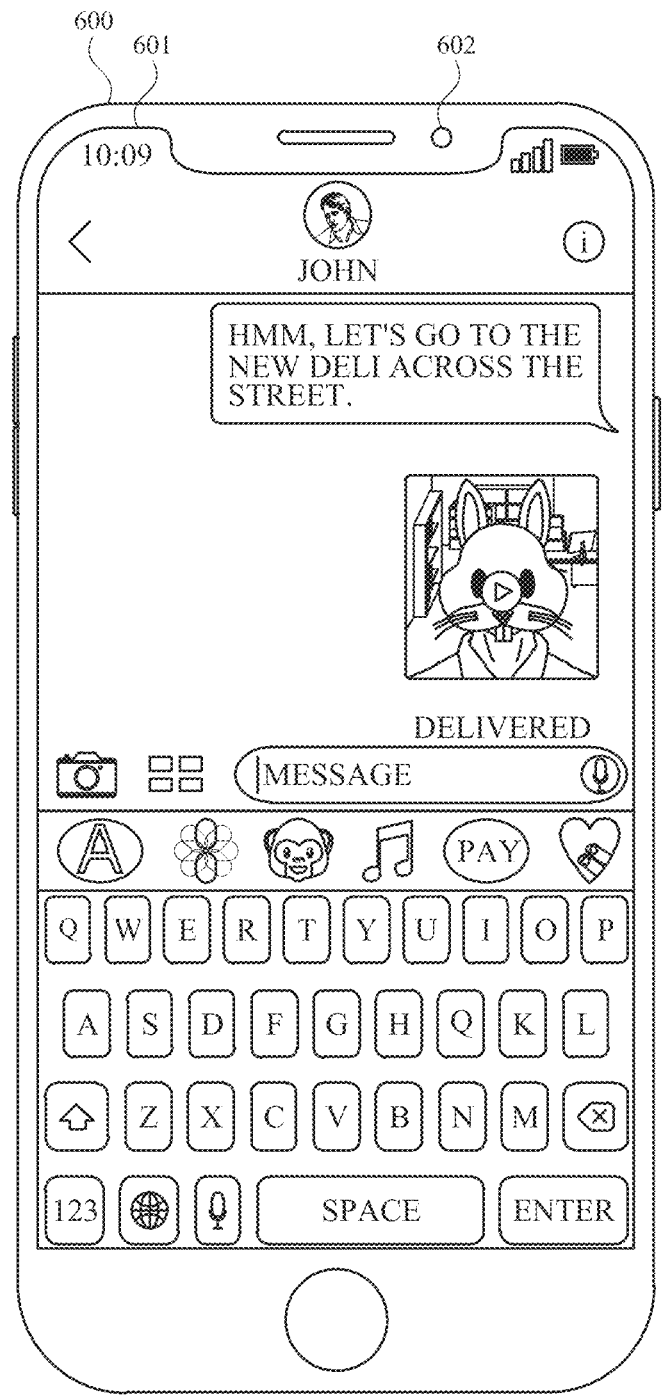

FIGS. 6Y-6Z show that a placed sticker (e.g., sticker 658-1) can be repositioned on the image display region 620 by dragging the sticker to a new location (see drag gesture 662 moving sticker 658-1 to a new position in FIG. 6Z).

FIG. 6AA shows that a placed sticker (e.g., sticker 658-1) can be rotated using two-finger gesture 664.

FIG. 6AB shows that a placed sticker (e.g., sticker 658-1) can be resized using a pinch or de-pinch gesture. In FIG. 6AB, helmet sticker 658-1 is enlarged in response to de-pinch gesture 666. The resized, rotated, and repositioned helmet sticker 658-1 is shown placed on robot avatar's head in FIG. 6AC.

In FIG. 6AD, device 600 detects input 668 (e.g. a tap gesture on display 601) on close icon 670 to close sticker options menu 656 and return to the camera application user interface 615 as shown in FIG. 6AE, which includes camera options region 625 showing capture affordance 621, visual effects option affordances 624, and highlighted effects affordance 622 indicating visual effects are enabled for display. In FIG. 6AE, device 600 shows the representation of the user in the image on image display region 620, but modified with visual effects that include robot avatar 633 (e.g., selected from avatar options menu 628) and helmet sticker 658-1 (e.g., selected from sticker options menu 656). The display of the visual effects is dynamic. For example, device 600 continuously modifies robot avatar 633 in response to detected changes in the user's face. In some embodiments, positioning of sticker 658-1 is also dynamic and changing based on the detected movements of the user, as discussed in greater detail below.

When visual effects are enabled for device 600 (e.g., effects affordance 622 is shown highlighted), applied visual effects (such as avatars and stickers, for example) can be removed or hidden from image display region 620 by un-selecting highlighted effects affordance 622 (e.g., selecting effects affordance 622 when it is highlighted to disable visual effects). For example, in FIG. 6AF, device detects input 672 (e.g., a tap gesture on display 601) on highlighted effects affordance 622. In response, device 600 removes the displayed visual effects (e.g., helmet sticker 658-1 and robot avatar 633 in FIG. 6AF) from image display region 620, as shown in FIG. 6AG, while maintaining display of the image stream (e.g., live camera preview 620-1) including subject 632 and background 636 in the field-of-view of camera 602.

In some embodiments, after the visual effects mode is disabled (e.g., by un-selecting highlighted effects affordance 622), the removed visual effects can be restored, for example, by reselecting effects affordance 622 within a predetermined amount of time. For example, in FIG. 6AH, device detects input 674 (e.g., a tap gesture on display 601) on non-highlighted effects affordance 622. In response to detecting input 674, device 600 highlights effects affordance 622 and re-displays helmet sticker 658-1 and robot avatar 633, while continuing to display the image stream (e.g., live camera preview 620-1) including the body of subject 632 and background 636, as shown in FIG. 6AI.

In FIG. 6AJ, device 600 detects input 676 (e.g., a tap gesture on display 601) on capture affordance 621. In response to detecting input 676, device 600 captures an image of the live camera preview 620-1 in FIG. 6AJ, and displays, in FIG. 6AK, media item 620-2 (e.g., a still image of the state of live camera preview 620-1 at the time device 600 detected input 676 on capture affordance 621).

In some embodiments, when the image is captured (e.g., stored as a media item), device 600 encodes depth data into the media item. Storing the depth data in the media permits the later application of depth-based effects (e.g., effects based on the location of objects (e.g., the user's face) in the z direction). In some embodiments, when the image is captured while an effect is applied, the effect is directly encoded in the visual (e.g., RGB) information for improved compatibility with other devices.

In FIG. 6AK, device 600 displays camera application user interface 615 showing the captured image (e.g., media item 620-2) in the image display region 620 (e.g., media item 620-2 replaces the live camera preview 620-1 shown in image display region 620). Media item 620-2 is a representation of the live camera preview 620-1 at the time the capture affordance 621 was selected. Thus, media item 620-2 includes helmet sticker 658-1 and robot avatar 633 displayed over the face of subject 632, and background 636.

Device 600 also replaces the camera-specific affordances (e.g., affordances 617 shown in FIG. 6AJ) with retake affordance 679 and recipient identifier 606, which indicates a currently selected recipient of media item 620-2, should the user subsequently send the media item as discussed below.

Device 600 displays camera options region 625, including visual effects option affordances 624. Visual effects option affordances 624 can be selected to display their respective option menus, which can be used to modify captured media item 620-2 (as well as recorded video media item 620-4 discussed below).

Device 600 also updates camera options region 625 to replace capture affordance 621 and camera selector affordance 627 with markup affordance 677, edit affordance 678, and send affordance 680. Markup affordance 677 allows a user to mark-up media item 620-2. Edit affordance 678 allows a user to edit media item 620-2 such as by cropping the image or adjusting other characteristics of media item 620-2. As seen in FIG. 6AK, the send affordance 680 is displayed within the same location/region in which capture affordance 621 was displayed, such that send affordance 680 replaces the capture affordance 621 on the display.

Send affordance 680 allows the user to immediately send media item 620-2 to the recipient indicated by recipient identifier 606. For example, in FIG. 6AL, device 600 detects input 682 (e.g., a tap gesture on display 601) on send affordance 680, and immediately sends media item 620-2 to John, the contact corresponding to recipient identifier 606, as shown in messaging user interface 603 of FIG. 6AM. In some embodiments, device 600 sends media item 620-2 without displaying messaging user interface 603. In some embodiments, such as that shown in FIG. 6AM, device sends media item 620-2 and displays messaging user interface 603 having media item 620-2 in message display region 604, to indicate media item 620-2 was sent to a participant in the message conversation (e.g., John), and displaying application dock 690 positioned above keyboard display region 612. Application dock 690 includes application affordances 692 that can be selected to access different applications.

In some embodiments, media item 620-2 is not immediately sent to the participant in the messaging conversation. For example, in FIG. 6AN, instead of selecting send affordance 680, the user selects done affordance 618. In response to detecting input 684 (e.g. tap gesture on display 601) on done affordance 618, device 600 displays representation of media item 685 in message-compose field 608 of messaging user interface 603, as shown in FIG. 6AO. In this embodiment (shown in FIGS. 6AO-6AR), instead of displaying application dock 690, device 600 displays text-suggestion region 614 along with keyboard display region 612 to allow the user to compose text (e.g., 687), or optionally add other message content (e.g., multimedia content), prior to sending the message. In response to detecting input 686 (e.g., a tap gesture on display 601) on send icon 688, device 600 sends representation of media item 685 to the participant in the message conversation, as shown in FIGS. 6AQ-6AR.

In some embodiments, sending media item 685 includes sending the media item with encoded depth data in the media item. Sending the media item with depth data in the media permits the later application (e.g., later application by the recipient) of depth-based effects (e.g., effects based on the location of objects (e.g., the user's face) in the z direction). In some embodiments, when the media item is sent, the effects are directly encoded in the visual (e.g., RGB) information for improved compatibility with other devices.

In some embodiments, after sending representation of media item 685, device 600 displays messaging user interface 603 as shown in FIG. 6AR having text-suggestion region 614 displayed above keyboard display region 612. In response to receiving input 694 (e.g., a tap gesture on display 601) on application dock affordance 610, device 600 replaces text-suggestion region 614 with application dock 690, as shown in FIG. 6AT.

In some embodiments, application dock 690 remains displayed in messaging user interface 603 until a user selects message compose field 608 or keyboard region 612 (actions associated with composing text for a message). For example, as shown in FIG. 6AU, device 600 detects input 696 (e.g., tap gesture on device 601) on keyboard display region 612. In response, as shown in FIG. 6AV, device 600 removes application dock 690 and displays text-suggestion region 614 above keyboard display region 612. In some embodiments, if input 696 is an input on message-compose field (instead of keyboard display region 612), device 600 also removes application dock 690 and displays text-suggestion region 614, as shown in FIG. 6AV

FIG. 6AW shows messaging user interface 603 after application dock affordance 610 is selected (e.g., in response to input 694 in FIG. 6AS). Application dock 690 is displayed above keyboard selection region 612 (e.g., replacing text-suggestion region 614). In response to detecting input 698 (e.g., a tap gesture on display 601) on application affordance 692-1, device 600 displays application display region 699 at a location that was previously occupied by text-suggestion region 614 and keyboard display region 612. Application display region 699 optionally includes application dock 690, which includes an indication 6100 of the selected application affordance (e.g., application affordance 692-1), as shown in FIG. 6AX.

In some embodiments, application display region 699 includes graphical objects 6102 that can be selected for use in messaging user interface 603. In some embodiments, the type of graphical object displayed in application display region 699 depends on the application affordance that was selected to invoke display of the application display region. In the embodiment illustrated in FIG. 6AX, selected application affordance 692-1 corresponds to an avatar application. Accordingly, graphical objects 6102-1 and 6102-2 displayed in application display region 699 correspond to avatars that can be selected for use in the messaging user interface. If the application affordance selected from application dock 610 corresponds to a sticker application, then graphical objects 6102 correspond to stickers that can be selected for use in the messaging user interface.

As previously mentioned, the foregoing embodiments described with respect to FIGS. 6C-6AX are discussed with respect to device 600 operating in the still image capture mode of operation associated with photo affordance 619-2. However, unless specified otherwise, these embodiments also apply to operation of device 600 when the device is operating in the video recording mode associated with video affordance 619-1. As such, the following description of FIGS. 6AY-6BQ, which illustrate many of the foregoing embodiments as applied to the device 600 when operating in the video recording mode associated with video affordance 619-1, is abbreviated where appropriate to avoid redundancy.

FIG. 6AY-6AZ shows device 600 switching to a video recording mode in response to detecting input 6104 on video affordance 619-1 in camera application user interface 615. When switching to video recording mode, device 600 removes camera specific affordances 617-2, 617-3, and 617-4 and displays timer 6122.

FIGS. 6AZ-6BB show device 600 enabling effects mode in response to input 6106 on effects affordance 622, and then displaying visual effects option affordances 624 in camera options region 625 while the video record mode is enabled.

FIGS. 6BC-6BE show device 600 displaying avatar options menu 628 in response to detecting input 6108 on avatar effects affordance 624-1. Avatar options menu 628 includes avatar options 630 that can be selected to display a corresponding avatar on the subject's face while in video mode. Robot avatar option 630-3 is selected, and device 600 displays robot avatar 633 on subject's face, while maintaining display of the subject's body and background 636. Close icon 650 is selected with input 6110 to close avatar options menu 628 and return to camera options region 625 having highlighted effects affordance 622 and displayed visual effects option affordances 624.

FIGS. 6BF-6BH show device 600 generating a recorded video of the image data represented in image display region 620. Device 600 detects input 6112 on capture affordance 621, which initiates capturing the image data represented in image display region 620. In some embodiments, device 600 generates a video recording of the image data based on a determination that the video recording mode of device 600 is enabled. In some embodiments, device 600 generates a video recording or optionally a still image capture based on input 6112 detected on capture affordance 621. For example, if input 6112 is detected as a tap gesture, device 600 captures a still image of the image data represented in image display region 620. If input 6112 is detected as a tap-and-hold gesture, device 600 captures a video recording of the image data, as discussed in greater detail above.

In FIG. 6BG, in response to detecting input 6112 on capture affordance 621, device 600 initiates a process for recording the image data represented in image display region 620, which includes the subject, background, and visual effects. Device 600 also modifies camera application user interface 615 by removing camera effects region 625, expanding image display region 620, and displaying stop affordance 6114 and, optionally, image capture affordance 6116 for capturing still images of the live camera recording. In FIGS. 6BG and 6BH, image display region 620 represents live camera recording 620-3 of objects within the field-of-view of camera 602, with the addition of visual effects (e.g., robot avatar 633) that are enabled in accordance with the various selections made as discussed above. These visual effects, which can also include stickers and full-screen effects, are displayed in image display region 620 as part of the live image data, and are recorded to form a portion of the resulting media item. As discussed herein, these visual effects can be optionally displayed or hidden in the media item after the media item is recorded.

In FIG. 6BH, device 600 detects changes in the user's face, and modifies robot avatar 633 based on the detected changes in the user's face, while recording the live image stream. In response to detecting input 6118 on stop affordance 6114, device 600 stops recording the image data represented in image display region 620, and displays the playback interface shown in FIG. 6BI.

In FIG. 6BI, device 600 displays recorded video media item 620-4 in image display region 620 and displays retake affordance 679 and recipient identifier 606, which indicates a currently selected recipient of video media item 620-4, should the user subsequently send the media item as discussed herein.

Device 600 also removes stop affordance 6114 and image capture affordance 6116, and displays camera options region 625 having video scrubber 6120 for recorded video media item 620-4, effects affordance 622, edit affordance 678, markup affordance 677, and send affordance 680. Camera options region 625 also includes visual effects option affordances 624. Visual effects option affordances 624 can be selected to display their respective option menus, which can be used to modify captured media item 620-4. FIGS. 6BJ-6BN illustrate an example of changing visual effects in the captured video media item 620-4. As seen in FIG. 6BI, the send affordance 680 is displayed within the same location/region in which capture affordance 6116 was displayed, such that send affordance 680 replaces the capture affordance 6116 on the display.

FIGS. 6BJ-6BN show device 600 displaying avatar options menu 628 in response to detecting input 6124 on avatar effects affordance 624-1. As seen in FIG. 6BK, avatar options menu 628 shows avatar options 630, including selected robot avatar option 630-3. As seen in FIG. 6BL, device 600 detects input 6126 to select rabbit avatar option 630-4, and updates video media item 620-4 to show rabbit avatar 634 positioned on the subject's head, while still displaying the subject's body and background 636, as seen in FIG. 6BM. As seen in FIG. 6BN, in response to detecting input 6128 on close icon 650, device 600 closes avatar options menu 628 and displays camera options region 625 of FIG. 6BO. Camera options region 625, including video scrubber 6120, updates from displaying robot avatar 633 in FIG. 6BJ, to showing rabbit avatar 634. In some embodiments, in response to an input directed to the video scrubber 6120 (e.g., a swipe or drag input including movement of a contact that starts at a location of video scrubber 6120), the device scrubs through recorded video (e.g., changing the appearance of the preview of the video and moving the scrubber or moving a playhead in the scrubber in accordance with the input). In some embodiments, scrubbing through the recorded video shows how the effects applied to the video change over time (e.g., how stickers and/or avatars move and/or change expression as the user's head/face moves and or changes expression in the field of view of the one or more cameras). In some embodiments, video scrubber 6120 includes selectable affordances for cropping the video (e.g., by dragging editing affordances at the ends of the video scrubber to change a starting or ending time for the video scrubber). For example, in response to a user input directed to video scrubber 8120 in FIG. 8AW, the device would scrub through the video with an avatar and stickers as shown in FIGS. 8AW-8AZ, but at a rate determined based on the change in the input (e.g., the magnitude and direction of the movement of the contact on the touch-sensitive display). The interaction with video scrubber 6120 described above (and video scrubber 8120 described below) optionally applies in a similar manner to interaction with other scrubbers described herein.

As discussed above with respect to FIGS. 6AK-6AO, video media item 620-4 can be immediately sent to a participant in the message conversation in response to detecting an input (e.g., input 6130) on send affordance 680, as shown in FIGS. 6BP and 6BQ. A representation of video media item 620-4 can be displayed in the message-compose field 608 in response to an input on done affordance 618.

FIGS. 7A and 7B are a flow diagram illustrating a method for displaying visual effects in a messaging application using an electronic device in accordance with some embodiments. Method 700 is performed at a device (e.g., 100, 300, 500, 600) with a camera, a display apparatus, and one or more input devices. Some operations in method 700 are, optionally, combined, the orders of some operations are, optionally, changed, and some operations are, optionally, omitted.

As described below, method 700 provides an intuitive way for displaying visual effects in a messaging application. The method reduces the cognitive burden on a user for applying visual effects to an image for sending in a messaging application, thereby creating a more efficient human-machine interface. For battery-operated computing devices, enabling a user to display visual effects in an image faster and more efficiently conserves power and increases the time between battery charges.

The electronic device (e.g., 600) displays (702), via the display apparatus (e.g., 601), a messaging user interface (e.g., 603) of a message conversation including at least a first participant, the messaging user interface including a camera affordance (e.g., 609, a selectable icon associated with a function for activating a camera application).

The electronic device (e.g., 600) detects (704), via the one or more input devices, a first input (e.g., 616, a touch gesture on a touch screen display at a location that corresponds to the camera affordance) directed to the camera affordance.

In response to detecting the first input (e.g., 616), the electronic device (e.g., 600) displays (706) a camera user interface (e.g., 615). The camera user interface includes (708) a capture affordance (e.g., 621, a selectable icon associated with a function for capturing image data using the camera of the electronic device).

In some embodiments, the camera user interface (e.g., 615) includes (710) an effects mode affordance (e.g., 622, a selectable icon associated with a function for activating a mode in which various visual effects are available for modifying image data) associated with a mode in which visual effects are enabled for display in the captured image data. Including an effects mode affordance in the camera user interface enables the user to recognize that certain effects (e.g., visual effects) can be applied to an image via the camera user interface. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the visual effects can be added to a representation of image data within a field-of-view of the camera. In some embodiments, the visual effects can be added to captured image data. In some embodiments, the visual effects are based on depth data. In some embodiments, the electronic device detects, via the one or more input devices, a selection (e.g., 623) of the effects mode affordance. In some embodiments, in response to detecting the selection of the effects mode affordance, the electronic device transitions the electronic device from a first camera mode (e.g., standard camera mode) to a second camera mode, different from the first camera mode (e.g., an effects camera mode; a mode in which various visual effects are available for modifying image data). In some embodiments, while the device is in the second camera mode, a visual indication that the second camera mode is operative is displayed (e.g., the effects mode affordance is highlighted).

In some embodiments, further in response to detecting selection (e.g., 623) of the effects mode affordance (e.g., 622), the electronic device (e.g., 600) ceases to display the one or more camera mode affordances. In some embodiments, further in response to detecting selection of the effects mode affordance, the electronic device displays a plurality of effects option affordances (e.g., 624, selectable icons each associated with a function for creating a visual effect). In some embodiments, the effects option affordances include a sticker affordance (e.g., 624-2) and/or an avatar affordance (e.g., 624-1) at a location in the camera user interface (e.g., 615) that was previously occupied by the one or more camera mode affordances. In some embodiments, the locations at which the effects option affordances are displayed are any locations in a particular region (e.g., camera effects region 625) in which the camera mode affordances were previously displayed. In some embodiments, the locations at which respective effects option affordances are displayed are the same locations that respective camera mode affordances were displayed in the region. In some embodiments, displaying the effects option affordances includes replacing the camera mode affordances with the effects option affordances).

In some embodiments, the electronic device (e.g., 600) detects, via the one or more input devices, selection (e.g., 654) of a first one of the effects option affordances (e.g., stickers affordance 624-2). In some embodiments, in response to detecting selection of the first one of the effects option affordances, the electronic device ceases to display the plurality of effects option affordances (e.g., 624) and displays a plurality of selectable graphical icons (e.g., 658, stickers). Ceasing to display the plurality of effects option affordances and displaying the plurality of selectable graphical icons in response to detecting selection of the first one of the effects option affordances enables the user to quickly and easily recognize that the first one of the effects option affordances relates to graphical icon (e.g., sticker) options, thereby enhancing the operability of the device and making the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, displaying the stickers includes displaying a region (e.g., sticker menu 656) over the effects option affordances, where the region includes a plurality of sticker options that can be selected for display on an image represented in the camera user interface. In some embodiments, a user selects (e.g., 660) a sticker (e.g., 658-1) by tapping on the sticker, and the sticker is automatically displayed on the image (e.g., at a default location such as the center of the image). In some embodiments, a user selects a sticker by touching the sticker and dragging it from the sticker menu onto the image. In some embodiments, while displaying the capture affordance and further in response to detecting selection of the first one of the effects option affordances, the electronic device ceases to display the capture affordance.

In some embodiments, the electronic device (e.g., 600) detects, via the one or more input devices, selection (e.g., 626) of a second one of the effects option affordances (e.g., avatar affordance 624-1). In some embodiments, in response to detecting selection of the second one of the effects option affordances, the electronic device ceases to display the plurality of effects option affordances (e.g., 624) and displays an avatar selection region (e.g., avatar menu 628) having a plurality of avatar affordances (e.g., 630, displayed in a linear arrangement) (e.g., affordances that represent avatars). Ceasing to display the plurality of effects option affordances and displaying an avatar selection region in response to detecting selection of the second one of the effects option affordances enables the user to quickly and easily recognize that the second of the effects option affordances relates to avatar selection, thereby enhancing the operability of the device and making the user-device interface more efficient (e.g., by helping the user to provide proper inputs and reducing user mistakes when operating/ interacting with the device) which, additionally, reduces power usage and improves battery life of the device by enabling the user to use the device more quickly and efficiently. In some embodiments, the avatar affordances correspond to avatars that are customizable, non-customizable, or a combination thereof. In some embodiments, displaying the avatar selection region includes displaying the region (e.g., avatar menu 628) over the effects option affordances, the region including a plurality of avatar affordances that can be selected to display a corresponding avatar on an image represented in the camera user interface.

In some embodiments, the electronic device (e.g., 600) detects, via the one or more input devices, a swipe input (e.g., 646, a vertical swipe gesture) on the avatar selection region (e.g., 628). In some embodiments, in response to detecting the swipe input on the avatar selection region, the electronic device increases a size of the avatar selection region (e.g., 628-1) and displays the plurality of avatar affordances (e.g., 630, arranged in a matrix. Increasing a size of the avatar selection region and displaying the plurality of avatar affordances arranged in a matrix in response to detecting the swipe input on the avatar selection region enables the user to (concurrently) view one or more additional selectable avatars that were not (concurrently) visible in the avatar selection region. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, increasing the size of the avatar display region includes extending the avatar display region in a vertical direction to present a full-screen display of the avatar display region, with the avatar affordances displayed in a matrix in the avatar display region.

In some embodiments, the camera user interface (e.g., 615) further includes a first representation of image data (e.g., a live camera preview 620-1). Providing the first representation of image data (e.g., a live camera preview) provides visual feedback about one or more modifications (to an image) made by the user prior to saving/confirming the modifications. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, further in response to detecting selection of the effects mode affordance (e.g., 624-1, 624-2), the electronic device (e.g., 600), in accordance with a determination that the first representation of image data corresponds to image data obtained from a second camera (e.g., a rear-facing camera), ceases to display the first representation of image data and displays a second representation of image data (e.g., a live camera preview), the second representation of image data corresponding to image data obtained from the camera (e.g., a front-facing camera). In some embodiments, a representation of image data corresponding to the front-facing camera includes a representation of a user positioned in the field-of-view of the front-facing camera.

In some embodiments, while the electronic device (e.g., 600) is in the second camera mode (e.g., an effects camera mode; a mode in which various visual effects are available for modifying image data), the electronic device receives a request to transition (e.g., a selection of an active visual effects affordance) to the first camera mode (e.g., the normal mode, a non-effects mode). In some embodiments, in response to receiving the request to transition to the first camera mode, the electronic device transitions the electronic device from the second camera mode to the first camera mode. In some embodiments, in accordance with a first visual effect being active (e.g., actively applied to captured image data or a preview of image data for capture), the electronic device deactivates (e.g., disabling, ceasing to display the displayed first visual effect) the first visual effect.

In some embodiments, after deactivating the first visual effect, the electronic device (e.g., 600) detects, via the one or more input devices, subsequent selection of the effects mode affordance (e.g., 624-1, 624-2). In some embodiments, in response to detecting the subsequent selection of the effects mode affordance, the electronic device, in accordance with a determination that the subsequent selection of the effects mode affordance occurs within a predetermined amount of time after deactivating the first visual effect, re-activates the first visual effect. Re-activating the first visual effect in accordance with the determination that the subsequent selection of the effects mode affordance occurs within a predetermined amount of time after deactivating the first visual effect enables a user to quickly and easily revert back to a previous visual effect (e.g., without having to re-select/re-create the effect). Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, after selecting the effects mode affordance to remove the visual effects from the image, if the effects mode affordance is selected again within a predetermined time period, the removed visual effects are restored to the image.

The electronic device (e.g., 600) detects (712), via the one or more input devices, a second input (e.g., 676, a touch gesture on a touch screen display at a location that corresponds to the capture affordance) directed to the capture affordance (e.g., 621).

In response to detecting the second input (714), the electronic device (e.g., 600) captures (716) image data using the camera (e.g., 602). In some embodiments, capturing the image data includes, in accordance with a value of a characteristic (e.g., a duration of contact) of the second input meeting a first capture mode criteria (e.g., less than a threshold duration), capturing the image data in a first image capture mode (e.g., a photo capture mode, a still image capture mode). In some embodiments, capturing the image data includes, in accordance with the value of the characteristic of the second input meeting a second capture mode criteria (e.g., greater than a second threshold duration), capturing the image data in a second image capture mode (e.g., a video capture mode, a continuous capture mode). In some embodiments, the capture affordance (e.g., 621) is a multi-function capture affordance. In some embodiments, the electronic device captures a photo (e.g., a still image) when a tap is detected on the capture affordance. In some embodiments, the electronic device captures a video (e.g., a continuous image) when a press-and-hold gesture is detected on the capture affordance.

In response to detecting the second input (e.g., 676) (714), the electronic device (e.g., 600) ceases (718) to display the capture affordance (e.g., 621).

In some embodiments, after capturing image data using the camera (e.g., 602), the electronic device (e.g., 600) displays a mark-up affordance (e.g., 677), an edit affordance (e.g., 678), and a retake affordance (e.g., 679). In some embodiments, while displaying the mark-up affordance, the edit affordance, and the retake affordance, the electronic device receives, via the one or more input devices, a fourth user input. In some embodiments, in response to detecting the fourth user input, in accordance with the fourth user input corresponding to the edit affordance, the electronic device initiates a process for editing the captured image data. In some embodiments, the process for editing includes displaying one or more affordances for editing the captured image data. In some embodiments, in response to detecting the fourth user input, in accordance with the fourth user input corresponding to the mark-up affordance, the electronic device initiates a process for marking-up the captured image data. In some embodiments, the process for editing includes displaying one or more affordances for marking up the captured image data. In some embodiments, in response to detecting the fourth user input, in accordance with the fourth user input corresponding to the retake affordance, the electronic device initiates a process for retaking the captured image data. In some embodiments, initiating the process for retaking the captured image data includes capturing new image data and replacing the captured image data with the new image data.

In response to detecting the second input (e.g., 676) (714), the electronic device (e.g., 600) displays (720) a send affordance (e.g., 680, a selectable icon associated with a function for sending captured image data to a participant in a conversation, or for presenting the captured image data in a compose region prior to subsequent sending) at a location in the camera user interface (e.g., 615) that was previously occupied by the capture affordance (e.g., 621). Displaying the send affordance at the location in the camera user interface that was previously occupied by the capture affordance provides visual feedback that the captured image is ready to be transmitted to an intended recipient. Providing visual feedback to the user without cluttering the UI enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the location at which the send affordance (e.g., 680) is displayed is any location in a particular region (e.g., camera effects region 625) in which the capture affordance was previously displayed. In some embodiments, the location at which the send affordance is displayed is the same location that the capture affordance was displayed in the region. In some embodiments, displaying the send affordance includes replacing the capture affordance with the send affordance.

In some embodiments, while displaying the send affordance (e.g., 680), the electronic device (e.g., 600) displays (722) a representation of the first participant (e.g., an icon, picture, avatar, or other identifier associated with the first participant). Displaying the representation of the first participant while displaying the send affordance enables the user to quickly and easily recognize the intended recipient, thereby enhancing the operability of the device and making the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the representation of the first participant serves as an indication to the user that the captured photo will be sent to the first participant). In some embodiments, the representation of the first participant is not displayed (724) prior to capturing the image data using the camera (e.g., 602). In some embodiments, the camera user interface (e.g., 615) includes camera-specific affordances (e.g., 619, corresponding to filters, lighting options, timer options, etc.) that are displayed prior to capturing the image data. In some embodiments, displaying the representation of the first participant replaces the displayed camera-specific affordances with the representation of the first participant.

The electronic device (e.g., 600) detects (726), via the one or more input devices, a third input (e.g., a touch gesture on a touch screen display at a location that corresponds to the send affordance 680) directed to the send affordance.

In response to detecting the third input, the electronic device (e.g., 600) initiates (728) a process (e.g., immediately sending or presenting the captured image data in a compose region prior to subsequent sending) to send the captured image data to the first participant.

In some embodiments, prior to detecting the third input directed to the send affordance (e.g., 680), the electronic device (e.g., 600) displays a done affordance (e.g., a selectable icon associated with a function for closing the camera user interface to display the messaging user interface). In some embodiments, the electronic device detects, via the one or more input devices, selection of the done affordance. In some embodiments, in response to detecting selection of the done affordance, the electronic device displays the messaging user interface (e.g., 603), the messaging user interface having a message-compose region (e.g., 608). In some embodiments, in response to detecting selection of the done affordance, the electronic device displays a representation of the captured image data in the message-compose region. In some embodiments, selecting the done affordance closes the camera user interface and displays the captured image data in a message-compose field of the messaging user interface, without sending the captured image data.

In some embodiments, prior to detecting the third user input, the electronic device (e.g., 600) is in a first image capture mode (e.g., photo capture mode, video capture mode). In some embodiments, further in response to detecting the third user input, the electronic device maintains the first image capture mode. In some embodiments, the electronic device can be configured (e.g., user configured) to capture image data according to a plurality of modes (e.g., photo capture mode, video capture mode). In some embodiments, a selection of a image capture mode is persistent, even when the electronic transitions from a first camera mode (e.g., a standard camera mode, a non-effects camera mode) to a second camera mode (e.g., an effects camera mode).

In some embodiments, initiating the process to send the captured image data to the first participant includes sending the captured image data to the first participant (e.g., without displaying the messaging user interface 615). In some embodiments, selecting the send affordance (e.g., 680) from the camera user interface immediately sends the captured image data to another participant in a message conversation without displaying any intermediate user interface or requiring further input from the user.

In some embodiments, initiating the process to send the captured image data to the first participant includes re-displaying the messaging user interface (e.g., 615), where the messaging user interface further includes a keyboard region (e.g., 612) and an application menu affordance (e.g., 610, a selectable icon associated with a function for displaying an application menu user interface). Re-displaying the messaging user interface as part of initiating the process to send the captured image data to the first participant provides visual feedback that the captured image data is being sent via the message conversation. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the application menu affordance is displayed adjacent a message-compose field in the messaging user interface. In some embodiments, the electronic device (e.g., 600) detects, via the one or more input devices, selection of the application menu affordance. In some embodiments, in response to detecting selection of the application menu affordance, the electronic device displays an application menu region adjacent (e.g., above) the keyboard region, where the application menu region has a plurality of application affordances (e.g., selectable icons each associated with a function for initiating an application associated with the respective application affordance). In some embodiments, the application affordances include stickers affordances and avatar affordances.

In some embodiments, the electronic device (e.g., 600) detects a fourth input on the messaging user interface (e.g., 615). In some embodiments, in accordance with a determination the fourth input corresponds to a location of the keyboard region (e.g., 612) or a location of a message-compose region (e.g., 608) in the messaging user interface, the electronic device ceases to display the application menu region and displays a text-suggestion region (e.g., a region having a listing of suggested words for convenient selection by a user) at a location in the messaging user interface that was previously occupied by the application menu region.

In some embodiments, the electronic device (e.g., 600) detects selection of one of the plurality of application affordances (e.g., a stickers affordance or an avatar affordance) in the application menu region. In some embodiments, in response to detecting selection of the application affordance (e.g., 610), the electronic device ceases to display the keyboard region (e.g., 612) and displays an application display region at a location in the messaging user interface (e.g., 615) that was previously occupied by the keyboard region, where the application display region includes a plurality of graphical objects (e.g., avatars or stickers) corresponding to the selected application affordance. In some embodiments, the selected application affordance is a stickers affordance and the graphical objects displayed in the application display region are stickers. In some embodiments, the selected application affordance is an avatar affordance and the graphical objects displayed in the application display region are avatars (e.g., customizable avatars and/or non-customizable avatars).

Note that details of the processes described above with respect to method 700 (e.g., FIGS. 7A-7B) are also applicable in an analogous manner to the methods described below. For example, methods 900, 1100, 1300, and 1500 optionally includes one or more of the characteristics of the various methods described above with reference to method 700. For example, visual effects such as stickers and virtual avatars are displayed in image data in a camera application user interface, in a media user interface, and in a user interface for live video communication sessions. For brevity, these details are not repeated below.

FIGS. 8A-8BQ illustrate exemplary user interfaces for displaying visual effects in a camera application, in accordance with some embodiments. The user interfaces in these figures are used to illustrate the processes described below, including the processes in FIGS. 9A and 9B.

In FIG. 8A, device 600 shows home screen 800 and detects input 801 on camera application affordance 802.

In FIG. 8B, in response to detecting input 801, device 600 launches a camera application associated with camera application affordance 802 and displays camera application user interface 815. Camera application user interface 815 is similar to camera application user interface 615 discussed above with respect to the embodiments shown in FIGS. 6A-6BQ.

Camera application user interface 815 includes image display region 820 which displays a representation of image data such as, for example, streamed image data (e.g., a live camera preview, live camera recording, or live video communications session) representing objects positioned within a field-of-view of a camera (e.g., a rear-facing camera or camera 602), or a media item such as, for example, a photograph or a video recording. In the embodiment illustrated in FIG. 8B, image display region 820 shows live camera preview 820-1' from a rear-facing camera of device 600.

Camera application user interface 815 also includes a region above image display region 820 that includes camera-specific affordances 817. Camera-specific affordances include affordance 817-1 associated with a camera flash function, affordance 817-2 associated with a camera mode function, affordance 817-3 associated with a timer function, and affordance 817-4 associated with a filter function.

Camera application user interface 815 also includes camera options region 825 (similar to camera options region 625) positioned below image display region 820 (similar to image display region 620). Camera options region 825 includes camera selector affordance 827 for switching between cameras (e.g., a rear-facing camera and camera 602), and camera option affordances 819 associated with different capture modes in which a camera can record image data. For example, video affordance 819-1 is associated with a function for activating a video recording capture mode of the camera, and photo affordance 819-2 is associated with a function for activating a still image capture mode of the camera. In the embodiments discussed below with respect to FIGS. 8B-8AQ, device 600 is in the still image capture mode of operation associated with photo affordance 819-2. However, unless specified otherwise, these embodiments also apply to the video recording mode associated with video affordance 819-1.

Camera options region 825 further includes effects affordance 822 for enabling and disabling a mode (visual effects mode, effects mode) of device 600 in which device 600 is enabled or disabled for displaying visual effects in image display region 820. Effects affordance 822 is similar to effects affordance 622 and, therefore, has the same functionality as effects affordance 622, unless specified otherwise. Accordingly, effects affordance 822 can be selected to enable display of visual effects, and deselected to disable display of visual effects.

Camera options region 825 also includes capture affordance 821, which functions in a manner similar to capture affordance 621 discussed above. Capture affordance 821 can be selected to capture image data represented in image display region 820. In some embodiments, device 600 captures the image data in a manner based on the currently enabled capture option (e.g., video recording capture mode or image capture mode). In some embodiments, device 600 captures the image data depending on the type of gesture detected on capture affordance 821. For example, if device 600 detects a tap gesture on capture affordance 821, device 600 captures a still image of the image data represented in image display region 820 at the time the tap gesture occurs. If device 600 detects a tap-and-hold gesture on capture affordance 821, device 600 captures a video recording of the image data represented in image display region 820 during a period of time for which the tap-and-hold gesture persists. In some embodiments, the video recording stops when the finger lifts off of the affordance. In some embodiments, the video recording continues until a subsequent input (e.g., a tap input) is detected at a location corresponding to the affordance. In some embodiments, the captured image (e.g., still image or video recording) can be shared with other devices, for example, using a messaging application.

Figure 8C:

In FIG. 8C, device 600 detects input 823 on effects affordance 822.

Figure 8D:
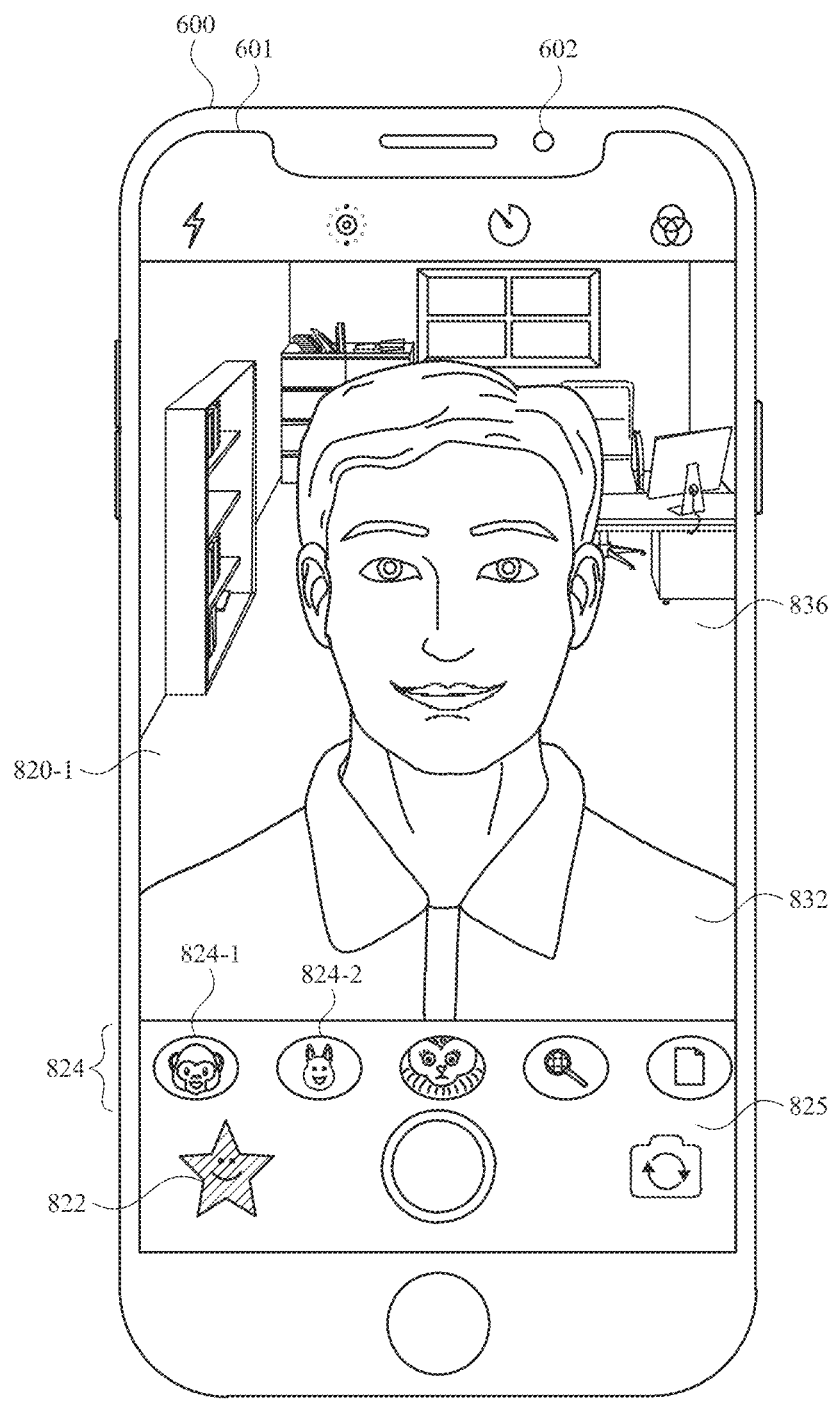

In FIG. 8D, in response to detecting input 823, device 600 activates camera 602 (e.g., switches from the rear-facing camera) and updates image display region 820 to display live camera preview 820-1 from camera 602, showing a representation of subject 832 positioned in the field of view of camera 602 and background 836 displayed behind subject 832. As discussed herein, image data captured using camera 602 includes, in some embodiments, depth data that can be used to determine a depth of objects in the field of view of camera 602. In some embodiments, device 600 parses objects (e.g., in image data) based on a detected depth of those objects, and uses this determination to apply the visual effects discussed herein. For example, device 600 can categorize subject 832 as being in the foreground of the live camera preview 820-1 and objects positioned behind the user as being in the background of the live camera preview 820-1. These background objects are referred to generally herein as background 836.

Device 600 also highlights effects affordance 822 to indicate visual effects are enabled for display, and updates camera options region 825 by replacing camera option affordances 819 with visual effects option affordances 824. The visual effects option affordances include avatar effects affordance 824-1 and sticker effects affordance 824-2. Visual effects option affordances 824 are similar to visual effects option affordances 624 described above. Visual effects option affordances 824 correspond to different visual effects that can be applied to the image displayed in image display region 820. By selecting one of the visual effect option affordances (e.g., 824-1 or 824-2) a menu is displayed with visual effects options corresponding to the selected visual effects option affordance.

Figure 8E:
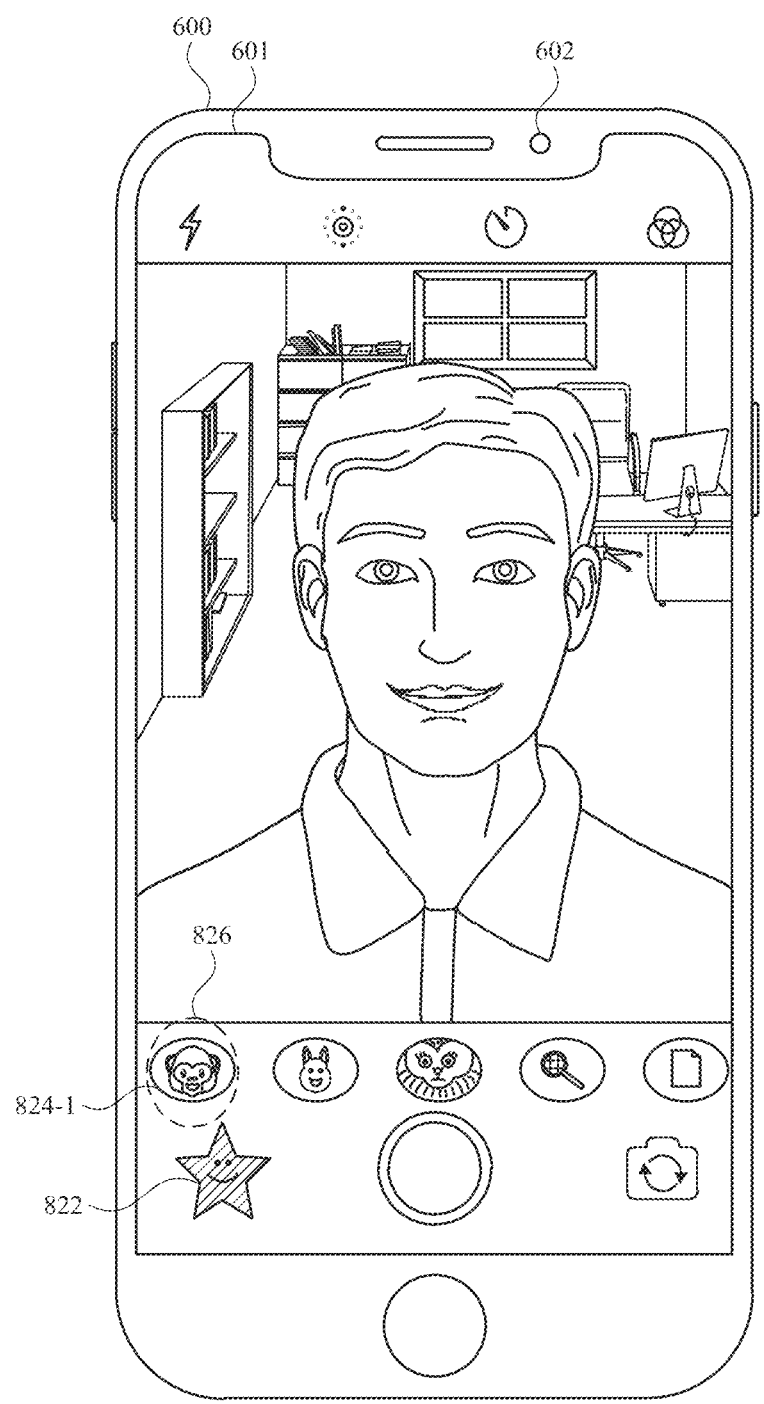
Figure 8F:

In FIGS. 8E-8F, device 600 detects input 826 on avatar effects affordance 824-1, and displays avatar options menu 828. Avatar options menu 828 is similar to avatar options menu 628. Avatar options menu 828 includes a scrollable listing of avatar options 830 and selection region 829 for indicating a selected one of avatar options 830. Displayed avatar options include customizable woman avatar 830-1, null avatar option 830-2, robot avatar option 830-3, rabbit avatar option 830-4, and a second customizable woman avatar 830-5. As shown in FIG. 8F, null avatar option 830-2 is selected as the default avatar option 830. Thus, the representation of subject 832 displayed in image display region 820 is shown with no avatar displayed on the subject's face. Avatar options 830 can be preconfigured, like avatar options 830-3 or 830-4, or they can be customizable avatar, such as avatar options 830-1 and 830-5.

Avatar options 830 have a similar functionality to avatar options 630. Thus, avatar options 830 correspond to a virtual avatar visual effect applied to a representation of the subject in image display region 820. Specifically, each avatar option 830 corresponds to a virtual avatar that, when selected, is transposed onto the face of the subject in the image display region, while other portions of the image in image display region (such as a background or other portions of the user, such as their body) remain displayed. A user (e.g., subject 832) positioned in the field-of-view of camera 602 can control visual aspects of the virtual avatar by changing the pose (e.g., rotation or orientation) of their face as discussed above.

Figure 8G:
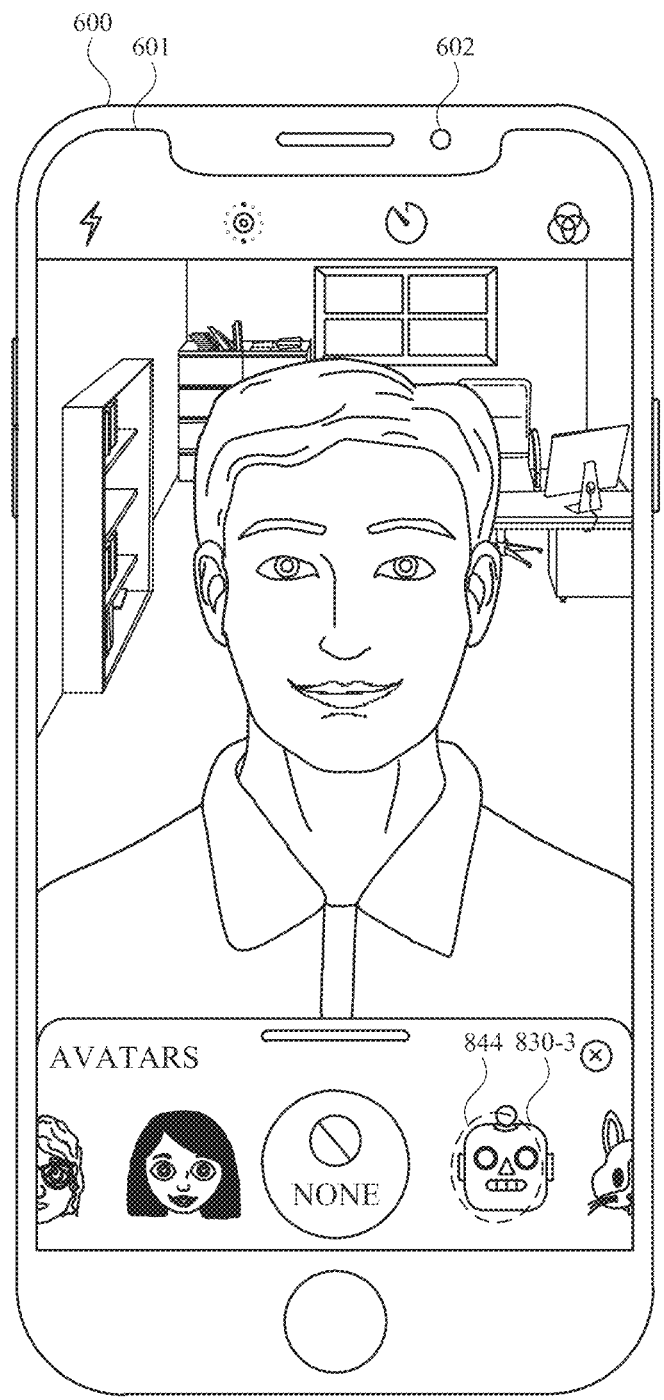
Figure 8H:
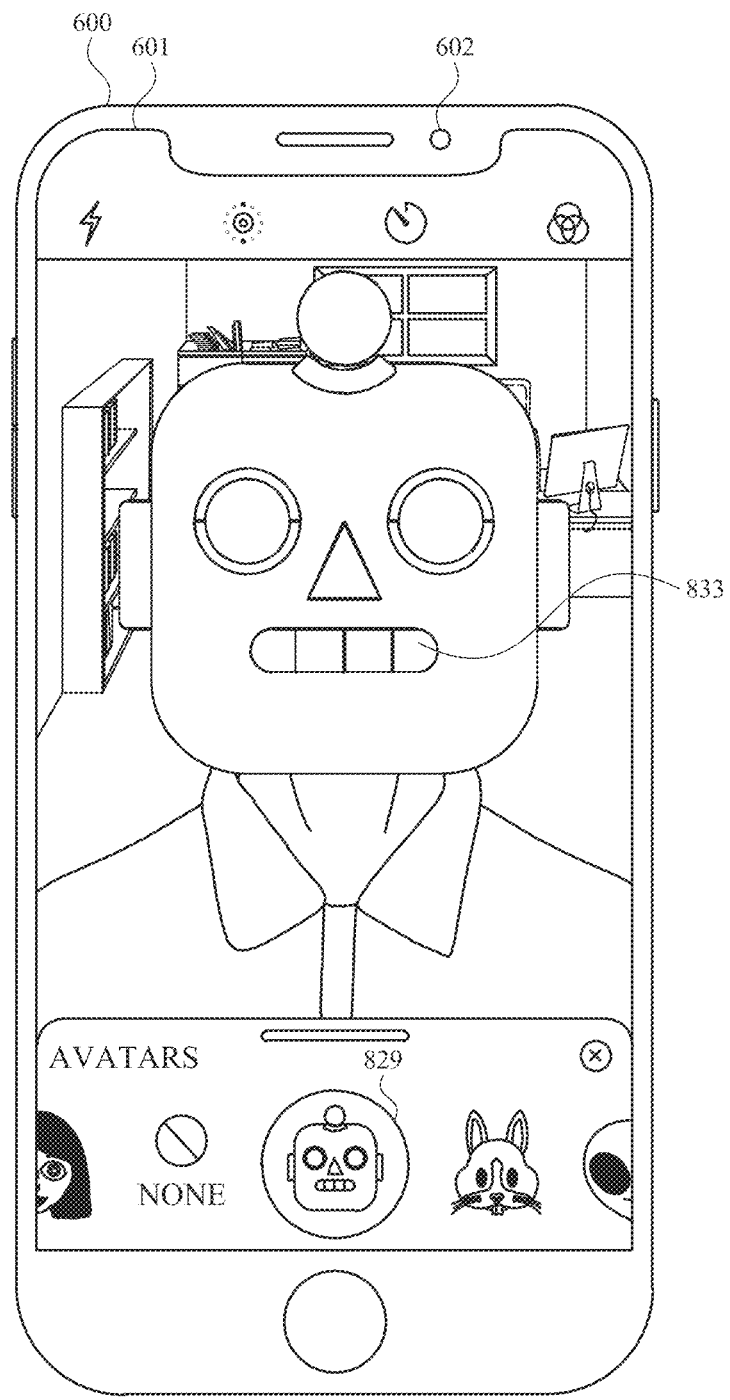
Figure 8I:
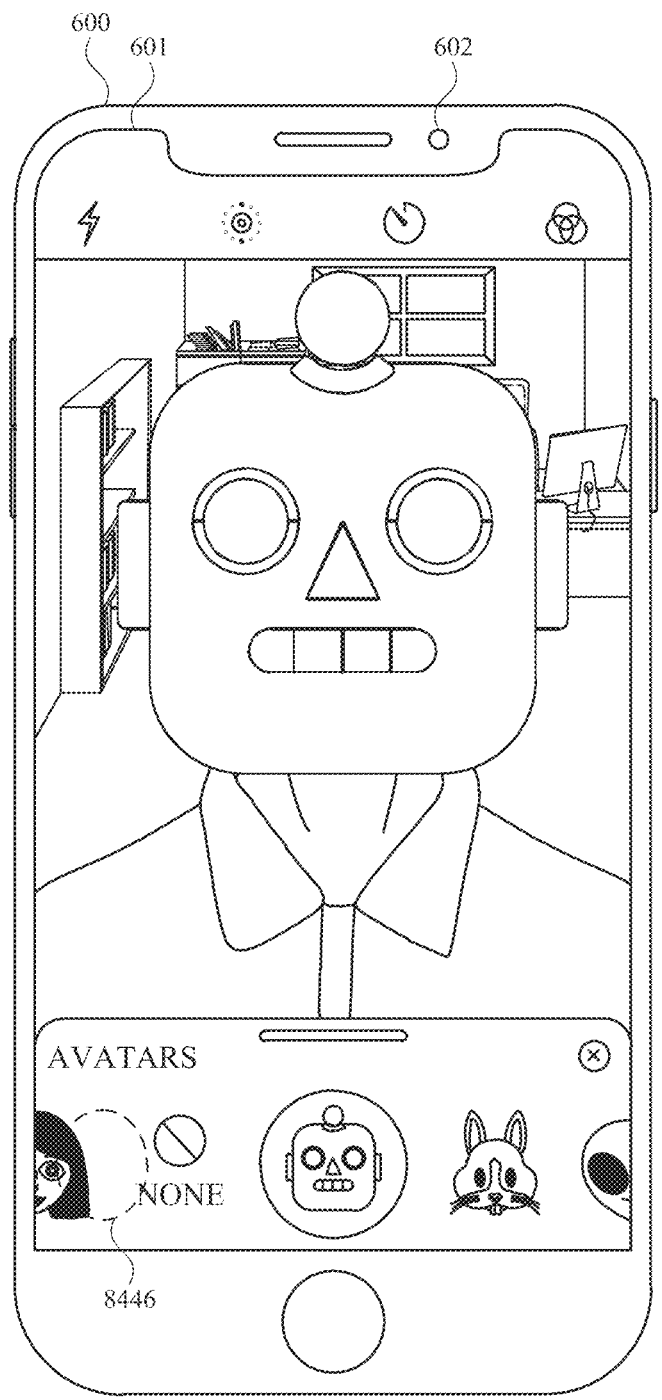
Figure 8J:
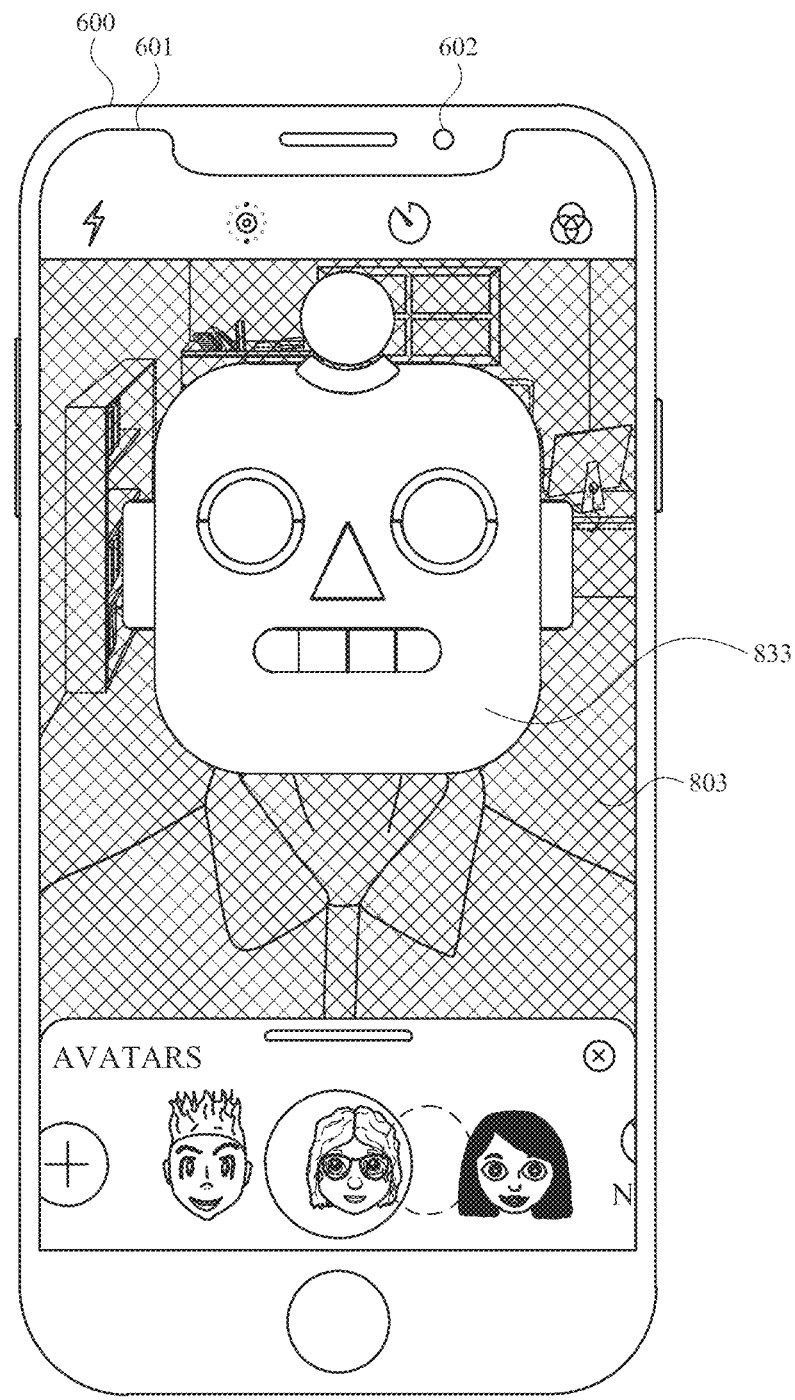

Avatar options 830 can be scrolled by gestures on the avatar options menu 828. For example, a horizontal gesture 844a is shown in FIG. 8G to select robot avatar option 830-3, which is then displayed as robot avatar 833 on the subject's face in image display region 820, as shown in FIG. 8H. Continued scrolling via horizontal gestures 844b, scrolls additional avatar options 830 onto the displayed avatar options menu 828. In some embodiments, as the user scrolls the avatar options 830, image display region 820 shows an avatar (e.g., robot avatar 833 in FIG. 8J) with blurred effect 803 applied to the represented image data behind the avatar.

Figure 8K:
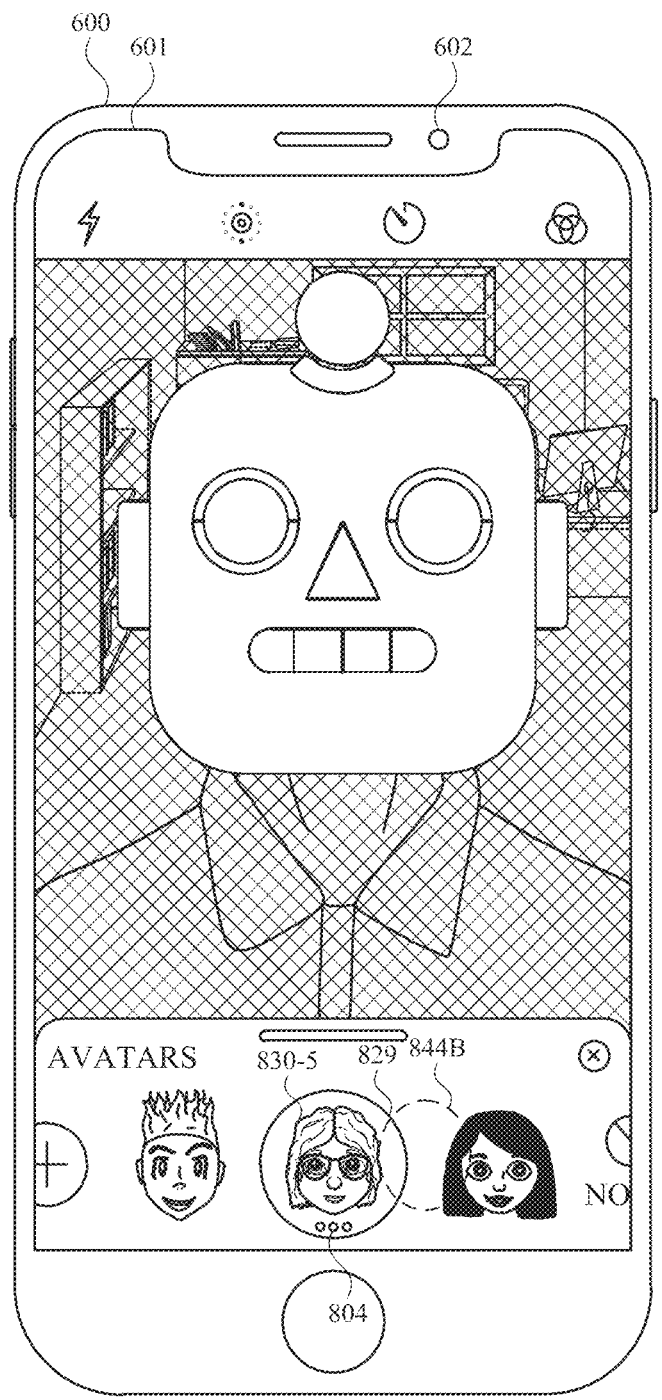

In FIG. 8K, device 600 displays customizable woman avatar option 830-5 positioned within selection region 829, just prior to being selected (e.g., gesture 844b has not yet terminated), and edit affordance 804 displayed below customizable woman avatar option 830-5. Device 600 continues to display robot avatar 833 with blurred effect 803. In some embodiments, device 600 displays edit affordance 804 in selection region 829 when a customizable avatar option is positioned in selection region 829. Edit affordance 804 can be selected to display an avatar editing user interface, such as that discussed below with respect to FIG. 8AA.

Figure 8L:
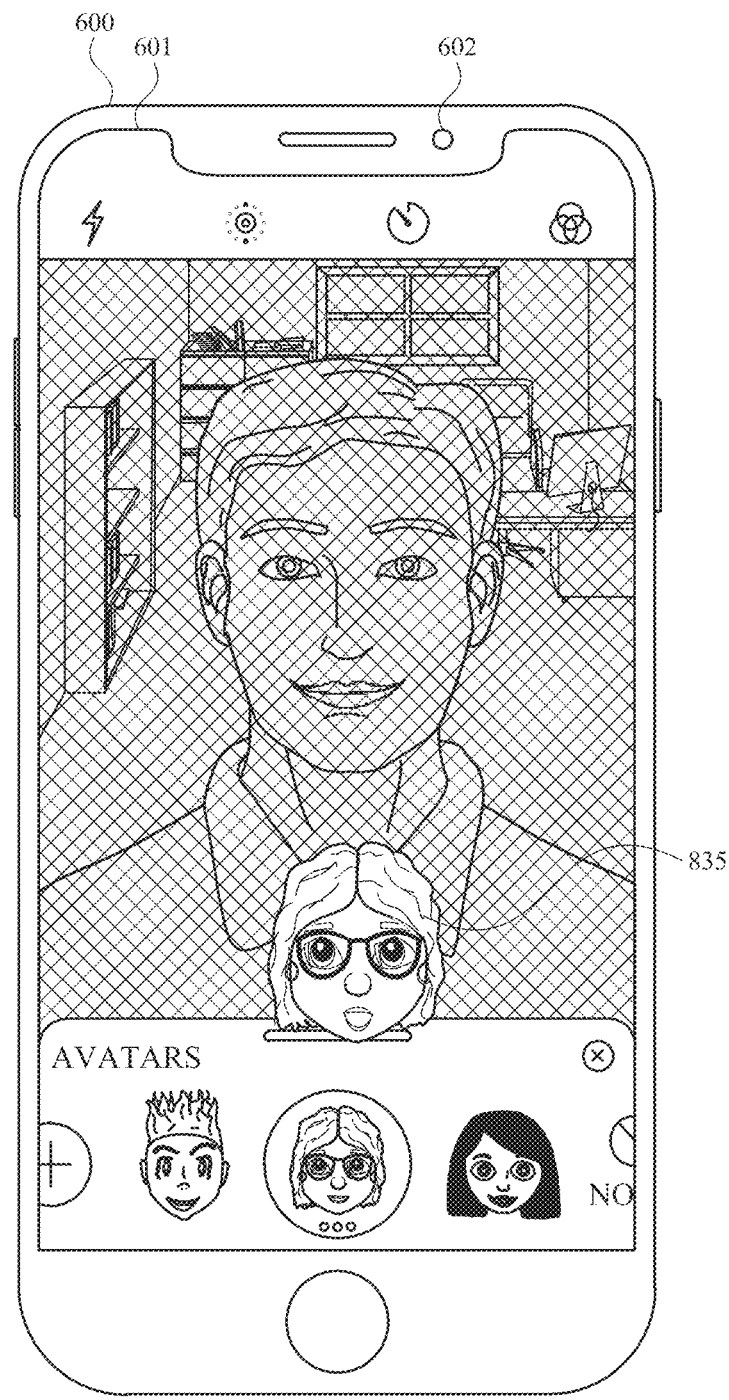

In FIG. 8L, after avatar option 830-5 is selected (e.g., gesture 844b is terminated). Device 600 removes robot avatar 833 from image display region 820 (while continuing the blurred effect 803) and displays an animation of customizable woman avatar 835 appearing from the avatar option 830-5 within selection region 829 and moving to image display region 820 (e.g., at a position at the center of image display region 820, or at a location corresponding to the subject's face), where avatar 835 is modified based on detected changes to the subject's face. In some embodiments, the animation includes the avatar (e.g., 835) starting out as a static appearance (e.g., similar to a sticker matching the displayed avatar option) and then transitioning into a dynamic state (shown in FIG. 8L) in which the avatar (e.g., 835) is modified based on device 600 detecting changes to a user's face. In some embodiments, the avatar's transition from static to dynamic occurs prior to the avatar moving from selection region. In some embodiments, the avatar's transition from static to dynamic occurs as the avatar is moving from selection region 829 to image display region 820.

Figure 8M:
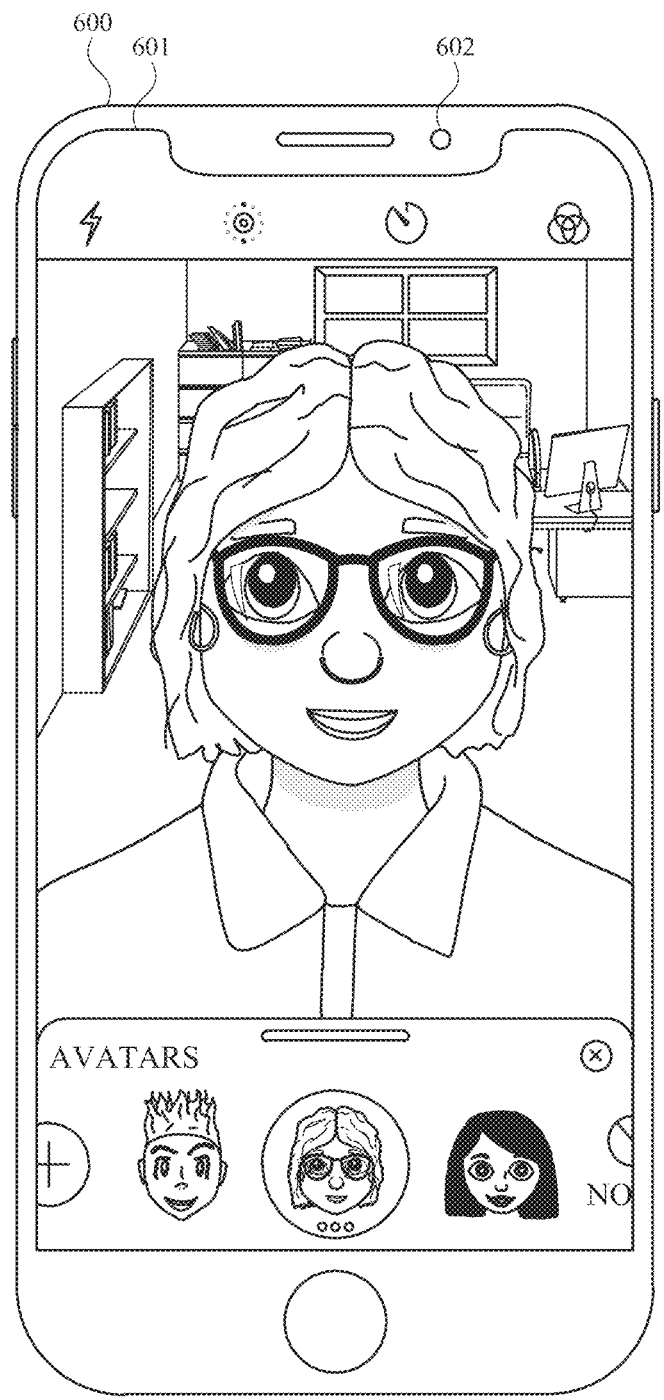
Figure 8N:
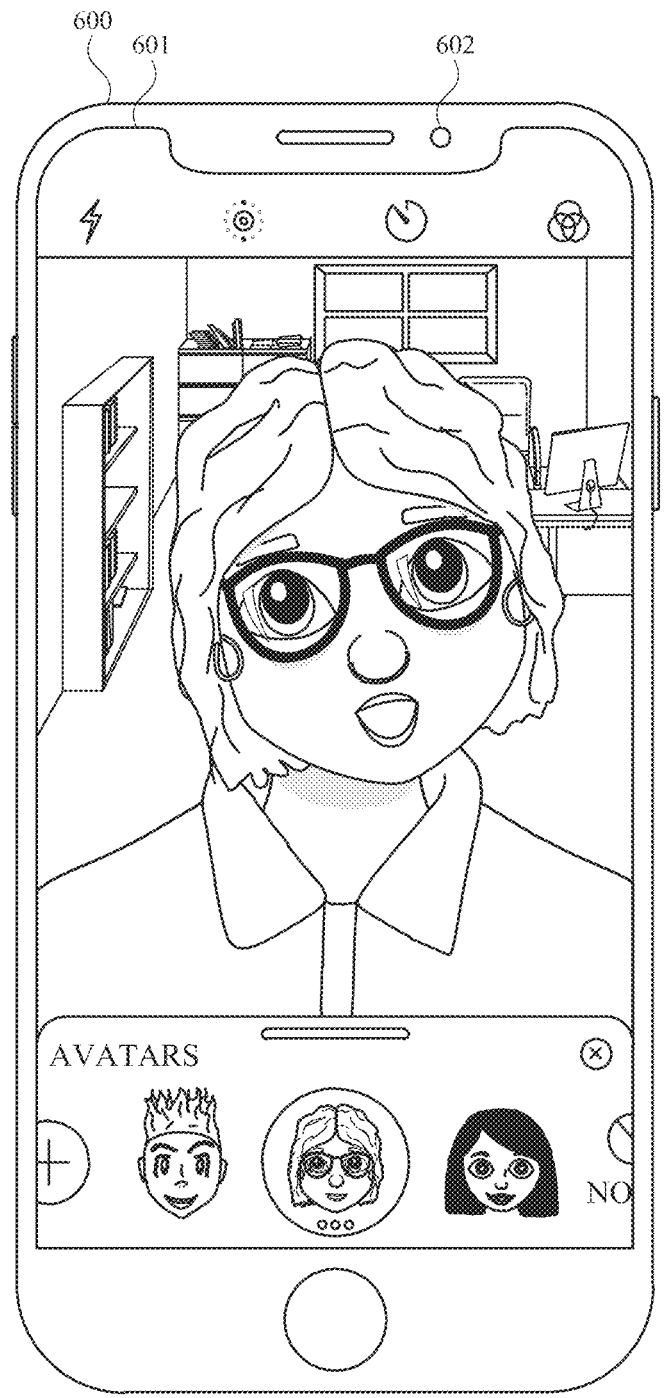
Figure 8O:
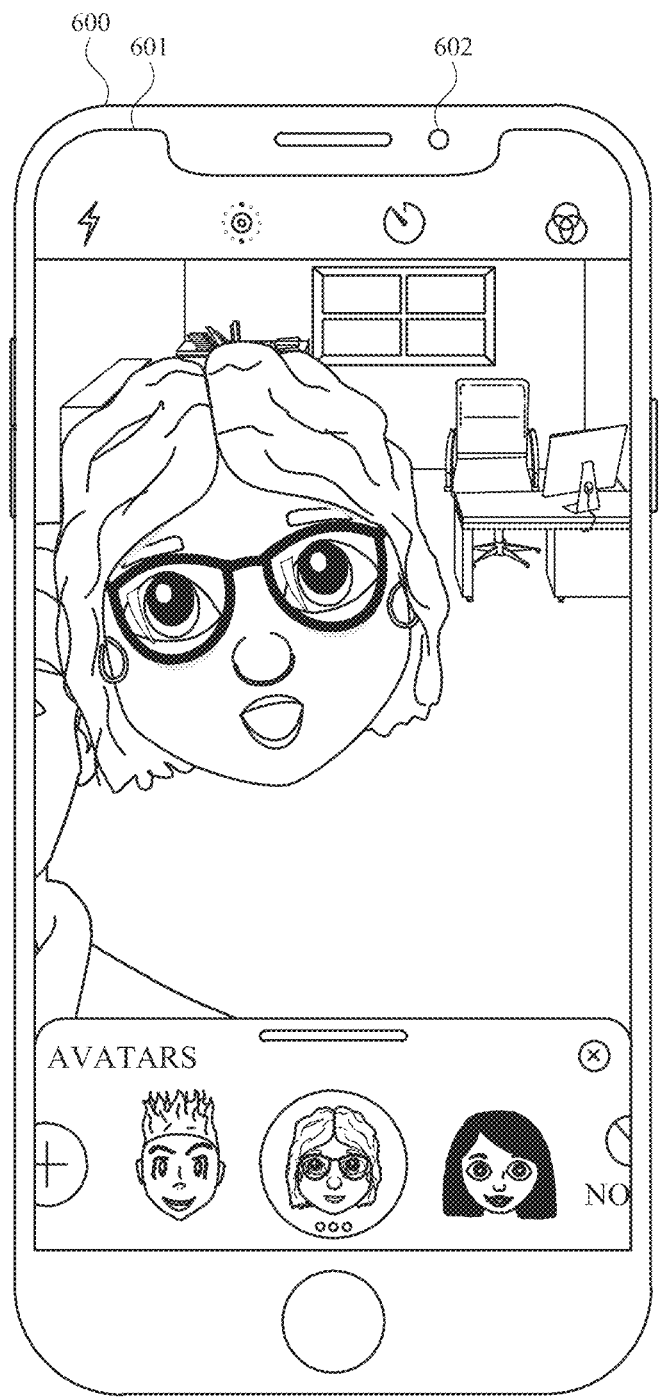

As shown in FIGS. 8M and 8N, when avatar 835 is applied to the subject's face, device 600 modifies avatar 835 based on detected changes to subject's face, including changes to the position of the face within the field of view of camera 602.

Figure 8P:
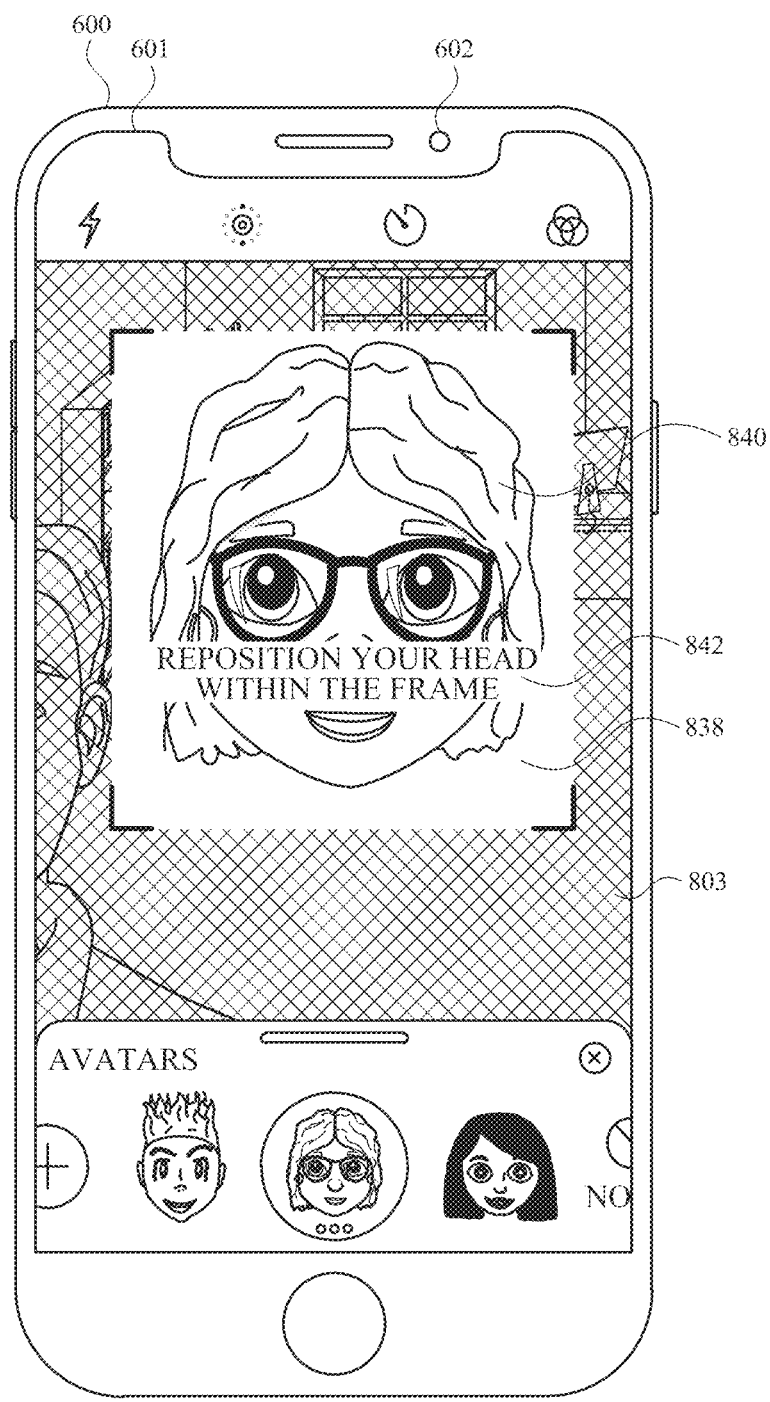
Figure 8Q:
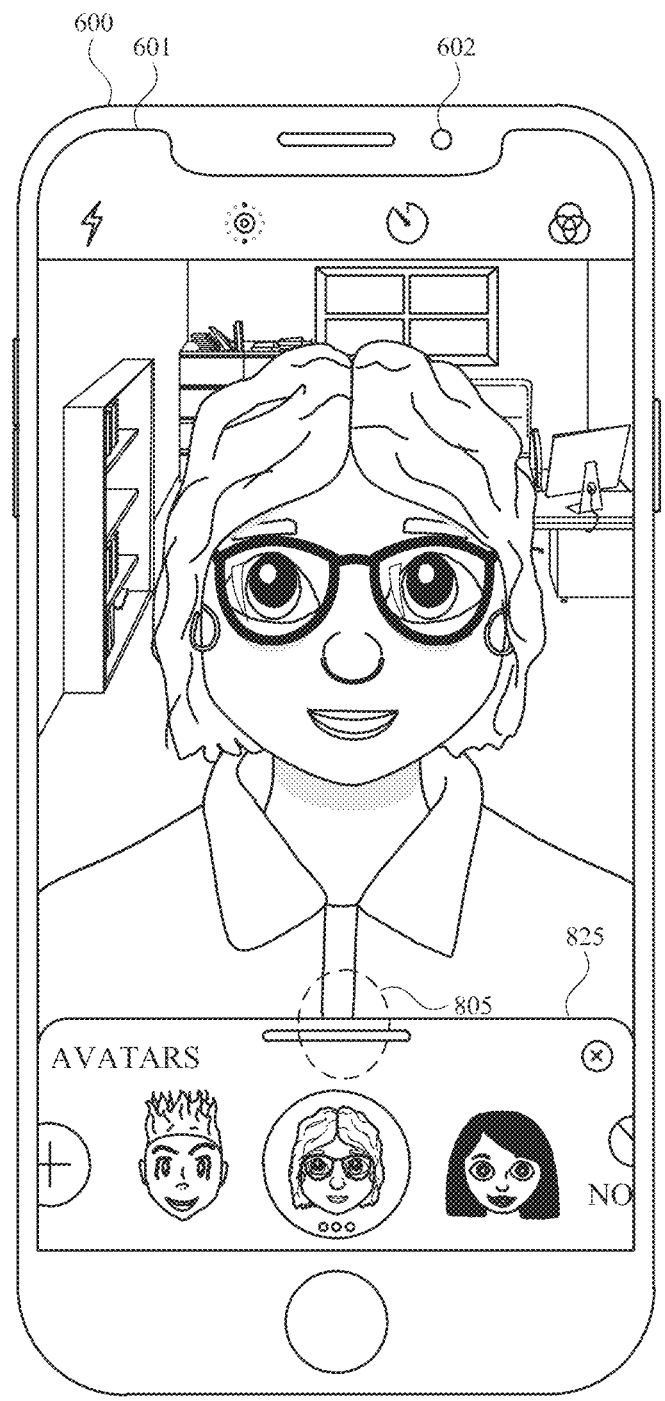
Figure 8R:
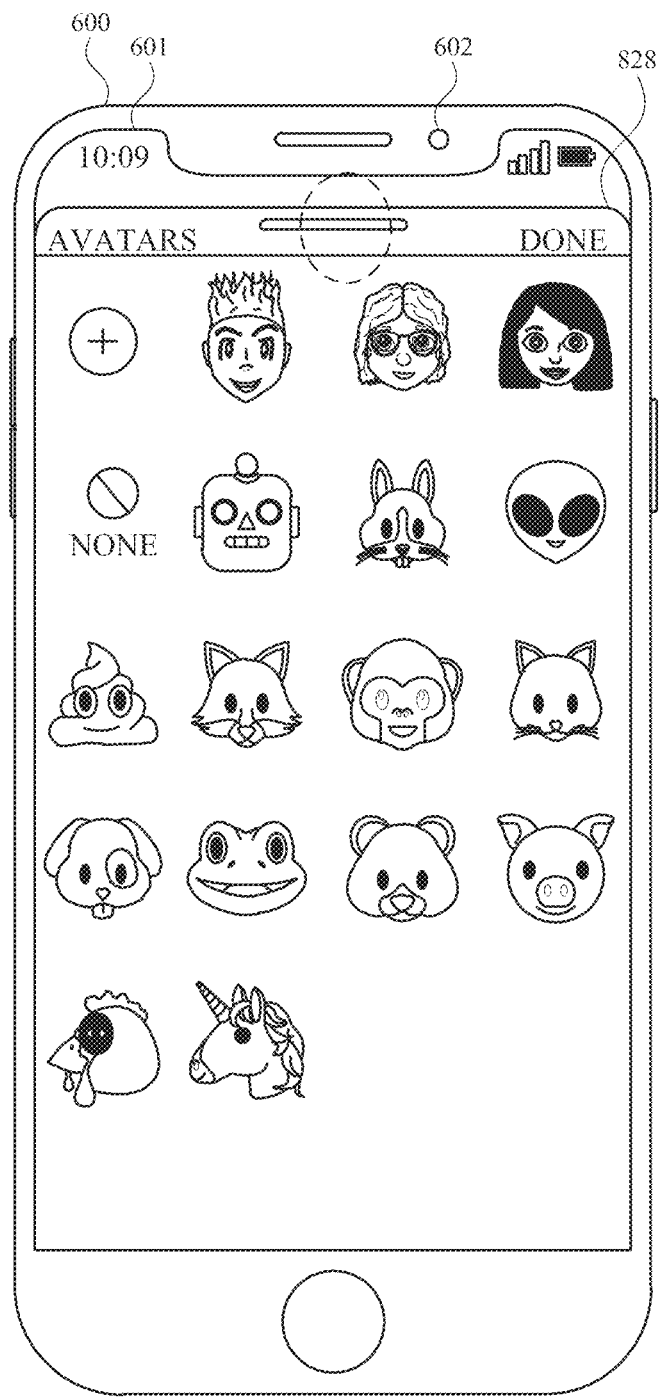
Figure 8S:
Figure 8T:
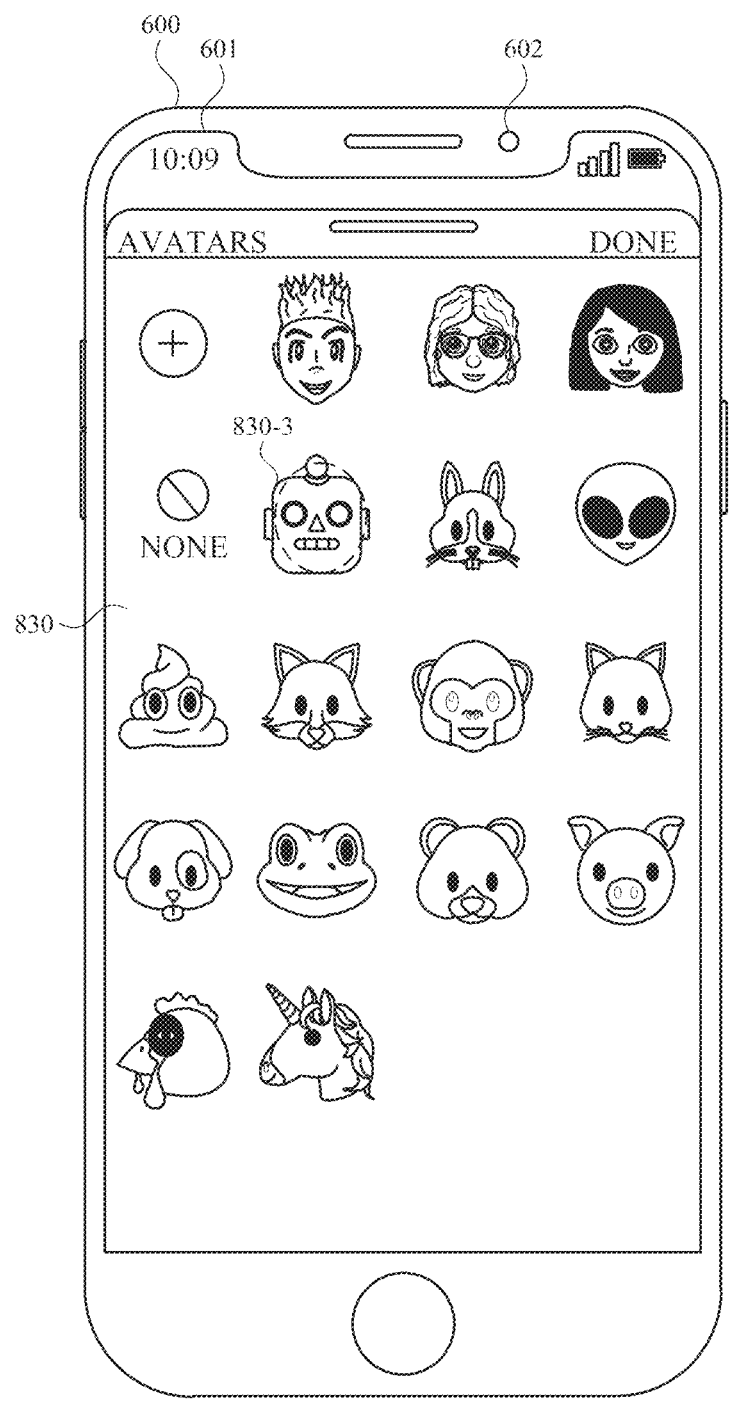

In some embodiments, when device 600 no longer detects the subject's face within the field-of-view of camera 602, device 600 again applies a blurring effect 803 (similar to the blurring effect 644) to the background and displays prompt 838 instructing the user to return their face to the field-of-view of camera 602. In the embodiment shown in FIG. 8P, device 600 displays prompt 838 containing representation 840 of the selected avatar (e.g., customizable woman avatar) and message 842 instructing the user to reposition their head in the field-of-view of camera 602. In some embodiments, displaying prompt 838 includes displaying an animation of the selected avatar (e.g., 835) returning to a center location of image display region 820, and showing a slowed movement of the avatar and its features as they appear to settle to a stop based on a physics model of the avatar features.

In some embodiments, when device 600 detects the user's face returning to the field-of-view of camera 602, device 600 displays avatar 835 moving from the center position of image display region 820 to the position of the user's face, and resumes modifying the avatar based on detected changes to the user's face.

Figure 8U:
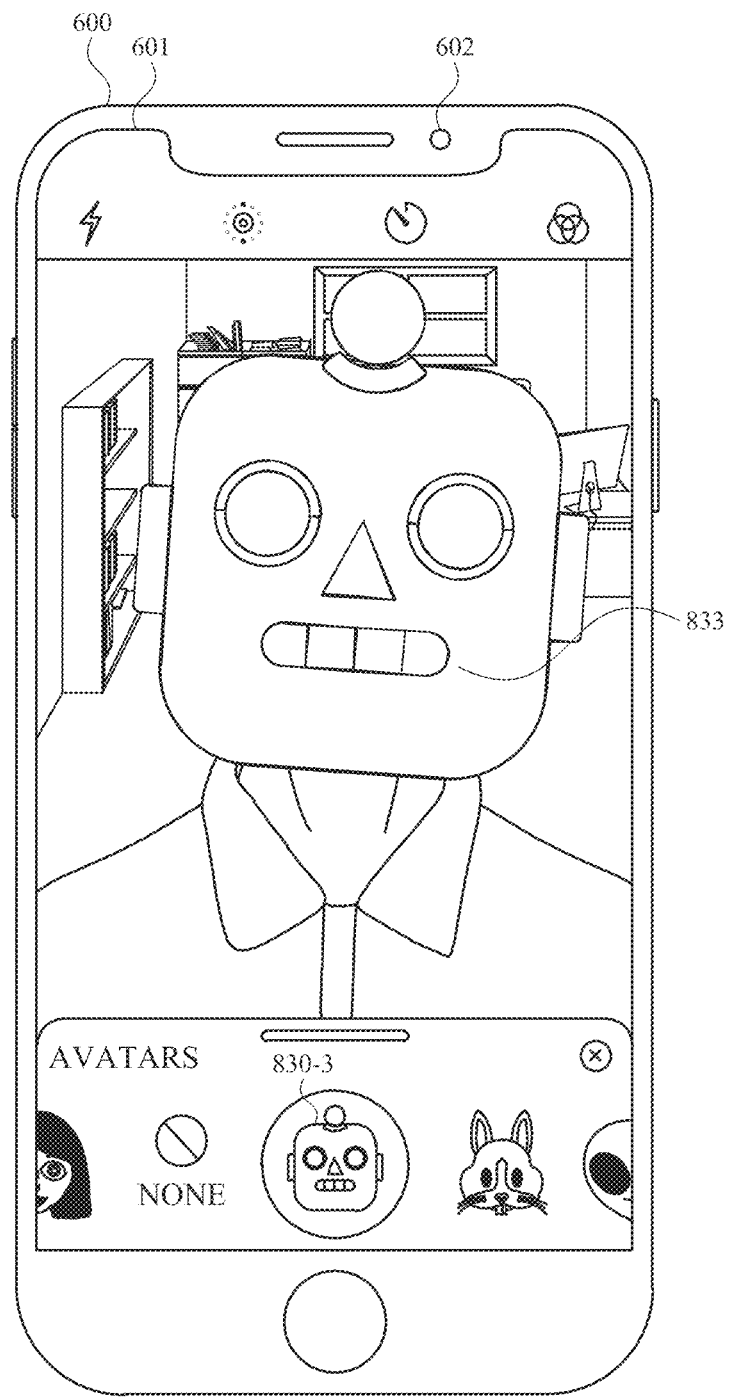

In some embodiments, avatar options menu 828 can be expanded with a vertical gesture (e.g., 805) to display an enlarged version of the avatar options menu as shown in FIGS. 8Q-8T. The enlarged version of the avatar options menu displays a greater number of avatar options 830, including avatars of different types (e.g., customizable and non-customizable). A new avatar option (e.g., robot avatar option 830-3) may be selected in the enlarged avatar display menu. Device 600 then displays the corresponding avatar (e.g., robot avatar 833) on the user's face when the enlarged version of the avatar options menu is returned to its original (e.g., condensed) state, as shown in FIG. 8U.

In some embodiments, device 600 displays different avatars on the user's head in response to detecting swipe gestures on image display region 820. For example, in FIG. 8V, device 600 detects swipe gesture 806 moving in a rightward direction across image display region 820. In response to detecting swipe gesture 806, device 600 scrolls avatar options 830 in avatar options menu 828. In some embodiments, the magnitude of the scroll is determined by the magnitude of the swipe gesture. Thus, a user can scroll through multiple avatars based on the magnitude of the swipe gesture. In addition, the direction of scroll, and the corresponding movement of avatars on image display region 820, is determined based on a direction of swipe gesture 806. Therefore, the scrolling of avatar options and corresponding movement of transitioning avatars can be in a leftward direction if the swipe is in a leftward direction, or can be in a rightward direction if the swipe is in a rightward direction (as shown in FIGS. 8V and 8W).

As the avatar options 830 begin to scroll, the currently selected avatar option (e.g. robot avatar option 830-3 in FIG. 8V) leaves selection region 829 and, as the scroll continues, a new avatar option (e.g., avatar option 830-1 in FIG. 8W) enters selection region 829. As the avatar options scroll, device 600 also displays, in image display region 820, an animation of the currently selected avatar (e.g., robot avatar 833) moving off of the user's face and exiting the right side of image display region 820 while a next avatar (e.g., customizable avatar 831) enters image display region 820 from the left, and moves to the user's face. In some embodiments, device 600 applies blurring effect 803 to the image display region 820 while the avatars are scrolled across image display region 820.

Figure 8V:
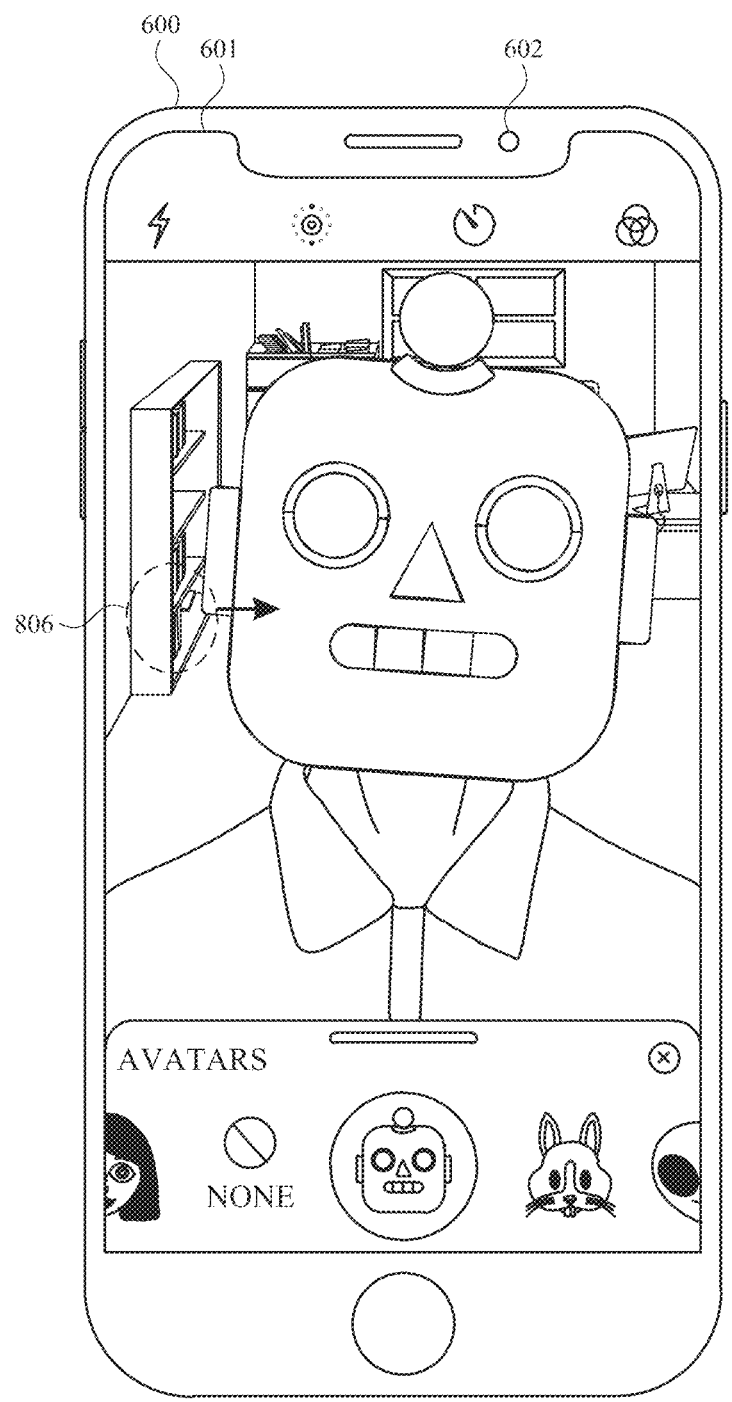
Figure 8W:
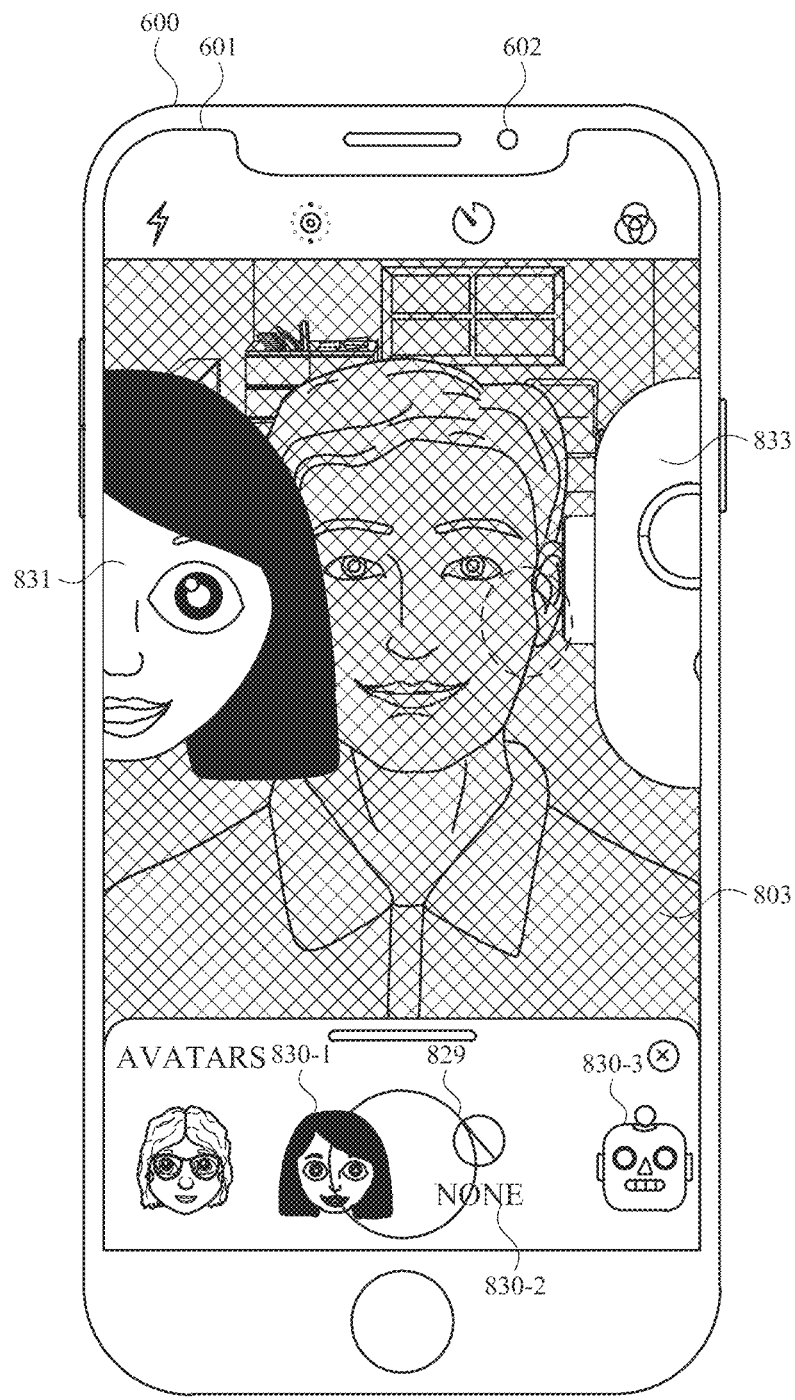

In the embodiment illustrated in FIGS. 8V and 8W, null avatar option 830-2 is not selected to better illustrate a transition from a currently selected avatar to a new avatar that appears on image display region 820. However, it should be understood that null avatar option 830-2 can be selected with a swipe gesture on image display region 820.

In such instances, the currently selected avatar is moved off screen while the background is blurred, and then the blurring effect is removed to display the user's face with no avatar.

Figure 8X:
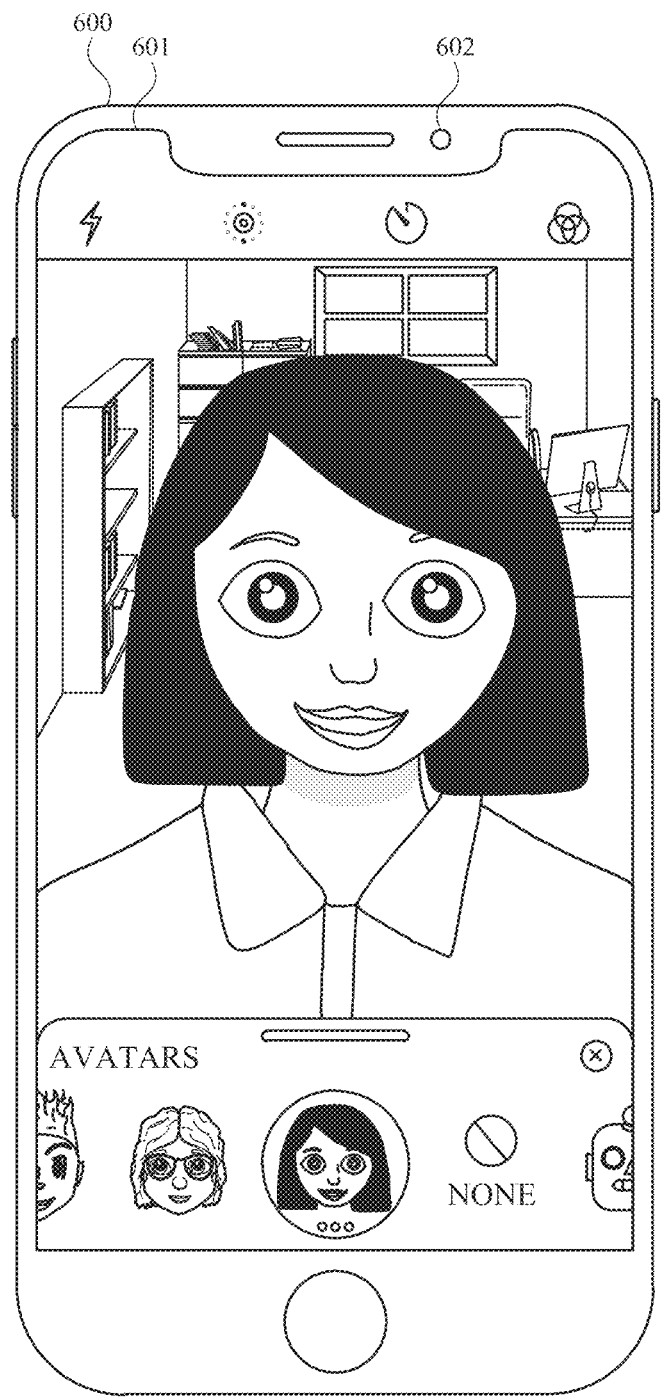
Figure 8Y:
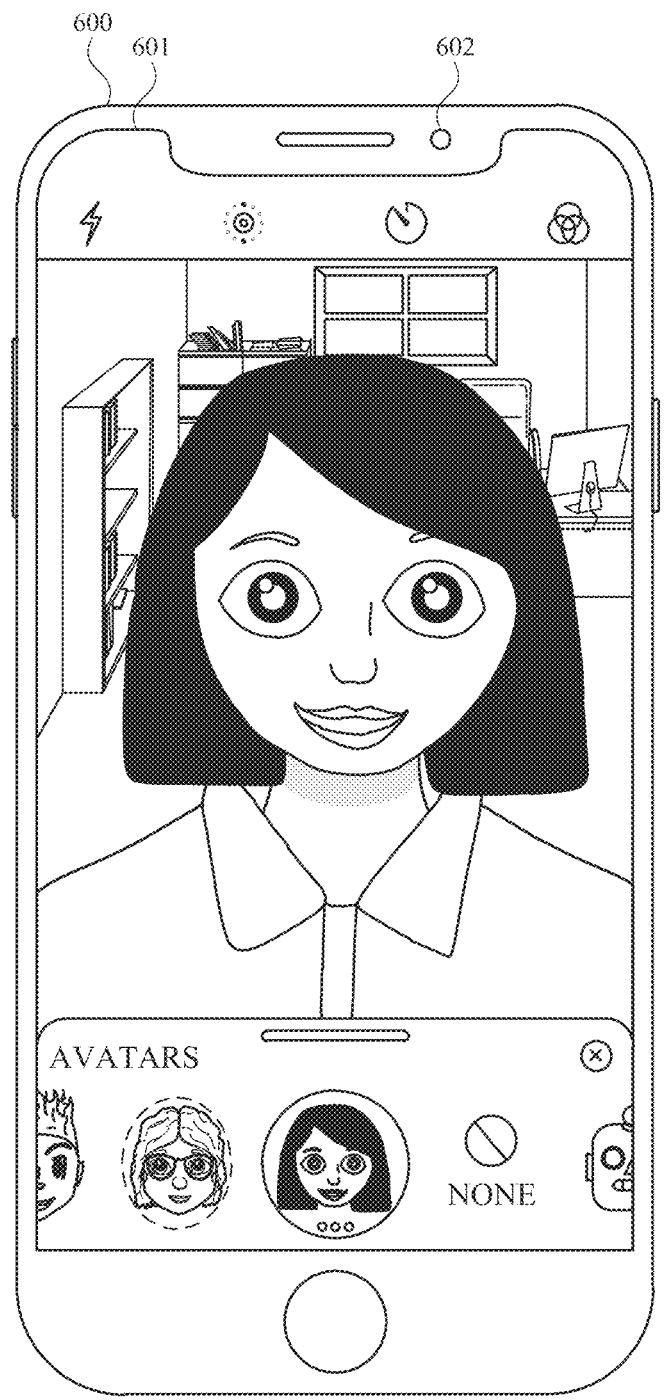
Figure 8Z:
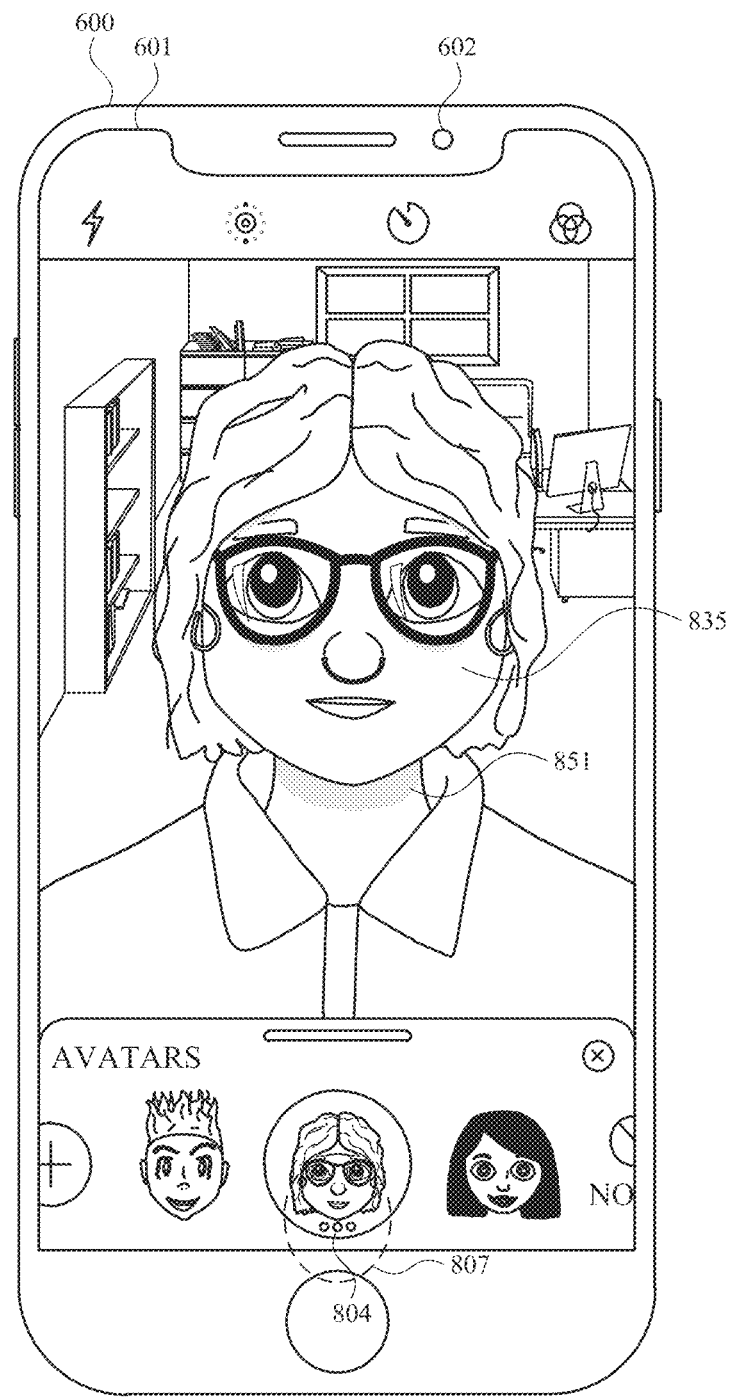
Figure 8A:
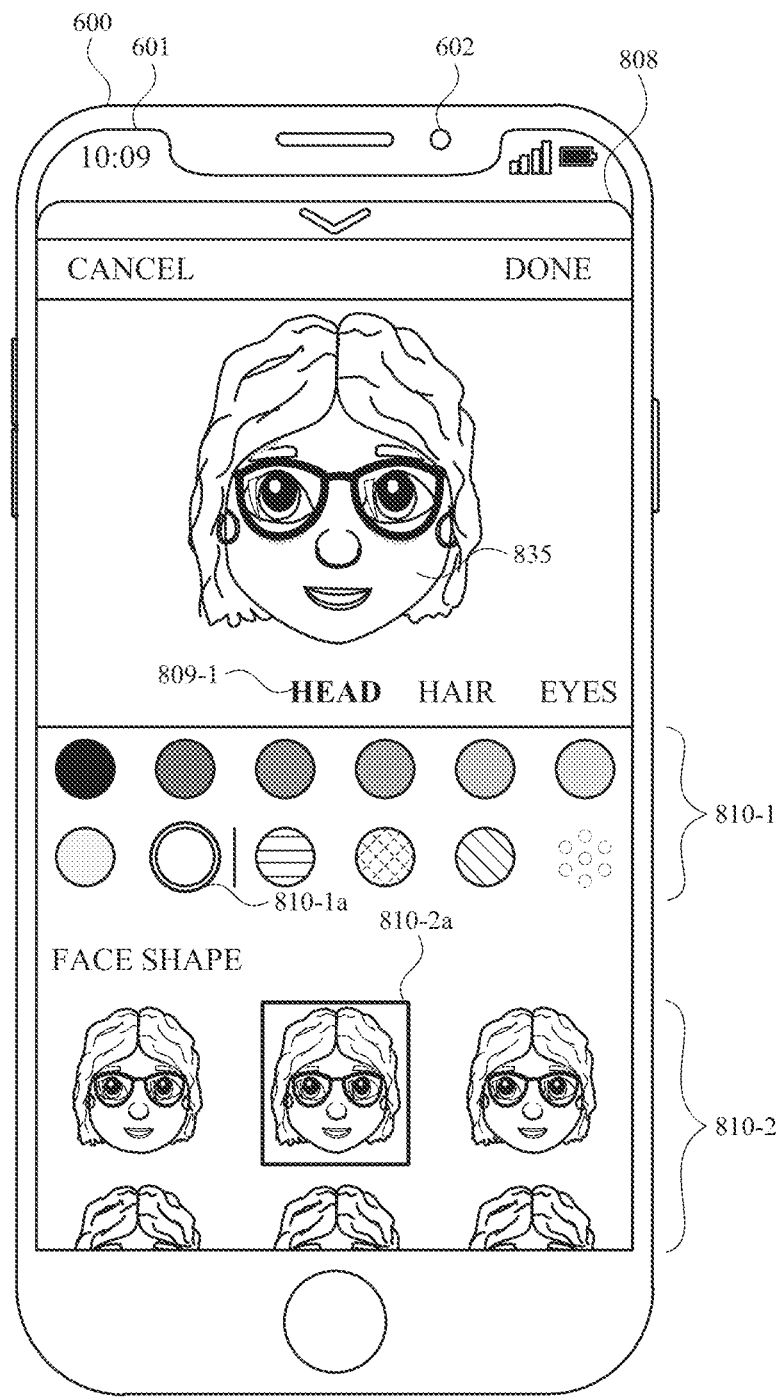
Figure 8A:
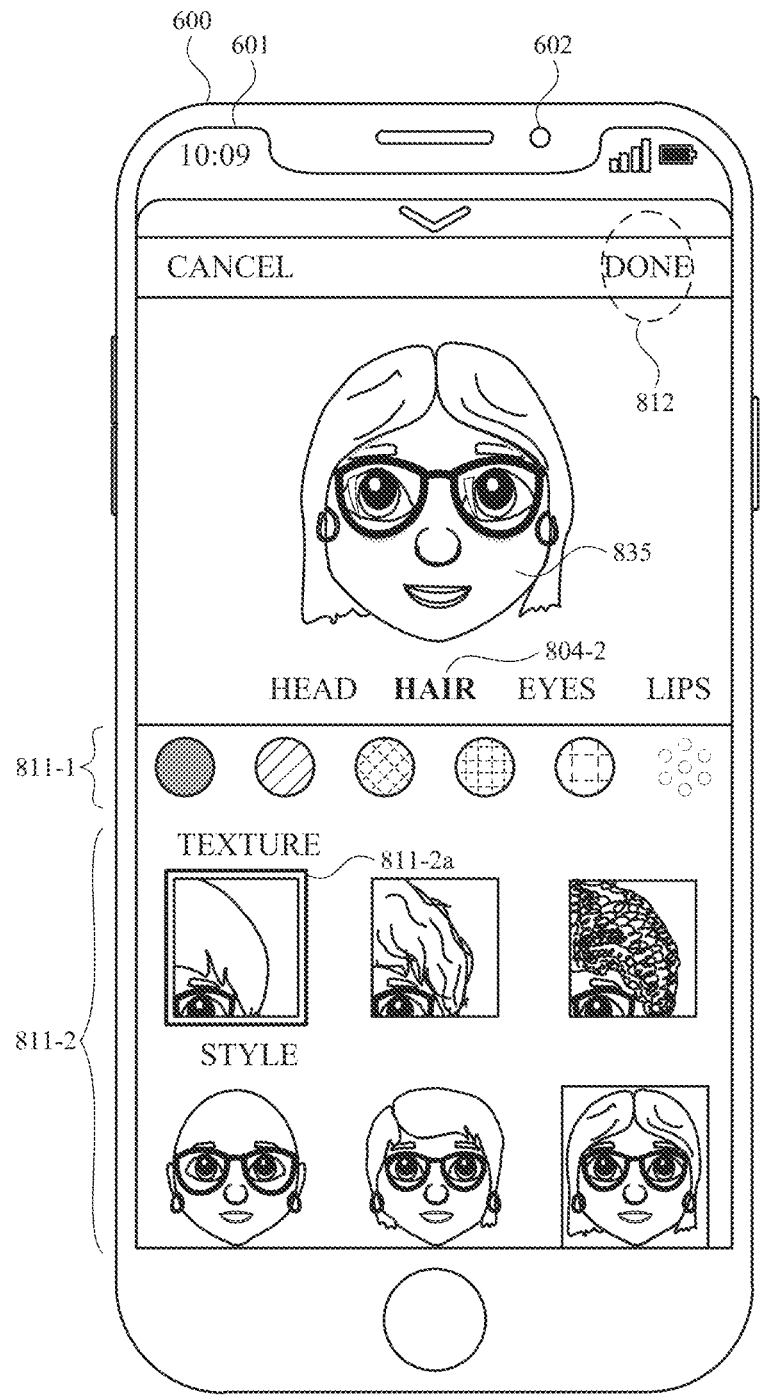
Figure 8A:
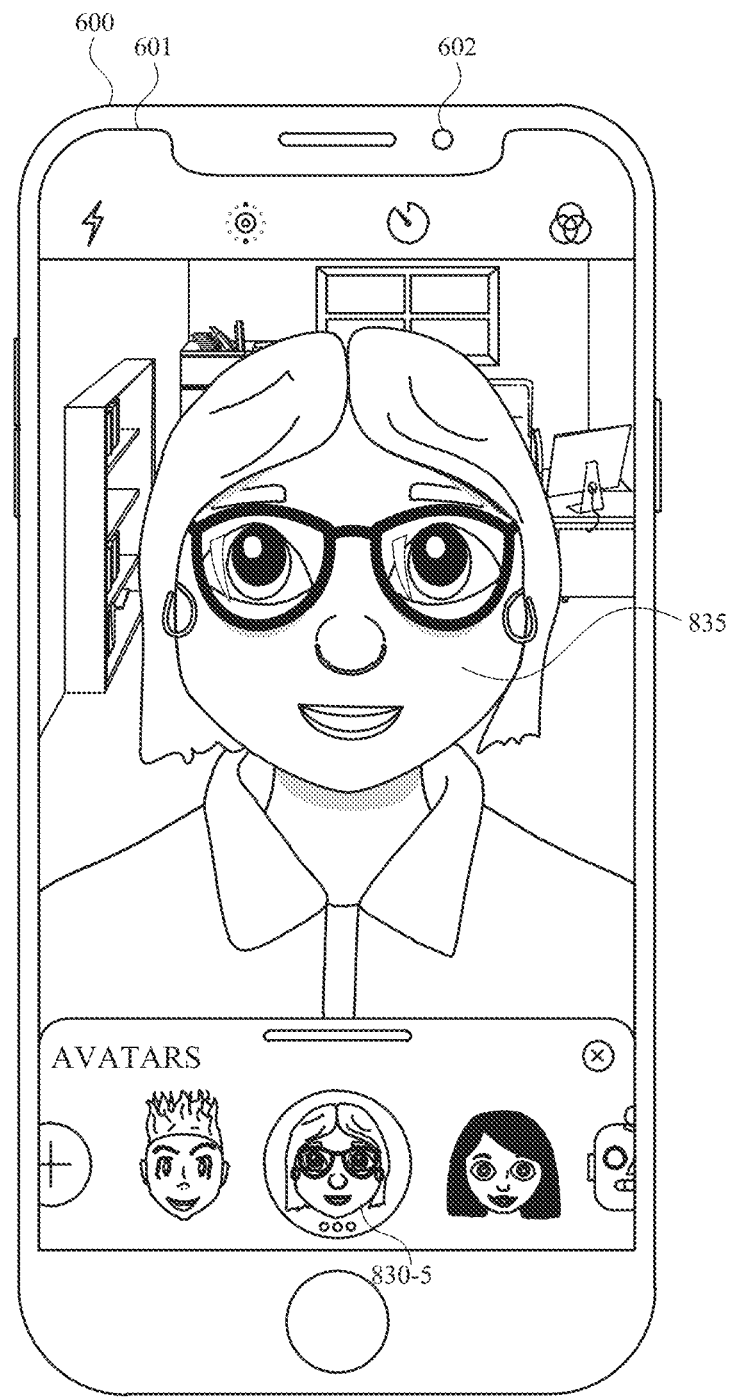
Figure 8A:
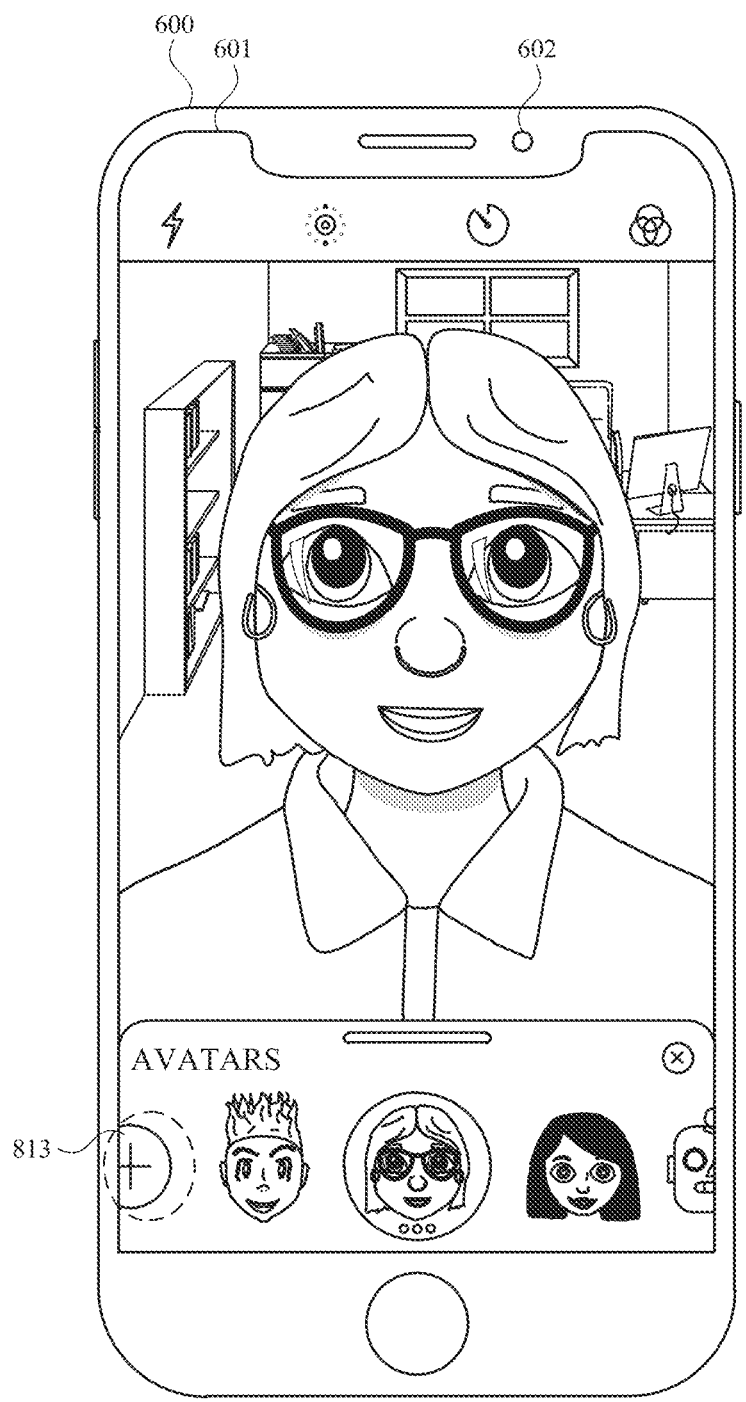
Figure 8A:
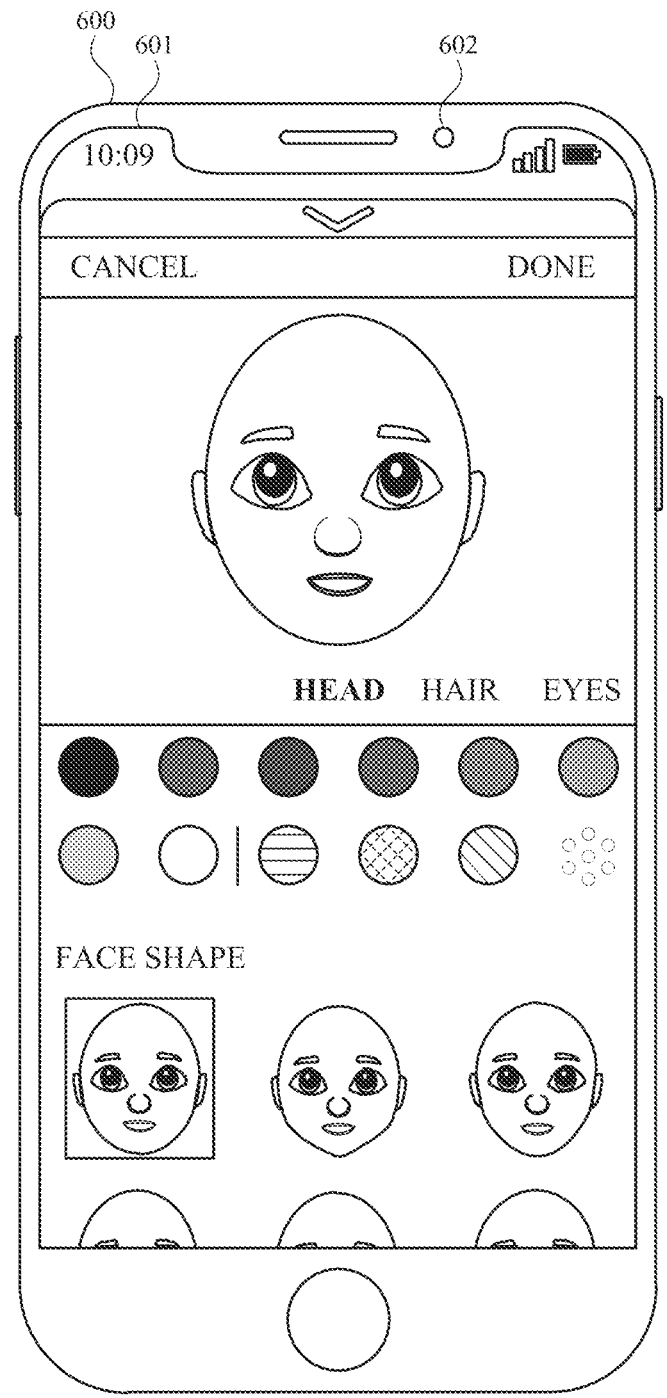
Figure 8A:
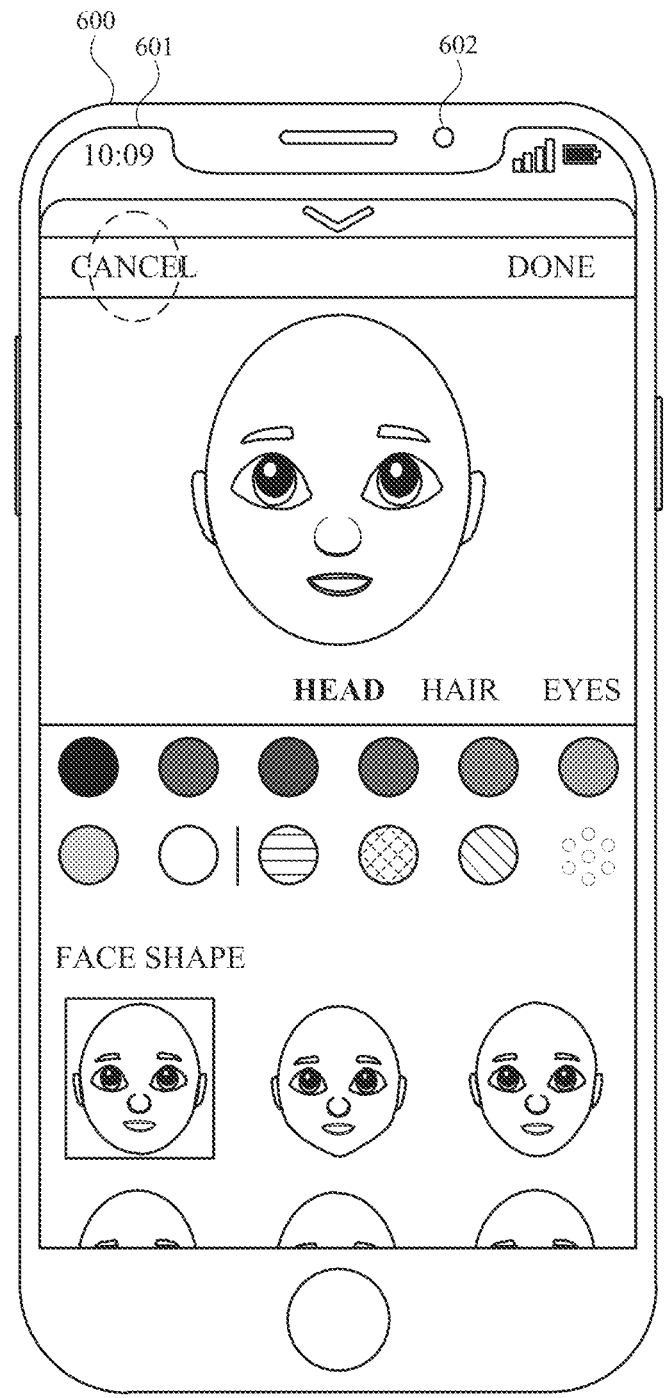
Figure 8A:
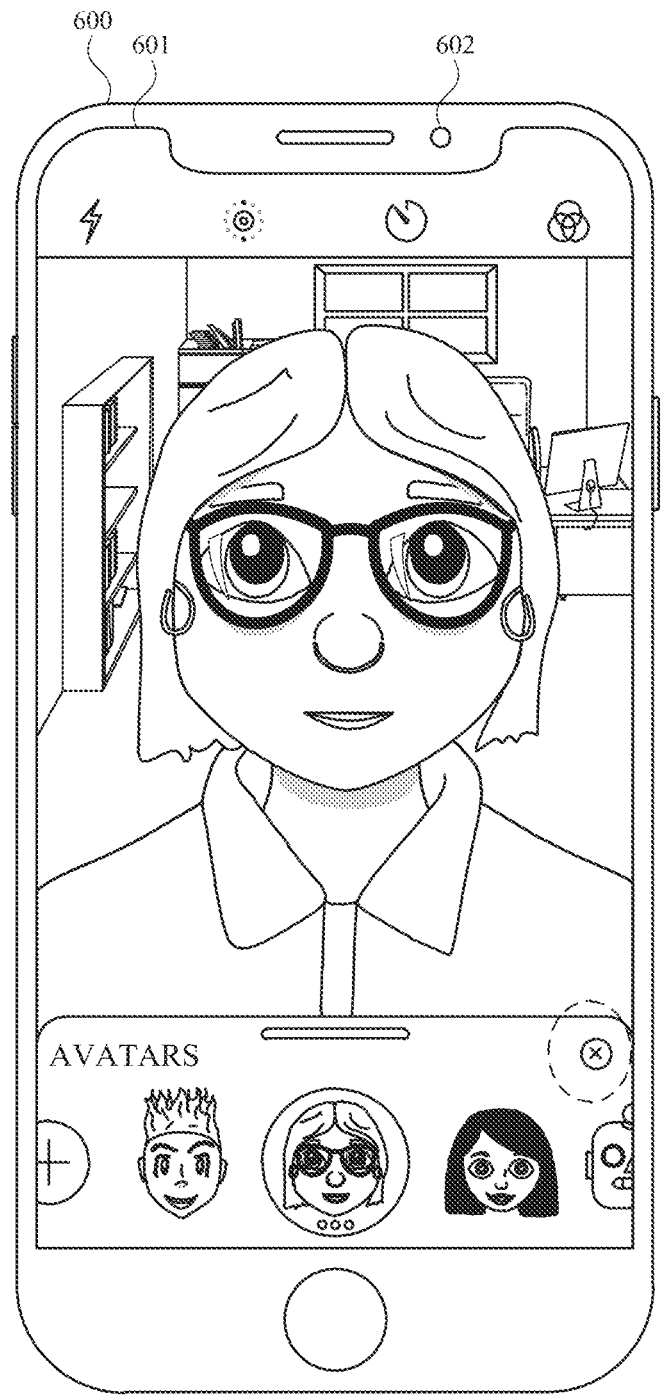
Figure 8A:
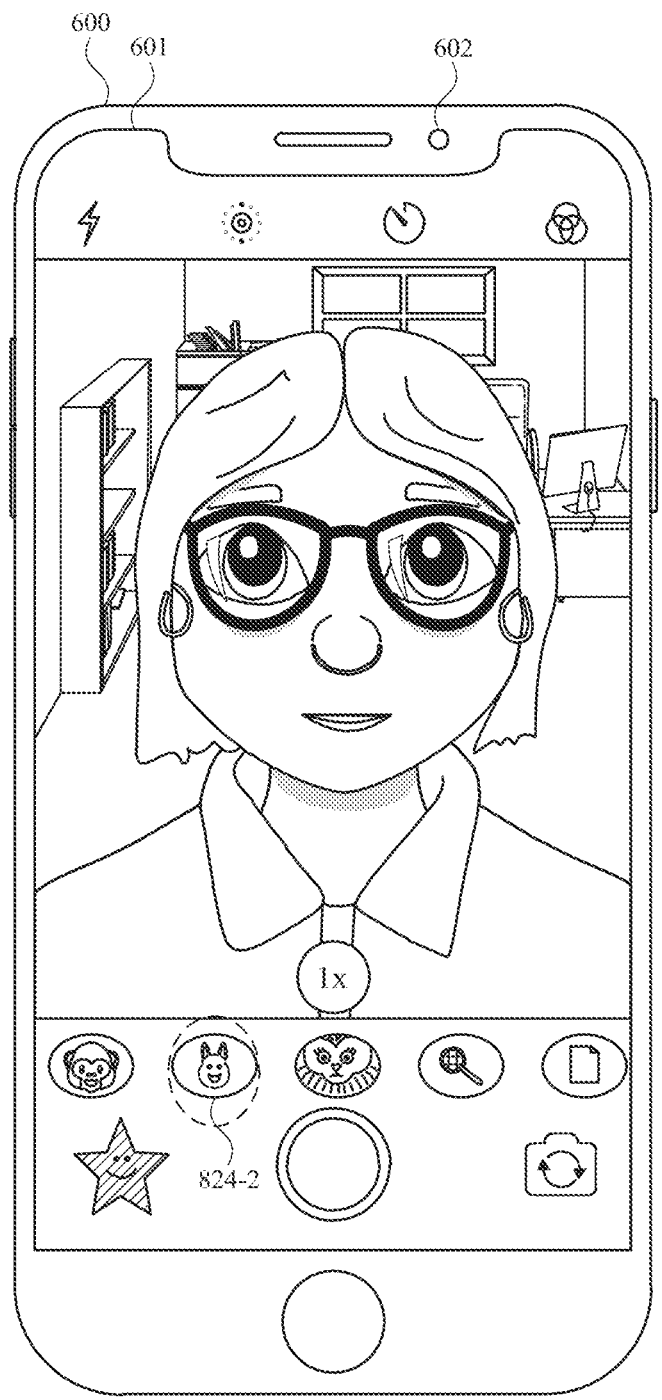
Figure 8A:
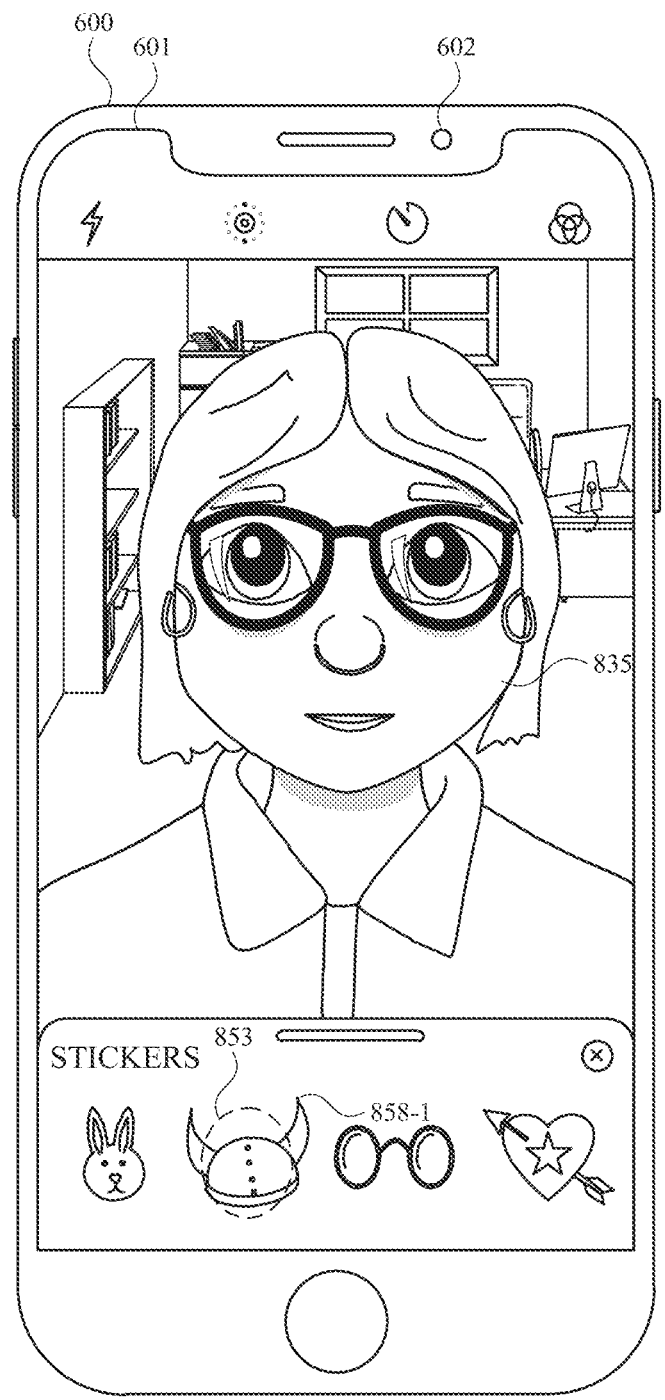
Figure 8A:
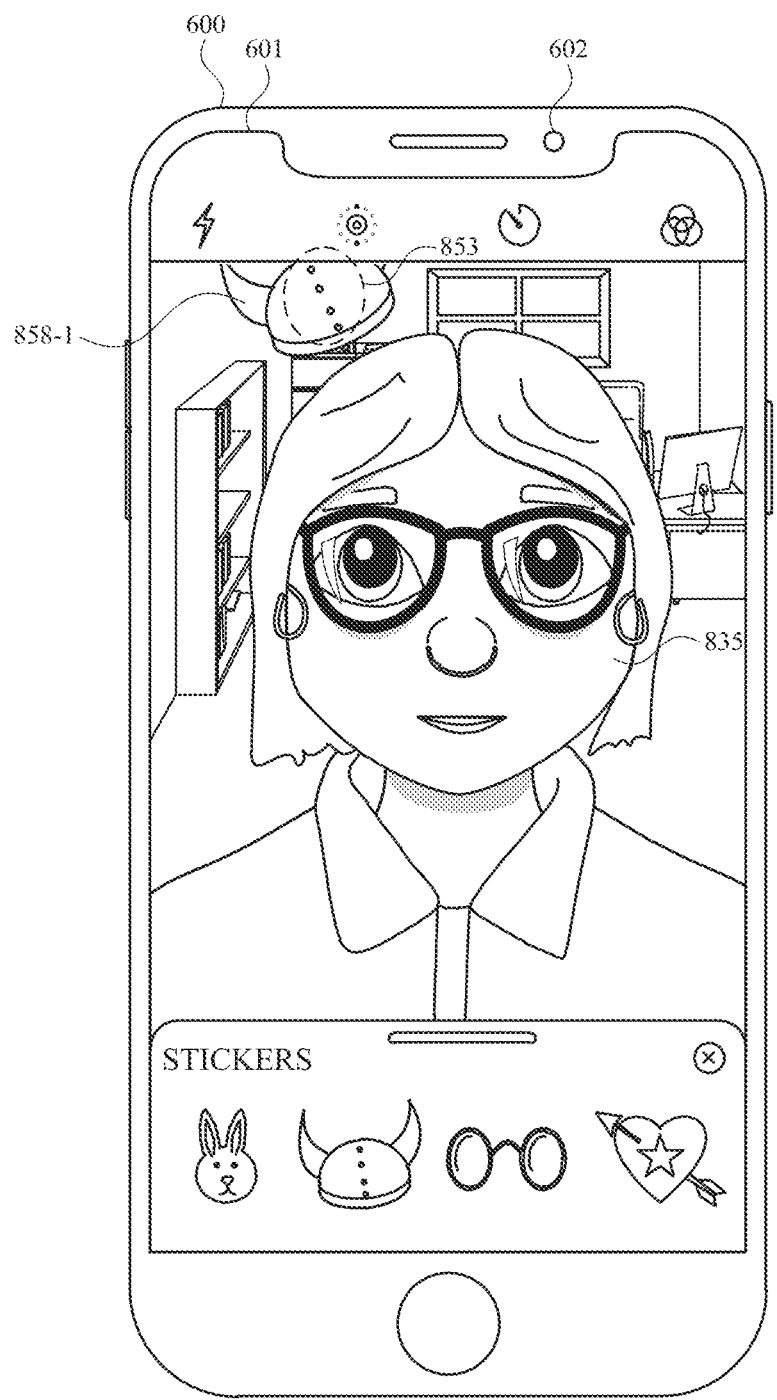
Figure 8A:
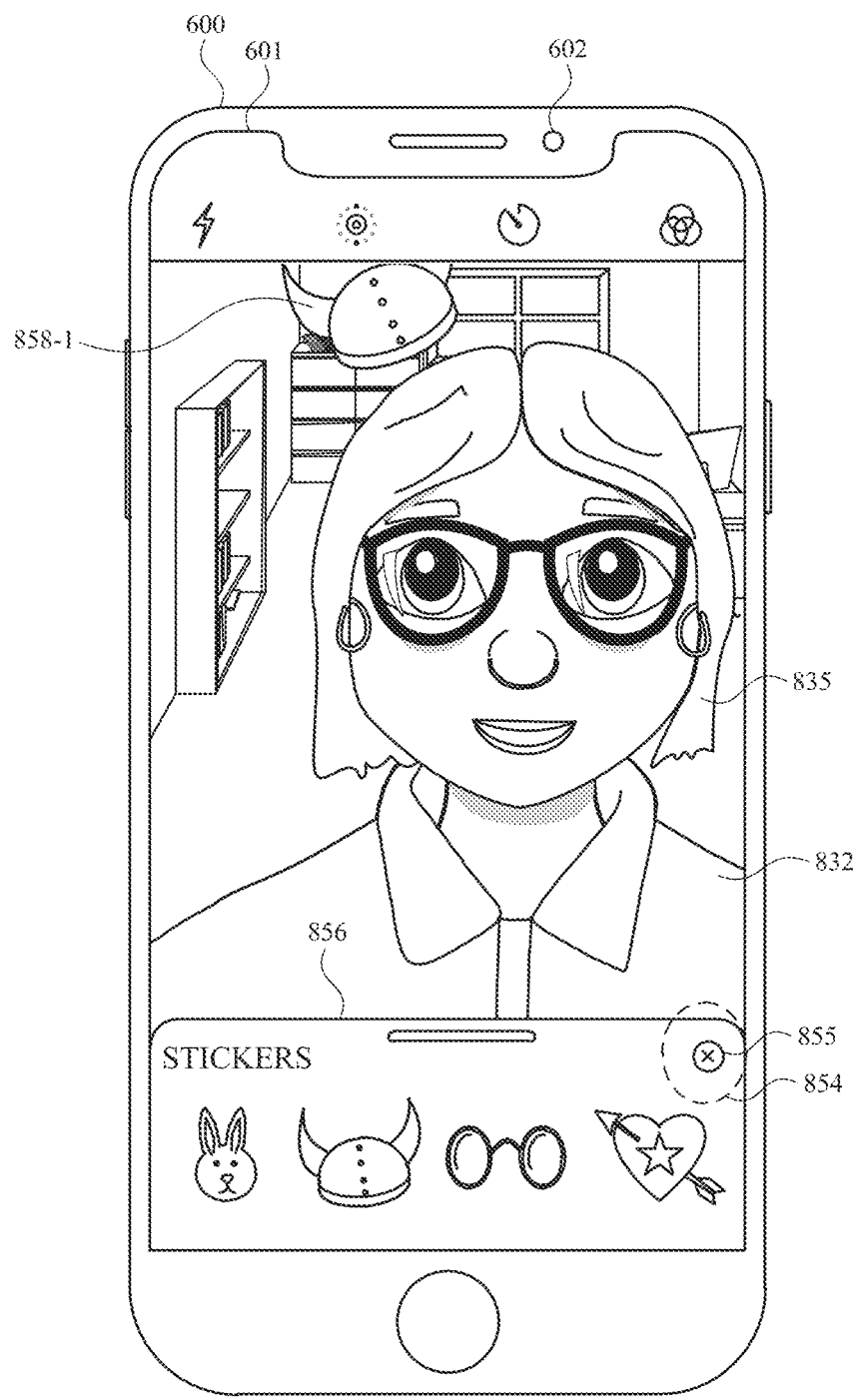
Figure 8A:
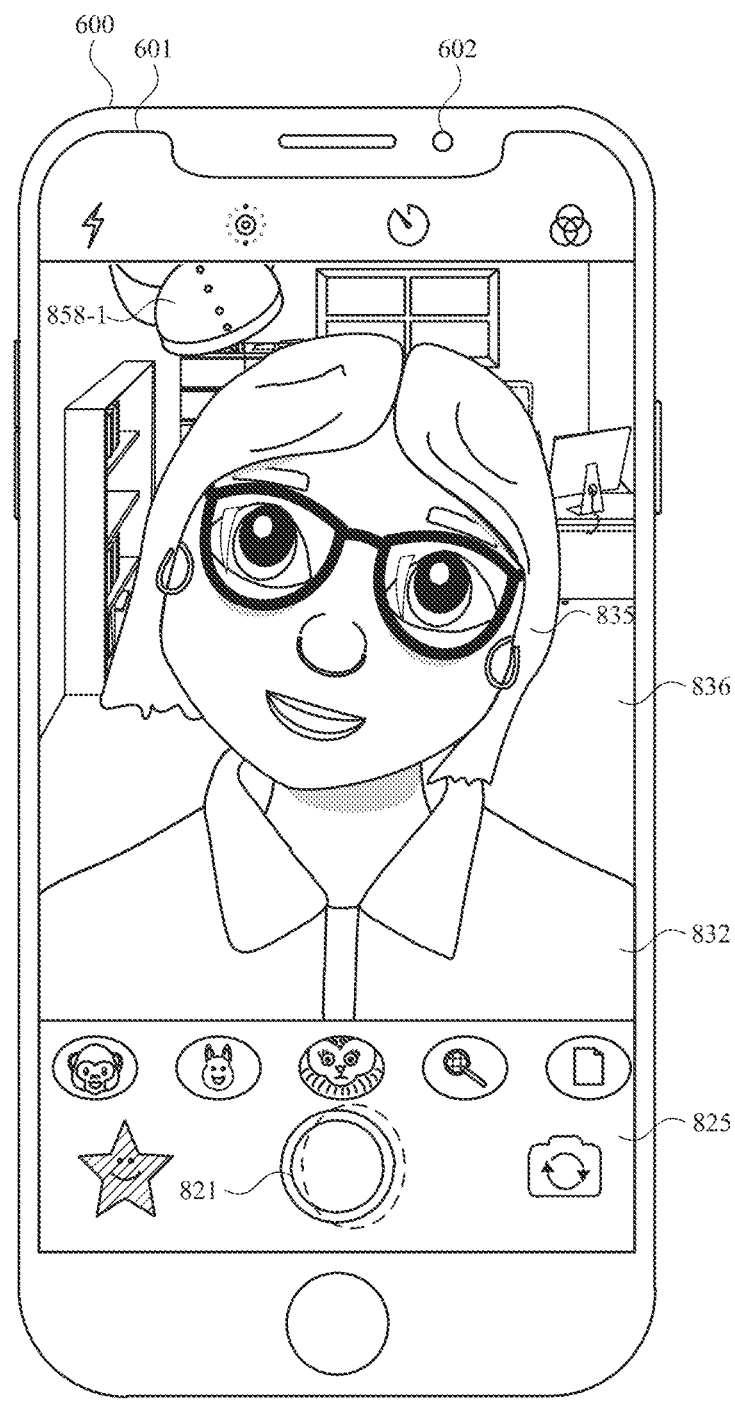
Figure 8A:
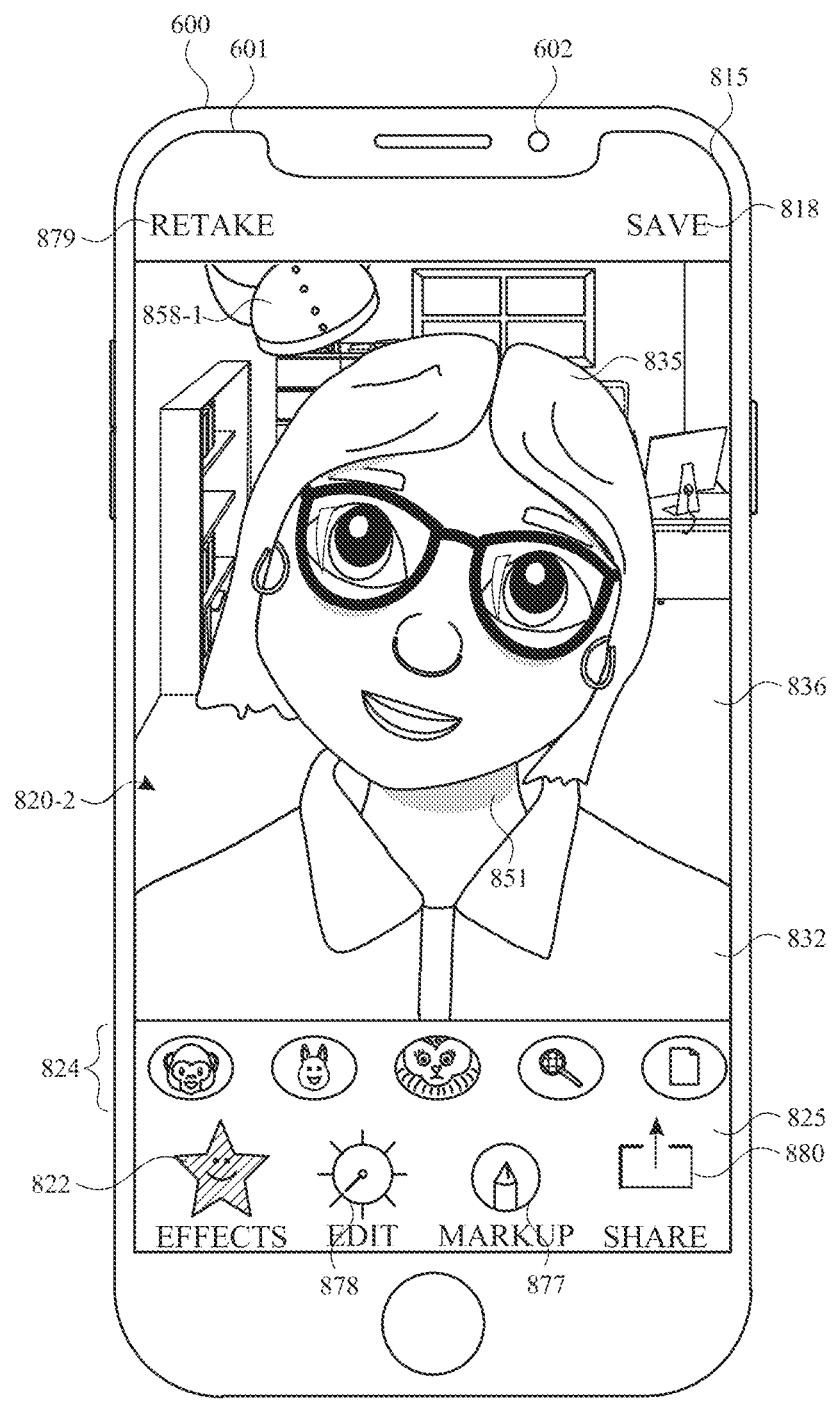
Figure 8A:
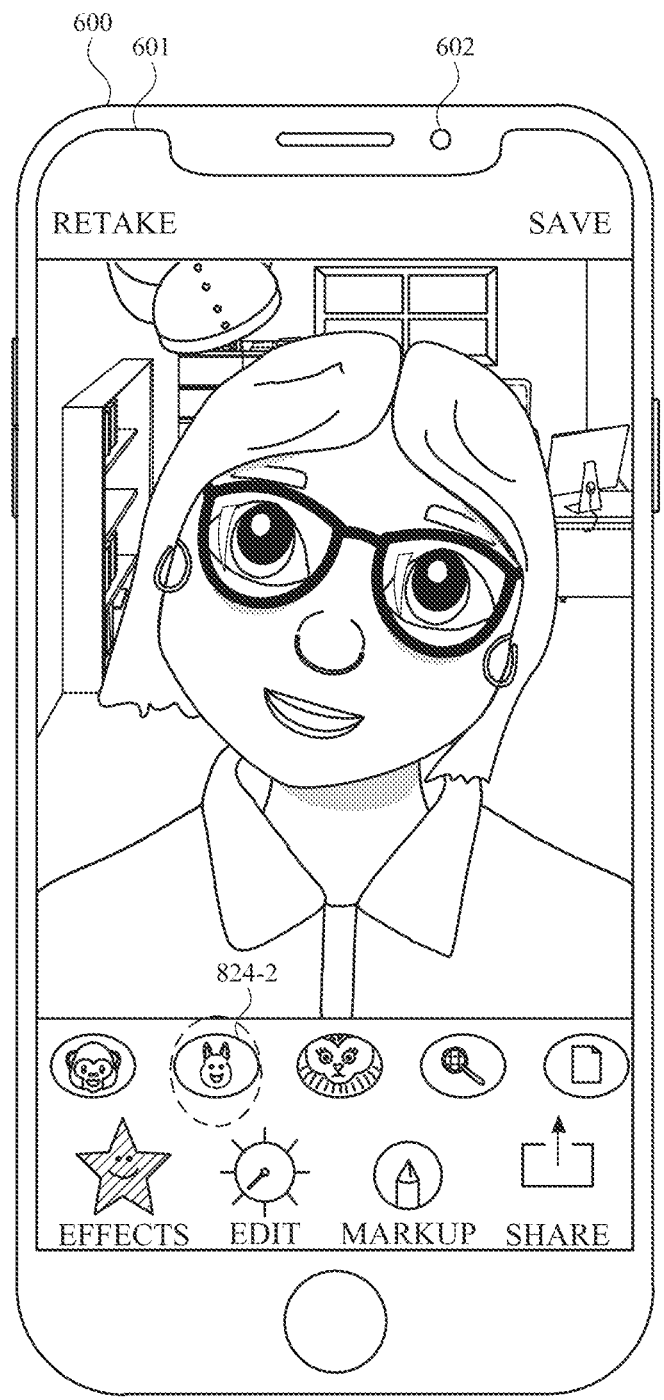
Figure 8A:
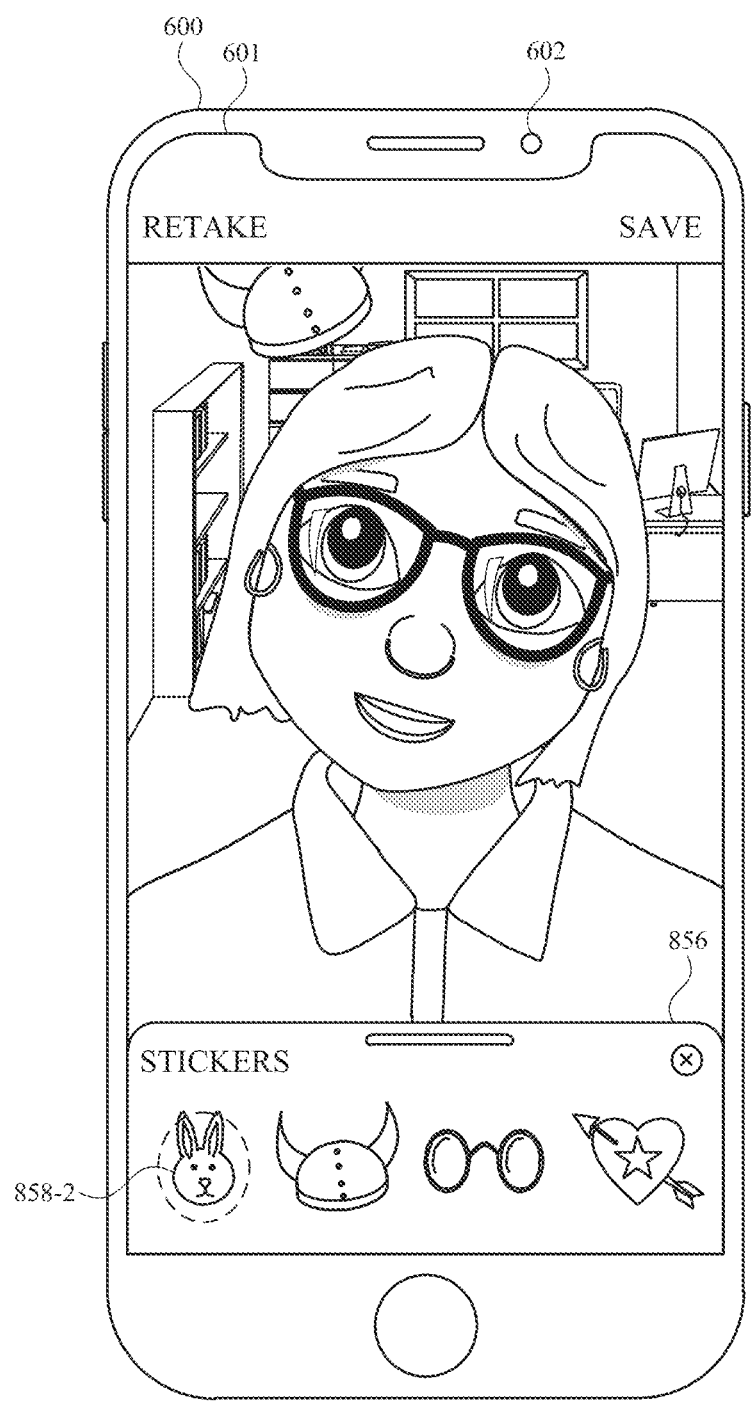
Figure 8A:
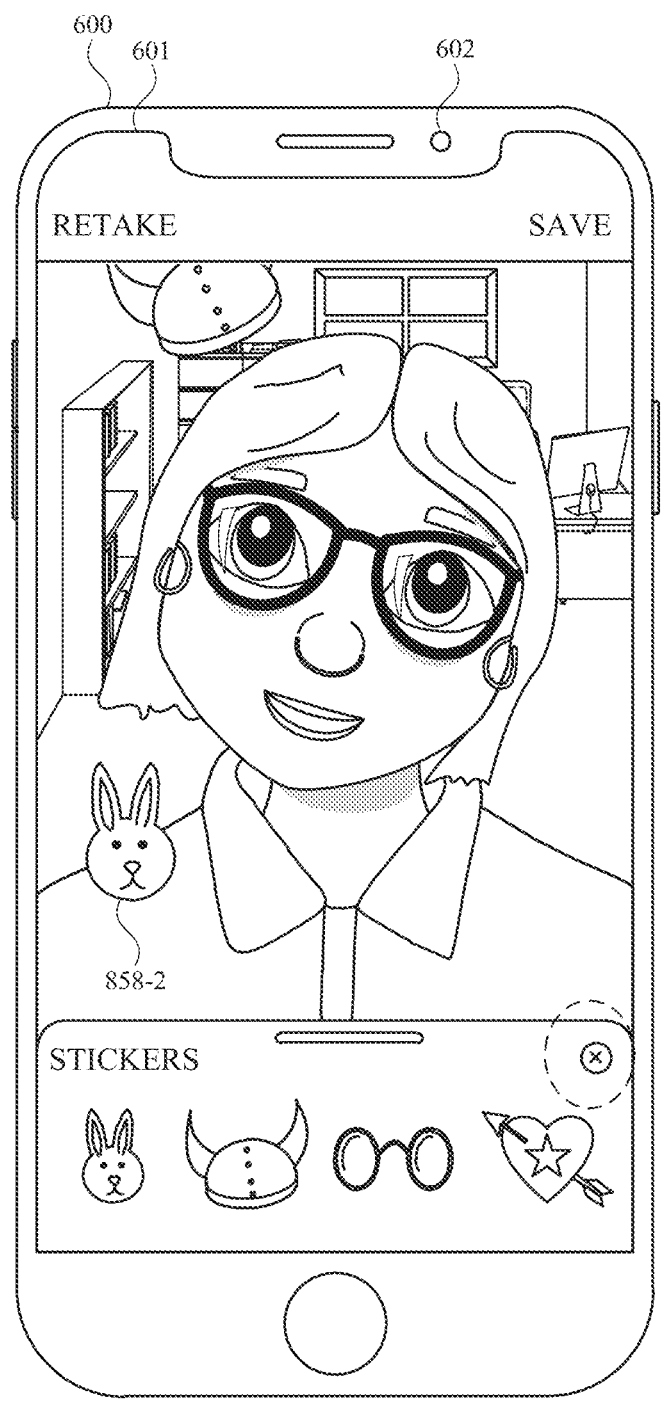
Figure 8A:
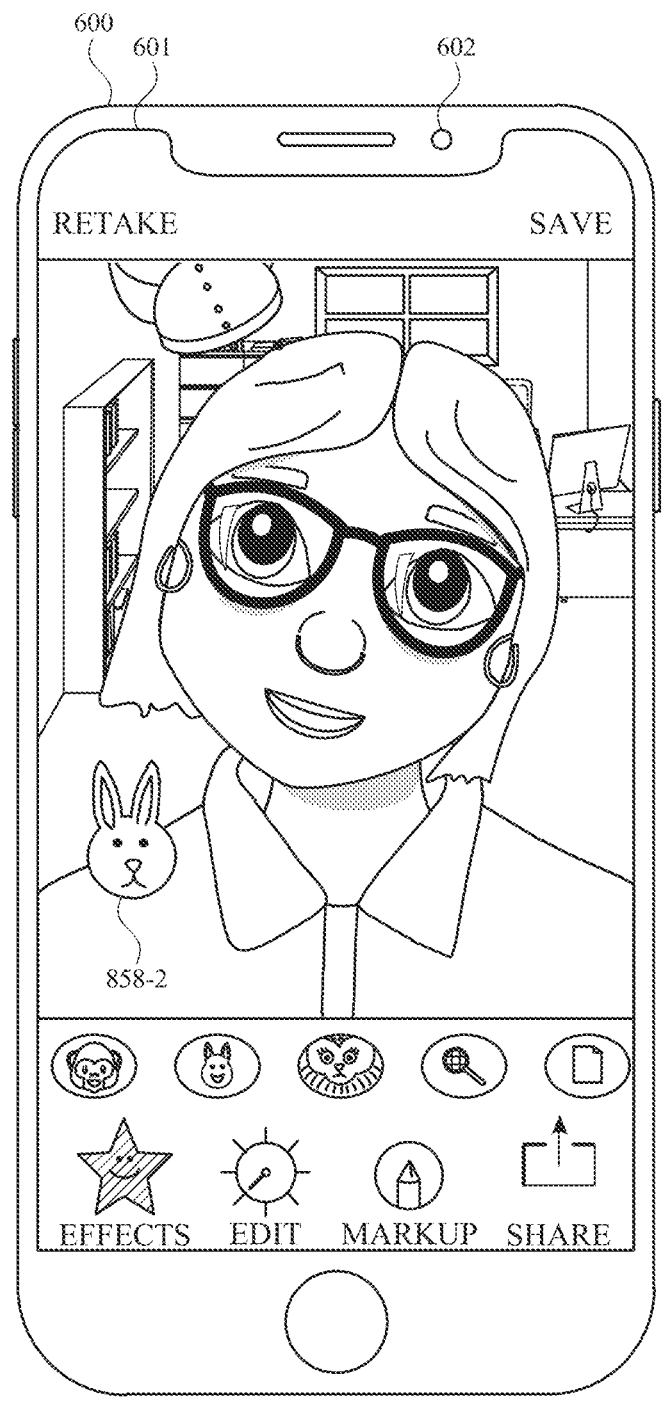
Figure 8A:
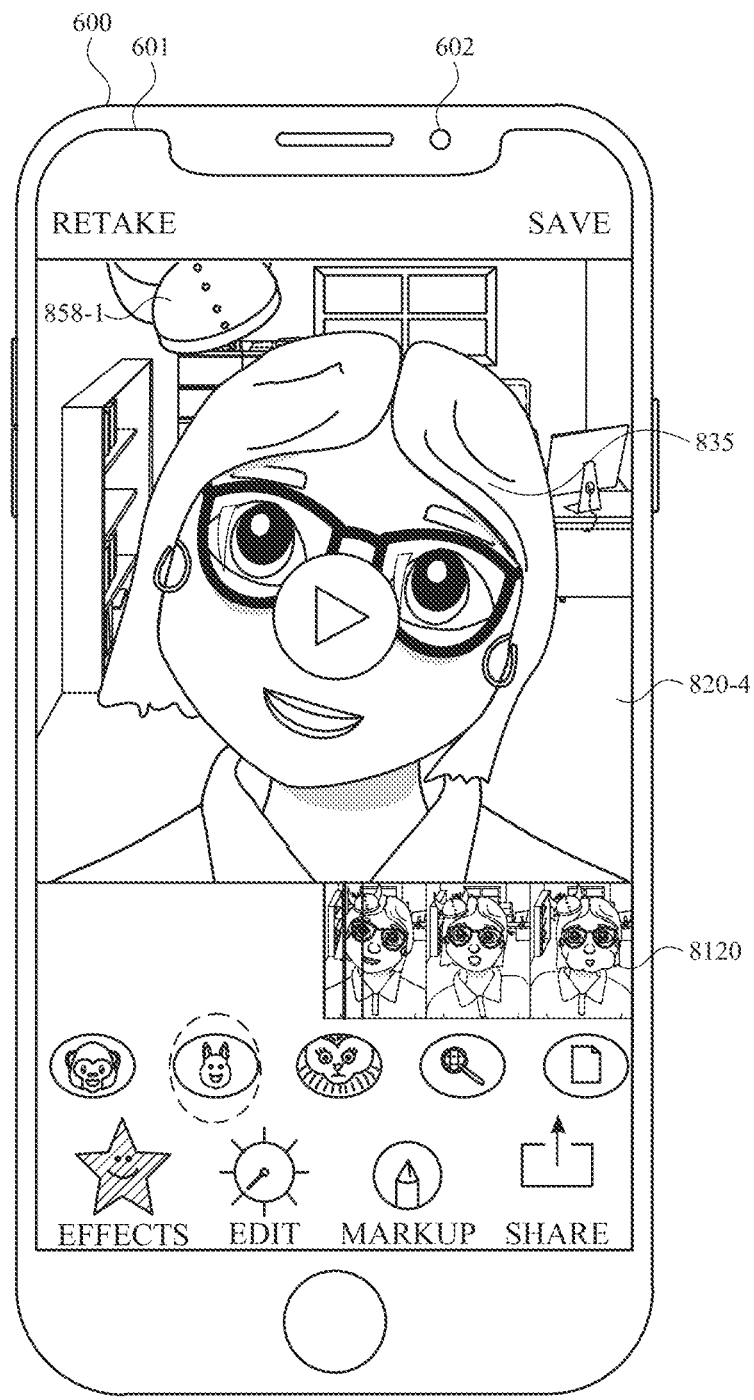
Figure 8A:
Figure 8A:
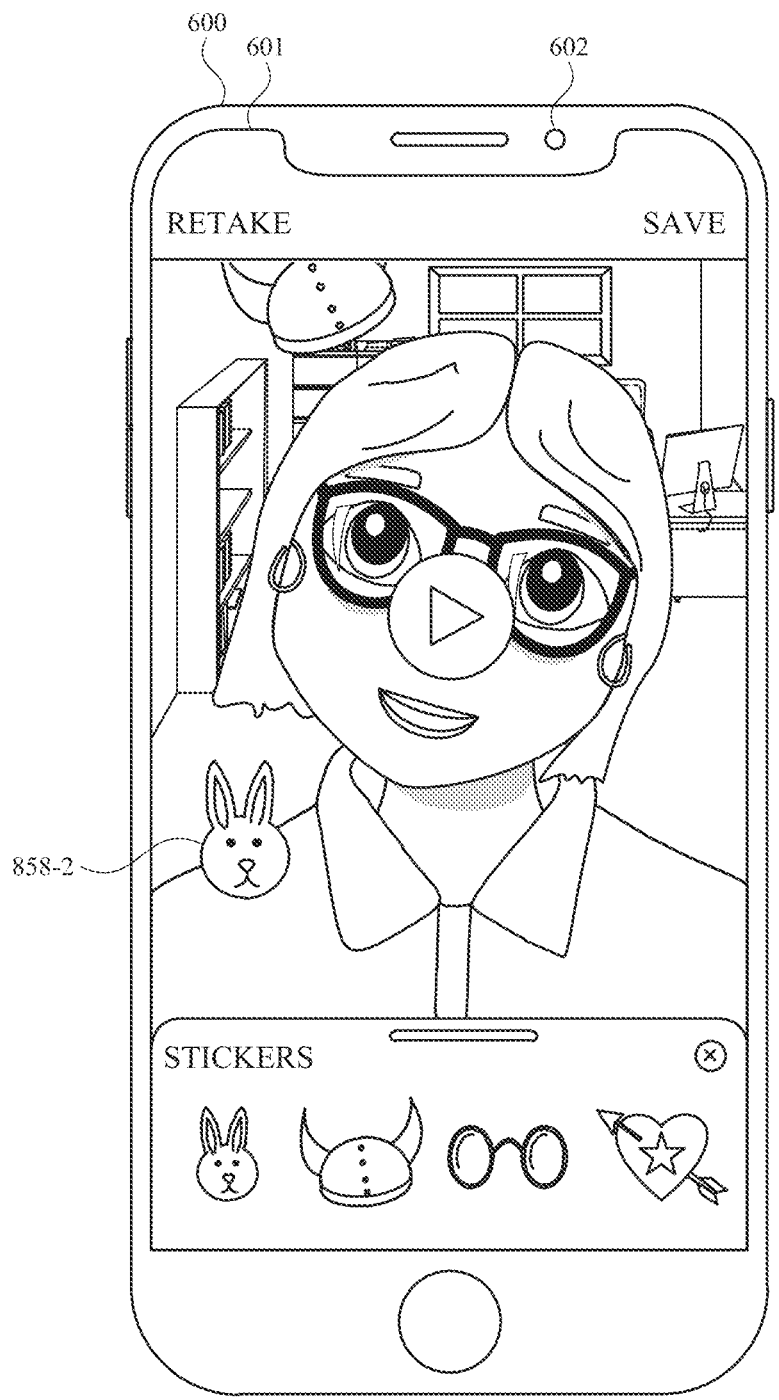
Figure 8A:
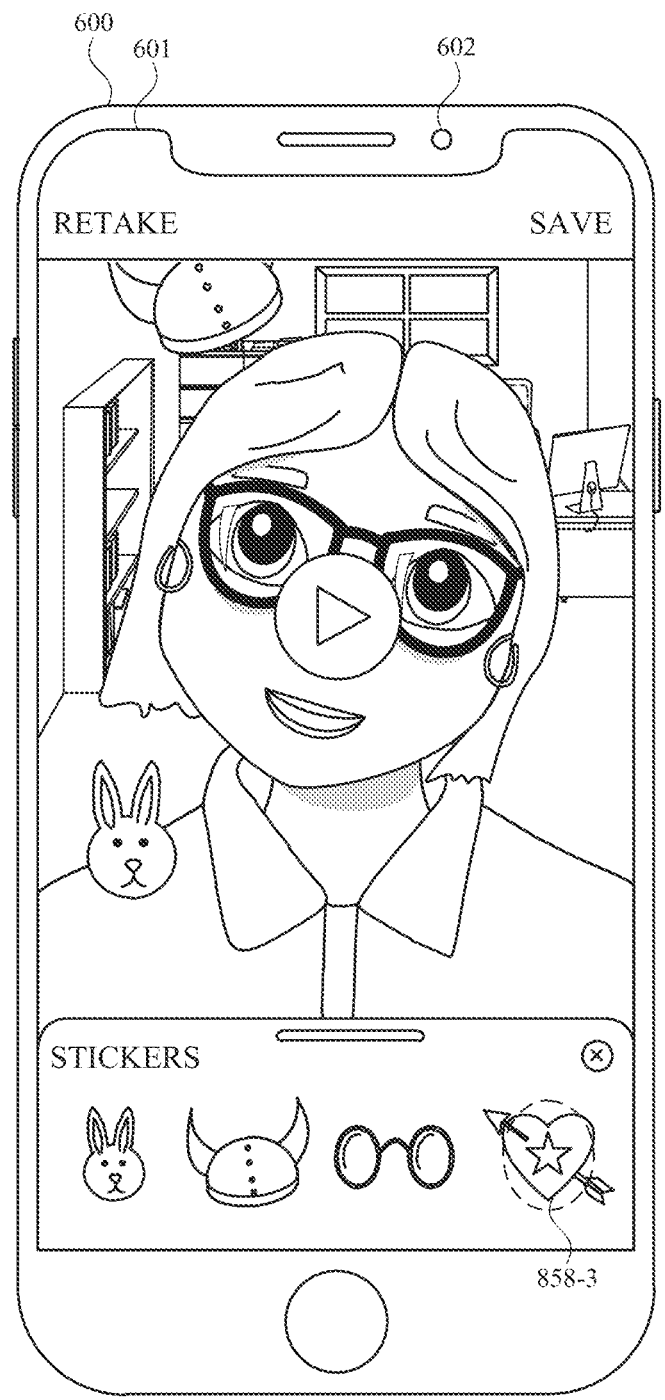
Figure 8A:
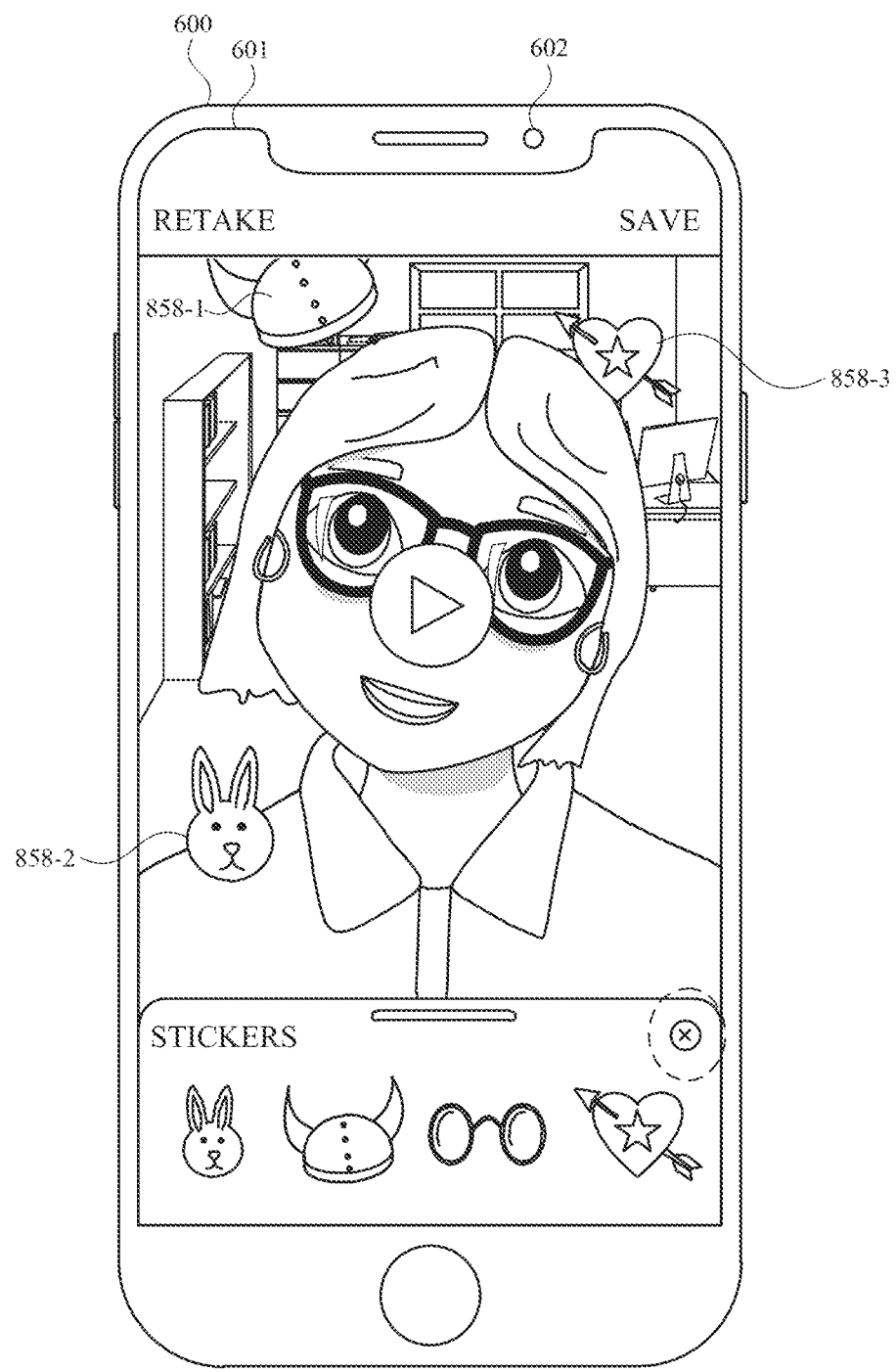
Figure 8A:
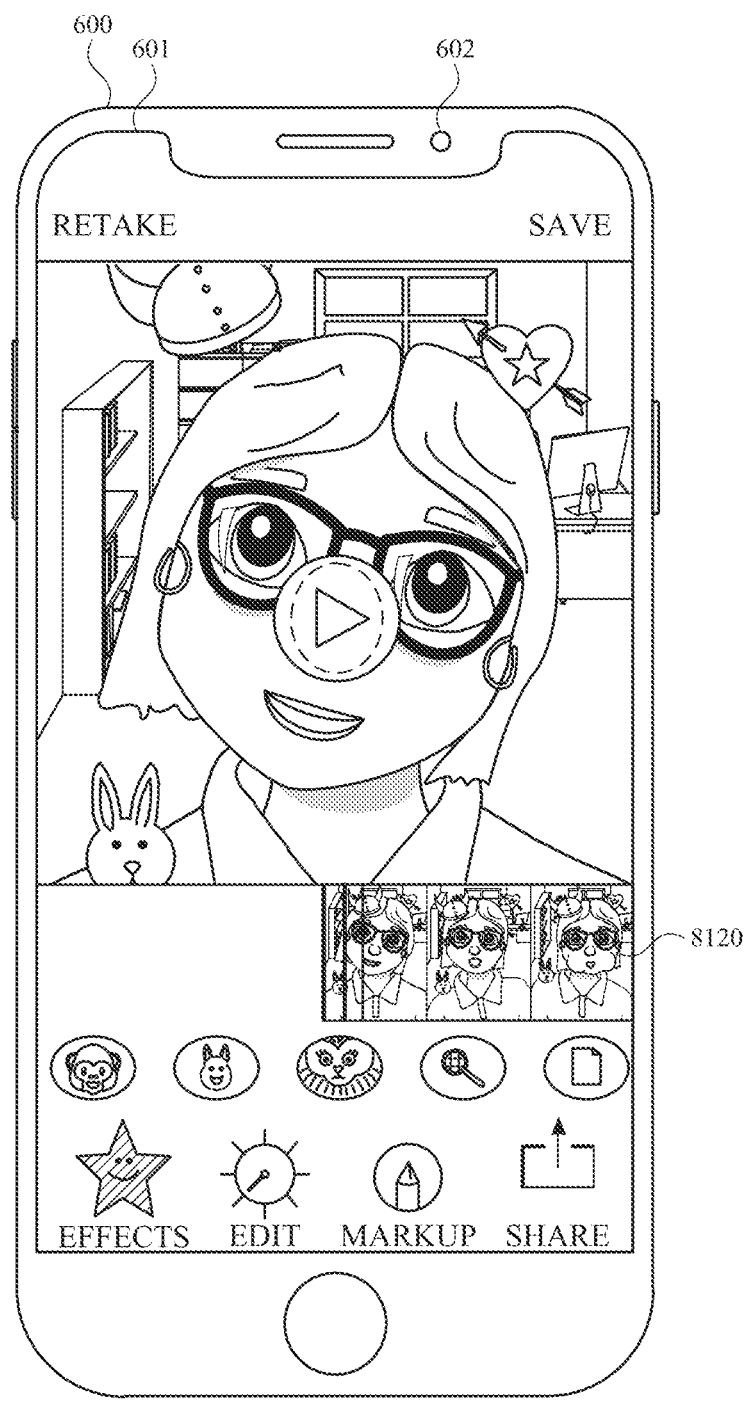
Figure 8A:
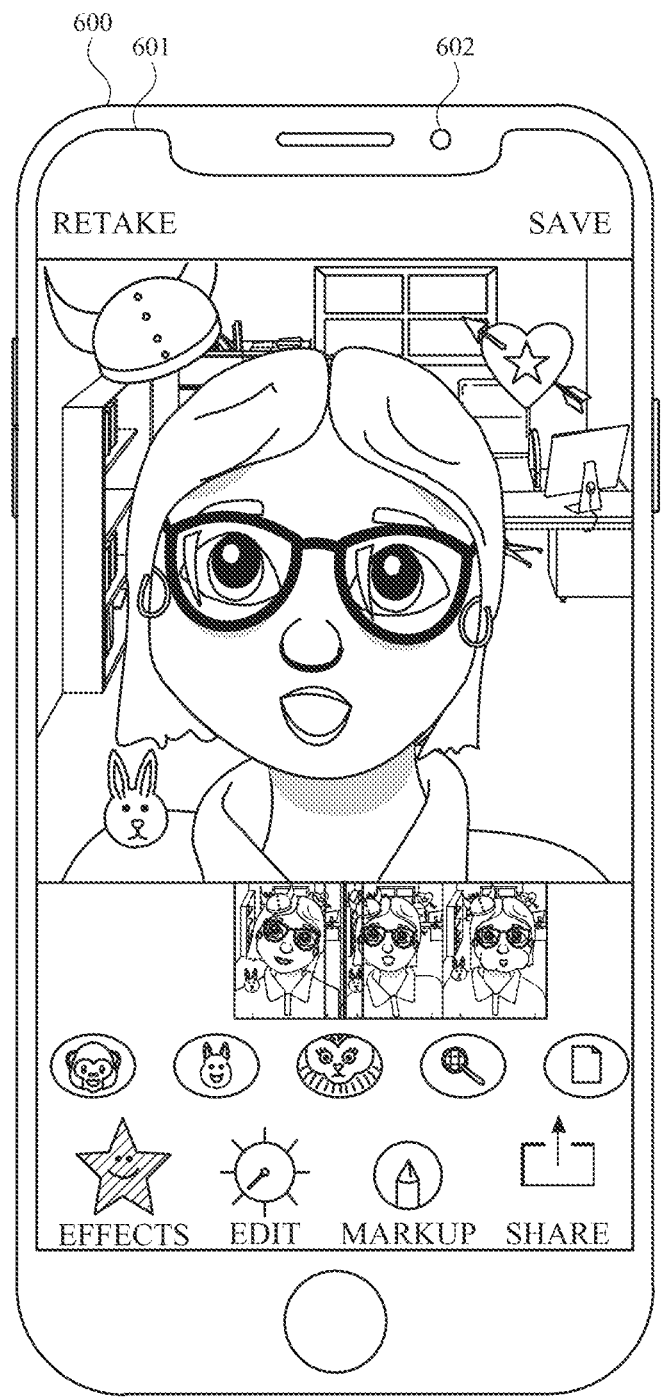
Figure 8A:
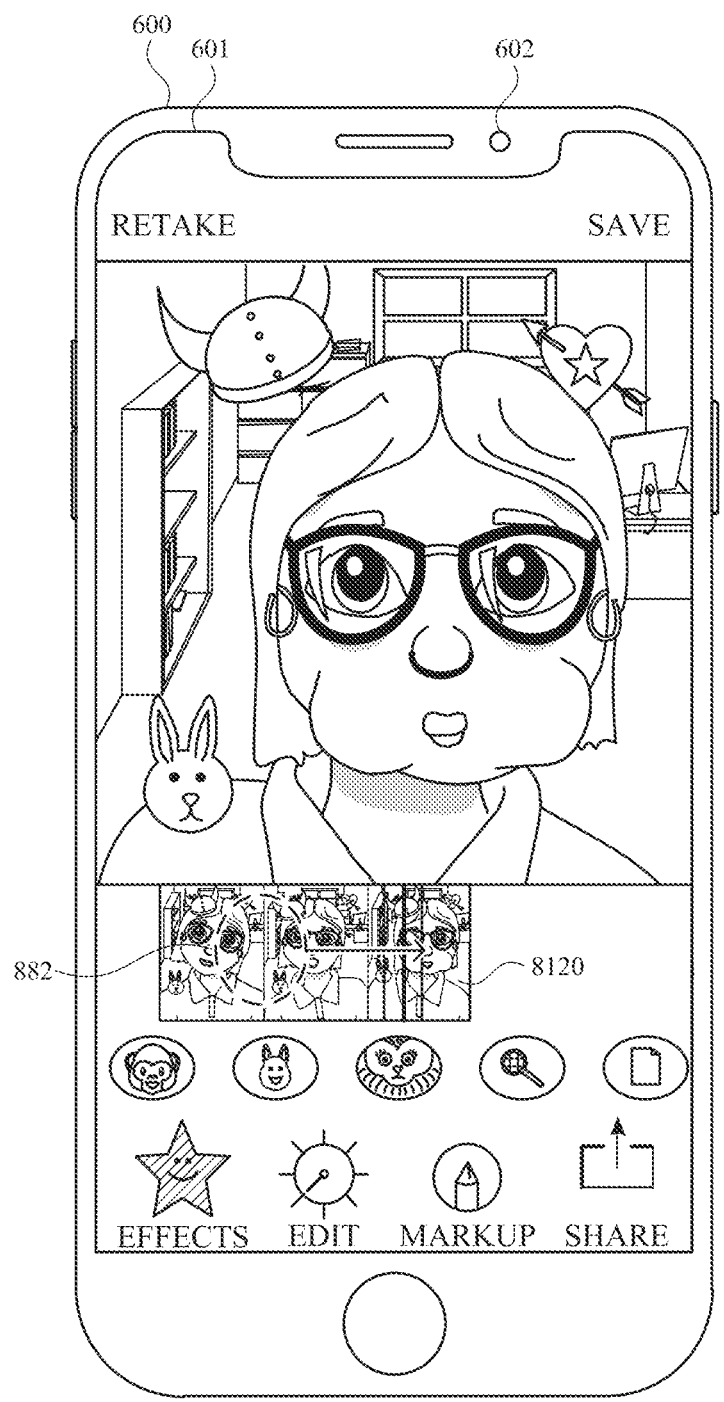
Figure 8A:
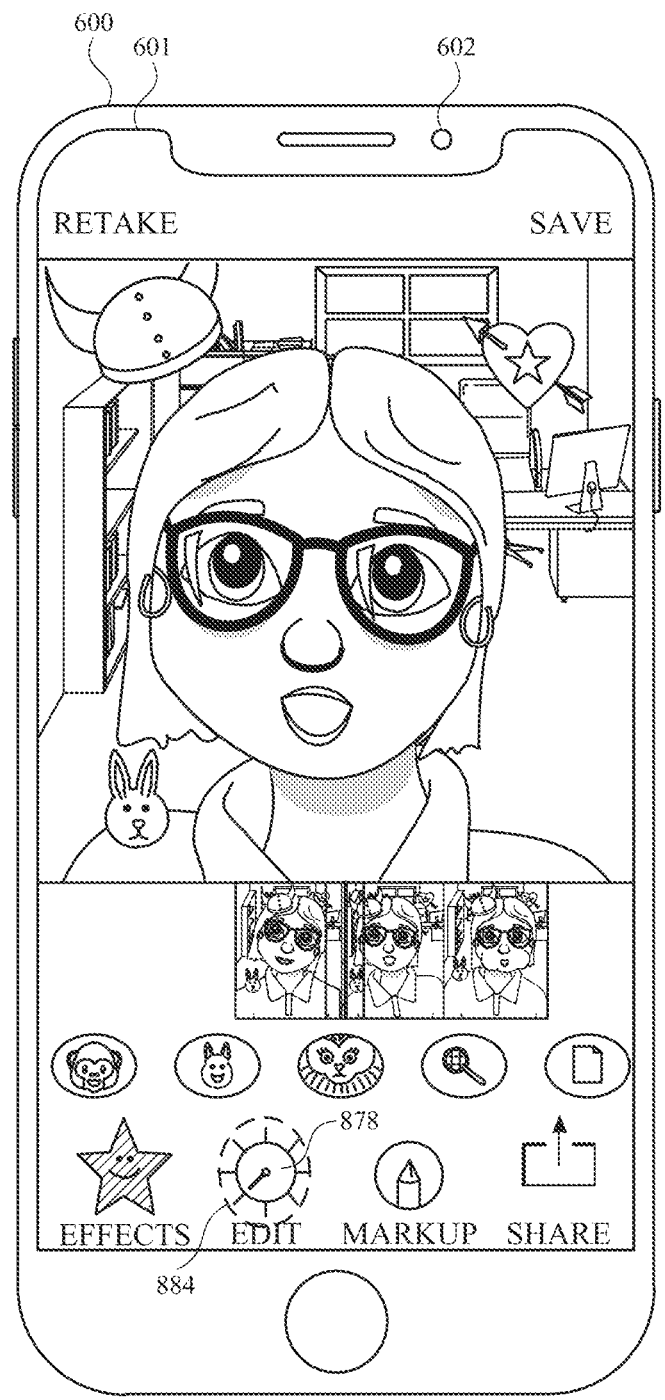
Figure 8B:
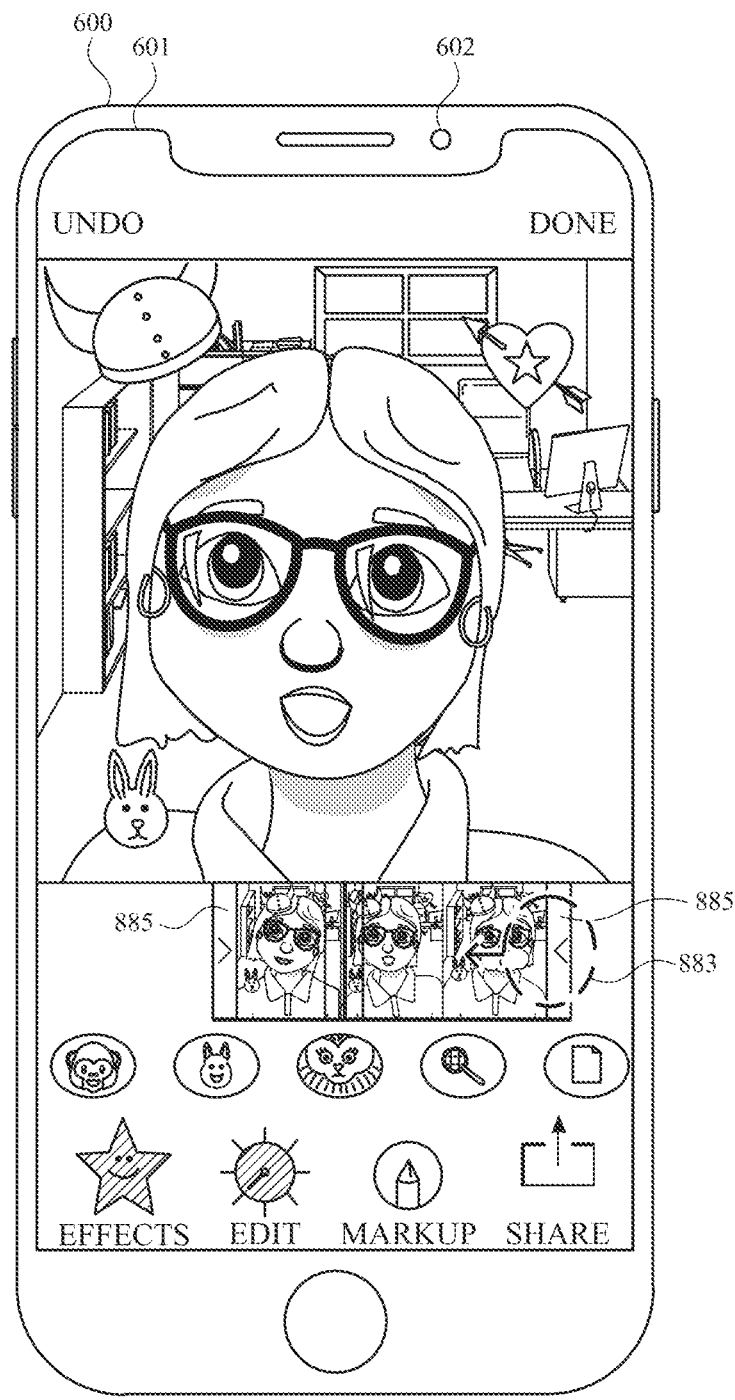
Figure 8B:
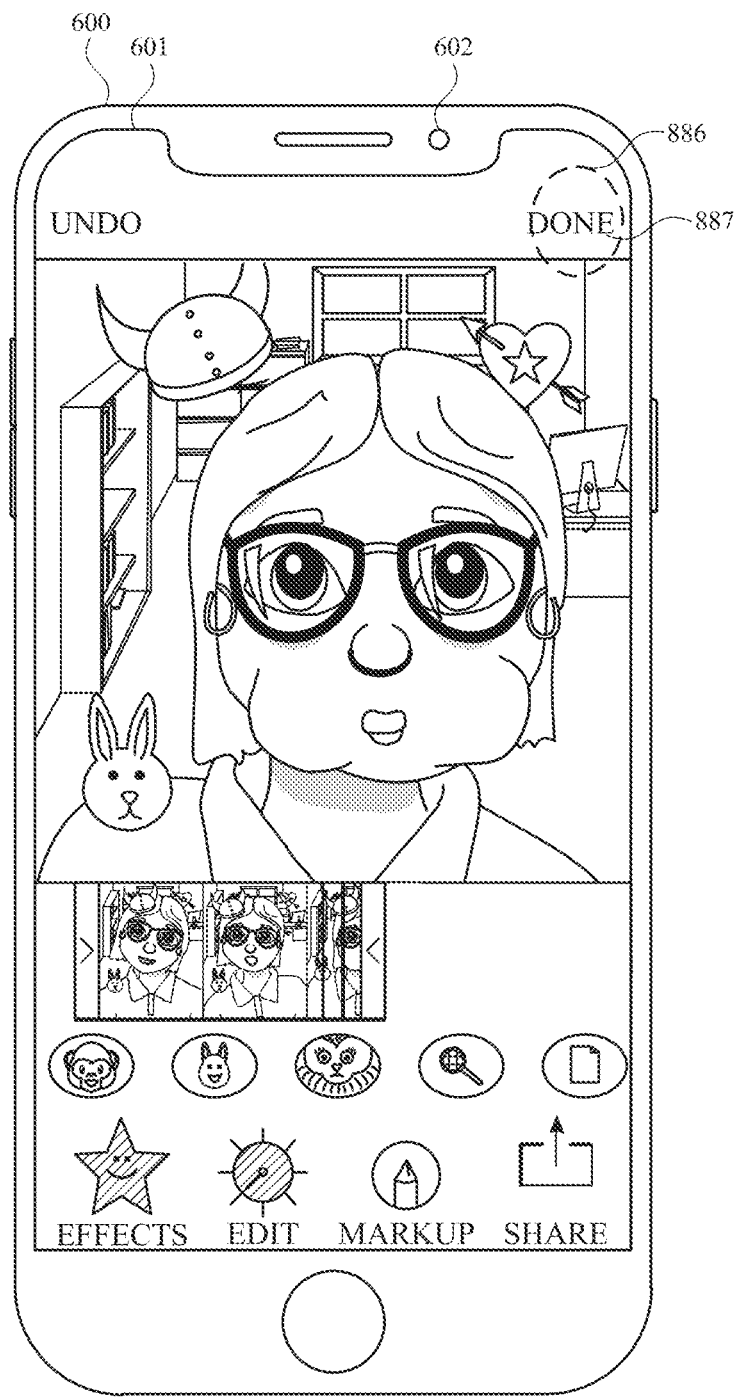
Figure 8B:
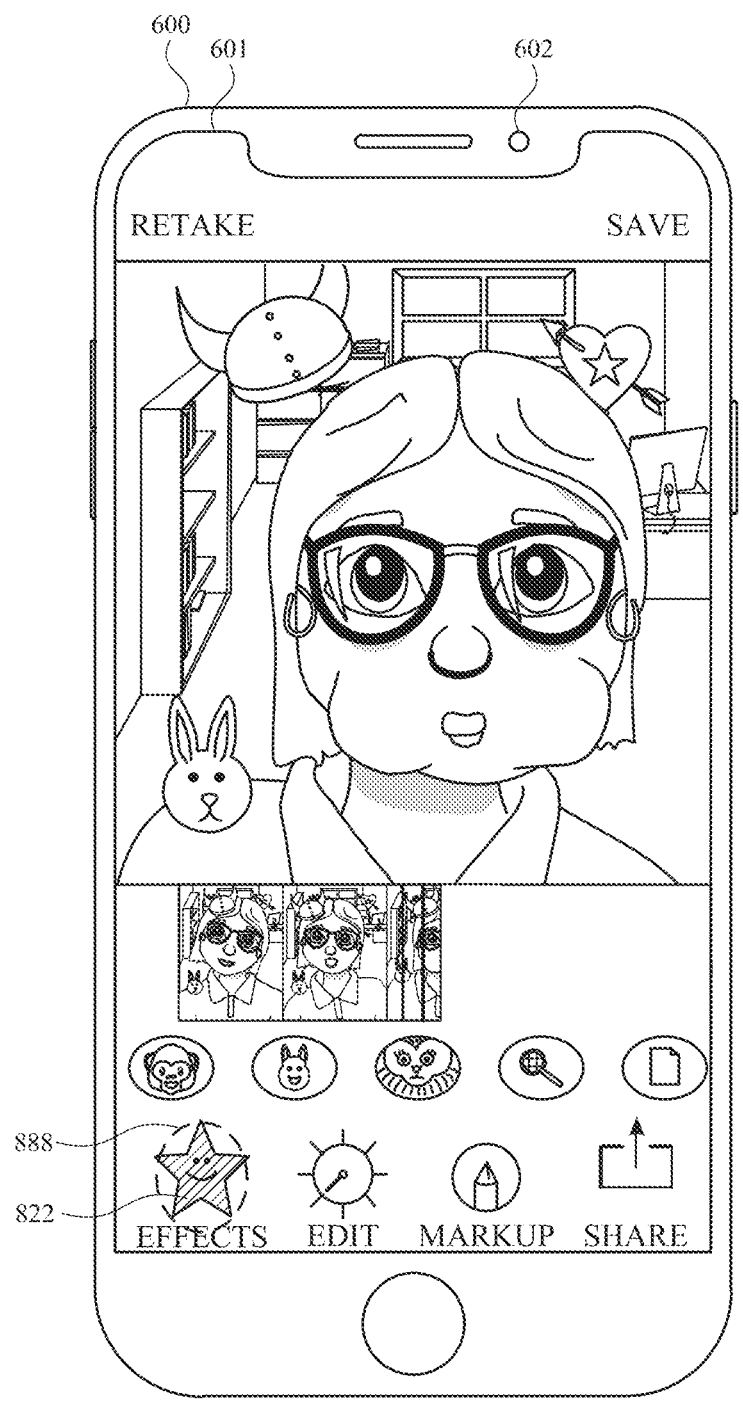
Figure 8B:
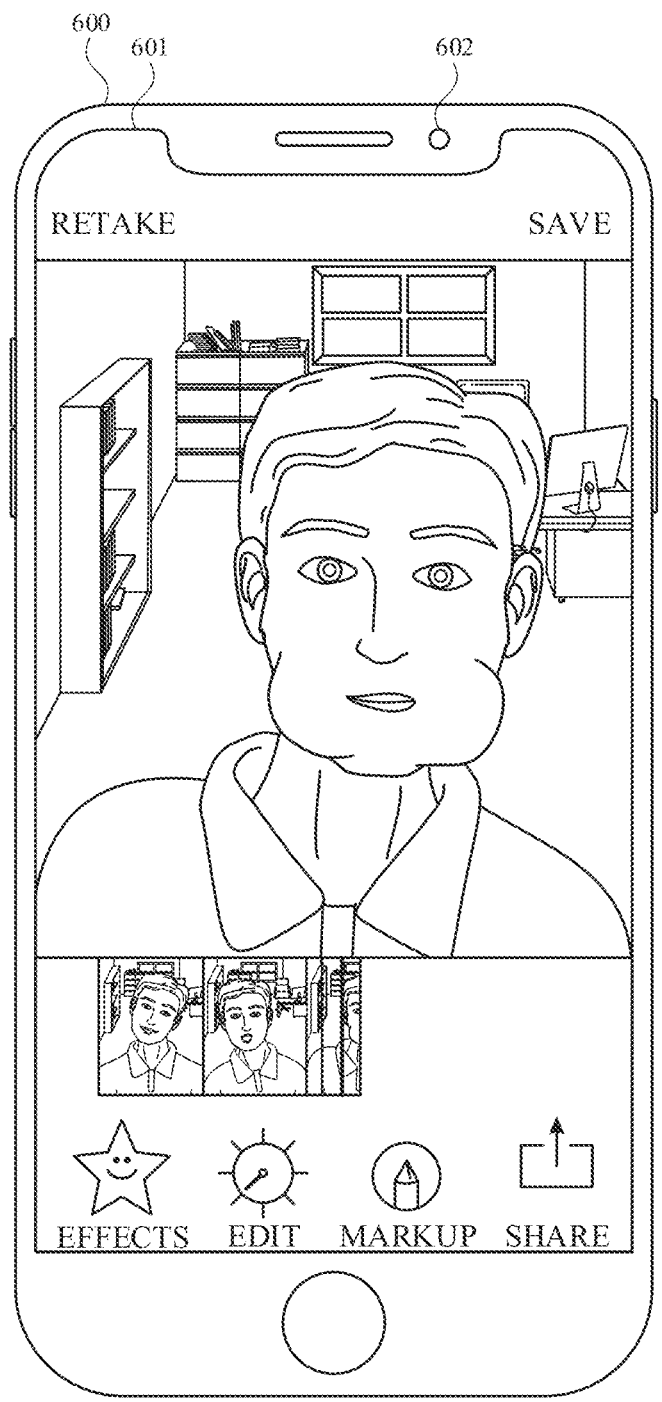
Figure 8B:
Figure 8B:
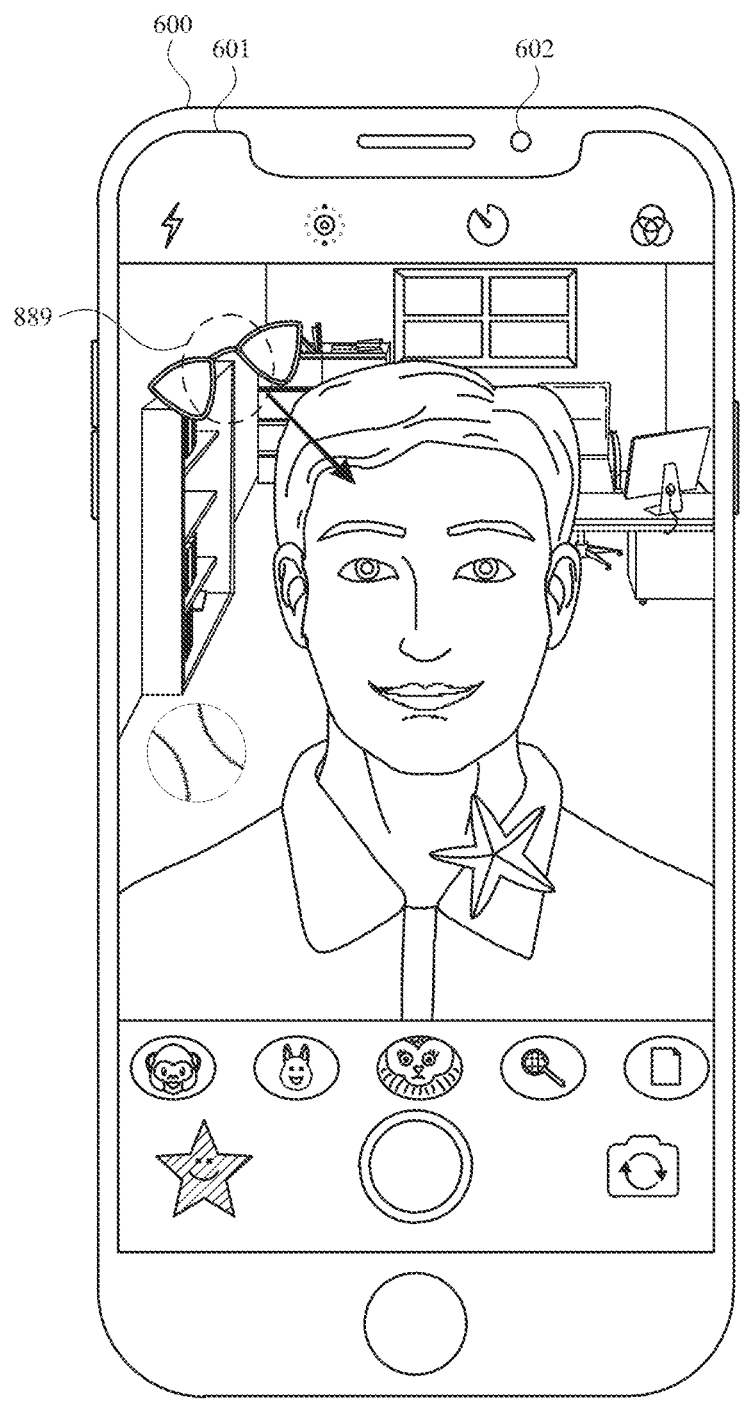
Figure 8B:
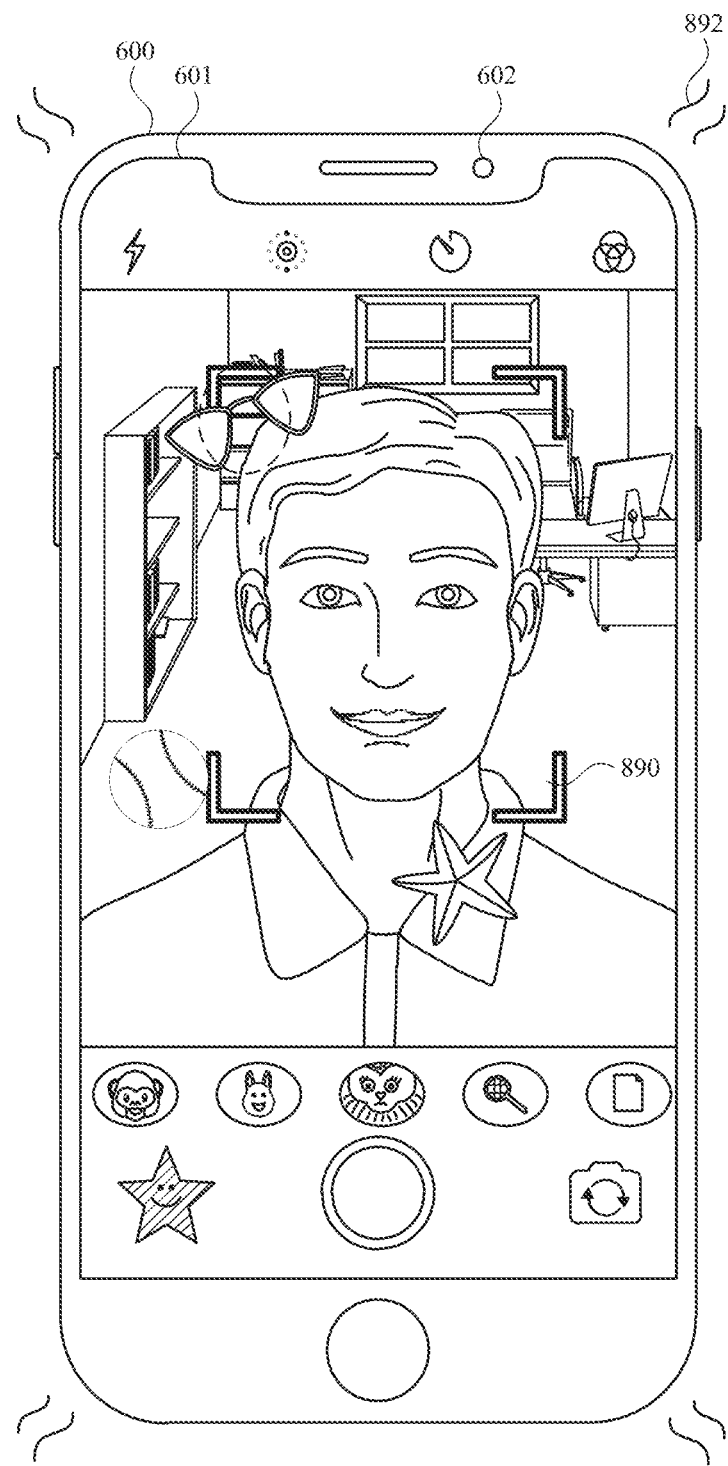
Figure 8B:
Figure 8B:

Figure 8B:
Figure 8B:
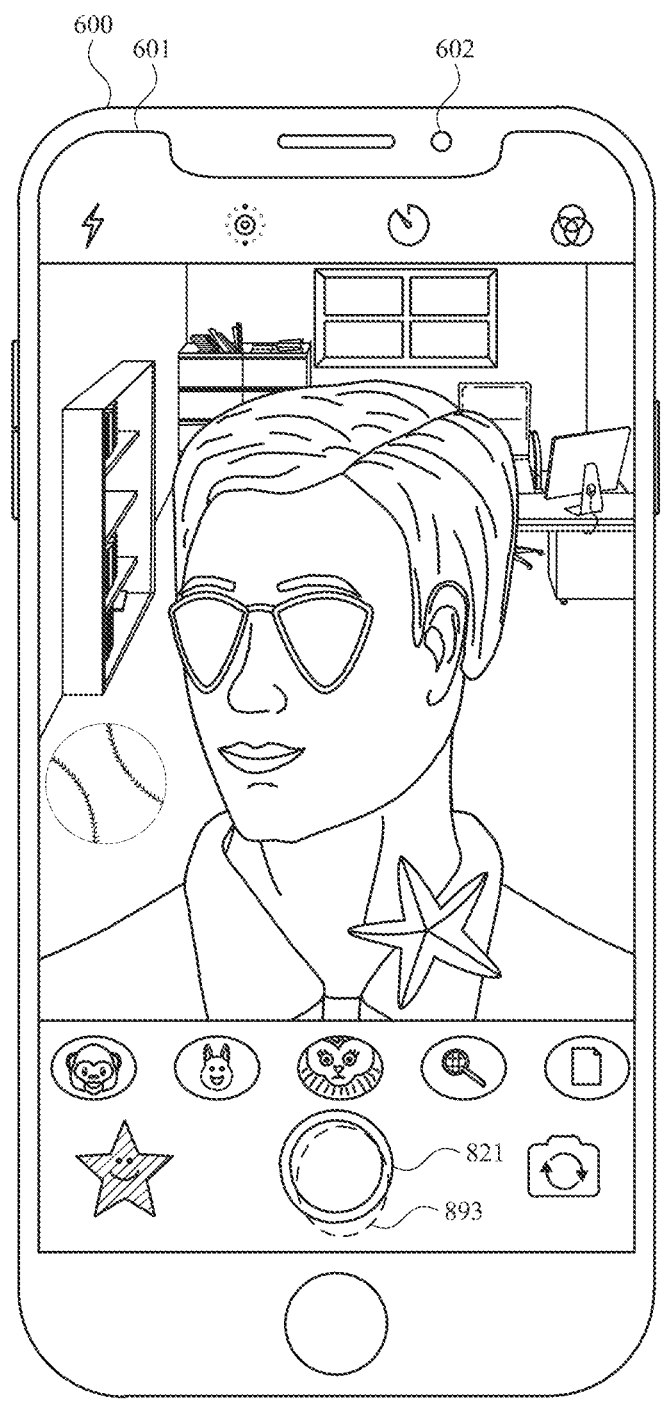
Figure 8B:
Figure 8B:
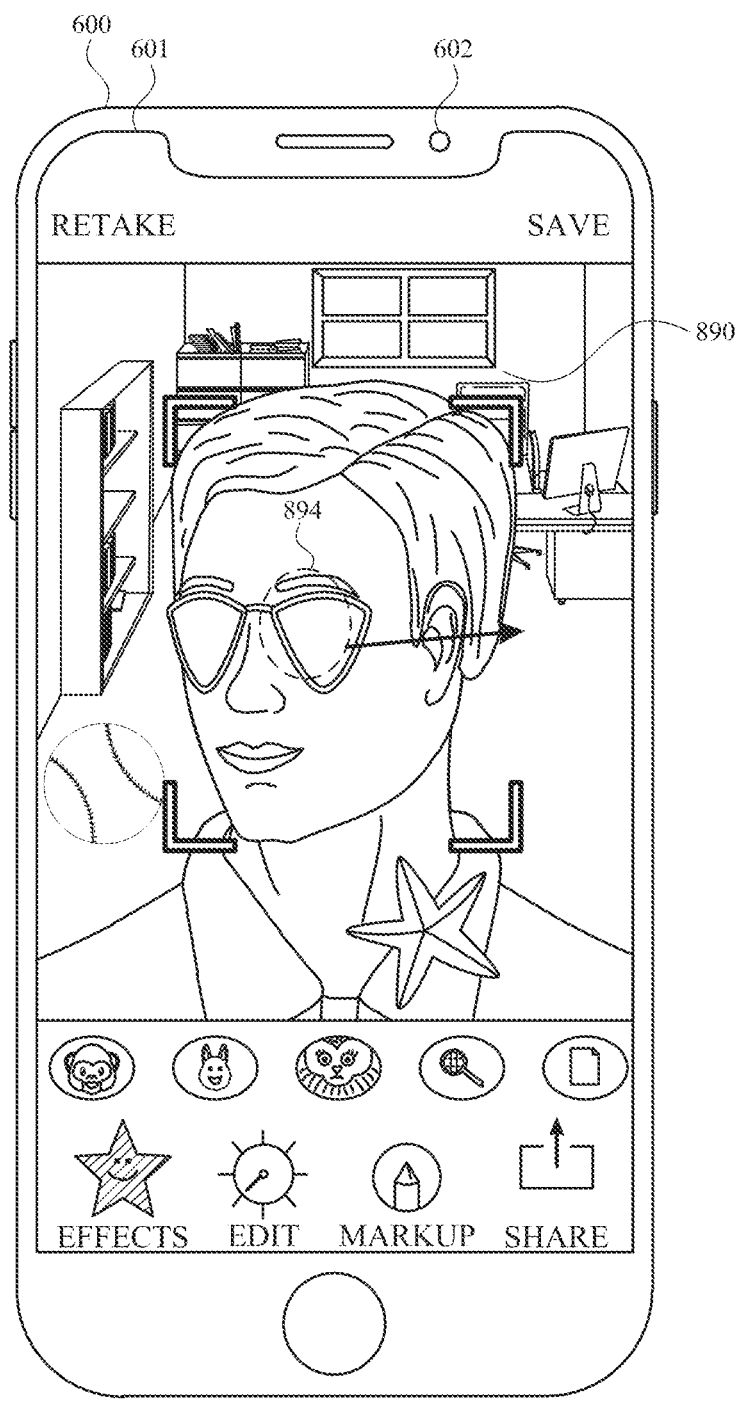
Figure 8B:
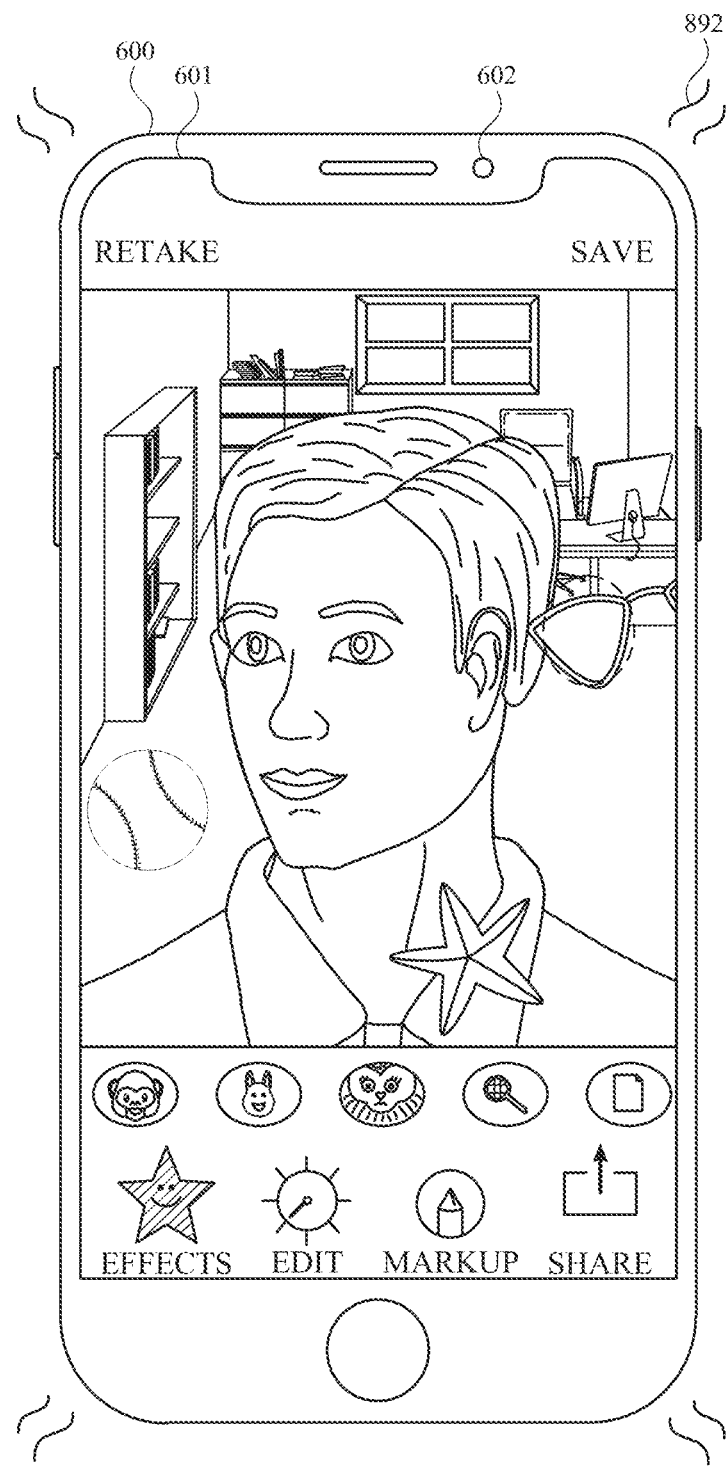
Figure 8B:
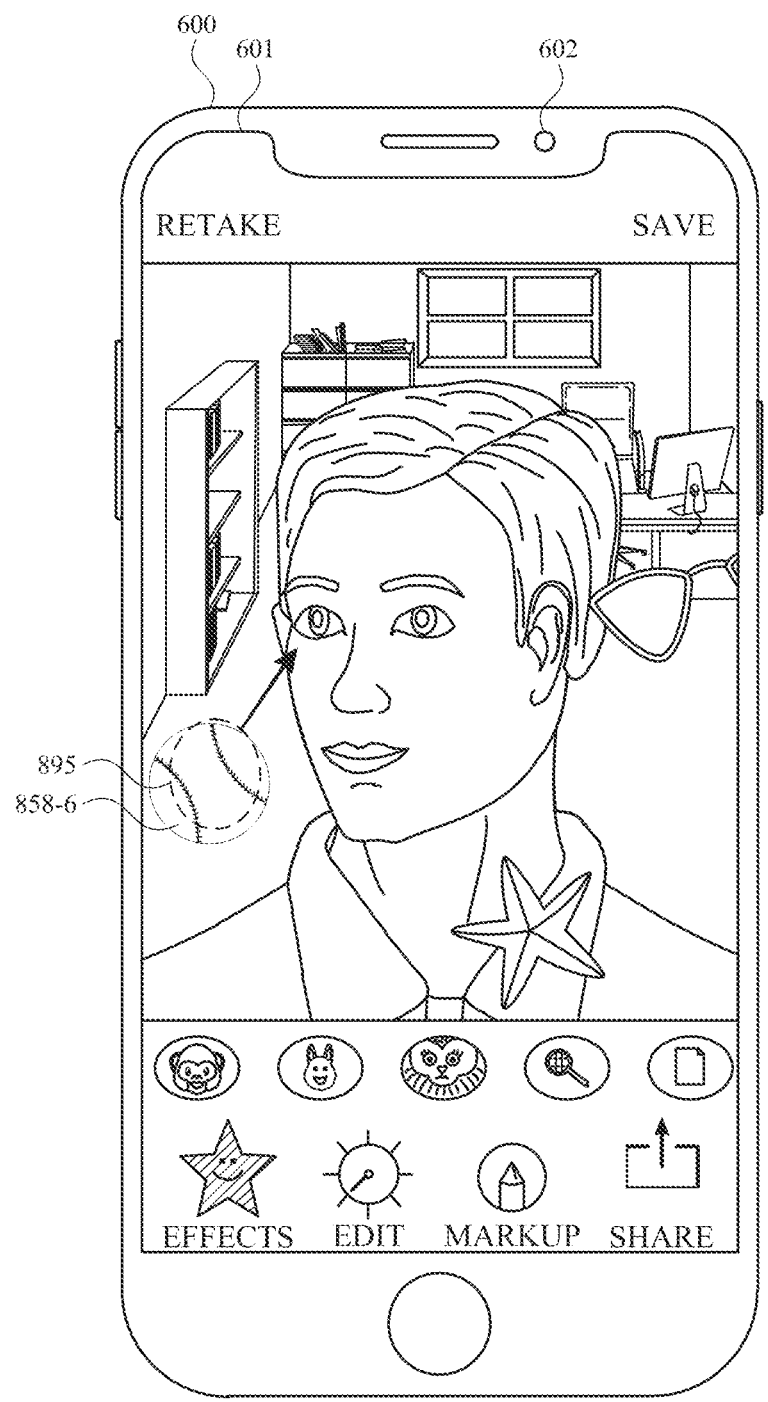
Figure 8B:
Figure 8B:
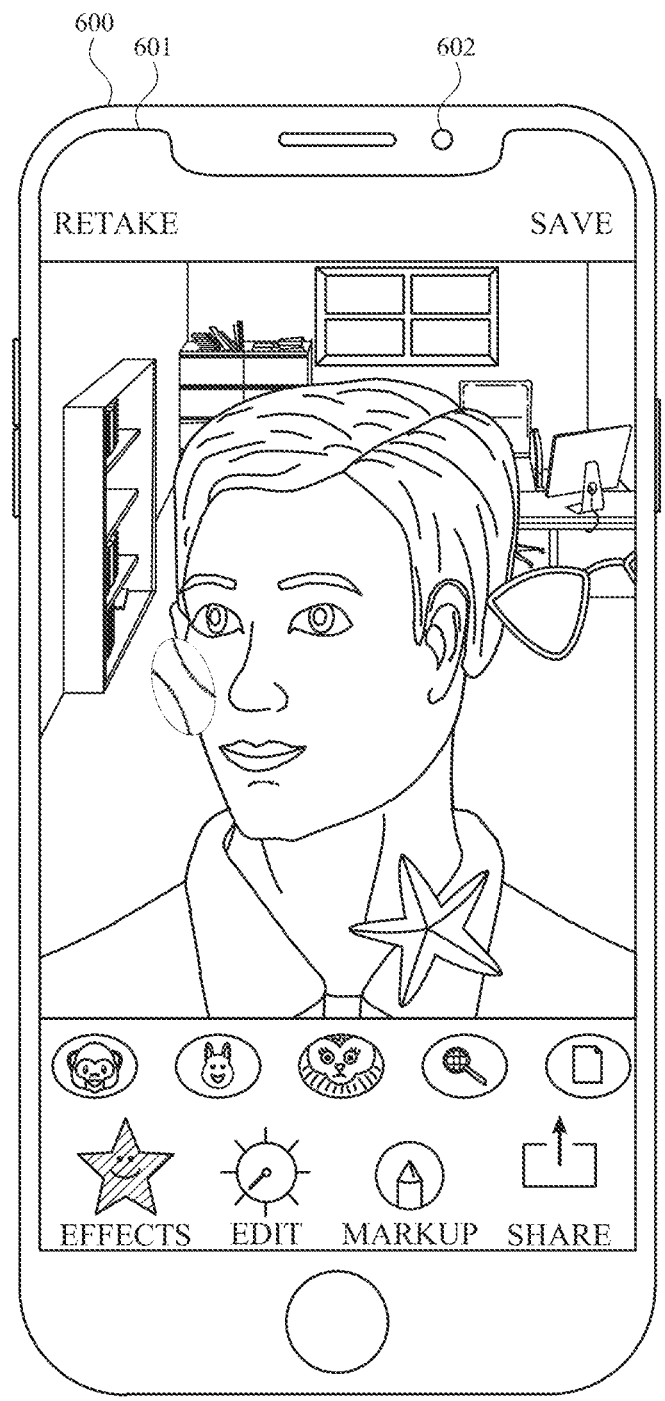

FIGS. 8X and 8Y show a selection of a different customizable avatar option (e.g., customizable avatar option 830-5) and the corresponding displayed customizable avatar 835. When customizable avatar option 830-5 is displayed in selection region 829, edit affordance 804 is displayed. Edit affordance 804 can be selected (e.g., via input 807) to display avatar editing user interface 808 shown in FIG. 8AA. Avatar editing user interface 808 provides an interface for editing the avatar (e.g. customizable avatar 835) corresponding to the customizable avatar option (e.g., 830-5) associated with the selected edit affordance 804.

In some embodiments, applied visual effects can include a lighting effect such as shadow 851 shown on the subject's neck below applied custom avatar 835 or light reflections on glasses. As device 600 modifies avatar 835 to mirror the real-time movements of the user, device 600 also modifies the lighting effects on avatar 835 and those projected onto the subject, including moving displayed locations of reflections shadows based on a relative position of a modeled light source and avatar 835.

As shown in FIG. 8AA, avatar editing user interface 808 includes a representation of customizable avatar 835 and various avatar feature options 810 (e.g., face color options 810-1 and face shape options 810-2) that represent currently selected avatar feature options and available feature options that can be selected to modify avatar 835. The avatar feature options correspond to values for aspects of a particular avatar feature, specifically a currently selected avatar feature, such as an avatar head feature indicated by highlighted avatar head affordance 809-1. Avatar editing user interface 808 indicates a selected face color option 810-1a and a selected face shape option 810-2a, which are represented in avatar 835. The displayed avatar feature options can be changed by selecting a different avatar feature. For example, in FIG. 8 AB, device 600 updates avatar editing user interface 808 to display different avatar hair feature options (e.g., hair texture options 811-1 and hair color options 811-2) when the avatar hair affordance 809-2 is selected.

Device 600 modifies avatar 835 when different avatar feature options are selected. For example, in FIG. 8AB, device 600 detects selection of straight hair texture option 811-2a, and updates avatar 835 to have the selected straight hair texture option. In some embodiments, device 600 modifies the representation of avatar 835 shown in avatar editing user interface 808 in response to detected changes in a user's face.

In response to detecting selection of done affordance 812, device 600 exits avatar editing user interface 808 and returns to camera application user interface 815 showing the selected avatar option 830-5 and corresponding avatar 835 updated based on the hair texture option selected in the avatar editing user interface.

FIGS. 8AD-8AF show an embodiment in which a new customized avatar can be created and added to avatar options menu 828. In response to detecting a selection of new avatar affordance 813, device 600 displays avatar editing user interface 808 having a representation of a default avatar with no selected avatar feature options, as shown in FIG. 8AE. Device 600 can modify the default avatar based on user selection of the avatar feature options and save the avatar as a new avatar that is selectable from the avatar options menu 828. In FIG. 8AF, device 600 detects selection of a cancel affordance and, therefore, foregoes saving the modified avatar in avatar options menu 828, as shown in FIG. 8AG.

In response to detecting selection of cancel icon 850 in FIG. 8AG, device 600 closes avatar options menu 828 and displays camera options region 825 as shown in FIG. 8AH.

In response to detecting selection of sticker effects affordance 824-2, device 600 displays sticker options menu 856 having a scrollable listing of sticker 858 in FIG. 8AI. Sticker options menu 856 and stickers 858 are similar to sticker options menu 656 and stickers 658 discussed above. The stickers are static graphical objects that may be selected by a user and applied to the image in image display region 820. In some embodiments a sticker can be selected by a tap gesture, and the corresponding sticker is then displayed at a position on the image display region 820. In some embodiments, a sticker can be selected by a touch-and-drag gesture that initiates on the selected sticker, drags the sticker to a desired location, and then places the sticker at the desired location by terminating the drag (e.g., lifting finger). An example of such an embodiment is illustrated in FIGS. 8AI-8AK, where helmet sticker 858-1 is selected (e.g., input 853), dragged to a position above (e.g., away from) custom avatar 835. In FIG. 8AK, device 600 detects subject 832 move laterally from the position shown in FIG. 8AJ. In response, device 600 displays helmet sticker 858-1 and avatar 835 both moving laterally based on the lateral movement (e.g., direction and magnitude) of the representation of the subject.

In FIG. 8AK, device 600 detects input 854 on close affordance 855. In response, device 600 closes sticker options menu 856 to display camera options region 825 in FIG. 8AL. In FIG. 8AL, device 600 shows that subject 832 is shifted back to the center of the screen with their head tilted. In response to detecting this movement of subject 832, device 600 displays helmet sticker 858-1 above customizable avatar 835 in FIG. 8AL and shifted laterally (from the position shown in FIG. 8AK) based on the movement of the subject's head to the center of the screen. Device 600 displays helmet sticker 858-1 maintaining the relative spacing with respect to avatar 835. However, helmet sticker 858-1 is not rotated (e.g., tilted) in response to the rotation (e.g., tilting) of the subject's head, whereas avatar 835 is rotated (e.g., tilted), as shown in FIG. 8AL.

In FIG. 8AL, device 600 detects a selection of capture affordance 821, which causes device 600 to capture an image of the live camera preview 820-1 displayed in image display region 820, including the visual effects (e.g., customized avatar 835 and helmet sticker 858-1), as well as other image data including subject 832 and background 836.

In FIG. 8AM, device 600 displays camera application user interface 815 showing the captured image (e.g., media item 820-2) in the image display region 820 (e.g., media item 820-2 replaces the live camera preview 820-1 shown in image display region 820). Media item 820-2 is a representation of the live camera preview 820-1 at the time the capture affordance 821 was selected. Thus, media item 820-2 includes helmet sticker 858-1 and avatar 835 displayed over the face of subject 832, and background 836.

Device 600 also replaces the camera-specific affordances (e.g., affordances 817 shown in FIG. 8AL) with retake affordance 879 and save affordance 818 for saving the captured media item 820-2.

Device 600 also updates camera options region 825 to replace capture affordance 821 and camera selector affordance 827 with markup affordance 877, edit affordance 878, and share affordance 880. Markup affordance 877 allows a user to mark-up media item 820-2. Edit affordance 878 allows a user to edit media item 820-2 such as by cropping the image or adjusting other characteristics of media item 820-2. Share affordance 880 allows a user to send media item 820-2 to another device, such as, for example in a messaging application or email application.

Device 600 displays camera options region 825, including visual effects option affordances 824. Visual effects option affordances 824 can be selected to display their respective option menus, which can be used to modify captured media item 820-2 (as well as recorded video media item 820-4 discussed below). For example, FIGS. 8AN-8AP illustrate device 600 adding a sticker to media item 820-2. Sticker effects affordance 824-2 is selected in FIG. 8AN, which causes device 600 to display sicker options menu 856 in FIG. 8AO, which also shows selection of rabbit sticker 858-2, which is positioned on subject 832 in media item 820-2, shown in FIG. 8AP. Sticker options menu 856 is closed in FIG. 8AP, displaying camera options region 825 in FIG. 8AQ.

In FIG. 8AQ, device 600 also displays media item 820-2 with rabbit sticker 858-2 positioned on subject 832, along with other visual effects (e.g., avatar 835 and helmet sticker 858-1).

Stickers can be added to recorded media items that are in a video format in a manner that is similar to that described above for media item 820-2 (still image). For example, FIG. 8AR shows an embodiment in which video media item 820-4 is a recorded video. Media item 820-4 can be created in a manner similar to that described above for media item 620-4.

In FIG. 8AR, device 600 displays recorded video media item 820-4 in image display region 820. Device 600 also displays camera options region 825 having video scrubber 8120 for recorded video media item 820-4, effects affordance 822, edit affordance 878, markup affordance 877, and share affordance 880. Camera options region 825 also includes visual effects option affordances 824. Visual effects option affordances 824 can be selected to display their respective option menus, which can be used to modify captured media item 820-4. For example, FIGS. 8AR-8AV illustrate device 600 adding stickers 858-2 and 858-3 to media item 820-4.

In some embodiments, displayed stickers can have different modeled behaviors in a video media item (or live video stream). For example, some stickers have an appearance of being applied to the display (e.g., 601) and remain static as objects in the image data move. An example of such a sticker is demonstrated by heart sticker 858-3 in FIGS. 8AX-8BC. In some embodiments, stickers have this static behavior when the sticker is placed in the media item (e.g., 820-4) or live camera preview (e.g., 820-1) when device 600 does not detect the presence of all or a portion (e.g., head or face) of the representation of the subject in the media item, live camera preview, or field of view of camera 602. For example, if a subject's face is completely off screen (e.g., not detected in the field of view of camera 602), and a sticker is placed on image display region 820, then, once the face is detected in the field of view of camera 602 and is displayed on image display region 820 with the previously placed sticker, the sticker is stationary and does not track any movement of the subject's face.

Other stickers have the appearance of being applied to the display and moving to follow an object (e.g., an item in the field of view of the camera including, for example, an avatar or a representation of the subject) in the image. In some embodiments, the sticker is placed at a location remote from the object the sticker follows. An example of such a sticker is demonstrated by helmet sticker 858-1 in FIGS. 8AK and 8AX-8BC. Helmet sticker 858-1 follows lateral movement of subject 832, but not rotational movement of the subject. Another example of such a sticker is demonstrated by starfish sticker 858-5 in FIGS. 8BE-8BQ. When positioned away from the subject's face, starfish sticker 858-5 follows movement of the subject's face while maintaining a relative position with respect to the face (e.g., starfish sticker 858-5 follows movement of the subject's face forwards, backwards, and side-to-side, but not rotational movement of the subject's face).

Yet other stickers have the appearance of being applied to an object in the field of view of camera 602 and move to follow the object within the field of view (e.g., having an appearance of depth as the sticker adjusts with the object in the image). An example of such a sticker is demonstrated by rabbit sticker 858-2 in FIGS. 8AX-8BC. Rabbit sticker 858-2 moves with lateral and rotational movement of the subject (specifically, the subject's shoulder). Another example of such a sticker is glasses sticker 858-4 in FIGS. 8BG-8BM. When positioned on the subject's face in FIGS. 8BG-8BM, glasses sticker 858-4 follows lateral movement (e.g., side to side, up/down) of the subject's face, movement of the subject's face forwards and backwards, and rotational movement of the subject's face. The glasses sticker 858-4 has the appearance of physically being applied (e.g., stuck) to the subject's face.

In some embodiments, a sticker's behavior changes based on its position relative to objects in the media item (or live camera preview or field of view of the camera). In some embodiments, the behavior of a sticker changes in response to detecting changes in the position of the sticker relative to the object. Examples of such stickers are shown in FIGS. 8BE-8BQ, described in greater detail below.

FIGS. 8AW-8BC show video playback and editing of media item 820-4, which includes avatar 835, helmet sticker 858-1, rabbit sticker 858-2, and heart sticker 858-3. As media item 820-4 advances during playback, heart sticker 858-3 remains static, having the appearance of being applied to display 601 and not moving. Helmet sticker 858-1 has the appearance of being applied to the display, but moves (e.g., translates) in response to changes in a position of avatar 835. Rabbit sticker 858-2 has the appearance of being applied on the shoulder of subject 832 in media item 820-4. As the shoulder moves, rabbit sticker 858-2 changes positions, including orientation and displayed size, to give the appearance of following the subject's shoulder during playback of media item 820-4.

In some embodiments, a sticker or other virtual object that is applied to a location of the representation of the field of view of one or more cameras that includes a respective object (e.g., a face, hand, or other body part of a user of the device) being tracked in three dimensions (e.g., via depth information from a depth sensor) is attached to the respective object such that the size and/or orientation of the virtual object changes as the distance of the respective object from the one or more cameras and/or the orientation of the respective object with respect to the one or more cameras changes in addition to moving laterally (e.g., side to side and/or up and down) as the respective object moves laterally (e.g., side to side and/or up and down) in the field of view of the one or more cameras. For example, as shown in FIGS. 8AS-8AT, rabbit sticker 858-2 is placed on the representation of the subject's shoulder. As the shoulder moves up and towards the camera in FIGS. 8AX-8AY, rabbit sticker 858-2 moves with the shoulder laterally (up) and enlarges as the shoulder moves towards the camera. In some embodiments, a sticker or other virtual object that is applied to a location of the representation of the field of view of one or more cameras that is away (e.g., remote) from a respective object (e.g., a face, hand, or other body part of a user of the device) being tracked in three dimensions (e.g., via depth information from a depth sensor) moves laterally (e.g., side to side and/or up and down) as the respective object moves laterally (e.g., side to side and/or up and down) in the field of view of the one or more cameras without being attached to the object such that the size and/or orientation of the virtual object does not change as the distance of the respective object from the one or more cameras and/or the orientation of the respective object with respect to the one or more cameras changes. For example, as shown in FIGS. 8AX and 8AY, helmet sticker 858-1 is placed at a location that is away from the representation of the subject. As the representation of the subject moves sideways and closer to the camera in FIGS. 8AX and 8AY, helmet sticker 858-1 moves laterally based on the movement of the representation of the user, but does not change in orientation or size.

In FIG. 8AY, device 600 detects input 882 (e.g., a swipe or drag gesture) on scrubber 8120, and scrubs through media item 820-4 based on the input. As shown in FIG. 8AZ, in response to input 882, device 600 reverses through media item 820-4 to display the portion of media item 820-4 that was previously displayed in FIG. 8AX. Device 600 detects input 884 on edit affordance 878.

In FIG. 8BA, device 600 enters an editing mode (for editing media item 820-4) and displays selectable affordances 885 for cropping the video by dragging affordances 885 at the ends of the video scrubber 8120 (via input 883) to change an ending time for the video scrubber.

As shown in FIG. 8BB, video scrubber 8120 is trimmed in response to input 883. Device 600 detects input 886 on done affordance 887 and exits the editing mode.

In FIG. 8BC, the video scrubber 8120 is shown trimmed (e.g., having a shorter length than prior to entering edit mode in FIG. 8AZ). Device 600 detects input 888 on effects affordance 822, which exits effects mode.

As demonstrated in FIG. 8BD, the visual effects displayed in media item 820-4 are hidden from display in response to detecting input 888 deselecting effects affordance 822.

In some embodiments, stickers can have a behavior that is determined based on conditions (e.g., position of the sticker relative to other objects, the presence (or absence) of objects when the sticker is placed, etc.) of the sticker's placement. For example, in some embodiments, a sticker can have a first type of behavior when positioned remote from an object or region, and a second type of behavior when positioned on the object or region. In some embodiments, a sticker can have a third type of behavior if an object is not present when the sticker is placed. In some embodiments, the behavior of the sticker can change based on changes to the sticker's placement (e.g., relative to an object).

For example, FIGS. 8BE-8BQ illustrate an example embodiment showing the behavior of various stickers displayed in live camera preview 820-1, and changes to the behavior of the stickers based on changes to the stickers' placement relative to the subject's face. In the embodiment illustrated in FIGS. 8BE-8BQ, the behavior of the stickers is determined based on the location of the stickers relative to the subject's face.

In FIG. 8BE, device 600 displays camera application user interface 815 having an appearance similar to that shown in FIG. 8D, but having stickers 858 displayed in image display region 820. Image display region 820 shows live camera preview 820-1 from camera 602, showing a representation of subject 832 positioned in the field of view of camera 602 and background 836 displayed behind subject 832. Glasses sticker 858-4, starfish sticker 858-5, and baseball sticker 858-6 are each displayed positioned away from (e.g., not on) the face of subject 832. The stickers shown in FIG. 8BE-8BQ can be placed and moved in the image display region in accordance with the various embodiments discussed herein.

When the stickers 858 are positioned away from (e.g., not on) the subject's face, they have a first type of behavior. For example, the stickers follow movement of the subject's face laterally (e.g., side to side and up/down), forwards (e.g., towards camera 602), and backwards (e.g., away from camera 602), but not rotational movement of the subject's face (e.g., not following the pitch and yaw of the subject's face).

In FIG. 8BF, device 600 detects input 889 (e.g., a touch and drag gesture on display 601) on glasses sticker 858-4. In response to detecting input 889, device 600 displays glasses sticker 858-4 moving with the input (e.g., in the direction and magnitude of movement of input 889), as shown in FIGS. 8BG and 8BH.

In some embodiments, device 600 provides an indication when the sticker moves to a location that corresponds to the object the sticker is following. For example, in FIG. 8BG, device 600 shows glasses sticker 858-4 moving from a location away from the subject's face to a location on the subject's face. Device 600 displays brackets 890 around the subject's face and, optionally, produces haptic feedback 892 (e.g., a tactile output, with or without an audio output) as glasses sticker 858-4 moves onto the subject's face. In some embodiments, brackets 890 provide a visual indication of a region in which glasses sticker 858-4 can be placed so that they will be displayed on the subject's face (resulting in modified behavior for glasses sticker 858-4). Thus, brackets 890 (and haptic feedback 892) can indicate to a user when they are dragging the sticker to a placement area (e.g., inside the brackets) that will position the sticker on the subject's face. In some embodiments, haptic feedback 892 indicates that the glasses sticker 858-4 has moved from the region outside the subject's face (e.g., a region in which the sticker has the first type of behavior) to the region on the subject's face (e.g., the region in which the sticker has the second type of behavior).

In some embodiments, when device 600 detects that the position of the sticker (or other visual effect) moves to a location that corresponds to the object the sticker is following, device 600 modifies the appearance of the sticker based on the position of the object and modifies the behavior of the sticker (in some embodiments, the behavior of the sticker is modified after detecting termination of input 889). Device 600 also modifies the appearance and behavior of the sticker in an opposite manner when the sticker is moved from the location that corresponds to the object the sticker is following, to a location remote from the object.

In FIG. 8BH, when device 600 detects the position of glasses sticker 858-4 on the subject's face (e.g., positioned within brackets 890), device 600 modifies the sticker based on the position (e.g., size and orientation) of the subject's face. For example, the glasses sticker 858-4 increases in size (e.g., to proportionally match the size of the subject's face), and rotates from its static position in FIG. BG, to match the position of the subject's face in FIG. 8BH. In some embodiments, the sticker is positioned on a plane that corresponds to the subject's nose and transforms coordinates of its position as the face moves. In some embodiments, a face mesh (e.g., a depth mask) is used to determine the point of the nose. In some embodiments, the sticker is positioned on the plane, but does not conform to the shape of the subject's face.

Device 600 also changes the behavior of the sticker to a second type of behavior (e.g., a behavior different than the first type of behavior). As shown in FIG. 8BH, a second type of behavior can include a behavior in which the sticker maintains its 3D position on the face, following rotational movement of the subject's face (e.g., following the pitch and yaw of the face), in addition to lateral movement and movement forwards/backwards. The behavior of other stickers is not changed. Thus, baseball sticker 858-6 and starfish sticker 858-5 continue to have the first type of behavior because they are not placed on the subject's face. Instead, starfish sticker 858-5 and baseball sticker 858-6 continue to maintain a relative spacing from the face.

In some embodiments, brackets 890 persist with input 889 while input 889 is positioned on the subject's face (e.g., within the brackets). Thus, when device 600 detects termination of input 889, device 600 ceases displaying brackets 890, as shown in FIG. 8BI.

FIGS. 8BI and 8BJ illustrate device 600 rotating glasses sticker 858-4 with the subject's face, while starfish sticker 858-5 and baseball sticker 858-6 remain stationary (unlike glasses sticker 858-4, they do not follow rotational movement of the subject's face).

In FIG. 8BK, the subject moves closer to camera 602. Glasses sticker 858-4 moves with the forward movement of the subject's face and maintains its rotated position with the subject's face. Similarly, baseball sticker 858-6 and starfish sticker 858-5 move with the forward movement of the subject's face, while maintaining a relative spacing with respect to the subject's face. Baseball sticker 858-6 and starfish sticker 858-5 do not rotate with the subject's face.

In FIG. 8BK, device 600 detects input 893 on capture affordance 821 and, in response, captures an image of live camera preview 820-1.

In FIG. 8BL, device 600 displays camera application user interface 815 showing the captured image (e.g., media item 820-5) in the image display region 820 (e.g., media item 820-5 replaces the live camera preview 820-1 shown in image display region 820). Media item 820-5 is a representation of the live camera preview 820-1 at the time the capture affordance 821 was selected. The embodiment shown in FIG. 8BL is similar to that shown in FIG. 8AM, but with media item 820-5 (instead of media item 820-2), which includes glasses sticker 858-4, starfish sticker 858-5, and baseball sticker 858-6 displayed relative to the face of subject 832 and background 836.

The display of visual effects, as discussed herein, is similar across different embodiments. For example, unless specified otherwise, visual effects can be displayed and manipulated in a similar manner in a camera application, a messaging application, an avatar editing application, a live video messaging application, or any other application discussed herein. Additionally, visual effects can be displayed and manipulated in a similar manner across different types of image data. For example, unless specified otherwise, visual effects can be displayed and manipulated in a similar manner in a live camera preview, a media item, streamed image data, or any other image data discussed herein. For example, FIGS. 8BL-8BQ illustrate displaying stickers in media item 820-5 in a manner similar to that discussed above for live camera preview 820-1. Specifically, FIGS. 8BL-8BQ demonstrate that stickers in a media item (e.g., 820-5) can be repositioned, and their respective behavior changed accordingly, in a manner similar to that discussed above with respect to live image preview 820-1.

In FIG. 8BM, device 600 detects input 894 on glasses sticker 858-4 and displays brackets 890. Input 894 moves glasses sticker 858-4 off of the subject's face in FIG. 8BN. As the glasses sticker is moved off the face, device 600 generates haptic feedback 892, ceases displaying brackets 890, and modifies glasses sticker 858-4 back to its original shape (e.g., the slightly tilted shape from when the glasses sticker was positioned remote from the subject's face in FIG. 8BE). Device 600 also modifies the behavior of glasses sticker 858-4 back to the first type of behavior (the behavior associated with a sticker placed remote from an object it tracks) and modifies the appearance of the sticker based on the changed behavior. Thus, glasses sticker 858-4 is displayed having a larger size in FIGS. 8BN-8BQ (compared to the size of glasses sticker 858-4 in FIGS. 8BE-8BG) to maintain the relative spacing of glasses sticker 858-4 to the position of the subject's face in media item 820-5, similar to the size changes of starfish sticker 858-5 and baseball sticker 858-6 based on forward movement of the subject's face in FIGS. 8BJ-8BK.

FIGS. 8BO-8BQ demonstrate placing a different sticker on the subject's face in media item 820-5, and that different sticker being modified based on a different behavior of the sticker in response to being moved onto the subject's face. For example, in FIG. 8BO, device 600 detects input 895 on baseball sticker 858-6. As baseball sticker 858-6 is dragged onto the subject's face in FIG. 8BP, device 600 displays brackets 890, generates haptic feedback 892 (e.g., a tactile output), and repositions baseball sticker 858-6 based on the angle of the subject's face. In other words, the behavior of baseball sticker 858-6 changes such that it follows rotational movement of the subject's face, similar to the way glasses sticker 858-4 followed rotational movement of the subject's face when it was placed on the subject's face.

In FIG. 8BQ, input 895 terminates and device 600 ceases displaying brackets 890.

FIGS. 9A and 9B are a flow diagram illustrating a method for displaying visual effects in a camera application using an electronic device in accordance with some embodiments. Method 900 is performed at a device (e.g., 100, 300, 500, 600) with a camera and a display apparatus. Some operations in method 900 are, optionally, combined, the orders of some operations are, optionally, changed, and some operations are, optionally, omitted.

As described below, method 900 provides an intuitive way for displaying visual effects in a camera application. The method reduces the cognitive burden on a user for applying visual effects to an image viewed in a camera application, thereby creating a more efficient human-machine interface. For battery-operated computing devices, enabling a user to display visual effects in an image faster and more efficiently conserves power and increases the time between battery charges.

The electronic device (e.g., 600) displays (902), via the display apparatus (e.g., 601), a camera user interface (e.g., 815). The camera user interface includes (904) a camera display region (e.g., 820) including a representation (e.g., 835) of image data captured via the camera (e.g., 602).

In some embodiments, the image data includes (906) depth data (e.g., image data that includes a depth aspect (e.g., depth data independent of RGB data) of a captured image or video. In some embodiments, the image data includes at least two components: an RGB component that encodes the visual characteristics of a captured image, and depth data that encodes information about the relative spacing relationship of elements within the captured image (e.g., the depth data encodes that a user is in the foreground, and background elements, such as a tree positioned behind the user, are in the background. In some embodiments, the depth data is a depth map. In some embodiments, a depth map (e.g., depth map image) contains information (e.g., values) that relates to the distance of objects in a scene from a viewpoint (e.g., a camera). In one embodiment of a depth map, each depth pixel defines the position in the viewpoint's z-axis where its corresponding two-dimensional pixel is located. In some examples, a depth map is composed of pixels wherein each pixel is defined by a value (e.g., 0-255). For example, the "0" value represents pixels that are located at the most distant place in a "three dimensional" scene and the "255" value represents pixels that are located closest to a viewpoint (e.g., camera) in the "three dimensional" scene. In other examples, a depth map represents the distance between an object in a scene and the plane of the viewpoint.) In some embodiments, the depth map includes information about the relative depth of various features of an object of interest in view of the depth camera (e.g., the relative depth of eyes, nose, mouth, ears of a user's face). In some embodiments, the depth map includes information that enables the device to determine contours of the object of interest in a z direction.

In some embodiments, the depth data has a first depth component (e.g., a first portion of depth data that encodes a spatial position of the subject in the camera display region; a plurality of depth pixels that form a discrete portion of the depth map, such as a foreground or a specific object) that includes the representation of the subject in the camera display region (e.g., 820). In some embodiments, the depth data has a second depth component (e.g., a second portion of depth data that encodes a spatial position of the background in the camera display region; a plurality of depth pixels that form a discrete portion of the depth map, such as a background), separate from the first depth component, the second depth aspect including the representation of the background in the camera display region. In some embodiments, the first depth aspect and second depth aspect are used to determine a spatial relationship between the subject in the camera display region and the background in the camera display region. This spatial relationship can be used to distinguish the subject from the background. This distinction can be exploited to, for example, apply different visual effects (e.g., visual effects having a depth component) to the subject and background). In some embodiments, all areas of the image data that do not correspond to the first depth component (e.g., areas of the image data that are out of range of the depth camera) are segmented out (e.g., excluded) from the depth map.

In some embodiments, the representation (e.g., 835) of image data captured via the camera (e.g., 602) is a live camera preview (e.g., a stream of image data that represents what is in the field of view of the camera).

In some embodiments, while the first camera display mode is active, the electronic device (e.g., 600) detects a swipe gesture on the camera display region (e.g., 820). In some embodiments, in response to detecting the swipe gesture on the camera display region (e.g., the electronic device (e.g., 600) changes an appearance of the displayed representation of the selected avatar option in the camera display region from a first appearance (e.g., an appearance based on the currently selected avatar option) to a second appearance (e.g., an appearance based on a different avatar option (e.g., a null avatar option or an avatar option corresponding to a different avatar, including avatars of different types (e.g., customizable, non-customizable))), where the second appearance corresponds to a different one of the plurality of avatar options (e.g., a different avatar option included in the avatar selection region). Changing the appearance of the displayed representation of the selected avatar option in response to detecting a swipe gesture on the camera display region provides the user with a quick and easy method to change a representation of a selected avatar. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently In some embodiments, when the different one of the plurality of avatar options is a null avatar option, the device (e.g., 600) ceases to display the representation of the avatar on the representation of the subject (e.g., the device foregoes replacing image data of the user's head with a virtual avatar). In some embodiments, when the different one of the plurality of avatar options is an avatar option of a different avatar character (including a customizable or non-customizable avatar character), the device replaces the selected avatar character with the different avatar character (e.g., the device replaces the representation of the avatar with a representation of a different avatar). In some embodiments, replacing the selected avatar character with the different avatar character includes displaying an animation of the different avatar character moving to the center of the screen. In some embodiments, replacing the selected avatar character with the different avatar character includes displaying an animation of the different avatar character moving to the user's head. In some embodiments, replacing the selected avatar character with the different avatar character includes blurring the background while the selected avatar is being replaced. Displaying an animation (e.g., the different avatar character moving to the center of the screen, the different avatar character moving to the user's head, blurring the background) once/while the selected avatar character is replaced with the different avatar character provides visual feedback that the avatar character is being changed. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the currently selected avatar option corresponds to an avatar of a first type (e.g., a customizable avatar), and the different avatar option corresponds to an avatar of a second type (e.g., a non-customizable avatar).

In some embodiments, changing the appearance of the displayed representation of the selected avatar option in the camera display region (e.g., 820) from the first appearance to the second appearance includes moving a first version of the representation of the selected avatar option, off of the display, the first version having the first appearance. In some embodiments, changing the appearance of the displayed representation of the selected avatar option in the camera display region from the first appearance to the second appearance includes moving a second version of the representation of the selected avatar option to substantially the center of the display, the second version having the second appearance. Moving the first version of the representation of the selected avatar option off of the display and moving the second version of the representation of the selected avatar option to substantially the center of the display provides visual feedback that the first version is being replaced by the second version. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, changing the appearance of the displayed representation of the selected avatar option from the first appearance to the second appearance includes moving a first version of the representation of the selected avatar off of the display, the first version having the first appearance. In some embodiments, changing the appearance of the displayed representation of the selected avatar option from the first appearance to the second appearance includes moving a second version of the representation of the selected avatar option to substantially the position of the representation of the subject displayed in the camera display region (e.g., 820), the second version having the second appearance. Moving the first version of the representation of the selected avatar option off of the display and moving the second version of the representation of the selected avatar option to substantially the position of the representation of the subject displayed in the camera display region provides visual feedback that the first version is being replaced by the second version. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, changing the appearance of the displayed representation of the selected avatar option from the first appearance to the second appearance includes modifying the visual appearance of the background displayed in the camera display region (e.g., 820) (e.g., blurring the background, desaturating the background).

The camera user interface also includes (908) a first affordance (e.g., an affordance that corresponds to a virtual avatar) associated with a first camera display mode (e.g., a mode in which image data of the user's head is replaced with a virtual avatar).

In some embodiments, the camera user interface (e.g., 815) further includes a sticker affordance (e.g., 824-2, an affordance that corresponds to a function for enabling the display of stickers) associated with a sticker display mode (e.g., a mode in which stickers are enabled to be applied to the image data). In some embodiments, while displaying the image data (and optionally a representation of the selected avatar option) in the camera display region (e.g., 820), the electronic device (e.g., 600) detects a gesture (e.g., FIG. 8AH) directed to the sticker affordance. In some embodiments, in response to detecting the gesture directed to the sticker affordance, the electronic device activates the sticker display mode, where activating the sticker display mode includes displaying a sticker selection region (e.g., 856) including a plurality of sticker options (e.g., 858, stickers), detecting a selection of one of the plurality of sticker options (e.g., 858-2, a sticker) in the sticker selection region, and, in response to detecting the selection, displaying a representation (e.g., 858-2) of the selected sticker option on the image data in the camera display region. In some embodiments, the selected sticker option displayed on the image data has the appearance of being placed on the display screen (e.g., 601) (e.g., similar to the appearance of a user placing a physical sticker on the screen of the device), and does not move or otherwise interact with objects represented in the image data. In some embodiments, the selected sticker option displayed on the image data has the appearance of being placed on the display screen (e.g., similar to the appearance of a user placing a physical sticker on the screen of the device), but does move based on movement of objects displayed in the image data. For example, a sticker appears as being placed on the display, and interacts with objects represented in the image data (e.g., a person), however movement of the sticker is restricted to movement along x- and y-axes. In other words, the sticker appears to be applied to the screen of the device, but can be moved on the screen by objects represented in the image data (e.g., a person in the image data appears to touch the sticker or drag it across the screen). In some embodiments, the selected sticker option displayed on the image data has the appearance of being inserted into the image data as an interactive object that forms a portion of the image data. Providing the appearance of being inserted into the image data as an interactive object that forms a portion of the image data provides visual feedback that the selected sticker can act as an interactive object within the image. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In such embodiments, the sticker appears to move based on interactions with objects represented in the image data. For example, the sticker can appear as an object sitting on a person's shoulders. As the person moves, the sticker moves with the person's shoulders to maintain the appearance of sitting on the person's shoulders. This includes movement along x- and y-axes, as well as movement along a z-axis.

In some embodiments, while displaying the representation of the selected sticker option (e.g., 858-1, 858-2, 858-3, 858-4, 858-5, 858-6) on the image data in the camera display region (e.g., 820), the device (e.g., 600) detects lateral movement of the subject (e.g., 832) in the field of view of the one or more cameras (e.g., 602). In response to detecting the lateral movement of the subject in the field of view of the one or more cameras, the device moves the representation of the selected sticker option laterally in accordance with the movement of the subject in the field of view of the one or more cameras (e.g., without regard to a relationship of the sticker to the subject) (e.g., see helmet sticker 858-1 in FIGS. 8AV-8AY). Moving the representation of the selected sticker option laterally in accordance with lateral movement of the subject in the field of view of the one or more cameras provides visual feedback that the selected sticker can act as an interactive object within the image. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the representation of the selected sticker option (e.g., 858-1, 858-2, 858-3, 858-4, 858-5, 858-6) on the image data in the camera display region (e.g., 820), the device (e.g., 600) detects rotation of the subject (e.g., 832) in the field of view of the one or more cameras (e.g., 602) (e.g., rotation relative to an axis perpendicular to the display; e.g., the subject turning their head). In response to detecting the rotation of the subject in the field of view of the one or more cameras, the device performs one or more of the following steps. In accordance with a determination that the representation of the selected sticker option has (e.g., was placed with) a first relationship to the subject (e.g., the sticker was initially (or is currently) placed at a location on the display that corresponds to the subject; e.g., the sticker is placed on the representation of the subject's face or other designated area (e.g., shown with brackets (e.g., 890))), the device rotates the representation of the selected sticker option in accordance with a magnitude and direction of the rotation of the subject (e.g., the sticker rotates and turns to follow the pitch and yaw of the subject's face) (e.g., see glasses sticker 858-4 in FIGS. 8BH-8BM). In accordance with a determination that the representation of the selected sticker option does not have (e.g., was not placed with) the first relationship to the subject (e.g., the sticker was initially (or is currently) placed at a location on the display that was away from the subject; e.g., the sticker was placed outside the representation of the subject's face or other designated area), the device forgoes rotating the representation of the selected sticker option in accordance with the magnitude and direction of the rotation of the subject (e.g., see starfish sticker 858-5 and baseball sticker 858-6 in FIGS. 8BE-8BN). Selectively rotating the representation of the selected sticker option based on whether the representation of the selected sticker option has the first relationship to the subject provides visual feedback about the behavior of the selected sticker option and indicates that it can act as an interactive object within the image. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the representation of the selected sticker option (e.g., 858-1, 858-2, 858-3, 858-4, 858-5, 858-6) on the image data in the camera display region (e.g., 820), the device (e.g., 600) detects movement of the subject (e.g., 832) toward (or away from) the one or more cameras (e.g., 602). In response to detecting the movement of the subject toward (or away from) the one or more cameras, the device performs one or more of the following steps. In accordance with a determination that the representation of the selected sticker option has (e.g., was placed with) the first relationship to the subject (e.g., the sticker was initially (or is currently) placed at a location on the display that corresponds to the subject; e.g., the sticker was placed when the representation of the subject's face was present (e.g., detected) within the field of view of the camera), the device enlarges (or shrinks) the representation of the selected sticker option in accordance with a magnitude of movement of the subject toward (or away from) the one or more cameras. For example, the rabbit sticker 858-2 enlarges as shown in FIGS. 8AX and 8AY in response to the representation of the subject's shoulder moving towards the camera. In another example, starfish sticker 858-5 and baseball sticker 858-6 enlarge as the subject moves towards the camera in FIGS. 8BJ-8BK. In accordance with a determination that the representation of the selected sticker option does not have (e.g., was not placed with) the first relationship to the subject (e.g., the sticker was initially (or is currently) placed at a location on the display that was away from the subject; e.g., the sticker was placed when the representation of the subject's face was not present (e.g., not detected) within the field of view of the camera), the device forgoes enlarging the representation of the selected sticker option in accordance with the magnitude of movement of the subject toward (or away from) the one or more cameras (e.g., see helmet sticker 858-1 and heart sticker 858-3 in FIGS. 8AV-8AY). Selectively enlarging (or shrinking) the representation of the selected sticker option based on whether the representation of the selected sticker option has the first relationship to the subject provides visual feedback about the behavior of the selected sticker option and indicates that it can act as an interactive object within the image. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

While a subject is positioned within a field of view of the camera (e.g., 602) and a representation of the subject and a background (e.g., objects in the field of view of the camera other than the subject) are displayed in the camera display region (e.g., 820), the electronic device (e.g., 600) detects (910) a gesture directed to the first affordance. In some embodiments, the electronic device detects (e.g., recognizes) that the subject is positioned in the field of view.

In some embodiments, the camera user interface (e.g., 815), while displaying the capture affordance, further includes a camera display region (e.g., 820) including a representation of a live preview of a field of view of the camera (e.g., a stream of image data that represents what is in the field of view of the camera). In some embodiments, while a subject is positioned within the field of view of the camera (e.g., the electronic device detects/recognizes that the subject is positioned in the field of view) and a representation of the subject and a background (e.g., objects in the field of view of the camera other than the subject) are displayed in the camera display region, the electronic device (e.g., 600) displays a representation of a selected avatar on the representation of the subject in the camera display region (e.g., a displayed head or face portion of the user is replaced with (or overlaid by (e.g., opaquely, transparently, translucently)) a head of a virtual avatar that corresponds to the selected avatar). In some embodiments, while displaying the representation of the selected avatar on the representation of the subject in the camera display region, the electronic device receives a request to display an avatar selection region. In some embodiments, in response to receiving the request to display an avatar selection region, the electronic device ceases to display the capture affordance and displays (e.g., at a location in the camera user interface that was previously occupied by the capture affordance) an avatar selection region (e.g., avatar menu 828) having a plurality of avatar affordances. In some embodiments, in response to (or in conjunction with) the avatar selection region no longer being displayed, the capture affordance is displayed (e.g., re-displayed).

In some embodiments, the camera user interface (e.g., 815), while displaying the capture affordance (e.g., 821), further includes a camera display region (e.g., 820) including a representation of a live preview of a field of view of the camera (e.g., a stream of image data that represents what is in the field of view of the camera). In some embodiments, while a subject is positioned within the field of view of the camera and a representation of the subject and a background (e.g., objects in the field of view of the camera other than the subject) are displayed in the camera display region, the electronic device (e.g., 600) displays a representation of a selected avatar on the representation of the subject in the camera display region (e.g., a displayed head or face portion of the user is replaced with (or overlaid by (e.g., opaquely, transparently, translucently)) a head of a virtual avatar that corresponds to the selected avatar). In some embodiments, the electronic device detects (e.g., recognizes) that the subject is positioned in the field of view. In some embodiments, while displaying the representation of the selected avatar on the representation of the subject in the camera display region, the electronic device detects a change in pose (e.g., position and/or orientation) of the subject. In some embodiments, the change in pose is detected when the user moves their head or any facial features. In some embodiments, in response to detecting the change in pose of the subject, the electronic device changes an appearance of the displayed representation of the selected avatar option based on the detected change in pose of the subject while maintaining display of the background (e.g., as described with respect to method 900 and FIGS. 9A-9B). Changing the appearance of the displayed representation of the selected avatar option based on the detected change in pose of the subject while maintaining display of the background enables the user to quickly and easily recognize that movements of the avatar correspond to and/or are based on detected movements of the user. Providing additional control options enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In response to detecting the gesture directed to the first affordance, the electronic device (e.g., 600) activates the first camera display mode. Activating the first camera display mode includes displaying (914) an avatar selection region (e.g., 829) (e.g., including a selected one of a plurality of avatar options (e.g., affordances that represent different virtual avatars that can be selected to appear over the user's head in the camera display region (e.g., 820) of the camera user interface (e.g., 815)).

In some embodiments, the avatar selection region (e.g., 829) further includes an option for ceasing to display the representation of the selected avatar option on the representation of the subject in the camera display. In some embodiments, the electronic device (e.g., 600) receives a user input corresponding to selection of the option for ceasing to display the representation of the selected avatar option on the representation of the subject in the camera display region (e.g., 820). In some embodiments, in response to receiving a user input corresponding to selection of the option for ceasing to display the representation of the selected avatar option on the representation of the subject in the camera display region, the electronic device ceases to display the representation of the selected avatar option on the representation of the subject in the camera display region.

In some embodiments, the avatar selection region (e.g., 829) includes a null avatar option (e.g., 830-2). When the null avatar option is selected, no avatar is displayed on the representation of the subject in the camera display region (e.g., 820) (e.g., the device forgoes replacing image data of the user's head with a virtual avatar). In some embodiments, the avatar selection region includes a "cancel" affordance (e.g., an "x" icon located in the corner of the avatar selection region). When the cancel affordance is selected, the device ceases to display the avatar selection region and, optionally, ceases to display any selected avatar on the representation of the subject (e.g., the device foregoes replacing image data of the user's head with a virtual avatar).

In some embodiments, activating the first camera display mode (e.g., an avatar display mode in which image data of the user's head is replaced with a virtual avatar) further includes, prior to displaying the representation of the selected avatar option on the representation of the subject in the camera display region (e.g., 820), displaying (916) the representation of the subject in the camera display region without displaying a representation of the selected avatar option on the representation of the subject. In some embodiments, after entering the avatar display mode, the device initially displays the representation of the subject without an avatar (e.g., the device foregoes replacing image data of the user's head with a virtual avatar). In some embodiments, the avatar option that is initially selected when entering the avatar display mode corresponds to a null avatar option. When the null avatar option is selected, the device foregoes replacing image data of the subject's head with a virtual avatar.

Activating the first camera display mode includes displaying (918) a representation of the selected avatar option on the representation of the subject in the camera display region (e.g., 820) (e.g., a displayed head or face portion of the user is replaced with (or overlaid by (e.g., opaquely, transparently, translucently)) a head of a virtual avatar that corresponds to the selected avatar option). Displaying the representation of the selected avatar option on the representation of the subject in the camera display region enables the user to quickly and easily recognize that selected avatar option relates to representation of the subject. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, displaying a representation of the selected avatar option on the representation of the subject includes using depth information obtained using one or more depth cameras of the electronic device (e.g., 600).

In some embodiments, activating the first camera display mode further includes displaying the selected avatar option with a static appearance (e.g., the avatar appearance does not change based on detected changes in the user's face) in the avatar selection region (e.g., 829). In some embodiments, activating the first camera display mode further includes updating the selected avatar option to have a dynamic appearance that changes based on the detected change in pose of the subject (e.g., the avatar changes to mirror the detected changes in the user's face). In some embodiments, activating the first camera display mode further includes displaying an animation of the selected avatar having the dynamic appearance moving from the avatar selection region to the representation of the subject (e.g., a representation of the user's face) in the camera display region (e.g., 820). In some embodiments, the avatar continues to track changes in the user's face during the animated movement from the avatar selection region to the user's face in the camera display region.

In some embodiments, updating the selected avatar option to have a dynamic appearance that changes based on the detected change in pose of the subject includes initially displaying the avatar option having the dynamic appearance with an initial pose that corresponds (e.g., matches) a pose of the avatar option having the static appearance, prior to changing the appearance of the avatar option based on the detected change in pose of the subject.

While the first camera display mode is active, the electronic device (e.g., 600) detects (920) a change in pose (e.g., position and/or orientation of the subject). In some embodiments, the change in pose is detected when the user moves their head or any facial features.

In response to detecting the change in pose of the subject, the electronic device (e.g., 600) changes (922) an appearance of the displayed representation of the selected avatar option based on the detected change in pose of the subject while maintaining display of the background (e.g., 836) (e.g., the virtual avatar displayed on the user is responsive to detected changes in the user's head and face such that a change in the user's head or face effects a change in the displayed virtual avatar while still displaying the background). Changing the appearance of the displayed representation of the selected avatar option based on the detected change in pose of the subject while maintaining display of the background enables the user to quickly and easily recognize that movements of the avatar correspond to and/or are based on detected movements of the user. Providing additional control options enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the camera user interface includes one or more features/functions of the camera user interface described with respect to the embodiment shown in FIGS. 6A-6BQ and the FIGS. 9A-9B. For example, the camera user interface (e.g., 815) can include an effects mode affordance (e.g., 622).

In some embodiments, the electronic device (e.g., 600) detects a horizontal swipe gesture on the avatar selection region (e.g., 829). In some embodiments, in response to detecting the horizontal swipe gesture, the electronic device displays an avatar creation affordance associated with a function for adding a new avatar option to the plurality of avatar options. Displaying the avatar creation affordance associated with a function for adding a new avatar option to the plurality of avatar options in response to detecting a horizontal swipe gesture enables the user to quickly and easily access the avatar creation affordance from the avatar selection region. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, a horizontal swipe gesture on the avatar selection region scrolls the displayed avatar options to reveal an avatar creation affordance. In some embodiments, the avatar creation affordance can be selected to create a new avatar. When the new avatar is created, a new avatar option representing the created avatar is added to the plurality of avatar options (e.g., 830) in the avatar selection region.

In some embodiments, while the first camera display mode is active, the electronic device (e.g., 600) detects a swipe gesture on the avatar selection region (e.g., 829). In some embodiments, in response to detecting the swipe gesture on the avatar selection region, the electronic device changes an appearance of the displayed representation of the selected avatar option in the camera display region (e.g., 820) from a first appearance (e.g., an appearance based on the currently selected avatar option) to a second appearance (e.g., an appearance based on a different avatar option (e.g., a null avatar option or an avatar option corresponding to a different avatar, including avatars of different types (e.g., customizable, non-customizable))), where the second appearance corresponds to a different one of the plurality of avatar options (e.g., a different avatar option included in the avatar selection region). Changing the appearance of the displayed representation of the selected avatar option in response to detecting a swipe gesture on the avatar selection region enables the user to quickly and easily change the appearance of the selected avatar option. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, when the different one of the plurality of avatar options is a null avatar option (e.g., 830-2), the device ceases to display the representation of the avatar on the representation of the subject (e.g., the device forgoes replacing image data of the user's head with a virtual avatar). In some embodiments, when the different one of the plurality of avatar options is an avatar option of a different avatar character (including a customizable or non-customizable avatar character), the device replaces the selected avatar character with the different avatar character (e.g., the device replaces the representation of the avatar with a representation of a different avatar). In some embodiments, replacing the selected avatar character with the different character includes displaying an animation of the different avatar character moving to the center of the screen. In some embodiments, replacing the selected avatar character with the different avatar character includes displaying an animation of the different avatar character moving to the user's head. In some embodiments, replacing the selected avatar character with the different avatar character includes blurring the background (e.g., 836) while the selected avatar is being replaced. In some embodiments, the currently selected avatar option corresponds to an avatar of a first type (e.g., a customizable avatar), and the different avatar option corresponds to an avatar of a second type (e.g., a non-customizable avatar).

In some embodiments, while the first camera display mode is active, in response to a determination that the subject is no longer positioned in the field of view of the camera (e.g., face tracking is lost), the electronic device (e.g., 600) displays an animation of the representation of the selected avatar option moving to a center location in the camera display region (e.g., 820). Displaying an animation of the representation of the selected avatar option moving to a center location in the camera display region in response to a determination that the subject is no longer positioned in the field of view of the camera provides visual feedback to the user that the user is no longer being detected by the camera. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, when the user is no longer detected in the field of view of the camera, the avatar moves to the center of the camera display region. In some embodiments, the background is blurred when the user is no longer detected in the field-of-view of the camera.

In some embodiments, while the first camera display mode is active, in response to a determination that the subject is no longer positioned in the field of view of the camera (e.g., face tracking is lost), the electronic device (e.g., 600) modifies the visual appearance of the background (e.g., 836) displayed in the camera display region (e.g., 820) (e.g., blurring the background, desaturating the background).

In some embodiments, while the first camera display mode is active and the representation of the selected avatar option (e.g., a representation of a customizable avatar option selected from the avatar selection region) is displayed on the representation of the subject in the camera display region (e.g., 820) (e.g., image data of the user's head is replaced with the customizable avatar), the electronic device (e.g., 600) detects a touch gesture (e.g., a tap gesture) on the selected avatar option in the avatar selection region (e.g., 829). In some embodiments, in response to detecting the touch gesture, the electronic device displays an avatar editing user interface (e.g., a user interface for editing one or more features of the selected avatar option (e.g., a selected customizable avatar) having a plurality of options (e.g., edit affordances that are selectable to modify various features of the customizable avatar) for editing the selected avatar option. Displaying an avatar editing user interface in response to detecting a touch gesture on the selected avatar option in the avatar selection region enables a user to quickly and easily access the avatar editing user interface to edit the avatar. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the camera user interface (e.g., 815) further includes a second affordance (e.g., 824-2, an affordance that corresponds to a function for displaying stickers) associated with a second camera display mode (e.g., a mode in which virtual effects (e.g., stickers) are applied to the image data). In some embodiments, while the subject is positioned within the field of view of the camera (e.g., 602) and the representation of the subject and the background (e.g., 836) are displayed in the camera display region (e.g., 820), the electronic device (e.g., 600) detects a gesture directed to the second affordance. In some embodiments, in response to detecting the gesture directed to the second affordance, the electronic device activates the second camera display mode, where activating the second camera display mode includes displaying a visual effects selection region including a plurality of graphical objects (e.g., stickers).

In some embodiments, while the second camera display mode is active, the electronic device (e.g., 600) detects a selection of one of the plurality of graphical objects (e.g., a sticker) in the visual effects selection region (e.g., 824). In some embodiments, in response to detecting the selection, the electronic device displays a representation of the selected graphical object in the camera display region (e.g., 820). In some embodiments, the selected sticker is displayed in the camera display region during a live camera preview (e.g., 820-1). In some embodiments, displaying the sticker in the live camera preview includes immediately displaying the sticker at a default location (e.g., the center of the screen) of the camera display region. In some embodiments, displaying the sticker in the live camera preview includes displaying an animation of the sticker moving from the visual effects selection region to a location on the camera display region. In some embodiments, this animation is determined based on a drag gesture of the user selection of the sticker (e.g., a gesture in which the user touches the sticker and drags it to a location on the camera display region).

In some embodiments, the representation of image data captured via the camera (e.g., 602) is a media item (e.g., 820-2, a still image or recorded video). In some embodiments, the camera user interface (e.g., 815) further includes a third affordance (e.g., an affordance that corresponds to a function for displaying stickers) associated with a third camera display mode (e.g., a mode in which virtual effects (e.g., stickers) are applied to a photograph or recorded video). In some embodiments, the electronic device (e.g., 600) detects a gesture directed to the third affordance. In some embodiments, in response to detecting the gesture directed to the third affordance, the electronic device activates the third camera display mode, where activating the third camera display mode includes displaying a visual effects selection region including a plurality of graphical objects (e.g., stickers).

In some embodiments, while the third camera display mode is active, the electronic device (e.g., 600) detects a selection of one of the plurality of graphical objects (e.g., a sticker) in the visual effects selection region. In some embodiments, in response to detecting the selection, the electronic device displays a representation of the selected graphical object on the media item (e.g., 820-2) in the camera display region (e.g., 820). In some embodiments, the selected sticker is displayed in the camera display region when viewing a photograph or recorded video. In some embodiments, displaying the sticker on the photograph or recorded video includes immediately displaying the sticker at a default location (e.g., the center of the screen) of the camera display region. In some embodiments, displaying the sticker in the photograph or recorded video includes displaying an animation of the sticker moving from the visual effects selection region to a location on the camera display region. In some embodiments, this animation is determined based on a drag gesture of the user selection of the sticker (e.g., a gesture in which the user touches the sticker and drags it to a location on the camera display region).

Note that details of the processes described above with respect to method 900 (e.g., FIGS. 9A and 9B) are also applicable in an analogous manner to the methods described above and below. For example, method 700 optionally includes one or more of the characteristics of the various methods described above with reference to method 900. For example, visual effects such as stickers and virtual avatars are displayed in image data in a messaging application user interface. For another example, method 1100 optionally includes one or more of the characteristics of the various methods described above with reference to method 900. For example, visual effects such as stickers and virtual avatars are displayed in image data in a media user interface. For another example, method 1300 optionally includes one or more of the characteristics of the various methods described above with reference to method 900. For example, visual effects such as stickers and virtual avatars are displayed in image data in a user interface for a live video communication session. For another example, method 1500 optionally includes one or more of the characteristics of the various methods described above with reference to method 900. For example, visual effects such as stickers and virtual avatars are displayed in image data for a camera user interface. For brevity, these details are not repeated below.

FIGS. 10A-10AL illustrate exemplary user interfaces for displaying visual effects in a media item viewing mode, in accordance with some embodiments. The user interfaces in these figures are used to illustrate the processes described below, including the processes in FIGS. 11A-11B.

In FIG. 10A, device 600 shows home screen 1000 and detects input 1001 on media viewer application affordance 1002.

Figure 10B:
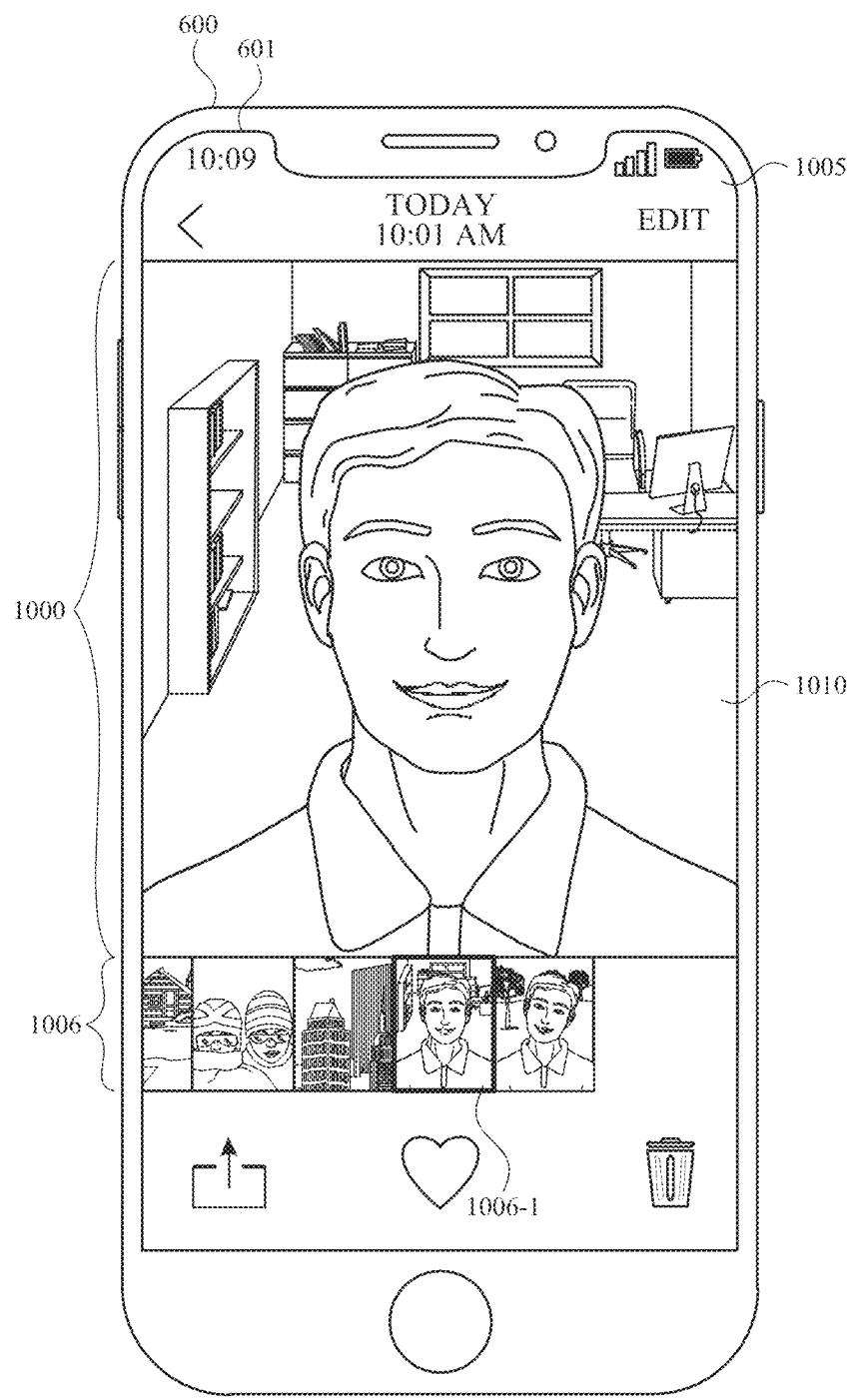

In FIG. 10B, in response to detecting input 1001, device 600 launches a media view application associated with media viewer application affordance 1002 and displays media user interface 1005. Media user interface 1005 includes a series of stored media items 1006 and a media display region 1008 for displaying a media item corresponding a selected one of stored media items 1006. In FIG. 10B, media display region 1008 shows media item 1010 corresponding to selected stored media item 1006-1.

Media item 1010 is an image that does not include encoded depth data (e.g., it was captured by a camera that does not encode depth data into captured media items (e.g., a camera other than camera 602)). Thus, media item 1010 does not include depth data, which, as discussed herein, is used to enable certain visual effects in an image.

Figure 10C:
Figure 10D:

In FIG. 10C, device 600 detects input 1011 on edit affordance 1012. In response, device 600 displays, in FIG. 10D, edit options display region 1014. Edit option display region includes effects affordance 1016 (similar to effects affordances 622, 822), media edit affordance 1018, and markup affordance 1020.

Figure 10E:
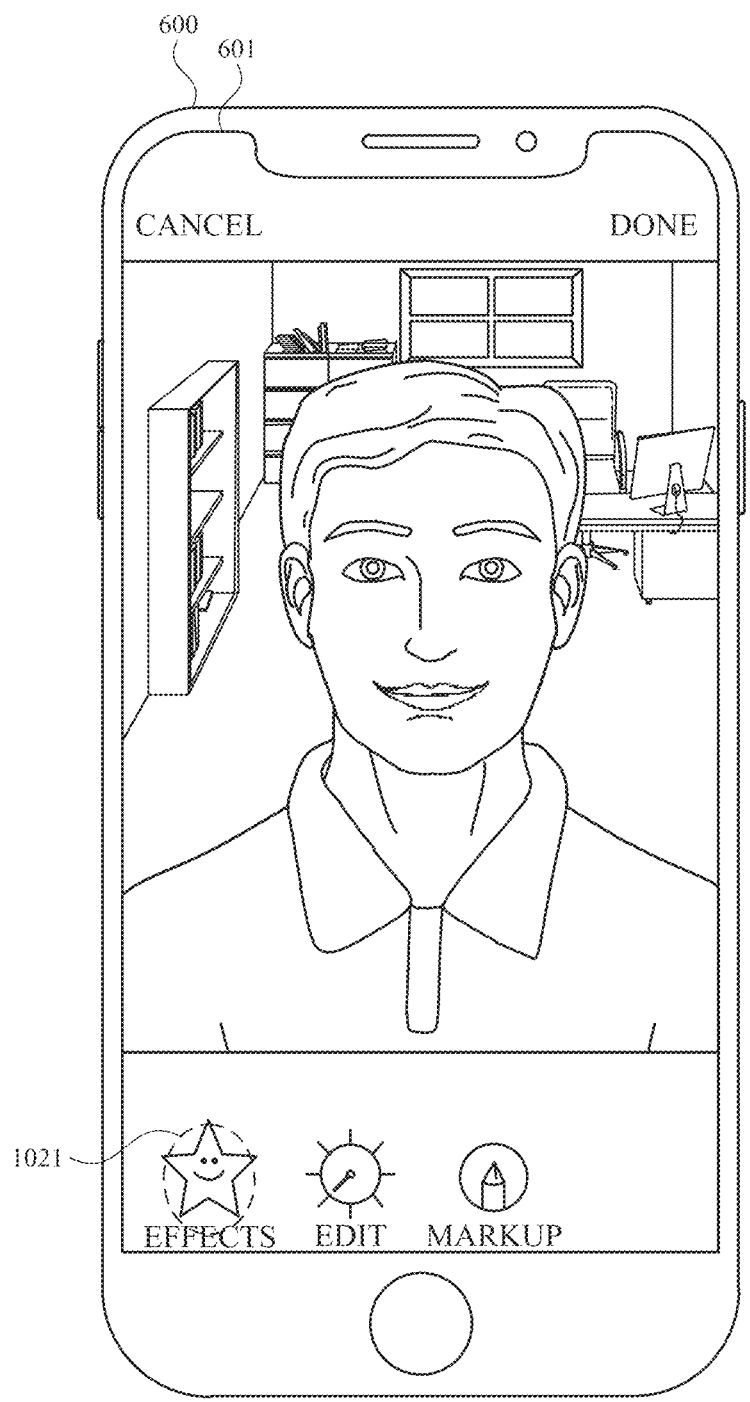

In FIG. 10E, device 600 detects input 1021 on effects affordance 1016, to enable a visual effects mode in which any visual effects associated with the displayed media item (e.g., media item 1010) are displayed. In the embodiment illustrated in FIG. 10E, media item 1010 does not include visual effects; in particular, image 1010 does note include depth-based visual effects because media item 1010 does not include depth data.

Figure 10F:
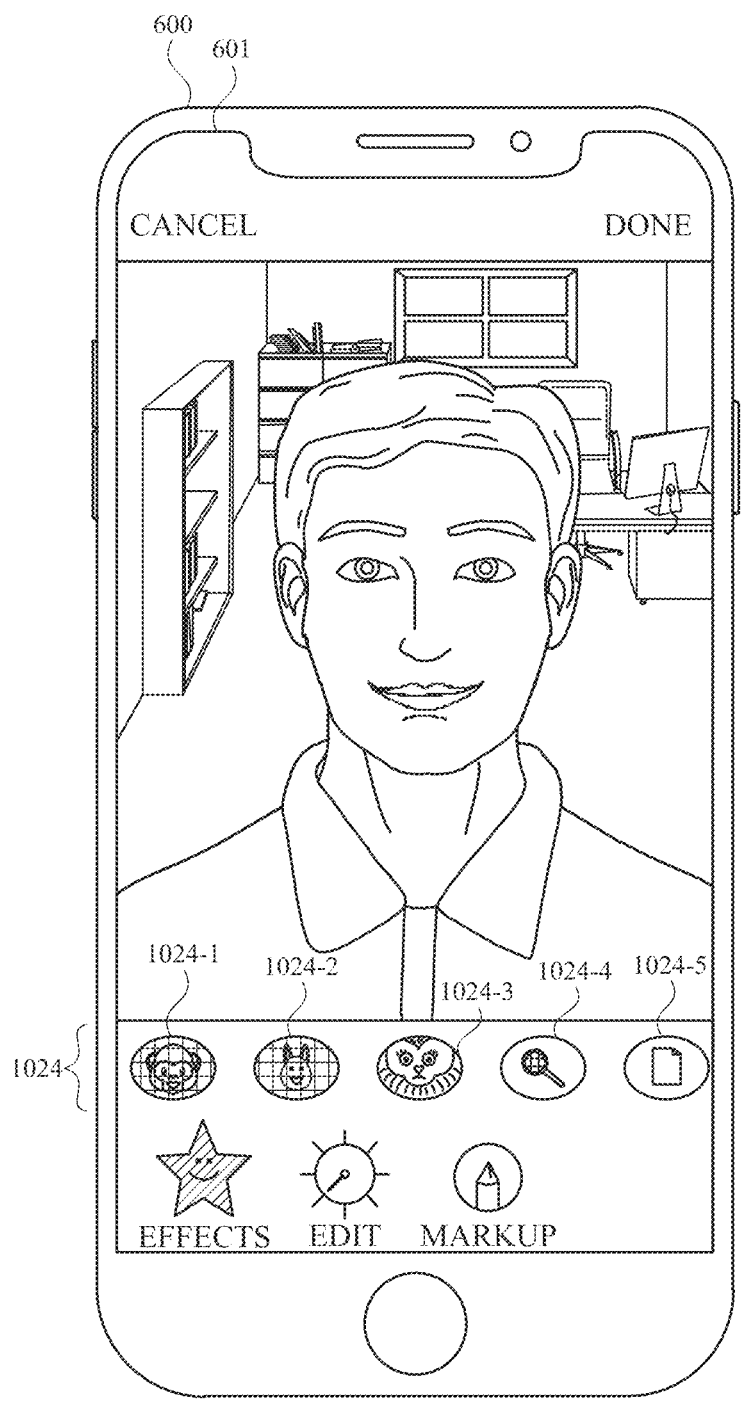

In FIG. 10F, in response to detecting input 1021 activating effects affordance 1016, device 600 highlights effects affordance 1016 and expands edit option display region 1014 to display effects option affordances 1024. In the embodiment illustrated in FIG. 10F, because media item 1010 does not include depth data to enable visual effects, avatar effects affordance 1024-1 and sticker effects affordance 1024-2 are shown as not selectable, whereas remaining visual effects option affordances 1024-3, 1024-4, and 1024-5 are selectable. In some embodiments, when the media item does not include depth data to enable visual effects, avatar effects affordance 1024-1 and sticker effects affordance 1024-2 are not displayed.

Because media item 1010 does not include depth data to enable depth-based visual effects, no depth-based visual effects are displayed in media item 1010 when effects affordance 1016 is selected. Thus, media item 1010 remains unchanged in FIG. 10F.

Figure 10G:
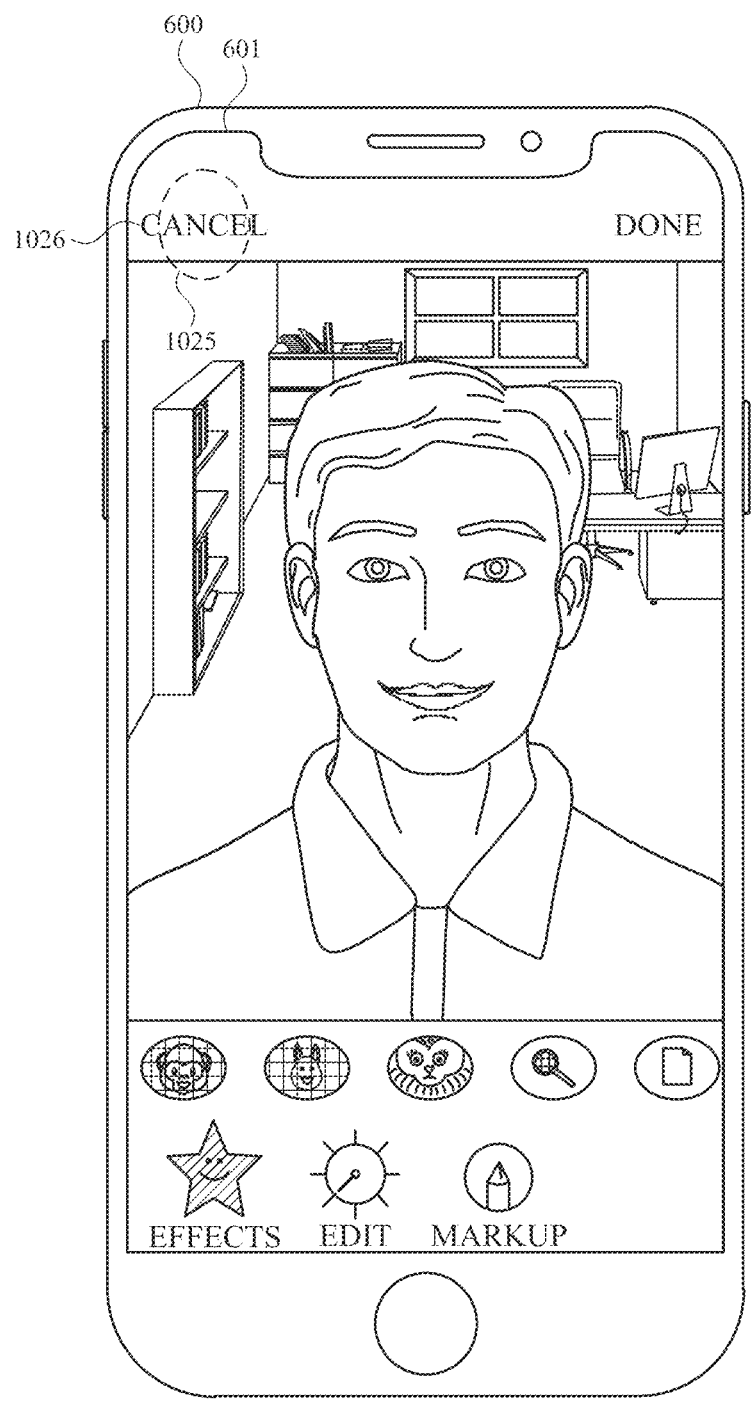
Figure 10H:
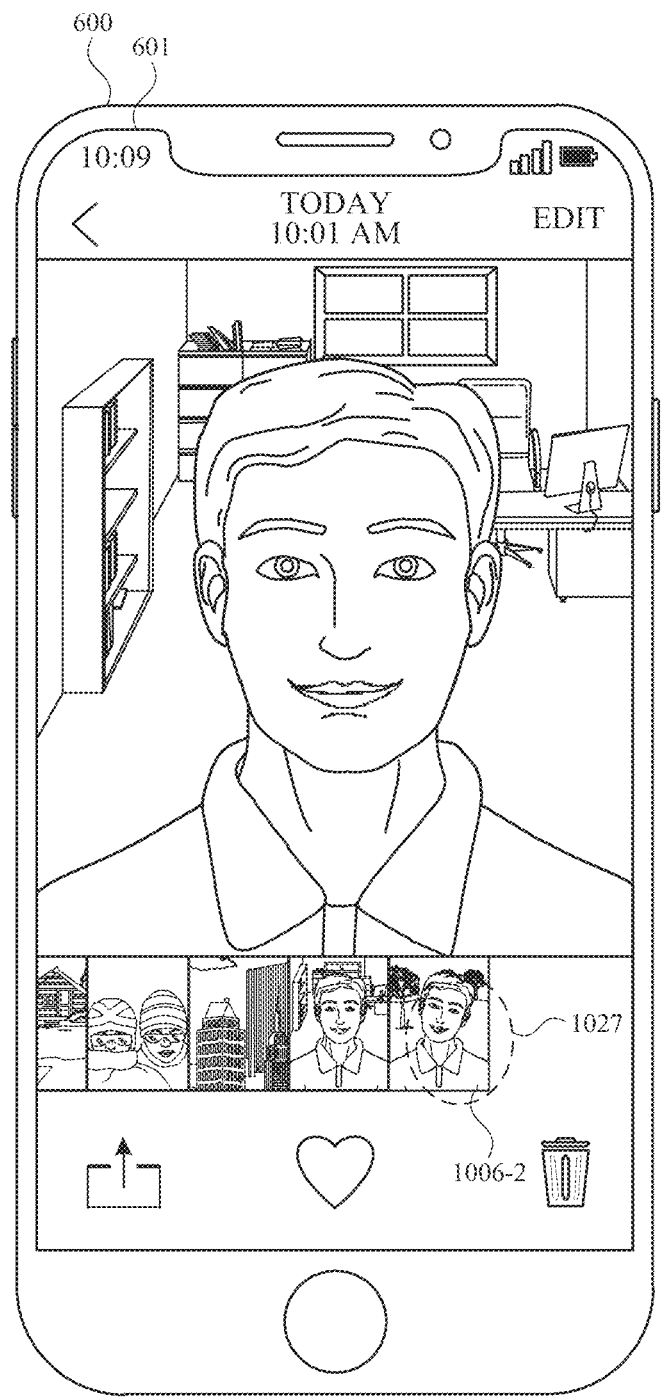

In FIG. 10G, device 600 detects input 1025 on cancel affordance 1026, and returns to the user interface shown in FIG. 10H.

In FIG. 10H, device 600 detects input 1027 on stored media item 1006-2 to select stored media item 1006-2.

Figure 10I:
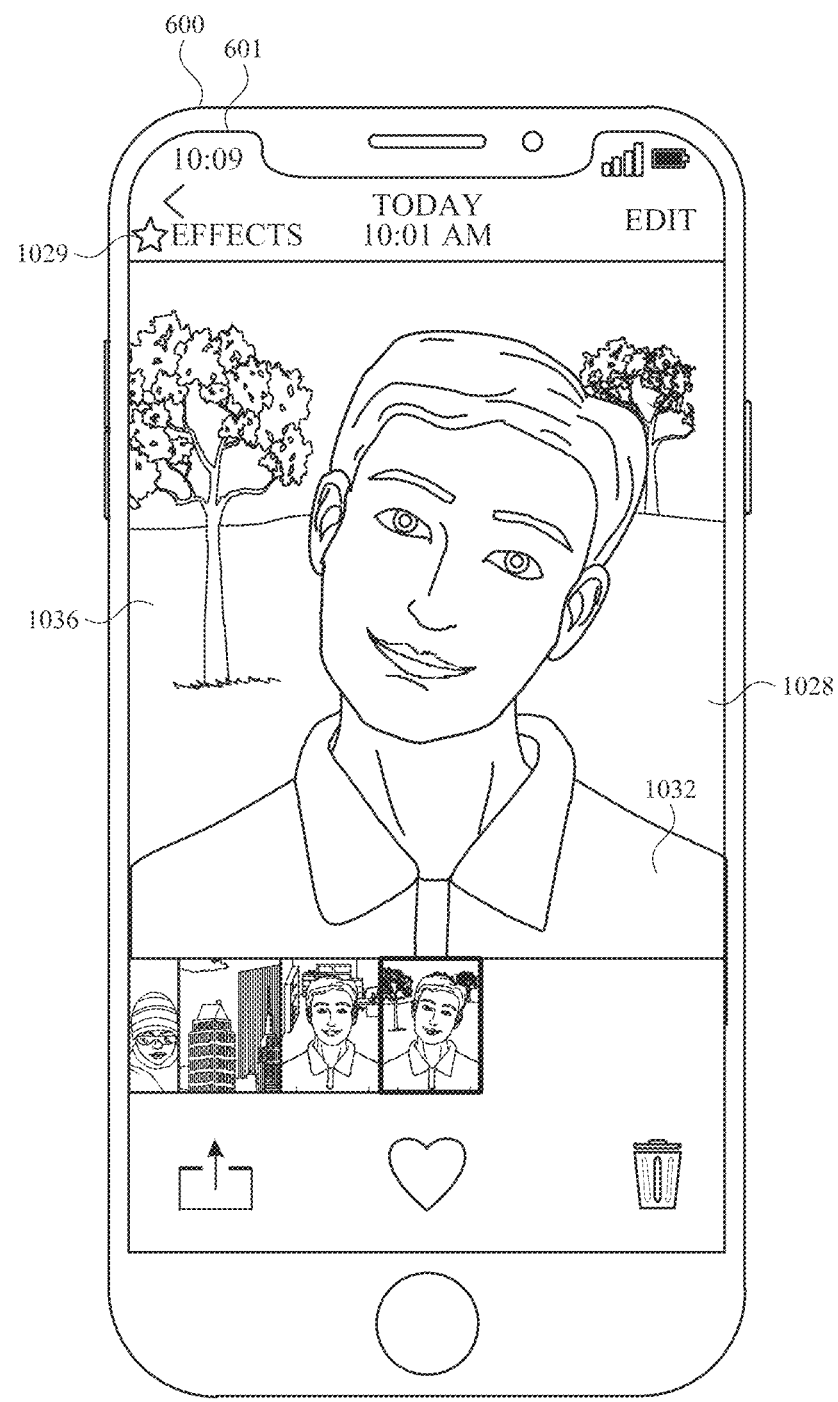

In FIG. 10I, device 600 displays media item 1028 in media display region 1008. Media item 1028 corresponds to selected stored media item 1006-2 showing a subject 1032 and background 1036. Media item 1028 is an image captured by a camera (e.g., camera 602) that encodes depth data into captured media items. As explained herein, the depth data encoded into media items enables display of visual effects, particularly visual effects having a depth component.

In FIG. 10I, visual effects are not displayed in media item 1028, because effects mode is not enabled for media item 1028. However, device 600 displays effects icon 1029, to indicate that media item 1028 contains depth data, and is capable of displaying visual effects.

Figure 10J:
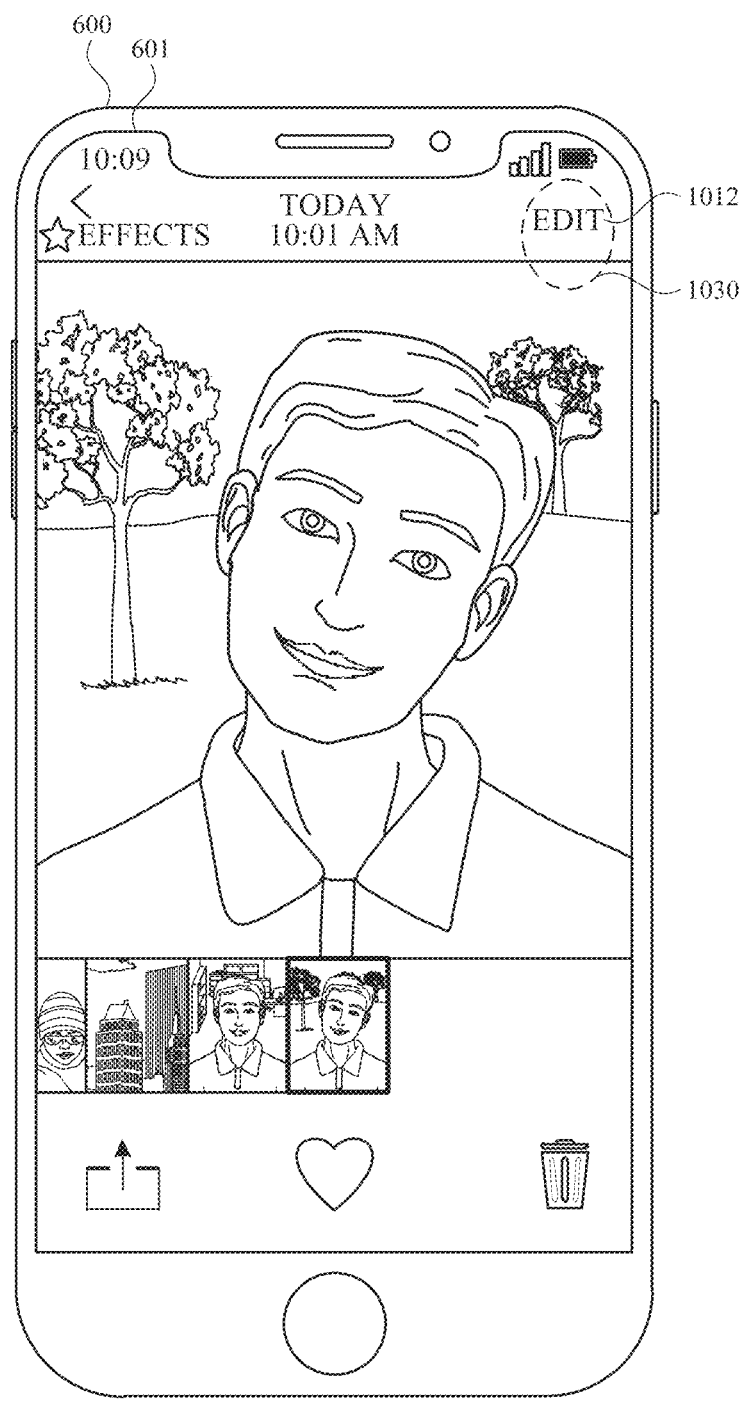
Figure 10K:

In FIG. 10J, device detects input 1030 on edit affordance 1012 and displays, in FIG. 10K, edit option display region 1014 showing effects affordance 1016 in a non-highlighted state to indicate that visual effects are not enabled for display in media item 1028.

Figure 10L:
Figure 10M:
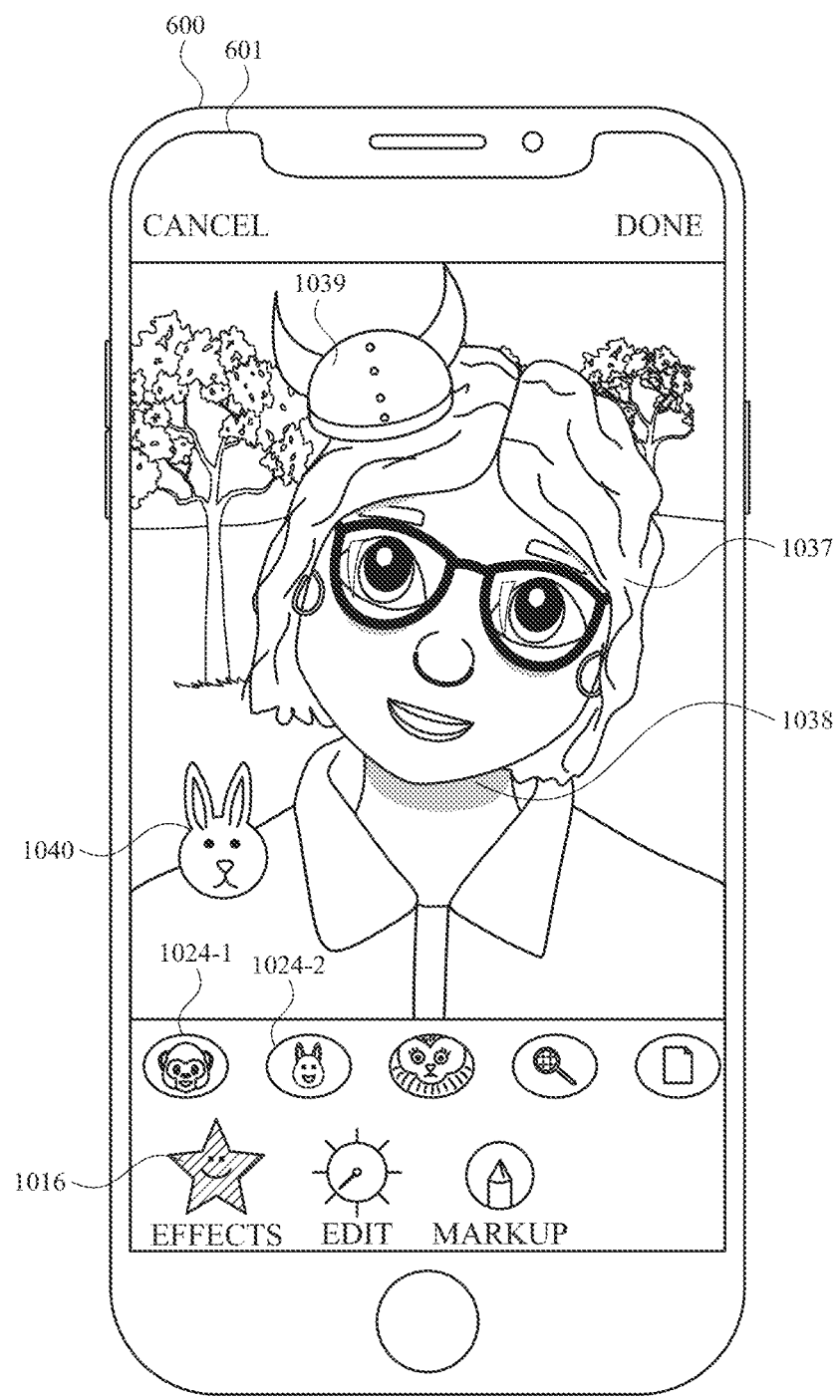

In FIG. 10L, device 600 detects input 1033 on effects affordance 1016 to enable visual effects mode. When visual effects mode is enabled, as shown in FIG. 10M, device 600 highlights effects affordance 1016 and expands edit option display region 1014 to display effects option affordances 1024. In the embodiment illustrated in FIG. 10M, because media item 1028 includes depth data to enable depth-based visual effects, avatar effects affordance 1024-1 and sticker effects affordance 1024-2 are shown as selectable, and visual effects are displayed in media item 1028. In the embodiment illustrated in FIG. 10M, the displayed visual effects include customizable avatar 1037, shadow 1038 displayed below avatar 1037 on the subject's neck, helmet sticker 1039, and rabbit sticker 1040.

In some embodiments, device 600 modifies avatar 1037 based on detected changes in a user's face positioned in the field-of-view of camera 602, which is encoded in the depth data of media item 1028. Thus, although media item 1028 is described in this embodiment as a still image, it should be appreciated that media item 1028 is not limited to a still image and may include other media items such as a recorded video, including a recorded video having depth data. Similarly, device 600 can modify the position of stickers applied to media item 1028 based on detected changes in the position of objects in the media item, which is encoded in the depth data.

Visual effects, including depth-based visual effects, can be applied to media item 1028 and edited in accordance with the embodiments discussed herein. For example, avatar effects affordance 1024-1 can be selected to remove, modify, and/or switch the selected avatar (e.g., avatar 1037) in accordance with the various embodiments disclosed herein. Additionally, sticker effects affordance 1024-2 can be selected to remove, modify, and/or add stickers to media item 1028 in accordance with the various embodiments disclosed herein.

Figure 10N:
Figure 10O:
Figure 10P:

FIGS. 10N-10P illustrate device 600 adding heart sticker 1042 to media item 1028. These processes are discussed in greater detail above with respect to FIGS. 6U-6AD, 8AH-8AK, and 8AR-8AY. For the sake of brevity, details of these processes are not repeated here.

Figure 10Q:
Figure 10R:
Figure 10S:
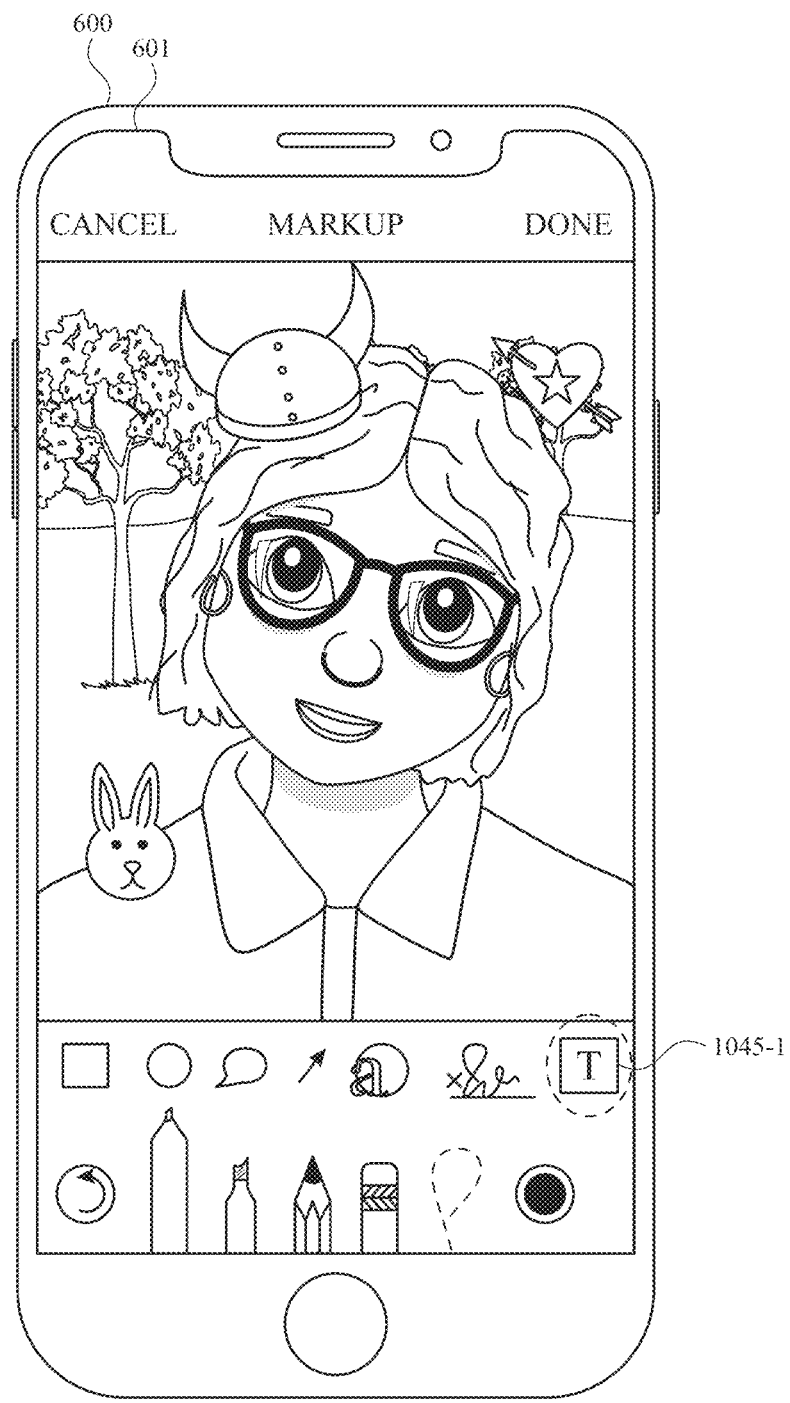
Figure 10T:
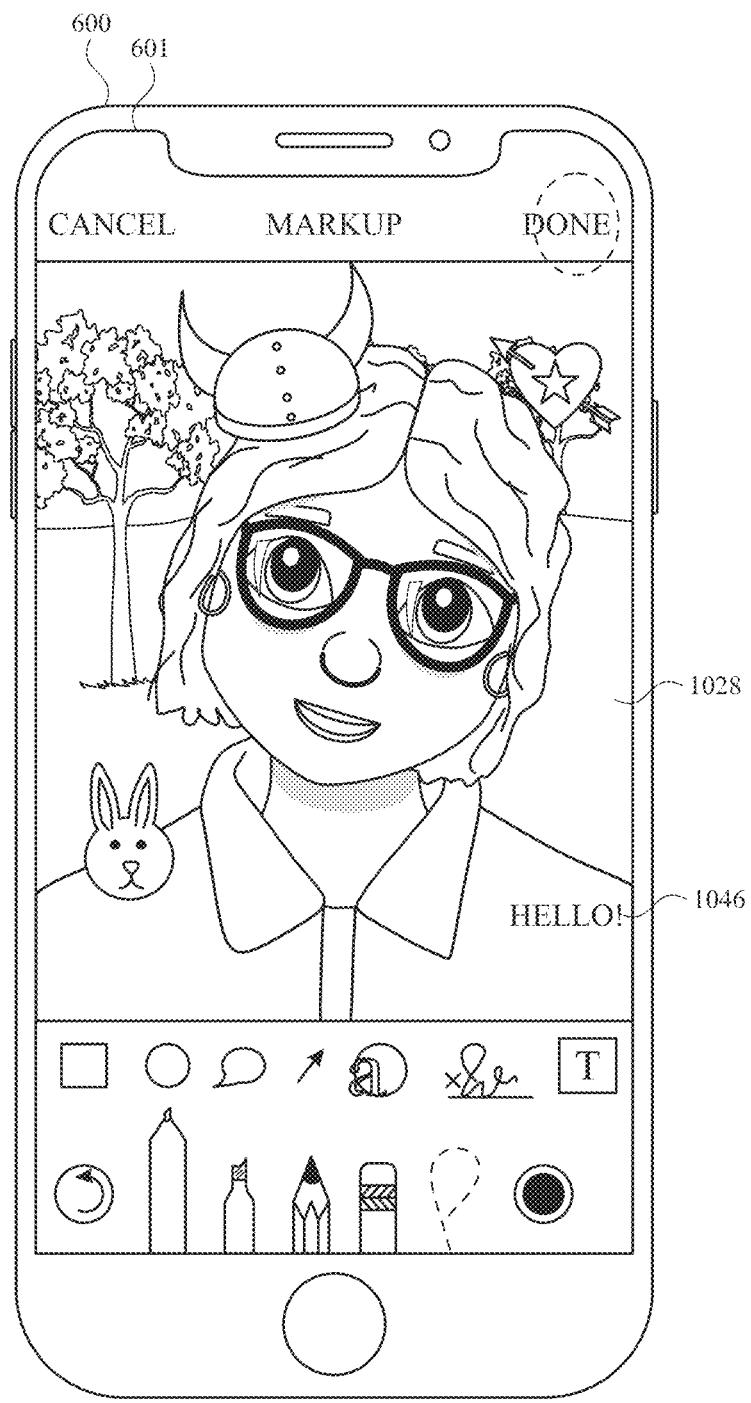

In FIG. 10Q, device 600 detects input 1043 on markup affordance 1020. In FIG. 10R, device 600 replaces the displayed edit option display region 1014 with markup option menu 1044 including various selectable markup options 1045 for adding markup effects to media item 1028. FIGS. 10S-10T show a process for adding text 1046 to media item 1028 by selecting text affordance 1045-1.

Figure 10U:
Figure 10V:
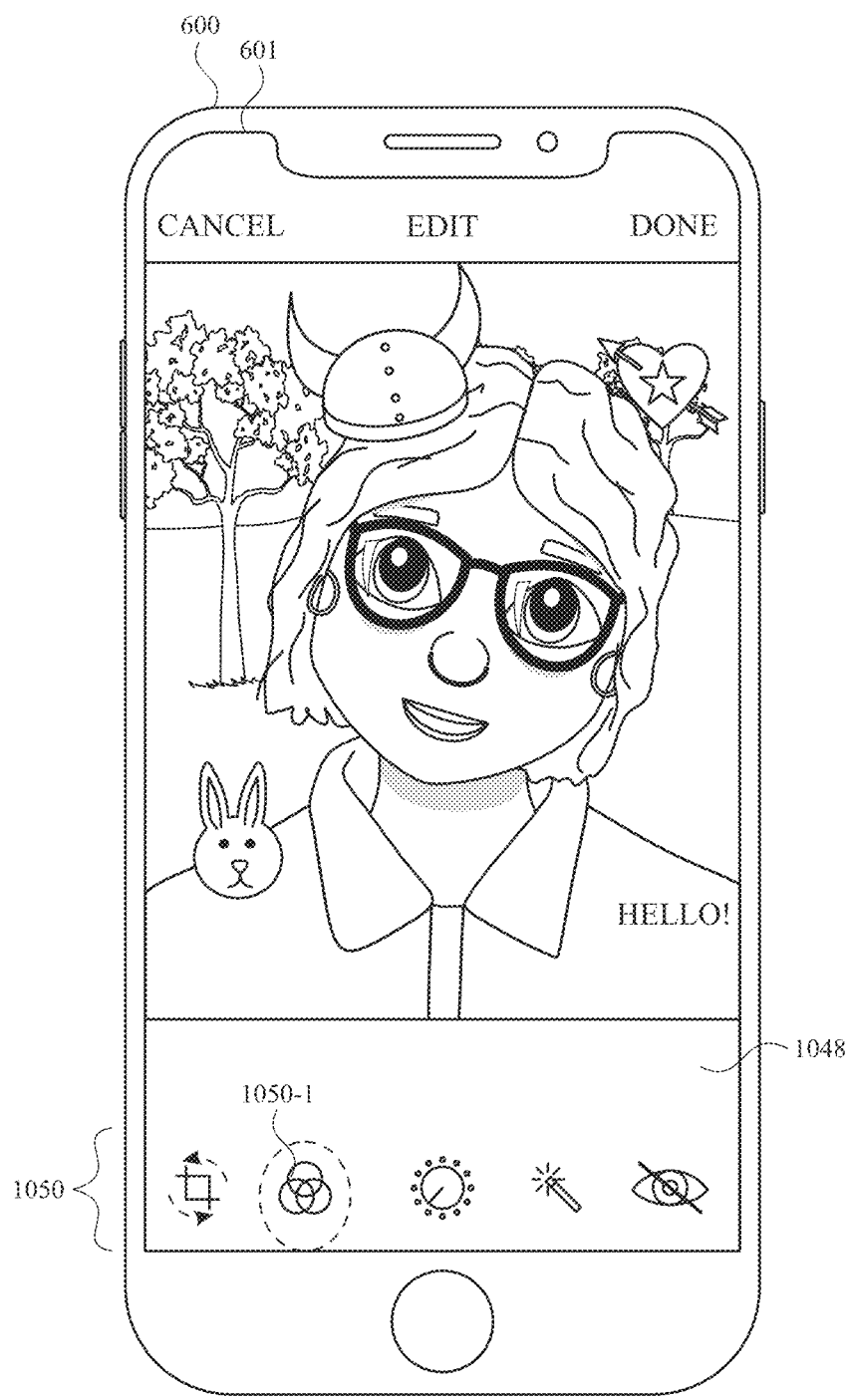
Figure 10W:
Figure 10X:
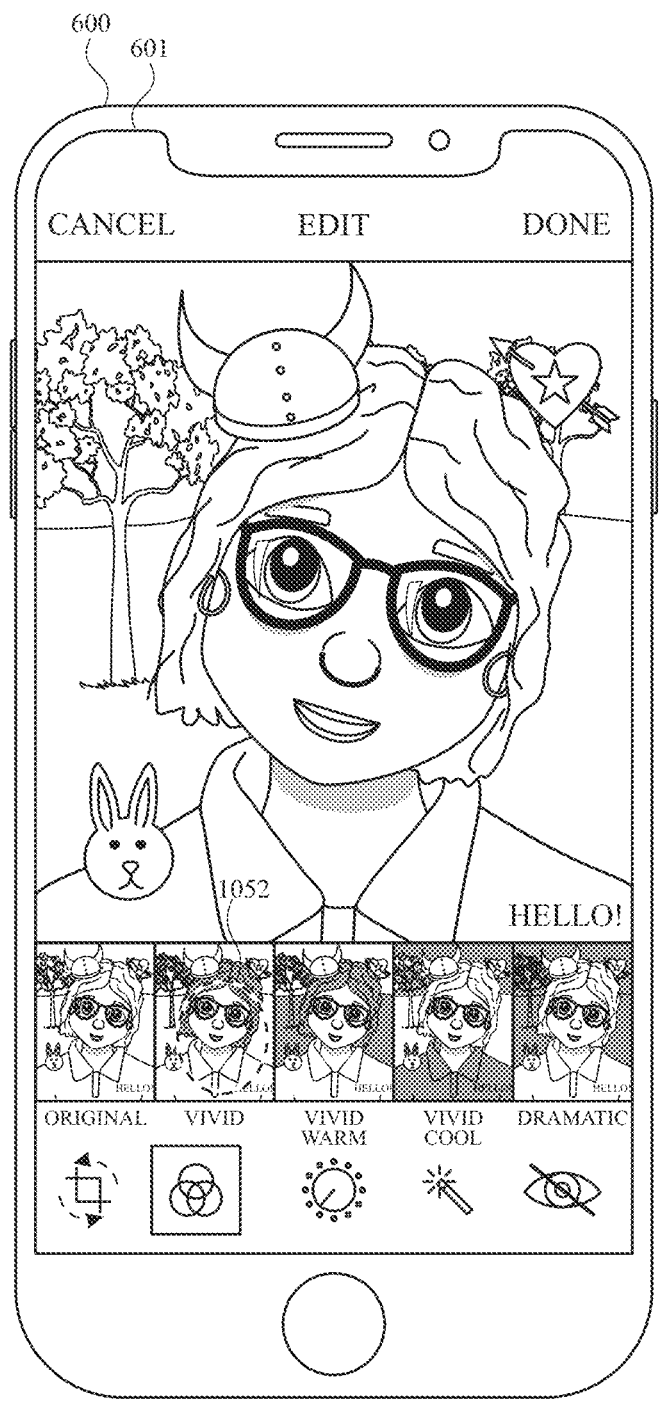
Figure 10Y:

In FIG. 10U, device 600 detects input 1047 on edit affordance 1012. In FIG. 10V, device 600 replaces the displayed edit option display region 1014 with image edit menu 1048 including various image edit affordances 1050. FIGS. 10V-10Y show a process for editing media item 1028 to apply a vivid color filter by selecting filter affordance 1050-1, and then selecting vivid filter option 1052. The vivid color filter applies changes to both the background 1036 in media item 1028 as well as the applied visual effects (e.g., the hair on avatar 1037). In some embodiments, the filter changes an appearance of the avatar and the representation of the field of view of the one or more cameras in a similar manner to increase the similarity between the avatar and the representation of the field of view of the one or more cameras (e.g., applying a comic book filter, a sketch drawing filter, a black and white filter, a greyscale filter, or the like). In some embodiments, the avatar has a cartoon-like appearance that does not match with the real world that is in the field of view of the one or more cameras, by applying a filter that changes both the appearance of the avatar and the representation of the field of view of the one or more cameras, the appearance of the avatar is unified with the rest of the representation of the field of view of the one or more cameras. In some embodiments, the filter is a filter that reduces a realism of the representation of the field of view of the one or more cameras (e.g., a sketch filter or a comic book filter). In some embodiments the filter is a filter that reduces a 3D effect (e.g., flattens) both the appearance of the avatar and the appearance of the representation of the field of view of the one or more cameras.

Figure 10Z:
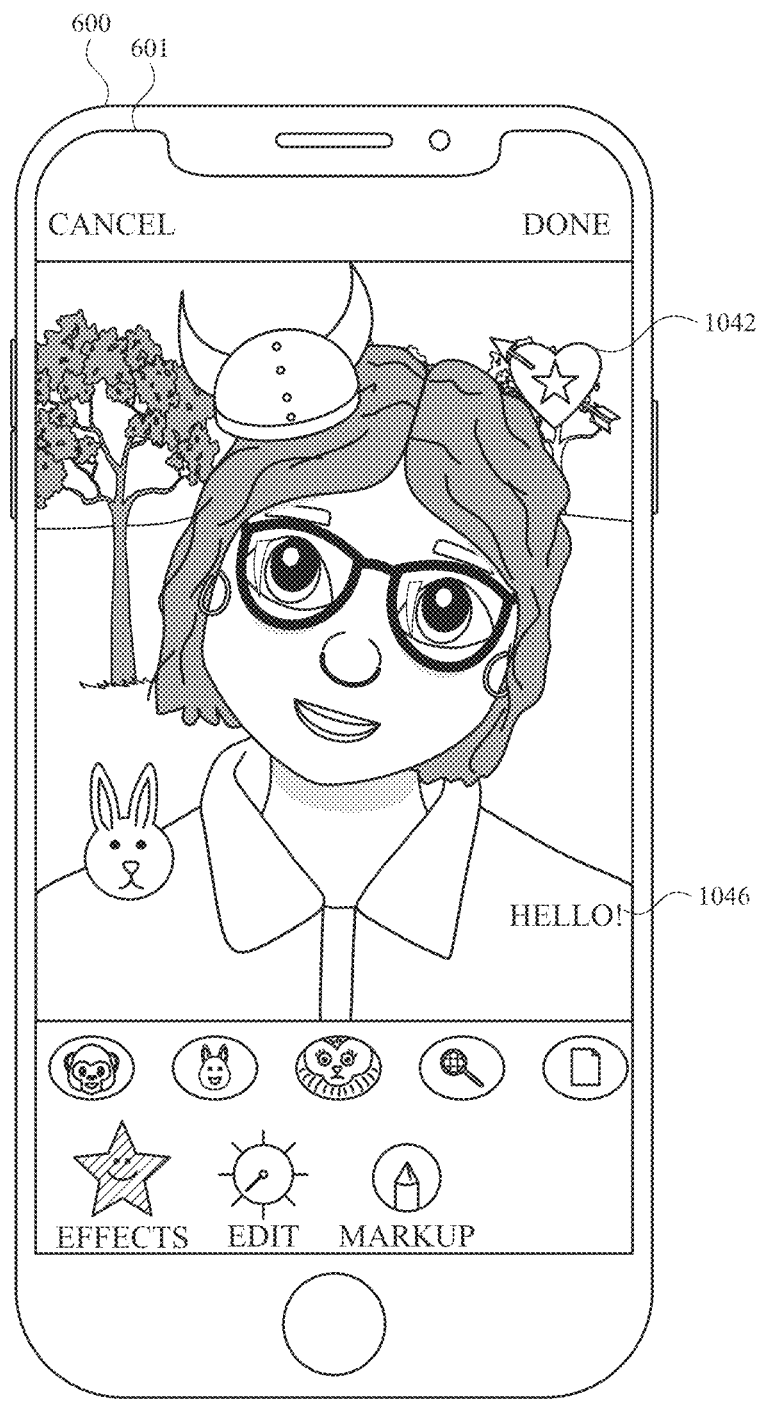
Figure 10A:
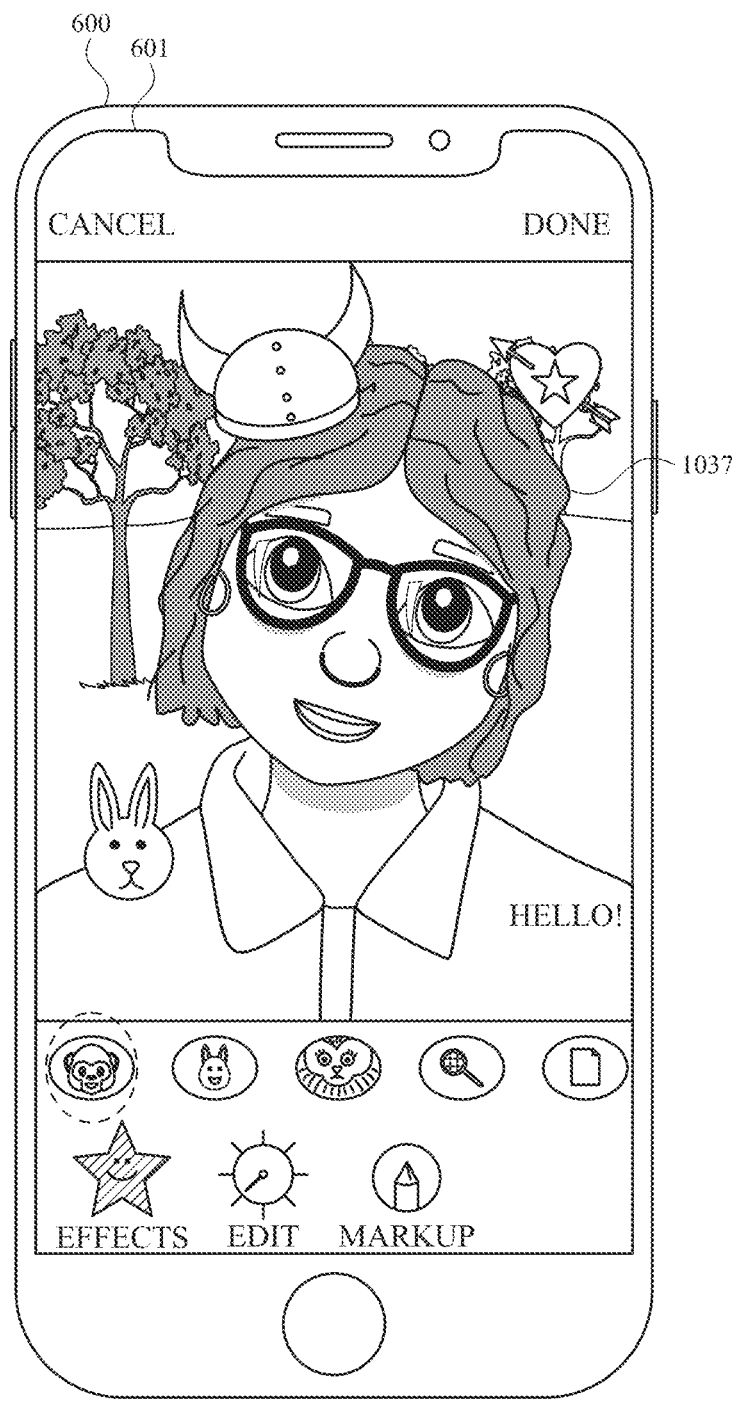
Figure 10A:
Figure 10A:
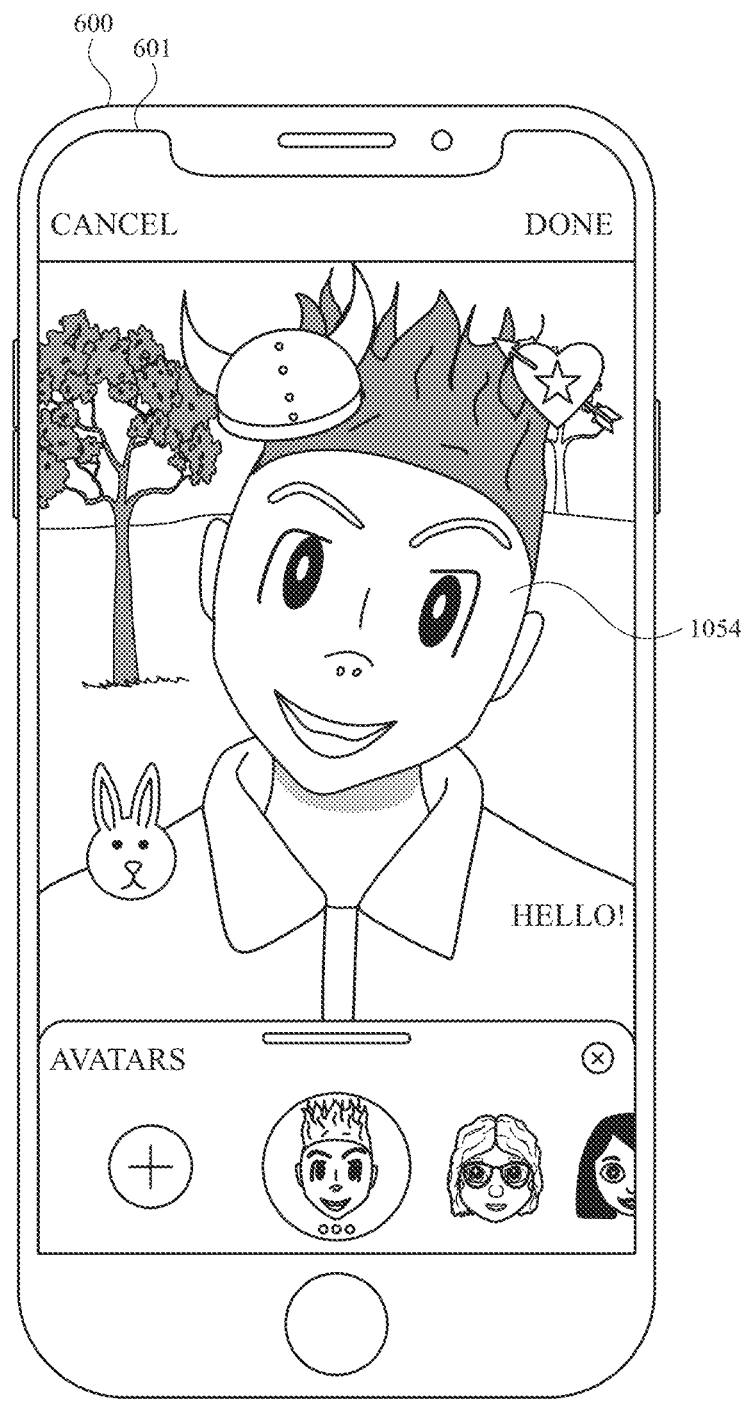
Figure 10A:
Figure 10A:
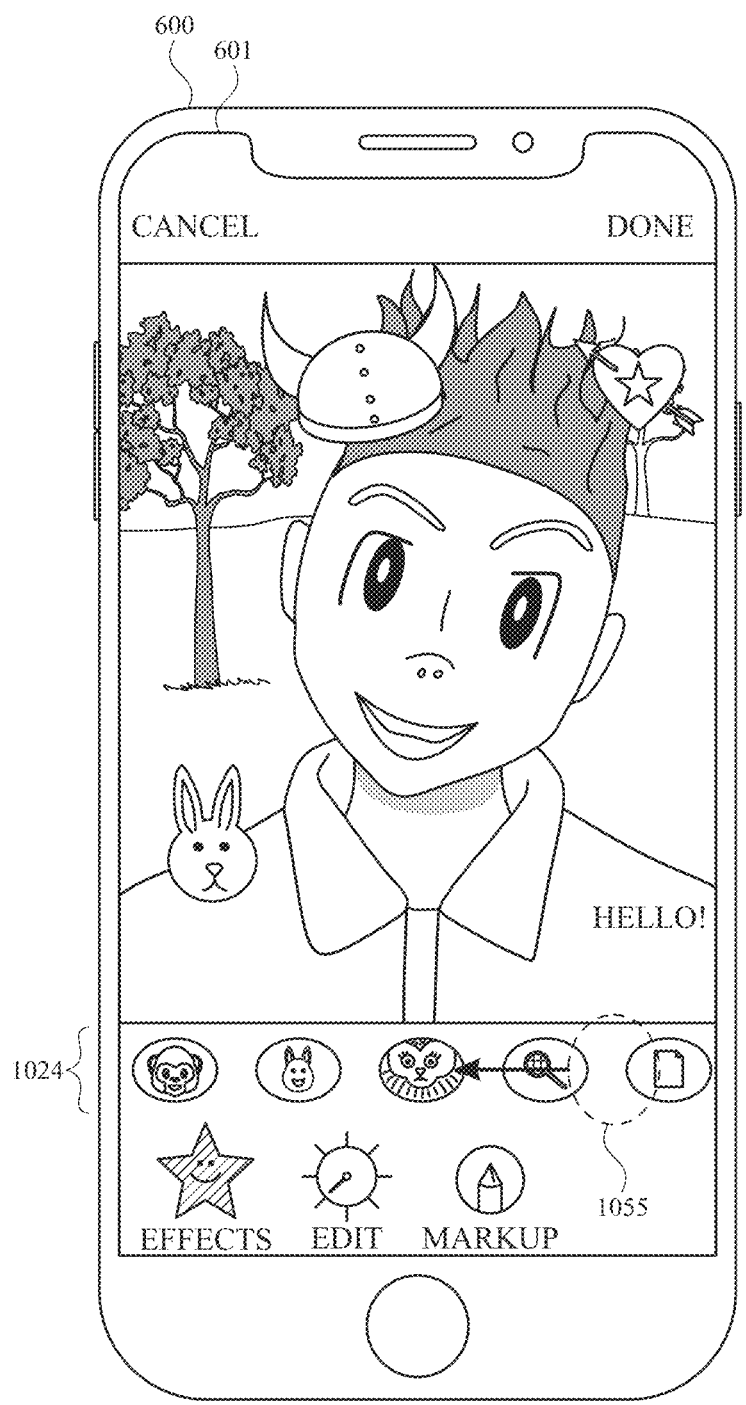
Figure 10A:
Figure 10A:
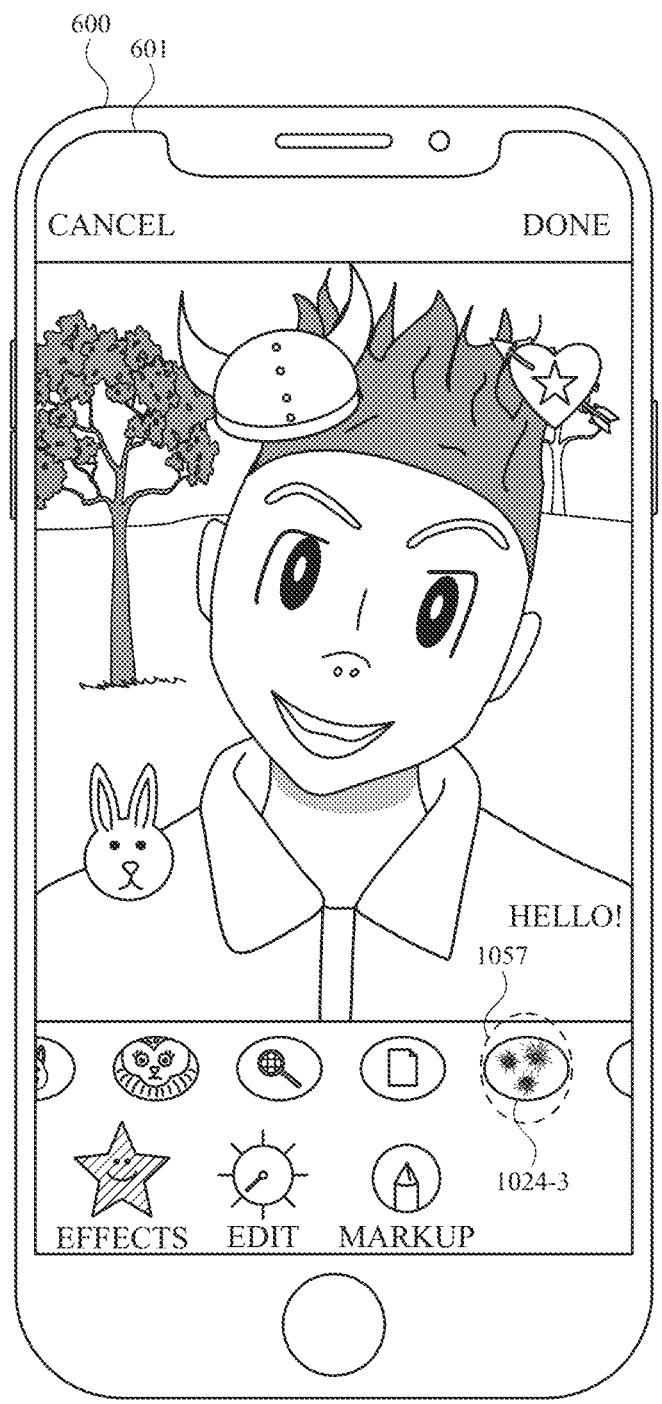
Figure 10A:
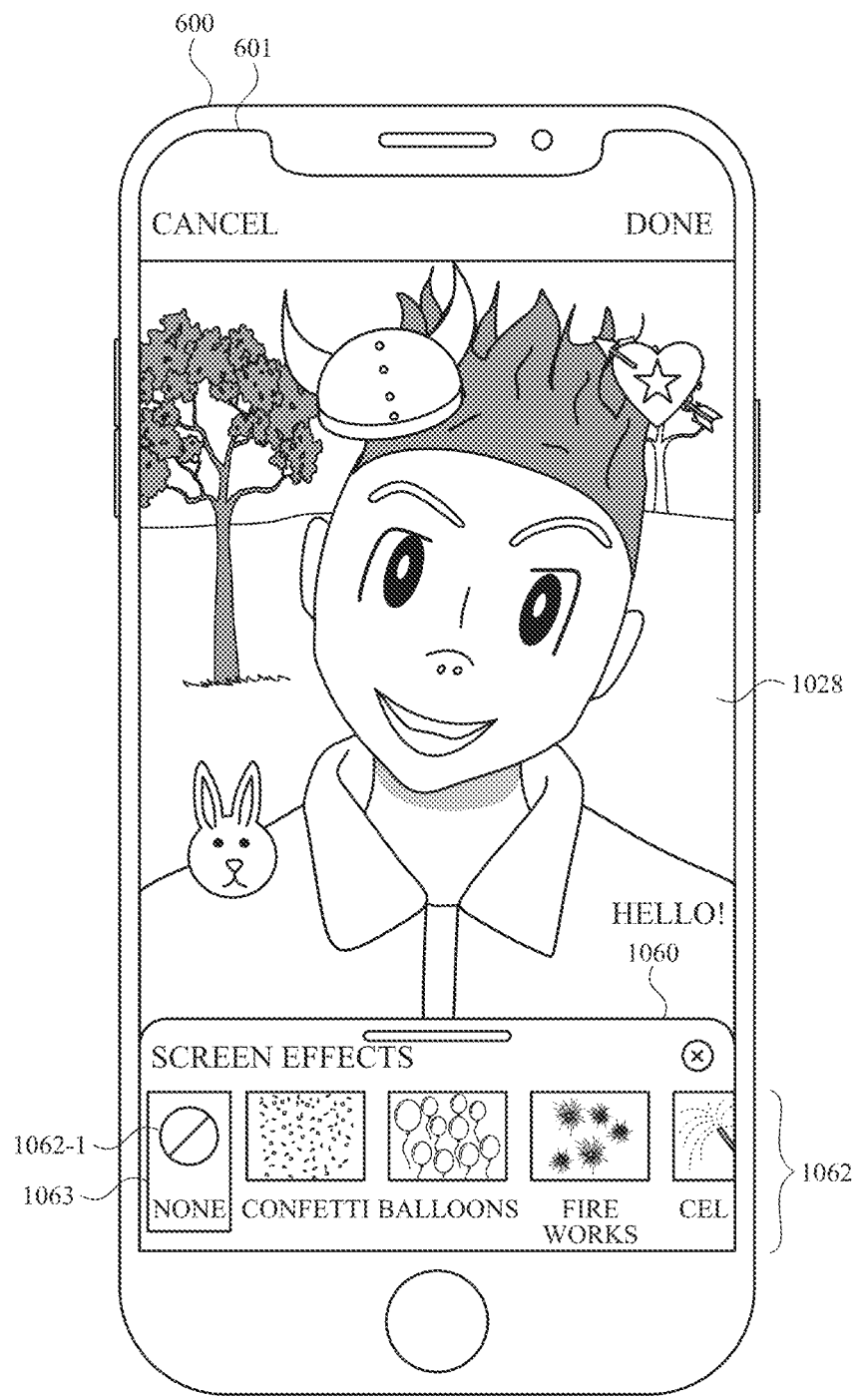
Figure 10A:
Figure 10A:
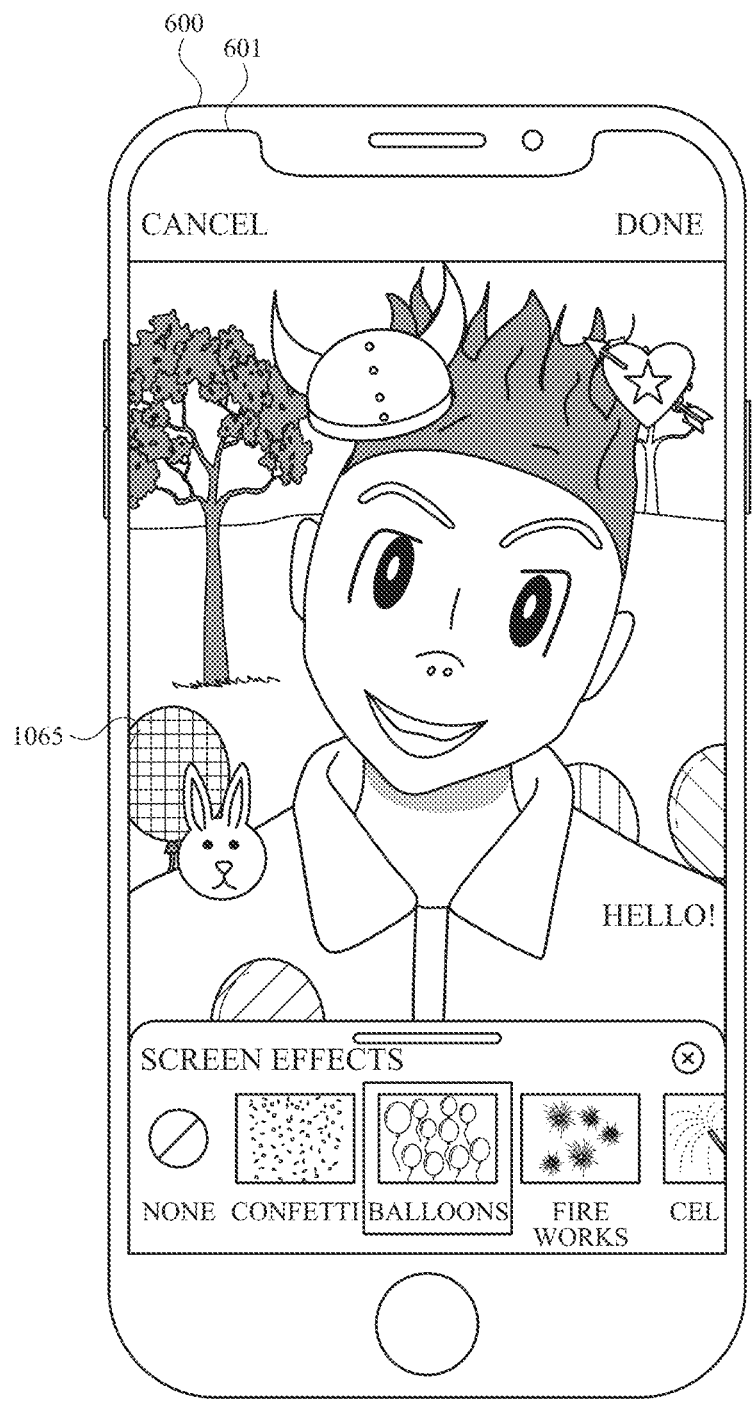
Figure 10A:
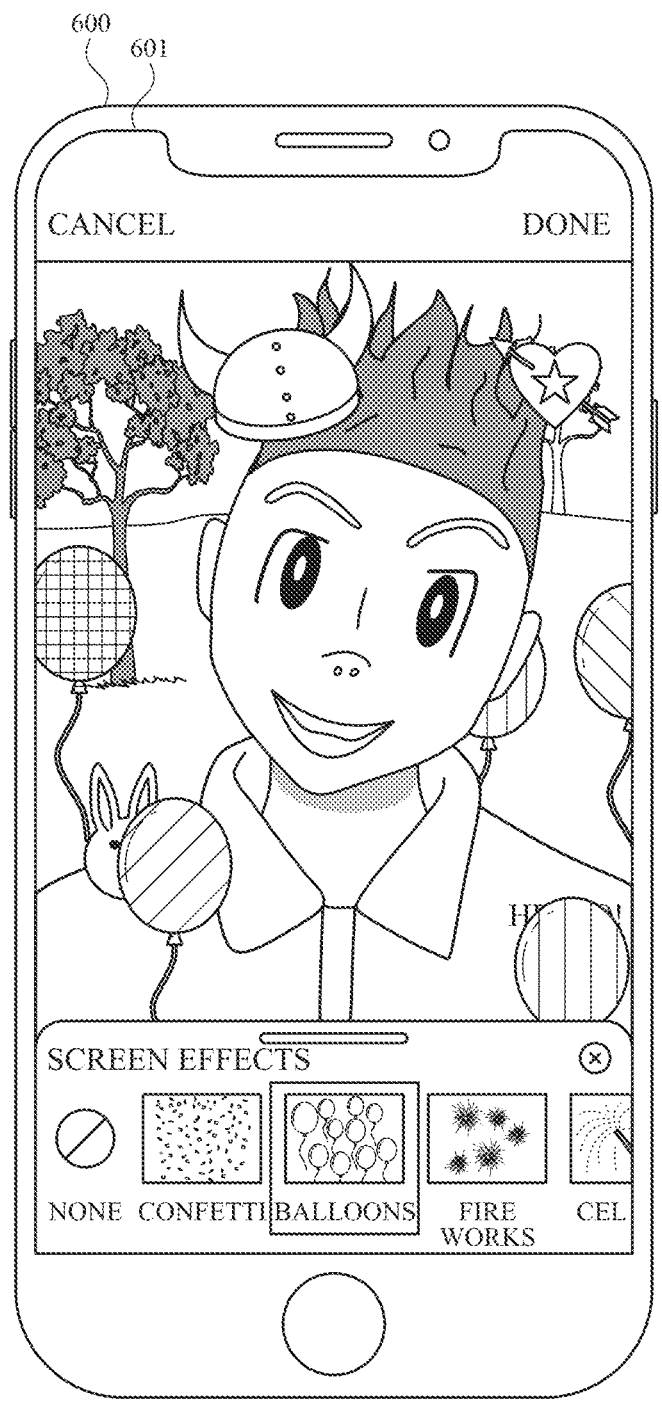
Figure 10A:
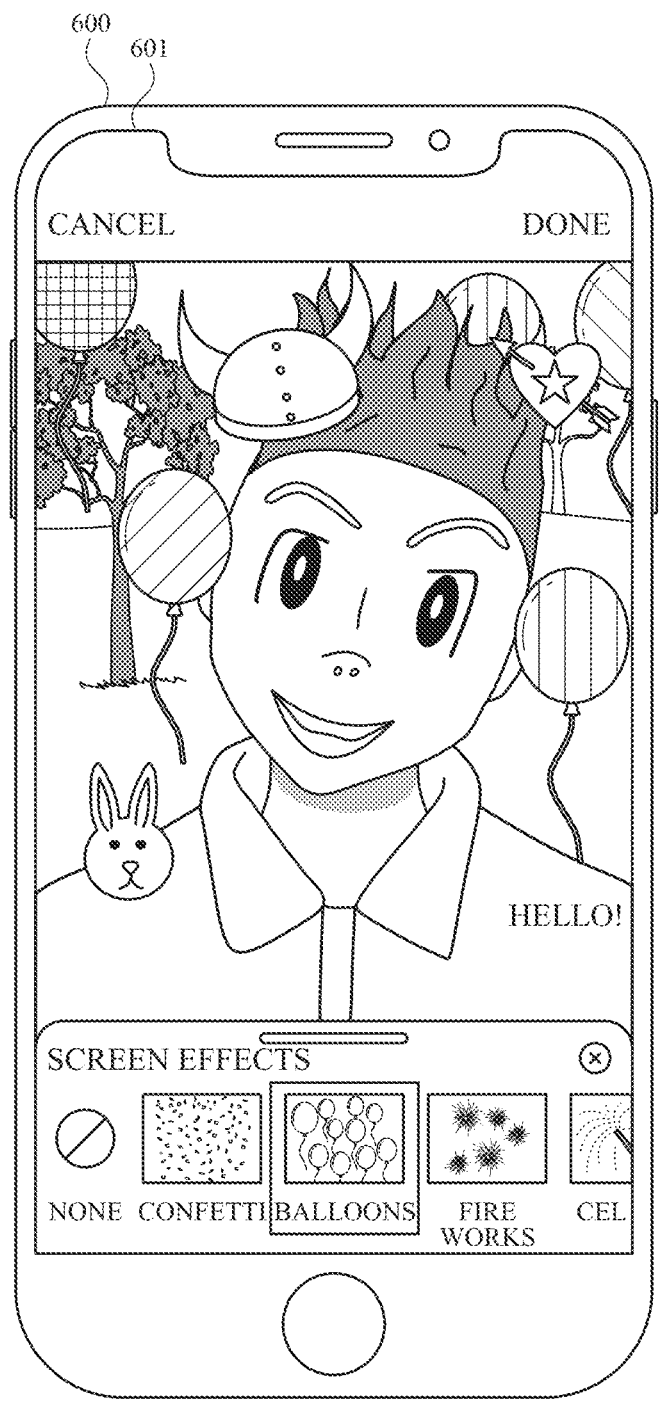

FIG. 10Z shows media item 1028 edited to display new heart sticker 1042, text 1046, and having vivid color filter applied.

FIGS. 10AA-10AD show device 600 switching from avatar 1037 to avatar 1054. These processes are discussed in greater detail above with respect to FIGS. 6G-6Q, 6BD-6BE, 6BK-6BN, and 8F-8AG. For the sake of brevity, details of these processes are not repeated here.

In FIG. 10AE, device 600 displays media item 1028 having stickers (e.g., 1039, 1040, 1042), avatar 1054, text 1046, and vivid color filter applied. The color filter in media item 1028 affects the hair of new avatar 1054 when new avatar 1054 is displayed in media item 1028.

In FIG. 10AE, device 600 detects swipe gesture 1055 on effects option affordances 1024 and, in response, scrolls effects option affordances 1024 to display screen effects affordance 1024-3 in FIG. 10AF.

In FIG. 10AG, device 600 detects input 1057 on screen effects affordance 1024-3 and, in response, displays screen effects menu 1060. Screen effects menu 1060 includes various screen effects options 1062, which are selectable to apply a full-screen visual effect to media item 1028. In FIG. 10AH, null effects option 1062-1 is selected (e.g., 1063) and device 600 displays no screen effects in media item 1028.

In FIG. 10AI, device 600 detects input 1064 on balloon effects option 1062-2. In FIGS. 10AJ-AL, device 600 displays an animated effect of balloons 1065 in media item 1028. In some embodiments, an animated effect is applied in a manner that emphasizes the depth data encoded in media item 1028. For example, in FIG. 10AJ-10AL, some of the balloons are displayed appearing in front of subject 1062 and visual effects (e.g., rabbit sticker 1040, avatar 1054, text 1046). Some of the balloons are displayed appearing at a depth behind subject 1062 and visual effects (e.g., rabbit sticker 1040, avatar 1054, heart sticker 1042).

In some embodiments, the screen effects can interact with visual effects and objects in media item 1028 based on the depth of the objects and visual effects in media item 1028. For example, a confetti screen effect can show confetti falling in front of, and behind, objects in media item 1028 (e.g., subject 1062) and visual effects (stickers and an avatar), and also falling on top of these objects and visual effects. For example, the confetti can be displayed falling on the avatar and falling off the side of the avatar based on a physics model of the falling confetti.

FIGS. 11A and 11B are a flow diagram illustrating a method for displaying visual effects in a media item viewing mode using an electronic device in accordance with some embodiments. Method 1100 is performed at a device (e.g., 100, 300, 500, 600) with a display apparatus. Some operations in method 1100 are, optionally, combined, the orders of some operations are, optionally, changed, and some operations are, optionally, omitted.

As described below, method 1100 provides an intuitive way for displaying visual effects in a media item viewing mode. The method reduces the cognitive burden on a user for displaying visual effects in an image or video, thereby creating a more efficient human-machine interface. For battery-operated computing devices, enabling a user to display visual effects faster and more efficiently conserves power and increases the time between battery charges.

The electronic device (e.g., 600) displays (1102), via the display apparatus (e.g., 601), a media user interface (e.g., 1005). The media user interface includes (1104) a media display region (e.g., 1008) including a representation (e.g., 1010) of a media item (e.g., a still image or video). In some embodiments, the depth data corresponding to the media item is obtained by a camera of the electronic device after detecting a prior selection of the effects affordance.

In some embodiments, the media item is a recorded image or video, and the effects are applied based on the depth data after the media item is recorded. In some embodiments, visual effects such as stickers, virtual avatars, and full screen effects can be added to image data, or changed to a different visual effect (e.g., replacing a sticker with a virtual avatar), after the image data is captured (e.g., recorded).

The media user interface (e.g., 1005) includes (1106) an effects affordance (e.g., 1016, an affordance associated with a function for activating an image display mode (e.g., a mode in which depth data is displayed when the image data contains depth data)).

The electronic device (e.g., 600) detects (1108) a gesture (e.g., 1021) directed to the effects affordance (e.g., 1016). In some embodiments, the respective effects option (e.g., 1024-1) corresponds (1110) to an effect for displaying an avatar in (e.g., overlaid on) the media item. In some embodiments, when displaying an avatar in the media item, image data of a person's head is replaced with a virtual avatar. Displaying the avatar in the media item, where image data of a person's head is replaced with a virtual avatar, provides visual feedback that the avatar relates to and/or is associated with the person being replaced. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the avatar is customizable. In some embodiments, the avatar is non-customizable.

In some embodiments, the respective effects option (e.g., 1024-3) corresponds (1112) to an effect for displaying a plurality of virtual objects (e.g., 1062, confetti, balloons, etc.) moving in (e.g., animatedly overlaid on) the media item. In some embodiments, a trajectory of the plurality of objects moving in the media item is modified based on a presence of at least one of an object in (e.g., represented in; identified in) the media item (e.g., an object that is encoded in the original media item, not an object that is the product of an effect applied to the media item, such as a person in the original image or video, but not a virtual avatar) or a visual effect (e.g., an avatar) applied to the media item. In some embodiments, objects such as confetti or balloons are displayed in front of, behind, and/or on a user in the image. In some embodiments, the image includes another effect, such as an avatar, and objects such as confetti or balloons are displayed in front of, behind, and/or landing on the avatar.

In some embodiments, the respective effects option (e.g., 1024-2) corresponds (1114) to an effect for displaying one or more selectable graphical icons (e.g., 1042, stickers) in (e.g., overlaid on) the media item.

In response to detecting the gesture directed to the effects affordance, the electronic device (e.g., 600) displays (1116) a plurality of effects options (e.g., stickers affordance, avatar affordance) for applying effects to the media item concurrently with a representation of the media item, including, in accordance with a determination (1118) that the media item is associated with corresponding depth data (e.g., as described herein), the plurality of effects options include a respective effects option (e.g., 1024) for applying effects (e.g., stickers, virtual avatars, full screen effects, etc.) based on the depth data. In some embodiments, in response to detecting the gesture, the electronic device activates an image display mode (e.g., a depth-data-based image display mode.

In some embodiments, a sticker affordance (e.g., 1024-2) is selectable to display a plurality of sticker options (e.g., 1042) that can be displayed on the media item (e.g., still image or video) based on depth data. For example, a sticker can be placed on the media item and modified based on depth data associated with the media item. In some embodiments, a sticker is associated with a relative position of an object in a video. Movement of the object in the video has a depth component that is used to modify a displayed aspect (e.g., size, orientation, position, etc.) of the sticker based on the movement of the object. For example, the sticker is displayed on the object, and as the object moves away from the camera (e.g., 602) (e.g., backwards), the sticker gets smaller to give the appearance the sticker is moving away from the camera with the object. In some embodiments, an avatar affordance (e.g., 1024-1) is selectable to display a plurality of avatar options (e.g., FIG. 10AB) that can be displayed on the media item based on depth data. For example, an avatar can be displayed on a face in an image or video and modified based on depth data associated with the face in the image or video. For example, as the face moves forwards, backwards, side-to-side, or in any other manner that affects a depth component of the image data, the avatar is displayed and modified based on the depth data. Thus, as the face moves, the avatar is displayed moving in the same manner.

In response to detecting the gesture directed to the effects affordance, the electronic device (e.g., 600) displays (1116) a plurality of effects options (e.g., 1024, stickers affordance, avatar affordance) for applying effects to the media item concurrently with a representation of the media item, including, in accordance with a determination (1120) that the image data does not include the depth data, the respective effects option is not available for activation in the plurality of effects options (e.g., the respective effects option is excluded from the displayed plurality of effects options or is disabled in the displayed plurality of effects options). The respective effects option not being available for activation in the plurality of effects options in accordance with a determination that the image data does not include the depth data provides feedback that the image data does not included needed depth data. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, affordances that correspond to depth data (e.g., the effects affordance) are not displayed or are not selectable when the image data does not include depth data.

In some embodiments, the plurality of effects options (e.g., 1024) includes an option (e.g., 1020) for adding labels to (e.g., overlaid on) the media item. In some embodiments, text labels can be added to the image or video. In some embodiments, the plurality of effects options includes an option for applying one or more image filters to (e.g., overlaid on) the media item.

Note that details of the processes described above with respect to method 1100 (e.g., FIGS. 11A-11B) are also applicable in an analogous manner to the methods described above and below. For example, method 700 optionally includes one or more of the characteristics of the various methods described above with reference to method 1100. For example, visual effects such as stickers and virtual avatars are displayed in image data in a messaging application user interface. For another example, method 900 optionally includes one or more of the characteristics of the various methods described above with reference to method 1100. For example, visual effects such as stickers and virtual avatars are displayed in image data in a user interface for a camera application user interface. For another example, method 1300 optionally includes one or more of the characteristics of the various methods described above with reference to method 1100. For example, visual effects such as stickers and virtual avatars are displayed in image data in a user interface for a live video communication session. For another example, method 1500 optionally includes one or more of the characteristics of the various methods described above with reference to method 1100. For example, visual effects such as stickers and virtual avatars are displayed in image data for a camera user interface. For brevity, these details are not repeated below.

FIGS. 12A-12AP illustrate exemplary user interfaces for displaying visual effects in a live video communication session, in accordance with some embodiments. The user interfaces in these figures are used to illustrate the processes described below, including the processes in FIGS. 13A-13B.

In FIG. 12A, device 600 shows a user interface 1200 for a live video communication session (e.g., a streamed video communication) between two or more participants. In user interface 1200, device displays participant image data 1204 representing a participant in the live video communication session. In window 1202, device 600 displays device image data 1201, which includes data obtained by a camera of device 600 (e.g., camera 602) and representative of video data being transmitted to other participants in the live video communication session. In FIG. 12A, device image data 1201 represents a user who is also a participant in the video communication session (e.g., using an external electronic device (e.g., a device similar to device 600)). In FIG. 12A, device image data 1201 is captured using camera 602 of device 600. In some embodiments, however, device image data 1201 can be captured using a rear-facing camera of device 600.

Figure 12B:
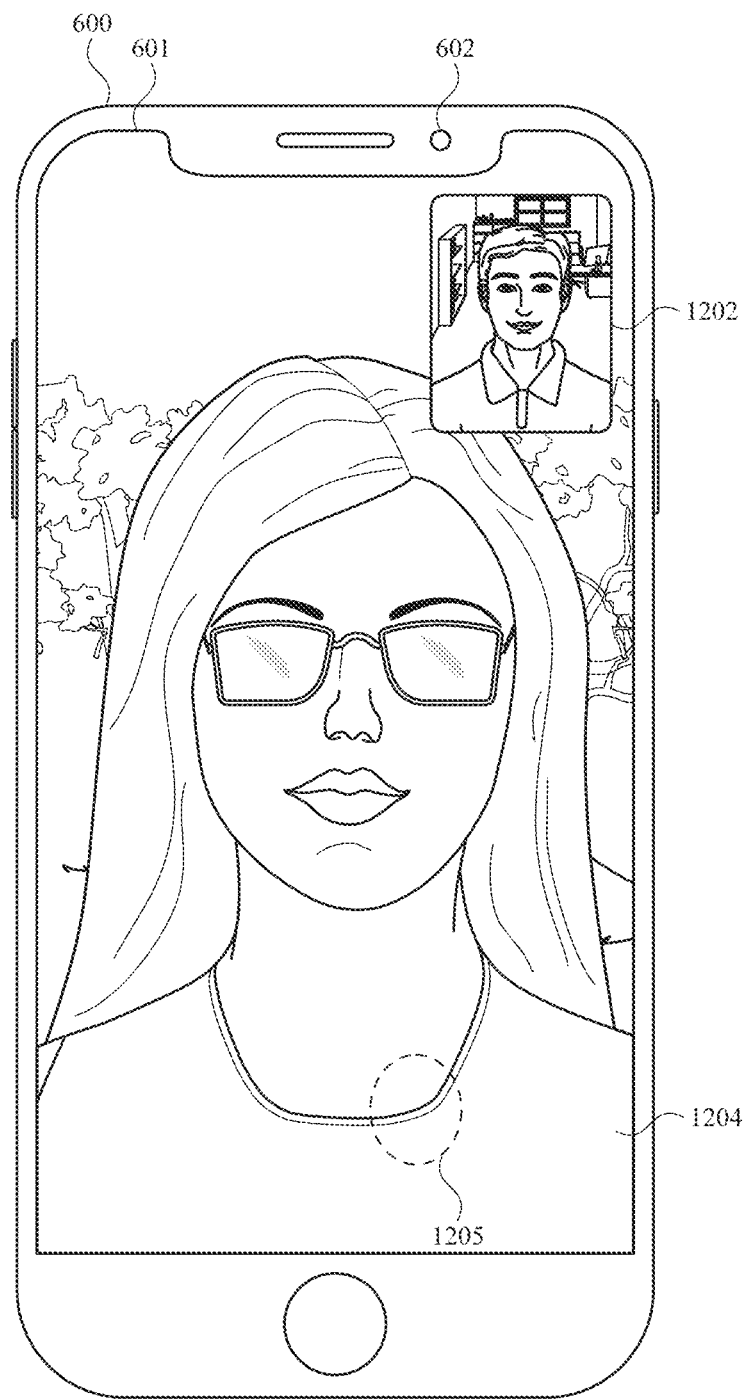
Figure 12C:
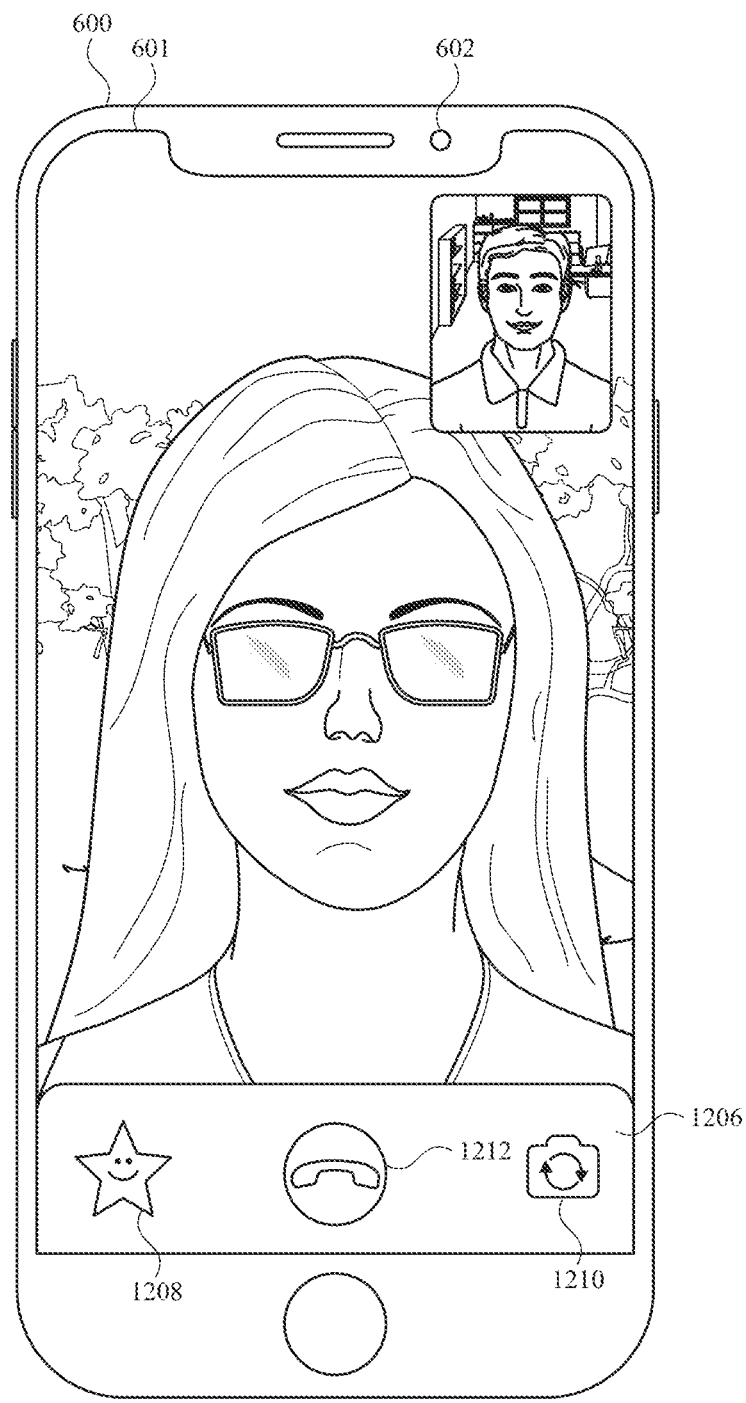

In FIG. 12B, device 600 detects input 1205 on user interface 1200 and, in response, displays, in FIG. 12C, options display region 1206 having effects affordance 1208, camera selector affordance 1210, and end affordance 1212. End affordance 1212 is associated with a function for terminating the live video communication session, and camera selector affordance 1210 is associated with a function for switching between cameras (e.g., a rear-facing camera and camera 602). Effects affordance 1208 is similar to effects affordance 622, 822, and 1016, and is selectable for enabling and disabling a mode (visual effect mode, effects mode) of device 600 in which device 600 is enabled or disabled for displaying visual effects in user interface 1200.

Figure 12D:
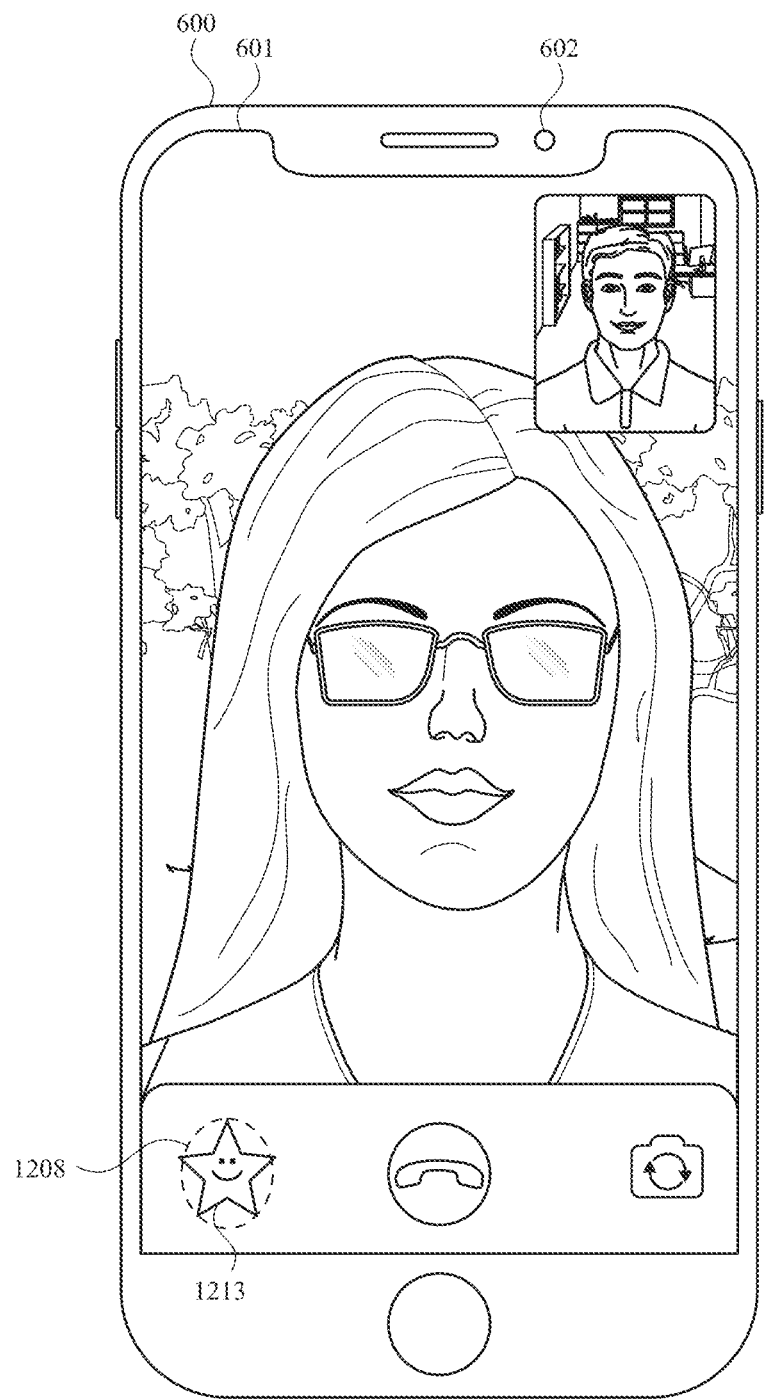

In FIG. 12D, device 600 detects input 1213 on effects affordance 1208.

Figure 12E:
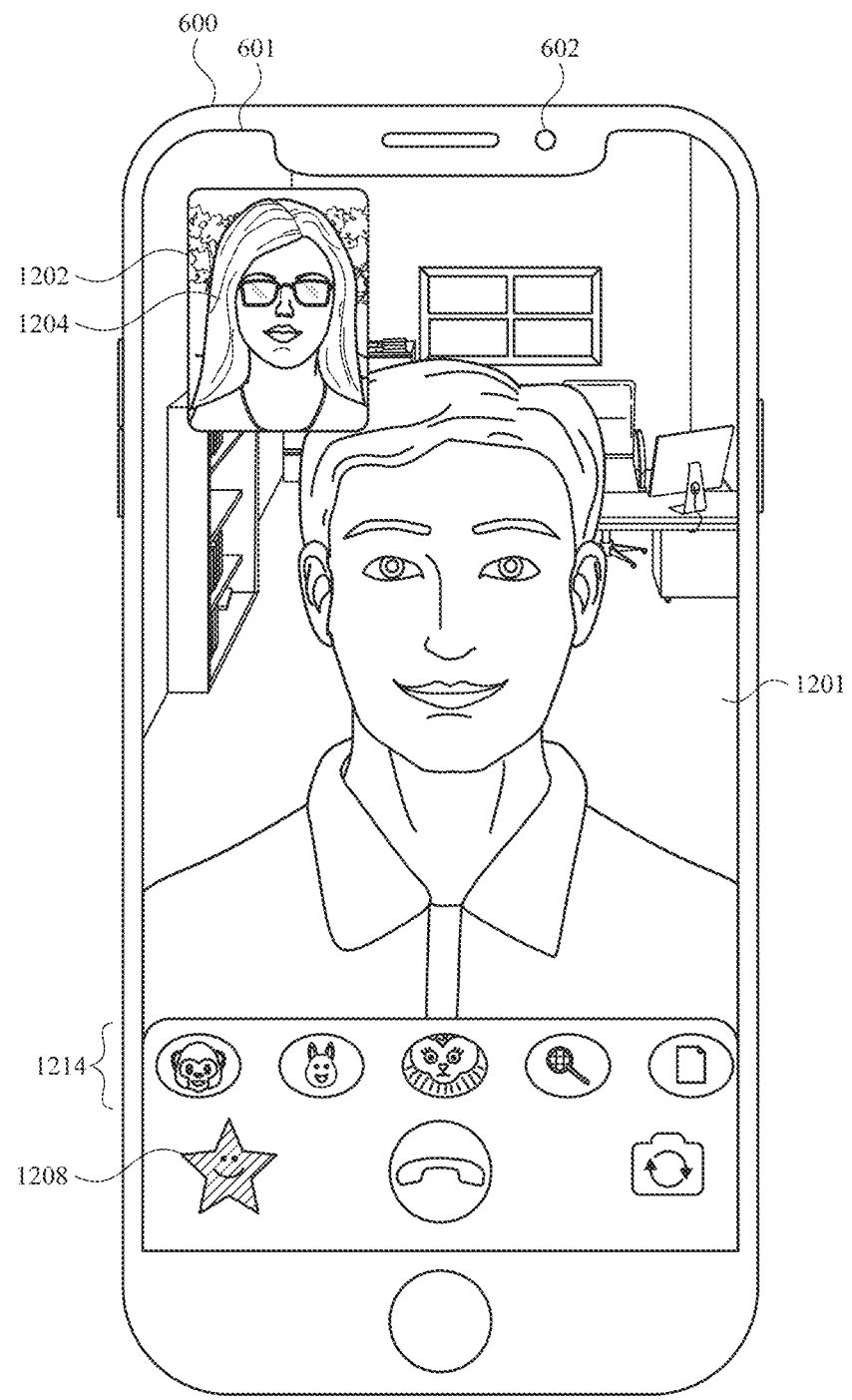

In FIG. 12E, in response to detecting input 1213, device 600 enables visual effects mode. Device 600 switches the displayed locations of device image data 1201 and participant image data 1204 by displaying participant image data 1204 in window 1202, which is optionally moved to another location in user interface 1200. Device 600 also highlights effects affordance 1208 and expands options display region 1206 to include visual effects option affordances 1214. Visual effects option affordances 1214 are similar to visual effects option affordances 624, 824, and 1024 discussed above, and are displayed when effects affordance 1208 is enabled.

Figure 12F:
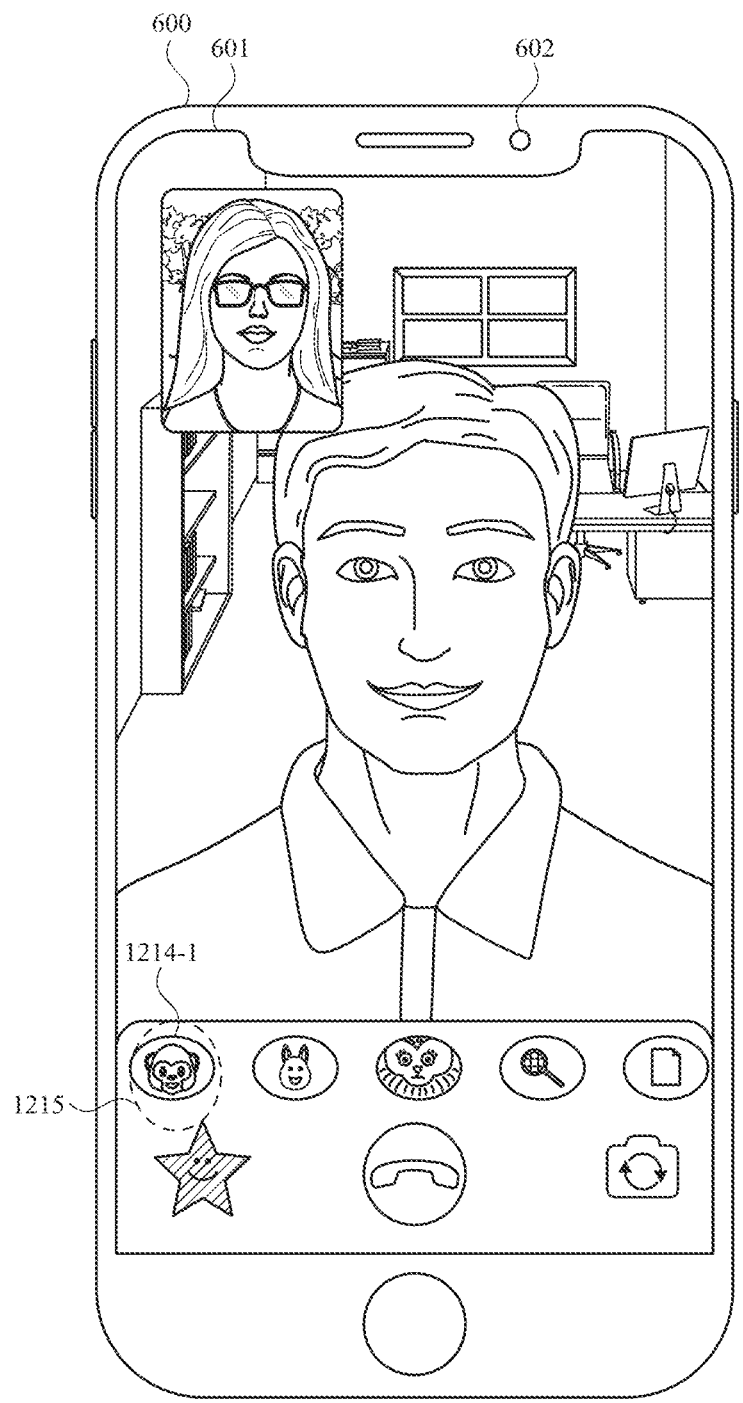
Figure 12G:
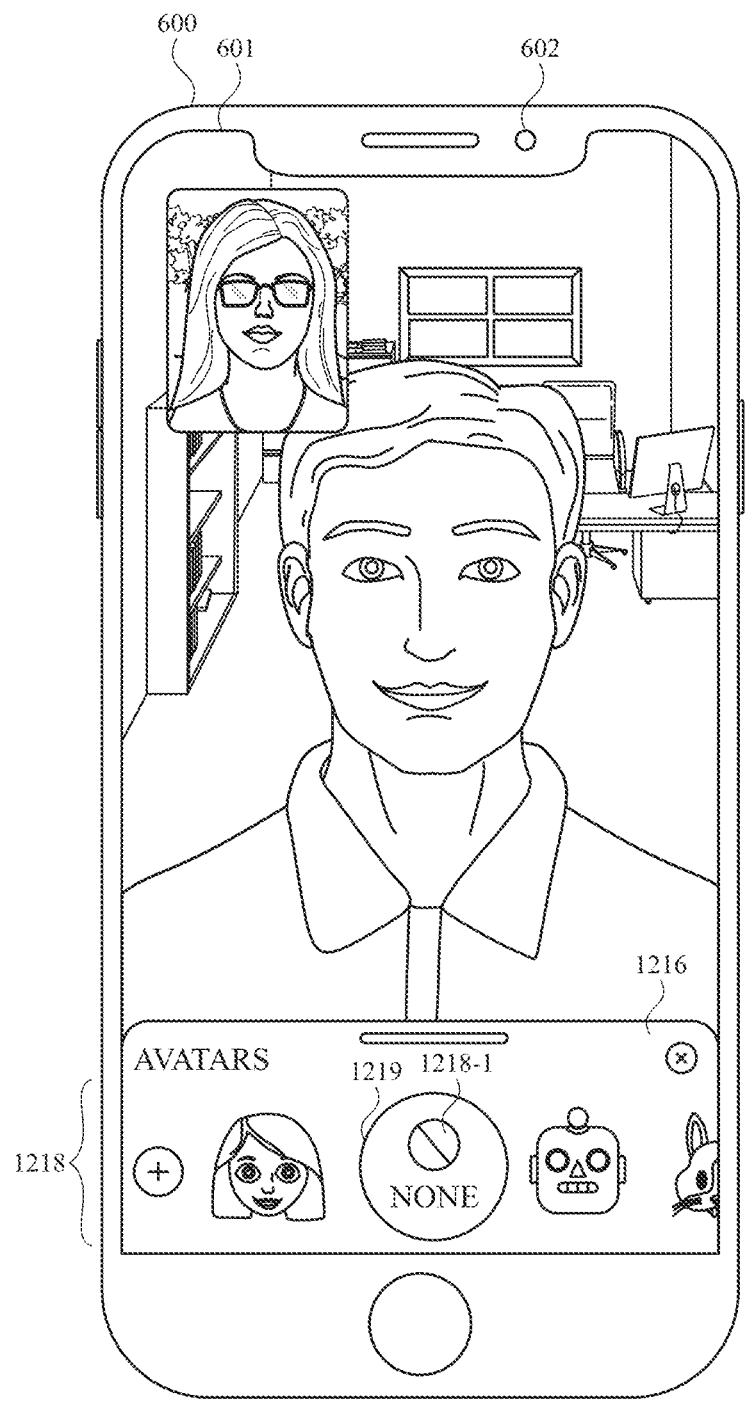
Figure 12H:
Figure 12I:
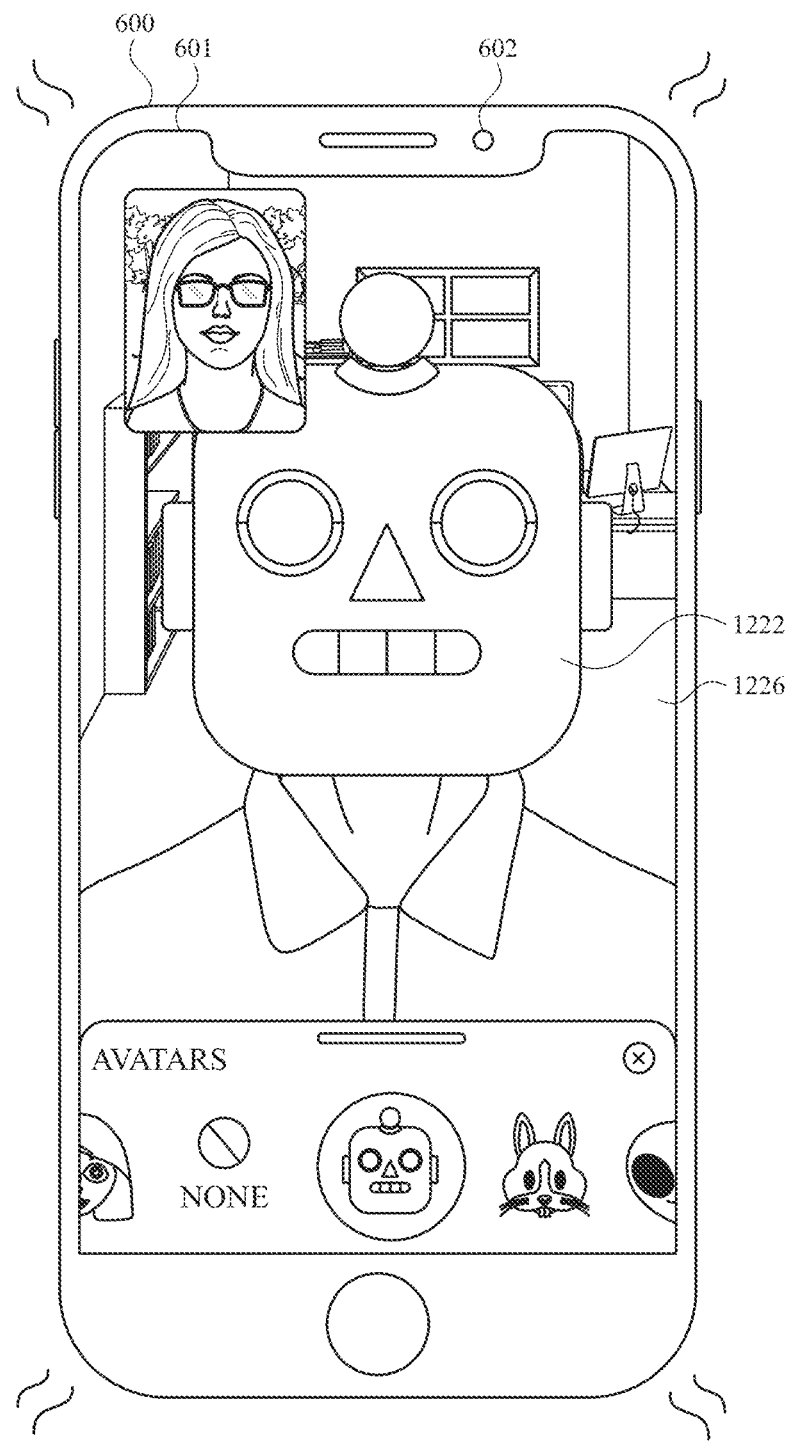
Figure 12J:
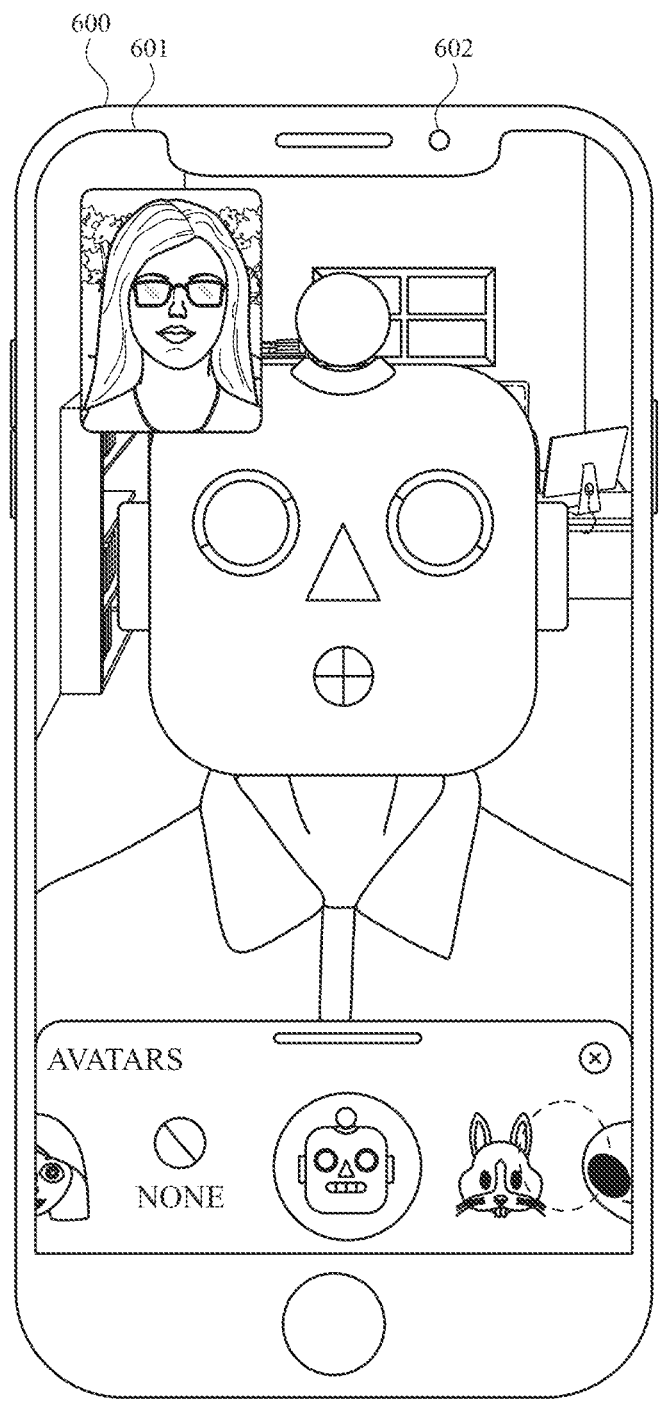
Figure 12K:
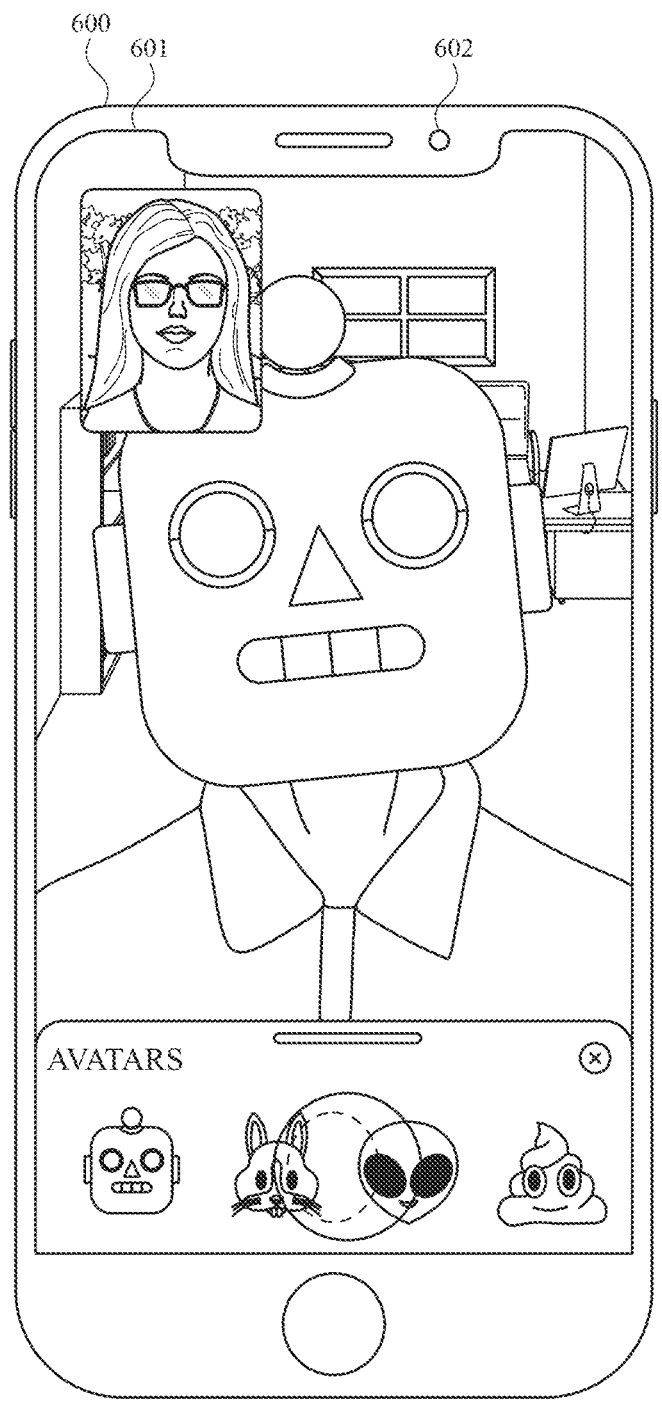
Figure 12L:
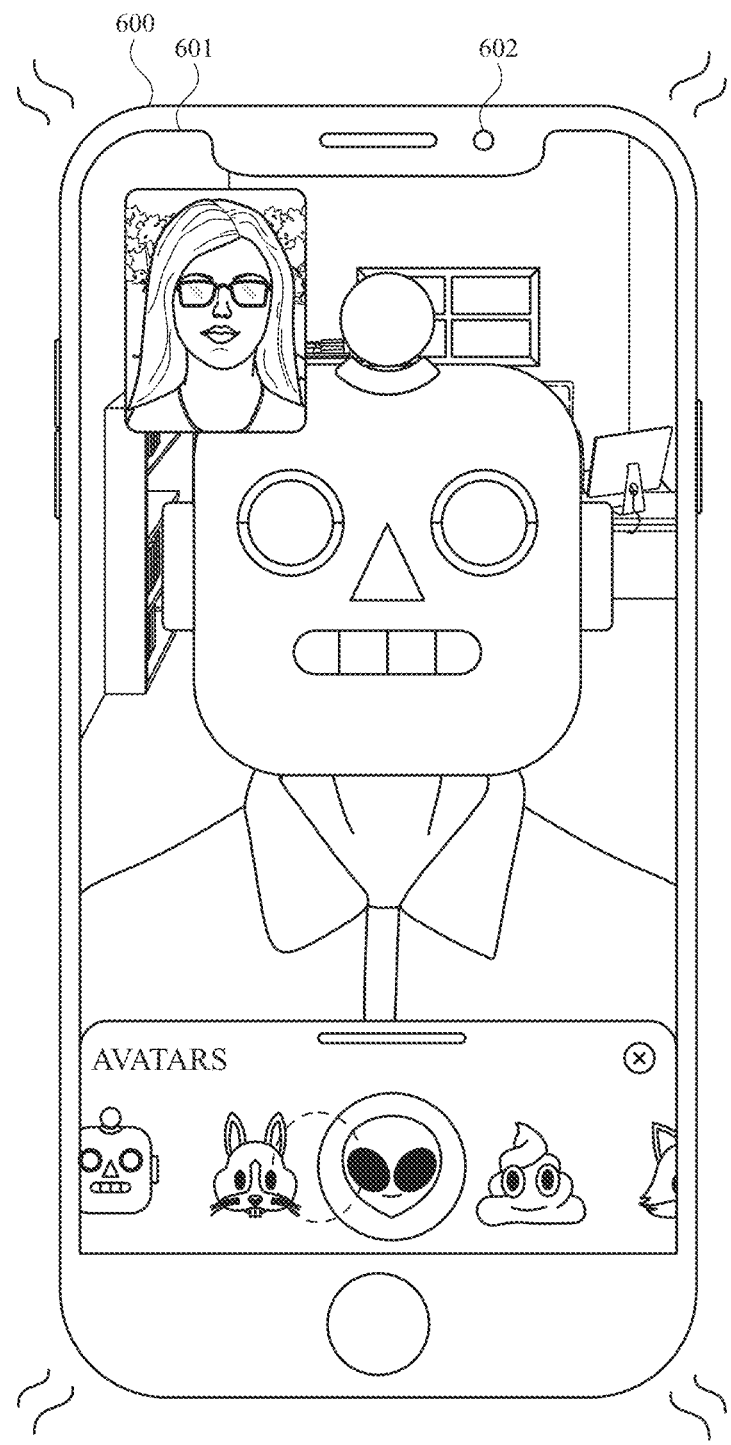
Figure 12M:
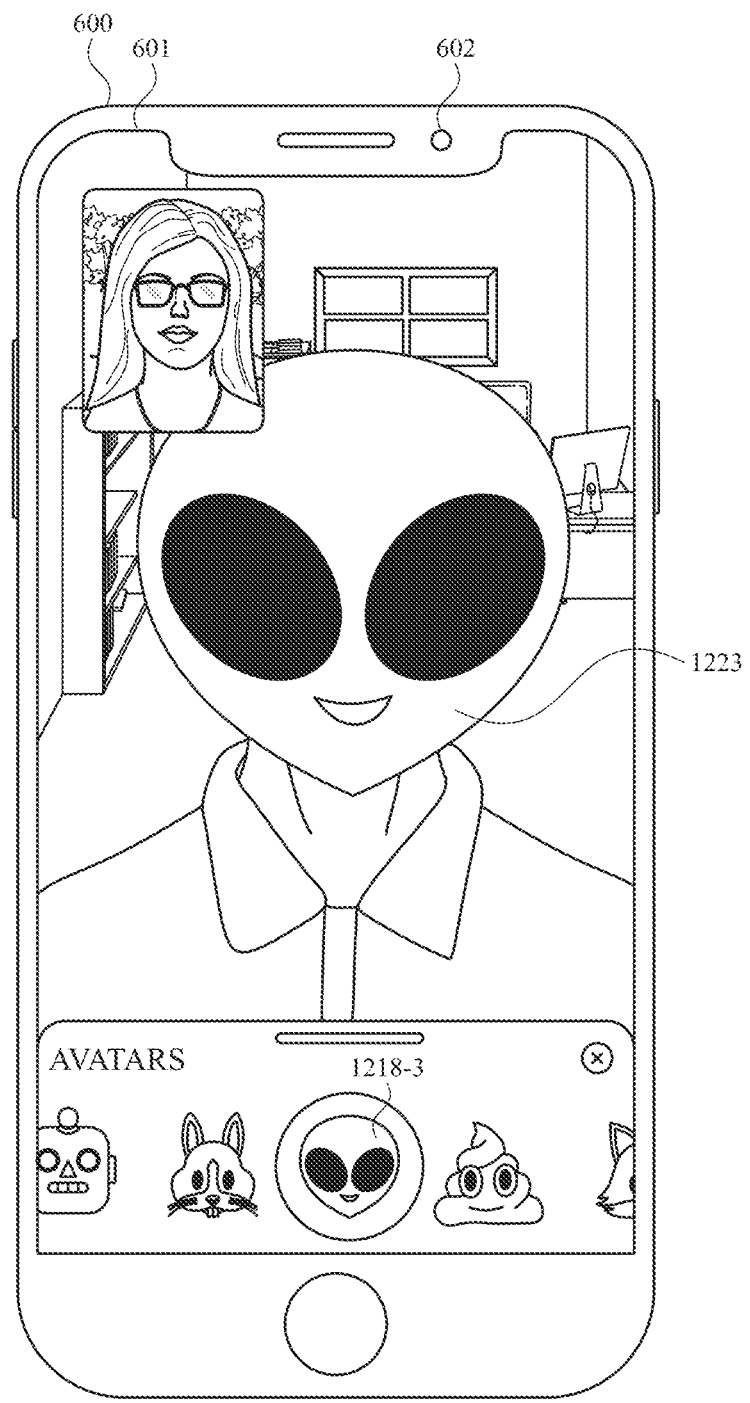
Figure 12N:
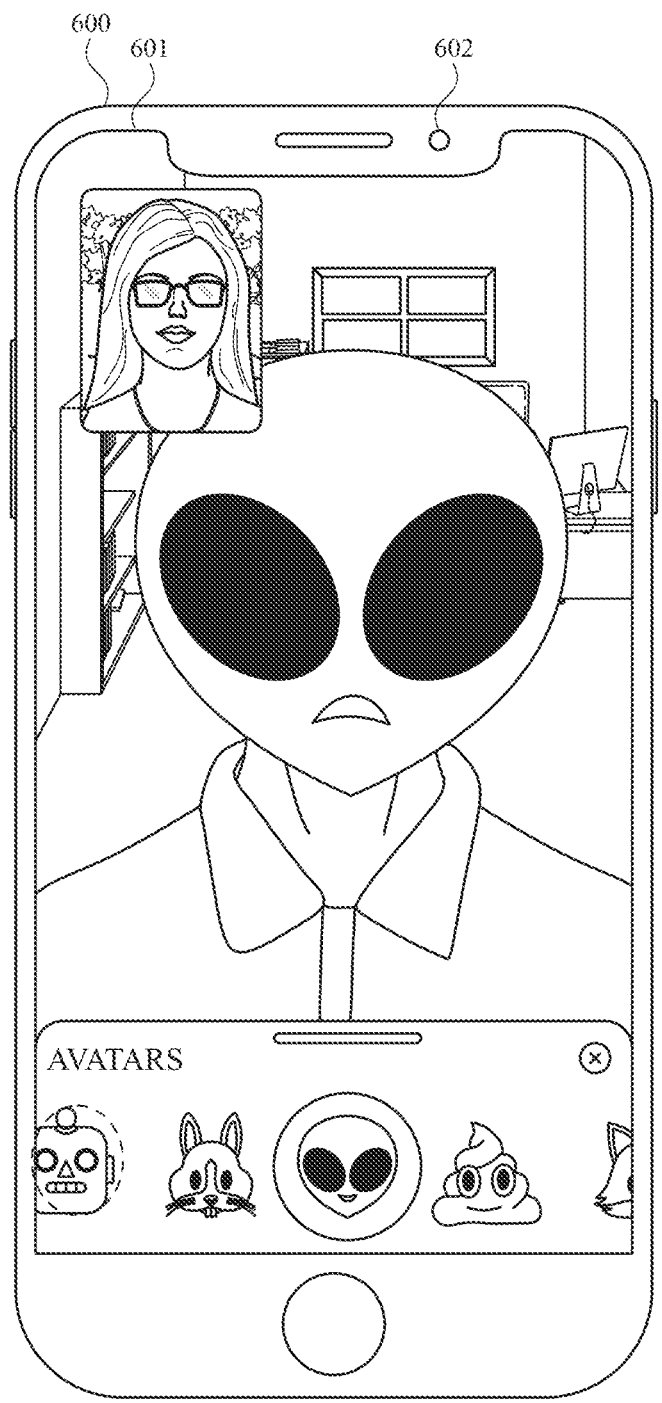
Figure 12O:
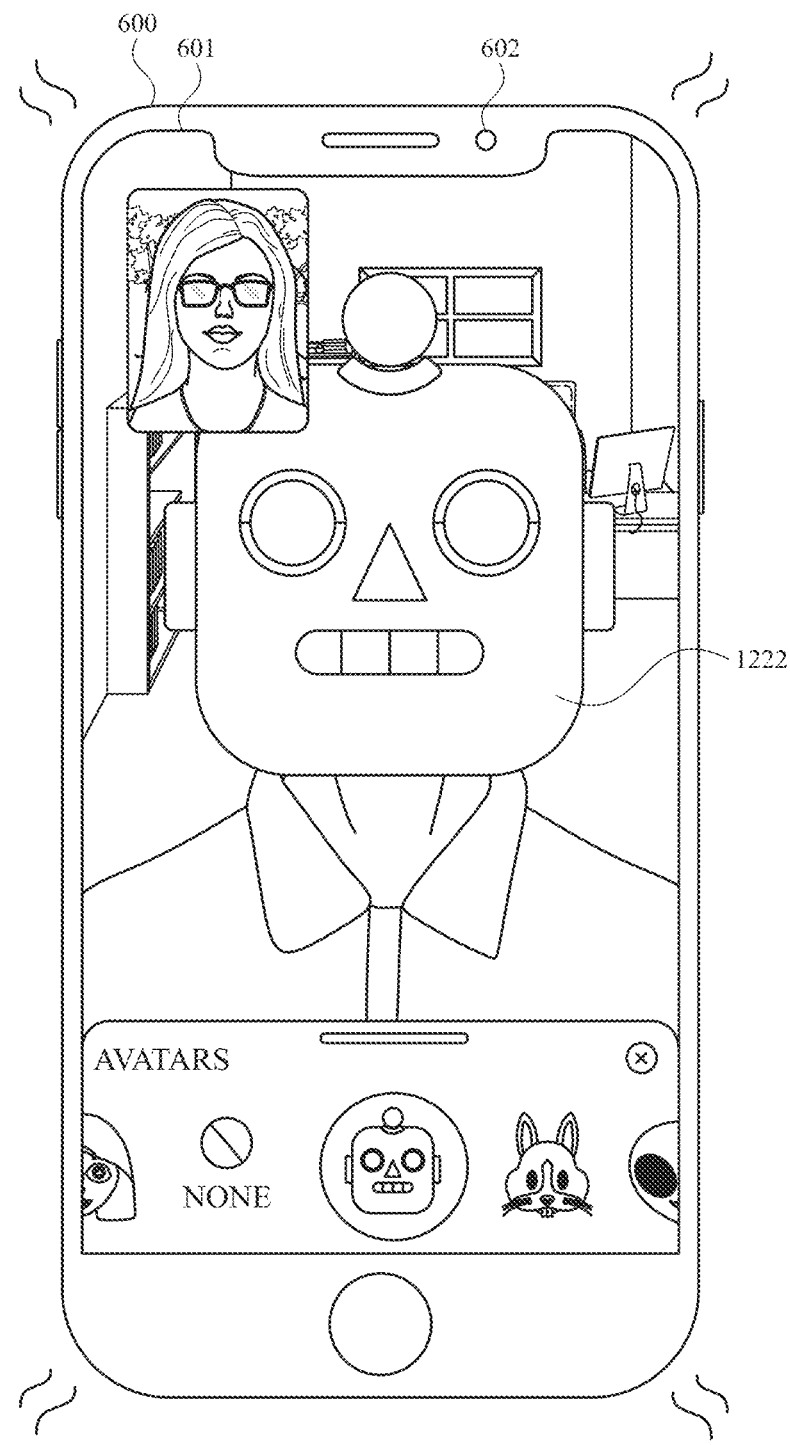

In FIG. 12F, device 600 detects input 1215 on avatar effects affordance 1214-1. In FIG. 12G, in response, device 600 displays avatar options menu 1216, which includes a scrollable listing of selectable avatar options 1218. Avatar options menu 1216 is similar to avatar option menus 628 and 828, and avatar options 1218 are similar to avatar options 630 and 830.

Avatar options 1218 may be selected to apply a corresponding avatar to the subject's face in device image data 1201 in a manner similar to that described above with respect to FIGS. 6G-6Q, 6BD-6BE, 6BK-6BN, and 8F-8AG. In some embodiments, avatar options 1218 may be selected to apply a corresponding avatar in a similar manner to the participant displayed in participant image data 1204.

In FIG. 12G, because null avatar option 1218-1 is selected (e.g., positioned within selection region 1219), no avatar is displayed on the user's face in device image data 1201.

FIGS. 12H-12P illustrate a process for selecting, and switching between, various avatar options to display corresponding avatars on the user's face in device image data 1201. For example, device 600 receives a selection of robot avatar option 1218-2 and displays robot avatar 1222 on the user's face in device image data 1201, while maintaining display of other objects (e.g., the user's body and background 1226) in device image data 1201. Device 600 modifies the appearance of robot avatar 1222 based on detected changes in the user's face using camera 602. Device 600 then receives a selection of alien avatar option 1218-3 and transitions the displayed avatar to alien avatar 1223. Device receives a subsequent selection of robot avatar option 1218-2 and again transitions the displayed avatar to robot avatar 1222. In some embodiments, a user can select to remove (or forego displaying) an avatar in device image data 1201 by selecting null avatar option 1218-0. These processes are discussed in greater detail above with respect to FIGS. 6G-6Q, 6BD-6BE, 6BK-6BN, and 8F-8AG. For the sake of brevity, details of these process are not repeated here.

Figure 12P:
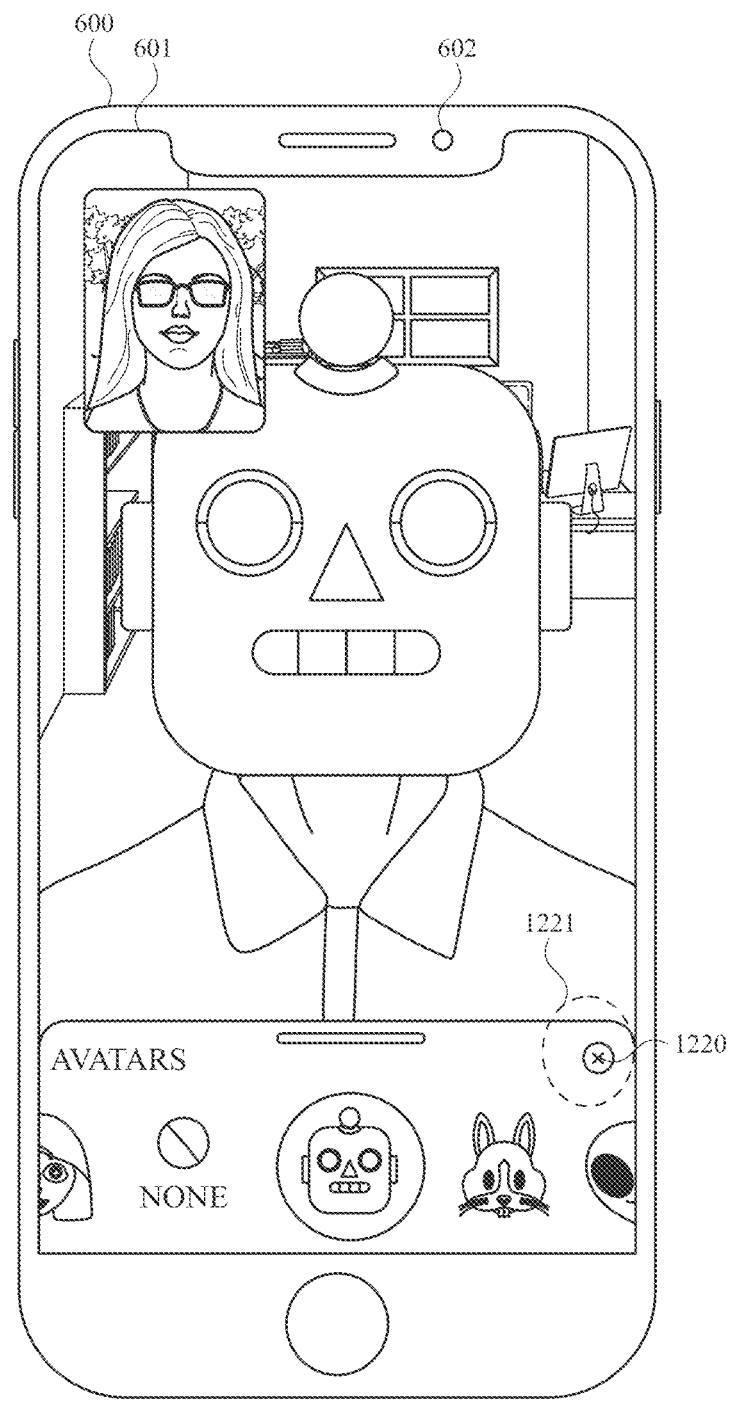
Figure 12Q:
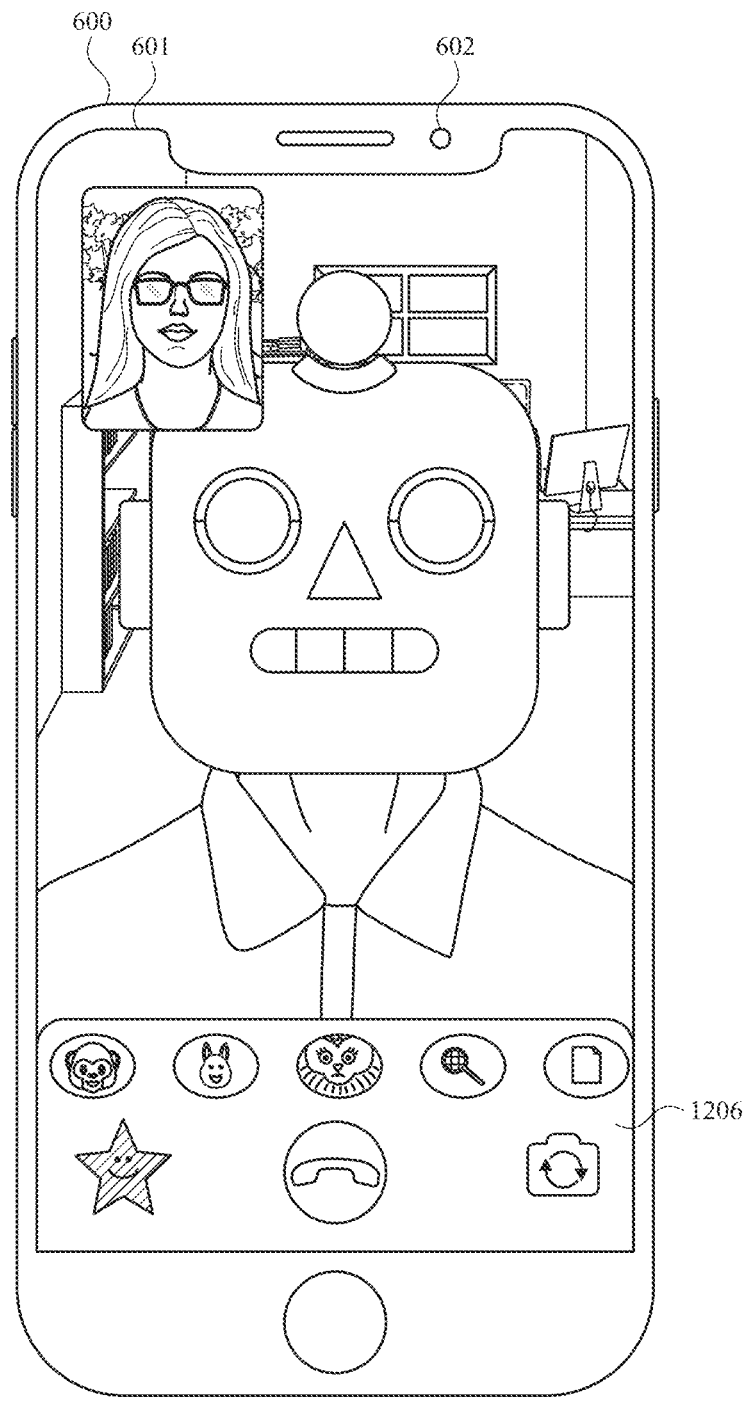

After detecting selection (via input 1221) of close icon 1220 in FIG. 12P, device 600 closes avatar options menu 1216 and again displays options display region 1206 in FIG. 12Q. Device 600 displays robot avatar 1222 on the user's head in device image data 1201 and modifies the avatar based on detected changes in the user's face using camera 602.

Figure 12R:
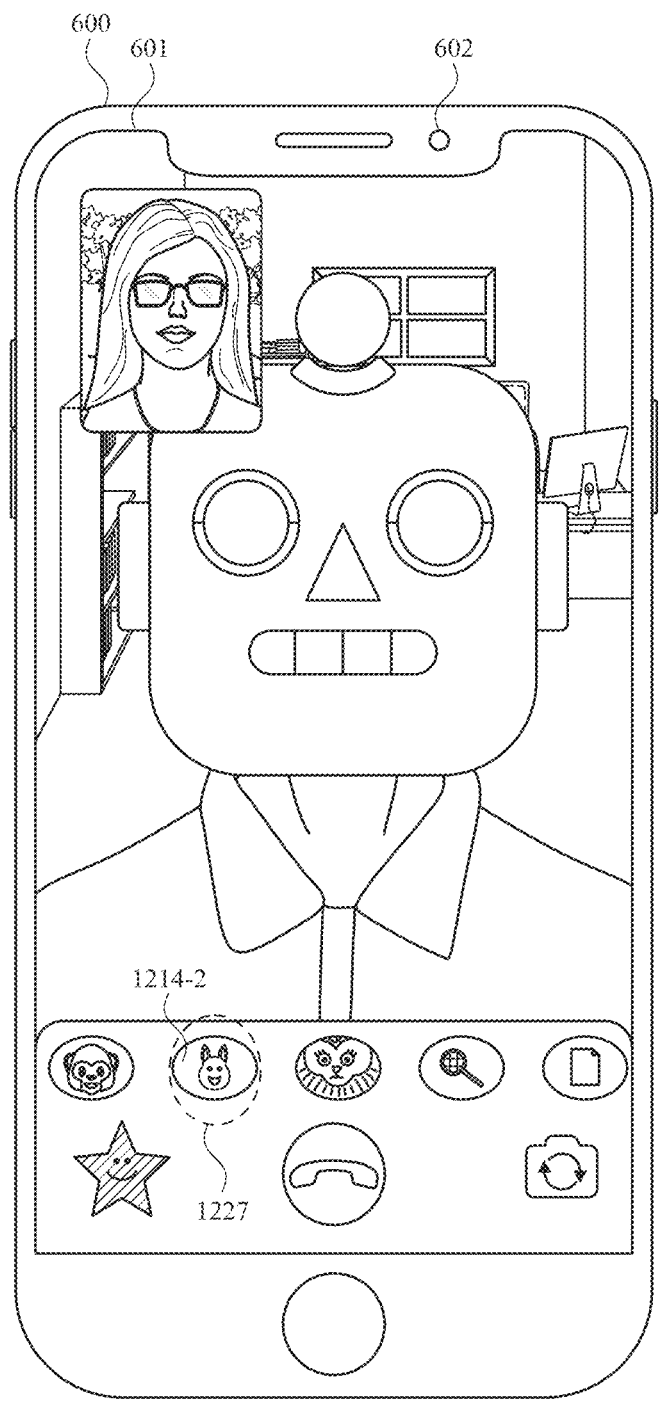
Figure 12S:
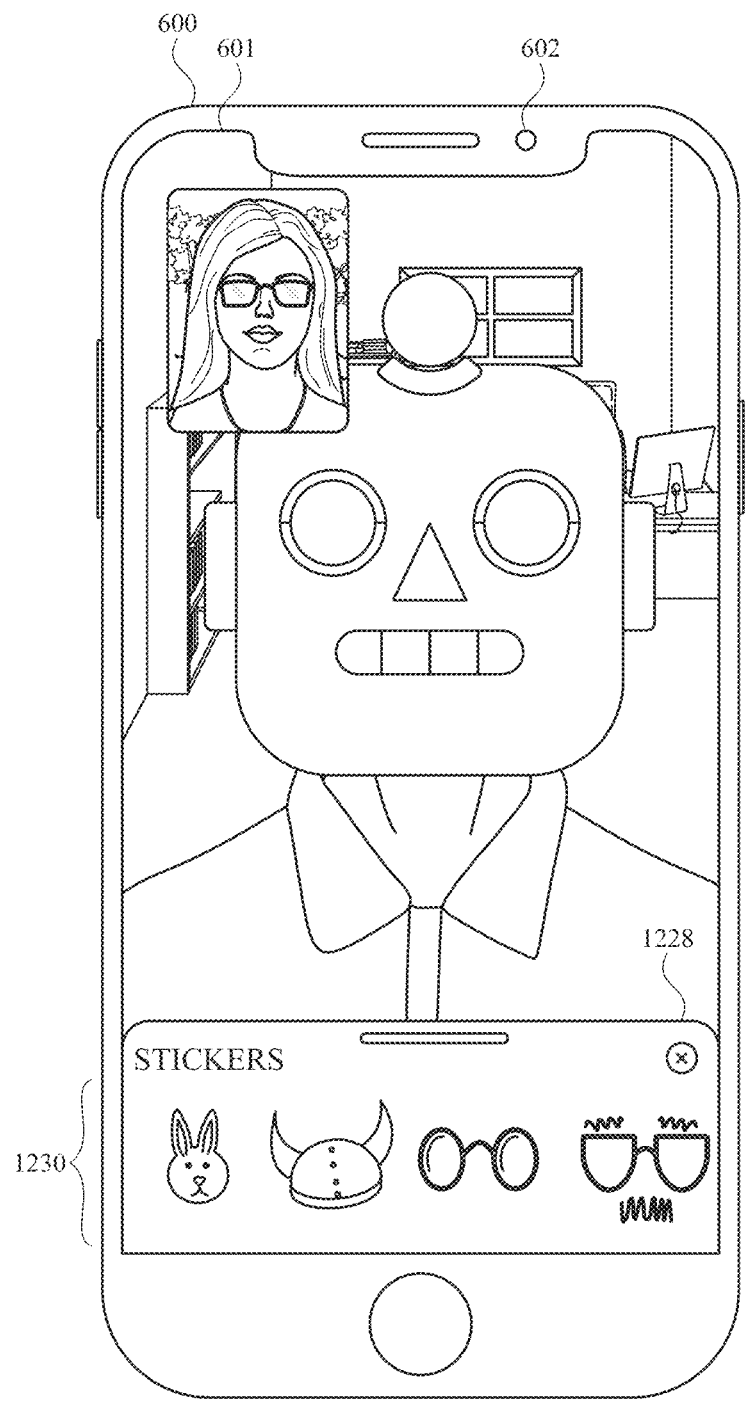

In FIG. 12R, device 600 detects selection 1227 of sticker effects affordance 1214-2, and displays, in FIG. 12S, sticker options menu 1228 having stickers 1230. Sticker options menu 1228 is similar to sticker options menu 656 and 856, and stickers 1230 are similar to stickers 658 and 858.

Stickers 1230 may be selected to apply a corresponding sticker to device image data 1201 in a manner similar to that described above with respect to FIGS. 6U-6AD, 8AH-8AK, and 8AR-8AY. In some embodiments, stickers 1230 may be applied to participant image data 1204.

Figure 12T:
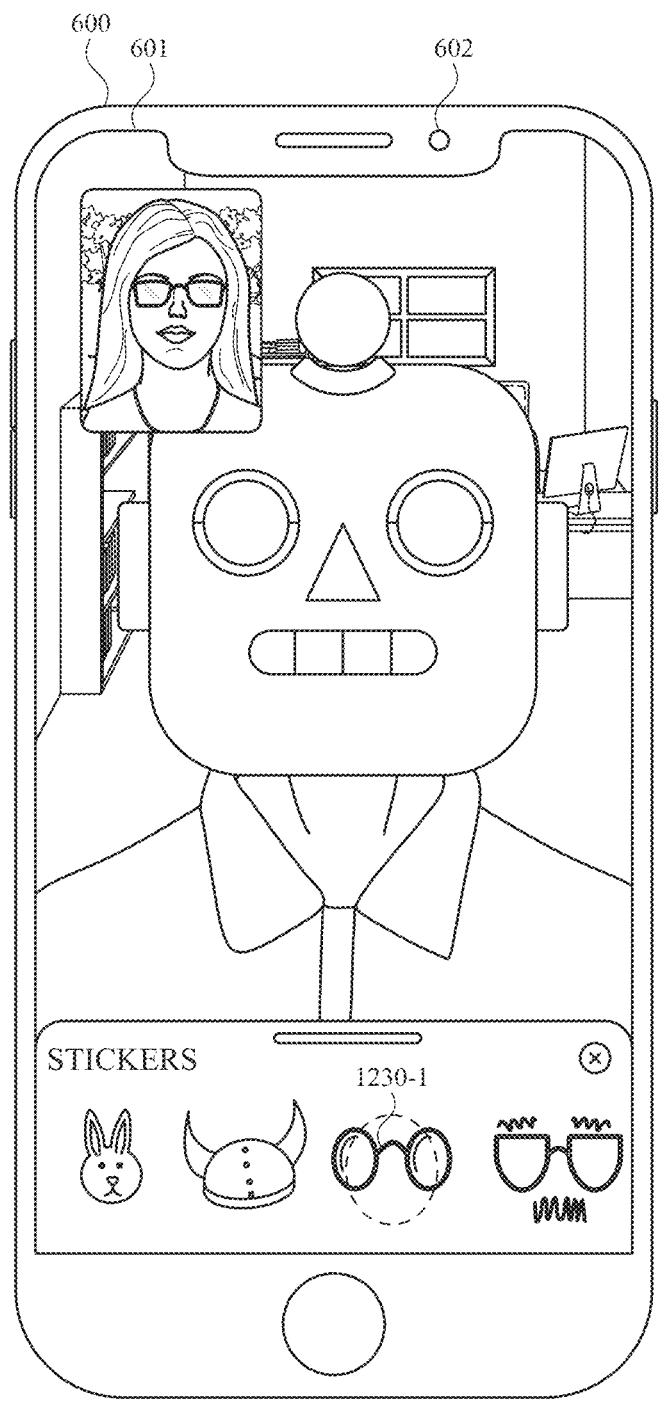
Figure 12U:
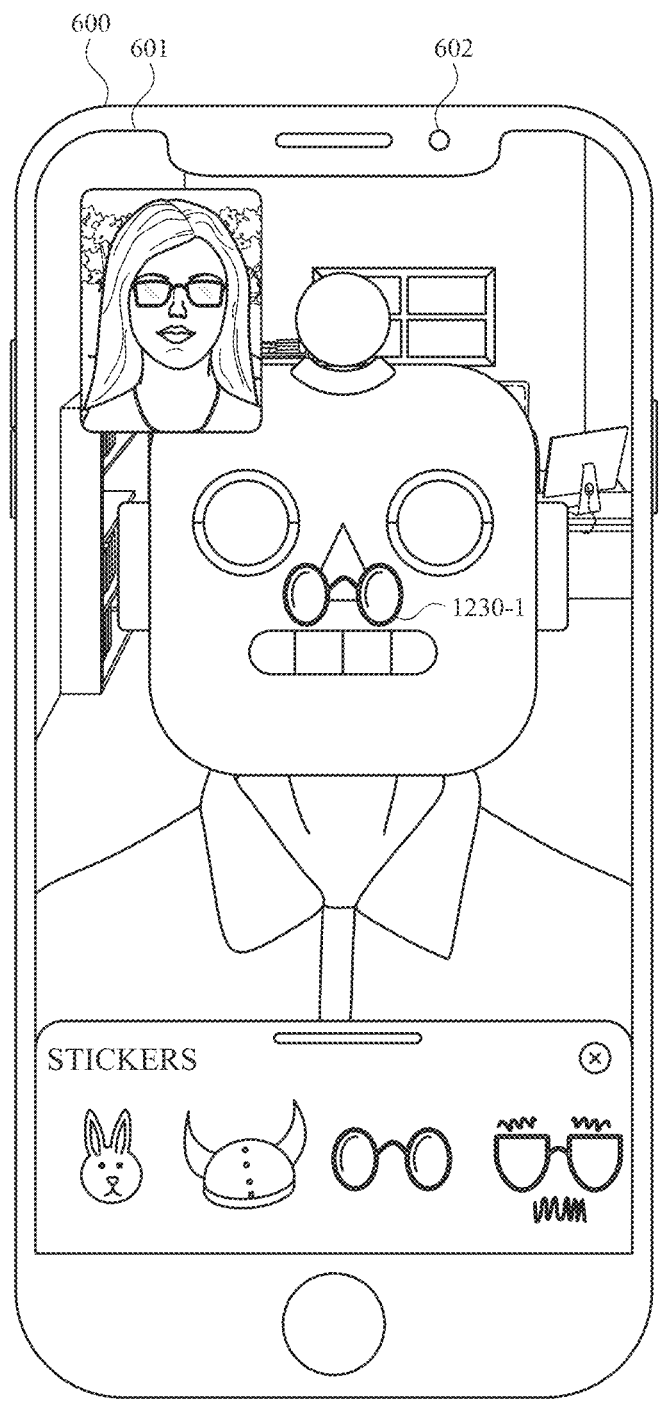
Figure 12V:
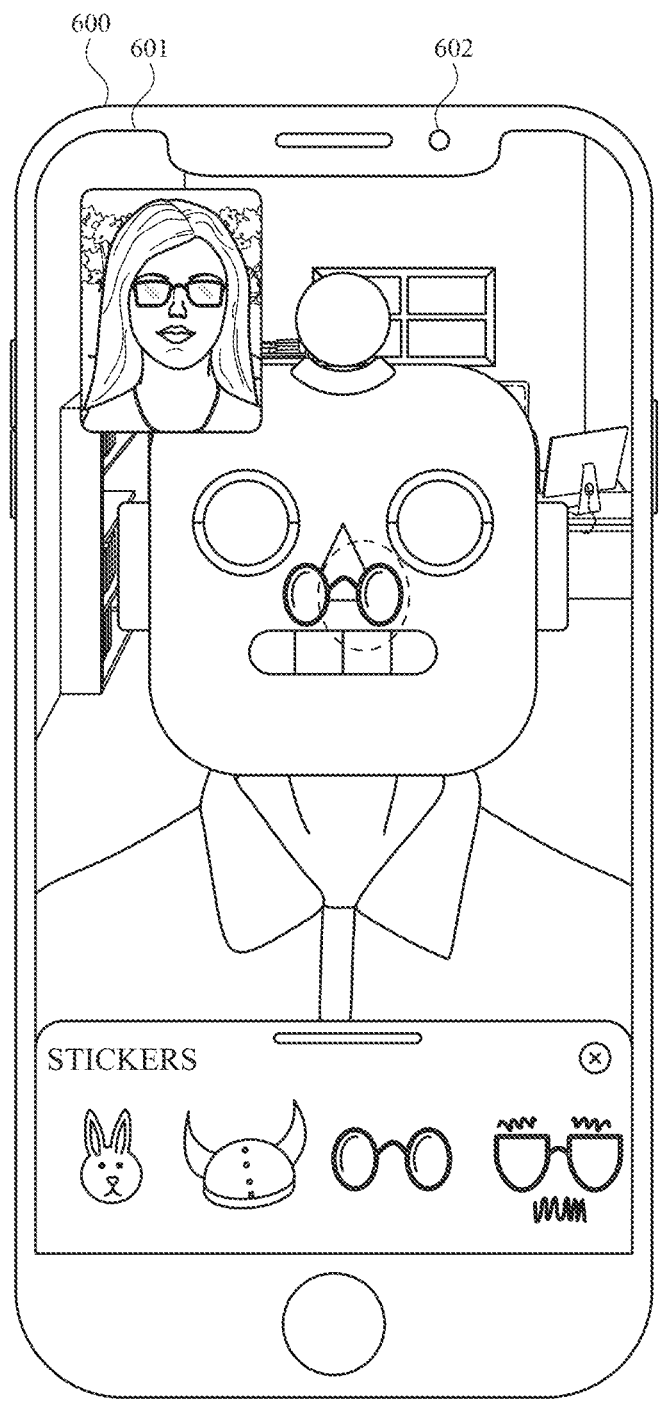
Figure 12W:
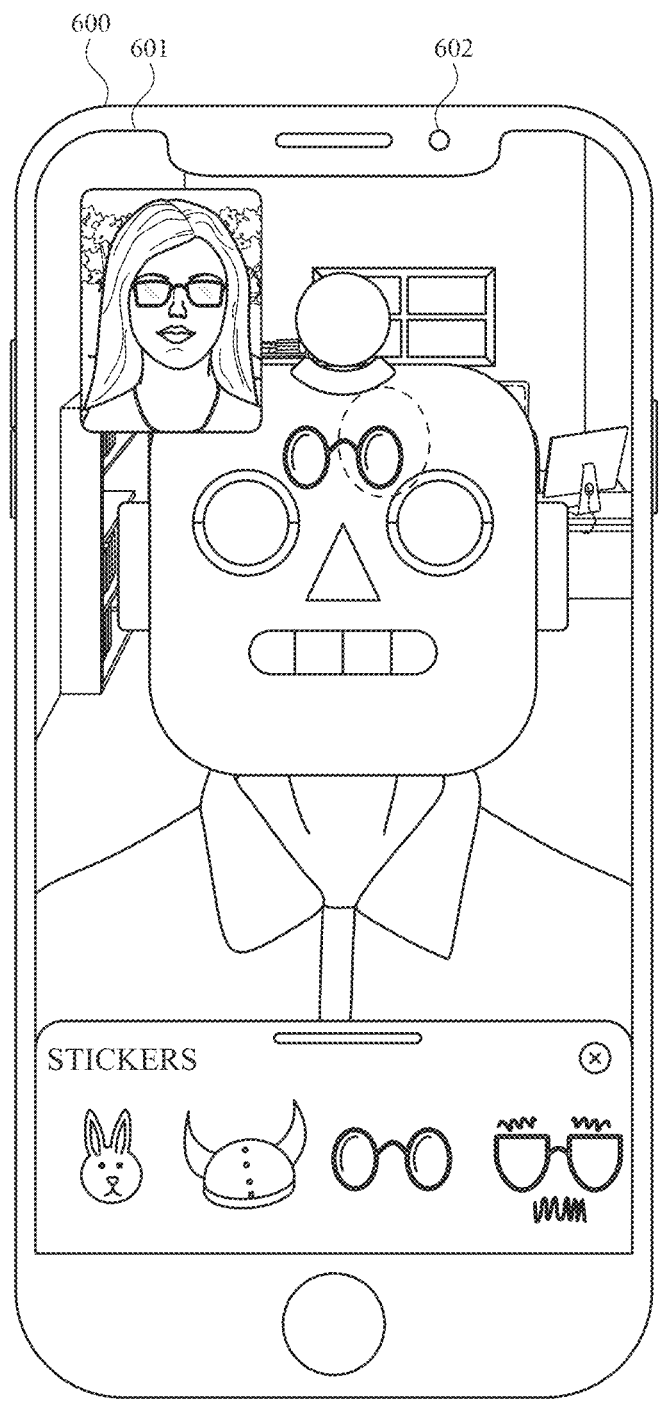
Figure 12X:
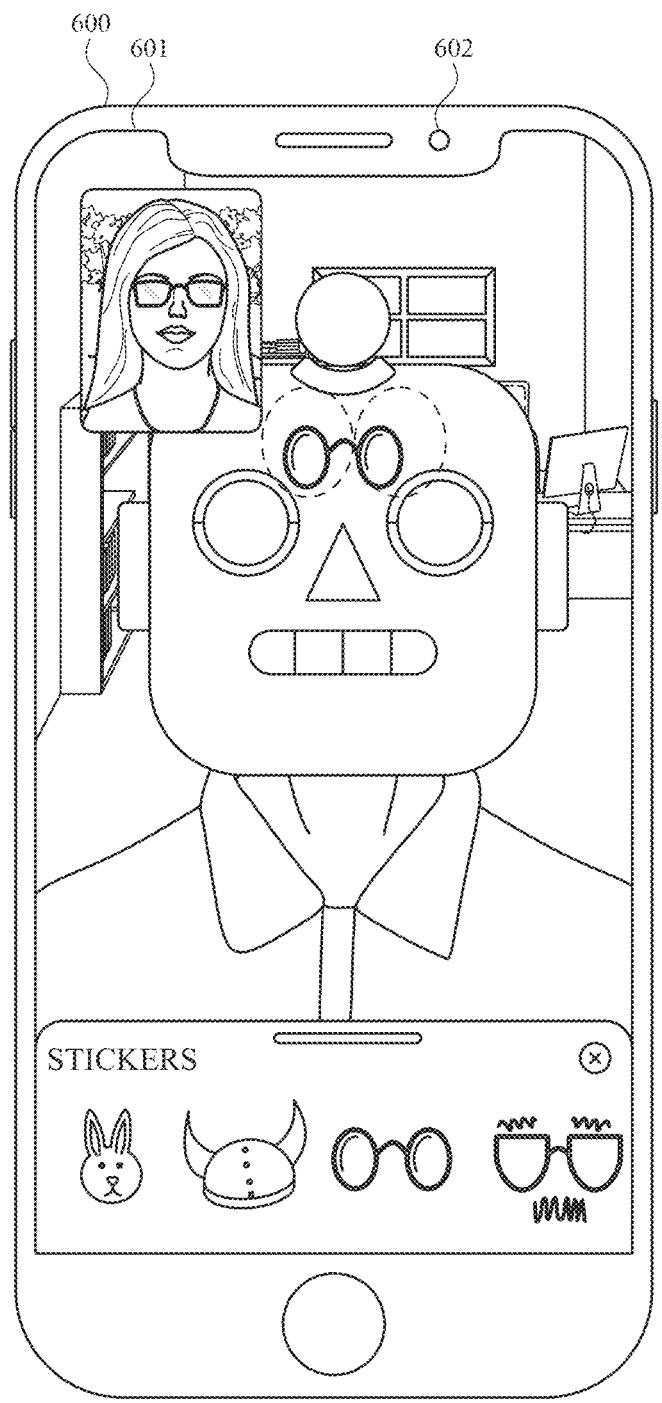
Figure 12Y:
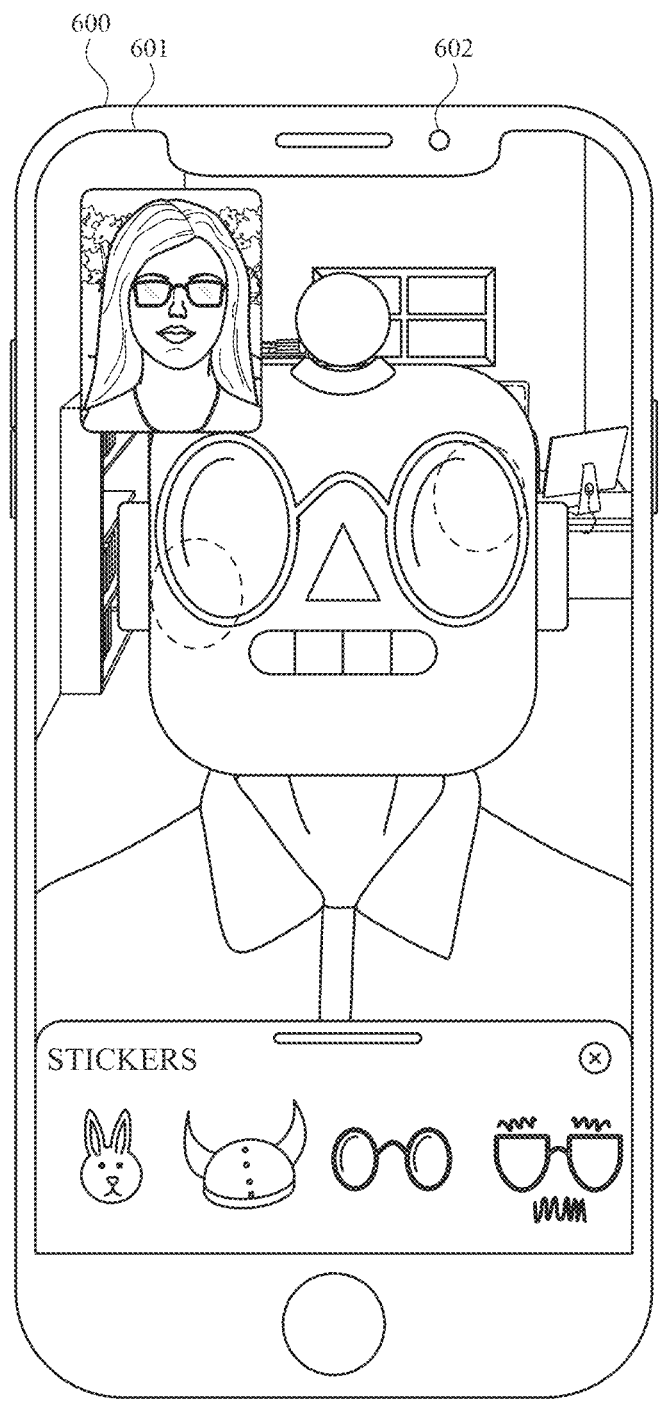
Figure 12Z:
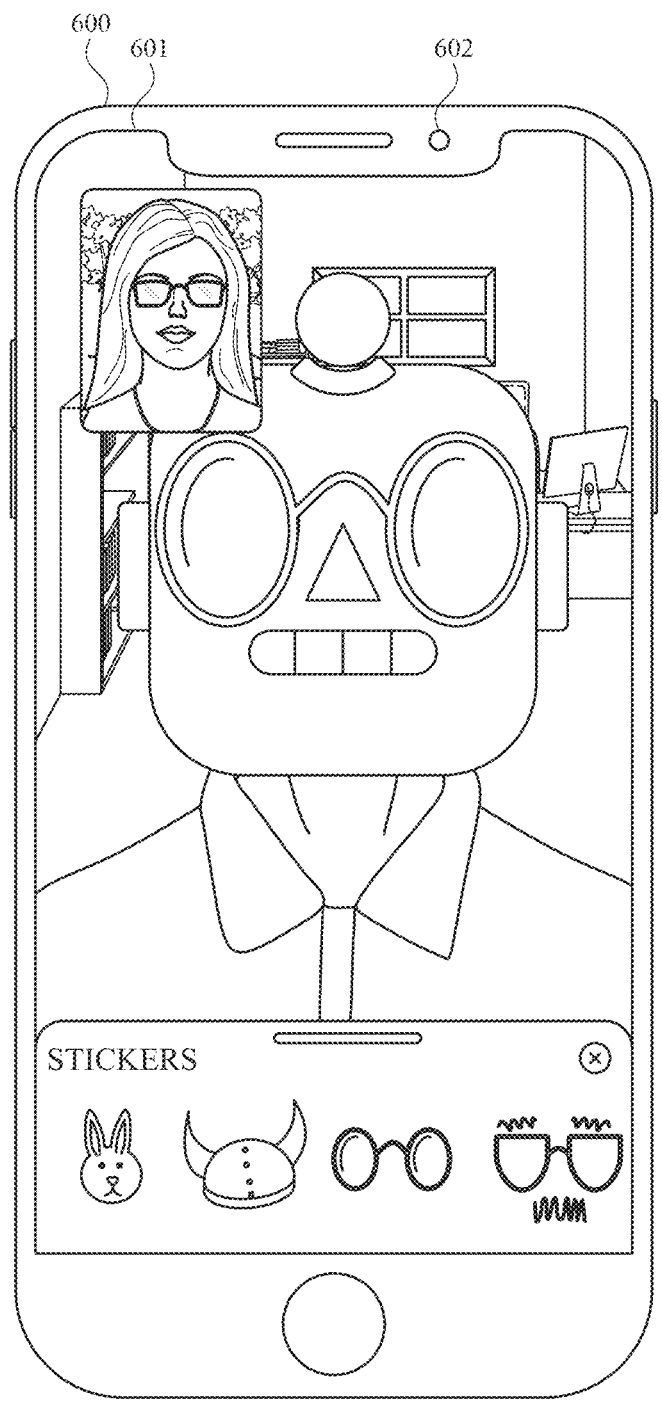
Figure 12A:
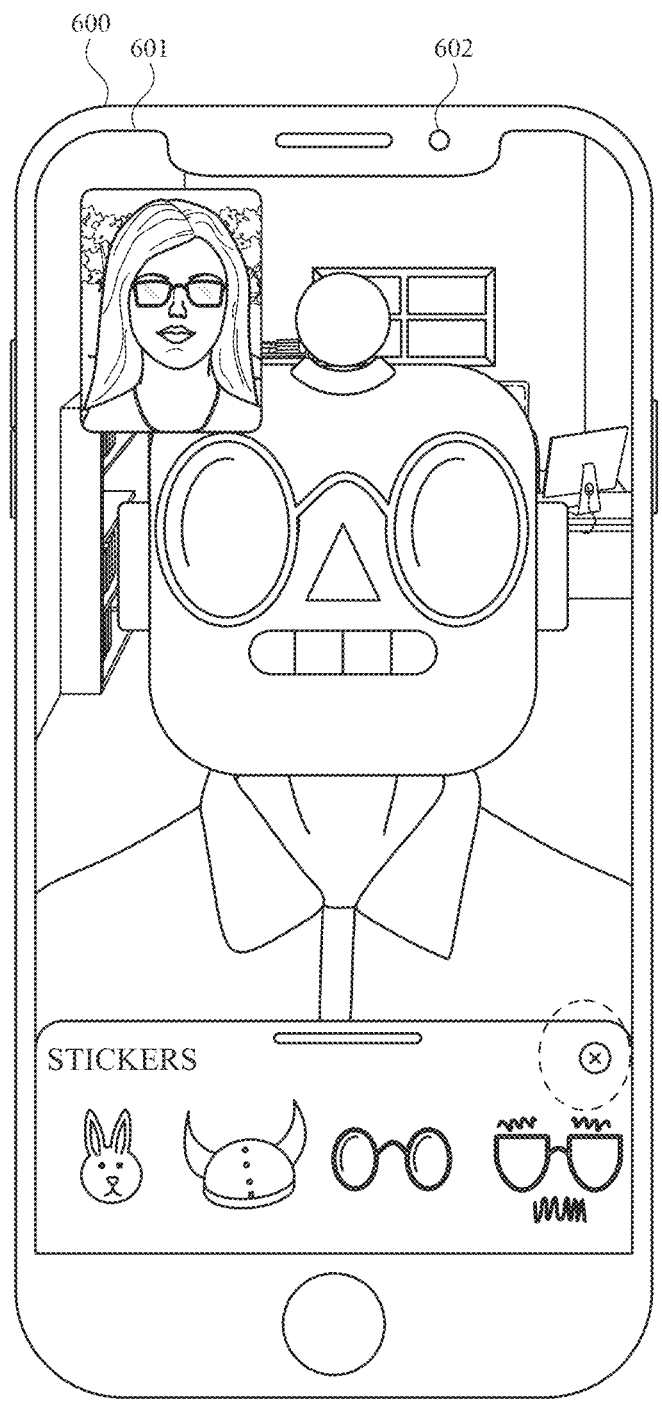
Figure 12A:
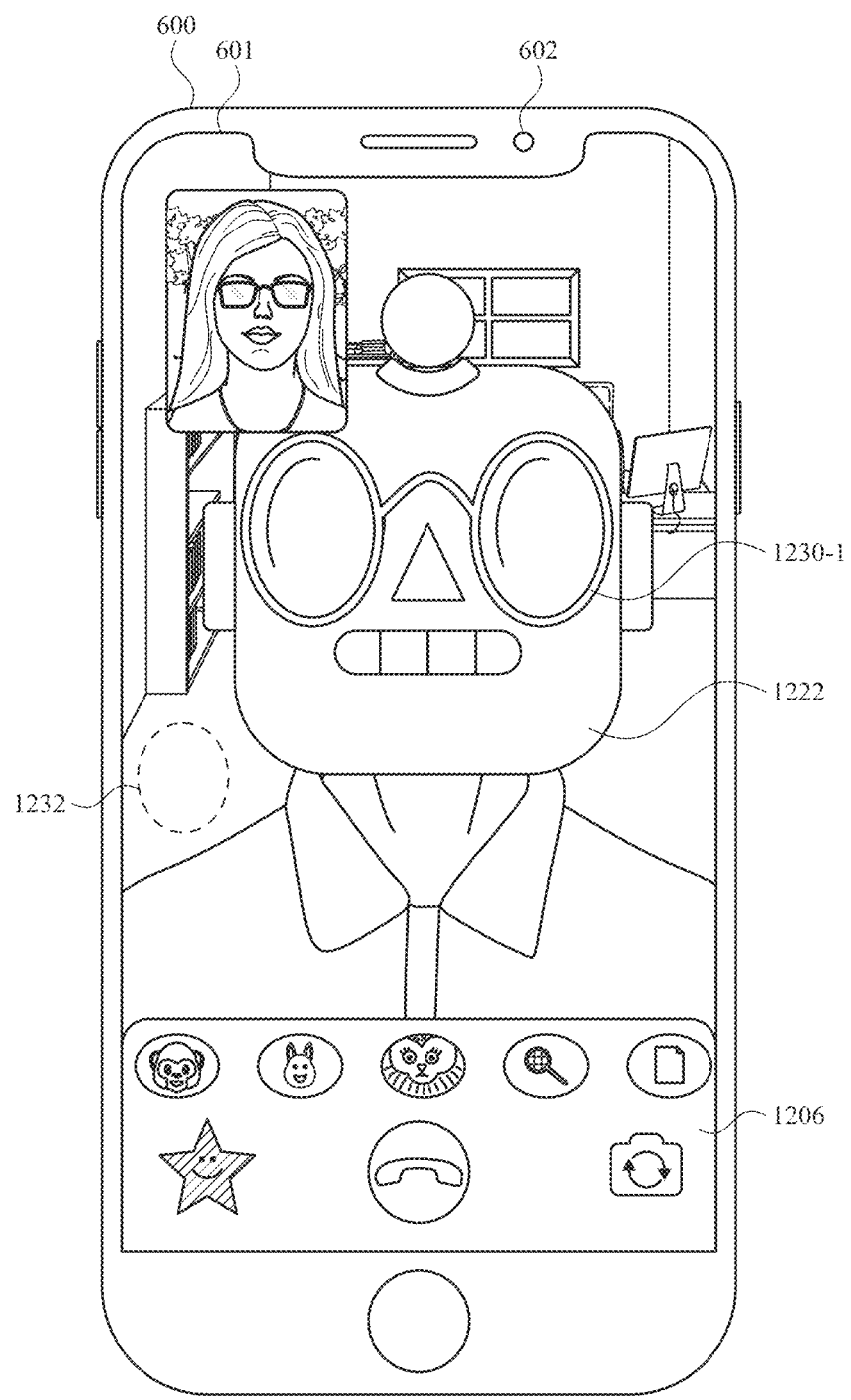
Figure 12A:
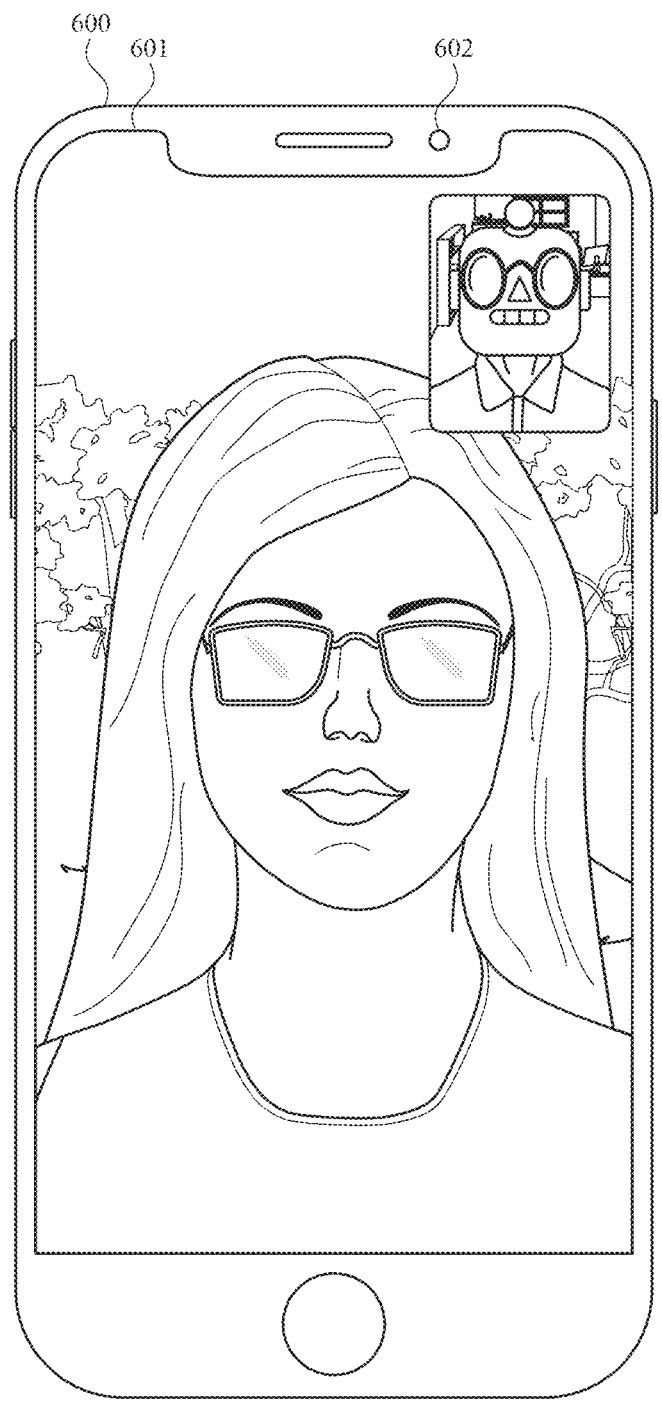
Figure 12A:
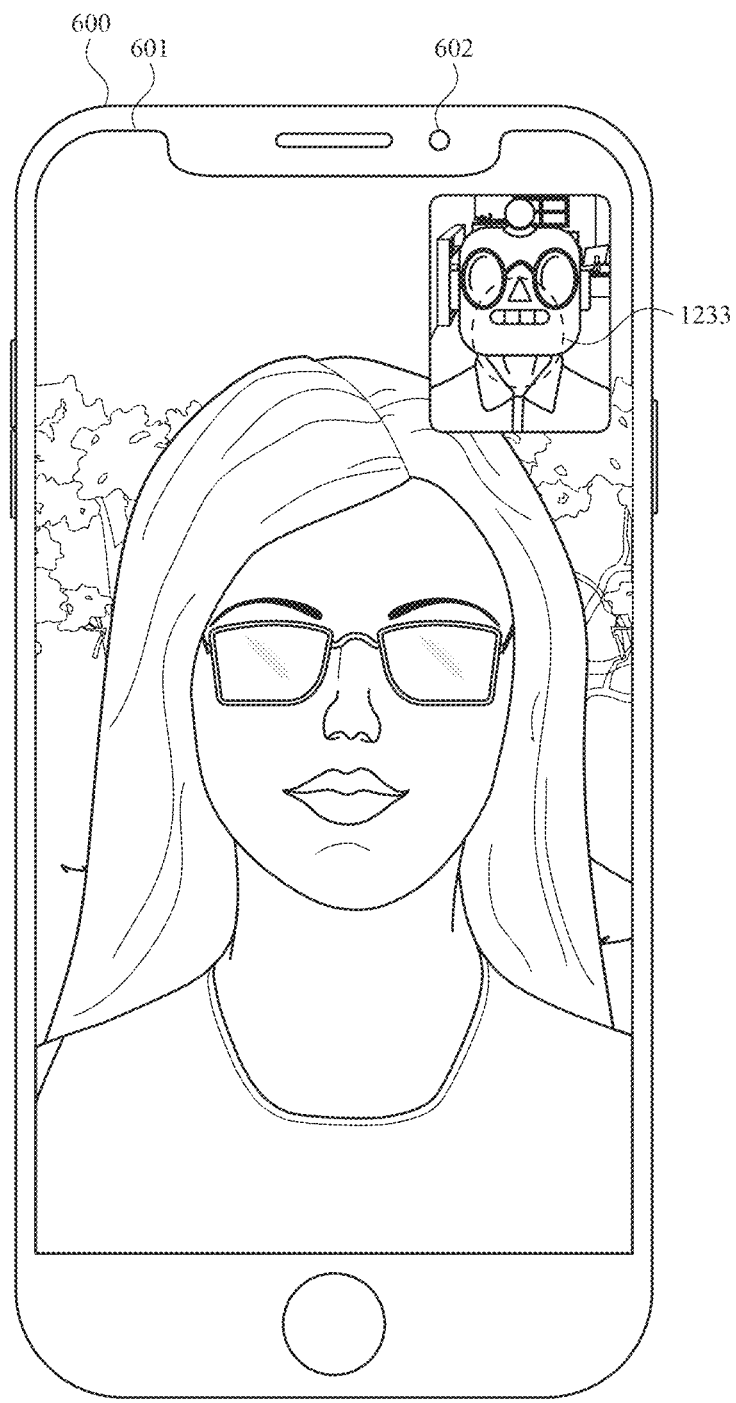
Figure 12A:
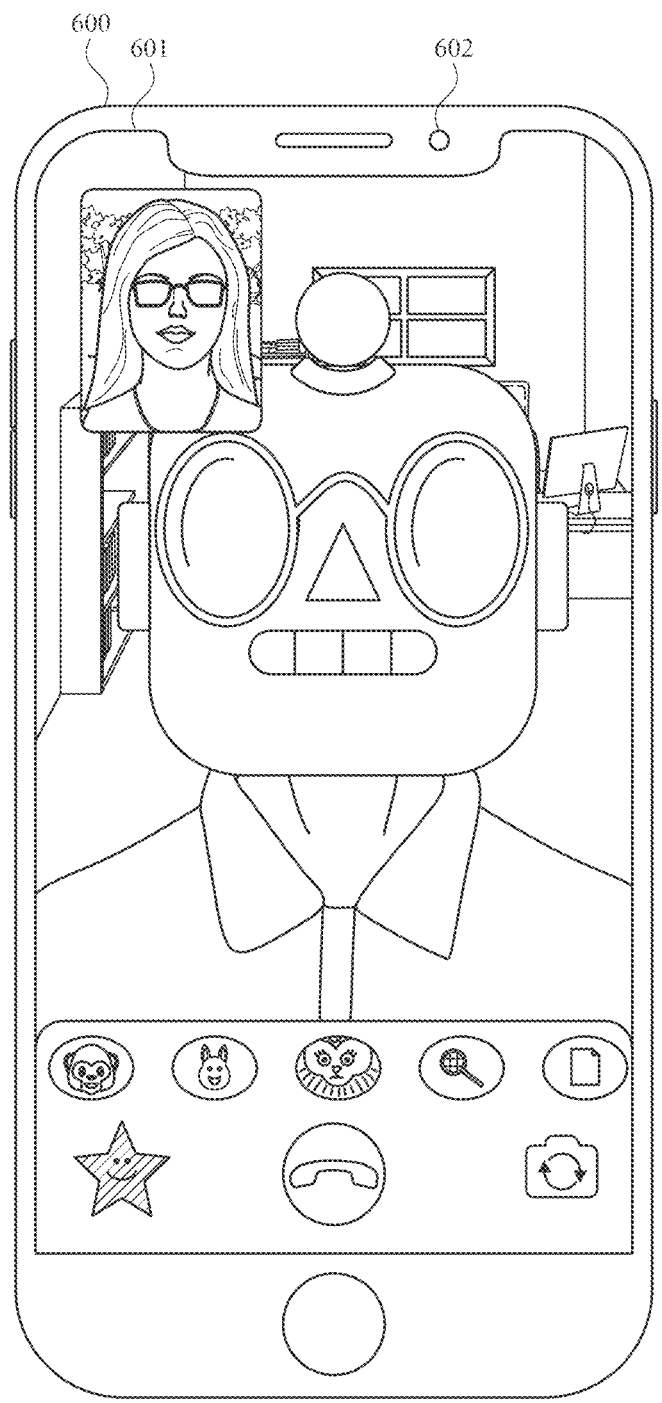
Figure 12A:
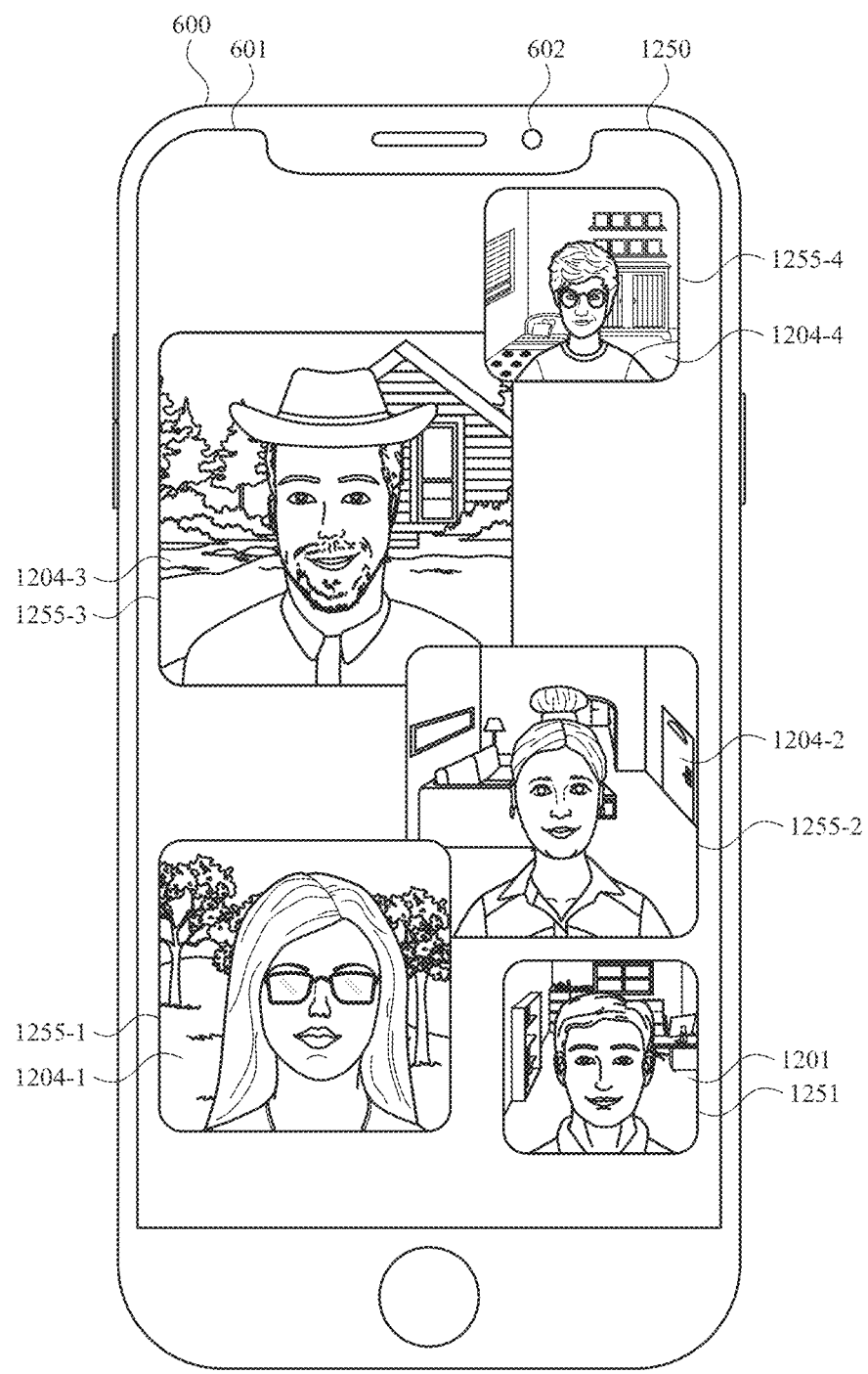
Figure 12A:
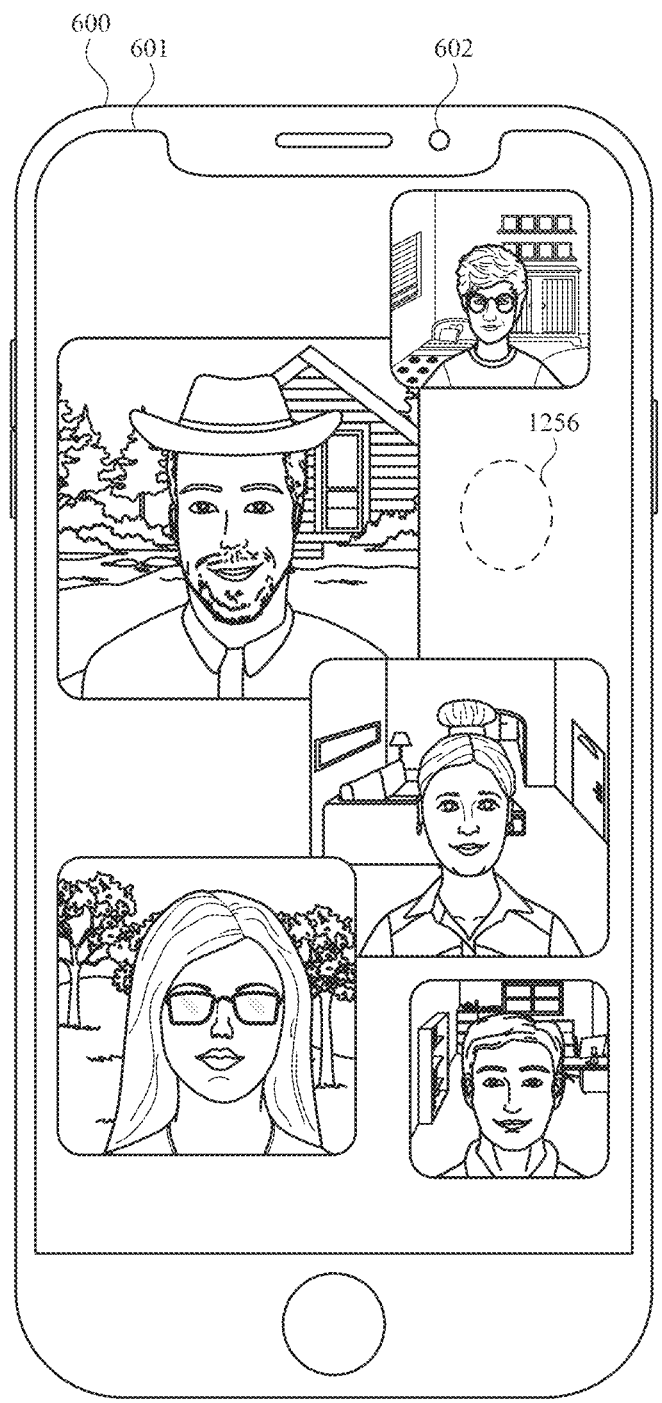
Figure 12A:
Figure 12A:
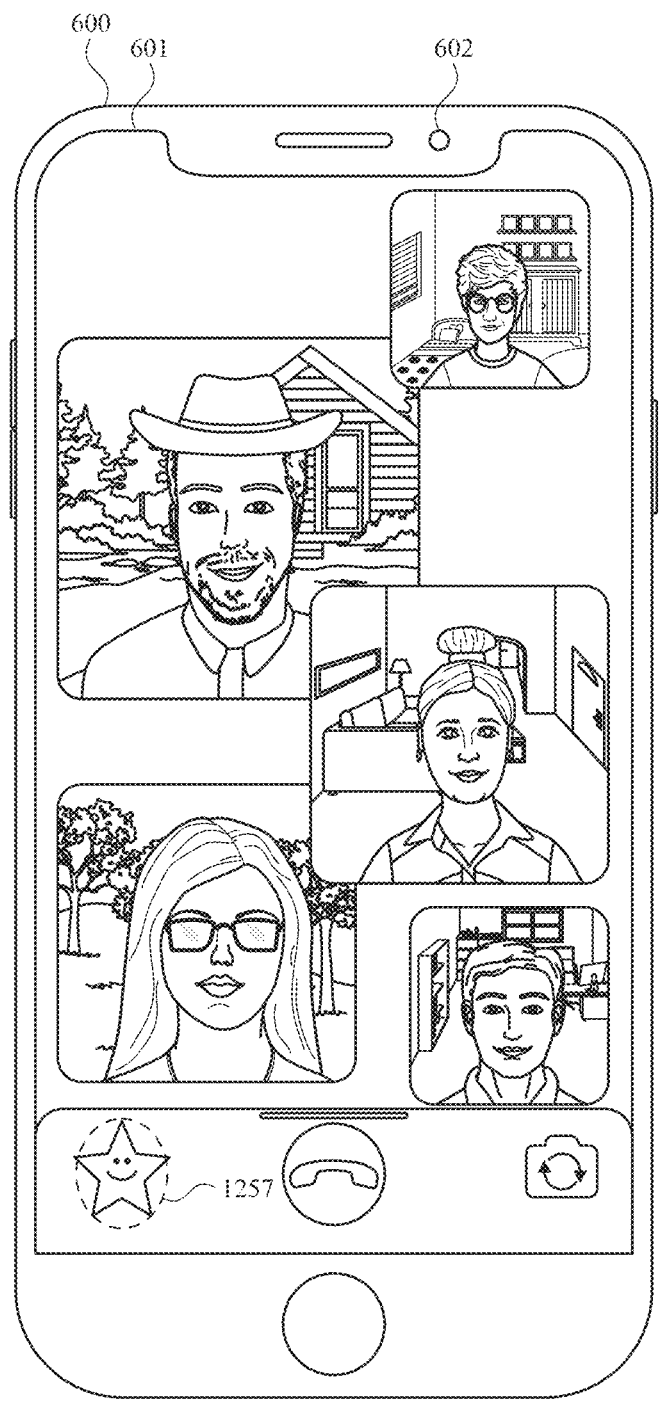
Figure 12A:
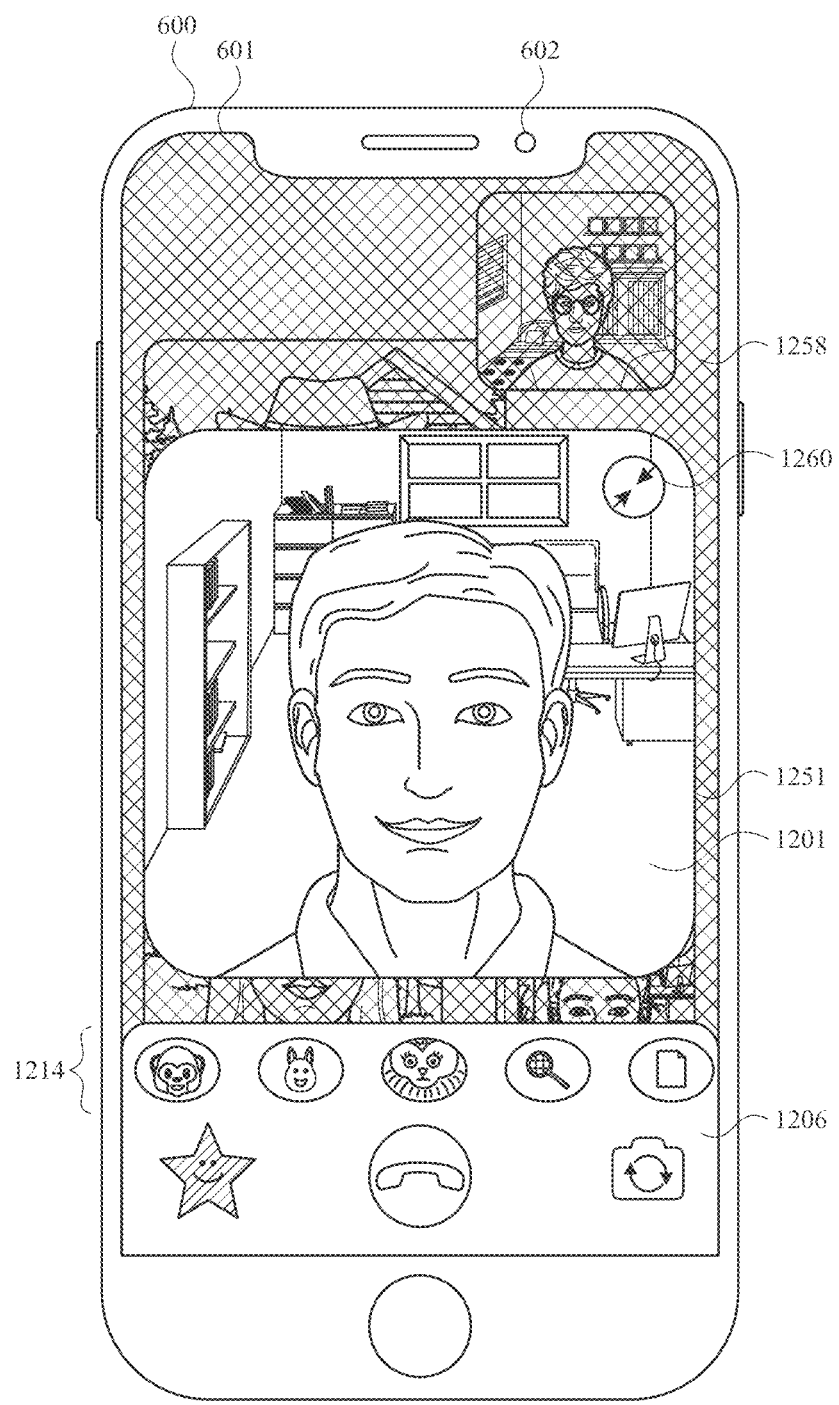
Figure 12A:
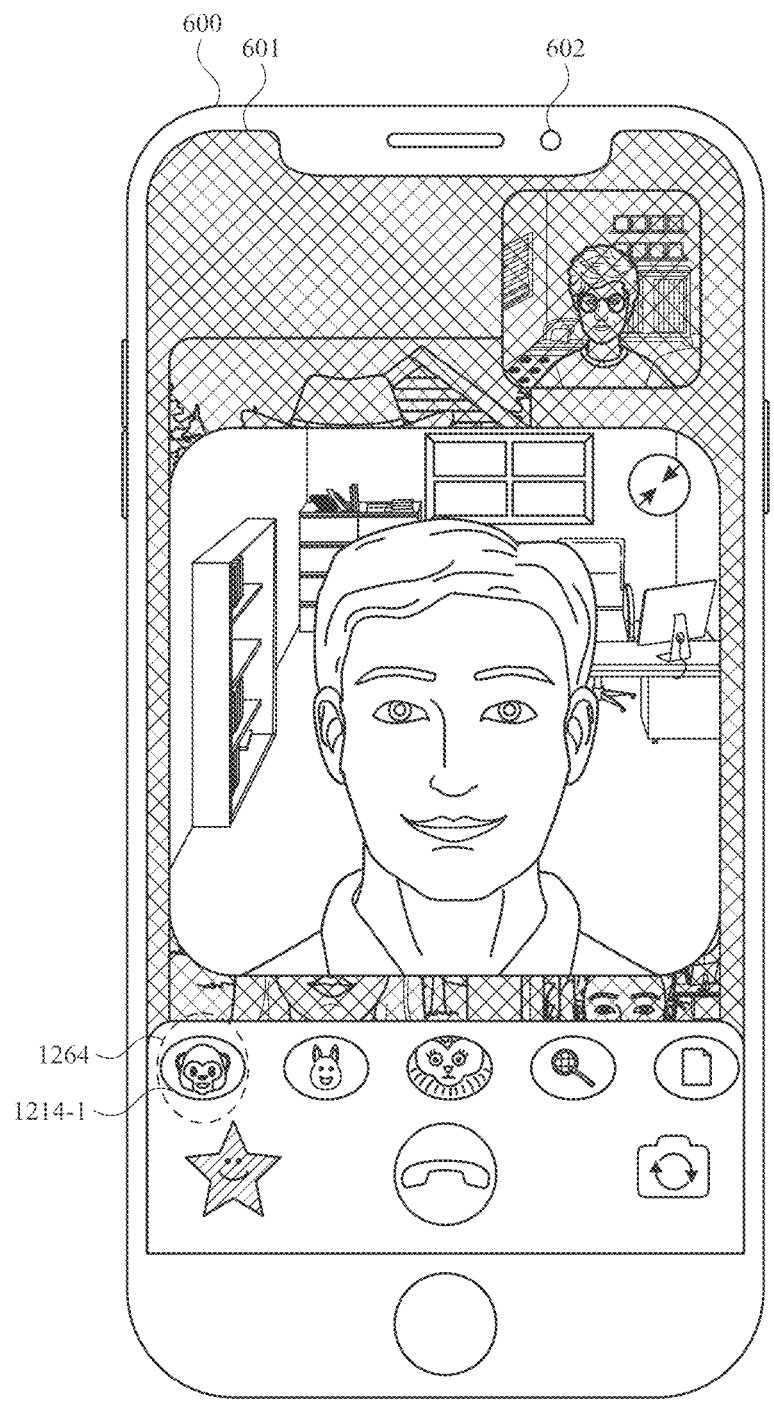
Figure 12A:
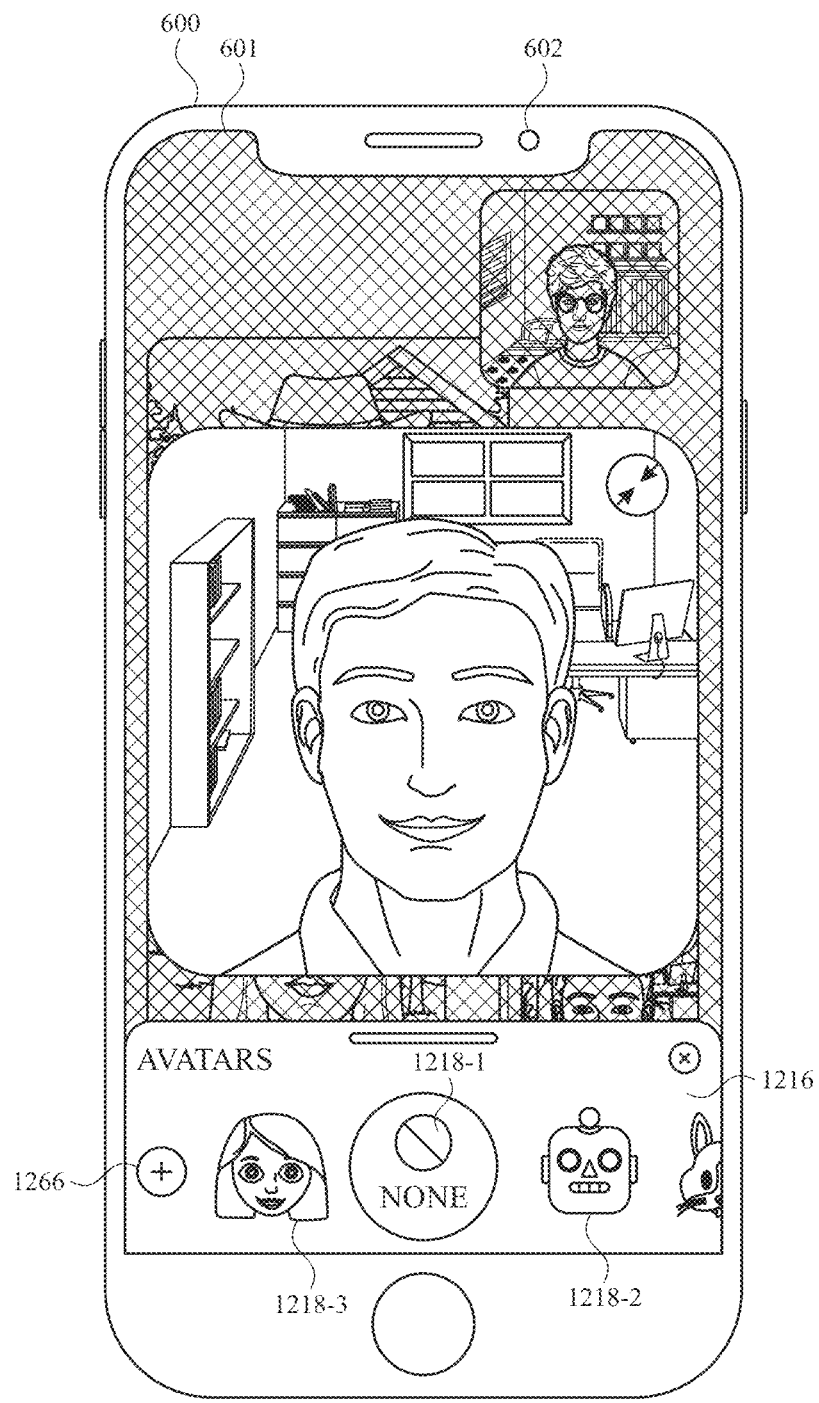
Figure 12A:
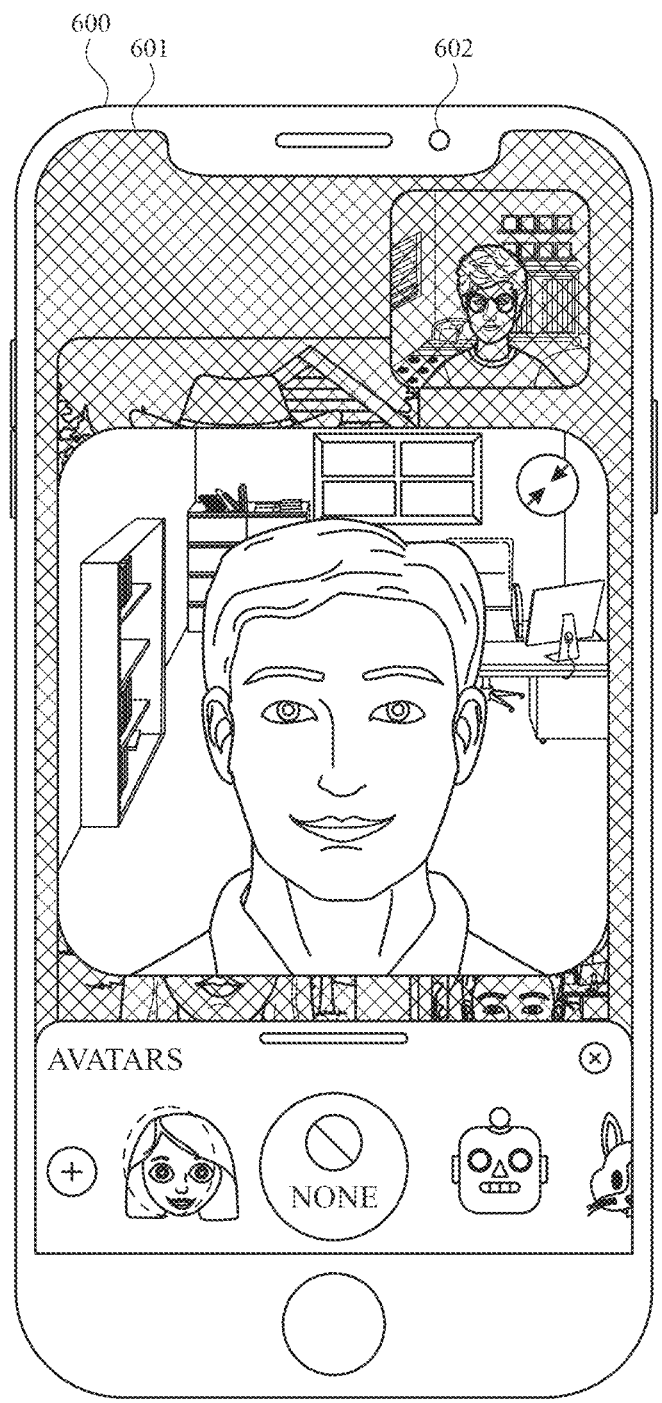
Figure 12A:
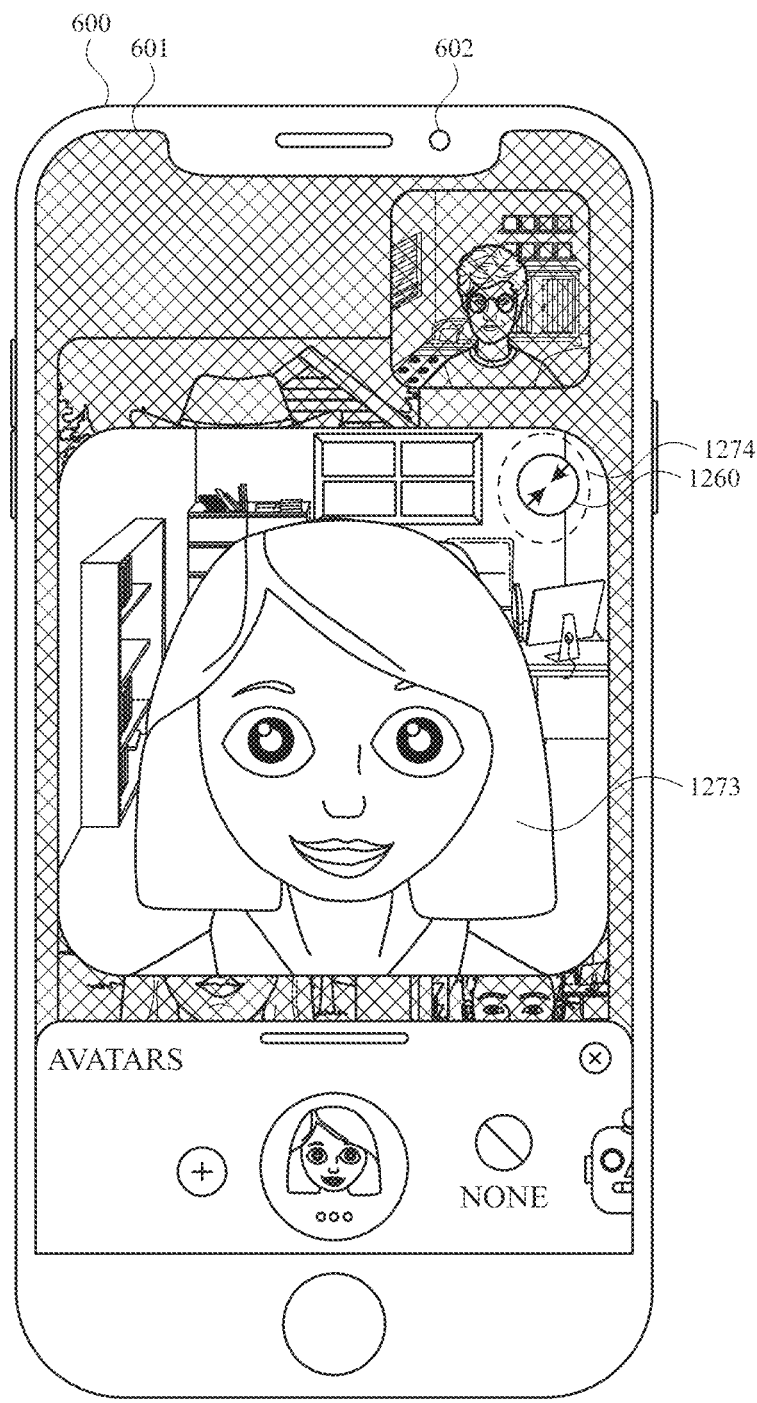
Figure 12A:
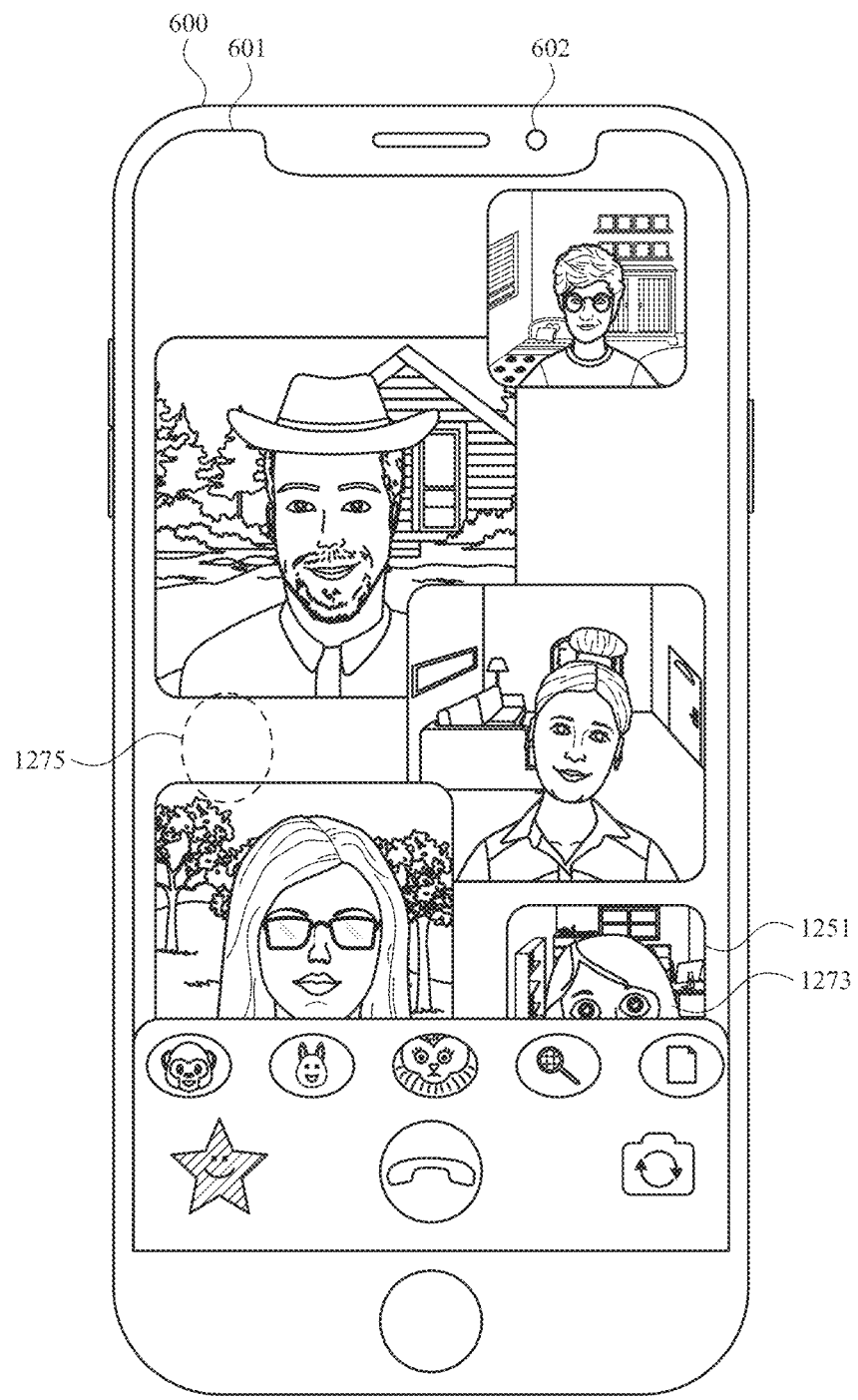
Figure 12A:
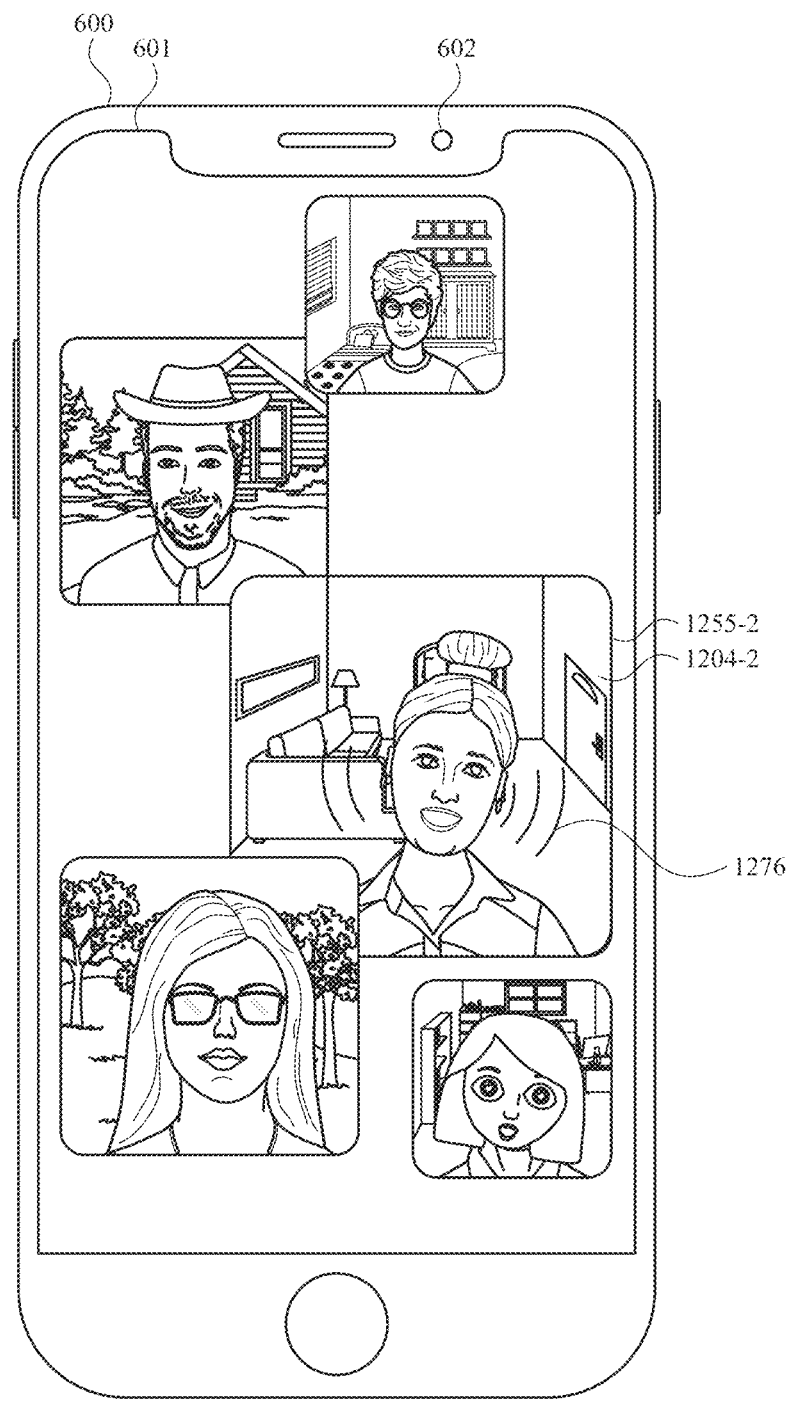

FIGS. 12T-12AA illustrate a process for applying and modifying stickers in device image data 1201. Device 600 detects selection of glasses sticker 1230-1, and displays glasses sticker 1230-1 in device image data 1201. Device 600 also detects subsequent gestures to move, resize, and position glasses sticker 1230-1 on robot avatar 1222. These processes are discussed in greater detail above with respect to FIGS. 6U-6AD, 8AH-8AK, and 8AR-8AY. For the sake of brevity, details of these process are not repeated here.

In some embodiments, selected stickers 1230 are not visible to other participants in the live communication session until the user places the sticker in device image data 1201. In some embodiments, modifications to placed stickers 1230 are not visible to other participants until the modification is complete. In some embodiments, once a selected sticker appears over device image data 1201 in user interface 1200, the sticker is visible to participants in the video communication session, even if the user has not yet placed the sticker 1230. Similarly, modifications to placed stickers are visible such that continued adjustments of the sticker are visible to other participants in the live video communication session, even if the user is still modifying placement of the sticker.

In FIG. 12AB, robot avatar 1222 and glasses sticker 1230-1 are applied to device image data 1201 and options display region 1206 is displayed. Device 600 detects gesture 1232 on user interface 1200 and, in response, switches the displayed locations of device image data 1201 and participant image data 1204, in FIG. 12AC, such that device image data 1201 is displayed in window 1202, which is optionally moved to another location in user interface 1200. The visual effects (e.g., robot avatar 1222 and glasses sticker 1230-1) are displayed in device image data 1201 positioned in window 1202.

Device image data 1201 can be enlarged again (by again switching positions with participant image data 1204) in response to receiving gesture 1233 on window 1202, as shown in FIG. 12AD. Device 600 shows device image data 1201 and participant image data 1204 switched in FIG. 12AE, with the displayed visual effects and options display region 1206. Because effects mode is enabled, when options display region 1206 is displayed, visual effects option affordances 1214 are also displayed.

The foregoing description for displaying visual effects in a live video communication session also applies to a live video communication session having three or more participants. FIGS. 12AF-12AP illustrate various methods for applying visual effects in such an embodiment.

In FIG. 12AF, device 600 displays user interface 1200 having device image data 1201 in user window 1251 and respective participant image data 1204-1 to 1204-4 in respective participant windows 1255-1 to 1255-4.

In FIG. 12AG, device 600 receives input 1256 on user interface 1200 and, in response, in FIG. 12AH, displays options display region 1206 having effects affordance 1208, camera selector affordance 1210, and end affordance 1212. Because effects mode is not enabled when device 600 receives input 1256, options display region 1206 is displayed without visual effects option affordances 1214.

In FIG. 12AI, device 600 detects input 1257 on effects affordance 1208, which enables visual effects mode. Device 600 then displays user window 1251 expanding to an enlarged view, as shown in FIG. 12AJ, while also applying a blurred effect 1258 behind window 1251, and expanding options display region 1206 to display visual effects option affordances 1214. Expanded window 1251 includes return icon 1260, which is selectable to return to the view shown in FIG. 12AI.

Visual effects can be applied to device image data 1201 using visual effects option affordances 1214, as explained above. For example, device 600 can apply stickers in a manner consistent with that described above with respect to FIGS. 12R-12AB. FIGS. 12AK-12AN illustrate a user adding customizable avatar 1262 to the user's face in device image data 1251. For example, avatar effects affordance 1214-1 is selected (1264) in FIG. 12AK, which causes device 600 to display avatar options menu 1216 having avatar options 1218, including null avatar option 1218-1 (selectable to forego displaying an avatar or removing a displayed avatar), non-customizable robot avatar option 1218-2, customizable avatar option 1218-3, and new avatar affordance 1266 (selectable to create a new avatar in a manner similar to new avatar affordance 813). Customizable avatar option 1218-3 can be customized in a manner similar to customizable avatar option 830-5 discussed above.

In FIGS. 12AM-12AN customizable avatar option 1218-3 is selected, and device 600 displays customizable avatar 1273 on the user's face in device image data 1201 displayed in window 1251. Device 600 modifies customizable avatar 1273 based on detected changes in the user's face positioned in a field-of-view of camera 602. Device indicates when the user's face is not detected within the field-of-view of camera 602, as explained with respect to previous embodiments discussed herein.

In FIG. 12AN, device 600 detects input 1274 on return icon 1260 and, in response, displays device image data 1201 in window 1251 as shown in FIG. 12AO, including the applied visual effects (e.g., customizable avatar 1273). In the embodiment illustrated in FIG. 12AO, device image data 1201 and applied visual effects are visible to other participants in the live video communication session. Because visual effects are enabled, options display region 1206 is displayed with visual effects option affordances 1214 and effects affordance 1208 highlighted.

In FIG. 12AO, device detects input 1275 on user interface 1200 and, in response, hides options display region 1206, and shifts and resizes the position of various participant windows 1255, as shown in FIG. 12AP. In some embodiments, device 600 enlarges a respective participant window when the participant is speaking. For example, in FIG. 12AP, device 600 detects audio 1276 (e.g., laughter) from the woman represented in participant image data 1204-2 and, in response, enlarges the woman's participant window 1255-2.

FIGS. 13A-13B are a flow diagram illustrating a method for displaying visual effects in a live video communication session using an electronic device in accordance with some embodiments. Method 1300 is performed at a device (e.g., 100, 300, 500, 600) with a display apparatus. Some operations in method 1300 are, optionally, combined, the orders of some operations are, optionally, changed, and some operations are, optionally, omitted.

As described below, method 1300 provides an intuitive way for displaying visual effects in a live video communication session. The method reduces the cognitive burden on a user for displaying visual effects, thereby creating a more efficient human-machine interface. For battery-operated computing devices, enabling a user to display visual effects faster and more efficiently conserves power and increases the time between battery charges.

The electronic device (e.g., 600) displays (1302), via the display apparatus (e.g., 601), a live video communication user interface (e.g., 1200) of a live video communication application. The live video communication user interface includes (1304) a representation (e.g., 1201) of a subject participating in a live video communication session. Including a representation of a subject participating in a live video communication session enables the user to quickly and easily recognize the other participant(s) of the live video communication session. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the representation of the subject participating in the live video communication session includes (1306) image data captured by a camera (e.g., 602) associated with the electronic device. In some embodiments, the subject is a user of the electronic device. In some embodiments, the representation of the subject participating in the live video communication session includes image data transmitted to the electronic device from a second electronic device. In some embodiments, the second electronic device is a device of another user, and the subject is the other user.

In some embodiments, the live video communication user interface (e.g., 1200) further includes a representation (e.g., 1204) of a second participant in the live video communication session and a representation of a third participant in the live video communication session. In some embodiments, displayed sizes of the representations of the second and third participants in the live video communication session are adjusted so all representations of the participants can fit on the screen. Adjusting the sizes of the representations of the second and third participants to fit on the screen allows the user to simultaneously view their reactions to the visual effects applied to the representation of the user, thereby enhancing the operability of the device and making the user-device interface more efficient (e.g., by allowing the user to easily view the reactions of other participants without manual inputs) which, additionally, reduces power usage and improves battery life of the device by enabling the user to use the device more quickly and efficiently.

The live video communication user interface (e.g., 1200) includes (1308) a first affordance (e.g., 1208, an effects affordance) (e.g., an affordance associated with a function for activating a camera effects mode (e.g., a mode in which various camera effects can be applied to the representation of a user in a live video communication session)).

In some embodiments, prior to displaying the first affordance (e.g., 1208), the electronic device (e.g., 600) detects a first input (e.g., 1205) on the live video communication user interface (e.g., 1200) (e.g., a tap gesture on the live video communication user interface to display video call options), the first input corresponding to a request to display one or more options (e.g., an option to end the call, an option to switch a camera view, etc.) associated with the live video communication session. In some embodiments, in response to detecting the first input, the electronic device displays the one or more options (e.g., 1208, 1210, 1212) associated with the live video communication session. In some embodiments, the electronic device displays the first affordance (e.g., 1208).

The electronic device (e.g., 600) detects (1310) a gesture (e.g., 1213) directed to the first affordance (e.g., 1208). In response to detecting (1312) the gesture directed to the first affordance, the electronic device activates (1314) a camera effects mode.

In some embodiments, in response to detecting the gesture directed to the first affordance (e.g., 1208), the electronic device (e.g., 600) displays a first visual-effect affordance associated with a first type of visual effect and a second visual-effect affordance associated with a second type of visual effect that is different from the first type of visual effect and, optionally, a third visual-effect affordance associated with a third type of visual effect that is different from the first type of visual effect and the second type of visual effect (e.g., a sticker affordance 1214-2, an avatar affordance 1214-1, an affordance associated with a full-screen effect). In some embodiments, a sticker affordance is associated with a visual effect in which a sticker is displayed in the representation of the subject participating in the live video communication session. In some embodiments, an avatar affordance is associated with a visual effect in which a virtual avatar is displayed on the representation of the subject participating in the live video communication session. In some embodiments, a full-screen effect includes a visual effect in which graphical objects such as confetti or balloons are displayed in front of, behind, and/or on a participant in the live video communication session.

In some embodiments, the electronic device (e.g., 600) detects a selection (e.g., 1215) of one of the affordances (e.g., a sticker affordance 1214-2, an avatar affordance 1214-1, an affordance associated with a full-screen effect) associated with a type of visual effect. In some embodiments, in response to detecting the selection of the affordance associated with the visual effect, the electronic device displays a plurality of visual effect options (e.g., 1218) corresponding to the visual effect. Displaying a plurality of visual effect options corresponding to the visual effect in response to detecting a selection of the affordance associated with the visual effect allows the user to quickly and easily access corresponding visual effect options. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, a sticker affordance is associated with a visual effect that includes displaying a representation of a static graphical object (e.g., a hat, a star, glasses, etc.) in image data (e.g., the representation of the subject participating in the live video communication session). In some embodiments, an avatar affordance is associated with a visual effect that includes displaying a representation of a virtual avatar (e.g., a customizable virtual avatar or a non-customizable virtual avatar) such that image data of a person's head is replaced with a graphical representation of the virtual avatar. In some embodiments, a full-screen effect includes a visual effect in which graphical objects such as confetti or balloons are displayed in front of, behind, and/or on a participant in the live video communication session.

In response to detecting (1312) the gesture directed to the first affordance, the electronic device (e.g., 600) increases (1316) a size of the representation (e.g., 1201) of the subject participating in the live video communication session. Increasing the size of the representation of the subject participating in the live video communication session in response to detecting (1312) the gesture directed to the first affordance enables the user to quickly and easily adjust the size of the representation of the subject. Providing additional control options without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, increasing the size of the representation of the subject includes switching the position of the displayed representation of the subject with the position of a displayed participant in the live video communication session.

In some embodiments, while the camera effects mode is activated (1318), the electronic device (e.g., 600) detects (1320) a selection of an effects option affordance (e.g., a selectable icon associated with a function for displaying a visual effect in the representation of the subject participating in the live video communication session). In some embodiments, the effects option affordance is a stickers affordance, an avatar affordance, or an affordance associated with a full-screen effect such as confetti or balloons.

In some embodiments, in response to detecting selection of the effects option affordance, the electronic device modifies (1322) an appearance of the representation of the subject participating in the live video communication session based on a visual effect (e.g., displaying a sticker, avatar, or full-screen effect) associated with the selected effects option affordance. Modifying an appearance of the representation of the subject participating in the live video communication session based on a visual effect associated with the selected effects option affordance provides visual feedback that application of the selected visual effect was successful. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, in response to detecting selection of a sticker affordance, the representation of the user participating in the live video communication session is modified to display a selected sticker. In some embodiments, in response to detecting selection of an avatar affordance, the representation of the user participating in the live video communication session is modified to display an avatar positioned on the face of the user. In some embodiments, in response to detecting selection of an affordance associated with a full-screen effect, a full-screen effect is displayed in the representation of the user participating in the live video communication session (e.g., confetti is displayed falling in front of, behind, and on the representation of the user).

In some embodiments, the electronic device (e.g., 600) detects a second input on the live video communication user interface (e.g., 1200), the second input corresponding to a request to reduce the size of the representation of the subject participating in the live video communication session. In some embodiments, in response to detecting the second input, the electronic device concurrently displays the representation of the subject participating in the live video communication session having the modified appearance based on the visual effect associated with the selected effects option affordance and one or more representations of respective participants in the live video communication session. Concurrently displaying the representation of the subject participating in the live video communication session and one or more representations of respective participants in the live video communication session in response to detecting the second input enables the user to quickly and easily view (simultaneously) other participants of the live video communication. Providing additional control options without cluttering the UI with additional displayed controls enhances the operability of the device and makes the user-device interface more efficient (e.g., by helping the user to provide proper inputs and reducing user mistakes when operating/ interacting with the device) which, additionally, reduces power usage and improves battery life of the device by enabling the user to use the device more quickly and efficiently. In some embodiments, the representation of the user in the live video communication session is reduced so that it is displayed on the screen with representations of other participants in the live video communication session.

In some embodiments, while the camera effects mode is activated (1318), the electronic device (e.g., 600) modifies (1324) an appearance of the representation (e.g., 1201) of the subject participating in the live video communication session to display one or more visual effects. In some embodiments, when the visual effect is a sticker effect, the appearance of the representation of the subject participating in the live video communication session is modified to include display of a static graphical object (e.g., a sticker). In some embodiments, the static graphical object (e.g., sticker) interacts with the representation of the subject participating in the live video communication session. In some embodiments, when the visual effect is an avatar effect, the appearance of the representation of the subject participating in the live video communication session is modified to display a representation of a virtual avatar (e.g., a customizable virtual avatar or a non-customizable virtual avatar) replacing the subject's head. In some embodiments, when the visual effect is a full-screen effect, the appearance of the representation of the subject participating in the live video communication session is modified to display graphical objects (e.g., graphical confetti or graphical balloons) displayed in front of, behind, and/or on a participant in the live video communication session).

In some embodiments, the modified appearance is sent/transmitted to other participants in the live video communication session. In some embodiments, transmitting the data includes transmitting the image data (e.g., a real-time stream of image data) from the field of view of the camera) along with data (e.g., separate data) representing the modifications made based on the selected visual effect. In some embodiments, transmitting the data includes transmitting composite video data that includes the image data from the field of view of the camera combined with data representing the modifications made based on the selected visual effect.

In some embodiments, while the camera effects mode is activated, the electronic device (e.g., 600) modifies an appearance of the representation (e.g., 1200) of the subject participating in the live video communication session to display a virtual avatar. In some embodiments, the electronic device detects a change in a face in a field of view of one or more cameras (e.g., 602) of the electronic device. In some embodiments, the electronic device changes an appearance of the virtual avatar based on the detected change in the face. Changing the appearance of the virtual avatar based on the detected change in the face provides visual feedback that the virtual avatar is based on/associated with the face. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the virtual avatar is modified to mirror movement of the subject participating in the live video communication session. In some embodiments, the change in the face is detected using one or more depth cameras and/or depth maps, as discussed herein.

In some embodiments, while the camera effects mode is activated, the electronic device (e.g., 600) displays a first visual effect (e.g., a sticker) in the representation of the subject participating in the live video communication session. In some embodiments, the electronic device detects an input (e.g., a touch input) corresponding to the first visual effect. In some embodiments, in response to detecting the input corresponding to the first visual effect, in accordance with a determination that the input is a first type (e.g., a touch-and-drag gesture), the electronic device modifies a location of the first visual effect in the representation of the subject participating in the live video communication session based on a magnitude (e.g., a distance the gesture is moved) and direction of the input. In some embodiments, in response to detecting the input corresponding to the first visual effect, in accordance with a determination that the input is a second type (e.g., a pinch or de-pinch gesture), the electronic device modifies a size of the first visual effect based on the magnitude (e.g., the adjusted distance between the contact points of the pinch/de-pinch gesture) of the input. Modifying the location of the first visual effect in the representation of the subject participating in the live video communication session based on a magnitude of the input or modifying the size of the first visual effect based on the magnitude (e.g., the adjusted distance between the contact points of the pinch/de-pinch gesture) of the input based on the type of the input enables the user to quickly and easily adjust the location or the size of a visual effect (by simply changing the type of the input). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, modifying the location of the first visual effect includes one or more of the following steps: prior to detecting termination of the input (e.g., 889), displaying movement of the first visual effect (e.g., 858-4) based on the magnitude and direction of the input; and in accordance with a determination that the first visual effect (e.g., a sticker (858-4)) moves across a border region of a predetermined location (e.g., a location corresponding to a portion of the representation of the subject (e.g., the subject's face)), generating an indication (e.g., display a bracket (e.g., 890) or generate a haptic response (e.g., 892)) that the first visual effect has crossed (e.g., or is crossing) the border region (e.g., displaying a bracket around the representation of the subject's face as shown in FIG. 8BG). In some embodiments, when (or after) crossing into the border region of the predetermined location, the device displays a bracket around the predetermined location and/or generates a haptic feedback (e.g., a tactile output) to indicate the sticker is positioned on the subject's face and will be placed on the subject's face upon termination of the gesture (e.g., the sticker will have a relationship to the representation of the subject's face; e.g., the sticker will have a behavior based on the relationship of the sticker to the user's face). In some embodiments, when (or after) crossing out of the border region of the predetermined location, the device displays a bracket around the predetermined location and/or generates a haptic feedback to indicate the sticker is no longer positioned on the subject's face and will not be placed on the subject's face upon termination of the gesture (e.g., the sticker will have a different relationship to the representation of the subject's face; e.g., the sticker will have a different behavior based on the relationship of the sticker to the user's face; e.g., the sticker will be positioned remote from the subject's face). In some embodiments, the indication is at least one of a haptic feedback (e.g., a tactile output and/or an audio output) or a visual feedback (e.g., a visual representation of the border region; a bracket displayed around the predetermined location).

Generating an indication that the first visual effect has crossed (or is crossing) the border region provides visual and/or haptic feedback to the user that the behavior and placement of the sticker has changed, without requiring the user to terminate the gesture and experiment with the modeled behavior. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, modifying the location of the first visual effect includes displaying movement of the first visual effect from a first location to a second location. In some embodiments, modifying the size of the first visual effect includes displaying a transition of the first visual effect from a first displayed size to a second displayed size. In some embodiments, when a sticker is being moved on the display or resized, the sticker movement and/or resizing is displayed such that the user and other participants in the live video communication session can see the changes, including the intermediate movement/resizing as the sticker is being modified.

In some embodiments, modifying the location of the first visual effect includes transitioning the first visual effect from appearing at a first location to appearing at a second location, without displaying the first visual effect appearing at an intermediate location. In some embodiments, modifying the size of the first visual effect includes transitioning the first visual effect from a first displayed size to a second displayed size, without displaying the first visual effect having an intermediate size. In some embodiments, when a sticker is being moved on the display or resized, the sticker movement and/or resizing is displayed such that only the user can see the changes, including the intermediate movement/resizing as the sticker is being modified, but other participants in the live video communication session cannot see the intermediate movement/resizing of the sticker. Thus, other participants only see the sticker (or updates to the sticker) after it has been modified.

In some embodiments, a plurality of participants are participating in the live video communication session, the plurality of participants including the subject (e.g., a user of the electronic device) and a first remote participant (e.g., a user of a second electronic device, remote from the first electronic device. In some embodiments, the live video communication user interface (e.g., 1200) further includes a representation of the first remote participant. In some embodiments, the representation of the first remote participant includes image or video data received from a remote device/a remote camera. In some embodiments, further in response to detecting the gesture directed to the first affordance, the electronic device reduces a size of the representation of the first remote participant.

In some embodiments, a plurality of participants are participating in the live video communication session, the plurality of participants including the subject (e.g., a user of the electronic device) and a first remote participant (e.g., a user of a second electronic device, remote from the first electronic device), and where the representation of the subject is a live preview of a field of view of a camera (e.g., 602) of the electronic device (e.g., 600) (e.g., a stream of image data that represents what is in the field of view of the camera). In some embodiments, after modifying the appearance of the representation (e.g., 1201) of the subject participating in the live video communication session based on a visual effect associated with the selected effects option affordance, the electronic device transmits data corresponding to the modified appearance of the representation of the subject participating in the live video communication session to at least the remote participant of the plurality of participants. In some embodiments, transmitting the data includes transmitting the image data (e.g., a real-time stream of image data) from the field of view of the camera) along with data (e.g., separate data) representing the modifications made based on the selected visual effect. In some embodiments, transmitting the data includes transmitting composite video data that includes the image data from the field of view of the camera combined with data representing the modifications made based on the selected visual effect.

In some embodiments, the electronic device (e.g., 600) displays the live video communication user interface (e.g., 1200) without the first affordance. In some embodiments, the electronic device detects a touch input on the live video communication user interface (e.g., 1206) (e.g., a tap gesture on the live video communication user interface to display video call options). In some embodiments, in response to detecting the touch input, in accordance with a determination that the camera effects mode is activated, the electronic device displays a live video communication options user interface including the first affordance and a plurality of visual effects affordances (e.g., a sticker affordance, an avatar affordance, an affordance associated with a full-screen effect). In some embodiments, in response to detecting the touch input, in accordance with a determination that the camera effects mode is not activated, the electronic device displays the live video communication options user interface including the first affordance and excluding the plurality of visual effects affordances. Displaying the live video communication options user interface including the first affordance and either including the plurality of visual effects affordances or excluding the plurality of visual effects affordances based on a determination that the camera effects mode is or is not activated indicates whether or not the camera effects mode is currently activated. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 1300 (e.g., FIGS. 13A-13B) are also applicable in an analogous manner to the methods described above and below. For example, method 700 optionally includes one or more of the characteristics of the various methods described above with reference to method 1300. For example, visual effects such as stickers and virtual avatars are displayed in image data in a messaging application user interface. For another example, method 900 optionally includes one or more of the characteristics of the various methods described above with reference to method 1300. For example, visual effects such as stickers and virtual avatars are displayed in image data in a camera user interface. For another example, method 1100 optionally includes one or more of the characteristics of the various methods described above with reference to method 1300. For example, visual effects such as stickers and virtual avatars are displayed in image data in a media user interface. For another example, method 1500 optionally includes one or more of the characteristics of the various methods described above with reference to method 1300. For example, visual effects such as stickers and virtual avatars are displayed in image data for a camera user interface. For brevity, these details are not repeated below.

FIGS. 14A-14M illustrate exemplary user interfaces for displaying visual effects in a camera application, in accordance with some embodiments. The user interfaces in these figures are used to illustrate the processes described below, including the processes in FIGS. 15A-15B.

Figure 14A:
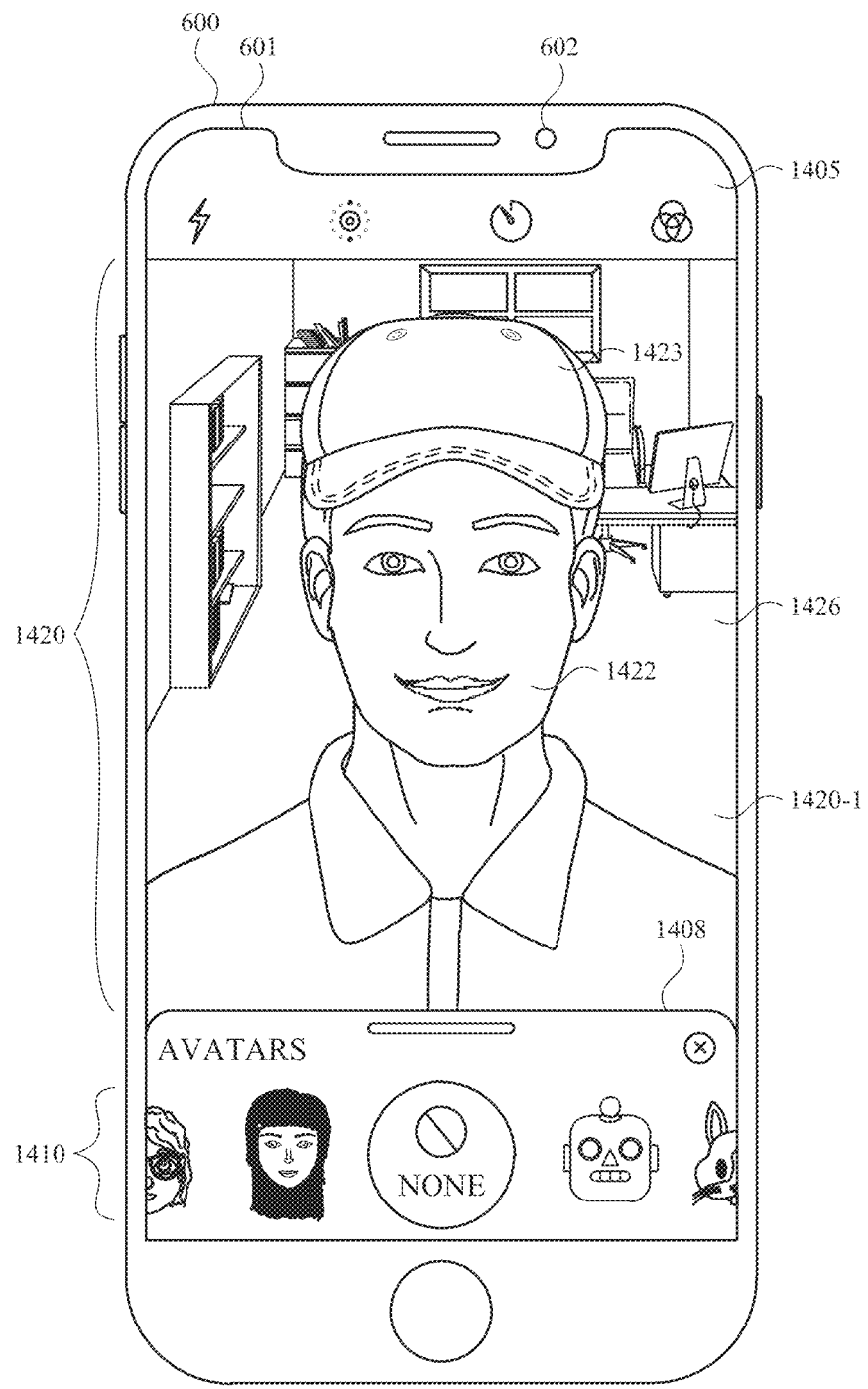
FIGS. 14A-14M illustrate exemplary user interfaces for displaying visual effects in a camera application.

FIG. 14A shows an embodiment of a camera application user interface 1405 similar to the camera application user interface 815 discussed above with respect to FIGS. 8A-8BQ. Camera application user interface 1405 includes image display region 1420 (similar to image display region 820) which displays a representation of image data such as, for example, streamed image data (e.g., a live camera preview, live camera recording, or live video communications session) representing objects positioned within a field-of-view of a camera (e.g., a rear-facing camera or camera 602), or a media item such as, for example, a photograph or a video recording. In the embodiment illustrated in FIG. 14A, image display region 1420 shows live camera preview 1420-1 from camera 602.

The embodiment illustrated in FIG. 14A is similar to that shown in FIG. 8F. Image display region 1420 shows a representation of subject 1422 positioned in the field of view of camera 602 and background 1426 displayed behind the representation of subject 1422. As discussed herein, image data captured using camera 602 includes, in some embodiments, depth data that can be used to determine a depth of objects in the field of view of camera 602. In some embodiments, device 600 parses objects (e.g., in image data) based on a detected depth of those objects, and uses this determination to apply the visual effects discussed herein. For example, device 600 can categorize representation of subject 1422 as being in the foreground of the live camera preview 1420-1 and objects positioned behind the user as being in the background of the live camera preview 1420-1. These background objects are referred to generally herein as background 1426.

Figure 14B:

In FIGS. 14A and 14B, representation of subject 1422 is shown wearing hat 1423, with a bill that sticks out in front of subject 1422, and no avatar is displayed on the representation of subject 1422. Device 600 displays avatar options menu 1408 (similar to avatar options menu 828) having avatar options 1410 that can be selected to display a virtual avatar in image display region 1420.

In FIG. 14B, device 600 detects input 1411 on avatar option 1410-1. In response, device 600 displays, in FIG. 14C, avatar option 1410-1 in selection region 1429 and generates haptic feedback 1412 (e.g., a tactile output, with or without an audio output) to indicate that avatar option 1410-1 is selected.

Figure 14C:
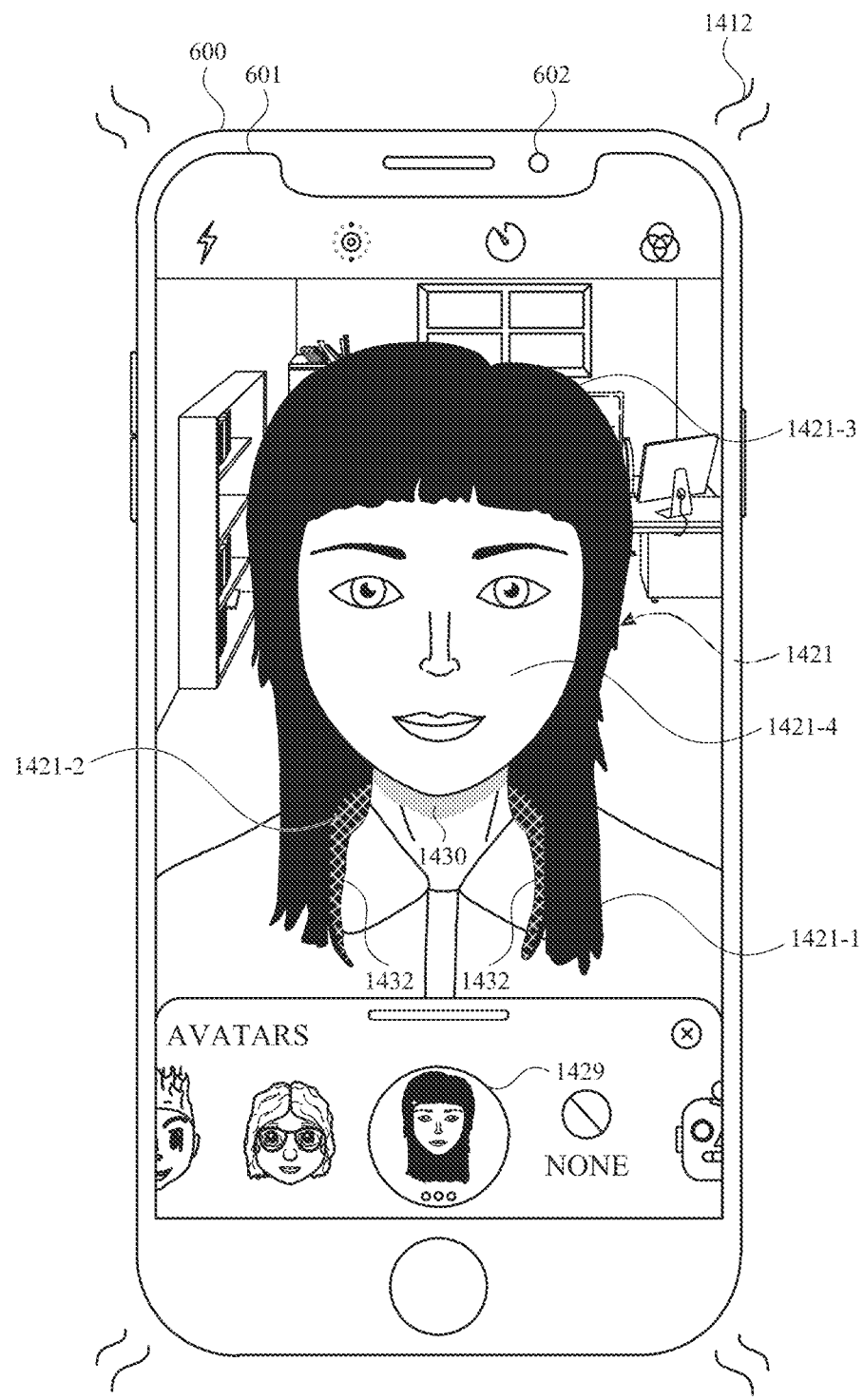

As shown in FIG. 14C, device 600 also updates live camera preview 1420-1 to display virtual avatar 1421 corresponding to selected avatar option 1410-1. Avatar 1421 is displayed overlaying portions of the representation of subject 1422, including subject's hat 1423, while maintaining display of other portions of representation of subject 1422 and background 1426. As shown in FIGS. 14A-14K, device 600 dynamically modifies avatar 1421 to hide or display certain portions of avatar 1421 depending on a spatial relationship determined for representation of subject 1422 and avatar 1421 (e.g., based on detected movements of the subject). This gives the appearance of avatar 1421 being physically placed onto the head of representation of subject 1422.

In some embodiments, the dynamic modification of avatar 1421 is achieved using one or more depth sensors (e.g., depth camera sensor 175) to capture an initial depth map of the objects in the field of view of camera 602 (including the subject (corresponding to representation of subject 1422) and background (corresponding to background 1426)). The initial depth map is then modified (e.g., using one or more of a blurring, fading, or smoothing transition of the initial depth map) to decrease instances of abrupt transitions between displaying and hiding portions of the avatar. This provides a more fluid, dynamic appearance of avatar 1421, particularly as various portions of the avatar are hidden or displayed in response to movement of the subject.

In FIG. 14C, avatar 1421 includes shadow 1430 positioned under the avatar head and displayed on the representation of the subject's neck, to represent a shadow cast by the presence of avatar 1421 on representation of subject 1422. In some embodiments, a position of shadow 1430 is determined based on a shape of the avatar and a relative position of representation of subject 1422, avatar 1421, and a light source (e.g., a light source detected in the field of view of camera 602 or a simulated light source).

Device 600 displays avatar 1421 having long hair that hangs in front of, and behind, the representation of the subject's shoulders. The position of certain portions of the hair, relative to the representation of the subject's shoulders, is determined based on depth data that indicates the spatial positioning of avatar 1421 (including the avatar hair) relative to the depth position of representation of subject 1422 (and specific portions of representation of subject 1422 (e.g., representations of the subject's neck and/or shoulders)). In some embodiments, portions of the avatar that are dynamically displayed (e.g., portions of the avatar that can be either displayed or hidden depending on the spatial relationship with representation of subject 1422) are shown having a blending effect 1432 at locations adjacent to representation of subject 1422. This blending effect smooths a displayed transition between the portion of the avatar and the representation of subject 1422.

Figure 14D:
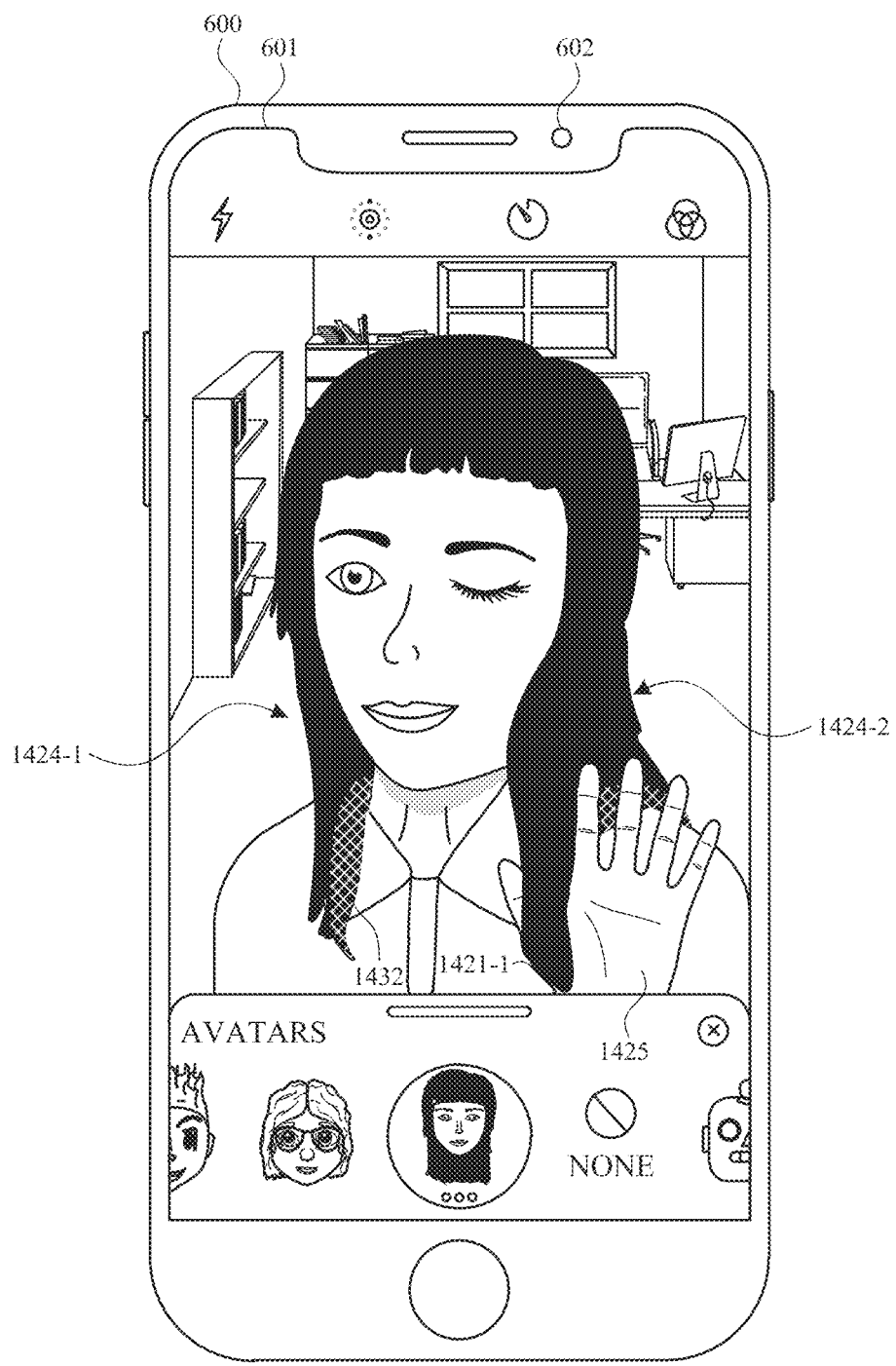
Figure 14E:
Figure 14F:
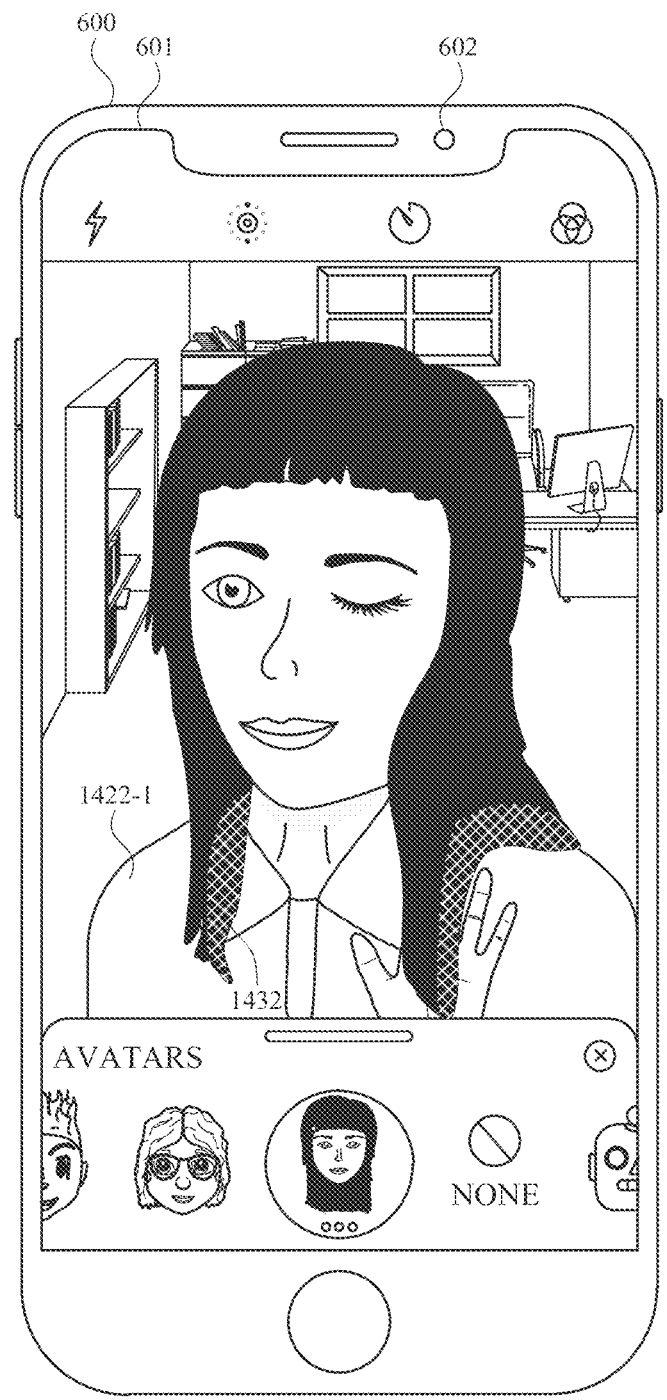

Device 600 modifies avatar 1421 in response to detected changes in the head and face of the subject. For example, as shown in FIGS. 14D-14F, device 600 detects the subject's head turned to the side, while winking and smiling and, in response, modifies avatar 1421 to reflect these same movements (e.g., avatar 1421 is shown with the avatar head turned to the side with a wink and smile), while also adjusting the position of shadow 1430 based on the movement of the avatar. Movement of the avatar head affects the spatial position of the avatar hair relative to representation of subject 1422. As a result, device 600 dynamically modifies some portions of the avatar based on the changed spatial relationship. For example, as the head turns, device 600 displays some of the avatar hair moving back over the representation of the subject's shoulder and/or behind the representation of the subject's neck (e.g., device 600 hides some portions of the avatar hair), as indicated at reference number 1424-1. Conversely, as the avatar head turns, device 600 also displays (e.g., reveals) portions of the avatar hair that were previously hidden prior to turning the avatar head (e.g., they were previously hidden behind the representation of the subject's neck or shoulder), as indicated at reference number 1424-2. Thus, device 600 hides or displays dynamic portions of the avatar (such as portions of avatar hair) based on the change in position of the user, which correspondingly affects movement of the avatar.

In some embodiments, portions of avatar 1421 are persistently displayed regardless of any spatial relationship to representation of subject 1422 or any other objects in the depth map. For example, although representation of subject 1422 is wearing hat 1423, which includes a bill that sticks out in front of representation of subject 1422, avatar head 1421-3 and avatar face 1421-4 are persistently displayed in front of the representation of the subject's head and hat 1423. This prevents objects in the field of view of camera 602, particularly objects on representation of subject 1422 (or portions of the representation of the subject), from appearing through portions of avatar 1421 (e.g., specifically, portions of avatar 1421 that should always be displayed to render an appearance of avatar 1421 positioned on representation of subject 1422). In some embodiments, the persistently displayed portions of avatar 1421 can include the avatar's face (1421-4), head (1421-3), and portions of the avatar's hair (1421-1).

As another example, FIG. 14D shows a representation of subject's hand 1425 held out in front of representation of subject 1422 towards camera 602. Although representation of hand 1425 is positioned far in front of representation of subject 1422, portion 1421-1 of avatar hair is displayed over of a portion of representation of hand 1425, even though the spatial position of representation of hand 1425 is clearly closer to camera 602 than the avatar hair portion 1421-1. To be clear, if avatar hair portion 1421-1 was dynamic (e.g., not persistently displayed), it would be hidden behind representation of hand 1425 in FIG. 14D similar to the dynamic portions of the avatar hair (e.g., 1421-2), which are discussed below.

FIG. 14E shows representation of hand 1425 moved back towards subject 1422, close to the representation of the subject's shoulder. As representation of hand 1425 moves closer to representation of subject 1422, device 600 determines that the spatial position of representation of hand 1425 moves into the dynamic portion of avatar hair. As a result, device 600 displays additional avatar hair 1421-2 positioned in front of representation of hand 1425. Similarly, FIG. 14F shows representation of hand 1425 positioned even closer towards representation of subject 1422 and a greater amount of hair displayed in front of representation of hand 1425. In FIGS. 14D-14F, the amount of hair positioned in front of representation of subject's right shoulder 1422-1 does not change because the spatial relationship of the avatar hair and representation of subject's right shoulder 1422-1 does not change after the head is turned.

Figure 14G:

In FIG. 14G, the subject returns to a forward facing position with a neutral facial expression, and device 600 modifies avatar 1421 accordingly.

Figure 14H:
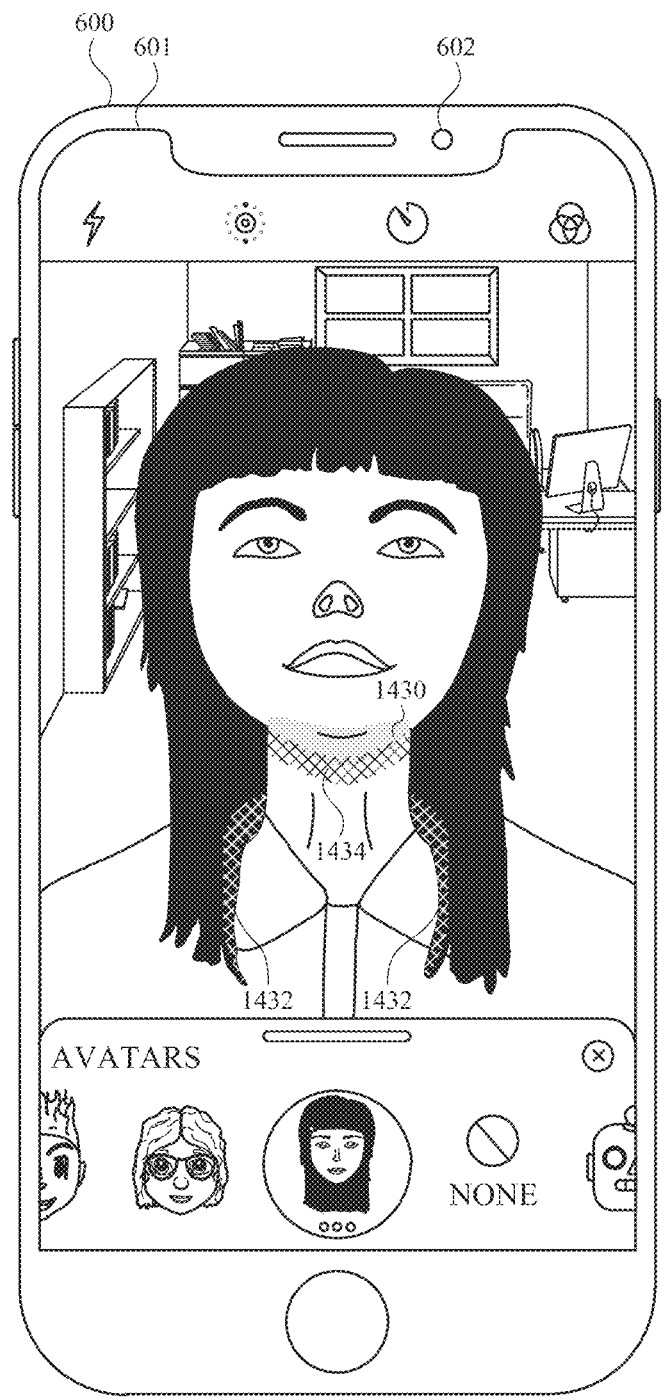

In FIG. 14H, the subject looks up, and device 600 modifies avatar 1421 accordingly. Device 600 shows avatar 1421 with a head tilting up to reveal the underside of the avatar's head, which includes blending effect 1434 at a location where the representation of the subject's neck intersects avatar 1421. In some embodiments, blending effect 1434 is similar to blending effect 1432. In FIG. 14H, shadow 1430 is also adjusted (e.g., moved under the avatar's chin) based on the tilted position of the avatar's head. When avatar 1421 is looking up, avatar hair positioned behind the representation of the subject's neck remains hidden behind the representation of the subject's neck and does not protrude through the representation of the subject's neck.

Figure 14I:
Figure 14J:
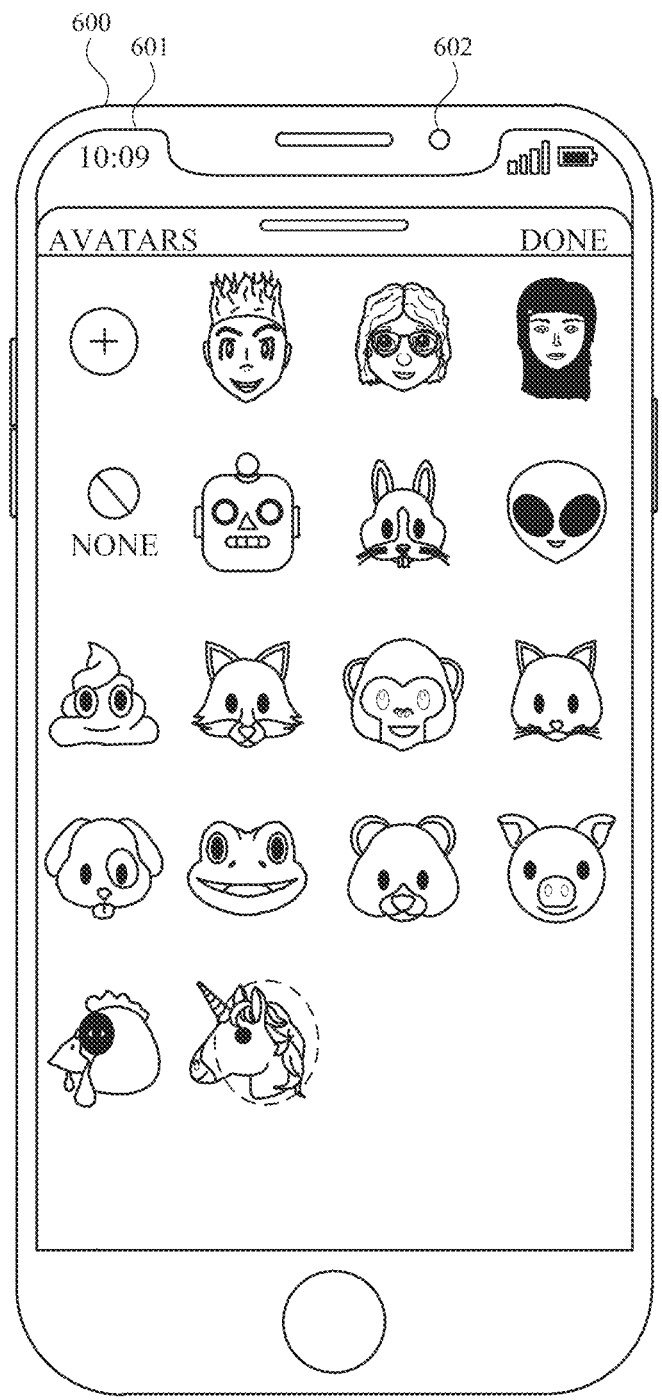

FIGS. 14I-14J illustrate selecting a different avatar in accordance with an embodiment of the present disclosure.

Figure 14K:
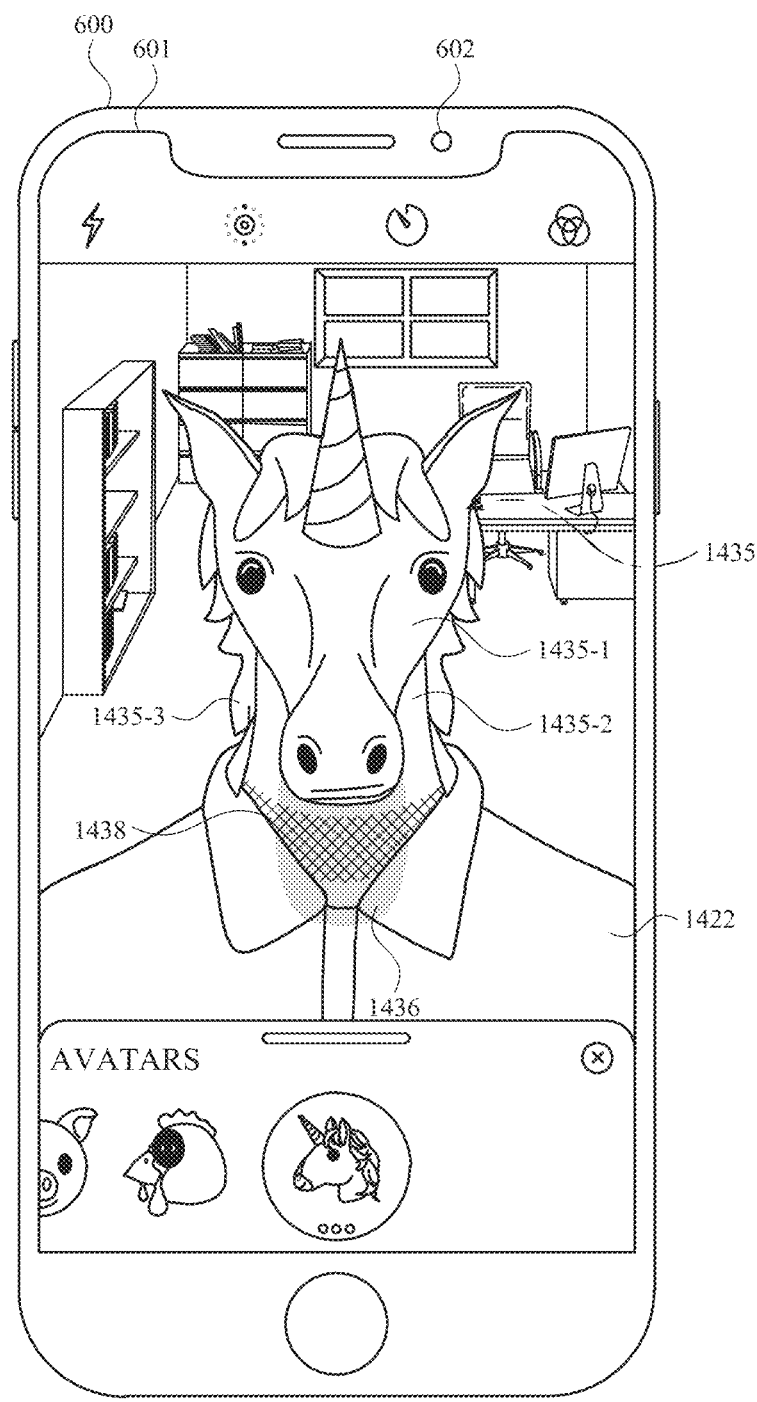
Figure 14L:
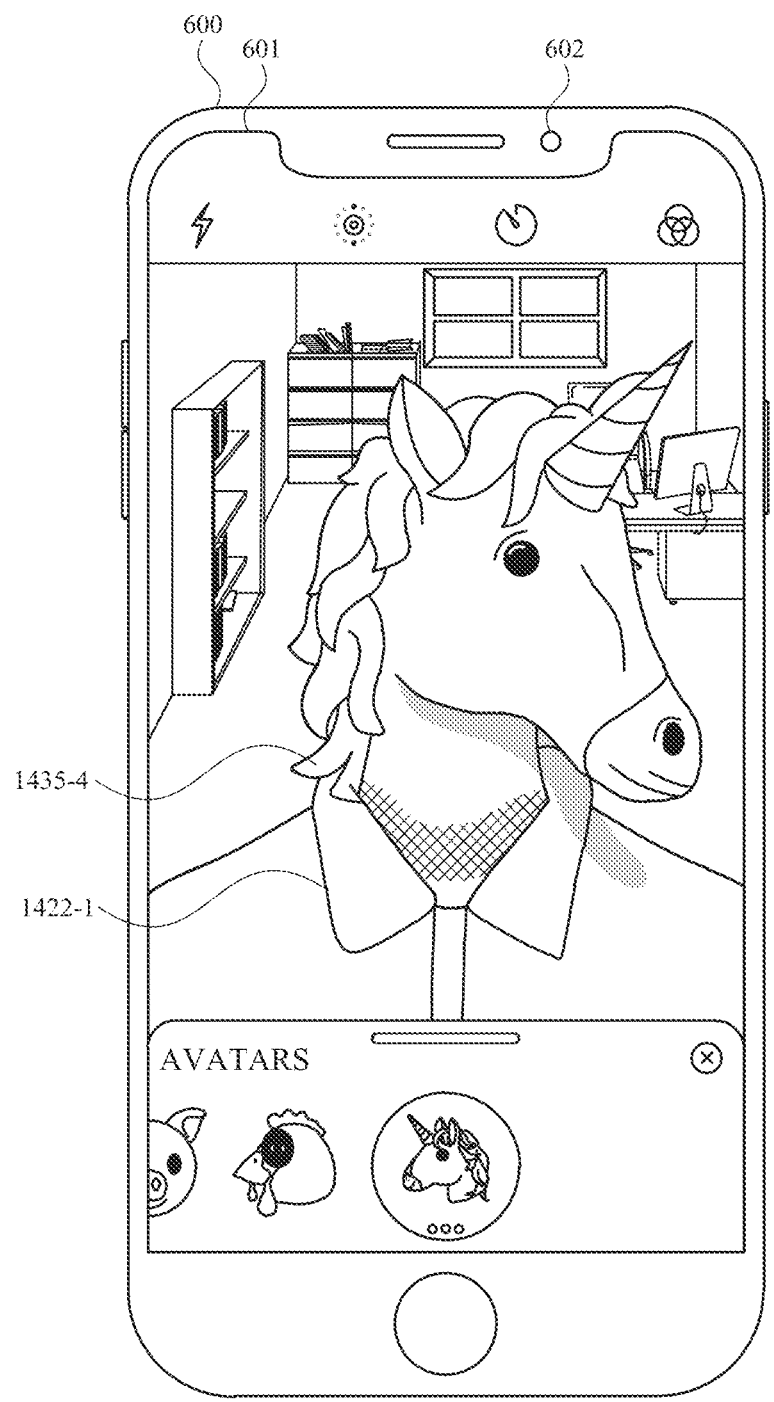
Figure 14M:

In FIGS. 14K-14M, device 600 shows representation of subject 1422 with unicorn avatar 1435 positioned over the representation of the subject's head and neck. Unicorn avatar 1435 includes a head portion 1435-1 and a neck portion 1435-2 including mane 1435-3. Neck portion 1435-2 is displayed around the representation of the subject's neck so that the representation of the subject's neck is not displayed. Blending effect 1438 is displayed where the unicorn neck portion 1435-2 meets the base of the representation of the subject's neck. Blending effect 1438 is similar to the other blending effects discussed herein.

Unicorn avatar 1435 also includes shadow 1436 displayed on a portion of unicorn avatar 1435 and on representation of subject 1432 (e.g., a representation of a shadow cast onto the representation of the subject by the avatar). In some embodiments, a displayed shadow has a shape and position determined based on the shape of the avatar and a relative position of the avatar and representation of subject 1432 to a light source (e.g., a light source detected in the field of view of camera 602 or a simulated light source). As shown in FIGS. 14K-14M, shadow 1436 moves in response to movement of unicorn avatar 1435. In FIG. 14K, shadow 1436 has an elongated shape (due to the elongated shape of the unicorn avatar's face) and is positioned on neck portion 1435-2 and the chest of representation of subject 1422. In FIG. 14L, head portion 1435-1 is turned to the side to reveal additional neck portion 1435-2 and mane 1435-3. A portion 1435-4 of mane 1435-3 that was positioned on the backside of unicorn avatar 1435 in FIG. 14K is now shown positioned in front of subject's shoulder 1422-1 and avatar neck portion 1435-2. Shadow 1436 is moved to the side to be positioned under head portion 1435-1 (e.g., on neck portion 1435-2), and partly on the shoulder of representation of subject 1422. In FIG. 14M, head portion 1435-1 is facing forward and tilted up, and shadow 1436 is positioned under head portion 1435-1 (on neck portion 1435-2) and having a reduced size due to the upward tilt of head portion 1435-1. Additionally, when the head is tilted up, the mane 1435-3 remains positioned on the backside of the neck portion 1435-2 and is not displayed through the neck portion.

FIGS. 15A-15B are a flow diagram illustrating a method for displaying visual effects in a camera application using an electronic device in accordance with some embodiments. Method 1500 is performed at a device (e.g., 100, 300, 500, 600) with one or more cameras and a display apparatus. Some operations in method 1500 are, optionally, combined, the orders of some operations are, optionally, changed, and some operations are, optionally, omitted.

As described below, method 1500 provides an intuitive way for displaying visual effects in a camera application. The method reduces the cognitive burden on a user for applying visual effects to an image viewed in a camera application, thereby creating a more efficient human-machine interface. For battery-operated computing devices, enabling a user to display visual effects in an image faster and more efficiently conserves power and increases the time between battery charges.

The electronic device (e.g., 600) displays (1502), via the display apparatus (e.g., 601), a representation of image data (e.g., 1420-1) captured via the one or more cameras (e.g., 602). In some embodiments, the representation includes a representation of a subject (e.g., 1422) (e.g., a representation of at least a portion of a subject) and the image data corresponds to depth data (e.g., the image data includes data captured by a visible light camera and a depth camera) that includes depth data for the subject (e.g., information about the relative depth positioning of one or more portions of the subject with respect to other portions of the subject and/or to other objects within the field of view of the one or more cameras). In some embodiments, depth data is in the form of a depth map or depth mask.

In some embodiments, the electronic device (e.g., 600) includes one or more depth sensors (e.g., 175, 602). In some embodiments, prior to displaying a representation of the virtual avatar (e.g., 1421), the electronic device captures initial depth data (e.g., an initial or unmodified depth map and/or depth mask corresponding to the image data captured by the one or more cameras (e.g., 602); an initial or unmodified depth mask of the subject) for the subject via the one or more depth sensors. The electronic device generates the depth data for the subject by modifying the initial depth data for the subject. In some embodiments, modifying the initial depth data can decrease instances of abrupt transitions between including and excluding the representation of the first portion of the virtual avatar (e.g., 1421-2), particularly as the pose of the subject changes with respect to the electronic device. Modifying the initial depth data for the subject allows for smoother transitions in displaying the representation of the virtual avatar as the pose of the user changes, thereby improving the visual feedback of detected changes in the subject (represented by the corresponding changes to the virtual avatar). Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, modifying the initial depth data for the subject includes performing one or more transformations on the initial depth data selected from the group consisting of blurring (e.g., defocusing the initial depth data to blend the transitions between different levels of the depth data; e.g., blurring the values (e.g., greyscale values) of an initial depth mask) the initial depth data, fading out (e.g., modulating the depth data downwards to reduce the depth values) to the initial depth data, and smoothing (e.g., applying a mathematical function to blend the initial depth data, particularly at the transitions between different depth layers of the initial depth data) the initial depth data.

The electronic device (e.g., 600) displays (1504), via the display apparatus (e.g., 601), a representation of a virtual avatar (e.g., 1421) (e.g., a visual representation of a virtual avatar construct that can include some or all of the construct, when represented) that is displayed in place of (e.g., occludes or is displayed on top of) at least a portion of (e.g., with at least a portion of the virtual avatar partially or completely overlaying (e.g., obscuring) at least a portion of the subject) the representation of the subject (e.g., 1422, 1423). Displaying a visual representation of the virtual avatar over at least a portion of the representation of the subject provides the user with visual feedback of how the virtual avatar looks when overlaid the subject. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the virtual avatar is placed at a simulated depth (e.g., at a location selected so that the virtual avatar is displayed slightly in front of the representation of the subject in a depth dimension of the user interface) relative to the representation of the subject as determined based on the depth data for the subject.

In some embodiments, in accordance with a determination, based on the depth data, that a first portion of the virtual avatar (e.g., 1421-2) (e.g., an avatar hair portion) satisfies a set of depth-based display criteria, device (e.g., 600) includes (1506) as part of the representation of the virtual avatar (e.g., 1421), a representation of the first portion of the virtual avatar (e.g., 1421-2) that is displayed in place of the first portion of the subject (e.g., the first portion of the representation of the subject) (for example, a portion 1421-2 of avatar hair is displayed over a portion of a representation of subject's hand 1425 as shown in FIG. 14E). When a first portion of the virtual avatar satisfies depth-based display criteria because it is not obscured by a portion of the subject, the first portion of the virtual avatar is displayed. Determining whether the first portion of the virtual avatar is obscured prior to displaying it allows the user-device interface to be more efficient by only displaying portions of the virtual avatar that will be visible to the user. Providing visual feedback of the visible portion of the virtual avatar allows the user to see the resulting image when the virtual avatar is overlaid over the subject. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the depth-based display criteria include a requirement that the depth data for the subject indicate that the first portion of the virtual avatar has a simulated depth that is in front of a corresponding first portion (e.g., a neck, shoulders and/or body) of the subject (e.g., a corresponding first portion of the representation of the subject), in order for the depth-based display criteria to be met (e.g., the set of depth-based criteria includes a criterion that is satisfied when the portion of the virtual avatar is to be displayed at a position that is not obscured by a portion of the subject (e.g., an ear of the subject)).

In some embodiments, in accordance with a determination, based on the depth data, that the first portion of the virtual avatar (e.g., 1421-2) does not satisfy the set of depth-based display criteria for the first portion of the subject (e.g., 1425) (e.g., because the depth data for the subject indicate that the first portion of the virtual avatar has a simulated depth that is behind the corresponding first portion of the subject), the device (e.g., 600) excludes (1508), from the representation of the virtual avatar (e.g., 1421), the representation of the first portion of the virtual avatar (e.g., hair is not displayed because it is positioned behind the subject's shoulder 1422-1 at region 1424-1) (e.g., additional avatar hair 1421-2 is not shown in FIG. 14D because it is positioned behind hand 1425). In some embodiments, the electronic device also displays the first portion of the subject (e.g., the first portion of the representation of the subject) in the region that would have been occupied by the first portion of the virtual avatar (e.g., forgo including as part of the representation of the virtual avatar, a representation of the first portion of the virtual avatar because that portion should be obscured by the subject). When the first portion of the virtual avatar does not satisfy depth-based display criteria because it is obscured by a portion of the subject, the first portion of the virtual avatar is excluded from the displayed representation of the virtual avatar. Determining whether the first portion of the virtual avatar is obscured prior to displaying it allows the user-device interface to be more efficient by excluding portions of the virtual avatar that will not be visible to the user. Providing visual feedback of the virtual avatar allows the user to see the resulting image when the virtual avatar is overlaid over the subject. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first portion of the virtual avatar (e.g., 1421) (e.g., an avatar head) moves based on movement of the subject. In some embodiments, the first portion of the virtual avatar moves based on the movement of the subject's head or the representation of the subject's head.

In some embodiments, the representation of the virtual avatar includes a representation of a second portion (e.g., 1421-1, 1421-3, 1421-4, 1435-1) (e.g., a top of an avatar head (1421-3)) of the virtual avatar that is displayed over a second portion (e.g., 1425, 1423) of the representation of the subject without regard to whether or not the depth data indicate that the second portion of the virtual avatar has a simulated depth that is in front of or behind the corresponding second portion of the representation of the subject. A representation of a second portion of the virtual avatar such as the top of the avatar's head is persistently displayed. This allows the second portion of the virtual avatar to always be displayed, even if the representation of the subject includes an object that is positioned closer to the camera (e.g., 602) than the avatar (e.g., a hat (1423) positioned on the representation of the subject's head will be covered by the avatar (1421)). Persistently displaying a portion of the virtual avatar provides the user with more control of the device by allowing the user to display a selected avatar without having to adjust depth settings of the device to ignore certain objects. Providing additional control of the device without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the second portion of the virtual avatar (e.g., an avatar head) is persistently displayed in place of the corresponding second portion of the representation of the subject. In some embodiments, portions of the avatar that are displayed irrespective of depth-based criteria are persistently displayed over the subject to avoid displaying portions of the representation of the subject (e.g., a hat (1423), the subject's hair) protruding through the virtual avatar, even when a spatial relationship of the portions of the virtual avatar and the portions of the representation of the subject would otherwise indicate that the portions of the virtual avatar should be obscured by the portions of the subject. In some embodiments, the second portion of the virtual avatar (e.g., an avatar head) moves based on movement of the subject (e.g., 1422) (e.g., based on movement of the subject's head or based on movement of the representation of the subject's head).

In some embodiments, the first portion of the virtual avatar (e.g., 1421-2) (e.g., a portion that is included or excluded based on depth data) is a first sub-portion of a first avatar feature (e.g., an element of the virtual avatar such as avatar hair, an avatar ear, an avatar accessory (e.g., avatar earrings)) and the second portion (e.g., 1421-1, 1421-3, 1421-4, 1435-1, 1435-2) of the virtual avatar (e.g., a portion that is not included or excluded based on depth data; that is included independent of the depth data) is a second sub-portion of the first avatar feature (e.g., avatar hair). In some embodiments, the first sub-portion is a portion (e.g., 1435-3) of the virtual avatar (e.g., 1435) that is positioned on the backside of the virtual avatar when the virtual avatar is in a neutral position (e.g., as shown in FIG. 14K) (e.g., a displayed position of the virtual avatar when no changes are detected in the pose of the subject's face or head) facing forward (e.g., facing the camera). In some embodiments, the second sub-portion (e.g., 1435-2) is a portion of the virtual avatar that is positioned on the front side of the virtual avatar or is otherwise not positioned on the backside of the virtual avatar when the virtual avatar is in a neutral position facing forward. In some embodiments, the first avatar feature is avatar hair, the second sub-portion is a front portion of the avatar hair (e.g., 1421-1) (e.g., bangs) displayed on the front of the virtual avatar's head (e.g., 1421-3), and the first sub-portion is a back portion of the avatar hair (e.g., long hair in the back) that is at least partially obscured by a portion of the subject (e.g., 1422), such as the subject's neck and/or shoulders (e.g., 1422-1).

In some embodiments, the virtual avatar (e.g., 1421, 1435) includes an avatar hair feature (e.g., avatar hair that is long) that includes the first portion (e.g., 1421-1) of the virtual avatar. The electronic device (e.g., 600) displays the representation of the virtual avatar by displaying a first portion of the avatar hair feature (e.g., 1421-1) and conditionally displays a second portion of the avatar hair feature (e.g., 1421-2) based on whether or not a simulated depth of the second portion of the avatar hair feature is in front of or behind a third portion of the representation of the subject (e.g., 1422-1) (e.g., neck, shoulders, and/or body) based on the depth data for the subject (e.g., displaying a representation of a persistent portion of the avatar hair feature and, variably including (or excluding) depending on depth, the first portion of the virtual avatar). Determining whether the first portion of the avatar hair feature and a second portion of the hair feature if it is in front of or behind a third portion of the representation of the subject, such as the neck, shoulders or body of the subject. Determining the visibility of the second portion of the hair feature prior to displaying allows the user-device interface to be more efficient in only displaying portions of the avatar hair feature that will be visible to the user. Providing visual feedback of the virtual avatar allows the user to see the resulting image when the avatar hair feature is displayed with the representation of the subject. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the virtual avatar includes an avatar neck feature (e.g., 1435-3) (e.g., a neck of an equine avatar (e.g., unicorn or horse); e.g., an avatar mane) that includes the first portion (e.g., 1435-4) of the virtual avatar. The electronic device displays the representation of the virtual avatar (e.g., 1435) by conditionally displaying a portion of the avatar neck feature based on whether or not a simulated depth of the portion of the avatar neck feature is in front of or behind a fourth portion (e.g., 1422-1) of the representation of the subject (e.g., neck or shoulder) based on the depth data for the subject (e.g., displaying a representation of a persistent portion of the avatar neck feature and, variably including (or excluding) depending on depth, the first portion of the virtual avatar). Determining whether the portion of the avatar neck feature if it is in front of or behind a fourth portion of the representation of the subject, such as the neck of the subject. Determining the visibility of the portion of the neck feature prior to displaying allows the user-device interface to be more efficient in only displaying portions of the avatar neck feature that will be visible to the user. Providing visual feedback of the virtual avatar allows the user to see the resulting image when the avatar hair feature is displayed with the representation of the subject. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first portion (e.g., 1421-2, 1435-3) of the virtual avatar (e.g., 1421, 1435) includes an obscured portion (e.g., 1435-4) of the virtual avatar (e.g., the back of the avatar's neck) that is not displayed when the portion of the representation of the subject (e.g., the subject's head) has a pose that (directly) faces the one or more cameras (e.g., the subject's head is positioned forward, facing the camera). Obscured portions of the avatar are not displayed because the user would not be able to see that portion of the avatar. Determining the visibility of the first portion of virtual avatar prior to displaying allows the user-device interface to be more efficient in only displaying portions of the avatar neck feature that will be visible to the user. Providing visual feedback of the virtual avatar allows the user to see the resulting image when the avatar hair feature is displayed with the representation of the subject. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the obscured portion of the virtual avatar includes the back of the avatar's neck (e.g., 1435-2, 1435-3) or portions of the virtual avatar (e.g., back of avatar hair) that are positioned behind the subject's neck or head. In some embodiments, this prevents the back of the avatar's neck (or portions of the avatar on the back of the avatar head or positioned behind the subject's neck) from being displayed protruding through the representation of the subject's neck when the subject's head is tilted up (e.g., looking up).

In some embodiments, displaying the representation of the virtual avatar (e.g., 1421) further includes modifying the visual appearance (e.g., blending, blurring, feathering, or otherwise gradually changing the degree of hiding) of a third portion (e.g., 1432) of the virtual avatar that is adjacent to the first portion (e.g., 1421-1) of the virtual avatar (e.g., and also adjacent at least a portion of the representation of the subject (e.g., 1422-1)) to an appearance that is based on both the appearance of the avatar and the appearance of the representation of the subject. In some embodiments, a portion of avatar hair (e.g., 1432) is blended with the representation of the subject (e.g., 1422) at a portion of the representation of the virtual avatar where the portion of the avatar hair intersects the shoulders (1422-1) of the displayed representation of the subject. In some embodiments, a bottom portion of the avatar head is blended (e.g., 1434) with the representation of the subject at a portion of the representation of the virtual avatar where the bottom portion of the avatar head intersects the displayed representation of the subject's neck (e.g., FIG. 14H).

In some embodiments, the electronic device (e.g., 600) detects a change in pose of a head portion of the subject (e.g., 1422) (e.g., the subject's head turns to the side). In response to the electronic device detecting the change in pose of the head portion of the subject, the electronic device modifies (e.g., increasing or decreasing), based on the depth data and the change in pose, an amount of the virtual avatar (e.g., 1421-2) that is excluded from (e.g., a size that is either included or excluded from the representation of the virtual avatar) the representation of the virtual avatar (e.g., the avatar's hair). Updating the displayed virtual avatar based on changes in the pose of the head portion of the subject provides visual feedback of the virtual avatar. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, modification includes increasing or decreasing an amount of the avatar's hair that is displayed in the representation of the virtual avatar (e.g., 1421) when the avatar's head (e.g., 1421-3) is turned to the side to match the movement of the subject's head. In some embodiments, the displayed amount of the first portion of the avatar (e.g., the avatar's hair) is modified depending on whether the portion of the avatar is obscured by a portion of the representation of the subject in response to the change in pose. For example, a displayed amount (e.g., size) of a portion of the avatar's hair is decreased when the portion of the avatar hair is obscured by the user's neck or shoulders (e.g., 1422-1) in response to turning the avatar's head (e.g., turning the avatar's head causes previously displayed hair positioned in front of the subject's shoulders to no longer be displayed because turning the head positioned the avatar hair behind the subject's shoulders (e.g., 1424-1)). Additionally, a displayed amount of the portion of the avatar's hair increases when the portion of the hair (e.g., 1424-2) that was previously hidden behind the subject's shoulders, neck, or head is visible as a result of the avatar head turning to the side (e.g., hair positioned behind the subject's shoulders is now visible because turning the avatar's head caused the avatar hair to be positioned in front of the subject's shoulders).

In some embodiments, the device (e.g., 600) detects (1510) a change in pose of the subject. In response to detecting the change in pose of the subject (e.g., 1422) (e.g., detecting a movement of a hand (e.g., 1425) over the user's shoulder (e.g., 1422-1; e.g., detecting a turning or tilting of the subject's head), the electronic device (e.g., 600) modifies (1512) the displayed representation of the virtual avatar (e.g., 1421) based on the change in pose. Updating the displayed virtual avatar based on changes in the pose of the subject provides visual feedback of the virtual avatar. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, in accordance with a determination, based on the depth data that takes into account the change in pose of the subject, that the first portion (e.g., 1421-2) of the virtual avatar (e.g., 1421) satisfies the set of depth-based display criteria, the electronic device updates (1514) an appearance of the representation of the virtual avatar from a first appearance (e.g., FIG. 14D) that excludes the first portion (e.g., 1421-2) of the virtual avatar (e.g., an appearance in which the first portion of the virtual avatar is not displayed because it is obscured by the representation of the subject (e.g., 1425) (e.g., a portion of the avatar's hair is hidden behind the subject's hand, neck, and/or shoulders) to a second appearance (e.g., FIG. 14E) that includes the first portion of the virtual avatar. In some embodiments, in accordance with a determination, based on the depth data that takes into account the change in pose of the subject, that the first portion of the virtual avatar does not satisfy the set of depth-based display criteria, the electronic device updates (1516) the appearance of the representation of the virtual avatar from a third appearance (e.g., FIG. 14C) that includes the first portion of the virtual avatar to a fourth appearance (e.g., FIG. 14D) that excludes the first portion of the virtual avatar (e.g., 1424-1 shows a reduction in the amount of displayed hair). In some embodiments, the first portion of the virtual avatar is dynamically hidden based on the subject's movement (e.g., a hidden portion of the avatar can become displayed, and a displayed portion of the avatar can become hidden, based on the subject's movement).

In some embodiments, the electronic device (e.g., 600) detects a change (e.g., a change in pose (e.g., orientation, rotation, translation, etc.); e.g., a change in a facial expression) in the portion of the representation of the subject (e.g., 1422). The electronic device changes an appearance of the virtual avatar (e.g., 1421, 1435) based on the detected change in the portion of the representation of the subject (e.g., modifying, in real time, a position and/or facial expression of the virtual avatar based on the detected change in the portion of the representation of the subject). Updating the displayed virtual avatar based on changes in the expressions of the subject provides visual feedback of the virtual avatar. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the electronic device (e.g., 600) displays, via the display apparatus (e.g., 601), a representation of a shadow (e.g., 1430, 1436) cast by the virtual avatar (e.g., 1421, 1435) that is displayed on at least a fifth portion (e.g., the subject's chest, neck, or shoulder) of the representation of the subject. The device displays a representation of a shadow cast by the virtual representation over a portion of the representation of the subject to provide a more realistic representation of the displayed virtual avatar with a simulated light source. Providing visual feedback of the virtual avatar allows the user to see the resulting image. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the representation of the shadow cast by the virtual avatar is overlaid on the representation of the subject with an opacity less than 100%. In some embodiments, a portion of the subject that is determined based on a relative position of the displayed virtual avatar and a simulated light source that is, optionally, determined based on a detected light source in the field of view of the camera. In some embodiments, one or more characteristics (e.g., position, intensity, shape, etc.) of the displayed representation of the shadow are based on a shape of the virtual avatar. In some embodiments, a shape of the displayed shadow is determined based on the shape of the virtual avatar such that different avatars appear to cast shadows of different shapes.

In some embodiments, one or more characteristics (e.g., position, intensity, shape, etc.) of the displayed representation of the shadow (e.g., 1430, 1436) are based on a lighting condition (e.g., a detected amount of ambient light, a detected light source, etc.) in the field of view of the one or more cameras (e.g., 602). In some embodiments, the position of the shadow is determined based on a position of a light source in the field of view of the camera. For example, if a light source (e.g., a detected light source or a modeled light source) is positioned behind the representation of the subject (e.g., 1422) in the field of view of the camera, the shadow is positioned on the representation of the subject opposite from the position of the light source relative to the representation of the subject. In some embodiments, the intensity of the shadow is determined based on the brightness of the lighting conditions detected in the field of view of the one or more cameras (e.g., the shadow is more intense (distinct, darker, etc.) for brighter lighting conditions, and less intense for darker lighting conditions).

In some embodiments, one or more characteristics (e.g., position, intensity, shape, etc.) of the displayed representation of the shadow (e.g., 1430, 1436) are based on the depth data. In some embodiments, the position and/or shape of the shadow is determined using the depth data (e.g., in the form of a depth map or depth mask) to provide a more realistic representation of the shadow effect that is based on the three-dimensional positioning of the representation of the subject (e.g., 1422) in the field of view of the one or more cameras (e.g., so that the shadow of the avatar appears to fall onto the subject based on a simulated distance from the avatar to the subject and a simulated distance from the light source to the avatar).

Note that details of the processes described above with respect to method 1500 (e.g., FIGS. 15A-15B) are also applicable in an analogous manner to the methods described above. For example, method 700 optionally includes one or more of the characteristics of the various methods described above with reference to method 1500. For example, visual effects such as virtual avatars are displayed in image data in a messaging application user interface. For another example, method 900 optionally includes one or more of the characteristics of the various methods described above with reference to method 1500. For example, visual effects such as virtual avatars are displayed in image data in a camera user interface. For another example, method 1100 optionally includes one or more of the characteristics of the various methods described above with reference to method 1500. For example, visual effects such as virtual avatars are displayed in image data in a media user interface. For another example, method 1300 optionally includes one or more of the characteristics of the various methods described above with reference to method 1500. For example, visual effects such as virtual avatars are displayed in image data in a user interface for a live video communication session. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources for sharing with other users. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to better represent a user in a conversation. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of sending an avatar, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

What is claimed is:

1. An electronic device, comprising:
a display apparatus;
one or more processors; and
memory storing one or more programs configured to be executed by the one or more processors, the one or more programs including instructions for:
displaying, via the display apparatus, a media user interface, the media user interface including:
a media display region including a representation of a media item; and
an effects affordance;
detecting a gesture directed to the effects affordance; and
in response to detecting the gesture directed to the effects affordance, displaying a plurality of effects options for applying effects to the media item concurrently with a representation of the media item, including:
in accordance with a determination that the media item is associated with corresponding depth data, the plurality of effects options include a respective effects option for applying effects based on the depth data; and
in accordance with a determination that the media item is not associated with corresponding depth data, the respective effects option is not available for activation in the plurality of effects options to apply one or more effects based on the depth data.

2. The electronic device of claim 1, wherein the respective effects option corresponds to an effect for displaying an avatar in the media item.

3. The electronic device of claim 1, wherein the respective effects option corresponds to an effect for displaying a plurality of virtual objects moving in the media item.

4. The electronic device of claim 3, wherein a trajectory of the plurality of virtual objects moving in the media item are modified based on a presence of at least one of an object in the media item or a visual effect applied to the media item.

5. The electronic device of claim 1, wherein the respective effects option corresponds to an effect for displaying one or more selectable graphical icons in the media item.

6. The electronic device of claim 1, wherein the plurality of effects options includes an option for adding labels to the media item.

7. The electronic device of claim 1, wherein the plurality of effects options includes an option for applying one or more image filters to the media item.

8. The electronic device of claim 1, wherein the depth data corresponding to the media item is obtained by a camera of the electronic device after detecting a prior selection of the effects affordance.

9. The electronic device of claim 1, wherein the media item is a recorded image or video, and wherein the effects are applied based on the depth data after the media item is recorded.

10. A non-transitory computer-readable storage medium storing one or more programs configured to be executed by one or more processors of an electronic device that is in communication with a display apparatus, the one or more programs including instructions for:
- displaying, via the display apparatus, a media user interface, the media user interface including:
  - a media display region including a representation of a media item; and
  - an effects affordance;
- detecting a gesture directed to the effects affordance; and
- in response to detecting the gesture directed to the effects affordance, displaying a plurality of effects options for applying effects to the media item concurrently with a representation of the media item, including:
  - in accordance with a determination that the media item is associated with corresponding depth data, the plurality of effects options include a respective effects option for applying effects based on the depth data; and
  - in accordance with a determination that the media item is not associated with corresponding depth data, the respective effects option is not available for activation in the plurality of effects options to apply one or more effects based on the depth data.

11. The non-transitory computer-readable storage medium of claim 10, wherein the respective effects option corresponds to an effect for displaying an avatar in the media item.

12. The non-transitory computer-readable storage medium of claim 10, wherein the respective effects option corresponds to an effect for displaying a plurality of virtual objects moving in the media item.

13. The non-transitory computer-readable storage medium of claim 12, wherein a trajectory of the plurality of virtual objects moving in the media item is modified based on a presence of at least one of an object in the media item or a visual effect applied to the media item.

14. The non-transitory computer-readable storage medium of claim 10, wherein the respective effects option corresponds to an effect for displaying one or more selectable graphical icons in the media item.

15. The non-transitory computer-readable storage medium of claim 10, wherein the plurality of effects options includes an option for adding labels to the media item.

16. The non-transitory computer-readable storage medium of claim 10, wherein the plurality of effects options includes an option for applying one or more image filters to the media item.

17. The non-transitory computer-readable storage medium of claim 10, wherein the depth data corresponding to the media item is obtained by a camera of the electronic device after detecting a prior selection of the effects affordance.

18. The non-transitory computer-readable storage medium of claim 10, wherein the media item is a recorded image or video, and wherein the effects are applied based on the depth data after the media item is recorded.

19. A method comprising:
at an electronic device having a display apparatus:
- displaying, via the display apparatus, a media user interface, the media user interface including:
  - a media display region including a representation of a media item; and
  - an effects affordance;
- detecting a gesture directed to the effects affordance; and
- in response to detecting the gesture directed to the effects affordance, displaying a plurality of effects options for applying effects to the media item concurrently with a representation of the media item, including:
  - in accordance with a determination that the media item is associated with corresponding depth data, the plurality of effects options include a respective effects option for applying effects based on the depth data; and
  - in accordance with a determination that the media item is not associated with corresponding depth data, the respective effects option is not available for activation in the plurality of effects options to apply one or more effects based on the depth data.

20. The method of claim 19, wherein the respective effects option corresponds to an effect for displaying an avatar in the media item.

21. The method of claim 19, wherein the respective effects option corresponds to an effect for displaying a plurality of virtual objects moving in the media item.

22. The method of claim 21, wherein a trajectory of the plurality of virtual objects moving in the media item is modified based on a presence of at least one of an object in the media item or a visual effect applied to the media item.

23. The method of claim 19, wherein the respective effects option corresponds to an effect for displaying one or more selectable graphical icons in the media item.

24. The method of claim 19, wherein the plurality of effects options includes an option for adding labels to the media item.

25. The method of claim 19, wherein the plurality of effects options includes an option for applying one or more image filters to the media item.

26. The method of claim 19, wherein the depth data corresponding to the media item is obtained by a camera of the electronic device after detecting a prior selection of the effects affordance.

27. The method of claim 19, wherein the media item is a recorded image or video, and wherein the effects are applied based on the depth data after the media item is recorded.

* * * * *

UNITED STATES PATENT AND TRADEMARK OFFICE
CERTIFICATE OF CORRECTION

| | | |
|---|---|---|
| PATENT NO. | : 11,722,764 B2 | Page 1 of 1 |
| APPLICATION NO. | : 17/525664 | |
| DATED | : August 8, 2023 | |
| INVENTOR(S) | : Marcel Van Os et al. | |

It is certified that error appears in the above-identified patent and that said Letters Patent is hereby corrected as shown below:

In the Claims

In Column 110, Line 57, Claim 4, delete "are" and insert -- is --, therefor.

Signed and Sealed this
Thirtieth Day of July, 2024

Katherine Kelly Vidal
*Director of the United States Patent and Trademark Office*